US008455239B2

(12) United States Patent
Feldman et al.

(10) Patent No.: US 8,455,239 B2
(45) **Date of Patent: *Jun. 4, 2013**

(54) YEAST ORGANISM PRODUCING ISOBUTANOL AT A HIGH YIELD

(75) Inventors: Reid M. Renny Feldman, San Marino, CA (US); Uvini Gunawardena, Irvine, CA (US); Jun Urano, Aurora, CO (US); Peter Meinhold, Denver, CO (US); Aristos Aristidou, Highlands Ranch, CO (US); Catherine Asleson Dundon, Englewood, CO (US); Christopher Smith, Englewood, CO (US)

(73) Assignee: Gevo, Inc., Englewood, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 12/820,505

(22) Filed: Jun. 22, 2010

(65) Prior Publication Data

US 2011/0020889 A1 Jan. 27, 2011

Related U.S. Application Data

(63) Continuation-in-part of application No. 12/696,645, filed on Jan. 29, 2010, which is a continuation of application No. 12/343,375, filed on Dec. 23, 2008, now Pat. No. 8,017,375.

(60) Provisional application No. 61/219,173, filed on Jun. 22, 2009, provisional application No. 61/016,483, filed on Dec. 23, 2007.

(51) Int. Cl.

| | |
|---|---|
| ***C12P 7/04*** | (2006.01) |
| ***C12P 7/16*** | (2006.01) |
| ***C12N 1/15*** | (2006.01) |
| ***C12N 1/16*** | (2006.01) |
| *C12N 15/00* | (2006.01) |
| *C12N 9/88* | (2006.01) |

(52) U.S. Cl.

USPC .................. 435/254.2; 435/254.21; 435/157; 435/160; 435/320.1; 435/232

(58) Field of Classification Search

USPC ....................... 435/254.2, 254.21, 320.1, 157

See application file for complete search history.

(56) References Cited

U.S. PATENT DOCUMENTS

| | | | |
|---|---|---|---|
| 6,660,507 | B2 | 12/2003 | Cheng et al. |
| 7,109,010 | B2 | 9/2006 | Rajgarhia et al. |
| 7,851,188 | B2 | 12/2010 | Donaldson et al. |
| 7,993,889 | B1 | 8/2011 | Donaldson et al. |
| 8,017,375 | B2 | 9/2011 | Feldman et al. |
| 2004/0029256 | A1 | 2/2004 | Rajgarhia et al. |
| 2004/0146996 | A1 | 7/2004 | Yocum et al. |
| 2005/0059136 | A1 | 3/2005 | van Maris et al. |
| 2006/0234364 | A1 | 10/2006 | Rajgarhia et al. |
| 2007/0092957 | A1 | 4/2007 | Donaldson et al. |
| 2009/0226691 | A1 | 9/2009 | Mankame et al. |
| 2009/0305363 | A1 | 12/2009 | Anthony et al. |
| 2010/0120105 | A1 | 5/2010 | Anthony et al. |
| 2011/0111472 | A1 | 5/2011 | Donaldson et al. |
| 2011/0112334 | A1 | 5/2011 | Donaldson et al. |
| 2011/0183392 | A1 | 7/2011 | Feldman et al. |
| 2011/0301388 | A1 | 12/2011 | Donaldson et al. |
| 2011/0313206 | A1 | 12/2011 | Donaldson et al. |
| 2011/0318799 | A1 | 12/2011 | Feldman et al. |
| 2012/0028323 | A1 | 2/2012 | Feldman et al. |

FOREIGN PATENT DOCUMENTS

| | | | |
|---|---|---|---|
| WO | WO 99/14335 | A1 | 3/1999 |
| WO | WO 03/102152 | A2 | 12/2003 |
| WO | WO 2004/099425 | A2 | 11/2004 |
| WO | WO 2006/102342 | A2 | 9/2006 |
| WO | WO 2007/032792 | A2 | 3/2007 |
| WO | WO 2007/061590 | A1 | 5/2007 |
| WO | WO 2008/042338 | A2 | 4/2008 |
| WO | WO 2008/052991 | A2 | 5/2008 |
| WO | WO 2008/063650 | A2 | 5/2008 |
| WO | WO 2008/080124 | A2 | 7/2008 |
| WO | WO 2008/098277 | A2 | 8/2008 |
| WO | WO 2008/121701 | A1 | 10/2008 |
| WO | WO 2008/130372 | A2 | 10/2008 |
| WO | WO 2009/103533 | A1 | 8/2009 |

OTHER PUBLICATIONS

Zhou et al., Cell Mol Life Sci 63(19-20):2260-2290, 2006.*
Kozak, M., Gene 234:187-208, 1999.*
Seffernick et al., J. Bacteriol. 183(8):2405-2410, 2001.*
Witkowski et al., Biochemistry 38:11643-11650, 1999.*
Branden et al, Introduction to Protein Structure, Garland Publishing Inc., New York, p. 247, 1991.*
Adachi, E, et al. (1998) Modification of Metabolic Pathways of *Saccharomyces cerevisiae* by the Expression of Lactate Dehydrogenase and Deletion of Pyruvate Decarboxylase Genes for the Lactic Acid Fermentation at Low pH Value. *Journal of Fermentation and Bioengineering* 86(3):284-9.
Atsumi, S, et al. (2008) "Non-fermentative pathways for synthesis of branched-chain higher alcohols as biofuels," *Nature* 451(7174):86-9.
Michnick, S, et al. (1997) "Modulation of Glycerol and Ethanol Yields During Alcoholic Fermentation in *Saccharomyces cerevisiae* Strains Overexpressed or Disrupted for GPD1 Encoding Glycerol 3-Phosphate Dehydrogenase," *Yeast* 13(9):783-93.
Nevoigt, E and Stahl, U. (1996) "Reduced pyruvate decarboxylase and increased glycerol-3-phosphate dehydrogenase [NAD+] levels enhance glycerol production in *Saccharomyces cerevisiae*," *Yeast* 12(13):1331-7.

(Continued)

*Primary Examiner* — Delia Ramirez
(74) *Attorney, Agent, or Firm* — Cooley LLP

(57) ABSTRACT

The present invention provides recombinant mircoorganisms comprising an isobutanol producing metabolic pathway and methods of using said recombinant microorganisms to produce isobutanol. In various aspects of the invention, the recombinant microorganisms may comprise a modification resulting in the reduction of pyruvate decarboxylase and/or glycerol-3-phosphate dehydrogenase activity. In various embodiments described herein, the recombinant microorganisms may be microorganisms of the *Saccharomyces* clade, Crabtree-negative yeast microorganisms, Crabtree-positive yeast microorganisms, post-WGD (whole genome duplication) yeast microorganisms, pre-WGD (whole genome duplication) yeast microorganisms, and non-fermenting yeast microorganisms.

9 Claims, 41 Drawing Sheets

OTHER PUBLICATIONS

Overkamp, KM, et al. (2002) "Metabolic Engineering of Glycerol Production in *Saccharomyces cerevisiae*," *Applied and Environmental Microbiology* 68(6):2814-21.
Porro D, et al. (1995) "Development of Metabolically Engineered *Saccharomyces cerevisiae* Cells for the Production of Lactic Acid," *Biotechnol Prog* 11:294-8.
Porro, D, et al. (1999) "Replacement of a Metabolic Pathway for Large-Scale Production of Lactic Acid from Engineered Yeasts," *Applied and Environmental Microbiology* 65(9), 4211-5.
Pronk, J.T., et al. (1996) "Pyruvate Metabolism in *Saccharomyces cerevisiae*," Yeast 12:1607-1633.
Salani, F and Bianchi, M. (2006) "Production of glucoamylase in pyruvate decarboxylase deletion mutants of the yeast *Kluyveromyces lactis*," *Applied Microbiology and Biotechnology* 69(5):564-72.
van Maris, AJA, et al. (2004) "Directed Evolution of Pyruvate Decarboxylase-Negative *Saccharomyces cerevisiae*, Yielding a $C_2$-Independent, Glucose-Tolerant, and Pyruvate-Hyperproducing Yeast," *Applied and Environmental Microbiology* 70(1):159-66.
Wang, Q, et al. (2005) "Metabolic engineering of *Torulopsis glabrata* for improved pyruvate production," *Enzyme and Microbial Technology* 36(5-6):832-9.
Yonehara, T and Mirata, R. (1994) "Fermentative Production of Pyruvic Acid by Yeast," *Baiosaiensu to Indasutori* 52(7):567-70.
Zelle, RM, et al. (2008) "Malic Acid Production by *Saccharomyces cerevisiae*: Engineering of Pyruvate Carboxylation, Oxaloacetate Reduction, and Malate Export," *Applied and Environmental Microbioloby* 74(9):2766-77.
International Search Report and Written Opinion mailed Jul. 23, 2009 in the International (PCT) Application No.: PCT/US08/88235, 10 pages.
International Search Report and Written Opinion mailed Aug. 30, 2010 in the International (PCT) Application No.: PCT/US10/39447, 9 pages.
Baburina, et al., "Reactivity at the substrate activation site of yeast pyruvate decarboxylase: inhibition by distortion of domain interactions," Biochemistry 37: 1245-55 (1998).
Butler, et al., "Identification of an upstream activation site in the pyruvate decarboxylase structural gene (PDC1) of *Saccharomyces cerevisiae*," Current Genetics 14: 405-12 (1988).
De La Plaza, et al., "Biochemical and molecular characterization of α-ketoisovalerate decarboxylase, an enzyme involved in the formation of aldehydes from amino acids by *Lactococcus lactis*," FEMS Microbiology Letters 238: 367-374 (Aug. 2004).
Eberhardt, et al., "Autoregulation of yeast pyruvate decarboxylase gene expression requires the enzyme but not its catalytic activity," Eur. J. Biochem. 262: 191-201 (1999).
Fernandez De Palencia, et al., "Diversity of amino acid converting enzymes in wild lactic acid bacteria," Enzyme and Microbiol Technology 38: 88-93 (Jan. 2006).
Hansen, et al., "Brewer's yeast: genetic structure and targets for improvement," Topics in Current Genetics, vol. 2., J.H. de Winde (Ed.): Functional Genetics of Industrial Yeasts (2003).
Joseph, et al., "Function of a conserved loop of the β-domain, not involved in thiamin diphosphate binding, in catalysis and substrate activation in yeast pyruvate decarboxylase," Biochemistry 45: 13517-27 (2006).
Kellermann, et al., "Analysis of the primary structure and promoter function of a pyruvate decarboxylase gene (PDC1) from *Saccharomyces cerevisiae*," Nuc. Acids Res. 14(22): 8963-77 (1986).
Kellermann, et al., "The glucose- and ethanol-dependent regulation of PDC1 from *Saccharomyces cerevisiae* are controlled by two distinct promoter regions," Current Genetics 14: 337-44 (1988).
Kutter, et al., "Covalently bound substrate at the regulatory site triggers allosteric enzyme activation," Nature Precedings: hdl:10101/npre.2008.1639.1 (Posted Feb. 27, 2008, Available Online Feb. 28, 2008); Available from Nature Precedings <http://hdl.handle.net/10101/npre.2008,1639.1>.
Langkjaer et al., "Yeast genome duplication was followed by asynchronous differentiation of duplicated genes," Nature 421:848-852 (2003).
Li, et al., "Effects of substitution of tryptophan 412 in the substrate activation pathway of yeast pyruvate decarboxylase," Biochemistry 38: 10004-10012 (1999).
Li, et al., "Role of glutamate 91 in information transfer during substrate activation of yeast pyruvate decarboxylase," Biochemistry 38: 9992-10003 (1999).
Merico et al., "Fermentative lifestyle in yeasts belonging to the *Saccharomyces* complex," FEBS Journal 274:976-989 (2007).
Sergienko, et al., "Catalytic acid-base groups in yeast pyruvate decarboxylase. 2. Insights into the specific roles of D28 and E477 from the rates and stereospecificity of formation of carboligase side products," Biochemistry 40: 7369-7381 (2001).
Serienko, et al., "Catalytic acid-base groups in yeast pyruvate decarboxylase. 3. A steady-state kinetic model consistent with the behavior of both wild-type and variant enzymes at all relevant pH values," Biochemistry 40: 7382-7403 (2001).
Serienko, et al., "Yeast pyruvate decarboxylase tetramers can dissociate into dimers along two interfaces. Hybrids of low-activity D28A (or D28N) and E477Q variants, with substitution of adjacent active center acidic groups from different subunits, display restored activity," Biochemistry 41: 6164-6169 (2002).
Smit, "Formation of amino acid derived cheese flavour compounds," Thesis Wageningen University, The Netherlands, 2004.
Smit, et al., "Identification, cloning, and characterization of a *Lactococcus lactis* branched-chain α-keto acid decarboxylase involved in flavor formation," Applied and Environmenta Microbiology 71(1): 303-311 (Jan. 2005).
Abbott et al., "Metabolic engineering of *Saccharomyces cerevisiae* for production of carboxylic acids: currnet status and challenges," FEMS Yeast Res. 9:1123-1136 (2009).
Björkqvist et al., "Physiological Response to Anaerobicity of Glycerol-3-Phosphate Dehydrogenase Mutants of *Saccharomyces cerevisiae*," Appl. Environ. Microbiol. 63(1):128-132 (1997).
Ishida et al., "The Effect of Pyruvate Decaroxylase Gene Knockout in *Saccharomyces cerevisiae* on L-Lactic Acid Production," Biosci. Biotechnol. Biochem. 70(5):1148-1153 (2006).
Nissen et al., "Anaerobic and aerobic batch cultivations of *Saccharomyces cerevisiae* mutants impaired in glycerol synthesis," Yeast 16:463-474 (2000).
Skory, "Lactic acid production by *Saccharomyces cerevisiae* expressing a *Rhizopus oryzae* lactate dehydrogenase gene," J. Ind. Microbial. Biotechnol. 30:22-27 (2003).
Boulton et al., Brewing Yeast & Fermentation, Chapters 3-4, first ed., Blackwell Science Ltd, Oxford, United Kingdom, pp. 69-259, 2001.
Chen, Ph.D. Thesis, McGill University (Montreal, Canada), Formation and Analysis of Fuse 1 Alcohols in Beer, Submitted to the Faculty of Graduate Studies and Research, Department of Agricultural Chemistry, 1978.
Hohmann et al., "Autoregulation may control the expression of yeast pyruvate decarboxylase structural genes PDCJ and PDC5," Eur. J. Biochem. 188:615-621, 1990.
Hohmann et al., "PDC6, a weakly expressed pyruvate decarboxylase gene from yeast, is activated when fused spontaneously under the control of the PDC1 promoter," Curr. Genet. 20:373-378, 1991.
Møller et al., "Pyruvate decarboxylases from the petite-negative yeast *Saccharomyces kfuyveri*," Mol. Gen. Genomics 270:558-568, 2004.
Oshita et al., "Clarification of the relationship between fusel alcohol formation and amino acid assimilation by brewing yeast using $^{13}$C-labeled amino acid," Proceedings of the European Brewery Convention Congress, pp. 387-394, 1995.
Rane et al., "Reversal of the Nucleotide Specificity of Ketol Acid Reductoisomerase by Site-Directed Mutagenesis Identifies the NADPH Binding Site," Arch. Biochem. Biophys. 338(1) :83-89 (1997).
Vuralhan et al., "Physiological characterization ofthe ARO10-Dependent, Broad-Substrate-Specificity 2-Oxo Acid Decarboxylase Activity of *Saccharomyces cerevisiae*," Appl. Environ. Micro. 71(6):3276-3284, 2005.
Yoshimoto et al., "Genetic and physiological analysis of branched-chain alcohols and isoamyl acetate production in *Saccharomyces cerevisiae*," Appl. Microbiol. Biotechnol. 59: 501-508, 2002.

Yoshimoto et al., "Pyruvate Decarbosylase Encoded by the PDC1 Gene Contributes, at Least Partially, to the Decarboxylation of α-Ketoisocaproate for Isoamyl Alcohol Formation in *Saccharomyces cerevisiae*," J. Biosci. Bioeng. 92:83-85 (2001).
Zelle et al., "Malic Acid Production by *Saccharomyces cerevisiae*: Engineering of Pyruvate Carboxylation, Oxaloacetate Reduction, and Malate Export," Appl. Environ. Microbiol. 74(9):2766-2777 (2008).
"Answer to Amended Complaint Answer to Amended Complaint, with Jury Demand, Counterclaim against Butamax(TM) Advanced Biofuels LLC, E.I. DuPont de Nemours and Co. by Gevo Inc.," Butamax™ *Advanced Biofuels LLC* v. *Gevo, Inc.* v. *E.I. DuPont de Nemours & Co.,* 1:11-cv-00054-SLR, United States District Court for the District of Delaware (filed Sep. 13, 2011).
"Sealed Answer to Answer to Amended Complaint, Counterclaim, Counterclaim against Gevo Inc. by E.I. DuPont de Nemours and Co., Butamax(TM) Advanced Biofuels LLC," Butamax™ *Advanced Biofuels LLC* v. *Gevo, Inc.* v. *E.I. DuPont de Nemours & Co.,* 1:11-cv-00054-SLR, United States District Court for the District of Delaware (filed Nov. 18, 2011).
"Objections and Responses to Gevo, Inc.'s Second Set of Interrogatories to Butamax Advanced Biofuels LLC (Nos. 8-16)" for Butamax™ *Advanced Biofuels LLC* v. *Gevo, Inc.* v. *E.I. DuPont de Nemours & Co.,* 1:11-cv-00054-SLR, United States District Court for the District of Delaware (dated Mar. 26, 2012).
"Sealed Opening Brief in Support re Sealed Motion for Leave to File Amended Answer to Counterclaims, Defenses, and Counter-Counterclaims filed by Butamax™ Advanced Biofuels LLC, E.I. DuPont de Nemours and Co.," Butamax™ *Advanced Biofuels LLC* v. *Gevo, Inc.* v. *E.I. DuPont de Nemours & Co.,* 1:11-cv-00054-SLR, United States District Court for the District of Delaware (filed Mar. 30, 2012).
"Answering Brief in Opposition re Sealed Motion for Leave to File Amended Answer to Counterclaims, Defenses, and Counter-Counterclaims filed by Gevo Inc.," Butamax™ *Advanced Biofuels LLC* v. *Gevo, Inc.* v. *E.I. DuPont de Nemours & Co.,* 1:11-cv-00054-SLR, United States District Court for the District of Delaware (filed Apr. 16, 2012).
"Sealed Reply Brief re Sealed Motion for Leave to File Amended Answer to Counterclaims, Defenses, and Counter-Counterclaims Reply Brief in Support of Plainitff'S and Counterclaim Defendants' Motion for Leave to Amend the Pleadings filed by Butamax(TM) Advanced Biofuels LLC, E.I. DuPont de Nemours and Co.," Butamax™ *Advanced Biofuels LLC* v. *Gevo, Inc. v. E.I. DuPont de Nemours & Co.,* 1:11-cv-00054-SLR, United States District Court for the District of Delaware (filed Apr. 26, 2012).
"First Supplemental Objections and Responses to Gevo, Inc.'s Second Set of Interrogatories to Butamax Advanced Biofuels LLC (Nos. 8-16)" for Butamax™ *Advanced Biofuels LLC* v. *Gevo, Inc.* v. *E.I. DuPont de Nemours & Co.,* 1:11-cv-00054-SLR, United States District Court for the District of Delaware (dated May 18, 2012).
"Request for Inter Partes Reexamination of U.S. Patent No. 8,017,375 Under 35 U.S.C. § 311 and 37 C.F.R. § 1.913," 3049 pages, U.S. Reexamination Control No. 95/002,158, filed Sep. 7, 2012.
"Order Granting Inter Partes Reexamination of U.S. Patent No. 8,017,375," 14 pages, U.S. Reexamination Control No. 95/002,158 (mailed Nov. 14, 2012).
"Office Action in Inter Partes U.S. Reexamination of U.S. Patent No. 8,017,375," 37 pages, U.S. Reexamination Control No. 95/002,158 (mailed Nov. 14, 2012).
Atsumi and Liao, "Metabolic engineering for advanced biofuels production from *Escherichia coli," Curr. Op. Biotechnol.* 19:414-419, Elsevier Ltd., England (2008).
Gevo's Opening Brief in Support of Gevo's Claim Constructions, Aug. 31, 2012, Butamax™ *Advanced Biofuels LLC* v. *Gevo, Inc.,* USDC—District of Delaware, No. 1:11-cv-00054-SLR.
Butamax's and DuPont's Responsive Brief in Support of Butamax's and DuPont's Claim Construction of the '375 and '376 Patents, Oct. 16, 2012, Butamax™ *Advanced Biofuels LLC* v. *Gevo, Inc.,*USDC—District of Delaware, No. 1:11-cv-00054-SLR.
Gevo's Reply Claim Construction Brief in Support of The Proper Construction of Disputed Terms of Gevo's '375 and '376 Patents, Oct. 17, 2012, Butamax™ *Advanced Biofuels LLC* v. *Gevo, Inc.,* USDC—District of Delaware, No. 1:11-cv-00054-SLR.
Butamax's and DuPont's Sur-Reply Brief in Support of Butamax's and DuPont's Claim Constructions of the '375 and '376 Patents, Nov. 6, 2012, Butamax™ *Advanced Biofuels LLLC* v. *Gevo, Inc.,* USDC—District of Delaware, No. 1:11-cv-00054-SLR.
U.S. Appl. No. 61/058,970, filed Jun. 5, 2008, Anthony et al.
Expert Report of Dr. Hans van Dijken, Ph.D., in Support of Butamax's Defense of Invalidity of United States Patent No. 8,017,375 Under 35 USC § 103, Aug. 31, 2012, Butamax™ *Advanced Biofuels LLC* v. *Gevo, Inc.,* USDC—District of Delaware, No. 1:11-cv-00054-SLR.
Expert Report of Professor Susan Henry, Aug. 31, 2012, Butamax™ *Advanced Biofuels LLC* v. *Gevo, Inc.,* USDC—District of Delaware, No. 1:11-cv-00054-SLR (Public Version).
Supplemental Expert Report of Corinne A. Michels, Ph.D., Oct. 24, 2012, Butamax™ *Advanced Biofuels LLC* v. *Gevo, Inc.,* USDC—District of Delaware, No. 1:11-cv-00054-SLR (Public Version).
Expert Report of Eleftherios Terry Papoutsakis, Ph.D., Oct. 12, 2012, Butamax™ *Advanced Biofuels LLC* v. *Gevo, Inc.,* USDC—District of Delaware, No. 1:11-cv-00054-SLR (Public Version).
Expert Rebuttal Report of Christopher Voigt, Ph.D., Oct. 12, 2012, Butamax™ *Advanced Biofuels LLC* v. *Gevo, Inc.,* USDC—District of Delaware, No. 1:11-cv-00054-SLR (Public Version).
Expert Report of Corinne Michels, Ph.D. in Support of Butamax's Defense of Invalidity of United States Patent No. 8,017,375 Under 35 USC §§ 102 and 103, Aug. 31, 2012, Butamax™ *Advanced Biofuels LLC* v. *Gevo, Inc.,* USDC—District of Delaware, No. 1:11-cv-00054-SLR (Public Version).
Bengtsson et al., "Xylose reductase from Pichia stipitis with altered coenzyme preference improves ethanolic xylose fermentation by recombinant Saccharomyces cerevisiae," Biotechnol. Biofuels 2:1-10 (2009).
Bode, "Valine inhibition β-isopropylmalate dehydrogenase takes part in the regulation of leucine biosynthesis in Candida maltosa," Antonie van Leeuwenhoek 60:125-130 (1991).
Connor et al., "Engineering of an *Escherichia coli* Strain for the Production of 3-Methyl-1-Butanol," Appl. Environ. Microbiol. 74(18):5769-5775 (2008).
Guo et al., "Interruption of glycerol pathway in industrial alcoholic yeasts to improve the ethanol production," Appl. Microbiol. Biotechnol. 82(2):287-292 (2009).
Lee et al., "Metabolic engineering of microorganisms for biofuels production: from bugs to synthetic biology to fuels," Curr. Opin. Biotechnol. 19(6):556-563 (2008).
Papini et al., "Systems Biology of Industrial Microorganisms," Adv. Biochem. Engin./Biotechnol. 120:51-99 (2010).
Van Vleet et al., "Yeast metabolic engineering for hemicellulosic ethanol production," Curr. Opin. Biotechnol. 20(3) :300-306 (2009).
Supplementary European Search Report, EP Appl. No. 10792562.0, 7 pages (Jan. 16, 2013).
"Patent Owner's Response to Office Action," 50 pages, U.S. Reexamination Control No. 95/002,158 (mailed Feb. 14, 2013).
Butamax and Dupont's Responsive and Reply Brief in Support of its Motion for Summary Judgment of Invalidity of the '375 and'376 Patents, 48 pages, Dec. 28, 2012, Butamax™ *Advanced Biofuels LLC* v. *Gevo, Inc.,* USDC—District of Delaware, No. 1:11-cv-00054-SLR (Public Version).
Gevo, Inc.'s Opposition to Butamax's Motion re Invalidity of the '375 and '376 Patents and Cross Motion for Summary Judgement of Written Description and Enablement of the '376 Patent, 45 pages, Dec. 14, 2012, Butamax™ *Advanced Biofuels LLC* v. *Gevo, Inc.,* USDC—District of Delaware, No. 1:11-cv-00054-SLR (Public Version).
Butamax and Dupont's Opening Brief in Support of Their Motion for Summary Judgment of Invalidity of the '375 and '376 Patents, 54 pages, Nov. 30, 2012, Butamax™ *Advanced Biofuels LLC* v. *Gevo, Inc.,* USDC—District of Delaware, No. 1:11-cv-00054-SLR (Public Version).

* cited by examiner

SEQUENCE LISTING

```
<160> NUMBER OF SEQ ID NOS: 78

<210> SEQ ID NO 1
<211> LENGTH: 4831
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

gcttagttta catttctttc ccaagtttaa ttcaatttct tcaacaaaga tttagagagt     60

atacttgcgc cgtcatcata ctggctgcct ttccgtttca tcaataaata tatgtattct    120

ctaattaatt ttatgctcat aatatatcgg ttgcacgaga tggtcattcc gatggtttca    180

gactctagtt aaaagaagaa gctagatgct gataatattg atttcggatg ttactgattg    240

aatattttga gctattataa taatatcaac aaagaaaatt ttaacgtggg ttgattctta    300

ggtttaaaaa gacccatcgt atatctcacc aaatatcggt accgtattcg aaggataagg    360

actaacgact taatctctaa cttgtggtaa ctaaatttag tcctttatct acaatttctc    420

tatagagcat tcaacaaaga ttgtggtttt tatctatcaa gtattattcc attactatta    480

atgtacttat aaaattctgt atatgaagag tatcaagaaa actgtgactt ctccacatca    540

gtatagtaaa gccaacaaag gggatacctt tgcagttgta gcaactattg gcgtaaacgt    600

ttcaaatggg gtaaaagaaa gaaataaaga gtatatcgtt catatatatc atttagaaat    660

caaatcacta aaattcgatt agttcttagc gttggtagca gcagtcaatt cgagctcata    720

gcttcaaaat gtttctactc cttttttact cttccagatt ttctcggact ccgcgcatcg    780

ccgtaccact tcaaaacacc caagcacagc atactaaatt tcccctcttt cttcctctag    840

ggtgtcgtta attacccgta ctaaaggttt ggaaaagaaa aaagagaccg cctcgtttct    900
```

```
ttttcttcgt cgaaaaaggc aataaaaatt tttatcacgt ttcttttttct tgaaaatttt    960
tttttgatt tttttctctt tcgatgacct cccattgata tttaagttaa taaacggtct   1020
tcaatttctc aagtttcagt ttcatttttc ttgttctatt acaacttttt ttacttcttg   1080
ctcattagaa agaaagcata gcaatctaat ctaagttttc tagtatgatt gaacaagatg   1140
gattgcacgc aggttctccg gccgcttggg tggagaggct attcggctat gactgggcac   1200
aacagacaat cggctgctct gatgccgccg tgttccggct gtcagcgcag gggcgcccgg   1260
ttctttttgt caagaccgac ctgtccggtg ccctgaatga actgcaggac gaggcagcgc   1320
ggctatcgtg gctggccacg acgggcgttc cttgcgcagc tgtgctcgac gttgtcactg   1380
aagcgggaag ggactggctg ctattgggcg aagtgccggg gcaggatctc ctgtcatctc   1440
accttgctcc tgccgagaaa gtatccatca tggctgatgc aatgcggcgg ctgcatacgc   1500
ttgatccggc tacctgccca ttcgaccacc aagcgaaaca tcgcatcgag cgagcacgta   1560
ctcggatgga agccggtctt gtcgatcagg atgatctgga cgaagagcat caggggctcg   1620
cgccagccga actgttcgcc aggctcaagg cgcgcatgcc cgacggcgag gatctcgtcg   1680
tgacccatgg cgatgcctgc ttgccgaata tcatggtgga aaatggccgc ttttctggat   1740
tcatcgactg tggccggctg ggtgtggcgg accgctatca ggacatagcg ttggctaccc   1800
gtgatattgc tgaagagctt ggcggcgaat gggctgaccg cttcctcgtg ctttacggta   1860
tcgccgctcc cgattcgcag cgcatcgcct tctatcgcct tcttgacgag ttcttctgaa   1920
ccggtagagt tctccgagaa caagcagagg ttcgagtgta ctcggatcag aagttacaag   1980
ttgatcgttt atatataaac tatacagaga tgttagagtg taatggcatt gcgtaagctt   2040
ggcgtaatca tggtcatagc tgtttcctgt gtgaaattgt tatccgctca caattccaca   2100
caacatacga gccggaagca taaagtgtaa agcctggggt gcctaatgag tgagctaact   2160
cacattaatt gcgttgcgct cactgcccgc tttccagtcg ggaaacctgt cgtgccagct   2220
gcattaatga atcggccaac gcgcggggag aggcggtttg cgtattgggc gctcttccgc   2280
ttcctcgctc actgactcgc tgcgctcggt cgttcggctg cggcgagcgg tatcagctca   2340
ctcaaaggcg gtaatacggt tatccacaga atcaggggat aacgcaggaa agaacatgtg   2400
agcaaaaggc cagcaaaagg ccaggaaccg taaaaaggcc gcgttgctgg cgtttttcca   2460
taggctccgc ccccctgacg agcatcacaa aaatcgacgc tcaagtcaga ggtggcgaaa   2520
cccgacagga ctataaagat accaggcgtt tccccctgga agctccctcg tgcgctctcc   2580
tgttccgacc ctgccgctta ccggatacct gtccgccttt ctcccttcgg gaagcgtggc   2640
gctttctcat agctcacgct gtaggtatct cagttcggtg taggtcgttc gctccaagct   2700
gggctgtgtg cacgaacccc ccgttcagcc cgaccgctgc gccttatccg gtaactatcg   2760
tcttgagtcc aacccggtaa gacacgactt atcgccactg gcagcagcca ctggtaacag   2820
gattagcaga gcgaggtatg taggcggtgc tacagagttc ttgaagtggt ggcctaacta   2880
cggctacact agaaggacag tatttggtat ctgcgctctg ctgaagccag ttaccttcgg   2940
aaaaagagtt ggtagctctt gatccggcaa acaaaccacc gctggtagcg gtggtttttt   3000
tgtttgcaag cagcagatta cgcgcagaaa aaaaggatct caagaagatc ctttgatctt   3060
ttctacgggg tctgacgctc agtggaacga aaactcacgt taagggattt tggtcatgag   3120
attatcaaaa aggatcttca cctagatcct tttaaattaa aaatgaagtt ttaaatcaat   3180
ctaaagtata tatgagtaaa cttggtctga cagttaccaa tgcttaatca gtgaggcacc   3240
tatctcagcg atctgtctat ttcgttcatc catagttgcc tgactccccg tcgtgtagat   3300
```

```
aactacgata cgggagggct taccatctgg ccccagtgct gcaatgatac cgcgagaccc   3360
acgctcaccg gctccagatt tatcagcaat aaaccagcca gccggaaggg ccgagcgcag   3420
aagtggtcct gcaactttat ccgcctccat ccagtctatt aattgttgcc gggaagctag   3480
agtaagtagt tcgccagtta atagtttgcg caacgttgtt gccattgcta caggcatcgt   3540
ggtgtcacgc tcgtcgtttg gtatggcttc attcagctcc ggttcccaac gatcaaggcg   3600
agttacatga tcccccatgt tgtgcaaaaa agcggttagc tccttcggtc ctccgatcgt   3660
tgtcagaagt aagttggccg cagtgttatc actcatggtt atggcagcac tgcataattc   3720
tcttactgtc atgccatccg taagatgctt ttctgtgact ggtgagtact caaccaagtc   3780
attctgagaa tagtgtatgc ggcgaccgag ttgctcttgc ccggcgtcaa tacgggataa   3840
taccgcgcca catagcagaa ctttaaaagt gctcatcatt ggaaaacgtt cttcggggcg   3900
aaaactctca aggatcttac cgctgttgag atccagttcg atgtaaccca ctcgtgcacc   3960
caactgatct tcagcatctt ttactttcac cagcgtttct gggtgagcaa aaacaggaag   4020
gcaaaatgcc gcaaaaaagg gaataagggc gacacggaaa tgttgaatac tcatactctt   4080
cctttttcaa tattattgaa gcatttatca gggttattgt ctcatgagcg gatacatatt   4140
tgaatgtatt tagaaaaata aacaaatagg ggttccgcgc acatttcccc gaaaagtgcc   4200
acctgacgtc acctggtaga ccaaagatgg tttgaacttc gacttgcttt aatctttcga   4260
acaagtaacg acctaatgta atttcagaca ttgtaattta agttggtttt gagttgtagt   4320
tttatcctta atattaatag ttaatactat aatatgtttg gctttagtgg atggtttttg   4380
aggtaatcaa aagtatataa ttaagattat gattaagaca tgatgggaaa ctctagccat   4440
tacagataat catgcccatg tatttatact ttatctgagt taactaaaaa aaatagaaag   4500
gtcatattca ccacccagcc agccctgcct ctcacctcac tctccccct taatggataa    4560
ttgacacaag tggtactact attccaacct taagatattc atgggccaat actacgtata   4620
caccttaaaa ggttgaatct tttcacaaat attgcataat ctatcccatg gttctacata   4680
gcaaatacag aatatgcaaa atacaggaca cgcacaaggg ccagcaatgg ttagctaatt   4740
tgaataattt ccaataccat gaaattatcc cacctttac cttggttgac tctcatttcc    4800
gattttctat accacagaaa ccgcacgtgt c                                  4831
```

<210> SEQ ID NO 2
<211> LENGTH: 7441
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
ccagttaact gtgggaatac tcaggtatcg taagatgcaa gagttcgaat ctcttagcaa     60
ccattatttt tttcctcaac ataacgagaa cacacagggg cgctatcgca cagaatcaaa    120
ttcgatgact ggaaattttt tgttaatttc agaggtcgcc tgacgcatat accttttca     180
actgaaaaat tgggagaaaa aggaaaggtg agagcgccgg aaccggcttt tcatatagaa    240
tagagaagcg ttcatgacta aatgcttgca tcacaatact tgaagttgac aatattattt    300
aaggacctat tgttttttcc aataggtggt tagcaatcgt cttactttct aacttttctt    360
accttttaca tttcagcaat atatatatat atatttcaag gatataccat tctaatgtct    420
gcccctaaga agatcgtcgt tttgccaggt gaccacgttg gtcaagaaat cacagccgaa    480
```

```
gccattaagg ttcttaaagc tatttctgat gttcgttcca atgtcaagtt cgatttcgaa    540
aatcatttaa ttggtggtgc tgctatcgat gctacaggtg ttccacttcc agatgaggcg    600
ctggaagcct ccaagaaggc tgatgccgtt ttgttaggtg ctgtgggtgg tcctaaatgg    660
ggtaccggta gtgttagacc tgaacaaggt ttactaaaaa tccgtaaaga acttcaattg    720
tacgccaact taagaccatg taactttgca tccgactctc ttttagactt atctccaatc    780
aagccacaat ttgctaaagg tactgacttc gttgttgtca gagaattagt gggaggtatt    840
tactttggta agagaaagga agacgatggt gatggtgtcg cttgggatag tgaacaatac    900
accgttccag aagtgcaaag aatcacaaga atggccgctt tcatggccct acaacatgag    960
ccaccattgc ctatttggtc cttggataaa gctaatgttt tggcctcttc aagattatgg   1020
agaaaaactg tggaggaaac catcaagaac gaattcccta cattgaaggt tcaacatcaa   1080
ttgattgatt ctgccgccat gatcctagtt aagaacccaa cccacctaaa tggtattata   1140
atcaccagca acatgtttgg tgatatcatc tccgatgaag cctccgttat cccaggttcc   1200
ttgggtttgt tgccatctgc gtccttggcc tctttgccag acaagaacac cgcatttggt   1260
ttgtacgaac catgccacgg ttctgctcca gatttgccaa agaataaggt caaccctatc   1320
gccactatct tgtctgctgc aatgatgttg aaattgtcat tgaacttgcc tgaagaaggt   1380
aaggccattg aagatgcagt taaaaaggtt ttggatgcag gtatcagaac tggtgattta   1440
ggtggttcca acagtaccac cgaagtcggt gatgctgtcg ccgaagaagt taagaaaatc   1500
cttgcttaaa aagattctct ttttttatga tatttgtaca taaactttat aaatgaaatt   1560
cataatagaa acgacacgaa attacaaaat ggaatatgtt catagggtag acgaaactat   1620
atacgcaatc tacatacatt tatcaagaag gagaaaaagg aggatgtaaa ggaatacagg   1680
taagcaaatt gatactaatg gctcaacgtg ataaggaaaa agaattgcac tttaacatta   1740
atattgacaa ggaggagggc accacacaaa aagttaggtg taacagaaaa tcatgaaact   1800
atgattccta atttatatat tggaggattt tctctaaaaa aaaaaaaata caacaaataa   1860
aaaacactca atgacctgac catttgatgg agttgccggc gatcacagcg gacggtggtg   1920
gcatgatggg gcttgcgatg ctatgtttgt ttgttttgtg atgatgtata ttattattga   1980
aaaacgatat cagacatttg tctgataatg cttcattatc agacaaatgt ctgatatcgt   2040
ttggagaaaa agaaaaggaa aacaaactaa atatctacta tataccactg tattttatac   2100
taatgacttt ctacgcctag tgtcaccctc tcgtgtaccc attgaccctg tatcggcgcg   2160
ttgcctcgcg ttcctgtacc atatattttt gtttatttag gtattaaaat ttactttcct   2220
catacaaata ttaaattcac caaacttctc aaaaactaat tattcgtagt tacaaactct   2280
attttacaat cacgtttatt caaccattct acatccaata accaaaatgc ccatgtacct   2340
ctcagcgaag tccaacggta ctgtccaata ttctcattaa atagtctttc atctatatat   2400
cagaaggtaa ttataattag agatttcgaa tcattaccgt gccgattcgc acgctgcaac   2460
ggcatgcatc actaatgaaa agcatacgac gcctgcgtct gacatgcact cattctgaag   2520
aagattctgg gcgcgtttcg ttctcgtttt cctctgtata ttgtactctg gtggacaatt   2580
tgaacataac gtctttcacc tcgccattct caataatggg ttccaattct atccaggtag   2640
cggttaattg acggtgctta agccgtatgc tcactctaac gctaccgttg tccaaacaac   2700
ggacccctttt gtgacgggtg taagacccat catgaagtaa aacatctcta acggtatgga   2760
aaagagtggt acggtcaagt ttcctggcac gagtcaattt tccctcttcg tgtagatcgg   2820
taccggccgc aaattaaagc cttcgagcgt cccaaaacct tctcaagcaa ggttttcagt   2880
```

```
ataatgttac atgcgtacac gcgtctgtac agaaaaaaaa gaaaaatttg aaatataaat   2940
aacgttctta atactaacat aactataaaa aaataaatag ggacctagac ttcaggttgt   3000
ctaactcctt ccttttcggt tagagcggat gtggggggag ggcgtgaatg taagcgtgac   3060
ataactaatt acatgactcg agcggccgcg gatcctcaat aaaactcttc aggcaataat   3120
ttttctgcta atttaatgtt atcagaatag tccaaaggaa cgtcaattac tactggtcca   3180
gtagtatctg ggattgattt aagaatttca gcaagttctt ctttgctgtg tgcacggtaa   3240
ccttttgctc ccattgcttc agcatatttt acgtaatcaa catagccaaa atcaacggct   3300
gctgaacgac catatttcat ttcttcttgg aatttaacca tatcataatg gccgtcattc   3360
cagataattt gaacgattgg aagattcaaa cgtacagctg tttccaactc ttgccctgtg   3420
aaaaggaagc ctccatcacc agagtgtgaa taaacttttt tacctgggcg caacaatgcg   3480
gctgtaattg cccaaggaag tgcaactcca agtgtttgca ttccgtttga gaagaggaga   3540
tgacgtggtt cgtatgattt gaaatgacgt gccatccaaa tgtagagtga acctacgtca   3600
acggttactg tttcatcatc tttaacgatt tcttggaaag tgctgaccaa atcaagaggg   3660
tgcattctac cttcttcagt attttcagta tcaaattcgt gttgctcagc aacttcatga   3720
aggccatcga gataatcttt tgttcctttt ggaattttgt atccacgaac agctggtaaa   3780
agattatcca atgttgctgc gatatcacca attaattcac gttctggttg gtagtaagta   3840
tcaatttcag caatggcatt atcaataacg ataattcgac tatcaatttc tgcattccag   3900
ttacgagctt catattcaat tgggtcataa ccaacagcaa taacaaggtc agaacgtttc   3960
agaagcatat ctcctggttg attgcggaaa agaccgatac gtccataaaa agtatgttct   4020
aaatcatgtg aaataacccc tgcaccttgg aatgtttcaa cgacaggaat attaacatga   4080
gttaatagat tacgcaatga tgaagcgact ttagcatctg aagcaccagc tccaaccaaa   4140
attactggca atacagcatt tttaattgct tgtgctaaat aattaatgtc atcaatagag   4200
gcattcccca ttttagggtc tgaaagtggt tgaatggcct tgattgatac ttcggcatcc   4260
gttacatctt gggggattga taagaaagtt gcacctggat gtcctgattt tgcaatacga   4320
taagcgttgg caattgattc agaaagtgta tcagggtcaa gaacttctgc tgaatatttt   4380
gttgctgatt gcatcattcc agcattatcc attgattggt gcgcacgttt aagacggtca   4440
cttcgtttaa cttgtccacc gatagccaaa atagcatcac cttctgaagt cgcggtcaaa   4500
agcggagtcg caaggtttga tacaccaggc ccactcgtaa caactactac accaggttcg   4560
ccagtcaaac gaccaacagc ttgagccatg aaagcagctc cttgctcatg acgagtcacg   4620
accatttgag ggccttcttc attttctaat aaatcaaaaa cccggtcaat ttttgctcct   4680
ggaatcccaa atacatactt cactttatgg ttaatcaaac tatcgacaac caagttcgcc   4740
ccaaattgtt tctcagacat gtcgacaccg atatacctgt atgtgtcacc accaatgtat   4800
ctataagtat ccatgctagt tctagaaaac ttagattaga ttgctatgct ttctttctaa   4860
tgagcaagaa gtaaaaaaag ttgtaataga acaagaaaaa tgaaactgaa acttgagaaa   4920
ttgaagaccg tttattaact taaatatcaa tgggaggtca tcgaaagaga aaaaaatcaa   4980
aaaaaaaatt ttcaagaaaa agaaacgtga taaaaatttt tattgccttt ttcgacgaag   5040
aaaaagaaac gaggcggtct ctttttttctt ttccaaacct ttagtacggg taattaacga   5100
caccctagag gaagaaagag gggaaattta gtatgctgtg cttgggtgtt ttgaagtggt   5160
acggcgatgc gcggagtccg agaaaatctg gaagagtaaa aaaggagtag aaacattttg   5220
aagctatgag ctccagcttt tgttcccttt agtgagggtt aattgcgcgc ttggcgtaat   5280
```

```
catggtcata gctgtttcct gtgtgaaatt gttatccgct cacaattcca cacaacatag   5340

gagccggaag cataaagtgt aaagcctggg gtgcctaatg agtgaggtaa ctcacattaa   5400

ttgcgttgcg ctcactgccc gctttccagt cgggaaacct gtcgtgccag ctgcattaat   5460

gaatcggcca acgcgcgggg agaggcggtt tgcgtattgg gcgctcttcc gcttcctcgc   5520

tcactgactc gctgcgctcg gtcgttcggc tgcggcgagc ggtatcagct cactcaaagg   5580

cggtaatacg gttatccaca gaatcagggg ataacgcagg aaagaacatg tgagcaaaag   5640

gccagcaaaa ggccaggaac cgtaaaaagg ccgcgttgct ggcgtttttc cataggctcc   5700

gcccccctga cgagcatcac aaaaatcgac gctcaagtca gaggtggcga aacccgacag   5760

gactataaag ataccaggcg tttccccctg gaagctccct cgtgcgctct cctgttccga   5820

ccctgccgct taccggatac ctgtccgcct ttctcccttc gggaagcgtg gcgctttctc   5880

atagctcacg ctgtaggtat ctcagttcgg tgtaggtcgt tcgctccaag ctgggctgtg   5940

tgcacgaacc ccccgttcag cccgaccgct gcgccttatc cggtaactat cgtcttgagt   6000

ccaacccggt aagacacgac ttatcgccac tggcagcagc cactggtaac aggattagca   6060

gagcgaggta tgtaggcggt gctacagagt tcttgaagtg gtggcctaac tacggctaca   6120

ctagaaggac agtatttggt atctgcgctc tgctgaagcc agttaccttc ggaaaaagag   6180

ttggtagctc ttgatccggc aaacaaacca ccgctggtag cggtggtttt tttgtttgca   6240

agcagcagat tacgcgcaga aaaaaaggat ctcaagaaga tcctttgatc ttttctacgg   6300

ggtctgacgc tcagtggaac gaaaactcac gttaagggat tttggtcatg agattatcaa   6360

aaaggatctt cacctagatc cttttaaatt aaaaatgaag ttttaaatca atctaaagta   6420

tatatgagta aacttggtct gacagttacc aatgcttaat cagtgaggca cctatctcag   6480

cgatctgtct atttcgttca tccatagttg cctgactccc cgtcgtgtag ataactacga   6540

tacgggaggg cttaccatct ggccccagtg ctgcaatgat accgcgagac ccacgctcac   6600

cggctccaga tttatcagca ataaaccagc cagccggaag ggccgagcgc agaagtggtc   6660

ctgcaacttt atccgcctcc atccagtcta ttaattgttg ccgggaagct agagtaagta   6720

gttcgccagt taatagtttg cgcaacgttg ttgccattgc tacaggcatc gtggtgtcac   6780

gctcgtcgtt tggtatggct tcattcagct ccggttccca acgatcaagg cgagttacat   6840

gatcccccat gttgtgcaaa aaagcggtta gctccttcgg tcctccgatc gttgtcagaa   6900

gtaagttggc cgcagtgtta tcactcatgg ttatggcagc actgcataat tctcttactg   6960

tcatgccatc cgtaagatgc ttttctgtga ctggtgagta ctcaaccaag tcattctgag   7020

aatagtgtat gcggcgaccg agttgctctt gcccggcgtc aatacgggat aataccgcgc   7080

cacatagcag aactttaaaa gtgctcatca ttggaaaacg ttcttcgggg cgaaaactct   7140

caaggatctt accgctgttg agatccagtt cgatgtaacc cactcgtgca cccaactgat   7200

cttcagcatc ttttactttc accagcgttt ctgggtgagc aaaaacagga aggcaaaatg   7260

ccgcaaaaaa gggaataagg gcgacacgga aatgttgaat actcatactc ttcctttttc   7320

aatattattg aagcatttat cagggttatt gtctcatgag cggatacata tttgaatgta   7380

tttagaaaaa taaacaaata ggggttccgc gcacatttcc ccgaaaagtg ccacctgacg   7440

t                                                                   7441
```

<210> SEQ ID NO 3
<211> LENGTH: 8949
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 3

```
caggcaagtg cacaaacaat acttaaataa atactactca gtaataacct atttcttagc     60
atttttgacg aaatttgcta ttttgttaga gtcttttaca ccatttgtct ccacacctcc    120
gcttacatca acaccaataa cgccatttaa tctaagcgca tcaccaacat tttctggcgt    180
cagtccacca gctaacataa aatgtaagct ttcggggctc tcttgccttc caacccagtc    240
agaaatcgag ttccaatcca aaagttcacc tgtcccacct gcttctgaat caaacaaggg    300
aataaacgaa tgaggtttct gtgaagctgc actgagtagt atgttgcagt cttttggaaa    360
tacgagtctt ttaataactg gcaaaccgag gaactcttgg tattcttgcc acgactcatc    420
tccatgcagt tggacgatat caatgccgta atcattgacc agagccaaaa catcctcctt    480
aggttgatta cgaaacacgc caaccaagta tttcggagtg cctgaactat tttatatgc     540
ttttacaaga cttgaaattt tccttgcaat aaccgggtca attgttctct ttctattggg    600
cacacatata atacccagca agtcagcatc ggaatctaga gcacattctg cggcctctgt    660
gctctgcaag ccgcaaactt tcaccaatgg accagaacta cctgtgaaat taataacaga    720
catactccaa gctgcctttg tgtgcttaat cacgtatact cacgtgctca atagtcacca    780
atgccctccc tcttggccct ctccttttct tttttcgacc gaattaattc ttaatcggca    840
aaaaaagaaa agctccggat caagattgta cgtaaggtga caagctattt ttcaataaag    900
aatatcttcc actactgcca tctggcgtca taactgcaaa gtacacatat attacgatgc    960
tgtctattaa atgcttccta tattatatat atagtaatgt cgttgacgtc gccggcgatc   1020
acagcggacg gtggtggcat gatggggctt gcgatgctat gtttgtttgt tttgtgatga   1080
tgtatattat tattgaaaaa cgatatcaga catttgtctg ataatgcttc attatcagac   1140
aaatgtctga tatcgtttgg agaaaaagaa aaggaaaaca aactaaatat ctactatata   1200
ccactgtatt ttatactaat gactttctac gcctagtgtc accctctcgt gtacccattg   1260
accctgtatc ggcgcgttgc ctcgcgttcc tgtaccatat atttttgttt atttaggtat   1320
taaaatttac tttcctcata caaatattaa attcaccaaa cttctcaaaa actaattatt   1380
cgtagttaca aactctattt tacaatcacg tttattcaac cattctacat ccaataacca   1440
aaatgcccat gtacctctca gcgaagtcca acggtactgt ccaatattct cattaaatag   1500
tctttcatct atatatcaga aggtaattat aattagagat ttcgaatcat taccgtgccg   1560
attcgcacgc tgcaacggca tgcatcacta atgaaaagca tacgacgcct gcgtctgaca   1620
tgcactcatt ctgaagaaga ttctgggcgc gtttcgttct cgttttcctc tgtatattgt   1680
actctggtgg acaatttgaa cataacgtct ttcacctcgc cattctcaat aatgggttcc   1740
aattctatcc aggtagcggt taattgacgg tgcttaagcc gtatgctcac tctaacgcta   1800
ccgttgtcca aacaacggac ccctttgtga cgggtgtaag acccatcatg aagtaaaaca   1860
tctctaacgg tatggaaaag agtggtacgg tcaagtttcc tggcacgagt caattttccc   1920
tcttcgtgta gatcggtacc ggccgcaaat taaagccttc gagcgtccca aaaccttctc   1980
aagcaaggtt ttcagtataa tgttacatgc gtacacgcgt ctgtacagaa aaaaaagaaa   2040
aatttgaaat ataaataacg ttcttaatac taacataact ataaaaaaat aaatagggac   2100
ctagacttca ggttgtctaa ctccttcctt ttcggttaga gcggatgtgg ggggagggcg   2160
tgaatgtaag cgtgacataa ctaattacat gactcgagcg gccgcggatc cttaacccgc   2220
aacagcaata cgtttcatat ctgtcatata gccgcgcagt ttcttaccta cctgctcaat   2280
```

```
cgcatggctg cgaatcgctt cgttcacatc acgcagttgc ccgttatcta ccgcgccttc   2340
cggaatagct ttacccaggt cgcccggttg cagctctgcc ataaacggtt tcagcaacgg   2400
cacacaagcg taagagaaca gatagttacc gtactcagcg gtatcagaga taaccacgtt   2460
catttcgtac agacgcttac gggcgatggt gttggcaatc agcggcagct cgtgcagtga   2520
ttcataatat gcagactctt caatgatgcc ggaatcgacc atggtttcga acgccagttc   2580
aacgcccgct ttcaccatcg caatcatcag tacgccttta tcgaagtact cctgctcgcc   2640
gattttgcct tcatactgcg gcgcggtttc aaacgcggtt ttgccggtct cttcacgcca   2700
ggtcagcagt ttcttatcat cgttggccca gtccgccatc ataccggaag agaattcgcc   2760
ggagatgatg tcgtccatat gtttctggaa caggggtgcc atgatctctt tcagctgttc   2820
agaaagcgca taagcacgca gtttcgccgg gttagagaga cggtccatca tcagggtgat   2880
gccgccctgt ttcagtgctt cggtgatggt ttcccaaccg aactgaatca gtttttctgc   2940
gtatgctgga tcggtacctt cttccaccag cttgtcgaag cacagcagag agccagcctg   3000
caacataccg cacaggatgg tttgctcgcc catcaggtca gatttcactt ccgcaacgaa   3060
ggacgattcc agcacacccg cacggtgacc accggttgca gccgcccagg ctttggcaat   3120
cgccatgcct tcgcctttcg gatcgttttc cgggtgaacg gcaatcagcg tcggtacgcc   3180
gaacccacgt ttgtactctt cacgcacttc ggtgcctggg catttcggcg caaccatcac   3240
tacggtgata tctttacgga tctgctcgcc cacttcgacg atgttgaaac cgtgcgagta   3300
gcccagcgcc gcgccgtctt tcatcagtgg ctgtacggtg cgcactacat cagagtgctg   3360
cttgtccggc gtcaggttaa tcaccagatc cgcctgtggg atcagttctt cgtaagtacc   3420
cactttaaaa ccattttcgg tcgctttacg ccaggacgcg cgcttctcgg caatcgcttc   3480
tttacgcaga gcgtaggaga tatcgagacc agaatcacgc atgttcaggc cctggttcag   3540
accctgtgcg ccacagccga cgatgactac ttttttaccc tgaaggtagc tcgcgccatc   3600
ggcgaattca tcgcggccca taaagcgaca tttgcccagc tgtgccagct gctggcgcag   3660
attcagtgta ttgaagtagt tagccatgtc gacaccatct tcttctgaga tgagtttttg   3720
ttccatgcta gttctagaat ccgtcgaaac taagttctgg tgttttaaaa ctaaaaaaaa   3780
gactaactat aaaagtagaa tttaagaagt ttaagaaata gatttacaga attacaatca   3840
atacctaccg tctttatata cttattagtc aagtagggga ataatttcag ggaactggtt   3900
tcaacctttt ttttcagctt tttccaaatc agagagagca gaaggtaata gaaggtgtaa   3960
gaaaatgaga tagatacatg cgtgggtcaa ttgccttgtg tcatcattta ctccaggcag   4020
gttgcatcac tccattgagg ttgtgcccgt tttttgcctg tttgtgcccc tgttctctgt   4080
agttgcgcta agagaatgga cctatgaact gatggttggt gaagaaaaca atattttggt   4140
gctgggattc tttttttttc tggatgccag cttaaaaagc gggctccatt atatttagtg   4200
gatgccagga ataaactgtt cacccagaca cctacgatgt tatatattct gtgtaacccg   4260
ccccctattt tgggcatgta cgggttacag cagaattaaa aggctaattt tttgactaaa   4320
taaagttagg aaaatcacta ctattaatta tttacgtatt ctttgaaatg gcgagtattg   4380
ataatgataa actgagctag atctgggccg cggatcctta accccccagt ttcgatttat   4440
cgcgcaccgc gcctttgtcg gcgctggttg ccaggctggc ataagcacgc agggcaaagg   4500
agacctgacg ttcacgattt ttcggcgtcc aggctttgtc acctcgagcg tcctgcgctt   4560
cacgacgcgc cgccagttcg gcatcgctta cctgtaactg aatgccacgg ttcgggatgt   4620
cgatagcgat caggtcacca tcttcaatca ggccaatgct gccgccgctt gccgcttccg   4680
```

```
gtgagacgtg gccgatggaa agaccagagg tgccaccaga gaaacgaccg tcggtgatca   4740
gcgcacaggc tttgccgaga cccattgatt tcaggaagct ggttgggtag agcatttcct   4800
gcatccccgg accgcctttc gggccttcat agcgaattac taccacatct ccggcgacaa   4860
ctttaccgcc gagaatcgct tctaccgcat cgtcctggct ttcgtacact ttcgccgggc   4920
cggtgaattt gaggatgctg tcatcgacgc ctgccgtttt cacgatgcag ccgttttccg   4980
caaagttacc gtagagcacc gccaggccgc cgtctttgct gtaggcgtgt tccagcgagc   5040
ggatacagcc attggcgcga tcgtcgtcca gcgtatccca acggcaatct tgcgagaatg   5100
cctgtgtggt acgaatgcct gcaggacctg cgcggaacat attttttacc gcgtcatcct   5160
gggtcagcat aacgtcgtat tgttccagcg tttgcggcaa cgtcaggcca agtacgtttt   5220
tcacatcacg gttcagtaac cccgcgcgat ccagttcgcc gagaataccg ataacaccac   5280
cagcacggtg aacatcttcc atatggtatt tctgggtgct cggcgcaact ttacacagct   5340
gtggaacctt gcgggaaagc ttatcgatat cactcatggt gaagtcgatt tccgcttcct   5400
gcgccgccgc cagcaggtga agtacggtgt tagtcgatcc acccatcgcg atatccagcg   5460
tcatggcgtt ttcaaacgcc gccttactgg cgatattacg cggcagtgca ctttcgtcgt   5520
tttgctcgta ataacgtttg gtcaattcaa caatgcgttt accagcatta aggaacagct   5580
gcttacggtc ggcgtgggtt gccagcagcg agccgttgcc cggctgcgac aggcccagcg   5640
cttcggtcag gcagttcatt gagttagcgg taaacatccc ggagcaggaa ccgcaggtcg   5700
gacacgcgga acgttcaacc tgatcgctct gggagtcaga tactttcggg tctgcgccct   5760
ggatcatcgc atcaaccaga tcgagcttga tgatctgatc ggaaagtttg gttttcccgg   5820
cctccatcgg gccgccggaa acaaagatca ccggaatatt caggcgcagg gaagccatca   5880
gcatccccgg ggtgattttg tcgcagttag agatgcagac catggcgtcg gcgcagtggg   5940
cgttgaccat atactcaacg gaatcagcga tcagttcgcg agatggcagt gaataaagca   6000
tccccccgtg gcccatggca atcccatcat ccaccgcaat ggtgttgaac tctttggcaa   6060
cgccgccagc cgcttcaatt tgttcggcga ccagtttacc gagatcgcgc agatggacgt   6120
gacccggtac aaattgggtg aacgagttca caaccgcgat aatcggctta ccgaaatcgg   6180
cgtcggtcat tccggtggcg cgccacagcg cacgagcacc cgccatatta cgaccatgag   6240
tggtggtggc ggaacggtac ttaggcatgt cgacaccgat atacctgtat gtgtcaccac   6300
caatgtatct ataagtatcc atgctagttc tagaaaactt agattagatt gctatgcttt   6360
ctttctaatg agcaagaagt aaaaaaagtt gtaatagaac aagaaaaatg aaactgaaac   6420
ttgagaaatt gaagaccgtt tattaactta aatatcaatg ggaggtcatc gaaagagaaa   6480
aaaatcaaaa aaaaaatttt caagaaaaag aaacgtgata aaaattttta ttgccttttt   6540
cgacgaagaa aaagaaacga ggcggtctct tttttctttt ccaaaccttt agtacgggta   6600
attaacgaca ccctagagga agaaagaggg gaaatttagt atgctgtgct tgggtgtttt   6660
gaagtggtac ggcgatgcgc ggagtccgag aaaatctgga agagtaaaaa aggagtagaa   6720
acattttgaa gctatgagct ccagcttttg ttccctttag tgagggttaa ttgcgcgctt   6780
ggcgtaatca tggtcatagc tgtttcctgt gtgaaattgt tatccgctca caattccaca   6840
caacatagga gccggaagca taaagtgtaa agcctggggt gcctaatgag tgaggtaact   6900
cacattaatt gcgttgcgct cactgcccgc tttccagtcg ggaaacctgt cgtgccagct   6960
gcattaatga atcggccaac gcgcggggag aggcggtttg cgtattgggc gctcttccgc   7020
ttcctcgctc actgactcgc tgcgctcggt cgttcggctg cggcgagcgg tatcagctca   7080
```

ctcaaaggcg gtaatacggt tatccacaga atcaggggat aacgcaggaa agaacatgtg 7140
agcaaaaggc cagcaaaagg ccaggaaccg taaaaaggcc gcgttgctgg cgtttttcca 7200
taggctccgc ccccctgacg agcatcacaa aaatcgacgc tcaagtcaga ggtggcgaaa 7260
cccgacagga ctataaagat accaggcgtt tccccctgga agctccctcg tgcgctctcc 7320
tgttccgacc ctgccgctta ccggatacct gtccgccttt ctcccttcgg gaagcgtggc 7380
gctttctcat agctcacgct gtaggtatct cagttcggtg taggtcgttc gctccaagct 7440
gggctgtgtg cacgaacccc ccgttcagcc cgaccgctgc gccttatccg gtaactatcg 7500
tcttgagtcc aacccggtaa gacacgactt atcgccactg gcagcagcca ctggtaacag 7560
gattagcaga gcgaggtatg taggcggtgc tacagagttc ttgaagtggt ggcctaacta 7620
cggctacact agaaggacag tatttggtat ctgcgctctg ctgaagccag ttaccttcgg 7680
aaaaagagtt ggtagctctt gatccggcaa acaaaccacc gctggtagcg gtggtttttt 7740
tgtttgcaag cagcagatta cgcgcagaaa aaaaggatct caagaagatc ctttgatctt 7800
ttctacgggg tctgacgctc agtggaacga aaactcacgt taagggattt tggtcatgag 7860
attatcaaaa aggatcttca cctagatcct tttaaattaa aaatgaagtt ttaaatcaat 7920
ctaaagtata tatgagtaaa cttggtctga cagttaccaa tgcttaatca gtgaggcacc 7980
tatctcagcg atctgtctat ttcgttcatc catagttgcc tgactccccg tcgtgtagat 8040
aactacgata cgggagggct taccatctgg ccccagtgct gcaatgatac cgcgagaccc 8100
acgctcaccg gctccagatt tatcagcaat aaaccagcca gccggaaggg ccgagcgcag 8160
aagtggtcct gcaactttat ccgcctccat ccagtctatt aattgttgcc gggaagctag 8220
agtaagtagt tcgccagtta atagtttgcg caacgttgtt gccattgcta caggcatcgt 8280
ggtgtcacgc tcgtcgtttg gtatggcttc attcagctcc ggttcccaac gatcaaggcg 8340
agttacatga tcccccatgt tgtgcaaaaa agcggttagc tccttcggtc ctccgatcgt 8400
tgtcagaagt aagttggccg cagtgttatc actcatggtt atggcagcac tgcataattc 8460
tcttactgtc atgccatccg taagatgctt ttctgtgact ggtgagtact caaccaagtc 8520
attctgagaa tagtgtatgc ggcgaccgag ttgctcttgc ccggcgtcaa tacgggataa 8580
taccgcgcca catagcagaa ctttaaaagt gctcatcatt ggaaaacgtt cttcggggcg 8640
aaaactctca aggatcttac cgctgttgag atccagttcg atgtaaccca ctcgtgcacc 8700
caactgatct tcagcatctt ttactttcac cagcgtttct gggtgagcaa aaacaggaag 8760
gcaaaatgcc gcaaaaaagg gaataagggc gacacggaaa tgttgaatac tcatactctt 8820
cctttttcaa tattattgaa gcatttatca gggttattgt ctcatgagcg gatacatatt 8880
tgaatgtatt tagaaaaata aacaaatagg ggttccgcgc acatttcccc gaaaagtgcc 8940
acctgacgt 8949

<210> SEQ ID NO 4
<211> LENGTH: 8800
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4
ctgattggaa agaccattct gctttacttt tagagcatct tggtcttctg agctcattat 60
acctcaatca aaactgaaat taggtgcctg tcacggctct ttttttactg tacctgtgac 120

```
ttcctttctt atttccaagg atgctcatca caatacgctt ctagatctat tatgcattat    180

aattaatagt tgtagctaca aaaggtaaaa gaaagtccgg ggcaggcaac aatagaaatc    240

ggcaaaaaaa actacagaaa tactaagagc ttcttcccca ttcagtcatc gcatttcgaa    300

acaagagggg aatggctctg gctagggaac taaccaccat cgcctgactc tatgcactaa    360

ccacgtgact acatatatgt gatcgttttt aacatttttc aaaggctgtg tgtctggctg    420

tttccattaa ttttcactga ttaagcagtc atattgaatc tgagctcatc accaacaaga    480

aatactaccg taaaagtgta aaagttcgtt taaatcattt gtaaactgga acagcaagag    540

gaagtatcat cagctagccc cataaactaa tcaaaggagg atgtctacta agagttactc    600

ggaaagagca gctgctcata gaagtccagt tgctgccaag cttttaaact tgatggaaga    660

gaagaagtca aacttatgtg cttctcttga tgttcgtaaa acagcagagt tgttaagatt    720

agttgaggtt ttgggtccat atatctgtct attgaagaca catgtagata tcttggagga    780

tttcagcttt gagaatacca ttgtgccgtt gaagcaatta gcagagaaac acaagttttt    840

gatatttgaa gacaggaagt ttgccgacat tgggaacact gttaaattac aatacacgtc    900

tggtgtatac cgtatcgccg aatggtctga tatcaccaat gcacacggtg tgactggtgc    960

gggcattgtt gctggtttga agcaaggtgc cgaggaagtt acgaaagaac ctagagggtt   1020

gttaatgctt gccgagttat cgtccaaggg gtctctagcg cacggtgaat acactcgtgg   1080

gaccgtggaa attgccaaga gtgataagga ctttgttatt ggatttattg ctcaaaacga   1140

tatgggtgga agagaagagg gctacgattg gttgatcatg acgccaggtg ttggtcttga   1200

tgacaaaggt gatgctttgg gacaacaata cagaactgtg gatgaagttg ttgccggtgg   1260

atcagacatc attattgttg gtagaggtct tttcgcaaag ggaagagatc ctgtagtgga   1320

aggtgagaga tacagaaagg cgggatggga cgcttacttg aagagagtag gcagatccgc   1380

ttaagagttc tccgagaaca agcagaggtt cgagtgtact cggatcagaa gttacaagtt   1440

gatcgtttat atataaacta tacagagatg ttagagtgta atggcattgc gtgccggcga   1500

tcacagcgga cggtggtggc atgatggggc ttgcgatgct atgtttgttt gttttgtgat   1560

gatgtatatt attattgaaa aacgatatca gacatttgtc tgataatgct tcattatcag   1620

acaaatgtct gatatcgttt ggagaaaaag aaaaggaaaa caaactaaat atctactata   1680

taccactgta ttttatacta atgactttct acgcctagtg tcaccctctc gtgtacccat   1740

tgaccctgta tcggcgcgtt gcctcgcgtt cctgtaccat atatttttgt ttatttaggt   1800

attaaaattt actttcctca tacaaatatt aaattcacca aacttctcaa aaactaatta   1860

ttcgtagtta caaactctat tttacaatca cgtttattca accattctac atccaataac   1920

caaaatgccc atgtacctct cagcgaagtc caacggtact gtccaatatt ctcattaaat   1980

agtctttcat ctatatatca gaaggtaatt ataattagag atttcgaatc attaccgtgc   2040

cgattcgcac gctgcaacgg catgcatcac taatgaaaag catacgacgc ctgcgtctga   2100

catgcactca ttctgaagaa gattctgggc gcgtttcgtt ctcgttttcc tctgtatatt   2160

gtactctggt ggacaatttg aacataacgt ctttcacctc gccattctca ataatgggtt   2220

ccaattctat ccaggtagcg gttaattgac ggtgcttaag ccgtatgctc actctaacgc   2280

taccgttgtc caaacaacgg accccttttgt gacgggtgta agacccatca tgaagtaaaa   2340

catctctaac ggtatggaaa agagtggtac ggtcaagttt cctggcacga gtcaattttc   2400

cctcttcgtg tagatcggta ccggccgcaa attaaagcct tcgagcgtcc caaaaccttc   2460

tcaagcaagg ttttcagtat aatgttacat gcgtacacgc gtctgtacag aaaaaaaaga   2520
```

-continued

```
aaaatttgaa atataaataa cgttcttaat actaacataa ctataaaaaa ataaataggg   2580

acctagactt caggttgtct aactccttcc ttttcggtta gagcggatgt gggggggaggg   2640

cgtgaatgta agcgtgacat aactaattac atgactcgag cggccgccta tttatggaat   2700

ttcttatcat aatcgaccaa agtaaatctg tatttgacgt ctccgctttc catccttgta   2760

aaggcatggc tgacgccttc ttcgctgatc ggaagttttt ccacccatat tttgacattc   2820

ttttcggaaa ctaatttcaa tagttgttcg atttccttcc tagatccgat agcactgctt   2880

gagattgata ctcccattag gcccaacggt tttaaaacaa gcttttcatt aacttcagga   2940

gcagcaattg aaacgatgga gcctccaatc ttcataatct taacgatact gtcaaaatta   3000

actttcgaca aagatgatga gcaaacgaca agaaggtcca aagcgttaga gtattgttct   3060

gtccagcctt tatcctccaa catagcaata tagtgatcag caccgagttt catagaatcc   3120

tcccgcttgg agtggcctcg cgaaaacgca taaacctcgg ctcccatagc tttagccaac   3180

agaatcccca tatgcccaat accaccgatg ccaacaatac ctaccctctt acctggacca   3240

cagccatttc ttagtagtgg agagaaaact gtaataccac cacacaataa tggagcggct   3300

agcggacttg gaatattttc tggtatttga atagcaaagt gttcatgaag cctcacgtgg   3360

gaggcaaagc ctccttgtga aatgtagccg tccttgtaag gagtccacat agtcaaaacg   3420

tggtcattgg tacagtattg ctcgttgtca cttttgcaac gttcacactc aaaacacgcc   3480

aaggcttggg caccaacacc aacacggtca ccgattttta ccccagtgtg gcacttggat   3540

ccaaccttca ccacgcggcc aattatttca tgtccaagga tttgattttc tgggactgga   3600

ccccaattac caacggctat atgaaaatca gatccgcaga taccacaggc ttcaatttca   3660

acatcaacgt catgatcgcc aaagggtttt gggtcaaaac tcactaattt aggatgcttc   3720

caatcctttg cgttggaaat accgatgccc tgaaattttt ctgggtaaag catgtcgaca   3780

ccatcttctt ctgagatgag tttttgttcc atgctagttc tagaatccgt cgaaactaag   3840

ttctggtgtt ttaaaactaa aaaaaagact aactataaaa gtagaattta agaagtttaa   3900

gaaatagatt tacagaatta caatcaatac ctaccgtctt tatatactta ttagtcaagt   3960

aggggaataa tttcagggaa ctggtttcaa cctttttttt cagcttttttc caaatcagag   4020

agagcagaag gtaatagaag gtgtaagaaa atgagataga tacatgcgtg ggtcaattgc   4080

cttgtgtcat catttactcc aggcaggttg catcactcca ttgaggttgt gcccgttttt   4140

tgcctgtttg tgcccctgtt ctctgtagtt gcgctaagag aatggaccta tgaactgatg   4200

gttggtgaag aaaacaatat tttggtgctg ggattctttt tttttctgga tgccagctta   4260

aaaagcgggc tccattatat ttagtggatg ccaggaataa actgttcacc cagacaccta   4320

cgatgttata tattctgtgt aacccgcccc ctattttggg catgtacggg ttacagcaga   4380

attaaaaggc taattttttg actaaataaa gttaggaaaa tcactactat taattattta   4440

cgtattcttt gaaatggcga gtattgataa tgataaactg aggatcctta ggatttattc   4500

tgttcagcaa acagcttgcc cattttcttc agtaccttcg gtgcgccttc tttcgccagg   4560

atcagttcga tccagtacat acggttcgga tcggcctggg cctctttcat cacgctcaca   4620

aattcgtttt cggtacgcac aattttagac acaacacggt cctcagttgc gccgaaggac   4680

tccggcagtt tagagtagtt ccacataggg atatcgttgt aagactggtt cggaccgtgg   4740

atctcacgct caacggtgta gccgtcattg ttaataatga agcaaatcgg gttgatcttt   4800

tcacgaattg ccagacccag ttcctgtacg gtcagctgca gggaaccgtc accgatgaac   4860

agcagatgac gagattcttt atcagcgatc tgagagccca gcgctgccgg gaaagtatag   4920
```

```
ccaatgctac cccacagcgg ctgaccgata aaatggcttt tggatttcag aaagatagaa   4980
gacgcgccga aaaagctcgt accttgttcc gccacgatgg tttcattgct ctgggtcagg   5040
ttctccacgg cctgccacag gcgatcctgg gacagcagtg cgttagatgg tacgaaatct   5100
tcttgctttt tgtcaatgta tttgccttta tactcgattt cggacaggtc cagcagagag   5160
ctgatcaggc tttcgaagtc gaagttctgg atacgctcgt tgaagatttt accctcgtcg   5220
atgttcaggc taatcatttt gttttcgttc agatggtgag tgaatgcacc ggtagaagag   5280
tcggtcagtt taacgcccag catcaggatg aagtccgcag attcaacaaa ttctttcagg   5340
ttcggttcgc tcagagtacc gttgtagatg cccaggaaag acggcagagc ctcgtcaaca   5400
gaggacttgc cgaagttcag ggtggtaatc ggcagtttgg ttttgctgat gaattgggtc   5460
acggtcttct ccagaccaaa agaaatgatt tcgtggccgg tgatcacgat tggtttcttt   5520
gcgtttttca gagactcctg gattttgttc aggatttcct ggtcgctagt gttagaagtg   5580
gagttttctt tcttcagcgg caggctcggt ttttccgctt tagctgccgc aacatccaca   5640
ggcaggttga tgtaaactgg tttgcgttct ttcagcagcg cagacagaac gcggtcgatt   5700
tccacagtag cgttctctgc agtcagcagc gtacgtgccg cagtcacagg ttcatgcatt   5760
ttcatgaagt gtttgaaatc gccgtcagcc agagtgtggt ggacgaattt accttcgttc   5820
tgaactttgc tcgttgggct gcctacgatc tccaccaccg gcaggttttc ggcgtaggag   5880
cccgccagac cgttgacggc gctcagttcg ccaacaccga aagtggtcag aaatgccgcg   5940
gctttcttgg tacgtgcata accatctgcc atgtagcttg cgttcagttc gttagcgtta   6000
cccacccatt tcatgtcttt atgagagatg atctgatcca ggaactgcag attgtaatca   6060
cccggaacgc cgaagatttc ttcgataccc agttcatgca gacggtccag cagataatca   6120
ccaacagtat acatgtcgac acccgcatag tcaggaacat cgtatgggta catgctagtt   6180
ctagaaaact tagattagat tgctatgctt tctttctaat gagcaagaag taaaaaaagt   6240
tgtaatagaa caagaaaaat gaaactgaaa cttgagaaat tgaagaccgt ttattaactt   6300
aaatatcaat gggaggtcat cgaaagagaa aaaaatcaaa aaaaaaattt tcaagaaaaa   6360
gaaacgtgat aaaaattttt attgcctttt tcgacgaaga aaaagaaacg aggcggtctc   6420
ttttttcttt tccaaacctt tagtacgggt aattaacgac accctagagg aagaaagagg   6480
ggaaatttag tatgctgtgc ttgggtgttt tgaagtggta cggcgatgcg cggagtccga   6540
gaaaatctgg aagagtaaaa aaggagtaga aacattttga agctatgagc tccagctttt   6600
gttcccttta gtgagggtta attgcgcgct tggcgtaatc atggtcatag ctgtttcctg   6660
tgtgaaattg ttatccgctc acaattccac acaacatagg agccggaagc ataaagtgta   6720
aagcctgggg tgcctaatga gtgaggtaac tcacattaat tgcgttgcgc tcactgcccg   6780
ctttccagtc gggaaacctg tcgtgccagc tgcattaatg aatcggccaa cgcgcgggga   6840
gaggcggttt gcgtattggg cgctcttccg cttcctcgct cactgactcg ctgcgctcgg   6900
tcgttcggct gcggcgagcg gtatcagctc actcaaaggc ggtaatacgg ttatccacag   6960
aatcagggga taacgcagga aagaacatgt gagcaaaagg ccagcaaaag gccaggaacc   7020
gtaaaaaggc cgcgttgctg gcgtttttcc ataggctccg cccccctgac gagcatcaca   7080
aaaatcgacg ctcaagtcag aggtggcgaa acccgacagg actataaaga taccaggcgt   7140
ttccccctgg aagctccctc gtgcgctctc ctgttccgac cctgccgctt accggatacc   7200
tgtccgcctt tctcccttcg ggaagcgtgg cgctttctca tagctcacgc tgtaggtatc   7260
tcagttcggt gtaggtcgtt cgctccaagc tgggctgtgt gcacgaaccc cccgttcagc   7320
```

```
ccgaccgctg cgccttatcc ggtaactatc gtcttgagtc caacccggta agacacgact   7380
tatcgccact ggcagcagcc actggtaaca ggattagcag agcgaggtat gtaggcggtg   7440
ctacagagtt cttgaagtgg tggcctaact acggctacac tagaaggaca gtatttggta   7500
tctgcgctct gctgaagcca gttaccttcg gaaaaagagt tggtagctct tgatccggca   7560
aacaaaccac cgctggtagc ggtggttttt ttgtttgcaa gcagcagatt acgcgcagaa   7620
aaaaaggatc tcaagaagat cctttgatct tttctacggg gtctgacgct cagtggaacg   7680
aaaactcacg ttaagggatt ttggtcatga gattatcaaa aaggatcttc acctagatcc   7740
ttttaaatta aaaatgaagt tttaaatcaa tctaaagtat atatgagtaa acttggtctg   7800
acagttacca atgcttaatc agtgaggcac ctatctcagc gatctgtcta tttcgttcat   7860
ccatagttgc ctgactcccc gtcgtgtaga taactacgat acgggagggc ttaccatctg   7920
gccccagtgc tgcaatgata ccgcgagacc cacgctcacc ggctccagat ttatcagcaa   7980
taaaccagcc agccggaagg gccgagcgca gaagtggtcc tgcaacttta tccgcctcca   8040
tccagtctat taattgttgc cgggaagcta gagtaagtag ttcgccagtt aatagtttgc   8100
gcaacgttgt tgccattgct acaggcatcg tggtgtcacg ctcgtcgttt ggtatggctt   8160
cattcagctc cggttcccaa cgatcaaggc gagttacatg atcccccatg ttgtgcaaaa   8220
aagcggttag ctccttcggt cctccgatcg ttgtcagaag taagttggcc gcagtgttat   8280
cactcatggt tatggcagca ctgcataatt ctcttactgt catgccatcc gtaagatgct   8340
tttctgtgac tggtgagtac tcaaccaagt cattctgaga atagtgtatg cggcgaccga   8400
gttgctcttg cccggcgtca atacgggata ataccgcgcc acatagcaga actttaaaag   8460
tgctcatcat tggaaaacgt tcttcggggc gaaaactctc aaggatctta ccgctgttga   8520
gatccagttc gatgtaaccc actcgtgcac ccaactgatc ttcagcatct tttactttca   8580
ccagcgtttc tgggtgagca aaaacaggaa ggcaaaatgc cgcaaaaaag ggaataaggg   8640
cgacacggaa atgttgaata ctcatactct tcctttttca atattattga agcatttatc   8700
agggttattg tctcatgagc ggatacatat ttgaatgtat ttagaaaaat aaacaaatag   8760
gggttccgcg cacatttccc cgaaaagtgc cacctgacgt                         8800
```

```
<210> SEQ ID NO 5
<211> LENGTH: 1677
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

gtcgacatgt ctgagaaaca atttggggcg aacttggttg tcgatagttt gattaaccat     60
aaagtgaagt atgtatttgg gattccagga gcaaaaattg accgggtttt tgatttatta    120
gaaaatgaag aaggccctca aatggtcgtg actcgtcatg agcaaggagc tgctttcatg    180
gctcaagctg ttggtcgttt gactggcgaa cctggtgtag tagttgttac gagtgggcct    240
ggtgtatcaa accttgcgac tccgcttttg accgcgactt cagaaggtga tgctattttg    300
gctatcggtg gacaagttaa acgaagtgac cgtcttaaac gtgcgcacca atcaatggat    360
aatgctggaa tgatgcaatc agcaacaaaa tattcagcag aagttcttga ccctgataca    420
ctttctgaat caattgccaa cgcttatcgt attgcaaaat caggacatcc aggtgcaact    480
ttcttatcaa tcccccaaga tgtaacggat gccgaagtat caatcaaggc cattcaacca    540
ctttcagacc ctaaaatggg gaatgcctct attgatgaca ttaattattt agcacaagca    600
```

```
attaaaaatg ctgtattgcc agtaattttg gttggagctg gtgcttcaga tgctaaagtc    660

gcttcatcat tgcgtaatct attaactcat gttaatattc ctgtcgttga aacattccaa    720

ggtgcagggg ttatttcaca tgatttagaa catacttttt atggacgtat cggtcttttc    780

cgcaatcaac caggagatat gcttctgaaa cgttctgacc ttgttattgc tgttggttat    840

gacccaattg aatatgaagc tcgtaactgg aatgcagaaa ttgatagtcg aattatcgtt    900

attgataatg ccattgctga aattgatact tactaccaac cagaacgtga attaattggt    960

gatatcgcag caacattgga taatctttta ccagctgttc gtggatacaa aattccaaaa   1020

ggaacaaaag attatctcga tggccttcat gaagttgctg agcaacacga atttgatact   1080

gaaaatactg aagaaggtag aatgcaccct cttgatttgg tcagcacttt ccaagaaatc   1140

gttaaagatg atgaaacagt aaccgttgac gtaggttcac tctacatttg gatggcacgt   1200

catttcaaat catacgaacc acgtcatctc ctcttctcaa acggaatgca aacacttgga   1260

gttgcacttc cttgggcaat tacagccgca ttgttgcgcc caggtaaaaa agtttattca   1320

cactctggtg atggaggctt ccttttcaca gggcaagagt tggaaacagc tgtacgtttg   1380

aatcttccaa tcgttcaaat tatctggaat gacggccatt atgatatggt taaattccaa   1440

gaagaaatga aatatggtcg ttcagcagcc gttgattttg gctatgttga ttacgtaaaa   1500

tatgctgaag caatgggagc aaaaggttac cgtgcacaca gcaaagaaga acttgctgaa   1560

attcttaaat caatcccaga tactactgga ccagtagtaa ttgacgttcc tttggactat   1620

tctgataaca ttaaattagc agaaaaatta ttgcctgaag agttttattg aggatcc      1677
```

<210> SEQ ID NO 6
<211> LENGTH: 1488
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
gtcgacatgg ctaactactt caatacactg aatctgcgcc agcagctggc acagctgggc     60

aaatgtcgct ttatgggccg cgatgaattc gccgatggcg cgagctacct tcagggtaaa    120

aaagtagtca tcgtcggctg tggcgcacag ggtctgaacc agggcctgaa catgcgtgat    180

tctggtctcg atatctccta cgctctgcgt aaagaagcga ttgccgagaa gcgcgcgtcc    240

tggcgtaaag cgaccgaaaa tggttttaaa gtgggtactt acgaagaact gatcccacag    300

gcggatctgg tgattaacct gacgccggac aagcagcact ctgatgtagt gcgcaccgta    360

cagccactga tgaaagacgg cgcggcgctg ggctactcgc acggtttcaa catcgtcgaa    420

gtgggcgagc agatccgtaa agatatcacc gtagtgatgg ttgcgccgaa atgcccaggc    480

accgaagtgc gtgaagagta caaacgtggg ttcggcgtac cgacgctgat tgccgttcac    540

ccggaaaacg atccgaaagg cgaaggcatg gcgattgcca aagcctgggc ggctgcaacc    600

ggtggtcacc gtgcgggtgt gctggaatcg tccttcgttg cggaagtgaa atctgacctg    660

atgggcgagc aaaccatcct gtgcggtatg ttgcaggctg gctctctgct gtgcttcgac    720

aagctggtgg aagaaggtac cgatccagca tacgcagaaa aactgattca gttcggttgg    780

gaaaccatca ccgaagcact gaaacagggc ggcatcaccc tgatgatgga ccgtctctct    840

aacccggcga aactgcgtgc ttatgcgctt tctgaacagc tgaaagagat catggcaccc    900

ctgttccaga aacatatgga cgacatcatc tccggcgaat tctcttccgg tatgatggcg    960
```

```
gactgggcca acgatgataa gaaactgctg acctggcgtg aagagaccgg caaaaccgcg   1020

tttgaaaccg cgccgcagta tgaaggcaaa atcggcgagc aggagtactt cgataaaggc   1080

gtactgatga ttgcgatggt gaaagcgggc gttgaactgg cgttcgaaac catggtcgat   1140

tccggcatca ttgaagagtc tgcatattat gaatcactgc acgagctgcc gctgattgcc   1200

aacaccatcg cccgtaagcg tctgtacgaa atgaacgtgg ttatctctga taccgctgag   1260

tacggtaact atctgttctc ttacgcttgt gtgccgttgc tgaaaccgtt tatggcagag   1320

ctgcaaccgg gcgacctggg taaagctatt ccggaaggcg cggtagataa cgggcaactg   1380

cgtgatgtga acgaagcgat tcgcagccat gcgattgagc aggtaggtaa gaaactgcgc   1440

ggctatatga cagatatgaa acgtattgct gttgcgggtt aaggatcc                1488
```

<210> SEQ ID NO 7
<211> LENGTH: 1863
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
gtcgacatgc ctaagtaccg ttccgccacc accactcatg gtcgtaatat ggcgggtgct     60

cgtgcgctgt ggcgcgccac cggaatgacc gacgccgatt tcggtaagcc gattatcgcg    120

gttgtgaact cgttcaccca atttgtaccg ggtcacgtcc atctgcgcga tctcggtaaa    180

ctggtcgccg aacaaattga agcggctggc ggcgttgcca aagagttcaa caccattgcg    240

gtggatgatg ggattgccat gggccacggg gggatgcttt attcactgcc atctcgcgaa    300

ctgatcgctg attccgttga gtatatggtc aacgcccact gcgccgacgc catggtctgc    360

atctctaact gcgacaaaat caccccgggg atgctgatgg cttccctgcg cctgaatatt    420

ccggtgatct ttgtttccgg cggcccgatg gaggccggga aaaccaaact ttccgatcag    480

atcatcaagc tcgatctggt tgatgcgatg atccagggcg cagacccgaa agtatctgac    540

tcccagagcg atcaggttga acgttccgcg tgtccgacct gcggttcctg ctccgggatg    600

tttaccgcta actcaatgaa ctgcctgacc gaagcgctgg gcctgtcgca gccgggcaac    660

ggctcgctgc tggcaaccca cgccgaccgt aagcagctgt tccttaatgc tggtaaacgc    720

attgttgaat tgaccaaacg ttattacgag caaaacgacg aaagtgcact gccgcgtaat    780

atcgccagta aggcggcgtt tgaaaacgcc atgacgctgg atatcgcgat gggtggatcg    840

actaacaccg tacttcacct gctggcggcg gcgcaggaag cggaaatcga cttcaccatg    900

agtgatatcg ataagctttc ccgcaaggtt ccacagctgt gtaaagttgc gccgagcacc    960

cagaaatacc atatggaaga tgttcaccgt gctggtggtg ttatcggtat tctcggcgaa   1020

ctggatcgcg cggggttact gaaccgtgat gtgaaaaacg tacttggcct gacgttgccg   1080

caaacgctgg aacaatacga cgttatgctg acccaggatg acgcggtaaa aaatatgttc   1140

cgcgcaggtc ctgcaggcat tcgtaccaca caggcattct cgcaagattg ccgttgggat   1200

acgctggacg acgatcgcgc caatggctgt atccgctcgc tggaacacgc ctacagcaaa   1260

gacggcggcc tggcggtgct ctacggtaac tttgcggaaa acggctgcat cgtgaaaacg   1320

gcaggcgtcg atgacagcat cctcaaattc accggcccgg cgaaagtgta cgaaagccag   1380

gacgatgcgg tagaagcgat tctcggcggt aaagttgtcg ccggagatgt ggtagtaatt   1440

cgctatgaag gcccgaaagg cggtccgggg atgcaggaaa tgctctaccc aaccagcttc   1500

ctgaaatcaa tgggtctcgg caaagcctgt gcgctgatca ccgacggtcg tttctctggt   1560
```

```
ggcacctctg gtctttccat cggccacgtc tcaccggaag cggcaagcgg cggcagcatt   1620

ggcctgattg aagatggtga cctgatcgct atcgacatcc cgaaccgtgg cattcagtta   1680

caggtaagcg atgccgaact ggcggcgcgt cgtgaagcgc aggacgctcg aggtgacaaa   1740

gcctggacgc cgaaaaatcg tgaacgtcag gtctcctttg ccctgcgtgc ttatgccagc   1800

ctggcaacca gcgccgacaa aggcgcggtg cgcgataaat cgaaactggg gggttaagga   1860

tcc                                                                 1863
```

<210> SEQ ID NO 8
<211> LENGTH: 1659
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
gtcgacatgt atactgttgg tgattatctg ctggaccgtc tgcatgaact gggtatcgaa     60

gaaatcttcg gcgttccggg tgattacaat ctgcagttcc tggatcagat catctctcat    120

aaagacatga aatgggtggg taacgctaac gaactgaacg caagctacat ggcagatggt    180

tatgcacgta ccaagaaagc cgcggcattt ctgaccactt tcggtgttgg cgaactgagc    240

gccgtcaacg gtctggcggg ctcctacgcc gaaaacctgc cggtggtgga gatcgtaggc    300

agcccaacga gcaaagttca gaacgaaggt aaattcgtcc accacactct ggctgacggc    360

gatttcaaac acttcatgaa aatgcatgaa cctgtgactg cggcacgtac gctgctgact    420

gcagagaacg ctactgtgga aatcgaccgc gttctgtctg cgctgctgaa agaacgcaaa    480

ccagtttaca tcaacctgcc tgtggatgtt gcggcagcta aagcggaaaa accgagcctg    540

ccgctgaaga aagaaaactc cacttctaac actagcgacc aggaaatcct gaacaaaatc    600

caggagtctc tgaaaaacgc aaagaaacca atcgtgatca ccggccacga aatcatttct    660

tttggtctgg agaagaccgt gacccaattc atcagcaaaa ccaaactgcc gattaccacc    720

ctgaacttcg gcaagtcctc tgttgacgag gctctgccgt ctttcctggg catctacaac    780

ggtactctga gcgaaccgaa cctgaaagaa tttgttgaat ctgcggactt catcctgatg    840

ctgggcgtta aactgaccga ctcttctacc ggtgcattca ctcaccatct gaacgaaaac    900

aaaatgatta gcctgaacat cgacgagggt aaaatcttca acgagcgtat ccagaacttc    960

gacttcgaaa gcctgatcag ctctctgctg gacctgtccg aaatcgagta taaaggcaaa   1020

tacattgaca aaaagcaaga agatttcgta ccatctaacg cactgctgtc ccaggatcgc   1080

ctgtggcagg ccgtggagaa cctgacccag agcaatgaaa ccatcgtggc ggaacaaggt   1140

acgagctttt tcggcgcgtc ttctatcttt ctgaaatcca aaagccattt tatcggtcag   1200

ccgctgtggg gtagcattgg ctatactttc ccggcagcgc tgggctctca gatcgctgat   1260

aaagaatctc gtcatctgct gttcatcggt gacggttccc tgcagctgac cgtacaggaa   1320

ctgggtctgg caattcgtga aaagatcaac ccgatttgct tcattattaa caatgacggc   1380

tacaccgttg agcgtgagat ccacggtccg aaccagtctt acaacgatat ccctatgtgg   1440

aactactcta aactgccgga gtccttcggc gcaactgagg accgtgttgt gtctaaaatt   1500

gtgcgtaccg aaaacgaatt tgtgagcgtg atgaaagagg cccaggccga tccgaaccgt   1560

atgtactgga tcgaactgat cctggcgaaa gaaggcgcac cgaaggtact gaagaaaatg   1620

ggcaagctgt ttgctgaaca gaataaatcc taaggatcc                          1659
```

<210> SEQ ID NO 9
<211> LENGTH: 1059
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
gtcgacatgt ctattccaga aactcaaaaa gccattatct tctacgaatc caacggcaag     60

ttggagcata aggatatccc agttccaaag ccaaagccca acgaattgtt aatcaacgtc    120

aagtactctg gtgtctgcca caccgatttg cacgcttggc atggtgactg gccattgcca    180

actaagttac cattagttgg tggtcacgaa ggtgccggtg tcgttgtcgg catgggtgaa    240

aacgttaagg gctggaagat cggtgactac gccggtatca aatggttgaa cggttcttgt    300

atggcctgtg aatactgtga attgggtaac gaatccaact gtcctcacgc tgacttgtct    360

ggttacaccc acgacggttc tttccaagaa tacgctaccg ctgacgctgt tcaagccgct    420

cacattcctc aaggtactga cttggctgaa gtcgcgccaa tcttgtgtgc tggtatcacc    480

gtatacaagg ctttgaagtc tgccaacttg agagcaggcc actgggcggc catttctggt    540

gctgctggtg gtctaggttc tttggctgtt caatatgcta aggcgatggg ttacagagtc    600

ttaggtattg atggtggtcc aggaaaggaa gaattgttta cctcgctcgg tggtgaagta    660

ttcatcgact tcaccaaaga gaaggacatt gttagcgcag tcgttaaggc taccaacggc    720

ggtgcccacg gtatcatcaa tgtttccgtt tccgaagccg ctatcgaagc ttctaccaga    780

tactgtaggg cgaacggtac tgttgtcttg gttggtttgc cagccggtgc aaagtgctcc    840

tctgatgtct tcaaccacgt tgtcaagtct atctccattg tcggctctta cgtggggaac    900

agagctgata ccagagaagc cttagatttc tttgccagag gtctagtcaa gtctccaata    960

aaggtagttg gcttatccag tttaccagaa atttacgaaa agatggagaa gggccaaatt   1020

gctggtagat acgttgttga cacttctaaa taaggatcc                          1059
```

<210> SEQ ID NO 10
<211> LENGTH: 9761
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataccac agcttttcaa ttcaattcat catttttttt ttattctttt ttttgatttc    240

ggtttctttg aaattttttt gattcggtaa tctccgaaca gaaggaagaa cgaaggaagg    300

agcacagact tagattggta tatatacgca tatgtagtgt tgaagaaaca tgaaattgcc    360

cagtattctt aacccaactg cacagaacaa aaacctgcag gaaacgaaga taaatcatgt    420

cgaaagctac atataaggaa cgtgctgcta ctcatcctag tcctgttgct gccaagctat    480

ttaatatcat gcacgaaaag caaacaaact tgtgtgcttc attggatgtt cgtaccacca    540

aggaattact ggagttagtt gaagcattag gtcccaaaat ttgtttacta aaaacacatg    600

tggatatctt gactgatttt tccatggagg gcacagttaa gccgctaaag gcattatccg    660
```

-continued

```
ccaagtacaa ttttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag gggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg gccgcaaatt aaagccttcg agcgtcccaa   2040
aaccttctca agcaaggttt tcagtataat gttacatgcg tacacgcgtc tgtacagaaa   2100
aaaaagaaaa atttgaaata taaataacgt tcttaatact aacataacta taaaaaaata   2160
aatagggacc tagacttcag gttgtctaac tccttccttt tcggttagag cggatgtggg   2220
gggagggcgt gaatgtaagc gtgacataac taattacatg actcgagcgg ccgcggatcc   2280
ttatttagaa gtgtcaacaa cgtatctacc agcaatttgg cccttctcca tcttttcgta   2340
aatttctggt aaactggata agccaactac ctttattgga gacttgacta gacctctggc   2400
aaagaaatct aaggcttctc tggtatcagc tctgttcccc acgtaagagc cgacaatgga   2460
gatagacttg acaacgtggt tgaagacatc agaggagcac tttgcaccgg ctggcaaacc   2520
aaccaagaca acagtaccgt tcgccctaca gtatctggta gaagcttcga tagcggcttc   2580
ggaaacggaa acattgatga taccgtgggc accgccgttg gtagccttaa cgactgcgct   2640
aacaatgtcc ttctctttgg tgaagtcgat gaatacttca ccaccgagcg aggtaaacaa   2700
ttcttccttt cctggaccac catcaatacc taagactctg taacccatcg ccttagcata   2760
ttgaacagcc aaagaaccta gaccaccagc agcaccagaa atggccgccc agtggcctgc   2820
tctcaagttg gcagacttca aagccttgta tacggtgata ccagcacaca agattggcgc   2880
gacttcagcc aagtcagtac cttgaggaat gtgagcggct tgaacagcgt cagcggtagc   2940
gtattcttgg aaagaaccgt cgtgggtgta accagacaag tcagcgtgag gacagttgga   3000
ttcgttaccc aattcacagt attcacaggc catacaagaa ccgttcaacc atttgatacc   3060
```

-continued

```
ggcgtagtca ccgatcttcc agcccttaac gttttcaccc atgccgacaa cgacaccggc   3120

accttcgtga ccaccaacta atggtaactt agttggcaat ggccagtcac catgccaagc   3180

gtgcaaatcg gtgtggcaga caccagagta cttgacgttg attaacaatt cgttgggctt   3240

tggctttgga actgggatat ccttatgctc caacttgccg ttggattcgt agaagataat   3300

ggctttttga gtttctggaa tagacatgtc gacaccatct tcttctgaga tgagtttttg   3360

ttccatgcta gttctagaat ccgtcgaaac taagttctgg tgttttaaaa ctaaaaaaaa   3420

gactaactat aaaagtagaa tttaagaagt ttaagaaata gatttacaga attacaatca   3480

atacctaccg tctttatata cttattagtc aagtagggga ataatttcag ggaactggtt   3540

tcaacctttt ttttcagctt tttccaaatc agagagagca gaaggtaata gaaggtgtaa   3600

gaaaatgaga tagatacatg cgtgggtcaa ttgccttgtg tcatcattta ctccaggcag   3660

gttgcatcac tccattgagg ttgtgcccgt tttttgcctg tttgtgcccc tgttctctgt   3720

agttgcgcta agagaatgga cctatgaact gatggttggt gaagaaaaca atattttggt   3780

gctgggattc tttttttttc tggatgccag cttaaaaagc gggctccatt atatttagtg   3840

gatgccagga ataaactgtt cacccagaca cctacgatgt tatatattct gtgtaacccg   3900

ccccctattt tgggcatgta cgggttacag cagaattaaa aggctaattt tttgactaaa   3960

taaagttagg aaaatcacta ctattaatta tttacgtatt ctttgaaatg gcgagtattg   4020

ataatgataa actgaggatc cttaggattt attctgttca gcaaacagct tgcccatttt   4080

cttcagtacc ttcggtgcgc cttctttcgc caggatcagt tcgatccagt acatacggtt   4140

cggatcggcc tgggcctctt tcatcacgct cacaaattcg ttttcggtac gcacaatttt   4200

agacacaaca cggtcctcag ttgcgccgaa ggactccggc agtttagagt agttccacat   4260

agggatatcg ttgtaagact ggttcggacc gtggatctca cgctcaacgg tgtagccgtc   4320

attgttaata atgaagcaaa tcgggttgat cttttcacga attgccagac ccagttcctg   4380

tacggtcagc tgcagggaac cgtcaccgat gaacagcaga tgacgagatt ctttatcagc   4440

gatctgagag cccagcgctg ccgggaaagt atagccaatg ctaccccaca gcggctgacc   4500

gataaaatgg cttttggatt tcagaaagat agaagacgcg ccgaaaaagc tcgtaccttg   4560

ttccgccacg atggtttcat tgctctgggt caggttctcc acggcctgcc acaggcgatc   4620

ctgggacagc agtgcgttag atggtacgaa atcttcttgc tttttgtcaa tgtatttgcc   4680

tttatactcg atttcggaca ggtccagcag agagctgatc aggctttcga agtcgaagtt   4740

ctggatacgc tcgttgaaga ttttaccctc gtcgatgttc aggctaatca ttttgttttc   4800

gttcagatgg tgagtgaatg caccggtaga agagtcggtc agtttaacgc ccagcatcag   4860

gatgaagtcc gcagattcaa caaattcttt caggttcggt tcgctcagag taccgttgta   4920

gatgcccagg aaagacggca gagcctcgtc aacagaggac ttgccgaagt tcagggtggt   4980

aatcggcagt ttggttttgc tgatgaattg ggtcacggtc ttctccagac caaaagaaat   5040

gatttcgtgg ccggtgatca cgattggttt ctttgcgttt ttcagagact cctggatttt   5100

gttcaggatt tcctggtcgc tagtgttaga agtggagttt tctttcttca gcggcaggct   5160

cggtttttcc gctttagctg ccgcaacatc cacaggcagg ttgatgtaaa ctggtttgcg   5220

ttctttcagc agcgcagaca gaacgcggtc gatttccaca gtagcgttct ctgcagtcag   5280

cagcgtacgt gccgcagtca caggttcatg cattttcatg aagtgtttga aatcgccgtc   5340

agccagagtg tggtggacga atttaccttc gttctgaact ttgctcgttg ggctgcctac   5400

gatctccacc accggcaggt tttcggcgta ggagcccgcc agaccgttga cggcgctcag   5460
```

-continued

```
ttcgccaaca ccgaaagtgg tcagaaatgc cgcggctttc ttggtacgtg cataaccatc   5520
tgccatgtag cttgcgttca gttcgttagc gttacccacc catttcatgt ctttatgaga   5580
gatgatctga tccaggaact gcagattgta atcacccgga acgccgaaga tttcttcgat   5640
acccagttca tgcagacggt ccagcagata atcaccaaca gtatacatgt cgacacccgc   5700
atagtcagga acatcgtatg ggtacatgct agttctagaa aacttagatt agattgctat   5760
gctttctttc taatgagcaa gaagtaaaaa aagttgtaat agaacaagaa aaatgaaact   5820
gaaacttgag aaattgaaga ccgtttatta acttaaatat caatgggagg tcatcgaaag   5880
agaaaaaaat caaaaaaaaa attttcaaga aaaagaaacg tgataaaaat ttttattgcc   5940
tttttcgacg aagaaaaaga aacgaggcgg tctctttttt cttttccaaa cctttagtac   6000
gggtaattaa cgacacccta gaggaagaaa gaggggaaat ttagtatgct gtgcttgggt   6060
gttttgaagt ggtacggcga tgcgcggagt ccgagaaaat ctggaagagt aaaaaaggag   6120
tagaaacatt ttgaagctat gagctccagc ttttgttccc tttagtgagg gttaattgcg   6180
cgcttggcgt aatcatggtc atagctgttt cctgtgtgaa attgttatcc gctcacaatt   6240
ccacacaaca taggagccgg aagcataaag tgtaaagcct ggggtgccta atgagtgagg   6300
taactcacat taattgcgtt gcgctcactg cccgctttcc agtcgggaaa cctgtcgtgc   6360
cagctgcatt aatgaatcgg ccaacgcgcg gggagaggcg gtttgcgtat tgggcgctct   6420
tccgcttcct cgctcactga ctcgctgcgc tcggtcgttc ggctgcggcg agcggtatca   6480
gctcactcaa aggcggtaat acggttatcc acagaatcag gggataacgc aggaaagaac   6540
atgtgagcaa aaggccagca aaaggccagg aaccgtaaaa aggccgcgtt gctggcgttt   6600
ttccataggc tccgcccccc tgacgagcat cacaaaaatc gacgctcaag tcagaggtgg   6660
cgaaacccga caggactata aagataccag gcgtttcccc ctggaagctc cctcgtgcgc   6720
tctcctgttc cgaccctgcc gcttaccgga tacctgtccg cctttctccc ttcgggaagc   6780
gtggcgcttt ctcatagctc acgctgtagg tatctcagtt cggtgtaggt cgttcgctcc   6840
aagctgggct gtgtgcacga accccccgtt cagcccgacc gctgcgcctt atccggtaac   6900
tatcgtcttg agtccaaccc ggtaagacac gacttatcgc cactggcagc agccactggt   6960
aacaggatta gcagagcgag gtatgtaggc ggtgctacag agttcttgaa gtggtggcct   7020
aactacggct acactagaag gacagtattt ggtatctgcg ctctgctgaa gccagttacc   7080
ttcggaaaaa gagttggtag ctcttgatcc ggcaaacaaa ccaccgctgg tagcggtggt   7140
ttttttgttt gcaagcagca gattacgcgc agaaaaaaag gatctcaaga agatcctttg   7200
atcttttcta cggggtctga cgctcagtgg aacgaaaact cacgttaagg gattttggtc   7260
atgagattat caaaaaggat cttcacctag atccttttaa attaaaaatg aagttttaaa   7320
tcaatctaaa gtatatatga gtaaacttgg tctgacagtt accaatgctt aatcagtgag   7380
gcacctatct cagcgatctg tctatttcgt tcatccatag ttgcctgact ccccgtcgtg   7440
tagataacta cgatacggga gggcttacca tctggcccca gtgctgcaat gataccgcga   7500
gacccacgct caccggctcc agatttatca gcaataaacc agccagccgg aagggccgag   7560
cgcagaagtg gtcctgcaac tttatccgcc tccatccagt ctattaattg ttgccgggaa   7620
gctagagtaa gtagttcgcc agttaatagt ttgcgcaacg ttgttgccat tgctacaggc   7680
atcgtggtgt cacgctcgtc gtttggtatg gcttcattca gctccggttc ccaacgatca   7740
aggcgagtta catgatcccc catgttgtgc aaaaaagcgg ttagctcctt cggtcctccg   7800
atcgttgtca gaagtaagtt ggccgcagtg ttatcactca tggttatggc agcactgcat   7860
```

```
aattctctta ctgtcatgcc atccgtaaga tgcttttctg tgactggtga gtactcaacc   7920

aagtcattct gagaatagtg tatgcggcga ccgagttgct cttgcccggc gtcaatacgg   7980

gataataccg cgccacatag cagaacttta aaagtgctca tcattggaaa acgttcttcg   8040

gggcgaaaac tctcaaggat cttaccgctg ttgagatcca gttcgatgta acccactcgt   8100

gcacccaact gatcttcagc atcttttact ttcaccagcg tttctgggtg agcaaaaaca   8160

ggaaggcaaa atgccgcaaa aaagggaata agggcgacac ggaaatgttg aatactcata   8220

ctcttccttt ttcaatatta ttgaagcatt tatcagggtt attgtctcat gagcggatac   8280

atatttgaat gtatttagaa aaataaacaa ataggggttc cgcgcacatt tccccgaaaa   8340

gtgccacctg aacgaagcat ctgtgcttca ttttgtagaa caaaaatgca acgcgagagc   8400

gctaattttt caaacaaaga atctgagctg catttttaca gaacagaaat gcaacgcgaa   8460

agcgctattt taccaacgaa gaatctgtgc ttcatttttg taaaacaaaa atgcaacgcg   8520

agagcgctaa tttttcaaac aaagaatctg agctgcattt ttacagaaca gaaatgcaac   8580

gcgagagcgc tattttacca acaaagaatc tatacttctt ttttgttcta caaaaatgca   8640

tcccgagagc gctatttttc taacaaagca tcttagatta cttttttttct cctttgtgcg   8700

ctctataatg cagtctcttg ataacttttt gcactgtagg tccgttaagg ttagaagaag   8760

gctactttgg tgtctatttt ctcttccata aaaaaagcct gactccactt cccgcgttta   8820

ctgattacta gcgaagctgc gggtgcattt tttcaagata aaggcatccc cgattatatt   8880

ctataccgat gtggattgcg catactttgt gaacagaaag tgatagcgtt gatgattctt   8940

cattggtcag aaaattatga acggtttctt ctattttgtc tctatatact acgtatagga   9000

aatgtttaca ttttcgtatt gttttcgatt cactctatga atagttctta ctacaatttt   9060

tttgtctaaa gagtaatact agagataaac ataaaaaatg tagaggtcga gtttagatgc   9120

aagttcaagg agcgaaaggt ggatgggtag gttatatagg gatatagcac agagatatat   9180

agcaaagaga tacttttgag caatgtttgt ggaagcggta ttcgcaatat tttagtagct   9240

cgttacagtc cggtgcgttt ttggtttttt gaaagtgcgt cttcagagcg cttttggttt   9300

tcaaaagcgc tctgaagttc ctatactttc tagagaatag gaacttcgga ataggaactt   9360

caaagcgttt ccgaaaacga gcgcttccga aaatgcaacg cgagctgcgc acatacagct   9420

cactgttcac gtcgcaccta tatctgcgtg ttgcctgtat atatatatac atgagaagaa   9480

cggcatagtg cgtgtttatg cttaaatgcg tacttatatg cgtctattta tgtaggatga   9540

aaggtagtct agtacctcct gtgatattat cccattccat gcggggtatc gtatgcttcc   9600

ttcagcacta ccctttagct gttctatatg ctgccactcc tcaattggat tagtctcatc   9660

cttcaatgct atcatttcct ttgatattgg atcatactaa gaaaccatta ttatcatgac   9720

attaacctat aaaaataggc gtatcacgag gccctttcgt c                       9761
```

<210> SEQ ID NO 11
<211> LENGTH: 7990
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180
```

```
accataaacg acattactat atatataata taggaagcat ttaatagaca gcatcgtaat    240
atatgtgtac tttgcagtta tgacgccaga tggcagtagt ggaagatatt ctttattgaa    300
aaatagcttg tcaccttacg tacaatcttg atccggagct ttctttttt tgccgattaa     360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact atagggcgaa ttgggtaccg gccgcaaatt aaagccttcg   1920
agcgtcccaa aaccttctca agcaaggttt tcagtataat gttacatgcg tacacgcgtc   1980
tgtacagaaa aaaaagaaaa atttgaaata taaataacgt tcttaatact aacataacta   2040
taaaaaaata aatagggacc tagacttcag gttgtctaac tccttccttt tcggttagag   2100
cggatgtggg ggagggcgt gaatgtaagc gtgacataac taattacatg actcgagcgg    2160
ccgcggatcc ttaacccgca acagcaatac gtttcatatc tgtcatatag ccgcgcagtt   2220
tcttacctac ctgctcaatc gcatggctgc gaatcgcttc gttcacatca cgcagttgcc   2280
cgttatctac cgcgccttcc ggaatagctt tacccaggtc gcccggttgc agctctgcca   2340
taaacggttt cagcaacggc acacaagcgt aagagaacag atagttaccg tactcagcgg   2400
tatcagagat aaccacgttc atttcgtaca gacgcttacg ggcgatggtg ttggcaatca   2460
gcggcagctc gtgcagtgat tcataaatatg cagactcttc aatgatgccg gaatcgacca  2520
tggtttcgaa cgccagttca acgcccgctt tcaccatcgc aatcatcagt acgcctttat   2580
```

```
cgaagtactc ctgctcgccg attttgcctt catactgcgg cgcggtttca aacgcggttt   2640

tgccggtctc ttcacgccag gtcagcagtt tcttatcatc gttggcccag tccgccatca   2700

taccggaaga gaattcgccg gagatgatgt cgtccatatg tttctggaac aggggtgcca   2760

tgatctcttt cagctgttca gaaagcgcat aagcacgcag tttcgccggg ttagagagac   2820

ggtccatcat cagggtgatg ccgccctgtt tcagtgcttc ggtgatggtt tcccaaccga   2880

actgaatcag tttttctgcg tatgctggat cggtaccttc ttccaccagc ttgtcgaagc   2940

acagcagaga gccagcctgc aacataccgc acaggatggt ttgctcgccc atcaggtcag   3000

atttcacttc cgcaacgaag gacgattcca gcacacccgc acggtgacca ccggttgcag   3060

ccgcccaggc tttggcaatc gccatgcctt cgcctttcgg atcgttttcc gggtgaacgg   3120

caatcagcgt cggtacgccg aacccacgtt tgtactcttc acgcacttcg gtgcctgggc   3180

atttcggcgc aaccatcact acggtgatat ctttacggat ctgctcgccc acttcgacga   3240

tgttgaaacc gtgcgagtag cccagcgccg cgccgtcttt catcagtggc tgtacggtgc   3300

gcactacatc agagtgctgc ttgtccggcg tcaggttaat caccagatcc gcctgtggga   3360

tcagttcttc gtaagtaccc actttaaaac cattttcggt cgctttacgc caggacgcgc   3420

gcttctcggc aatcgcttct ttacgcagag cgtaggagat atcgagacca gaatcacgca   3480

tgttcaggcc ctggttcaga ccctgtgcgc cacagccgac gatgactact tttttaccct   3540

gaaggtagct cgcgccatcg gcgaattcat cgcggcccat aaagcgacat ttgcccagct   3600

gtgccagctg ctggcgcaga ttcagtgtat tgaagtagtt agccatgtcg acaccatctt   3660

cttctgagat gagtttttgt tccatgctag ttctagaatc cgtcgaaact aagttctggt   3720

gttttaaaac taaaaaaaag actaactata aaagtagaat ttaagaagtt taagaaatag   3780

atttacagaa ttacaatcaa tacctaccgt ctttatatac ttattagtca agtaggggaa   3840

taatttcagg gaactggttt caaccttttt tttcagcttt ttccaaatca gagagagcag   3900

aaggtaatag aaggtgtaag aaaatgagat agatacatgc gtgggtcaat tgccttgtgt   3960

catcatttac tccaggcagg ttgcatcact ccattgaggt tgtgcccgtt ttttgcctgt   4020

ttgtgcccct gttctctgta gttgcgctaa gagaatggac ctatgaactg atggttggtg   4080

aagaaaacaa tattttggtg ctgggattct ttttttttct ggatgccagc ttaaaaagcg   4140

ggctccatta tatttagtgg atgccaggaa taaactgttc acccagacac ctacgatgtt   4200

atatattctg tgtaacccgc cccctatttt gggcatgtac gggttacagc agaattaaaa   4260

ggctaatttt ttgactaaat aaagttagga aaatcactac tattaattat ttacgtattc   4320

tttgaaatgg cgagtattga taatgataaa ctgagctaga tctgggcccg agctccagct   4380

tttgttccct ttagtgaggg ttaattgcgc gcttggcgta atcatggtca tagctgtttc   4440

ctgtgtgaaa ttgttatccg ctcacaattc cacacaacat aggagccgga agcataaagt   4500

gtaaagcctg gggtgcctaa tgagtgaggt aactcacatt aattgcgttg cgctcactgc   4560

ccgctttcca gtcgggaaac ctgtcgtgcc agctgcatta atgaatcggc caacgcgcgg   4620

ggagaggcgg tttgcgtatt gggcgctctt ccgcttcctc gctcactgac tcgctgcgct   4680

cggtcgttcg gctgcggcga gcggtatcag ctcactcaaa ggcggtaata cggttatcca   4740

cagaatcagg ggataacgca ggaaagaaca tgtgagcaaa aggccagcaa aaggccagga   4800

accgtaaaaa ggccgcgttg ctggcgtttt tccataggct ccgcccccct gacgagcatc   4860

acaaaaatcg acgctcaagt cagaggtggc gaaacccgac aggactataa agataccagg   4920

cgtttccccc tggaagctcc ctcgtgcgct ctcctgttcc gaccctgccg cttaccggat   4980
```

```
acctgtccgc ctttctccct tcgggaagcg tggcgctttc tcatagctca cgctgtaggt   5040
atctcagttc ggtgtaggtc gttcgctcca agctgggctg tgtgcacgaa ccccccgttc   5100
agcccgaccg ctgcgcctta tccggtaact atcgtcttga gtccaacccg gtaagacacg   5160
acttatcgcc actggcagca gccactggta acaggattag cagagcgagg tatgtaggcg   5220
gtgctacaga gttcttgaag tggtggccta actacggcta cactagaagg acagtatttg   5280
gtatctgcgc tctgctgaag ccagttacct tcggaaaaag agttggtagc tcttgatccg   5340
gcaaacaaac caccgctggt agcggtggtt tttttgtttg caagcagcag attacgcgca   5400
gaaaaaaagg atctcaagaa gatcctttga tcttttctac ggggtctgac gctcagtgga   5460
acgaaaactc acgttaaggg attttggtca tgagattatc aaaaaggatc ttcacctaga   5520
tccttttaaa ttaaaaatga agttttaaat caatctaaag tatatatgag taaacttggt   5580
ctgacagtta ccaatgctta atcagtgagg cacctatctc agcgatctgt ctatttcgtt   5640
catccatagt tgcctgactc cccgtcgtgt agataactac gatacgggag ggcttaccat   5700
ctggccccag tgctgcaatg ataccgcgag acccacgctc accggctcca gatttatcag   5760
caataaacca gccagccgga agggccgagc gcagaagtgg tcctgcaact ttatccgcct   5820
ccatccagtc tattaattgt tgccgggaag ctagagtaag tagttcgcca gttaatagtt   5880
tgcgcaacgt tgttgccatt gctacaggca tcgtggtgtc acgctcgtcg tttggtatgg   5940
cttcattcag ctccggttcc caacgatcaa ggcgagttac atgatccccc atgttgtgca   6000
aaaaagcggt tagctccttc ggtcctccga tcgttgtcag aagtaagttg gccgcagtgt   6060
tatcactcat ggttatggca gcactgcata attctcttac tgtcatgcca tccgtaagat   6120
gcttttctgt gactggtgag tactcaacca agtcattctg agaatagtgt atgcggcgac   6180
cgagttgctc ttgcccggcg tcaatacggg ataataccgc gccacatagc agaactttaa   6240
aagtgctcat cattggaaaa cgttcttcgg ggcgaaaact ctcaaggatc ttaccgctgt   6300
tgagatccag ttcgatgtaa cccactcgtg cacccaactg atcttcagca tcttttactt   6360
tcaccagcgt ttctgggtga gcaaaaacag gaaggcaaaa tgccgcaaaa aagggaataa   6420
gggcgacacg gaaatgttga atactcatac tcttcctttt tcaatattat tgaagcattt   6480
atcagggtta ttgtctcatg agcggataca tatttgaatg tatttagaaa aataaacaaa   6540
taggggttcc gcgcacattt ccccgaaaag tgccacctga acgaagcatc tgtgcttcat   6600
tttgtagaac aaaaatgcaa cgcgagagcg ctaatttttc aaacaaagaa tctgagctgc   6660
atttttacag aacagaaatg caacgcgaaa gcgctatttt accaacgaag aatctgtgct   6720
tcatttttgt aaaacaaaaa tgcaacgcga gagcgctaat ttttcaaaca aagaatctga   6780
gctgcatttt tacagaacag aaatgcaacg cgagagcgct attttaccaa caaagaatct   6840
atacttcttt tttgttctac aaaaatgcat cccgagagcg ctatttttct aacaaagcat   6900
cttagattac tttttttctc ctttgtgcgc tctataatgc agtctcttga taactttttg   6960
cactgtaggt ccgttaaggt tagaagaagg ctactttggt gtctattttc tcttccataa   7020
aaaaagcctg actccacttc ccgcgtttac tgattactag cgaagctgcg ggtgcatttt   7080
ttcaagataa aggcatcccc gattatattc tataccgatg tggattgcgc atactttgtg   7140
aacagaaagt gatagcgttg atgattcttc attggtcaga aaattatgaa cggtttcttc   7200
tattttgtct ctatatacta cgtataggaa atgtttacat tttcgtattg ttttcgattc   7260
actctatgaa tagttcttac tacaattttt ttgtctaaag agtaatacta gagataaaca   7320
taaaaaatgt agaggtcgag tttagatgca agttcaagga gcgaaaggtg gatgggtagg   7380
```

```
ttatataggg atatagcaca gagatatata gcaaagagat acttttgagc aatgtttgtg   7440

gaagcggtat tcgcaatatt ttagtagctc gttacagtcc ggtgcgtttt tggtttttg   7500

aaagtgcgtc ttcagagcgc ttttggtttt caaaagcgct ctgaagttcc tatactttct   7560

agagaatagg aacttcggaa taggaacttc aaagcgtttc cgaaaacgag cgcttccgaa   7620

aatgcaacgc gagctgcgca catacagctc actgttcacg tcgcacctat atctgcgtgt   7680

tgcctgtata tatatataca tgagaagaac ggcatagtgc gtgtttatgc ttaaatgcgt   7740

acttatatgc gtctatttat gtaggatgaa aggtagtcta gtacctcctg tgatattatc   7800

ccattccatg cggggtatcg tatgcttcct tcagcactac cctttagctg ttctatatgc   7860

tgccactcct caattggatt agtctcatcc ttcaatgcta tcatttcctt tgatattgga   7920

tcatattaag aaaccattat tatcatgaca ttaacctata aaaataggcg tatcacgagg   7980

ccctttcgtc                                                          7990
```

```
<210> SEQ ID NO 12
<211> LENGTH: 8167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctctag tacactctat attttttat gcctcggtaa tgattttcat    360

ttttttttt cccctagcgg atgactcttt ttttttctta gcgattggca ttatcacata    420

atgaattata cattatataa agtaatgtga tttcttcgaa gaatatacta aaaaatgagc    480

aggcaagata aacgaaggca aagatgacag agcagaaagc cctagtaaag cgtattacaa    540

atgaaaccaa gattcagatt gcgatctctt taaagggtgg tcccctagcg atagagcact    600

cgatcttccc agaaaaagag gcagaagcag tagcagaaca ggccacacaa tcgcaagtga    660

ttaacgtcca cacaggtata gggtttctgg accatatgat acatgctctg gccaagcatt    720

ccggctggtc gctaatcgtt gagtgcattg gtgacttaca catagacgac catcacacca    780

ctgaagactg cgggattgct ctcggtcaag cttttaaaga ggccctaggg gccgtgcgtg    840

gagtaaaaag gtttggatca ggatttgcgc ctttggatga ggcactttcc agagcggtgg    900

tagatctttc gaacaggccg tacgcagttg tcgaacttgg tttgcaaagg gagaaagtag    960

gagatctctc ttgcgagatg atcccgcatt ttcttgaaag ctttgcagag gctagcagaa   1020

ttaccctcca cgttgattgt ctgcgaggca agaatgatca tcaccgtagt gagagtgcgt   1080

tcaaggctct tgcggttgcc ataagagaag ccacctcgcc caatggtacc aacgatgttc   1140

cctccaccaa aggtgttctt atgtagtgac accgattatt taaagctgca gcatacgata   1200

tatatacatg tgtatatatg tatacctatg aatgtcagta agtatgtata cgaacagtat   1260

gatactgaag atgacaaggt aatgcatcat tctatacgtg tcattctgaa cgaggcgcgc   1320

tttccttttt tctttttgct tttctttttt ttttctcttg aactcgacgg atctatgcgg   1380
```

-continued

```
tgtgaaatac cgcacagatg cgtaaggaga aaataccgca tcaggaaatt gtaaacgtta   1440
atattttgtt aaaattcgcg ttaaattttt gttaaatcag ctcatttttt aaccaatagg   1500
ccgaaatcgg caaaatccct tataaatcaa aagaatagac cgagataggg ttgagtgttg   1560
ttccagtttg gaacaagagt ccactattaa agaacgtgga ctccaacgtc aaagggcgaa   1620
aaaccgtcta tcagggcgat ggcccactac gtgaaccatc accctaatca agttttttgg   1680
ggtcgaggtg ccgtaaagca ctaaatcgga accctaaagg gagcccccga tttagagctt   1740
gacggggaaa gccggcgaac gtggcgagaa aggaagggaa gaaagcgaaa ggagcgggcg   1800
ctagggcgct ggcaagtgta gcggtcacgc tgcgcgtaac caccacaccc gccgcgctta   1860
atgcgccgct acagggcgcg tcgcgccatt cgccattcag gctgcgcaac tgttgggaag   1920
ggcgatcggt gcgggcctct tcgctattac gccagctggc gaaaggggga tgtgctgcaa   1980
ggcgattaag ttgggtaacg ccagggtttt cccagtcacg acgttgtaaa acgacggcca   2040
gtgagcgcgc gtaatacgac tcactatagg gcgaattggg taccggccgc aaattaaagc   2100
cttcgagcgt cccaaaacct tctcaagcaa ggttttcagt ataatgttac atgcgtacac   2160
gcgtctgtac agaaaaaaaa gaaaaatttg aaatataaat aacgttctta atactaacat   2220
aactataaaa aaataaatag ggacctagac ttcaggttgt ctaactcctt ccttttcggt   2280
tagagcggat gtgggggag ggcgtgaatg taagcgtgac ataactaatt acatgactcg   2340
agcggccgcg gatcctcaat aaaactcttc aggcaataat tttctgcta atttaatgtt   2400
atcagaatag tccaaaggaa cgtcaattac tactggtcca gtagtatctg ggattgattt   2460
aagaatttca gcaagttctt ctttgctgtg tgcacggtaa ccttttgctc ccattgcttc   2520
agcatatttt acgtaatcaa catagccaaa atcaacggct gctgaacgac catatttcat   2580
ttcttcttgg aatttaacca tatcataatg gccgtcattc cagataattt gaacgattgg   2640
aagattcaaa cgtacagctg tttccaactc ttgccctgtg aaaaggaagc ctccatcacc   2700
agagtgtgaa taaacttttt tacctgggcg caacaatgcg gctgtaattg cccaaggaag   2760
tgcaactcca agtgtttgca ttccgtttga gaagaggaga tgacgtggtt cgtatgattt   2820
gaaatgacgt gccatccaaa tgtagagtga acctacgtca acggttactg tttcatcatc   2880
tttaacgatt tcttggaaag tgctgaccaa atcaagaggg tgcattctac cttcttcagt   2940
attttcagta tcaaattcgt gttgctcagc aacttcatga aggccatcga gataatcttt   3000
tgttcctttt ggaattttgt atccacgaac agctggtaaa agattatcca atgttgctgc   3060
gatatcacca attaattcac gttctggttg gtagtaagta tcaatttcag caatggcatt   3120
atcaataacg ataattcgac tatcaatttc tgcattccag ttacgagctt catattcaat   3180
tgggtcataa ccaacagcaa taacaaggtc agaacgtttc agaagcatat ctcctggttg   3240
attgcggaaa agaccgatac gtccataaaa agtatgttct aaatcatgtg aaataacccc   3300
tgcaccttgg aatgtttcaa cgacaggaat attaacatga gttaatagat tacgcaatga   3360
tgaagcgact ttagcatctg aagcaccagc tccaaccaaa attactggca atacagcatt   3420
tttaattgct tgtgctaaat aattaatgtc atcaatagag gcattcccca ttttagggtc   3480
tgaaagtggt tgaatggcct tgattgatac ttcggcatcc gttacatctt gggggattga   3540
taagaaagtt gcacctggat gtcctgattt tgcaatacga taagcgttgg caattgattc   3600
agaaagtgta tcagggtcaa gaacttctgc tgaatatttt gttgctgatt gcatcattcc   3660
agcattatcc attgattggt gcgcacgttt aagacggtca cttcgtttaa cttgtccacc   3720
gatagccaaa atagcatcac cttctgaagt cgcggtcaaa agcggagtcg caaggtttga   3780
```

-continued

```
tacaccaggc ccactcgtaa caactactac accaggttcg ccagtcaaac gaccaacagc   3840
ttgagccatg aaagcagctc cttgctcatg acgagtcacg accatttgag ggccttcttc   3900
attttctaat aaatcaaaaa cccggtcaat ttttgctcct ggaatcccaa atacatactt   3960
cactttatgg ttaatcaaac tatcgacaac caagttcgcc ccaaattgtt tctcagacat   4020
gtcgacaccg atatacctgt atgtgtcacc accaatgtat ctataagtat ccatgctagc   4080
cctaggttta tgtgatgatt gattgattga ttgtacagtt tgtttttctt aatatctatt   4140
tcgatgactt ctatatgata ttgcactaac aagaagatat tataatgcaa ttgatacaag   4200
acaaggagtt atttgcttct cttttatatg attctgacaa tccatattgc gttggtagtc   4260
tttttgctg gaacggttca gcggaaaaga cgcatcgctc tttttgcttc tagaagaaat   4320
gccagcaaaa gaatctcttg acagtgactg acagcaaaaa tgtctttttc taactagtaa   4380
caaggctaag atatcagcct gaaataaagg gtggtgaagt aataattaaa tcatccgtat   4440
aaacctatac acatatatga ggaaaaataa tacaaaagtg ttttaaatac agatacatac   4500
atgaacatat gcacgtatag cgcccaaatg tcggtaatgg gatcggcgag ctccagcttt   4560
tgttcccttt agtgagggtt aattgcgcgc ttggcgtaat catggtcata gctgtttcct   4620
gtgtgaaatt gttatccgct cacaattcca cacaacatag gagccggaag cataaagtgt   4680
aaagcctggg gtgcctaatg agtgaggtaa ctcacattaa ttgcgttgcg ctcactgccc   4740
gctttccagt cgggaaacct gtcgtgccag ctgcattaat gaatcggcca acgcgcgggg   4800
agaggcggtt tgcgtattgg gcgctcttcc gcttcctcgc tcactgactc gctgcgctcg   4860
gtcgttcggc tgcggcgagc ggtatcagct cactcaaagg cggtaatacg gttatccaca   4920
gaatcagggg ataacgcagg aaagaacatg tgagcaaaag gccagcaaaa ggccaggaac   4980
cgtaaaaagg ccgcgttgct ggcgtttttc cataggctcc gcccccctga cgagcatcac   5040
aaaaatcgac gctcaagtca gaggtggcga aacccgacag gactataaag ataccaggcg   5100
tttccccctg gaagctccct cgtgcgctct cctgttccga ccctgccgct taccggatac   5160
ctgtccgcct ttctcccttc gggaagcgtg gcgctttctc atagctcacg ctgtaggtat   5220
ctcagttcgg tgtaggtcgt tcgctccaag ctgggctgtg tgcacgaacc ccccgttcag   5280
cccgaccgct gcgccttatc cggtaactat cgtcttgagt ccaacccggt aagacacgac   5340
ttatcgccac tggcagcagc cactggtaac aggattagca gagcgaggta tgtaggcggt   5400
gctacagagt tcttgaagtg gtggcctaac tacggctaca ctagaaggac agtatttggt   5460
atctgcgctc tgctgaagcc agttaccttc ggaaaaagag ttggtagctc ttgatccggc   5520
aaacaaacca ccgctggtag cggtggtttt tttgtttgca agcagcagat tacgcgcaga   5580
aaaaaaggat ctcaagaaga tcctttgatc ttttctacgg ggtctgacgc tcagtggaac   5640
gaaaactcac gttaagggat tttggtcatg agattatcaa aaaggatctt cacctagatc   5700
cttttaaatt aaaaatgaag ttttaaatca atctaaagta tatatgagta aacttggtct   5760
gacagttacc aatgcttaat cagtgaggca cctatctcag cgatctgtct atttcgttca   5820
tccatagttg cctgactccc cgtcgtgtag ataactacga tacgggaggg cttaccatct   5880
ggccccagtg ctgcaatgat accgcgagac ccacgctcac cggctccaga tttatcagca   5940
ataaaccagc cagccggaag ggccgagcgc agaagtggtc ctgcaacttt atccgcctcc   6000
atccagtcta ttaattgttg ccgggaagct agagtaagta gttcgccagt taatagtttg   6060
cgcaacgttg ttgccattgc tacaggcatc gtggtgtcac gctcgtcgtt tggtatggct   6120
tcattcagct ccggttccca acgatcaagg cgagttacat gatcccccat gttgtgcaaa   6180
```

```
aaagcggtta gctccttcgg tcctccgatc gttgtcagaa gtaagttggc cgcagtgtta   6240

tcactcatgg ttatggcagc actgcataat tctcttactg tcatgccatc cgtaagatgc   6300

ttttctgtga ctggtgagta ctcaaccaag tcattctgag aatagtgtat gcggcgaccg   6360

agttgctctt gcccggcgtc aatacgggat aataccgcgc cacatagcag aactttaaaa   6420

gtgctcatca ttggaaaacg ttcttcgggg cgaaaactct caaggatctt accgctgttg   6480

agatccagtt cgatgtaacc cactcgtgca cccaactgat cttcagcatc ttttactttc   6540

accagcgttt ctgggtgagc aaaaacagga aggcaaaatg ccgcaaaaaa gggaataagg   6600

gcgacacgga aatgttgaat actcatactc ttcctttttc aatattattg aagcatttat   6660

cagggttatt gtctcatgag cggatacata tttgaatgta tttagaaaaa taaacaaata   6720

ggggttccgc gcacatttcc ccgaaaagtg ccacctgaac gaagcatctg tgcttcattt   6780

tgtagaacaa aaatgcaacg cgagagcgct aatttttcaa acaaagaatc tgagctgcat   6840

ttttacagaa cagaaatgca acgcgaaagc gctattttac caacgaagaa tctgtgcttc   6900

atttttgtaa aacaaaaatg caacgcgaga gcgctaattt ttcaaacaaa gaatctgagc   6960

tgcattttta cagaacagaa atgcaacgcg agagcgctat tttaccaaca aagaatctat   7020

acttcttttt tgttctacaa aaatgcatcc cgagagcgct atttttctaa caaagcatct   7080

tagattactt tttttctcct ttgtgcgctc tataatgcag tctcttgata actttttgca   7140

ctgtaggtcc gttaaggtta gaagaaggct actttggtgt ctattttctc ttccataaaa   7200

aaagcctgac tccacttccc gcgtttactg attactagcg aagctgcggg tgcatttttt   7260

caagataaag gcatccccga ttatattcta taccgatgtg gattgcgcat actttgtgaa   7320

cagaaagtga tagcgttgat gattcttcat tggtcagaaa attatgaacg gtttcttcta   7380

ttttgtctct atatactacg tataggaaat gtttacattt tcgtattgtt ttcgattcac   7440

tctatgaata gttcttacta caattttttt gtctaaagag taatactaga gataaacata   7500

aaaaatgtag aggtcgagtt tagatgcaag ttcaaggagc gaaaggtgga tgggtaggtt   7560

atatagggat atagcacaga gatatatagc aaagagatac ttttgagcaa tgtttgtgga   7620

agcggtattc gcaatatttt agtagctcgt tacagtccgg tgcgtttttg gttttttgaa   7680

agtgcgtctt cagagcgctt ttggttttca aaagcgctct gaagttccta tactttctag   7740

agaataggaa cttcggaata ggaacttcaa agcgtttccg aaaacgagcg cttccgaaaa   7800

tgcaacgcga gctgcgcaca tacagctcac tgttcacgtc gcacctatat ctgcgtgttg   7860

cctgtatata tatatacatg agaagaacgg catagtgcgt gtttatgctt aaatgcgtac   7920

ttatatgcgt ctatttatgt aggatgaaag gtagtctagt acctcctgtg atattatccc   7980

attccatgcg gggtatcgta tgcttccttc agcactaccc tttagctgtt ctatatgctg   8040

ccactcctca attggattag tctcatcctt caatgctatc atttcctttg atattggatc   8100

atctaagaaa ccattattat catgacatta acctataaaa ataggcgtat cacgaggccc   8160

tttcgtc                                                            8167
```

<210> SEQ ID NO 13
<211> LENGTH: 9598
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
tcgcgcgttt cggtgatgac ggtgaaaacc tctgacacat gcagctcccg gagacggtca     60
```

-continued cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatcga ctacgtcgta aggccgtttc tgacagagta aaattcttga gggaactttc 240
accattatgg gaaatgcttc aagaaggtat tgacttaaac tccatcaaat ggtcaggtca 300
ttgagtgttt tttatttgtt gtattttttt ttttttagag aaaatcctcc aatatcaaat 360
taggaatcgt agtttcatga ttttctgtta cacctaactt tttgtgtggt gccctcctcc 420
ttgtcaatat taatgttaaa gtgcaattct ttttccttat cacgttgagc cattagtatc 480
aatttgctta cctgtattcc tttactatcc tcctttttct ccttcttgat aaatgtatgt 540
agattgcgta tatagtttcg tctaccctat gaacatattc cattttgtaa tttcgtgtcg 600
tttctattat gaatttcatt tataaagttt atgtacaaat atcataaaaa aagagaatct 660
ttttaagcaa ggattttctt aacttcttcg gcgacagcat caccgacttc ggtggtactg 720
ttggaaccac ctaaatcacc agttctgata cctgcatcca aaaccttttt aactgcatct 780
tcaatggcct taccttcttc aggcaagttc aatgacaatt tcaacatcat tgcagcagac 840
aagatagtgg cgatagggtc aaccttattc tttggcaaat ctggagcaga accgtggcat 900
ggttcgtaca aaccaaatgc ggtgttcttg tctggcaaag aggccaagga cgcagatggc 960
aacaaaccca aggaacctgg gataacggag gcttcatcgg agatgatatc accaaacatg 1020
ttgctggtga ttataatacc atttaggtgg gttgggttct taactaggat catggcggca 1080
gaatcaatca attgatgttg aaccttcaat gtagggaatt cgttcttgat ggtttcctcc 1140
acagtttttc tccataatct tgaagaggcc aaaagattag ctttatccaa ggaccaaata 1200
ggcaatggtg gctcatgttg tagggccatg aaagcggcca ttcttgtgat tctttgcact 1260
tctggaacgg tgtattgttc actatcccaa gcgacaccat caccatcgtc ttcctttctc 1320
ttaccaaagt aaatacctcc cactaattct ctgacaacaa cgaagtcagt acctttagca 1380
aattgtggct tgattggaga taagtctaaa agagagtcgg atgcaaagtt acatggtctt 1440
aagttggcgt acaattgaag ttctttacgg atttttagta aaccttgttc aggtctaaca 1500
ctaccggtac cccatttagg accagccaca gcacctaaca aaacggcatc aaccttcttg 1560
gaggcttcca gcgcctcatc tggaagtggg acacctgtag catcgatagc agcaccacca 1620
attaaatgat tttcgaaatc gaacttgaca ttggaacgaa catcagaaat agctttaaga 1680
accttaatgg cttcggctgt gatttcttga ccaacgtggt cacctggcaa aacgacgatc 1740
ttcttagggg cagacatagg ggcagacatt agaatggtat atccttgaaa tatatatata 1800
tattgctgaa atgtaaaagg taagaaaagt tagaaagtaa gacgattgct aaccacctat 1860
tggaaaaaac aataggtcct taaataatat tgtcaacttc aagtattgtg atgcaagcat 1920
ttagtcatga acgcttctct attctatatg aaaagccggt tccggcctct cacctttcct 1980
ttttctccca atttttcagt tgaaaaaggt atatgcgtca ggcgacctct gaaattaaca 2040
aaaaatttcc agtcatcgaa tttgattctg tgcgatagcg cccctgtgtg ttctcgttat 2100
gttgaggaaa aaaataatgg ttgctaagag attcgaactc ttgcatctta cgatacctga 2160
gtattcccac agttaactgc ggtcaagata tttcttgaat caggcgcctt agaccgctcg 2220
gccaaacaac caattacttg ttgagaaata gagtataatt atcctataaa tataacgttt 2280
ttgaacacac atgaacaagg aagtacagga caattgattt tgaagagaat gtggattttg 2340
atgtaattgt tgggattcca tttttaataa ggcaataata ttaggtatgt ggatatacta 2400
gaagttctcc tcgaccgtcg atatgcggtg tgaaataccg cacagatgcg taaggagaaa 2460

-continued

```
ataccgcatc aggaaattgt aaacgttaat attttgttaa aattcgcgtt aaatttttgt   2520
taaatcagct cattttttaa ccaataggcc gaaatcggca aaatccctta taaatcaaaa   2580
gaatagaccg agatagggtt gagtgttgtt ccagtttgga acaagagtcc actattaaag   2640
aacgtggact ccaacgtcaa agggcgaaaa accgtctatc agggcgatgg cccactacgt   2700
gaaccatcac cctaatcaag ttttttgggg tcgaggtgcc gtaaagcact aaatcggaac   2760
cctaaaggga gcccccgatt tagagcttga cggggaaagc cggcgaacgt ggcgagaaag   2820
gaagggaaga aagcgaaagg agcgggcgct agggcgctgg caagtgtagc ggtcacgctg   2880
cgcgtaacca ccacacccgc cgcgcttaat gcgccgctac agggcgcgtc gcgccattcg   2940
ccattcaggc tgcgcaactg ttgggaaggg cgatcggtgc gggcctcttc gctattacgc   3000
cagctggcga aagggggatg tgctgcaagg cgattaagtt gggtaacgcc agggttttcc   3060
cagtcacgac gttgtaaaac gacggccagt gagcgcgcgt aatacgactc actatagggc   3120
gaattgggta ccggccgcaa attaaagcct tcgagcgtcc caaaaccttc tcaagcaagg   3180
ttttcagtat aatgttacat gcgtacacgc gtctgtacag aaaaaaaaga aaaatttgaa   3240
atataaataa cgttcttaat actaacataa ctataaaaaa ataaataggg acctagactt   3300
caggttgtct aactccttcc ttttcggtta gagcggatgt ggggggaggg cgtgaatgta   3360
agcgtgacat aactaattac atgactcgag cggccgcgga tccttaaccc cccagtttcg   3420
atttatcgcg caccgcgcct ttgtcggcgc tggttgccag gctggcataa gcacgcaggg   3480
caaaggagac ctgacgttca cgatttttcg gcgtccaggc tttgtcacct cgagcgtcct   3540
gcgcttcacg acgcgccgcc agttcggcat cgcttacctg taactgaatg ccacggttcg   3600
ggatgtcgat agcgatcagg tcaccatctt caatcaggcc aatgctgccg ccgcttgccg   3660
cttccggtga gacgtggccg atggaaagac cagaggtgcc accagagaaa cgaccgtcgg   3720
tgatcagcgc acaggctttg ccgagaccca ttgatttcag gaagctggtt gggtagagca   3780
tttcctgcat ccccggaccg cctttcgggc cttcatagcg aattactacc acatctccgg   3840
cgacaacttt accgccgaga atcgcttcta ccgcatcgtc ctggctttcg tacactttcg   3900
ccgggccggt gaatttgagg atgctgtcat cgacgcctgc cgttttcacg atgcagccgt   3960
tttccgcaaa gttaccgtag agcaccgcca ggccgccgtc tttgctgtag gcgtgttcca   4020
gcgagcggat acagccattg gcgcgatcgt cgtccagcgt atcccaacgg caatcttgcg   4080
agaatgcctg tgtggtacga atgcctgcag gacctgcgcg gaacatattt tttaccgcgt   4140
catcctgggt cagcataacg tcgtattgtt ccagcgtttg cggcaacgtc aggccaagta   4200
cgtttttcac atcacggttc agtaaccccg cgcgatccag ttcgccgaga ataccgataa   4260
caccaccagc acggtgaaca tcttccatat ggtatttctg ggtgctcggc gcaactttac   4320
acagctgtgg aaccttgcgg gaaagcttat cgatatcact catggtgaag tcgatttccg   4380
cttcctgcgc cgccgccagc aggtgaagta cggtgttagt cgatccaccc atcgcgatat   4440
ccagcgtcat ggcgttttca aacgccgcct tactggcgat attacgcggc agtgcacttt   4500
cgtcgttttg ctcgtaataa cgtttggtca attcaacaat gcgtttacca gcattaagga   4560
acagctgctt acggtcggcg tgggttgcca gcagcgagcc gttgcccggc tgcgacaggc   4620
ccagcgcttc ggtcaggcag ttcattgagt tagcggtaaa catcccggag caggaaccgc   4680
aggtcggaca cgcggaacgt tcaacctgat cgctctggga gtcagatact ttcgggtctg   4740
cgccctggat catcgcatca accagatcga gcttgatgat ctgatcggaa agtttggttt   4800
tcccggcctc catcgggccg ccggaaacaa agatcaccgg aatattcagg cgcagggaag   4860
```

```
ccatcagcat ccccggggtg attttgtcgc agttagagat gcagaccatg gcgtcggcgc   4920
agtgggcgtt gaccatatac tcaacggaat cagcgatcag ttcgcgagat ggcagtgaat   4980
aaagcatccc cccgtggccc atggcaatcc catcatccac cgcaatggtg ttgaactctt   5040
tggcaacgcc gccagccgct tcaatttgtt cggcgaccag tttaccgaga tcgcgcagat   5100
ggacgtgacc cggtacaaat tgggtgaacg agttcacaac cgcgataatc ggcttaccga   5160
aatcggcgtc ggtcattccg gtggcgcgcc acagcgcacg agcacccgcc atattacgac   5220
catgagtggt ggtggcggaa cggtacttag gcatgtcgac accatcttct tctgagatga   5280
gtttttgttc catgctagtt ctagaatccg tcgaaactaa gttctggtgt tttaaaacta   5340
aaaaaaagac taactataaa agtagaattt aagaagttta agaaatagat ttacagaatt   5400
acaatcaata cctaccgtct ttatatactt attagtcaag taggggaata atttcaggga   5460
actggtttca accttttttt tcagcttttt ccaaatcaga gagagcagaa ggtaatagaa   5520
ggtgtaagaa aatgagatag atacatgcgt gggtcaattg ccttgtgtca tcatttactc   5580
caggcaggtt gcatcactcc attgaggttg tgcccgtttt ttgcctgttt gtgcccctgt   5640
tctctgtagt tgcgctaaga gaatggacct atgaactgat ggttggtgaa gaaaacaata   5700
ttttggtgct gggattcttt ttttttctgg atgccagctt aaaaagcggg ctccattata   5760
tttagtggat gccaggaata aactgttcac ccagacacct acgatgttat atattctgtg   5820
taacccgccc cctattttgg gcatgtacgg gttacagcag aattaaaagg ctaatttttt   5880
gactaaataa agttaggaaa atcactacta ttaattattt acgtattctt tgaaatggcg   5940
agtattgata atgataaact gagctagatc tgggcccgag ctccagcttt tgttcccttt   6000
agtgagggtt aattgcgcgc ttggcgtaat catggtcata gctgtttcct gtgtgaaatt   6060
gttatccgct cacaattcca cacaacatag gagccggaag cataaagtgt aaagcctggg   6120
gtgcctaatg agtgaggtaa ctcacattaa ttgcgttgcg ctcactgccc gctttccagt   6180
cgggaaacct gtcgtgccag ctgcattaat gaatcggcca acgcgcgggg agaggcggtt   6240
tgcgtattgg gcgctcttcc gcttcctcgc tcactgactc gctgcgctcg gtcgttcggc   6300
tgcggcgagc ggtatcagct cactcaaagg cggtaatacg gttatccaca gaatcagggg   6360
ataacgcagg aaagaacatg tgagcaaaag gccagcaaaa ggccaggaac cgtaaaaagg   6420
ccgcgttgct ggcgtttttc cataggctcc gcccccctga cgagcatcac aaaaatcgac   6480
gctcaagtca gaggtggcga aacccgacag gactataaag ataccaggcg tttccccctg   6540
gaagctccct cgtgcgctct cctgttccga ccctgccgct taccggatac ctgtccgcct   6600
ttctcccttc gggaagcgtg gcgctttctc atagctcacg ctgtaggtat ctcagttcgg   6660
tgtaggtcgt tcgctccaag ctgggctgtg tgcacgaacc ccccgttcag cccgaccgct   6720
gcgccttatc cggtaactat cgtcttgagt ccaacccggt aagacacgac ttatcgccac   6780
tggcagcagc cactggtaac aggattagca gagcgaggta tgtaggcggt gctacagagt   6840
tcttgaagtg gtggcctaac tacggctaca ctagaaggac agtatttggt atctgcgctc   6900
tgctgaagcc agttaccttc ggaaaaagag ttggtagctc ttgatccggc aaacaaacca   6960
ccgctggtag cggtggtttt tttgtttgca agcagcagat tacgcgcaga aaaaaaggat   7020
ctcaagaaga tcctttgatc ttttctacgg ggtctgacgc tcagtggaac gaaaactcac   7080
gttaagggat tttggtcatg agattatcaa aaaggatctt cacctagatc cttttaaatt   7140
aaaaatgaag ttttaaatca atctaaagta tatatgagta aacttggtct gacagttacc   7200
aatgcttaat cagtgaggca cctatctcag cgatctgtct atttcgttca tccatagttg   7260
```

```
cctgactccc cgtcgtgtag ataactacga tacgggaggg cttaccatct ggccccagtg   7320

ctgcaatgat accgcgagac ccacgctcac cggctccaga tttatcagca ataaaccagc   7380

cagccggaag ggccgagcgc agaagtggtc ctgcaacttt atccgcctcc atccagtcta   7440

ttaattgttg ccgggaagct agagtaagta gttcgccagt taatagtttg cgcaacgttg   7500

ttgccattgc tacaggcatc gtggtgtcac gctcgtcgtt tggtatggct tcattcagct   7560

ccggttccca acgatcaagg cgagttacat gatcccccat gttgtgcaaa aaagcggtta   7620

gctccttcgg tcctccgatc gttgtcagaa gtaagttggc cgcagtgtta tcactcatgg   7680

ttatggcagc actgcataat tctcttactg tcatgccatc cgtaagatgc ttttctgtga   7740

ctggtgagta ctcaaccaag tcattctgag aatagtgtat gcggcgaccg agttgctctt   7800

gcccggcgtc aatacgggat aataccgcgc cacatagcag aactttaaaa gtgctcatca   7860

ttggaaaacg ttcttcgggg cgaaaactct caaggatctt accgctgttg agatccagtt   7920

cgatgtaacc cactcgtgca cccaactgat cttcagcatc ttttactttc accagcgttt   7980

ctgggtgagc aaaaacagga aggcaaaatg ccgcaaaaaa gggaataagg gcgacacgga   8040

aatgttgaat actcatactc ttcctttttc aatattattg aagcatttat cagggttatt   8100

gtctcatgag cggatacata tttgaatgta tttagaaaaa taaacaaata ggggttccgc   8160

gcacatttcc ccgaaaagtg ccacctgaac gaagcatctg tgcttcattt tgtagaacaa   8220

aaatgcaacg cgagagcgct aatttttcaa acaaagaatc tgagctgcat ttttacagaa   8280

cagaaatgca acgcgaaagc gctattttac caacgaagaa tctgtgcttc atttttgtaa   8340

aacaaaaatg caacgcgaga gcgctaattt ttcaaacaaa gaatctgagc tgcattttta   8400

cagaacagaa atgcaacgcg agagcgctat tttaccaaca aagaatctat acttcttttt   8460

tgttctacaa aaatgcatcc cgagagcgct atttttctaa caaagcatct tagattactt   8520

tttttctcct ttgtgcgctc tataatgcag tctcttgata actttttgca ctgtaggtcc   8580

gttaaggtta gaagaaggct actttggtgt ctattttctc ttccataaaa aaagcctgac   8640

tccacttccc gcgtttactg attactagcg aagctgcggg tgcatttttt caagataaag   8700

gcatccccga ttatattcta taccgatgtg gattgcgcat actttgtgaa cagaaagtga   8760

tagcgttgat gattcttcat tggtcagaaa attatgaacg gtttcttcta ttttgtctct   8820

atatactacg tataggaaat gtttacattt tcgtattgtt ttcgattcac tctatgaata   8880

gttcttacta caattttttt gtctaaagag taatactaga gataaacata aaaaatgtag   8940

aggtcgagtt tagatgcaag ttcaaggagc gaaaggtgga tgggtaggtt atatagggat   9000

atagcacaga gatatatagc aaagagatac ttttgagcaa tgtttgtgga agcggtattc   9060

gcaatatttt agtagctcgt tacagtccgg tgcgtttttg gttttttgaa agtgcgtctt   9120

cagagcgctt ttggttttca aaagcgctct gaagttccta tactttctag agaataggaa   9180

cttcggaata ggaacttcaa agcgtttccg aaaacgagcg cttccgaaaa tgcaacgcga   9240

gctgcgcaca tacagctcac tgttcacgtc gcacctatat ctgcgtgttg cctgtatata   9300

tatatacatg agaagaacgg catagtgcgt gtttatgctt aaatgcgtac ttatatgcgt   9360

ctatttatgt aggatgaaag gtagtctagt acctcctgtg atattatccc attccatgcg   9420

ggtatcgta tgcttccttc agcactaccc tttagctgtt ctatatgctg ccactcctca    9480

attggattag tctcatcctt caatgctatc atttcctttg atattggatc atactaagaa   9540

accattatta tcatgacatt aacctataaa aataggcgta tcacgaggcc ctttcgtc     9598
```

```
<210> SEQ ID NO 14
<211> LENGTH: 8698
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

ctgattggaa agaccattct gctttacttt tagagcatct tggtcttctg agctcattat     60

acctcaatca aaactgaaat taggtgcctg tcacggctct ttttttactg tacctgtgac    120

ttcctttctt atttccaagg atgctcatca caatacgctt ctagatctat tatgcattat    180

aattaatagt tgtagctaca aaaggtaaaa gaaagtccgg ggcaggcaac aatagaaatc    240

ggcaaaaaaa actacagaaa tactaagagc ttcttcccca ttcagtcatc gcatttcgaa    300

acaagagggg aatggctctg gctagggaac taaccaccat cgcctgactc tatgcactaa    360

ccacgtgact acatatatgt gatcgttttt aacatttttc aaaggctgtg tgtctggctg    420

tttccattaa ttttcactga ttaagcagtc atattgaatc tgagctcatc accaacaaga    480

aatactaccg taaaagtgta aaagttcgtt taaatcattt gtaaactgga acagcaagag    540

gaagtatcat cagctagccc cataaactaa tcaaaggagg atgtctacta agagttactc    600

ggaaagagca gctgctcata gaagtccagt tgctgccaag cttttaaact tgatggaaga    660

gaagaagtca aacttatgtg cttctcttga tgttcgtaaa acagcagagt tgttaagatt    720

agttgaggtt ttgggtccat atatctgtct attgaagaca catgtagata tcttggagga    780

tttcagcttt gagaatacca ttgtgccgtt gaagcaatta gcagagaaac acaagttttt    840

gatatttgaa gacaggaagt ttgccgacat tgggaacact gttaaattac aatacacgtc    900

tggtgtatac cgtatcgccg aatggtctga tatcaccaat gcacacggtg tgactggtgc    960

gggcattgtt gctggtttga agcaaggtgc cgaggaagtt acgaaagaac ctagagggtt   1020

gttaatgctt gccgagttat cgtccaaggg gtctctagcg cacggtgaat acactcgtgg   1080

gaccgtggaa attgccaaga gtgataagga ctttgttatt ggatttattg ctcaaaacga   1140

tatgggtgga agagaagagg gctacgattg gttgatcatg acgccaggtg ttggtcttga   1200

tgacaaaggt gatgctttgg gacaacaata cagaactgtg gatgaagttg ttgccggtgg   1260

atcagacatc attattgttg gtagaggtct tttcgcaaag ggaagagatc ctgtagtgga   1320

aggtgagaga tacagaaagg cgggatggga cgcttacttg aagagagtag gcagatccgc   1380

ttaagagttc tccgagaaca agcagaggtt cgagtgtact cggatcagaa gttacaagtt   1440

gatcgtttat atataaacta tacagagatg ttagagtgta atggcattgc gtgccggcga   1500

tcacagcgga cggtggtggc atgatggggc ttgcgatgct atgtttgttt gttttgtgat   1560

gatgtatatt attattgaaa aacgatatca gacatttgtc tgataatgct tcattatcag   1620

acaaatgtct gatatcgttt ggagaaaaag aaaaggaaaa caaactaaat atctactata   1680

taccactgta ttttatacta atgactttct acgcctagtg tcaccctctc gtgtacccat   1740

tgaccctgta tcggcgcgtt gcctcgcgtt cctgtaccat atatttttgt ttatttaggt   1800

attaaaattt actttcctca tacaaatatt aaattcacca aacttctcaa aaactaatta   1860

ttcgtagtta caaactctat tttacaatca cgtttattca accattctac atccaataac   1920

caaaatgccc atgtacctct cagcgaagtc caacggtact gtccaatatt ctcattaaat   1980

agtctttcat ctatatatca gaaggtaatt ataattagag atttcgaatc attaccgtgc   2040

cgattcgcac gctgcaacgg catgcatcac taatgaaaag catacgacgc ctgcgtctga   2100
```

```
catgcactca ttctgaagaa gattctgggc gcgtttcgtt ctcgttttcc tctgtatatt   2160
gtactctggt ggacaatttg aacataacgt cttttcacctc gccattctca ataatgggtt   2220
ccaattctat ccaggtagcg gttaattgac ggtgcttaag ccgtatgctc actctaacgc   2280
taccgttgtc caaacaacgg acccctttgt gacgggtgta agacccatca tgaagtaaaa   2340
catctctaac ggtatggaaa agagtggtac ggtcaagttt cctggcacga gtcaattttc   2400
cctcttcgtg tagatcggta ccggccgcaa attaaagcct tcgagcgtcc caaaaccttc   2460
tcaagcaagg ttttcagtat aatgttacat gcgtacacgc gtctgtacag aaaaaaaaga   2520
aaaatttgaa atataaataa cgttcttaat actaacataa ctataaaaaa ataaataggg   2580
acctagactt caggttgtct aactccttcc ttttcggtta gagcggatgt ggggggaggg   2640
cgtgaatgta agcgtgacat aactaattac atgagcggcc gcctatttat ggaatttctt   2700
atcataatcg accaaagtaa atctgtattt gacgtctccg ctttccatcc ttgtaaaggc   2760
atggctgacg ccttcttcgc tgatcggaag tttttccacc catattttga cattcttttc   2820
ggaaactaat ttcaatagtt gttcgatttc cttcctagat ccgatagcac tgcttgagat   2880
tgatactccc attaggccca acggttttaa aacaagcttt tcattaactt caggagcagc   2940
aattgaaacg atggagcctc caatcttcat aatcttaacg atactgtcaa aattaacttt   3000
cgacaaagat gatgagcaaa cgacaagaag gtccaaagcg ttagagtatt gttctgtcca   3060
gcctttatcc tccaacatag caatatagtg atcagcaccg agtttcatag aatcctcccg   3120
cttggagtgg cctcgcgaaa acgcataaac ctcggctccc atagctttag ccaacagaat   3180
ccccatatgc ccaataccac cgatgccaac aatacctacc ctcttacctg gaccacagcc   3240
atttcttagt agtggagaga aaactgtaat accaccacac aataatggag cggctagcgg   3300
acttggaata ttttctggta tttgaatagc aaagtgttca tgaagcctca cgtgggaggc   3360
aaagcctcct tgtgaaatgt agccgtcctt gtaaggagtc cacatagtca aaacgtggtc   3420
attggtacag tattgctcgt tgtcactttt gcaacgttca cactcaaaac acgccaaggc   3480
ttgggcacca acaccaacac ggtcaccgat ttttacccca gtgtggcact tggatccaac   3540
cttcaccacg cggccaatta tttcatgtcc aaggatttga ttttctggga ctggacccca   3600
attaccaacg gctatatgaa aatcagatcc gcagatacca caggcttcaa tttcaacatc   3660
aacgtcatga tcgccaaagg gttttgggtc aaaactcact aatttaggat gcttccaatc   3720
ctttgcgttg gaaataccga tgccctgaaa tttttctggg taaagcatgt cgagtcgaaa   3780
ctaagttctg gtgttttaaa actaaaaaaa agactaacta taaaagtaga atttaagaag   3840
tttaagaaat agatttacag aattacaatc aatacctacc gtctttatat acttattagt   3900
caagtagggg aataatttca gggaactggt ttcaaccttt tttttcagct ttttccaaat   3960
cagagagagc agaaggtaat agaaggtgta agaaaatgag atagatacat gcgtgggtca   4020
attgccttgt gtcatcattt actccaggca ggttgcatca ctccattgag gttgtgcccg   4080
ttttttgcct gtttgtgccc ctgttctctg tagttgcgct aagagaatgg acctatgaac   4140
tgatggttgg tgaagaaaac aatattttgg tgctgggatt cttttttttt ctggatgcca   4200
gcttaaaaag cgggctccat tatatttagt ggatgccagg aataaactgt tcacccagac   4260
acctacgatg ttatatattc tgtgtaaccc gccccctatt ttgggcatgt acgggttaca   4320
gcagaattaa aaggctaatt ttttgactaa ataaagttag gaaaatcact actattaatt   4380
atttacgtat tctttgaaat ggcgagtatt gataatgata aactggatcc ttaggattta   4440
ttctgttcag caaacagctt gcccattttc ttcagtacct tcggtgcgcc ttctttcgcc   4500
```

```
aggatcagtt cgatccagta catacggttc ggatcggcct gggcctcttt catcacgctc   4560
acaaattcgt tttcggtacg cacaatttta gacacaacac ggtcctcagt tgcgccgaag   4620
gactccggca gtttagagta gttccacata gggatatcgt tgtaagactg gttcggaccg   4680
tggatctcac gctcaacggt gtagccgtca ttgttaataa tgaagcaaat cgggttgatc   4740
ttttcacgaa ttgccagacc cagttcctgt acggtcagct gcagggaacc gtcaccgatg   4800
aacagcagat gacgagattc tttatcagcg atctgagagc ccagcgctgc cgggaaagta   4860
tagccaatgc taccccacag cggctgaccg ataaaatggc ttttggattt cagaaagata   4920
gaagacgcgc cgaaaaagct cgtaccttgt tccgccacga tggtttcatt gctctgggtc   4980
aggttctcca cggcctgcca caggcgatcc tgggacagca gtgcgttaga tggtacgaaa   5040
tcttcttgct tttgtcaat gtatttgcct ttatactcga tttcggacag gtccagcaga    5100
gagctgatca ggctttcgaa gtcgaagttc tggatacgct cgttgaagat tttaccctcg   5160
tcgatgttca ggctaatcat tttgttttcg ttcagatggt gagtgaatgc accggtagaa   5220
gagtcggtca gtttaacgcc cagcatcagg atgaagtccg cagattcaac aaattctttc   5280
aggttcggtt cgctcagagt accgttgtag atgcccagga aagacggcag agcctcgtca   5340
acagaggact tgccgaagtt cagggtggta atcggcagtt tggttttgct gatgaattgg   5400
gtcacggtct tctccagacc aaaagaaatg atttcgtggc cggtgatcac gattggtttc   5460
tttgcgtttt tcagagactc ctggattttg ttcaggattt cctggtcgct agtgttagaa   5520
gtggagtttt ctttcttcag cggcaggctc ggtttttccg ctttagctgc cgcaacatcc   5580
acaggcaggt tgatgtaaac tggtttgcgt tctttcagca gcgcagacag aacgcggtcg   5640
atttccacag tagcgttctc tgcagtcagc agcgtacgtg ccgcagtcac aggttcatgc   5700
attttcatga agtgtttgaa atcgccgtca gccagagtgt ggtggacgaa tttaccttcg   5760
ttctgaactt tgctcgttgg gctgcctacg atctccacca ccggcaggtt ttcggcgtag   5820
gagcccgcca gaccgttgac ggcgctcagt tcgccaacac cgaaagtggt cagaaatgcc   5880
gcggctttct tggtacgtgc ataaccatct gccatgtagc ttgcgttcag ttcgttagcg   5940
ttacccaccc atttcatgtc tttatgagag atgatctgat ccaggaactg cagattgtaa   6000
tcacccggaa cgccgaagat ttcttcgata cccagttcat gcagacggtc cagcagataa   6060
tcaccaacag tatacatgtc gacaaactta gattagattg ctatgctttc tttctaatga   6120
gcaagaagta aaaaaagttg taatagaaca agaaaaatga aactgaaact tgagaaattg   6180
aagaccgttt attaacttaa atatcaatgg gaggtcatcg aaagagaaaa aaatcaaaaa   6240
aaaaatttc aagaaaaaga aacgtgataa aaatttttat tgcctttttc gacgaagaaa    6300
aagaaacgag gcggtctctt ttttcttttc caaaccttta gtacgggtaa ttaacgacac   6360
cctagaggaa gaaagagggg aaatttagta tgctgtgctt gggtgttttg aagtggtacg   6420
gcgatgcgcg gagtccgaga aaatctggaa gagtaaaaaa ggagtagaaa catttgaag    6480
ctatgagctc cagcttttgt tccctttagt gagggttaat tgcgcgcttg gcgtaatcat   6540
ggtcatagct gtttcctgtg tgaaattgtt atccgctcac aattccacac aacataggag   6600
ccggaagcat aaagtgtaaa gcctggggtg cctaatgagt gaggtaactc acattaattg   6660
cgttgcgctc actgcccgct ttccagtcgg gaaacctgtc gtgccagctg cattaatgaa   6720
tcggccaacg cgcggggaga ggcggtttgc gtattgggcg ctcttccgct tcctcgctca   6780
ctgactcgct gcgctcggtc gttcggctgc ggcgagcggt atcagctcac tcaaaggcgg   6840
taatacggtt atccacagaa tcaggggata acgcaggaaa gaacatgtga gcaaaaggcc   6900
```

```
agcaaaaggc caggaaccgt aaaaaggccg cgttgctggc gtttttccat aggctccgcc   6960

cccctgacga gcatcacaaa aatcgacgct caagtcagag gtggcgaaac ccgacaggac   7020

tataaagata ccaggcgttt ccccctggaa gctccctcgt gcgctctcct gttccgaccc   7080

tgccgcttac cggatacctg tccgcctttc tcccttcggg aagcgtggcg ctttctcata   7140

gctcacgctg taggtatctc agttcggtgt aggtcgttcg ctccaagctg ggctgtgtgc   7200

acgaaccccc cgttcagccc gaccgctgcg ccttatccgg taactatcgt cttgagtcca   7260

acccggtaag acacgactta tcgccactgg cagcagccac tggtaacagg attagcagag   7320

cgaggtatgt aggcggtgct acagagttct tgaagtggtg gcctaactac ggctacacta   7380

gaaggacagt atttggtatc tgcgctctgc tgaagccagt taccttcgga aaaagagttg   7440

gtagctcttg atccggcaaa caaaccaccg ctggtagcgg tggttttttt gtttgcaagc   7500

agcagattac gcgcagaaaa aaaggatctc aagaagatcc tttgatcttt tctacggggt   7560

ctgacgctca gtggaacgaa aactcacgtt aagggatttt ggtcatgaga ttatcaaaaa   7620

ggatcttcac ctagatcctt ttaaattaaa aatgaagttt taaatcaatc taaagtatat   7680

atgagtaaac ttggtctgac agttaccaat gcttaatcag tgaggcacct atctcagcga   7740

tctgtctatt tcgttcatcc atagttgcct gactccccgt cgtgtagata actacgatac   7800

gggagggctt accatctggc cccagtgctg caatgatacc gcgagaccca cgctcaccgg   7860

ctccagattt atcagcaata aaccagccag ccggaagggc cgagcgcaga agtggtcctg   7920

caactttatc cgcctccatc cagtctatta attgttgccg ggaagctaga gtaagtagtt   7980

cgccagttaa tagtttgcgc aacgttgttg ccattgctac aggcatcgtg gtgtcacgct   8040

cgtcgtttgg tatggcttca ttcagctccg gttcccaacg atcaaggcga gttacatgat   8100

cccccatgtt gtgcaaaaaa gcggttagct ccttcggtcc tccgatcgtt gtcagaagta   8160

agttggccgc agtgttatca ctcatggtta tggcagcact gcataattct cttactgtca   8220

tgccatccgt aagatgcttt tctgtgactg gtgagtactc aaccaagtca ttctgagaat   8280

agtgtatgcg gcgaccgagt tgctcttgcc cggcgtcaat acgggataat accgcgccac   8340

atagcagaac tttaaaagtg ctcatcattg gaaaacgttc ttcggggcga aaactctcaa   8400

ggatcttacc gctgttgaga tccagttcga tgtaacccac tcgtgcaccc aactgatctt   8460

cagcatcttt tactttcacc agcgtttctg ggtgagcaaa aacaggaagg caaaatgccg   8520

caaaaaaggg aataagggcg acacggaaat gttgaatact catactcttc ctttttcaat   8580

attattgaag catttatcag ggttattgtc tcatgagcgg atacatattt gaatgtattt   8640

agaaaaataa acaaataggg gttccgcgca catttccccg aaaagtgcca cctgacgt     8698
```

```
<210> SEQ ID NO 15
<211> LENGTH: 6012
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
```

```
caggcaagtg cacaaacaat acttaaataa atactactca gtaataacct atttcttagc     60

atttttgacg aaatttgcta ttttgttaga gtcttttaca ccatttgtct ccacacctcc    120

gcttacatca acaccaataa cgccatttaa tctaagcgca tcaccaacat tttctggcgt    180

cagtccacca gctaacataa aatgtaagct ttcggggctc tcttgccttc caacccagtc    240

agaaatcgag ttccaatcca aaagttcacc tgtcccacct gcttctgaat caaacaaggg    300
```

```
aataaacgaa tgaggtttct gtgaagctgc actgagtagt atgttgcagt cttttggaaa    360
tacgagtctt ttaataactg gcaaaccgag gaactcttgg tattcttgcc acgactcatc    420
tccatgcagt tggacgatat caatgccgta atcattgacc agagccaaaa catcctcctt    480
aggttgatta cgaaacacgc caaccaagta tttcggagtg cctgaactat ttttatatgc    540
ttttacaaga cttgaaattt tccttgcaat aaccgggtca attgttctct ttctattggg    600
cacacatata atacccagca agtcagcatc ggaatctaga gcacattctg cggcctctgt    660
gctctgcaag ccgcaaactt tcaccaatgg accagaacta cctgtgaaat taataacaga    720
catactccaa gctgcctttg tgtgcttaat cacgtatact cacgtgctca atagtcacca    780
atgccctccc tcttggccct ctccttttct tttttcgacc gaattaattc ttaatcggca    840
aaaaaagaaa agctccggat caagattgta cgtaaggtga caagctattt ttcaataaag    900
aatatcttcc actactgcca tctggcgtca taactgcaaa gtacacatat attacgatgc    960
tgtctattaa atgcttccta tattatatat atagtaatgt cgttgacgtc gccggcgaac   1020
gtggcgagaa aggaagggaa gaaagcgaaa ggagcgggcg ctagggcgct ggcaagtgta   1080
gcggtcacgc tgcgcgtaac caccacaccc gccgcgctta atgcgccgct acagggcgcg   1140
tcgcgccatt cgccattcag gctgcgcaac tgttgggaag ggcgatcggt gcgggcctct   1200
tcgctattac gccagctggc gaaaggggga tgtgctgcaa ggcgattaag ttgggtaacg   1260
ccagggtttt cccagtcacg acgttgtaaa acgacggcca gtgagcgcgc gtaatacgac   1320
tcactatagg gcgaattggg taccggccgc aaattaaagc cttcgagcgt cccaaaacct   1380
tctcaagcaa ggttttcagt ataatgttac atgcgtacac gcgtctgtac agaaaaaaaa   1440
gaaaaatttg aaatataaat aacgttctta atactaacat aactataaaa aaataaatag   1500
ggacctagac ttcaggttgt ctaactcctt ccttttcggt tagagcggat gtgggggagg   1560
ggcgtgaatg taagcgtgac ataactaatt acatgactcg agcggccgcg gatccctaga   1620
gagctttcgt tttcatgagt tccccgaatt ctttcggaag cttgtcactt gctaaattaa   1680
cgttatcact gtagtcaacc gggacatcaa tgatgacagg cccctcagcg ttcatgcctt   1740
gacgcagaac atctgccagc tggtctggtg attctacgcg taagccagtt gctccgaagc   1800
tttccgcgta tttcacgata tcgatatttc cgaaatcgac cgcagatgta cgattatatt   1860
ttttcaattg ctggaatgca accatgtcat atgtgctgtc gttccataca atgtgtacaa   1920
ttggtgcttt taaacgaact gctgtctcta attccatagc tgagaataag aaaccgccat   1980
caccggagac tgatactact tttctcccg gtttcaccaa tgaagcgccg attgcccaag   2040
gaagcgcaac gccgagtgtt tgcataccgt tactaatcat taatgttaac ggctcgtagc   2100
tgcggaaata acgtgacatc caaatcgcgt gtgaaccgat atcgcaagtc actgtaacat   2160
gatcatcgac tgcgtttcgc aattctttaa cgatttcaag aggatgcact ctgtctgatt   2220
tccaatctgc aggcacctgc tcaccctcat gcatatattg ttttaaatca gaaaggatct   2280
tctgctcacg ttccgcaaag tctactttca cagcatcgtg ttcgatatga ttgatcgtag   2340
atggaatatc accgatcagt tcaagatccg gctggtaagc atgatcaatg tcagccagaa   2400
tctcgtctaa atggatgatc gtccggtctc cattgacatt ccagaatttc ggatcatatt   2460
caattgggtc atagccgatt gtcagaacaa catcagcctg ctcaagcagc agatcgccag   2520
gctggttgcg gaataaaccg atccggccaa aatactgatc ctctaaatct ctcgtaagag   2580
taccggcagc ttgatatgtt tcaacgaatg gaagctgcac ttttttcaat agcttgcgaa   2640
ccgctttaat cgcttccggt cttccgccct tcatgccgac taaaacgaca ggaagttttg   2700
```

```
ctgtttgaat ttttgcaatg gccatactga ttgcgtcatc tgctgcggga ccaagttttg   2760
gcgctgcgac agcacgtacg ttttttgtat ttgtgacttc attcacaaca tcttgcggaa   2820
aactcacaaa agcggcccca gcctgccctg ctgacgctat cctaaacgca tttgtaacag   2880
cttccggtat attttttaca tcttgaactt ctacactgta ttttgtaatc ggctggaata   2940
gcgccgcatt atccaaagat tgatgtgtcc gttttaaacg atctgcacgg atcacgttcc   3000
cagcaagcgc aacgacaggg tcaccttcag tgtttgctgt cagcagtcct gttgccaagt   3060
tcgaagcacc tggtcctgat gtgactaaca cgactcccgg ttttccagtt aaacggccga   3120
ctgcttgcgc cataaatgct gcattttgtt catgccgggc aacgataatt tcaggccctt   3180
tatcttgtaa agcgtcaaat accgcatcaa tttttgcacc tggaatgcca aatacatgtg   3240
tgacaccttg ctccgctaag caatcaacaa caagctccgc ccctctgctt ttcacaaggg   3300
atttttgttc ttttgttgct tttgtcaaca tgtcgacttt atgtgatgat tgattgattg   3360
attgtacagt ttgtttttct taatatctat ttcgatgact tctatatgat attgcactaa   3420
caagaagata ttataatgca attgatacaa gacaaggagt tatttgcttc tcttttatat   3480
gattctgaca atccatattg cgttggtagt ctttttttgct ggaacggttc agcggaaaag   3540
acgcatcgct ctttttgctt ctagaagaaa tgccagcaaa agaatctctt gacagtgact   3600
gacagcaaaa atgtcttttt ctaactagta acaaggctaa gatatcagcc tgaaataaag   3660
ggtggtgaag taataattaa atcatccgta taaacctata cacatatatg aggaaaaata   3720
atacaaaagt gttttaaata cagatacata catgaacata tgcacgtata gcgcccaaat   3780
gtcggtaatg ggatcggcga gctccagctt ttgttccctt tagtgagggt taattgcgcg   3840
cttggcgtaa tcatggtcat agctgtttcc tgtgtgaaat tgttatccgc tcacaattcc   3900
acacaacata ggagccggaa gcataaagtg taaagcctgg ggtgcctaat gagtgaggta   3960
actcacatta attgcgttgc gctcactgcc cgctttccag tcgggaaacc tgtcgtgcca   4020
gctgcattaa tgaatcggcc aacgcgcggg gagaggcggt ttgcgtattg ggcgctcttc   4080
cgcttcctcg ctcactgact cgctgcgctc ggtcgttcgg ctgcggcgag cggtatcagc   4140
tcactcaaag gcggtaatac ggttatccac agaatcaggg gataacgcag gaaagaacat   4200
gtgagcaaaa ggccagcaaa aggccaggaa ccgtaaaaag gccgcgttgc tggcgttttt   4260
ccataggctc cgcccccctg acgagcatca caaaaatcga cgctcaagtc agaggtggcg   4320
aaacccgaca ggactataaa gataccaggc gtttccccct ggaagctccc tcgtgcgctc   4380
tcctgttccg accctgccgc ttaccggata cctgtccgcc tttctccctt cgggaagcgt   4440
ggcgctttct catagctcac gctgtaggta tctcagttcg gtgtaggtcg ttcgctccaa   4500
gctgggctgt gtgcacgaac cccccgttca gcccgaccgc tgcgccttat ccggtaacta   4560
tcgtcttgag tccaacccgg taagacacga cttatcgcca ctggcagcag ccactggtaa   4620
caggattagc agagcgaggt atgtaggcgg tgctacagag ttcttgaagt ggtggcctaa   4680
ctacggctac actagaagga cagtatttgg tatctgcgct ctgctgaagc cagttacctt   4740
cggaaaaaga gttggtagct cttgatccgg caaacaaacc accgctggta gcggtggttt   4800
ttttgtttgc aagcagcaga ttacgcgcag aaaaaaagga tctcaagaag atcctttgat   4860
cttttctacg gggtctgacg ctcagtggaa cgaaaactca cgttaaggga ttttggtcat   4920
gagattatca aaaaggatct tcacctagat ccttttaaat taaaaatgaa gttttaaatc   4980
aatctaaagt atatatgagt aaacttggtc tgacagttac caatgcttaa tcagtgaggc   5040
acctatctca gcgatctgtc tatttcgttc atccatagtt gcctgactcc ccgtcgtgta   5100
```

```
gataactacg atacgggagg gcttaccatc tggccccagt gctgcaatga taccgcgaga   5160
cccacgctca ccggctccag atttatcagc aataaaccag ccagccggaa gggccgagcg   5220
cagaagtggt cctgcaactt tatccgcctc catccagtct attaattgtt gccgggaagc   5280
tagagtaagt agttcgccag ttaatagttt gcgcaacgtt gttgccattg ctacaggcat   5340
cgtggtgtca cgctcgtcgt ttggtatggc ttcattcagc tccggttccc aacgatcaag   5400
gcgagttaca tgatccccca tgttgtgcaa aaaagcggtt agctccttcg gtcctccgat   5460
cgttgtcaga agtaagttgg ccgcagtgtt atcactcatg gttatggcag cactgcataa   5520
ttctcttact gtcatgccat ccgtaagatg cttttctgtg actggtgagt actcaaccaa   5580
gtcattctga gaatagtgta tgcggcgacc gagttgctct tgcccggcgt caatacggga   5640
taataccgcg ccacatagca gaactttaaa agtgctcatc attggaaaac gttcttcggg   5700
gcgaaaactc tcaaggatct taccgctgtt gagatccagt tcgatgtaac ccactcgtgc   5760
acccaactga tcttcagcat cttttacttt caccagcgtt tctgggtgag caaaaacagg   5820
aaggcaaaat gccgcaaaaa agggaataag ggcgacacgg aaatgttgaa tactcatact   5880
cttccttttt caatattatt gaagcattta tcagggttat tgtctcatga gcggatacat   5940
atttgaatgt atttagaaaa ataaacaaat aggggttccg cgcacatttc cccgaaaagt   6000
gccacctgac gt                                                       6012
```

<210> SEQ ID NO 16
<211> LENGTH: 8969
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
ccagttaact gtgggaatac tcaggtatcg taagatgcaa gagttcgaat ctcttagcaa     60
ccattatttt tttcctcaac ataacgagaa cacacagggg cgctatcgca cagaatcaaa    120
ttcgatgact ggaaattttt tgttaatttc agaggtcgcc tgacgcatat acctttttca    180
actgaaaaat tgggagaaaa aggaaaggtg agagcgccgg aaccggcttt tcatatagaa    240
tagagaagcg ttcatgacta aatgcttgca tcacaatact tgaagttgac aatattattt    300
aaggacctat tgtttttttcc aataggtggt tagcaatcgt cttactttct aacttttctt   360
acctttttaca tttcagcaat atatatatat atatttcaag gatataccat tctaatgtct   420
gcccctaaga agatcgtcgt tttgccaggt gaccacgttg gtcaagaaat cacagccgaa    480
gccattaagg ttcttaaagc tatttctgat gttcgttcca atgtcaagtt cgatttcgaa    540
aatcatttaa ttggtggtgc tgctatcgat gctacaggtg ttccacttcc agatgaggcg    600
ctggaagcct ccaagaaggc tgatgccgtt ttgttaggtg ctgtgggtgg tcctaaatgg    660
ggtaccggta gtgttagacc tgaacaaggt ttactaaaaa tccgtaaaga acttcaattg    720
tacgccaact taagaccatg taactttgca tccgactctc ttttagactt atctccaatc    780
aagccacaat ttgctaaagg tactgacttc gttgttgtca gagaattagt gggaggtatt    840
tactttggta agagaaagga agacgatggt gatggtgtcg cttgggatag tgaacaatac    900
accgttccag aagtgcaaag aatcacaaga atggccgctt tcatggccct acaacatgag    960
ccaccattgc ctatttggtc cttggataaa gctaatgttt tggcctcttc aagattatgg   1020
agaaaaactg tggaggaaac catcaagaac gaattcccta cattgaaggt tcaacatcaa   1080
```

-continued

```
ttgattgatt ctgccgccat gatcctagtt aagaacccaa cccacctaaa tggtattata   1140
atcaccagca acatgtttgg tgatatcatc tccgatgaag cctccgttat cccaggttcc   1200
ttgggtttgt tgccatctgc gtccttggcc tctttgccag acaagaacac cgcatttggt   1260
ttgtacgaac catgccacgg ttctgctcca gatttgccaa agaataaggt caaccctatc   1320
gccactatct tgtctgctgc aatgatgttg aaattgtcat tgaacttgcc tgaagaaggt   1380
aaggccattg aagatgcagt taaaaaggtt ttggatgcag gtatcagaac tggtgattta   1440
ggtggttcca acagtaccac cgaagtcggt gatgctgtcg ccgaagaagt taagaaaatc   1500
cttgcttaaa aagattctct ttttttatga tatttgtaca taaactttat aaatgaaatt   1560
cataatagaa acgacacgaa attacaaaat ggaatatgtt catagggtag acgaaactat   1620
atacgcaatc tacatacatt tatcaagaag gagaaaaagg aggatgtaaa ggaatacagg   1680
taagcaaatt gatactaatg gctcaacgtg ataaggaaaa agaattgcac tttaacatta   1740
atattgacaa ggaggagggc accacacaaa aagttaggtg taacagaaaa tcatgaaact   1800
atgattccta atttatatat tggaggattt tctctaaaaa aaaaaaaata caacaaataa   1860
aaaacactca atgacctgac catttgatgg agttgccggc gaacgtggcg agaaaggaag   1920
ggaagaaagc gaaaggagcg ggcgctaggg cgctggcaag tgtagcggtc acgctgcgcg   1980
taaccaccac acccgccgcg cttaatgcgc cgctacaggg cgcgtcgcgc cattcgccat   2040
tcaggctgcg caactgttgg gaagggcgat cggtgcgggc ctcttcgcta ttacgccagc   2100
tggcgaaagg gggatgtgct gcaaggcgat taagttgggt aacgccaggg ttttcccagt   2160
cacgacgttg taaaacgacg gccagtgagc gcgcgtaata cgactcacta tagggcgaat   2220
tgggtaccgg ccgcaaatta aagccttcga gcgtcccaaa accttctcaa gcaaggtttt   2280
cagtataatg ttacatgcgt acacgcgtct gtacagaaaa aaaagaaaaa tttgaaatat   2340
aaataacgtt cttaatacta acataactat aaaaaaataa atagggacct agacttcagg   2400
ttgtctaact ccttcctttt cggttagagc ggatgtgggg ggagggcgtg aatgtaagcg   2460
tgacataact aattacatga gcggccgcag atctttaacc cgcaacagca atacgtttca   2520
tatctgtcat atagccgcgc agtttcttac ctacctgctc aatcgcatgg ctgcgaatcg   2580
cttcgttcac atcacgcagt tgcccgttat ctaccgcgcc ttccggaata gctttaccca   2640
ggtcgcccgg ttgcagctct gccataaacg gtttcagcaa cggcacacaa gcgtaagaga   2700
acagatagtt accgtactca gcggtatcag agataaccac gttcatttcg tacagacgct   2760
tacgggcgat ggtgttggca atcagcggca gctcgtgcag tgattcataa tatgcagact   2820
cttcaatgat gccggaatcg accatggttt cgaacgccag ttcaacgccc gctttcacca   2880
tcgcaatcat cagtacgcct ttatcgaagt actcctgctc gccgattttg ccttcatact   2940
gcggcgcggt ttcaaacgcg gttttgccgg tctcttcacg ccaggtcagc agtttcttat   3000
catcgttggc ccagtccgcc atcataccgg aagagaattc gccggagatg atgtcgtcca   3060
tatgtttctg gaacaggggt gccatgatct ctttcagctg ttcagaaagc gcataagcac   3120
gcagtttcgc cgggttagag agacggtcca tcatcagggt gatgccgccc tgtttcagtg   3180
cttcggtgat ggtttcccaa ccgaactgaa tcagtttttc tgcgtatgct ggatcggtac   3240
cttcttccac cagcttgtcg aagcacagca gagagccagc ctgcaacata ccgcacagga   3300
tggtttgctc gcccatcagg tcagatttca cttccgcaac gaaggacgat tccagcacac   3360
ccgcacggtg accaccggtt gcagccgccc aggctttggc aatcgccatg ccttcgcctt   3420
tcggatcgtt ttccgggtga acggcaatca gcgtcggtac gccgaaccca cgtttgtact   3480
```

```
cttcacgcac ttcggtgcct gggcatttcg gcgcaaccat cactacggtg atatctttac   3540
ggatctgctc gcccacttcg acgatgttga aaccgtgcga gtagcccagc gccgcgccgt   3600
ctttcatcag tggctgtacg gtgcgcacta catcagagtg ctgcttgtcc ggcgtcaggt   3660
taatcaccag atccgcctgt gggatcagtt cttcgtaagt acccacttta aaaccatttt   3720
cggtcgcttt acgccaggac gcgcgcttct cggcaatcgc ttctttacgc agagcgtagg   3780
agatatcgag accagaatca cgcatgttca ggccctggtt cagaccctgt gcgccacagc   3840
cgacgatgac tactttttta ccctgaaggt agctcgcgcc atcggcgaat tcatcgcggc   3900
ccatctcgag tcgaaactaa gttctggtgt tttaaaacta aaaaaaagac taactataaa   3960
agtagaattt aagaagttta agaaatagat ttacagaatt acaatcaata cctaccgtct   4020
ttatatactt attagtcaag taggggaata atttcaggga actggtttca accttttttt   4080
tcagcttttt ccaaatcaga gagagcagaa ggtaatagaa ggtgtaagaa aatgagatag   4140
atacatgcgt gggtcaattg ccttgtgtca tcatttactc caggcaggtt gcatcactcc   4200
attgaggttg tgcccgtttt ttgcctgttt gtgcccctgt tctctgtagt tgcgctaaga   4260
gaatggacct atgaactgat ggttggtgaa gaaaacaata ttttggtgct gggattcttt   4320
ttttttctgg atgccagctt aaaaagcggg ctccattata tttagtggat gccaggaata   4380
aactgttcac ccagacacct acgatgttat atattctgtg taacccgccc cctattttgg   4440
gcatgtacgg gttacagcag aattaaaagg ctaatttttt gactaaataa agttaggaaa   4500
atcactacta ttaattattt acgtattctt tgaaatggcg agtattgata atgataaact   4560
ggatcctcat ccacccaact tcgatttgtc tcttactgcc cccttatcgg ctgaagtagc   4620
caatgaagca taagccctaa gggcgaaact tacttgacgt tctctatttt taggagtcca   4680
agccttatct cctctggcat cttgtgcttc tcttcttgca gccaattcag cgtctgagac   4740
ttgtaattgg atacctctat ttgggatatc tatggcgatc aaatctccat cttcaatcaa   4800
tccaatcgaa ccaccagaag ctgcctctgg tgatacgtga ccgatactta aacccgaagt   4860
gccaccagag aatctaccgt cagtgataag ggcacaagct tttcctagtc ccatggactt   4920
caaaaatgaa gttgggtaaa gcatttcctg catacctggt cctccctttg gtccctcata   4980
tcttatcact accacgtctc ctgctaccac ctttccgcca agtatagcct caacagcatc   5040
gtcttgactt tcgtaaactt tagcgggtcc agtaaatttc aaaatactat catctacacc   5100
agcagttttc acaatgcaac cattttcagc gaagtttcca tataatactg ctaaaccacc   5160
atccttacta taagcatgct caagcgatct tatacatcca tttgctctat catcgtccaa   5220
agtgtcccac ctacagtctt gcgagaatgc ttgggtggtt ctgatccctg ctggacctgc   5280
cctgaacatg tttttcacgg catcatcttg agttaacatg acatcgtatt gctctaatgt   5340
ctgtggaagt gttaaaccca atacattctt cacatccctg tttaaaagac cggctctgtc   5400
caactcccct aaaataccaa taacccctcc tgcacgatga acgtcttcca tgtgatactt   5460
ttgagttgat ggtgcaacct tacataactg tggaacctta cgtgaaagct tgtcgatatc   5520
agacatggtg aaatctatct cagcttcttg ggctgcagct agaagatgta agaccgtgtt   5580
tgtactacca cccattgcaa tatccaatgt catggcattt tcgaatgcag cctttgaagc   5640
tatattcctc ggtaatgctg attcatcatt ttgttcgtaa taccttttcg ttagttccac   5700
aattcttttt ccggcattta agaacaattg ctttctgtct gcatgggtcg ctaataatga   5760
accatttcct ggttgagata aacctagagc ttcagtcaag caattcatag agttagccgt   5820
gaacattcca ctgcaagaac cacaagttgg acatgcactt ctttcaactt ggtctgactg   5880
```

```
cgagtctgaa acttttggat ctgcaccttg aatcattgca tccacaagat caagtttgat   5940
gatctgatca cttaacttag ttttaccagc ctccattggg ccgccagata cgaagattac   6000
tgggatgttc aatctcaagg acgccatcaa cataccaggc gttatcttat cacaattaga   6060
gatacaaacc attgcatcgg cacaatgagc attaaccata tattcgactg agtctgcaat   6120
taattctctc gatggtaaag agtataacat accgccatgc cccatagcta taccgtcgtc   6180
cacagcaata gtattaaact cttttgcgac accacctgca gcttcaattt gttcggcaac   6240
aagcttacct agatcacgca aatggacatg acccggaacg aattgtgtaa aagagttgac   6300
gacggcaatg attggctttc cgaaatctgc atcagtcatg ccagtcatgt cgacaaactt   6360
agattagatt gctatgcttt ctttctaatg agcaagaagt aaaaaaagtt gtaatagaac   6420
aagaaaaatg aaactgaaac ttgagaaatt gaagaccgtt tattaactta aatatcaatg   6480
ggaggtcatc gaaagagaaa aaaatcaaaa aaaaaatttt caagaaaaag aaacgtgata   6540
aaaattttta ttgccttttt cgacgaagaa aaagaaacga ggcggtctct tttttctttt   6600
ccaaaccttt agtacgggta attaacgaca ccctagagga agaaagaggg gaaatttagt   6660
atgctgtgct tgggtgtttt gaagtggtac ggcgatgcgc ggagtccgag aaaatctgga   6720
agagtaaaaa aggagtagaa acattttgaa gctatgagct ccagcttttg ttccctttag   6780
tgagggttaa ttgcgcgctt ggcgtaatca tggtcatagc tgtttcctgt gtgaaattgt   6840
tatccgctca caattccaca caacatagga gccggaagca taaagtgtaa agcctggggt   6900
gcctaatgag tgaggtaact cacattaatt gcgttgcgct cactgcccgc tttccagtcg   6960
ggaaacctgt cgtgccagct gcattaatga atcggccaac gcgcggggag aggcggtttg   7020
cgtattgggc gctcttccgc ttcctcgctc actgactcgc tgcgctcggt cgttcggctg   7080
cggcgagcgg tatcagctca ctcaaaggcg gtaatacggt tatccacaga atcaggggat   7140
aacgcaggaa agaacatgtg agcaaaaggc cagcaaaagg ccaggaaccg taaaaaggcc   7200
gcgttgctgg cgtttttcca taggctccgc ccccctgacg agcatcacaa aaatcgacgc   7260
tcaagtcaga ggtggcgaaa cccgacagga ctataaagat accaggcgtt tccccctgga   7320
agctccctcg tgcgctctcc tgttccgacc ctgccgctta ccggatacct gtccgccttt   7380
ctcccttcgg gaagcgtggc gctttctcat agctcacgct gtaggtatct cagttcggtg   7440
taggtcgttc gctccaagct gggctgtgtg cacgaacccc ccgttcagcc cgaccgctgc   7500
gccttatccg gtaactatcg tcttgagtcc aacccggtaa gacacgactt atcgccactg   7560
gcagcagcca ctggtaacag gattagcaga gcgaggtatg taggcggtgc tacagagttc   7620
ttgaagtggt ggcctaacta cggctacact agaaggacag tatttggtat ctgcgctctg   7680
ctgaagccag ttaccttcgg aaaaagagtt ggtagctctt gatccggcaa acaaaccacc   7740
gctggtagcg gtggtttttt tgtttgcaag cagcagatta cgcgcagaaa aaaaggatct   7800
caagaagatc ctttgatctt ttctacgggg tctgacgctc agtggaacga aaactcacgt   7860
taagggattt tggtcatgag attatcaaaa aggatcttca cctagatcct tttaaattaa   7920
aaatgaagtt ttaaatcaat ctaaagtata tatgagtaaa cttggtctga cagttaccaa   7980
tgcttaatca gtgaggcacc tatctcagcg atctgtctat ttcgttcatc catagttgcc   8040
tgactccccg tcgtgtagat aactacgata cgggagggct taccatctgg ccccagtgct   8100
gcaatgatac cgcgagaccc acgctcaccg gctccagatt tatcagcaat aaaccagcca   8160
gccggaaggg ccgagcgcag aagtggtcct gcaactttat ccgcctccat ccagtctatt   8220
aattgttgcc gggaagctag agtaagtagt tcgccagtta atagtttgcg caacgttgtt   8280
```

```
gccattgcta caggcatcgt ggtgtcacgc tcgtcgtttg gtatggcttc attcagctcc   8340

ggttcccaac gatcaaggcg agttacatga tcccccatgt tgtgcaaaaa agcggttagc   8400

tccttcggtc ctccgatcgt tgtcagaagt aagttggccg cagtgttatc actcatggtt   8460

atggcagcac tgcataattc tcttactgtc atgccatccg taagatgctt ttctgtgact   8520

ggtgagtact caaccaagtc attctgagaa tagtgtatgc ggcgaccgag ttgctcttgc   8580

ccggcgtcaa tacgggataa taccgcgcca catagcagaa ctttaaaagt gctcatcatt   8640

ggaaaacgtt cttcggggcg aaaactctca aggatcttac cgctgttgag atccagttcg   8700

atgtaaccca ctcgtgcacc caactgatct tcagcatctt ttactttcac cagcgtttct   8760

gggtgagcaa aaacaggaag gcaaaatgcc gcaaaaaagg gaataagggc gacacggaaa   8820

tgttgaatac tcatactctt cctttttcaa tattattgaa gcatttatca gggttattgt   8880

ctcatgagcg gatacatatt tgaatgtatt tagaaaaata aacaaatagg ggttccgcgc   8940

acatttcccc gaaaagtgcc acctgacgt                                     8969
```

<210> SEQ ID NO 17
<211> LENGTH: 5853
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgcgtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctctag tacactctat atttttttat gcctcggtaa tgattttcat    360

tttttttttt cccctagcgg atgactcttt ttttttctta gcgattggca ttatcacata    420

atgaattata cattatataa agtaatgtga tttcttcgaa gaatatacta aaaaatgagc    480

aggcaagata aacgaaggca aagatgacag agcagaaagc cctagtaaag cgtattacaa    540

atgaaaccaa gattcagatt gcgatctctt taaagggtgg tcccctagcg atagagcact    600

cgatcttccc agaaaaagag gcagaagcag tagcagaaca ggccacacaa tcgcaagtga    660

ttaacgtcca cacaggtata gggtttctgg accatatgat acatgctctg gccaagcatt    720

ccggctggtc gctaatcgtt gagtgcattg gtgacttaca catagacgac catcacacca    780

ctgaagactg cgggattgct ctcggtcaag cttttaaaga ggccctaggg gccgtgcgtg    840

gagtaaaaag gtttggatca ggatttgcgc ctttggatga ggcactttcc agagcggtgg    900

tagatctttc gaacaggccg tacgcagttg tcgaacttgg tttgcaaagg gagaaagtag    960

gagatctctc ttgcgagatg atcccgcatt ttcttgaaag ctttgcagag gctagcagaa   1020

ttaccctcca cgttgattgt ctgcgaggca agaatgatca tcaccgtagt gagagtgcgt   1080

tcaaggctct tgcggttgcc ataagagaag ccacctcgcc caatggtacc aacgatgttc   1140

cctccaccaa aggtgttctt atgtagtgac accgattatt taaagctgca gcatacgata   1200

tatatacatg tgtatatatg tatacctatg aatgtcagta agtatgtata cgaacagtat   1260

gatactgaag atgacaaggt aatgcatcat tctatacgtg tcattctgaa cgaggcgcgc   1320

tttccttttt tctttttgct tttlctttt ttttctcttg aactcgacgg atctatgcgg   1380
```

```
tgtgaaatac cgcacagatg cgtaaggaga aaataccgca tcaggaaatt gtaaacgtta   1440
atattttgtt aaaattcgcg ttaaattttt gttaaatcag ctcatttttt aaccaatagg   1500
ccgaaatcgg caaaatccct tataaatcaa aagaatagac cgagataggg ttgagtgttg   1560
ttccagtttg gaacaagagt ccactattaa agaacgtgga ctccaacgtc aaagggcgaa   1620
aaaccgtcta tcagggcgat ggcccactac gtgaaccatc accctaatca agttttttgg   1680
ggtcgaggtg ccgtaaagca ctaaatcgga accctaaagg gagcccccga tttagagctt   1740
gacggggaaa gccggcgaac gtggcgagaa aggaagggaa gaaagcgaaa ggagcgggcg   1800
ctagggcgct ggcaagtgta gcggtcacgc tgcgcgtaac caccacaccc gccgcgctta   1860
atgcgccgct acagggcgcg tcgcgccatt cgccattcag gctgcgcaac tgttgggaag   1920
ggcgatcggt gcgggcctct tcgctattac gccagctggc gaaaggggga tgtgctgcaa   1980
ggcgattaag ttgggtaacg ccagggtttt cccagtcacg acgttgtaaa acgacggcca   2040
gtgagcgcgc gtaatacgac tcactatagg gcgaattggg taccggccgc aaattaaagc   2100
cttcgagcgt cccaaaacct tctcaagcaa ggttttcagt ataatgttac atgcgtacac   2160
gcgtctgtac agaaaaaaaa gaaaaatttg aaatataaat aacgttctta atactaacat   2220
aactataaaa aaataaatag ggacctagac ttcaggttgt ctaactcctt ccttttcggt   2280
tagagcggat gtggggggag ggcgtgaatg taagcgtgac ataactaatt acatgactcg   2340
aggtcgacgg tatcgataag cttgatatcg aattcctgca gcccggggga tccactagtt   2400
ctagaatccg tcgaaactaa gttctggtgt tttaaaacta aaaaaaagac taactataaa   2460
agtagaattt aagaagttta agaaatagat ttacagaatt acaatcaata cctaccgtct   2520
ttatatactt attagtcaag taggggaata atttcaggga actggtttca accttttttt   2580
tcagcttttt ccaaatcaga gagagcagaa ggtaatagaa ggtgtaagaa aatgagatag   2640
atacatgcgt gggtcaattg ccttgtgtca tcatttactc caggcaggtt gcatcactcc   2700
attgaggttg tgcccgtttt ttgcctgttt gtgcccctgt tctctgtagt tgcgctaaga   2760
gaatggacct atgaactgat ggttggtgaa gaaaacaata ttttggtgct gggattcttt   2820
tttttctgg atgccagctt aaaaagcggg ctccattata tttagtggat gccaggaata   2880
aactgttcac ccagacacct acgatgttat atattctgtg taacccgccc cctattttgg   2940
gcatgtacgg gttacagcag aattaaaagg ctaatttttt gactaaataa agttaggaaa   3000
atcactacta ttaattattt acgtattctt tgaaatggcg agtattgata atgataaact   3060
gagctccagc ttttgttccc tttagtgagg gttaattgcg cgcttggcgt aatcatggtc   3120
atagctgttt cctgtgtgaa attgttatcc gctcacaatt ccacacaaca taggagccgg   3180
aagcataaag tgtaaagcct ggggtgccta atgagtgagg taactcacat taattgcgtt   3240
gcgctcactg cccgctttcc agtcgggaaa cctgtcgtgc cagctgcatt aatgaatcgg   3300
ccaacgcgcg gggagaggcg gtttgcgtat tgggcgctct tccgcttcct cgctcactga   3360
ctcgctgcgc tcggtcgttc ggctgcggcg agcggtatca gctcactcaa aggcggtaat   3420
acggttatcc acagaatcag gggataacgc aggaaagaac atgtgagcaa aaggccagca   3480
aaaggccagg aaccgtaaaa aggccgcgtt gctggcgttt ttccataggc tccgcccccc   3540
tgacgagcat cacaaaaatc gacgctcaag tcagaggtgg cgaaacccga caggactata   3600
aagataccag gcgtttcccc ctggaagctc cctcgtgcgc tctcctgttc cgaccctgcc   3660
gcttaccgga tacctgtccg cctttctccc ttcgggaagc gtggcgcttt ctcatagctc   3720
acgctgtagg tatctcagtt cggtgtaggt cgttcgctcc aagctgggct gtgtgcacga   3780
```

```
acccccgtt cagcccgacc gctgcgcctt atccggtaac tatcgtcttg agtccaaccc   3840

ggtaagacac gacttatcgc cactggcagc agccactggt aacaggatta gcagagcgag   3900

gtatgtaggc ggtgctacag agttcttgaa gtggtggcct aactacggct acactagaag   3960

gacagtattt ggtatctgcg ctctgctgaa gccagttacc ttcggaaaaa gagttggtag   4020

ctcttgatcc ggcaaacaaa ccaccgctgg tagcggtggt ttttttgttt gcaagcagca   4080

gattacgcgc agaaaaaaag gatctcaaga agatcctttg atcttttcta cggggtctga   4140

cgctcagtgg aacgaaaact cacgttaagg gattttggtc atgagattat caaaaaggat   4200

cttcacctag atccttttaa attaaaaatg aagttttaaa tcaatctaaa gtatatatga   4260

gtaaacttgg tctgacagtt accaatgctt aatcagtgag gcacctatct cagcgatctg   4320

tctatttcgt tcatccatag ttgcctgact ccccgtcgtg tagataacta cgatacggga   4380

gggcttacca tctggcccca gtgctgcaat gataccgcga gacccacgct caccggctcc   4440

agatttatca gcaataaacc agccagccgg aagggccgag cgcagaagtg gtcctgcaac   4500

tttatccgcc tccatccagt ctattaattg ttgccgggaa gctagagtaa gtagttcgcc   4560

agttaatagt ttgcgcaacg ttgttgccat tgctacaggc atcgtggtgt cacgctcgtc   4620

gtttggtatg gcttcattca gctccggttc ccaacgatca aggcgagtta catgatcccc   4680

catgttgtgc aaaaaagcgg ttagctcctt cggtcctccg atcgttgtca gaagtaagtt   4740

ggccgcagtg ttatcactca tggttatggc agcactgcat aattctctta ctgtcatgcc   4800

atccgtaaga tgcttttctg tgactggtga gtactcaacc aagtcattct gagaatagtg   4860

tatgcggcga ccgagttgct cttgcccggc gtcaatacgg gataataccg cgccacatag   4920

cagaacttta aaagtgctca tcattggaaa acgttcttcg gggcgaaaac tctcaaggat   4980

cttaccgctg ttgagatcca gttcgatgta acccactcgt gcacccaact gatcttcagc   5040

atcttttact ttcaccagcg tttctgggtg agcaaaaaca ggaaggcaaa atgccgcaaa   5100

aaagggaata agggcgacac ggaaatgttg aatactcata ctcttccttt ttcaatatta   5160

ttgaagcatt tatcagggtt attgtctcat gagcggatac atatttgaat gtatttagaa   5220

aaataaacaa ataggggttc cgcgcacatt tccccgaaaa gtgccacctg ggtccttttc   5280

atcacgtgct ataaaaataa ttataattta aattttttaa tataaatata taaattaaaa   5340

atagaaagta aaaaaagaaa ttaaagaaaa aatagttttt gttttccgaa gatgtaaaag   5400

actctagggg gatcgccaac aaatactacc ttttatcttg ctcttcctgc tctcaggtat   5460

taatgccgaa ttgtttcatc ttgtctgtgt agaagaccac acacgaaaat cctgtgattt   5520

tacattttac ttatcgttaa tcgaatgtat atctatttaa tctgcttttc ttgtctaata   5580

aatatatatg taaagtacgc tttttgttga aattttttaa acctttgttt attttttttt   5640

cttcattccg taactcttct accttcttta tttactttct aaaatccaaa tacaaaacat   5700

aaaaataaat aaacacagag taaattccca aattattcca tcattaaaag atacgaggcg   5760

cgtgtaagtt acaggcaagc gatccgtcct aagaaaccat tattatcatg acattaacct   5820

ataaaaatag gcgtatcacg aggccctttc gtc                                5853
```

```
<210> SEQ ID NO 18
<211> LENGTH: 5778
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 18

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataccac agcttttcaa ttcaattcat cattttttt ttattctttt ttttgatttc     240
ggtttctttg aaattttttt gattcggtaa tctccgaaca gaaggaagaa cgaaggaagg     300
agcacagact tagattggta tatatacgca tatgtagtgt tgaagaaaca tgaaattgcc     360
cagtattctt aacccaactg cacagaacaa aaacctgcag gaaacgaaga taaatcatgt     420
cgaaagctac atataaggaa cgtgctgcta ctcatcctag tcctgttgct gccaagctat     480
ttaatatcat gcacgaaaag caaacaaact tgtgtgcttc attggatgtt cgtaccacca     540
aggaattact ggagttagtt gaagcattag gtcccaaaat ttgtttacta aaaacacatg     600
tggatatctt gactgatttt tccatggagg gcacagttaa gccgctaaag gcattatccg     660
ccaagtacaa tttttactc ttcgaagaca gaaaatttgc tgacattggt aatacagtca     720
aattgcagta ctctgcgggt gtatacagaa tagcagaatg ggcagacatt acgaatgcac     780
acggtgtggt gggcccaggt attgttagcg gtttgaagca ggcggcagaa gaagtaacaa     840
aggaacctag aggccttttg atgttagcag aattgtcatg caagggctcc ctatctactg     900
gagaatatac taagggtact gttgacattg cgaagagcga caaagatttt gttatcggct     960
ttattgctca aagagacatg ggtggaagag atgaaggtta cgattggttg attatgacac    1020
ccggtgtggg tttagatgac aagggagacg cattgggtca acagtataga accgtggatg    1080
atgtggtctc tacaggatct gacattatta ttgttggaag aggactattt gcaaagggaa    1140
gggatgctaa ggtagagggt gaacgttaca gaaaagcagg ctgggaagca tatttgagaa    1200
gatgcggcca gcaaaactaa aaaactgtat tataagtaaa tgcatgtata ctaaactcac    1260
aaattagagc ttcaatttaa ttatatcagt tattacccta tgcggtgtga aataccgcac    1320
agatgcgtaa ggagaaaata ccgcatcagg aaattgtaaa cgttaatatt ttgttaaaat    1380
tcgcgttaaa tttttgttaa atcagctcat tttttaacca ataggccgaa atcggcaaaa    1440
tcccttataa atcaaaagaa tagaccgaga tagggttgag tgttgttcca gtttggaaca    1500
agagtccact attaaagaac gtggactcca acgtcaaagg gcgaaaaacc gtctatcagg    1560
gcgatggccc actacgtgaa ccatcaccct aatcaagttt tttggggtcg aggtgccgta    1620
aagcactaaa tcggaaccct aaagggagcc cccgatttag agcttgacgg ggaaagccgg    1680
cgaacgtggc gagaaaggaa gggaagaaag cgaaaggagc gggcgctagg gcgctggcaa    1740
gtgtagcggt cacgctgcgc gtaaccacca cacccgccgc gcttaatgcg ccgctacagg    1800
gcgcgtcgcg ccattcgcca ttcaggctgc gcaactgttg ggaagggcga tcggtgcggg    1860
cctcttcgct attacgccag ctggcgaaag gggggatgtgc tgcaaggcga ttaagttggg    1920
taacgccagg gttttcccag tcacgacgtt gtaaaacgac ggccagtgag cgcgcgtaat    1980
acgactcact atagggcgaa ttgggtaccg gccgcaaatt aaagccttcg agcgtcccaa    2040
aaccttctca agcaaggttt tcagtataat gttacatgcg tacacgcgtc tgtacagaaa    2100
aaaaagaaaa atttgaaata taaataacgt tcttaatact aacataacta taaaaaaata    2160
aatagggacc tagacttcag gttgtctaac tccttccttt tcggttagag cggatgtggg    2220
gggagggcgt gaatgtaagc gtgacataac taattacatg actcgaggtc gacggtatcg    2280
ataagcttga tatcgaattc ctgcagcccg ggggatccac tagttctaga atccgtcgaa    2340
```

-continued

```
actaagttct ggtgttttaa aactaaaaaa aagactaact ataaaagtag aatttaagaa   2400
gtttaagaaa tagatttaca gaattacaat caatacctac cgtctttata tacttattag   2460
tcaagtaggg gaataatttc agggaactgg tttcaacctt ttttttcagc tttttccaaa   2520
tcagagagag cagaaggtaa tagaaggtgt aagaaaatga gatagataca tgcgtgggtc   2580
aattgccttg tgtcatcatt tactccaggc aggttgcatc actccattga ggttgtgccc   2640
gtttttttgcc tgtttgtgcc cctgttctct gtagttgcgc taagagaatg gacctatgaa   2700
ctgatggttg gtgaagaaaa caatattttg gtgctgggat tctttttttt tctggatgcc   2760
agcttaaaaa gcgggctcca ttatatttag tggatgccag gaataaactg ttcacccaga   2820
cacctacgat gttatatatt ctgtgtaacc cgccccctat tttgggcatg tacgggttac   2880
agcagaatta aaaggctaat tttttgacta aataaagtta ggaaaatcac tactattaat   2940
tatttacgta ttctttgaaa tggcgagtat tgataatgat aaactgagct ccagcttttg   3000
ttccctttag tgagggttaa ttgcgcgctt ggcgtaatca tggtcatagc tgtttcctgt   3060
gtgaaattgt tatccgctca caattccaca caacatagga gccggaagca taaagtgtaa   3120
agcctggggt gcctaatgag tgaggtaact cacattaatt gcgttgcgct cactgcccgc   3180
tttccagtcg ggaaacctgt cgtgccagct gcattaatga atcggccaac gcgcggggag   3240
aggcggtttg cgtattgggc gctcttccgc ttcctcgctc actgactcgc tgcgctcggt   3300
cgttcggctg cggcgagcgg tatcagctca ctcaaaggcg gtaatacggt tatccacaga   3360
atcaggggat aacgcaggaa agaacatgtg agcaaaaggc cagcaaaagg ccaggaaccg   3420
taaaaaggcc gcgttgctgg cgtttttcca taggctccgc ccccctgacg agcatcacaa   3480
aaatcgacgc tcaagtcaga ggtggcgaaa cccgacagga ctataaagat accaggcgtt   3540
tccccctgga agctccctcg tgcgctctcc tgttccgacc ctgccgctta ccggatacct   3600
gtccgccttt ctcccttcgg gaagcgtggc gctttctcat agctcacgct gtaggtatct   3660
cagttcggtg taggtcgttc gctccaagct gggctgtgtg cacgaacccc ccgttcagcc   3720
cgaccgctgc gccttatccg gtaactatcg tcttgagtcc aacccggtaa gacacgactt   3780
atcgccactg gcagcagcca ctggtaacag gattagcaga gcgaggtatg taggcggtgc   3840
tacagagttc ttgaagtggt ggcctaacta cggctacact agaaggacag tatttggtat   3900
ctgcgctctg ctgaagccag ttaccttcgg aaaaagagtt ggtagctctt gatccggcaa   3960
acaaaccacc gctggtagcg gtggtttttt tgtttgcaag cagcagatta cgcgcagaaa   4020
aaaaggatct caagaagatc ctttgatctt ttctacgggg tctgacgctc agtggaacga   4080
aaactcacgt taagggattt tggtcatgag attatcaaaa aggatcttca cctagatcct   4140
tttaaattaa aaatgaagtt ttaaatcaat ctaaagtata tatgagtaaa cttggtctga   4200
cagttaccaa tgcttaatca gtgaggcacc tatctcagcg atctgtctat ttcgttcatc   4260
catagttgcc tgactccccg tcgtgtagat aactacgata cgggagggct taccatctgg   4320
ccccagtgct gcaatgatac cgcgagaccc acgctcaccg gctccagatt tatcagcaat   4380
aaaccagcca gccggaaggg ccgagcgcag aagtggtcct gcaactttat ccgcctccat   4440
ccagtctatt aattgttgcc gggaagctag agtaagtagt tcgccagtta atagtttgcg   4500
caacgttgtt gccattgcta caggcatcgt ggtgtcacgc tcgtcgtttg gtatggcttc   4560
attcagctcc ggttcccaac gatcaaggcg agttacatga tcccccatgt tgtgcaaaaa   4620
agcggttagc tccttcggtc ctccgatcgt tgtcagaagt aagttggccg cagtgttatc   4680
actcatggtt atggcagcac tgcataattc tcttactgtc atgccatccg taagatgctt   4740
```

```
ttctgtgact ggtgagtact caaccaagtc attctgagaa tagtgtatgc ggcgaccgag   4800

ttgctcttgc ccggcgtcaa tacgggataa taccgcgcca catagcagaa ctttaaaagt   4860

gctcatcatt ggaaaacgtt cttcggggcg aaaactctca aggatcttac cgctgttgag   4920

atccagttcg atgtaaccca ctcgtgcacc caactgatct tcagcatctt ttactttcac   4980

cagcgtttct gggtgagcaa aaacaggaag gcaaaatgcc gcaaaaaagg gaataagggc   5040

gacacggaaa tgttgaatac tcatactctt cctttttcaa tattattgaa gcatttatca   5100

gggttattgt ctcatgagcg gatacatatt tgaatgtatt tagaaaaata aacaaatagg   5160

ggttccgcgc acatttcccc gaaaagtgcc acctgggtcc ttttcatcac gtgctataaa   5220

aataattata atttaaattt tttaatataa atatataaat taaaaataga aagtaaaaaa   5280

agaaattaaa gaaaaaatag tttttgtttt ccgaagatgt aaaagactct agggggatcg   5340

ccaacaaata ctacctttta tcttgctctt cctgctctca ggtattaatg ccgaattgtt   5400

tcatcttgtc tgtgtagaag accacacacg aaaatcctgt gattttacat tttacttatc   5460

gttaatcgaa tgtatatcta tttaatctgc ttttcttgtc taataaatat atatgtaaag   5520

tacgcttttt gttgaaattt tttaaacctt tgtttatttt tttttcttca ttccgtaact   5580

cttctacctt ctttatttac tttctaaaat ccaaatacaa aacataaaaa taaataaaca   5640

cagagtaaat tcccaaatta ttccatcatt aaaagatacg aggcgcgtgt aagttacagg   5700

caagcgatcc gtcctaagaa accattatta tcatgacatt aacctataaa aataggcgta   5760

tcacgaggcc ctttcgtc                                                 5778
```

<210> SEQ ID NO 19
<211> LENGTH: 6362
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataccac agcttttcaa ttcaattcat catttttttt ttattctttt ttttgatttc    240

ggtttctttg aaattttttt gattcggtaa tctccgaaca gaaggaagaa cgaaggaagg    300

agcacagact tagattggta tatatacgca tatgtagtgt tgaagaaaca tgaaattgcc    360

cagtattctt aacccaactg cacagaacaa aaacctgcag gaaacgaaga taaatcatgt    420

cgaaagctac atataaggaa cgtgctgcta ctcatcctag tcctgttgct gccaagctat    480

ttaatatcat gcacgaaaag caaacaaact tgtgtgcttc attggatgtt cgtaccacca    540

aggaattact ggagttagtt gaagcattag gtcccaaaat ttgtttacta aaaacacatg    600

tggatatctt gactgatttt tccatggagg gcacagttaa gccgctaaag gcattatccg    660

ccaagtacaa tttttttactc ttcgaagaca gaaaatttgc tgacattggt aatacagtca    720

aattgcagta ctctgcgggt gtatacagaa tagcagaatg ggcagacatt acgaatgcac    780

acggtgtggt gggcccaggt attgttagcg gtttgaagca ggcggcagaa gaagtaacaa    840

aggaacctag aggccttttg atgttagcag aattgtcatg caagggctcc ctatctactg    900

gagaatatac taagggtact gttgacattg cgaagagcga caaagatttt gttatcggct    960

ttattgctca aagagacatg ggtggaagag atgaaggtta cgattggttg attatgacac   1020
```

```
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg gccgcaaatt aaagccttcg agcgtcccaa   2040
aaccttctca agcaaggttt tcagtataat gttacatgcg tacacgcgtc tgtacagaaa   2100
aaaaagaaaa atttgaaata taaataacgt tcttaatact aacataacta taaaaaaata   2160
aatagggacc tagacttcag gttgtctaac tccttccttt tcggttagag cggatgtggg   2220
gggagggcgt gaatgtaagc gtgacataac taattacatg actcgagcgg ccgcggatcc   2280
cgggaattcg tcgacacccg catagtcagg aacatcgtat gggtacatgc tagttctaga   2340
aaacttagat tagattgcta tgctttcttt ctaatgagca agaagtaaaa aaagttgtaa   2400
tagaacaaga aaaatgaaac tgaaacttga gaaattgaag accgtttatt aacttaaata   2460
tcaatgggag gtcatcgaaa gagaaaaaaa tcaaaaaaaa aattttcaag aaaaagaaac   2520
gtgataaaaa tttttattgc ctttttcgac gaagaaaaag aaacgaggcg gtctcttttt   2580
tcttttccaa acctttagta cgggtaatta acgacaccct agaggaagaa agaggggaaa   2640
tttagtatgc tgtgcttggg tgttttgaag tggtacggcg atgcgcggag tccgagaaaa   2700
tctggaagag taaaaaagga gtagaaacat tttgaagcta tgagctccag cttttgttcc   2760
ctttagtgag ggttaattgc gcgcttggcg taatcatggt catagctgtt tcctgtgtga   2820
aattgttatc cgctcacaat tccacacaac ataggagccg gaagcataaa gtgtaaagcc   2880
tggggtgcct aatgagtgag gtaactcaca ttaattgcgt tgcgctcact gcccgctttc   2940
cagtcgggaa acctgtcgtg ccagctgcat taatgaatcg gccaacgcgc ggggagaggc   3000
ggtttgcgta ttgggcgctc ttccgcttcc tcgctcactg actcgctgcg ctcggtcgtt   3060
cggctgcggc gagcggtatc agctcactca aaggcggtaa tacggttatc cacagaatca   3120
ggggataacg caggaaagaa catgtgagca aaaggccagc aaaaggccag gaaccgtaaa   3180
aaggccgcgt tgctggcgtt tttccatagg ctccgccccc ctgacgagca tcacaaaaat   3240
cgacgctcaa gtcagaggtg gcgaaacccg acaggactat aaagatacca ggcgtttccc   3300
cctggaagct ccctcgtgcg ctctcctgtt ccgaccctgc cgcttaccgg atacctgtcc   3360
gcctttctcc cttcgggaag cgtggcgctt tctcatagct cacgctgtag gtatctcagt   3420
```

```
tcggtgtagg tcgttcgctc caagctgggc tgtgtgcacg aaccccccgt tcagcccgac   3480
cgctgcgcct tatccggtaa ctatcgtctt gagtccaacc cggtaagaca cgacttatcg   3540
ccactggcag cagccactgg taacaggatt agcagagcga ggtatgtagg cggtgctaca   3600
gagttcttga agtggtggcc taactacggc tacactagaa ggacagtatt tggtatctgc   3660
gctctgctga agccagttac cttcggaaaa agagttggta gctcttgatc cggcaaacaa   3720
accaccgctg gtagcggtgg tttttttgtt tgcaagcagc agattacgcg cagaaaaaaa   3780
ggatctcaag aagatccttt gatcttttct acggggtctg acgctcagtg gaacgaaaac   3840
tcacgttaag ggattttggt catgagatta tcaaaaagga tcttcaccta gatcctttta   3900
aattaaaaat gaagttttaa atcaatctaa agtatatatg agtaaacttg gtctgacagt   3960
taccaatgct taatcagtga ggcacctatc tcagcgatct gtctatttcg ttcatccata   4020
gttgcctgac tccccgtcgt gtagataact acgatacggg agggcttacc atctggcccc   4080
agtgctgcaa tgataccgcg agacccacgc tcaccggctc cagatttatc agcaataaac   4140
cagccagccg gaagggccga gcgcagaagt ggtcctgcaa ctttatccgc ctccatccag   4200
tctattaatt gttgccggga agctagagta agtagttcgc cagttaatag tttgcgcaac   4260
gttgttgcca ttgctacagg catcgtggtg tcacgctcgt cgtttggtat ggcttcattc   4320
agctccggtt cccaacgatc aaggcgagtt acatgatccc ccatgttgtg caaaaaagcg   4380
gttagctcct tcggtcctcc gatcgttgtc agaagtaagt tggccgcagt gttatcactc   4440
atggttatgg cagcactgca taattctctt actgtcatgc catccgtaag atgcttttct   4500
gtgactggtg agtactcaac caagtcattc tgagaatagt gtatgcggcg accgagttgc   4560
tcttgcccgg cgtcaatacg ggataatacc gcgccacata gcagaacttt aaaagtgctc   4620
atcattggaa aacgttcttc ggggcgaaaa ctctcaagga tcttaccgct gttgagatcc   4680
agttcgatgt aacccactcg tgcacccaac tgatcttcag catcttttac tttcaccagc   4740
gtttctgggt gagcaaaaac aggaaggcaa aatgccgcaa aaaagggaat aagggcgaca   4800
cggaaatgtt gaatactcat actcttcctt tttcaatatt attgaagcat ttatcagggt   4860
tattgtctca tgagcggata catatttgaa tgtatttaga aaaataaaca aataggggtt   4920
ccgcgcacat ttccccgaaa agtgccacct gaacgaagca tctgtgcttc attttgtaga   4980
acaaaaatgc aacgcgagag cgctaatttt tcaaacaaag aatctgagct gcatttttac   5040
agaacagaaa tgcaacgcga aagcgctatt ttaccaacga agaatctgtg cttcattttt   5100
gtaaaacaaa aatgcaacgc gagagcgcta atttttcaaa caaagaatct gagctgcatt   5160
tttacagaac agaaatgcaa cgcgagagcg ctattttacc aacaaagaat ctatacttct   5220
tttttgttct acaaaaatgc atcccgagag cgctattttt ctaacaaagc atcttagatt   5280
actttttttc tcctttgtgc gctctataat gcagtctctt gataactttt tgcactgtag   5340
gtccgttaag gttagaagaa ggctactttg gtgtctattt tctcttccat aaaaaaagcc   5400
tgactccact tcccgcgttt actgattact agcgaagctg cgggtgcatt ttttcaagat   5460
aaaggcatcc ccgattatat tctataccga tgtggattgc gcatactttg tgaacagaaa   5520
gtgatagcgt tgatgattct tcattggtca gaaaattatg aacggtttct tctattttgt   5580
ctctatatac tacgtatagg aaatgtttac attttcgtat tgttttcgat tcactctatg   5640
aatagttctt actacaattt ttttgtctaa agagtaatac tagagataaa cataaaaaat   5700
gtagaggtcg agtttagatg caagttcaag gagcgaaagg tggatgggta ggttatatag   5760
ggatatagca cagagatata tagcaaagag atacttttga gcaatgtttg tggaagcggt   5820
```

```
attcgcaata ttttagtagc tcgttacagt ccggtgcgtt tttggttttt tgaaagtgcg   5880
tcttcagagc gcttttggtt ttcaaaagcg ctctgaagtt cctatacttt ctagagaata   5940
ggaacttcgg aataggaact tcaaagcgtt tccgaaaacg agcgcttccg aaaatgcaac   6000
gcgagctgcg cacatacagc tcactgttca cgtcgcacct atatctgcgt gttgcctgta   6060
tatatatata catgagaaga acggcatagt gcgtgtttat gcttaaatgc gtacttatat   6120
gcgtctattt atgtaggatg aaaggtagtc tagtacctcc tgtgatatta tcccattcca   6180
tgcggggtat cgtatgcttc cttcagcact accctttagc tgttctatat gctgccactc   6240
ctcaattgga ttagtctcat ccttcaatgc tatcatttcc tttgatattg gatcatacta   6300
agaaaccatt attatcatga cattaaccta taaaaatagg cgtatcacga ggccctttcg   6360
tc                                                                  6362
```

<210> SEQ ID NO 20
<211> LENGTH: 6690
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctctag tacactctat atttttttat gcctcggtaa tgattttcat    360
tttttttttt cccctagcgg atgactcttt ttttttctta gcgattggca ttatcacata    420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctaggg gccgtgcgtg    840
gagtaaaaag gtttggatca ggatttgcgc ctttggatga ggcactttcc agagcggtgg    900
tagatctttc gaacaggccg tacgcagttg tcgaacttgg tttgcaaagg gagaaagtag    960
gagatctctc ttgcgagatg atcccgcatt ttcttgaaag ctttgcagag gctagcagaa   1020
ttaccctcca cgttgattgt ctgcgaggca agaatgatca tcaccgtagt gagagtgcgt   1080
tcaaggctct tgcggttgcc ataagagaag ccacctcgcc caatggtacc aacgatgttc   1140
cctccaccaa aggtgttctt atgtagtgac accgattatt taaagctgca gcatacgata   1200
tatatacatg tgtatatatg tatacctatg aatgtcagta agtatgtata cgaacagtat   1260
gatactgaag atgacaaggt aatgcatcat tctatacgtg tcattctgaa cgaggcgcgc   1320
tttccttttt tctttttgct tttctttttt ttttctcttg aactcgacgg atctatgcgg   1380
tgtgaaatac cgcacagatg cgtaaggaga aaataccgca tcaggaaatt gtaaacgtta   1440
```

-continued

```
atattttgtt aaaattcgcg ttaaattttt gttaaatcag ctcatttttt aaccaatagg   1500
ccgaaatcgg caaaatccct tataaatcaa aagaatagac cgagataggg ttgagtgttg   1560
ttccagtttg gaacaagagt ccactattaa agaacgtgga ctccaacgtc aaagggcgaa   1620
aaaccgtcta tcagggcgat ggcccactac gtgaaccatc accctaatca agttttttgg   1680
ggtcgaggtg ccgtaaagca ctaaatcgga accctaaagg gagcccccga tttagagctt   1740
gacggggaaa gccggcgaac gtggcgagaa aggaagggaa gaaagcgaaa ggagcgggcg   1800
ctagggcgct ggcaagtgta gcggtcacgc tgcgcgtaac caccacaccc gccgcgctta   1860
atgcgccgct acagggcgcg tcgcgccatt cgccattcag gctgcgcaac tgttgggaag   1920
ggcgatcggt gcgggcctct tcgctattac gccagctggc gaaaggggga tgtgctgcaa   1980
ggcgattaag ttgggtaacg ccagggtttt cccagtcacg acgttgtaaa acgacggcca   2040
gtgagcgcgc gtaatacgac tcactatagg gcgaattggg taccggccgc aaattaaagc   2100
cttcgagcgt cccaaaacct tctcaagcaa ggttttcagt ataatgttac atgcgtacac   2160
gcgtctgtac agaaaaaaaa gaaaaatttg aaatataaat aacgttctta atactaacat   2220
aactataaaa aaataaatag ggacctagac ttcaggttgt ctaactcctt ccttttcggt   2280
tagagcggat gtgggggggag ggcgtgaatg taagcgtgac ataactaatt acatgactcg   2340
agcggccgcg gatcccggga attcgtcgac accatcttct tctgagatga gtttttgttc   2400
catgctagtt ctagaatccg tcgaaactaa gttctggtgt tttaaaacta aaaaaaagac   2460
taactataaa agtagaattt aagaagttta agaaatagat ttacagaatt acaatcaata   2520
cctaccgtct ttatatactt attagtcaag taggggaata atttcaggga actggtttca   2580
accttttttt tcagcttttt ccaaatcaga gagagcagaa ggtaatagaa ggtgtaagaa   2640
aatgagatag atacatgcgt gggtcaattg ccttgtgtca tcatttactc caggcaggtt   2700
gcatcactcc attgaggttg tgcccgtttt ttgcctgttt gtgcccctgt tctctgtagt   2760
tgcgctaaga gaatggacct atgaactgat ggttggtgaa gaaaacaata ttttggtgct   2820
gggattcttt ttttttctgg atgccagctt aaaaagcggg ctccattata tttagtggat   2880
gccaggaata aactgttcac ccagacacct acgatgttat atattctgtg taacccgccc   2940
cctattttgg gcatgtacgg gttacagcag aattaaaagg ctaatttttt gactaaataa   3000
agttaggaaa atcactacta ttaattattt acgtattctt tgaaatggcg agtattgata   3060
atgataaact gagctccagc ttttgttccc tttagtgagg gttaattgcg cgcttggcgt   3120
aatcatggtc atagctgttt cctgtgtgaa attgttatcc gctcacaatt ccacacaaca   3180
taggagccgg aagcataaag tgtaaagcct ggggtgccta atgagtgagg taactcacat   3240
taattgcgtt gcgctcactg cccgctttcc agtcgggaaa cctgtcgtgc cagctgcatt   3300
aatgaatcgg ccaacgcgcg gggagaggcg gtttgcgtat tgggcgctct tccgcttcct   3360
cgctcactga ctcgctgcgc tcggtcgttc ggctgcggcg agcggtatca gctcactcaa   3420
aggcggtaat acggttatcc acagaatcag gggataacgc aggaaagaac atgtgagcaa   3480
aaggccagca aaaggccagg aaccgtaaaa aggccgcgtt gctggcgttt ttccataggc   3540
tccgcccccc tgacgagcat cacaaaaatc gacgctcaag tcagaggtgg cgaaacccga   3600
caggactata aagataccag gcgtttcccc ctggaagctc cctcgtgcgc tctcctgttc   3660
cgaccctgcc gcttaccgga tacctgtccg cctttctccc ttcgggaagc gtggcgcttt   3720
ctcatagctc acgctgtagg tatctcagtt cggtgtaggt cgttcgctcc aagctgggct   3780
gtgtgcacga accccccgtt cagcccgacc gctgcgcctt atccggtaac tatcgtcttg   3840
```

```
agtccaaccc ggtaagacac gacttatcgc cactggcagc agccactggt aacaggatta   3900
gcagagcgag gtatgtaggc ggtgctacag agttcttgaa gtggtggcct aactacggct   3960
acactagaag gacagtattt ggtatctgcg ctctgctgaa gccagttacc ttcggaaaaa   4020
gagttggtag ctcttgatcc ggcaaacaaa ccaccgctgg tagcggtggt ttttttgttt   4080
gcaagcagca gattacgcgc agaaaaaaag gatctcaaga agatcctttg atcttttcta   4140
cggggtctga cgctcagtgg aacgaaaact cacgttaagg gattttggtc atgagattat   4200
caaaaaggat cttcacctag atccttttaa attaaaaatg aagttttaaa tcaatctaaa   4260
gtatatatga gtaaacttgg tctgacagtt accaatgctt aatcagtgag gcacctatct   4320
cagcgatctg tctatttcgt tcatccatag ttgcctgact ccccgtcgtg tagataacta   4380
cgatacggga gggcttacca tctggcccca gtgctgcaat gataccgcga gacccacgct   4440
caccggctcc agatttatca gcaataaacc agccagccgg aagggccgag cgcagaagtg   4500
gtcctgcaac tttatccgcc tccatccagt ctattaattg ttgccgggaa gctagagtaa   4560
gtagttcgcc agttaatagt ttgcgcaacg ttgttgccat tgctacaggc atcgtggtgt   4620
cacgctcgtc gtttggtatg gcttcattca gctccggttc ccaacgatca aggcgagtta   4680
catgatcccc catgttgtgc aaaaaagcgg ttagctcctt cggtcctccg atcgttgtca   4740
gaagtaagtt ggccgcagtg ttatcactca tggttatggc agcactgcat aattctctta   4800
ctgtcatgcc atccgtaaga tgcttttctg tgactggtga gtactcaacc aagtcattct   4860
gagaatagtg tatgcggcga ccgagttgct cttgcccggc gtcaatacgg gataataccg   4920
cgccacatag cagaacttta aaagtgctca tcattggaaa acgttcttcg gggcgaaaac   4980
tctcaaggat cttaccgctg ttgagatcca gttcgatgta acccactcgt gcacccaact   5040
gatcttcagc atcttttact ttcaccagcg tttctgggtg agcaaaaaca ggaaggcaaa   5100
atgccgcaaa aaagggaata agggcgacac ggaaatgttg aatactcata ctcttccttt   5160
ttcaatatta ttgaagcatt tatcagggtt attgtctcat gagcggatac atatttgaat   5220
gtatttagaa aaataaacaa ataggggttc cgcgcacatt tccccgaaaa gtgccacctg   5280
aacgaagcat ctgtgcttca ttttgtagaa caaaaatgca acgcgagagc gctaattttt   5340
caaacaaaga atctgagctg catttttaca gaacagaaat gcaacgcgaa agcgctattt   5400
taccaacgaa gaatctgtgc ttcatttttg taaaacaaaa atgcaacgcg agagcgctaa   5460
tttttcaaac aaagaatctg agctgcattt ttacagaaca gaaatgcaac gcgagagcgc   5520
tattttacca acaaagaatc tatacttctt ttttgttcta caaaaatgca tcccgagagc   5580
gctatttttc taacaaagca tcttagatta cttttttttct cctttgtgcg ctctataatg   5640
cagtctcttg ataacttttt gcactgtagg tccgttaagg ttagaagaag gctactttgg   5700
tgtctatttt ctcttccata aaaaaagcct gactccactt cccgcgttta ctgattacta   5760
gcgaagctgc gggtgcattt tttcaagata aaggcatccc cgattatatt ctataccgat   5820
gtggattgcg catactttgt gaacagaaag tgatagcgtt gatgattctt cattggtcag   5880
aaaattatga acggtttctt ctattttgtc tctatatact acgtatagga aatgtttaca   5940
ttttcgtatt gttttcgatt cactctatga atagttctta ctacaatttt tttgtctaaa   6000
gagtaatact agagataaac ataaaaaatg tagaggtcga gtttagatgc aagttcaagg   6060
agcgaaaggt ggatgggtag gttatatagg gatatagcac agagatatat agcaaagaga   6120
tacttttgag caatgtttgt ggaagcggta ttcgcaatat tttagtagct cgttacagtc   6180
cggtgcgttt ttggtttttt gaaagtgcgt cttcagagcg cttttggttt tcaaaagcgc   6240
```

```
tctgaagttc ctatactttc tagagaatag gaacttcgga ataggaactt caaagcgttt   6300

ccgaaaacga gcgcttccga aaatgcaacg cgagctgcgc acatacagct cactgttcac   6360

gtcgcaccta tatctgcgtg ttgcctgtat atatatatac atgagaagaa cggcatagtg   6420

cgtgtttatg cttaaatgcg tacttatatg cgtctattta tgtaggatga aaggtagtct   6480

agtacctcct gtgatattat cccattccat gcggggtatc gtatgcttcc ttcagcacta   6540

ccctttagct gttctatatg ctgccactcc tcaattggat tagtctcatc cttcaatgct   6600

atcatttcct ttgatattgg atcatctaag aaaccattat tatcatgaca ttaacctata   6660

aaaataggcg tatcacgagg ccctttcgtc                                     6690
```

<210> SEQ ID NO 21
<211> LENGTH: 6506
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataaacg acattactat atatataata taggaagcat ttaatagaca gcatcgtaat    240

atatgtgtac tttgcagtta tgacgccaga tggcagtagt ggaagatatt ctttattgaa    300

aaatagcttg tcaccttacg tacaatcttg atccggagct tttctttttt tgccgattaa    360

gaattaattc ggtcgaaaaa agaaaaggag agggccaaga gggagggcat tggtgactat    420

tgagcacgtg agtatacgtg attaagcaca caaaggcagc ttggagtatg tctgttatta    480

atttcacagg tagttctggt ccattggtga aagtttgcgg cttgcagagc acagaggccg    540

cagaatgtgc tctagattcc gatgctgact tgctgggtat tatatgtgtg cccaatagaa    600

agagaacaat tgacccggtt attgcaagga aaatttcaag tcttgtaaaa gcatataaaa    660

atagttcagg cactccgaaa tacttggttg gcgtgtttcg taatcaacct aaggaggatg    720

ttttggctct ggtcaatgat tacggcattg atatcgtcca actgcatgga gatgagtcgt    780

ggcaagaata ccaagagttc ctcggtttgc cagttattaa aagactcgta tttccaaaag    840

actgcaacat actactcagt gcagcttcac agaaacctca ttcgtttatt cccttgtttg    900

attcagaagc aggtgggaca ggtgaacttt tggattggaa ctcgatttct gactgggttg    960

gaaggcaaga gagccccgaa agcttacatt ttatgttagc tggtggactg acgccagaaa   1020

atgttggtga tgcgcttaga ttaaatggcg ttattggtgt tgatgtaagc ggaggtgtgg   1080

agacaaatgg tgtaaaagac tctaacaaaa tagcaaattt cgtcaaaaat gctaagaaat   1140

aggttattac tgagtagtat ttatttaagt attgtttgtg cacttgccta tgcggtgtga   1200

aataccgcac agatgcgtaa ggagaaaata ccgcatcagg aaattgtaaa cgttaatatt   1260

ttgttaaaat tcgcgttaaa tttttgttaa atcagctcat tttttaacca ataggccgaa   1320

atcggcaaaa tcccttataa atcaaaagaa tagaccgaga tagggttgag tgttgttcca   1380

gtttggaaca agagtccact attaaagaac gtggactcca acgtcaaagg gcgaaaaacc   1440

gtctatcagg gcgatggccc actacgtgaa ccatcaccct aatcaagttt tttggggtcg   1500

aggtgccgta aagcactaaa tcggaaccct aaagggagcc cccgatttag agcttgacgg   1560

ggaaagccgg cgaacgtggc gagaaaggaa gggaagaaag cgaaaggagc gggcgctagg   1620
```

```
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact atagggcgaa ttgggtaccg gccgcaaatt aaagccttcg   1920
agcgtcccaa aaccttctca agcaaggttt tcagtataat gttacatgcg tacacgcgtc   1980
tgtacagaaa aaaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgagcgg   2160
ccgcggatcc cgggaattcg tcgacaccat cttcttctga gatgagtttt tgttccatgc   2220
tagttctaga atccgtcgaa actaagttct ggtgttttaa aactaaaaaa aagactaact   2280
ataaaagtag aatttaagaa gtttaagaaa tagatttaca gaattacaat caatacctac   2340
cgtctttata tacttattag tcaagtaggg gaataatttc agggaactgg tttcaacctt   2400
ttttttcagc tttttccaaa tcagagagag cagaaggtaa tagaaggtgt aagaaaatga   2460
gatagataca tgcgtgggtc aattgccttg tgtcatcatt tactccaggc aggttgcatc   2520
actccattga ggttgtgccc gtttttttgcc tgtttgtgcc cctgttctct gtagttgcgc   2580
taagagaatg gacctatgaa ctgatggttg gtgaagaaaa caatattttg gtgctgggat   2640
tctttttttt tctggatgcc agcttaaaaa gcgggctcca ttatatttag tggatgccag   2700
gaataaactg ttcacccaga cacctacgat gttatatatt ctgtgtaacc cgccccctat   2760
tttgggcatg tacgggttac agcagaatta aaaggctaat tttttgacta aataaagtta   2820
ggaaaatcac tactattaat tatttacgta ttctttgaaa tggcgagtat tgataatgat   2880
aaactgagct ccagcttttg ttccctttag tgagggttaa ttgcgcgctt ggcgtaatca   2940
tggtcatagc tgtttcctgt gtgaaattgt tatccgctca caattccaca caacatagga   3000
gccggaagca taaagtgtaa agcctggggt gcctaatgag tgaggtaact cacattaatt   3060
gcgttgcgct cactgcccgc tttccagtcg ggaaacctgt cgtgccagct gcattaatga   3120
atcggccaac gcgcggggag aggcggtttg cgtattgggc gctcttccgc ttcctcgctc   3180
actgactcgc tgcgctcggt cgttcggctg cggcgagcgg tatcagctca ctcaaaggcg   3240
gtaatacggt tatccacaga atcaggggat aacgcaggaa agaacatgtg agcaaaaggc   3300
cagcaaaagg ccaggaaccg taaaaaggcc gcgttgctgg cgtttttcca taggctccgc   3360
ccccctgacg agcatcacaa aaatcgacgc tcaagtcaga ggtggcgaaa cccgacagga   3420
ctataaagat accaggcgtt tccccctgga agctccctcg tgcgctctcc tgttccgacc   3480
ctgccgctta ccggatacct gtccgccttt ctcccttcgg gaagcgtggc gctttctcat   3540
agctcacgct gtaggtatct cagttcggtg taggtcgttc gctccaagct gggctgtgtg   3600
cacgaacccc ccgttcagcc cgaccgctgc gccttatccg gtaactatcg tcttgagtcc   3660
aacccggtaa gacacgactt atcgccactg gcagcagcca ctggtaacag gattagcaga   3720
gcgaggtatg taggcggtgc tacagagttc ttgaagtggt ggcctaacta cggctacact   3780
agaaggacag tatttggtat ctgcgctctg ctgaagccag ttaccttcgg aaaaagagtt   3840
ggtagctctt gatccggcaa acaaaccacc gctggtagcg gtggtttttt tgtttgcaag   3900
cagcagatta cgcgcagaaa aaaaggatct caagaagatc ctttgatctt ttctacgggg   3960
tctgacgctc agtggaacga aaactcacgt taagggattt tggtcatgag attatcaaaa   4020
```

```
aggatcttca cctagatcct tttaaattaa aaatgaagtt ttaaatcaat ctaaagtata   4080
tatgagtaaa cttggtctga cagttaccaa tgcttaatca gtgaggcacc tatctcagcg   4140
atctgtctat ttcgttcatc catagttgcc tgactccccg tcgtgtagat aactacgata   4200
cgggagggct taccatctgg ccccagtgct gcaatgatac cgcgagaccc acgctcaccg   4260
gctccagatt tatcagcaat aaaccagcca gccggaaggg ccgagcgcag aagtggtcct   4320
gcaactttat ccgcctccat ccagtctatt aattgttgcc gggaagctag agtaagtagt   4380
tcgccagtta atagtttgcg caacgttgtt gccattgcta caggcatcgt ggtgtcacgc   4440
tcgtcgtttg gtatggcttc attcagctcc ggttcccaac gatcaaggcg agttacatga   4500
tcccccatgt tgtgcaaaaa agcggttagc tccttcggtc ctccgatcgt tgtcagaagt   4560
aagttggccg cagtgttatc actcatggtt atggcagcac tgcataattc tcttactgtc   4620
atgccatccg taagatgctt ttctgtgact ggtgagtact caaccaagtc attctgagaa   4680
tagtgtatgc ggcgaccgag ttgctcttgc ccggcgtcaa tacgggataa taccgcgcca   4740
catagcagaa ctttaaaagt gctcatcatt ggaaaacgtt cttcggggcg aaaactctca   4800
aggatcttac cgctgttgag atccagttcg atgtaaccca ctcgtgcacc caactgatct   4860
tcagcatctt ttactttcac cagcgtttct gggtgagcaa aaacaggaag gcaaaatgcc   4920
gcaaaaaagg gaataagggc gacacggaaa tgttgaatac tcatactctt cctttttcaa   4980
tattattgaa gcatttatca gggttattgt ctcatgagcg gatacatatt tgaatgtatt   5040
tagaaaaata aacaaatagg ggttccgcgc acatttcccc gaaaagtgcc acctgaacga   5100
agcatctgtg cttcatttg tagaacaaaa atgcaacgcg agagcgctaa tttttcaaac   5160
aaagaatctg agctgcattt ttacagaaca gaaatgcaac gcgaaagcgc tattttacca   5220
acgaagaatc tgtgcttcat ttttgtaaaa caaaaatgca acgcgagagc gctaattttt   5280
caaacaaaga atctgagctg catttttaca gaacagaaat gcaacgcgag agcgctattt   5340
taccaacaaa gaatctatac ttcttttttg ttctacaaaa atgcatcccg agagcgctat   5400
ttttctaaca aagcatctta gattactttt tttctccttt gtgcgctcta taatgcagtc   5460
tcttgataac tttttgcact gtaggtccgt taaggttaga agaaggctac tttggtgtct   5520
attttctctt ccataaaaaa agcctgactc cacttcccgc gtttactgat tactagcgaa   5580
gctgcgggtg catttttca agataaaggc atccccgatt atattctata ccgatgtgga   5640
ttgcgcatac tttgtgaaca gaaagtgata gcgttgatga ttcttcattg gtcagaaaat   5700
tatgaacggt ttcttctatt ttgtctctat atactacgta taggaaatgt ttacattttc   5760
gtattgtttt cgattcactc tatgaatagt tcttactaca atttttttgt ctaaagagta   5820
atactagaga taaacataaa aaatgtagag gtcgagttta gatgcaagtt caaggagcga   5880
aaggtggatg ggtaggttat atagggatat agcacagaga tatatagcaa agagatactt   5940
ttgagcaatg tttgtggaag cggtattcgc aatattttag tagctcgtta cagtccggtg   6000
cgtttttggt tttttgaaag tgcgtcttca gagcgctttt ggttttcaaa agcgctctga   6060
agttcctata ctttctagag aataggaact tcggaatagg aacttcaaag cgtttccgaa   6120
aacgagcgct tccgaaaatg caacgcgagc tgcgcacata cagctcactg ttcacgtcgc   6180
acctatatct gcgtgttgcc tgtatatata tatacatgag aagaacggca tagtgcgtgt   6240
ttatgcttaa atgcgtactt atatgcgtct atttatgtag gatgaaaggt agtctagtac   6300
ctcctgtgat attatcccat tccatgcggg gtatcgtatg cttccttcag cactaccctt   6360
tagctgttct atatgctgcc actcctcaat tggattagtc tcatccttca atgctatcat   6420
```

```
ttcctttgat attggatcat attaagaaac cattattatc atgacattaa cctataaaaa   6480

taggcgtatc acgaggccct ttcgtc                                         6506
```

<210> SEQ ID NO 22
<211> LENGTH: 6616
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataccac agcttttcaa ttcaattcat catttttttt ttattctttt ttttgatttc    240

ggtttctttg aaattttttt gattcggtaa tctccgaaca gaaggaagaa cgaaggaagg    300

agcacagact tagattggta tatatacgca tatgtagtgt tgaagaaaca tgaaattgcc    360

cagtattctt aacccaactg cacagaacaa aaacctgcag gaaacgaaga taaatcatgt    420

cgaaagctac atataaggaa cgtgctgcta ctcatcctag tcctgttgct gccaagctat    480

ttaatatcat gcacgaaaag caaacaaact tgtgtgcttc attggatgtt cgtaccacca    540

aggaattact ggagttagtt gaagcattag gtcccaaaat ttgtttacta aaaacacatg    600

tggatatctt gactgatttt tccatggagg gcacagttaa gccgctaaag gcattatccg    660

ccaagtacaa tttttttactc ttcgaagaca gaaaatttgc tgacattggt aatacagtca    720

aattgcagta ctctgcgggt gtatacagaa tagcagaatg ggcagacatt acgaatgcac    780

acggtgtggt gggcccaggt attgttagcg gtttgaagca ggcggcagaa gaagtaacaa    840

aggaacctag aggccttttg atgttagcag aattgtcatg caagggctcc ctatctactg    900

gagaatatac taagggtact gttgacattg cgaagagcga caaagatttt gttatcggct    960

ttattgctca aagagacatg ggtggaagag atgaaggtta cgattggttg attatgacac   1020

ccggtgtggg tttagatgac aagggagacg cattgggtca acagtataga accgtggatg   1080

atgtggtctc tacaggatct gacattatta ttgttggaag aggactattt gcaaagggaa   1140

gggatgctaa ggtagagggt gaacgttaca gaaaagcagg ctgggaagca tatttgagaa   1200

gatgcggcca gcaaaactaa aaaactgtat tataagtaaa tgcatgtata ctaaactcac   1260

aaattagagc ttcaatttaa ttatatcagt tattacccta tgcggtgtga aataccgcac   1320

agatgcgtaa ggagaaaata ccgcatcagg aaattgtaaa cgttaatatt ttgttaaaat   1380

tcgcgttaaa tttttgttaa atcagctcat tttttaacca ataggccgaa atcggcaaaa   1440

tcccttataa atcaaaagaa tagaccgaga tagggttgag tgttgttcca gtttggaaca   1500

agagtccact attaaagaac gtggactcca acgtcaaagg gcgaaaaacc gtctatcagg   1560

gcgatggccc actacgtgaa ccatcaccct aatcaagttt tttggggtcg aggtgccgta   1620

aagcactaaa tcggaaccct aaagggagcc cccgatttag agcttgacgg ggaaagccgg   1680

cgaacgtggc gagaaaggaa gggaagaaag cgaaaggagc gggcgctagg gcgctggcaa   1740

gtgtagcggt cacgctgcgc gtaaccacca cacccgccgc gcttaatgcg ccgctacagg   1800

gcgcgtcgcg ccattcgcca ttcaggctgc gcaactgttg ggaagggcga tcggtgcggg   1860

cctcttcgct attacgccag ctggcgaaag ggggatgtgc tgcaaggcga ttaagttggg   1920
```

```
taacgccagg gttttcccag tcacgacgtt gtaaaacgac ggccagtgag cgcgcgtaat   1980
acgactcact atagggcgaa ttgggtaccg gccgcaaatt aaagccttcg agcgtcccaa   2040
aaccttctca agcaaggttt tcagtataat gttacatgcg tacacgcgtc tgtacagaaa   2100
aaaaagaaaa atttgaaata taaataacgt tcttaatact aacataacta taaaaaaata   2160
aatagggacc tagacttcag gttgtctaac tccttccttt tcggttagag cggatgtggg   2220
gggagggcgt gaatgtaagc gtgacataac taattacatg actcgagcgg ccgcggatcc   2280
cgggaattcg tcgacaccat cttcttctga gatgagtttt tgttccatgc tagttctaga   2340
atccgtcgaa actaagttct ggtgttttaa aactaaaaaa aagactaact ataaaagtag   2400
aatttaagaa gtttaagaaa tagatttaca gaattacaat caatacctac cgtctttata   2460
tacttattag tcaagtaggg gaataatttc agggaactgg tttcaacctt ttttttcagc   2520
tttttccaaa tcagagagag cagaaggtaa tagaaggtgt aagaaaatga gatagataca   2580
tgcgtgggtc aattgccttg tgtcatcatt tactccaggc aggttgcatc actccattga   2640
ggttgtgccc gtttttgcc tgtttgtgcc cctgttctct gtagttgcgc taagagaatg   2700
gacctatgaa ctgatggttg gtgaagaaaa caatattttg gtgctgggat tctttttttt   2760
tctggatgcc agcttaaaaa gcgggctcca ttatatttag tggatgccag gaataaactg   2820
ttcacccaga cacctacgat gttatatatt ctgtgtaacc cgccccctat tttgggcatg   2880
tacgggttac agcagaatta aaaggctaat tttttgacta aataaagtta ggaaaatcac   2940
tactattaat tatttacgta ttctttgaaa tggcgagtat tgataatgat aaactgagct   3000
ccagcttttg ttccctttag tgagggttaa ttgcgcgctt ggcgtaatca tggtcatagc   3060
tgtttcctgt gtgaaattgt tatccgctca caattccaca caacatagga gccggaagca   3120
taaagtgtaa agcctggggt gcctaatgag tgaggtaact cacattaatt gcgttgcgct   3180
cactgcccgc tttccagtcg ggaaacctgt cgtgccagct gcattaatga atcggccaac   3240
gcgcggggag aggcggtttg cgtattgggc gctcttccgc ttcctcgctc actgactcgc   3300
tgcgctcggt cgttcggctg cggcgagcgg tatcagctca ctcaaaggcg gtaatacggt   3360
tatccacaga atcaggggat aacgcaggaa agaacatgtg agcaaaaggc cagcaaaagg   3420
ccaggaaccg taaaaaggcc gcgttgctgg cgtttttcca taggctccgc ccccctgacg   3480
agcatcacaa aaatcgacgc tcaagtcaga ggtggcgaaa cccgacagga ctataaagat   3540
accaggcgtt tccccctgga agctccctcg tgcgctctcc tgttccgacc ctgccgctta   3600
ccggatacct gtccgccttt ctcccttcgg gaagcgtggc gctttctcat agctcacgct   3660
gtaggtatct cagttcggtg taggtcgttc gctccaagct gggctgtgtg cacgaacccc   3720
ccgttcagcc cgaccgctgc gccttatccg gtaactatcg tcttgagtcc aacccggtaa   3780
gacacgactt atcgccactg gcagcagcca ctggtaacag gattagcaga gcgaggtatg   3840
taggcggtgc tacagagttc ttgaagtggt ggcctaacta cggctacact agaaggacag   3900
tatttggtat ctgcgctctg ctgaagccag ttaccttcgg aaaaagagtt ggtagctctt   3960
gatccggcaa acaaaccacc gctggtagcg gtggtttttt tgtttgcaag cagcagatta   4020
cgcgcagaaa aaaaggatct caagaagatc ctttgatctt ttctacgggg tctgacgctc   4080
agtggaacga aaactcacgt taagggattt tggtcatgag attatcaaaa aggatcttca   4140
cctagatcct tttaaattaa aaatgaagtt ttaaatcaat ctaaagtata tatgagtaaa   4200
cttggtctga cagttaccaa tgcttaatca gtgaggcacc tatctcagcg atctgtctat   4260
ttcgttcatc catagttgcc tgactccccg tcgtgtagat aactacgata cgggagggct   4320
```

-continued

```
taccatctgg ccccagtgct gcaatgatac cgcgagaccc acgctcaccg gctccagatt   4380
tatcagcaat aaaccagcca gccggaaggg ccgagcgcag aagtggtcct gcaactttat   4440
ccgcctccat ccagtctatt aattgttgcc gggaagctag agtaagtagt tcgccagtta   4500
atagtttgcg caacgttgtt gccattgcta caggcatcgt ggtgtcacgc tcgtcgtttg   4560
gtatggcttc attcagctcc ggttcccaac gatcaaggcg agttacatga tcccccatgt   4620
tgtgcaaaaa agcggttagc tccttcggtc ctccgatcgt tgtcagaagt aagttggccg   4680
cagtgttatc actcatggtt atggcagcac tgcataattc tcttactgtc atgccatccg   4740
taagatgctt ttctgtgact ggtgagtact caaccaagtc attctgagaa tagtgtatgc   4800
ggcgaccgag ttgctcttgc ccggcgtcaa tacgggataa taccgcgcca catagcagaa   4860
ctttaaaagt gctcatcatt ggaaaacgtt cttcggggcg aaaactctca aggatcttac   4920
cgctgttgag atccagttcg atgtaaccca ctcgtgcacc caactgatct tcagcatctt   4980
ttactttcac cagcgtttct gggtgagcaa aaacaggaag gcaaaatgcc gcaaaaaagg   5040
gaataagggc gacacggaaa tgttgaatac tcatactctt cctttttcaa tattattgaa   5100
gcatttatca gggttattgt ctcatgagcg gatacatatt tgaatgtatt tagaaaaata   5160
aacaaatagg ggttccgcgc acatttcccc gaaaagtgcc acctgaacga agcatctgtg   5220
cttcattttg tagaacaaaa atgcaacgcg agagcgctaa tttttcaaac aaagaatctg   5280
agctgcattt ttacagaaca gaaatgcaac gcgaaagcgc tattttacca acgaagaatc   5340
tgtgcttcat ttttgtaaaa caaaaatgca acgcgagagc gctaattttt caaacaaaga   5400
atctgagctg catttttaca gaacagaaat gcaacgcgag agcgctattt taccaacaaa   5460
gaatctatac ttcttttttg ttctacaaaa atgcatcccg agagcgctat ttttctaaca   5520
aagcatctta gattactttt tttctccttt gtgcgctcta taatgcagtc tcttgataac   5580
tttttgcact gtaggtccgt taaggttaga agaaggctac tttggtgtct attttctctt   5640
ccataaaaaa agcctgactc cacttcccgc gtttactgat tactagcgaa gctgcgggtg   5700
catttttca agataaaggc atccccgatt atattctata ccgatgtgga ttgcgcatac   5760
tttgtgaaca gaaagtgata gcgttgatga ttcttcattg gtcagaaaat tatgaacggt   5820
ttcttctatt ttgtctctat atactacgta taggaaatgt ttacattttc gtattgtttt   5880
cgattcactc tatgaatagt tcttactaca atttttttgt ctaaagagta atactagaga   5940
taaacataaa aaatgtagag gtcgagttta gatgcaagtt caaggagcga aaggtggatg   6000
ggtaggttat atagggatat agcacagaga tatatagcaa agagatactt ttgagcaatg   6060
tttgtggaag cggtattcgc aatattttag tagctcgtta cagtccggtg cgtttttggt   6120
tttttgaaag tgcgtcttca gagcgctttt ggttttcaaa agcgctctga agttcctata   6180
ctttctagag aataggaact tcggaatagg aacttcaaag cgtttccgaa aacgagcgct   6240
tccgaaaatg caacgcgagc tgcgcacata cagctcactg ttcacgtcgc acctatatct   6300
gcgtgttgcc tgtatatata tatacatgag aagaacggca tagtgcgtgt ttatgcttaa   6360
atgcgtactt atatgcgtct atttatgtag gatgaaaggt agtctagtac ctcctgtgat   6420
attatcccat tccatgcggg gtatcgtatg cttccttcag cactaccctt tagctgttct   6480
atatgctgcc actcctcaat tggattagtc tcatccttca atgctatcat ttcctttgat   6540
attggatcat actaagaaac cattattatc atgacattaa cctataaaaa taggcgtatc   6600
acgaggccct ttcgtc                                                    6616
```

<210> SEQ ID NO 23

<211> LENGTH: 7974
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataaacg acattactat atatataata taggaagcat ttaatagaca gcatcgtaat    240

atatgtgtac tttgcagtta tgacgccaga tggcagtagt ggaagatatt ctttattgaa    300

aaatagcttg tcaccttacg tacaatcttg atccggagct tttctttttt tgccgattaa    360

gaattaattc ggtcgaaaaa agaaaaggag agggccaaga gggagggcat tggtgactat    420

tgagcacgtg agtatacgtg attaagcaca caaaggcagc ttggagtatg tctgttatta    480

atttcacagg tagttctggt ccattggtga aagtttgcgg cttgcagagc acagaggccg    540

cagaatgtgc tctagattcc gatgctgact tgctgggtat tatatgtgtg cccaatagaa    600

agagaacaat tgacccggtt attgcaagga aaatttcaag tcttgtaaaa gcatataaaa    660

atagttcagg cactccgaaa tacttggttg gcgtgtttcg taatcaacct aaggaggatg    720

ttttggctct ggtcaatgat tacggcattg atatcgtcca actgcatgga gatgagtcgt    780

ggcaagaata ccaagagttc ctcggtttgc cagttattaa aagactcgta tttccaaaag    840

actgcaacat actactcagt gcagcttcac agaaacctca ttcgtttatt cccttgtttg    900

attcagaagc aggtgggaca ggtgaacttt tggattggaa ctcgatttct gactgggttg    960

gaaggcaaga gagccccgaa agcttacatt ttatgttagc tggtggactg acgccagaaa   1020

atgttggtga tgcgcttaga ttaaatggcg ttattggtgt tgatgtaagc ggaggtgtgg   1080

agacaaatgg tgtaaaagac tctaacaaaa tagcaaattt cgtcaaaaat gctaagaaat   1140

aggttattac tgagtagtat ttatttaagt attgtttgtg cacttgccta tgcggtgtga   1200

aataccgcac agatgcgtaa ggagaaaata ccgcatcagg aaattgtaaa cgttaatatt   1260

ttgttaaaat tcgcgttaaa tttttgttaa atcagctcat tttttaacca ataggccgaa   1320

atcggcaaaa tcccttataa atcaaaagaa tagaccgaga tagggttgag tgttgttcca   1380

gtttggaaca agagtccact attaaagaac gtggactcca acgtcaaagg gcgaaaaacc   1440

gtctatcagg gcgatggccc actacgtgaa ccatcaccct aatcaagttt tttggggtcg   1500

aggtgccgta aagcactaaa tcggaaccct aaagggagcc cccgatttag agcttgacgg   1560

ggaaagccgg cgaacgtggc gagaaaggaa gggaagaaag cgaaaggagc gggcgctagg   1620

gcgctggcaa gtgtagcggt cacgctgcgc gtaaccacca cacccgccgc gcttaatgcg   1680

ccgctacagg gcgcgtcgcg ccattcgcca ttcaggctgc gcaactgttg ggaagggcga   1740

tcggtgcggg cctcttcgct attacgccag ctggcgaaag ggggatgtgc tgcaaggcga   1800

ttaagttggg taacgccagg gttttcccag tcacgacgtt gtaaaacgac ggccagtgag   1860

cgcgcgtaat acgactcact atagggcgaa ttgggtaccg gccgcaaatt aaagccttcg   1920

agcgtcccaa aaccttctca agcaaggttt tcagtataat gttacatgcg tacacgcgtc   1980

tgtacagaaa aaaaagaaaa atttgaaata taaataacgt tcttaatact aacataacta   2040

taaaaaaata aatagggacc tagacttcag gttgtctaac tccttccttt tcggttagag   2100

cggatgtggg gggagggcgt gaatgtaagc gtgacataac taattacatg actcgagcgg   2160
```

```
ccgcggatcc ctagagagct ttcgttttca tgagttcccc gaattctttc ggaagcttgt   2220
cacttgctaa attaacgtta tcactgtagt caaccgggac atcaatgatg acaggcccct   2280
cagcgttcat gccttgacgc agaacatctg ccagctggtc tggtgattct acgcgtaagc   2340
cagttgctcc gaagctttcc gcgtatttca cgatatcgat atttccgaaa tcgaccgcag   2400
atgtacgatt atattttttc aattgctgga atgcaaccat gtcatatgtg ctgtcgttcc   2460
atacaatgtg tacaattggt gcttttaaac gaactgctgt ctctaattcc atagctgaga   2520
ataagaaacc gccatcaccg gagactgata ctacttttc tcccggtttc accaatgaag   2580
cgccgattgc ccaaggaagc gcaacgccga gtgtttgcat accgttacta atcattaatg   2640
ttaacggctc gtagctgcgg aaataacgtg acatccaaat cgcgtgtgaa ccgatatcgc   2700
aagtcactgt aacatgatca tcgactgcgt ttcgcaattc tttaacgatt tcaagaggat   2760
gcactctgtc tgatttccaa tctgcaggca cctgctcacc ctcatgcata tattgtttta   2820
aatcagaaag gatcttctgc tcacgttccg caaagtctac tttcacagca tcgtgttcga   2880
tatgattgat cgtagatgga atatcaccga tcagttcaag atccggctgg taagcatgat   2940
caatgtcagc cagaatctcg tctaaatgga tgatcgtccg gtctccattg acattccaga   3000
atttcggatc atattcaatt gggtcatagc cgattgtcag aacaacatca gcctgctcaa   3060
gcagcagatc gccaggctgg ttgcggaata aaccgatccg gccaaaatac tgatcctcta   3120
aatctctcgt aagagtaccg gcagcttgat atgtttcaac gaatggaagc tgcacttttt   3180
tcaatagctt gcgaaccgct ttaatcgctt ccggtcttcc gcccttcatg ccgactaaaa   3240
cgacaggaag ttttgctgtt tgaatttttg caatggccat actgattgcg tcatctgctg   3300
cgggaccaag ttttggcgct gcgacagcac gtacgttttt tgtatttgtg acttcattca   3360
caacatcttg cggaaaactc acaaaagcgg ccccagcctg ccctgctgac gctatcctaa   3420
acgcatttgt aacagcttcc ggtatatttt ttacatcttg aacttctaca ctgtattttg   3480
taatcggctg gaatagcgcc gcattatcca aagattgatg tgtccgtttt aaacgatctg   3540
cacggatcac gttcccagca agcgcaacga cagggtcacc ttcagtgttt gctgtcagca   3600
gtcctgttgc caagttcgaa gcacctggtc ctgatgtgac taacacgact cccggttttc   3660
cagttaaacg gccgactgct tgcgccataa atgctgcatt ttgttcatgc cgggcaacga   3720
taatttcagg cccctttatct tgtaaagcgt caaataccgc atcaattttt gcacctggaa   3780
tgccaaatac atgtgtgaca ccttgctccg ctaagcaatc aacaacaagc tccgcccctc   3840
tgcttttcac aagggatttt tgttcttttg ttgcttttgt caacatgtcg actttatgtg   3900
atgattgatt gattgattgt acagtttgtt tttcttaata tctatttcga tgacttctat   3960
atgatattgc actaacaaga agatattata atgcaattga tacaagacaa ggagttattt   4020
gcttctcttt tatatgattc tgacaatcca tattgcgttg gtagtctttt ttgctggaac   4080
ggttcagcgg aaaagacgca tcgctctttt tgcttctaga agaaatgcca gcaaaagaat   4140
ctcttgacag tgactgacag caaaaatgtc tttttctaac tagtaacaag gctaagatat   4200
cagcctgaaa taaagggtgg tgaagtaata attaaatcat ccgtataaac ctatacacat   4260
atatgaggaa aaataataca aaagtgtttt aaatacagat acatacatga acatatgcac   4320
gtatagcgcc caaatgtcgg taatgggatc ggcgagctcc agcttttgtt ccctttagtg   4380
agggttaatt gcgcgcttgg cgtaatcatg gtcatagctg tttcctgtgt gaaattgtta   4440
tccgctcaca attccacaca acataggagc cggaagcata aagtgtaaag cctggggtgc   4500
ctaatgagtg aggtaactca cattaattgc gttgcgctca ctgcccgctt tccagtcggg   4560
```

```
aaacctgtcg tgccagctgc attaatgaat cggccaacgc gcggggagag gcggtttgcg   4620
tattgggcgc tcttccgctt cctcgctcac tgactcgctg cgctcggtcg ttcggctgcg   4680
gcgagcggta tcagctcact caaaggcggt aatacggtta tccacagaat caggggataa   4740
cgcaggaaag aacatgtgag caaaaggcca gcaaaaggcc aggaaccgta aaaaggccgc   4800
gttgctggcg tttttccata ggctccgccc ccctgacgag catcacaaaa atcgacgctc   4860
aagtcagagg tggcgaaacc cgacaggact ataaagatac caggcgtttc cccctggaag   4920
ctccctcgtg cgctctcctg ttccgaccct gccgcttacc ggatacctgt ccgcctttct   4980
cccttcggga agcgtggcgc tttctcatag ctcacgctgt aggtatctca gttcggtgta   5040
ggtcgttcgc tccaagctgg gctgtgtgca cgaacccccc gttcagcccg accgctgcgc   5100
cttatccggt aactatcgtc ttgagtccaa cccggtaaga cacgacttat cgccactggc   5160
agcagccact ggtaacagga ttagcagagc gaggtatgta ggcggtgcta cagagttctt   5220
gaagtggtgg cctaactacg gctacactag aaggacagta tttggtatct gcgctctgct   5280
gaagccagtt accttcggaa aaagagttgg tagctcttga tccggcaaac aaaccaccgc   5340
tggtagcggt ggtttttttg tttgcaagca gcagattacg cgcagaaaaa aaggatctca   5400
agaagatcct ttgatctttt ctacggggtc tgacgctcag tggaacgaaa actcacgtta   5460
agggattttg gtcatgagat tatcaaaaag gatcttcacc tagatccttt taaattaaaa   5520
atgaagtttt aaatcaatct aaagtatata tgagtaaact tggtctgaca gttaccaatg   5580
cttaatcagt gaggcaccta tctcagcgat ctgtctattt cgttcatcca tagttgcctg   5640
actccccgtc gtgtagataa ctacgatacg ggagggctta ccatctggcc ccagtgctgc   5700
aatgataccg cgagacccac gctcaccggc tccagattta tcagcaataa accagccagc   5760
cggaagggcc gagcgcagaa gtggtcctgc aactttatcc gcctccatcc agtctattaa   5820
ttgttgccgg gaagctagag taagtagttc gccagttaat agtttgcgca acgttgttgc   5880
cattgctaca ggcatcgtgg tgtcacgctc gtcgtttggt atggcttcat tcagctccgg   5940
ttcccaacga tcaaggcgag ttacatgatc ccccatgttg tgcaaaaaag cggttagctc   6000
cttcggtcct ccgatcgttg tcagaagtaa gttggccgca gtgttatcac tcatggttat   6060
ggcagcactg cataattctc ttactgtcat gccatccgta agatgctttt ctgtgactgg   6120
tgagtactca accaagtcat tctgagaata gtgtatgcgg cgaccgagtt gctcttgccc   6180
ggcgtcaata cgggataata ccgcgccaca tagcagaact ttaaaagtgc tcatcattgg   6240
aaaacgttct tcggggcgaa aactctcaag gatcttaccg ctgttgagat ccagttcgat   6300
gtaacccact cgtgcaccca actgatcttc agcatctttt actttcacca gcgtttctgg   6360
gtgagcaaaa acaggaaggc aaaatgccgc aaaaaaggga ataagggcga cacggaaatg   6420
ttgaatactc atactcttcc tttttcaata ttattgaagc atttatcagg gttattgtct   6480
catgagcgga tacatatttg aatgtattta gaaaaataaa caaatagggg ttccgcgcac   6540
atttccccga aaagtgccac ctgaacgaag catctgtgct tcattttgta gaacaaaaat   6600
gcaacgcgag agcgctaatt tttcaaacaa agaatctgag ctgcattttt acagaacaga   6660
aatgcaacgc gaaagcgcta ttttaccaac gaagaatctg tgcttcattt ttgtaaaaca   6720
aaaatgcaac gcgagagcgc taatttttca aacaaagaat ctgagctgca tttttacaga   6780
acagaaatgc aacgcgagag cgctatttta ccaacaaaga atctatactt cttttttgtt   6840
ctacaaaaat gcatcccgag agcgctattt ttctaacaaa gcatcttaga ttactttttt   6900
tctcctttgt gcgctctata atgcagtctc ttgataactt tttgcactgt aggtccgtta   6960
```

aggttagaag aaggctactt tggtgtctat tttctcttcc ataaaaaaag cctgactcca 7020
cttcccgcgt ttactgatta ctagcgaagc tgcgggtgca ttttttcaag ataaaggcat 7080
ccccgattat attctatacc gatgtggatt gcgcatactt tgtgaacaga aagtgatagc 7140
gttgatgatt cttcattggt cagaaaatta tgaacggttt cttctatttt gtctctatat 7200
actacgtata ggaaatgttt acattttcgt attgttttcg attcactcta tgaatagttc 7260
ttactacaat ttttttgtct aaagagtaat actagagata aacataaaaa atgtagaggt 7320
cgagtttaga tgcaagttca aggagcgaaa ggtggatggg taggttatat agggatatag 7380
cacagagata tatagcaaag agatactttt gagcaatgtt tgtggaagcg gtattcgcaa 7440
tattttagta gctcgttaca gtccggtgcg tttttggttt tttgaaagtg cgtcttcaga 7500
gcgcttttgg ttttcaaaag cgctctgaag ttcctatact ttctagagaa taggaacttc 7560
ggaataggaa cttcaaagcg tttccgaaaa cgagcgcttc cgaaaatgca acgcgagctg 7620
cgcacataca gctcactgtt cacgtcgcac ctatatctgc gtgttgcctg tatatatata 7680
tacatgagaa gaacggcata gtgcgtgttt atgcttaaat gcgtacttat atgcgtctat 7740
ttatgtagga tgaaaggtag tctagtacct cctgtgatat tatcccattc catgcggggt 7800
atcgtatgct tccttcagca ctacccttta gctgttctat atgctgccac tcctcaattg 7860
gattagtctc atccttcaat gctatcattt cctttgatat tggatcatat taagaaacca 7920
ttattatcat gacattaacc tataaaaata ggcgtatcac gaggcccttt cgtc 7974

<210> SEQ ID NO 24
<211> LENGTH: 9692
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24
ttggatcata ctaagaaacc attattatca tgacattaac ctataaaaat aggcgtatca 60
cgaggccctt tcgtctcgcg cgtttcggtg atgacggtga aaacctctga cacatgcagc 120
tcccggagac ggtcacagct tgtctgtaag cggatgccgg gagcagacaa gcccgtcagg 180
gcgcgtcagc gggtgttggc gggtgtcggg gctggcttaa ctatgcggca tcagagcaga 240
ttgtactgag agtgcaccat accacagctt ttcaattcaa ttcatcattt ttttttatt 300 ctttttttg atttcggttt ctttgaaatt tttttgattc ggtaatctcc gaacagaagg 360
aagaacgaag gaaggagcac agacttagat tggtatatat acgcatatgt agtgttgaag 420
aaacatgaaa ttgcccagta ttcttaaccc aactgcacag aacaaaaacc tgcaggaaac 480
gaagataaat catgtcgaaa gctacatata aggaacgtgc tgctactcat cctagtcctg 540
ttgctgccaa gctatttaat atcatgcacg aaaagcaaac aaacttgtgt gcttcattgg 600
atgttcgtac caccaaggaa ttactggagt tagttgaagc attaggtccc aaaatttgtt 660
tactaaaaac acatgtggat atcttgactg atttttccat ggagggcaca gttaagccgc 720
taaaggcatt atccgccaag tacaattttt tactcttcga agacagaaaa tttgctgaca 780
ttggtaatac agtcaaattg cagtactctg cgggtgtata cagaatagca gaatgggcag 840
acattacgaa tgcacacggt gtggtgggcc caggtattgt tagcggtttg aagcaggcgg 900
cagaagaagt aacaaaggaa cctagaggcc ttttgatgtt agcagaattg tcatgcaagg 960
gctccctatc tactggagaa tatactaagg gtactgttga cattgcgaag agcgacaaag 1020

-continued atttgttat cggctttatt gctcaaagag acatgggtgg aagagatgaa ggttacgatt 1080
ggttgattat gacacccggt gtgggtttag atgacaaggg agacgcattg ggtcaacagt 1140
atagaaccgt ggatgatgtg gtctctacag gatctgacat tattattgtt ggaagaggac 1200
tatttgcaaa gggaagggat gctaaggtag agggtgaacg ttacagaaaa gcaggctggg 1260
aagcatattt gagaagatgc ggccagcaaa actaaaaaac tgtattataa gtaaatgcat 1320
gtatactaaa ctcacaaatt agagcttcaa tttaattata tcagttatta ccctatgcgg 1380
tgtgaaatac cgcacagatg cgtaaggaga aaataccgca tcaggaaatt gtaaacgtta 1440
atattttgtt aaaattcgcg ttaaattttt gttaaatcag ctcatttttt aaccaatagg 1500
ccgaaatcgg caaaatccct tataaatcaa aagaatagac cgagataggg ttgagtgttg 1560
ttccagtttg gaacaagagt ccactattaa agaacgtgga ctccaacgtc aaagggcgaa 1620
aaaccgtcta tcagggcgat ggcccactac gtgaaccatc accctaatca agttttttgg 1680
ggtcgaggtg ccgtaaagca ctaaatcgga accctaaagg gagcccccga tttagagctt 1740
gacggggaaa gccggcgaac gtggcgagaa aggaagggaa gaaagcgaaa ggagcgggcg 1800
ctagggcgct ggcaagtgta gcggtcacgc tgcgcgtaac caccacaccc gccgcgctta 1860
atgcgccgct acagggcgcg tcgcgccatt cgccattcag gctgcgcaac tgttgggaag 1920
ggcgatcggt gcgggcctct tcgctattac gccagctggc gaaaggggga tgtgctgcaa 1980
ggcgattaag ttgggtaacg ccagggtttt cccagtcacg acgttgtaaa acgacggcca 2040
gtgagcgcgc gtaatacgac tcactatagg gcgaattggg taccggccgc aaattaaagc 2100
cttcgagcgt cccaaaacct tctcaagcaa ggttttcagt ataatgttac atgcgtacac 2160
gcgtctgtac agaaaaaaaa gaaaaatttg aaatataaat aacgttctta atactaacat 2220
aactataaaa aaataaatag ggacctagac ttcaggttgt ctaactcctt ccttttcggt 2280
tagagcggat gtgggggag ggcgtgaatg taagcgtgac ataactaatt acatgagcgg 2340
ccgcctattt atggaatttc ttatcataat cgaccaaagt aaatctgtat ttgacgtctc 2400
cgctttccat ccttgtaaag gcatggctga cgccttcttc gctgatcgga agtttttcca 2460
cccatatttt gacattcttt tcggaaacta atttcaatag ttgttcgatt tccttcctag 2520
atccgatagc actgcttgag attgatactc ccattaggcc caacggtttt aaaacaagct 2580
tttcattaac ttcaggagca gcaattgaaa cgatggagcc tccaatcttc ataatcttaa 2640
cgatactgtc aaaattaact ttcgacaaag atgatgagca aacgacaaga aggtccaaag 2700
cgttagagta ttgttctgtc cagcctttat cctccaacat agcaatatag tgatcagcac 2760
cgagtttcat agaatcctcc cgcttggagt ggcctcgcga aaacgcataa acctcggctc 2820
ccatagcttt agccaacaga atccccatat gcccaatacc accgatgcca acaataccta 2880
ccctcttacc tggaccacag ccatttctta gtagtggaga gaaaactgta ataccaccac 2940
acaataatgg agcggctagc ggacttggaa tattttctgg tatttgaata gcaaagtgtt 3000
catgaagcct cacgtgggag gcaaagcctc cttgtgaaat gtagccgtcc ttgtaaggag 3060
tccacatagt caaaacgtgg tcattggtac agtattgctc gttgtcactt ttgcaacgtt 3120
cacactcaaa acacgccaag gcttgggcac caacaccaac acggtcaccg atttttaccc 3180
cagtgtggca cttggatcca accttcacca cgcggccaat tatttcatgt ccaaggattt 3240
gattttctgg gactggaccc caattaccaa cggctatatg aaaatcagat ccgcagatac 3300
cacaggcttc aatttcaaca tcaacgtcat gatcgccaaa gggttttggg tcaaaactca 3360
ctaatttagg atgcttccaa tcctttgcgt tggaaatacc gatgccctga aatttttctg 3420

-continued

```
ggtaaagcat gtcgagtcga aactaagttc tggtgtttta aaactaaaaa aaagactaac   3480
tataaaagta gaatttaaga agtttaagaa atagatttac agaattacaa tcaataccta   3540
ccgtctttat atacttatta gtcaagtagg ggaataattt cagggaactg gtttcaacct   3600
tttttttcag ctttttccaa atcagagaga gcagaaggta atagaaggtg taagaaaatg   3660
agatagatac atgcgtgggt caattgcctt gtgtcatcat ttactccagg caggttgcat   3720
cactccattg aggttgtgcc cgtttttttgc ctgtttgtgc ccctgttctc tgtagttgcg   3780
ctaagagaat ggacctatga actgatggtt ggtgaagaaa acaatatttt ggtgctggga   3840
ttcttttttt ttctggatgc cagcttaaaa agcgggctcc attatattta gtggatgcca   3900
ggaataaact gttcacccag acacctacga tgttatatat tctgtgtaac ccgcccccta   3960
ttttgggcat gtacgggtta cagcagaatt aaaaggctaa ttttttgact aaataaagtt   4020
aggaaaatca ctactattaa ttatttacgt attctttgaa atggcgagta ttgataatga   4080
taaactggat ccttaggatt tattctgttc agcaaacagc ttgcccattt tcttcagtac   4140
cttcggtgcg ccttctttcg ccaggatcag ttcgatccag tacatacggt tcggatcggc   4200
ctgggcctct ttcatcacgc tcacaaattc gttttcggta cgcacaattt tagacacaac   4260
acggtcctca gttgcgccga aggactccgg cagtttagag tagttccaca tagggatatc   4320
gttgtaagac tggttcggac cgtggatctc acgctcaacg gtgtagccgt cattgttaat   4380
aatgaagcaa atcgggttga tcttttcacg aattgccaga cccagttcct gtacggtcag   4440
ctgcagggaa ccgtcaccga tgaacagcag atgacgagat tctttatcag cgatctgaga   4500
gcccagcgct gccgggaaag tatagccaat gctaccccac agcggctgac cgataaaatg   4560
gcttttggat ttcagaaaga tagaagacgc gccgaaaaag ctcgtacctt gttccgccac   4620
gatggtttca ttgctctggg tcaggttctc cacggcctgc cacaggcgat cctgggacag   4680
cagtgcgtta gatggtacga aatcttcttg ctttttgtca atgtatttgc ctttatactc   4740
gatttcggac aggtccagca gagagctgat caggctttcg aagtcgaagt tctggatacg   4800
ctcgttgaag attttaccct cgtcgatgtt caggctaatc attttgtttt cgttcagatg   4860
gtgagtgaat gcaccggtag aagagtcggt cagtttaacg cccagcatca ggatgaagtc   4920
cgcagattca acaaattctt tcaggttcgg ttcgctcaga gtaccgttgt agatgcccag   4980
gaaagacggc agagcctcgt caacagagga cttgccgaag ttcagggtgg taatcggcag   5040
tttggttttg ctgatgaatt gggtcacggt cttctccaga ccaaaagaaa tgatttcgtg   5100
gccggtgatc acgattggtt tctttgcgtt tttcagagac tcctggattt tgttcaggat   5160
ttcctggtcg ctagtgttag aagtggagtt ttctttcttc agcggcaggc tcggtttttc   5220
cgctttagct gccgcaacat ccacaggcag gttgatgtaa actggtttgc gttctttcag   5280
cagcgcagac agaacgcggt cgatttccac agtagcgttc tctgcagtca gcagcgtacg   5340
tgccgcagtc acaggttcat gcattttcat gaagtgtttg aaatcgccgt cagccagagt   5400
gtggtggacg aatttacctt cgttctgaac tttgctcgtt gggctgccta cgatctccac   5460
caccggcagg ttttcggcgt aggagcccgc cagaccgttg acggcgctca gttcgccaac   5520
accgaaagtg gtcagaaatg ccgcggcttt cttggtacgt gcataaccat ctgccatgta   5580
gcttgcgttc agttcgttag cgttacccac ccatttcatg tctttatgag agatgatctg   5640
atccaggaac tgcagattgt aatcacccgg aacgccgaag atttcttcga tacccagttc   5700
atgcagacgg tccagcagat aatcaccaac agtatacatg tcgacaaact tagattagat   5760
tgctatgctt tctttctaat gagcaagaag taaaaaaagt tgtaatagaa caagaaaaat   5820
```

```
gaaactgaaa cttgagaaat tgaagaccgt ttattaactt aaatatcaat gggaggtcat   5880

cgaaagagaa aaaaatcaaa aaaaaaattt tcaagaaaaa gaaacgtgat aaaaattttt   5940

attgcctttt tcgacgaaga aaaagaaacg aggcggtctc ttttttcttt tccaaacctt   6000

tagtacgggt aattaacgac accctagagg aagaaagagg ggaaatttag tatgctgtgc   6060

ttgggtgttt tgaagtggta cggcgatgcg cggagtccga gaaaatctgg aagagtaaaa   6120

aaggagtaga aacattttga agctatgagc tccagctttt gttcccttta gtgagggtta   6180

attgcgcgct tggcgtaatc atggtcatag ctgtttcctg tgtgaaattg ttatccgctc   6240

acaattccac acaacatagg agccggaagc ataaagtgta aagcctgggg tgcctaatga   6300

gtgaggtaac tcacattaat tgcgttgcgc tcactgcccg ctttccagtc gggaaacctg   6360

tcgtgccagc tgcattaatg aatcggccaa cgcgcgggga gaggcggttt gcgtattggg   6420

cgctcttccg cttcctcgct cactgactcg ctgcgctcgg tcgttcggct gcggcgagcg   6480

gtatcagctc actcaaaggc ggtaatacgg ttatccacag aatcagggga taacgcagga   6540

aagaacatgt gagcaaaagg ccagcaaaag gccaggaacc gtaaaaaggc cgcgttgctg   6600

gcgtttttcc ataggctccg cccccctgac gagcatcaca aaaatcgacg ctcaagtcag   6660

aggtggcgaa acccgacagg actataaaga taccaggcgt ttccccctgg aagctccctc   6720

gtgcgctctc ctgttccgac cctgccgctt accggatacc tgtccgcctt tctcccttcg   6780

ggaagcgtgg cgctttctca tagctcacgc tgtaggtatc tcagttcggt gtaggtcgtt   6840

cgctccaagc tgggctgtgt gcacgaaccc cccgttcagc ccgaccgctg cgccttatcc   6900

ggtaactatc gtcttgagtc caacccggta agacacgact tatcgccact ggcagcagcc   6960

actggtaaca ggattagcag agcgaggtat gtaggcggtg ctacagagtt cttgaagtgg   7020

tggcctaact acggctacac tagaaggaca gtatttggta tctgcgctct gctgaagcca   7080

gttaccttcg gaaaaagagt tggtagctct tgatccggca aacaaaccac cgctggtagc   7140

ggtggttttt ttgtttgcaa gcagcagatt acgcgcagaa aaaaaggatc tcaagaagat   7200

cctttgatct tttctacggg gtctgacgct cagtggaacg aaaactcacg ttaagggatt   7260

ttggtcatga gattatcaaa aaggatcttc acctagatcc ttttaaatta aaaatgaagt   7320

tttaaatcaa tctaaagtat atatgagtaa acttggtctg acagttacca atgcttaatc   7380

agtgaggcac ctatctcagc gatctgtcta tttcgttcat ccatagttgc ctgactcccc   7440

gtcgtgtaga taactacgat acgggagggc ttaccatctg gccccagtgc tgcaatgata   7500

ccgcgagacc cacgctcacc ggctccagat ttatcagcaa taaaccagcc agccggaagg   7560

gccgagcgca gaagtggtcc tgcaacttta tccgcctcca tccagtctat taattgttgc   7620

cgggaagcta gagtaagtag ttcgccagtt aatagtttgc gcaacgttgt tgccattgct   7680

acaggcatcg tggtgtcacg ctcgtcgttt ggtatggctt cattcagctc cggttcccaa   7740

cgatcaaggc gagttacatg atcccccatg ttgtgcaaaa aagcggttag ctccttcggt   7800

cctccgatcg ttgtcagaag taagttggcc gcagtgttat cactcatggt tatggcagca   7860

ctgcataatt ctcttactgt catgccatcc gtaagatgct tttctgtgac tggtgagtac   7920

tcaaccaagt cattctgaga atagtgtatg cggcgaccga gttgctcttg cccggcgtca   7980

atacgggata ataccgcgcc acatagcaga actttaaaag tgctcatcat tggaaaacgt   8040

tcttcggggc gaaaactctc aaggatctta ccgctgttga gatccagttc gatgtaaccc   8100

actcgtgcac ccaactgatc ttcagcatct tttactttca ccagcgtttc tgggtgagca   8160

aaaacaggaa ggcaaaatgc cgcaaaaaag ggaataaggg cgacacggaa atgttgaata   8220
```

```
ctcatactct tcctttttca atattattga agcatttatc agggttattg tctcatgagc   8280

ggatacatat ttgaatgtat ttagaaaaat aaacaaatag gggttccgcg cacatttccc   8340

cgaaaagtgc cacctgaacg aagcatctgt gcttcatttt gtagaacaaa aatgcaacgc   8400

gagagcgcta atttttcaaa caaagaatct gagctgcatt tttacagaac agaaatgcaa   8460

cgcgaaagcg ctattttacc aacgaagaat ctgtgcttca tttttgtaaa acaaaaatgc   8520

aacgcgagag cgctaatttt tcaaacaaag aatctgagct gcatttttac agaacagaaa   8580

tgcaacgcga gagcgctatt ttaccaacaa agaatctata cttctttttt gttctacaaa   8640

aatgcatccc gagagcgcta tttttctaac aaagcatctt agattacttt ttttctcctt   8700

tgtgcgctct ataatgcagt ctcttgataa ctttttgcac tgtaggtccg ttaaggttag   8760

aagaaggcta ctttggtgtc tattttctct tccataaaaa aagcctgact ccacttcccg   8820

cgtttactga ttactagcga agctgcgggt gcattttttc aagataaagg catccccgat   8880

tatattctat accgatgtgg attgcgcata ctttgtgaac agaaagtgat agcgttgatg   8940

attcttcatt ggtcagaaaa ttatgaacgg tttcttctat tttgtctcta tatactacgt   9000

ataggaaatg tttacatttt cgtattgttt tcgattcact ctatgaatag ttcttactac   9060

aatttttttg tctaaagagt aatactagag ataaacataa aaaatgtaga ggtcgagttt   9120

agatgcaagt tcaaggagcg aaaggtggat gggtaggtta tatagggata tagcacagag   9180

atatatagca aagagatact tttgagcaat gtttgtggaa gcggtattcg caatatttta   9240

gtagctcgtt acagtccggt gcgtttttgg tttttttgaaa gtgcgtcttc agagcgcttt   9300

tggttttcaa aagcgctctg aagttcctat actttctaga gaataggaac ttcggaatag   9360

gaacttcaaa gcgtttccga aaacgagcgc ttccgaaaat gcaacgcgag ctgcgcacat   9420

acagctcact gttcacgtcg cacctatatc tgcgtgttgc ctgtatatat atatacatga   9480

gaagaacggc atagtgcgtg tttatgctta aatgcgtact tatatgcgtc tatttatgta   9540

ggatgaaagg tagtctagta cctcctgtga tattatccca ttccatgcgg ggtatcgtat   9600

gcttccttca gcactaccct ttagctgttc tatatgctgc cactcctcaa ttggattagt   9660

ctcatccttc aatgctatca tttcctttga ta                                 9692
```

<210> SEQ ID NO 25
<211> LENGTH: 5439
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataaacg acattactat atatataata taggaagcat ttaatagaca gcatcgtaat    240

atatgtgtac tttgcagtta tgacgccaga tggcagtagt ggaagatatt ctttattgaa    300

aaatagcttg tcaccttacg tacaatcttg atccggagct tttctttttt tgccgattaa    360

gaattaattc ggtcgaaaaa agaaaaggag agggccaaga gggagggcat tggtgactat    420

tgagcacgtg agtatacgtg attaagcaca caaaggcagc ttggagtatg tctgttatta    480

atttcacagg tagttctggt ccattggtga aagtttgcgg cttgcagagc acagaggccg    540

cagaatgtgc tctagattcc gatgctgact tgctgggtat tatatgtgtg cccaatagaa    600
```

```
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact atagggcgaa ttgggtaccg gccgcaaatt aaagccttcg   1920
agcgtcccaa aaccttctca agcaaggttt tcagtataat gttacatgcg tacacgcgtc   1980
tgtacagaaa aaaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgagcgg   2160
ccgcggatcc cgggaattcg tcgactttat gtgatgattg attgattgat tgtacagttt   2220
gtttttctta atatctattt cgatgacttc tatatgatat tgcactaaca agaagatatt   2280
ataatgcaat tgatacaaga caaggagtta tttgcttctc ttttatatga ttctgacaat   2340
ccatattgcg ttggtagtct tttttgctgg aacggttcag cggaaaagac gcatcgctct   2400
ttttgcttct agaagaaatg ccagcaaaag aatctcttga cagtgactga cagcaaaaat   2460
gtctttttct aactagtaac aaggctaaga tatcagcctg aaataaaggg tggtgaagta   2520
ataattaaat catccgtata aacctataca catatatgag gaaaaataat acaaaagtgt   2580
tttaaataca gatacataca tgaacatatg cacgtatagc gcccaaatgt cggtaatggg   2640
atcggcgagc tccagctttt gttcccttta gtgagggtta attgcgcgct tggcgtaatc   2700
atggtcatag ctgtttcctg tgtgaaattg ttatccgctc acaattccac acaacatagg   2760
agccggaagc ataaagtgta aagcctgggg tgcctaatga gtgaggtaac tcacattaat   2820
tgcgttgcgc tcactgcccg ctttccagtc gggaaacctg tcgtgccagc tgcattaatg   2880
aatcggccaa cgcgcgggga gaggcggttt gcgtattggg cgctcttccg cttcctcgct   2940
cactgactcg ctgcgctcgg tcgttcggct gcggcgagcg gtatcagctc actcaaaggc   3000
```

```
ggtaatacgg ttatccacag aatcagggga taacgcagga aagaacatgt gagcaaaagg   3060
ccagcaaaag gccaggaacc gtaaaaaggc cgcgttgctg gcgtttttcc ataggctccg   3120
cccccctgac gagcatcaca aaaatcgacg ctcaagtcag aggtggcgaa acccgacagg   3180
actataaaga taccaggcgt ttccccctgg aagctccctc gtgcgctctc ctgttccgac   3240
cctgccgctt accggatacc tgtccgcctt tctcccttcg ggaagcgtgg cgctttctca   3300
tagctcacgc tgtaggtatc tcagttcggt gtaggtcgtt cgctccaagc tgggctgtgt   3360
gcacgaaccc cccgttcagc ccgaccgctg cgccttatcc ggtaactatc gtcttgagtc   3420
caacccggta agacacgact tatcgccact ggcagcagcc actggtaaca ggattagcag   3480
agcgaggtat gtaggcggtg ctacagagtt cttgaagtgg tggcctaact acggctacac   3540
tagaaggaca gtatttggta tctgcgctct gctgaagcca gttaccttcg gaaaaagagt   3600
tggtagctct tgatccggca aacaaaccac cgctggtagc ggtggttttt ttgtttgcaa   3660
gcagcagatt acgcgcagaa aaaaaggatc tcaagaagat cctttgatct tttctacggg   3720
gtctgacgct cagtggaacg aaaactcacg ttaagggatt ttggtcatga gattatcaaa   3780
aaggatcttc acctagatcc ttttaaatta aaaatgaagt tttaaatcaa tctaaagtat   3840
atatgagtaa acttggtctg acagttacca atgcttaatc agtgaggcac ctatctcagc   3900
gatctgtcta tttcgttcat ccatagttgc ctgactcccc gtcgtgtaga taactacgat   3960
acgggagggc ttaccatctg gccccagtgc tgcaatgata ccgcgagacc cacgctcacc   4020
ggctccagat ttatcagcaa taaaccagcc agccggaagg gccgagcgca gaagtggtcc   4080
tgcaacttta tccgcctcca tccagtctat taattgttgc cgggaagcta gagtaagtag   4140
ttcgccagtt aatagtttgc gcaacgttgt tgccattgct acaggcatcg tggtgtcacg   4200
ctcgtcgttt ggtatggctt cattcagctc cggttcccaa cgatcaaggc gagttacatg   4260
atcccccatg ttgtgcaaaa aagcggttag ctccttcggt cctccgatcg ttgtcagaag   4320
taagttggcc gcagtgttat cactcatggt tatggcagca ctgcataatt ctcttactgt   4380
catgccatcc gtaagatgct tttctgtgac tggtgagtac tcaaccaagt cattctgaga   4440
atagtgtatg cggcgaccga gttgctcttg cccggcgtca atacgggata ataccgcgcc   4500
acatagcaga actttaaaag tgctcatcat tggaaaacgt tcttcggggc gaaaactctc   4560
aaggatctta ccgctgttga gatccagttc gatgtaaccc actcgtgcac ccaactgatc   4620
ttcagcatct tttactttca ccagcgtttc tgggtgagca aaaacaggaa ggcaaaatgc   4680
cgcaaaaaag ggaataaggg cgacacggaa atgttgaata ctcatactct tcctttttca   4740
atattattga agcatttatc agggttattg tctcatgagc ggatacatat ttgaatgtat   4800
ttagaaaaat aaacaaatag gggttccgcg cacatttccc cgaaaagtgc cacctgggtc   4860
cttttcatca cgtgctataa aaataattat aatttaaatt ttttaatata aatatataaa   4920
ttaaaaatag aaagtaaaaa aagaaattaa agaaaaaata gtttttgttt tccgaagatg   4980
taaaagactc tagggggatc gccaacaaat actacctttt atcttgctct tcctgctctc   5040
aggtattaat gccgaattgt ttcatcttgt ctgtgtagaa gaccacacac gaaaatcctg   5100
tgattttaca ttttacttat cgttaatcga atgtatatct atttaatctg cttttcttgt   5160
ctaataaata tatatgtaaa gtacgctttt tgttgaaatt ttttaaacct ttgtttattt   5220
tttttcttc attccgtaac tcttctacct tctttattta ctttctaaaa tccaaataca   5280
aaacataaaa ataaataaac acagagtaaa ttcccaaatt attccatcat taaaagatac   5340
gaggcgcgtg taagttacag gcaagcgatc cgtcctaaga aaccattatt atcatgacat   5400
```

taacctataa aaataggcgt atcacgaggc cctttcgtc 5439

<210> SEQ ID NO 26
<211> LENGTH: 7146
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaacg acattactat atatataata taggaagcat ttaatagaca gcatcgtaat 240
atatgtgtac tttgcagtta tgacgccaga tggcagtagt ggaagatatt ctttattgaa 300
aaatagcttg tcaccttacg tacaatcttg atccggagct tttctttttt tgccgattaa 360
gaattaattc ggtcgaaaaa agaaaaggag agggccaaga gggagggcat tggtgactat 420
tgagcacgtg agtatacgtg attaagcaca caaaggcagc ttggagtatg tctgttatta 480
atttcacagg tagttctggt ccattggtga aagtttgcgg cttgcagagc acagaggccg 540
cagaatgtgc tctagattcc gatgctgact tgctgggtat tatatgtgtg cccaatagaa 600
agagaacaat tgacccggtt attgcaagga aaatttcaag tcttgtaaaa gcatataaaa 660
atagttcagg cactccgaaa tacttggttg gcgtgtttcg taatcaacct aaggaggatg 720
ttttggctct ggtcaatgat tacggcattg atatcgtcca actgcatgga gatgagtcgt 780
ggcaagaata ccaagagttc ctcggtttgc cagttattaa aagactcgta tttccaaaag 840
actgcaacat actactcagt gcagcttcac agaaacctca ttcgtttatt cccttgtttg 900
attcagaagc aggtgggaca ggtgaacttt tggattggaa ctcgatttct gactgggttg 960
gaaggcaaga gagccccgaa agcttacatt ttatgttagc tggtggactg acgccagaaa 1020
atgttggtga tgcgcttaga ttaaatggcg ttattggtgt tgatgtaagc ggaggtgtgg 1080
agacaaatgg tgtaaaagac tctaacaaaa tagcaaattt cgtcaaaaat gctaagaaat 1140
aggttattac tgagtagtat ttatttaagt attgtttgtg cacttgccta tgcggtgtga 1200
aataccgcac agatgcgtaa ggagaaaata ccgcatcagg aaattgtaaa cgttaatatt 1260
ttgttaaaat tcgcgttaaa tttttgttaa atcagctcat tttttaacca ataggccgaa 1320
atcggcaaaa tcccttataa atcaaaagaa tagaccgaga tagggttgag tgttgttcca 1380
gtttggaaca agagtccact attaaagaac gtggactcca acgtcaaagg gcgaaaaacc 1440
gtctatcagg gcgatggccc actacgtgaa ccatcaccct aatcaagttt tttggggtcg 1500
aggtgccgta aagcactaaa tcggaaccct aaagggagcc cccgatttag agcttgacgg 1560
ggaaagccgg cgaacgtggc gagaaaggaa gggaagaaag cgaaaggagc gggcgctagg 1620
gcgctggcaa gtgtagcggt cacgctgcgc gtaaccacca cacccgccgc gcttaatgcg 1680
ccgctacagg gcgcgtcgcg ccattcgcca ttcaggctgc gcaactgttg ggaagggcga 1740
tcggtgcggg cctcttcgct attacgccag ctggcgaaag ggggatgtgc tgcaaggcga 1800
ttaagttggg taacgccagg gttttcccag tcacgacgtt gtaaaacgac ggccagtgag 1860
cgcgcgtaat acgactcact atagggcgaa ttgggtaccg gccgcaaatt aaagccttcg 1920
agcgtcccaa aaccttctca agcaaggttt tcagtataat gttacatgcg tacacgcgtc 1980

-continued

```
tgtacagaaa aaaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgagcgg   2160
ccgcggatcc ctagagagct ttcgttttca tgagttcccc gaattctttc ggaagcttgt   2220
cacttgctaa attaacgtta tcactgtagt caaccgggac atcaatgatg acaggcccct   2280
cagcgttcat gccttgacgc agaacatctg ccagctggtc tggtgattct acgcgtaagc   2340
cagttgctcc gaagctttcc gcgtatttca cgatatcgat atttccgaaa tcgaccgcag   2400
atgtacgatt atattttttc aattgctgga atgcaaccat gtcatatgtg ctgtcgttcc   2460
atacaatgtg tacaattggt gcttttaaac gaactgctgt ctctaattcc atagctgaga   2520
ataagaaacc gccatcaccg gagactgata ctactttttc tcccggtttc accaatgaag   2580
cgccgattgc ccaaggaagc gcaacgccga gtgtttgcat accgttacta atcattaatg   2640
ttaacggctc gtagctgcgg aaataacgtg acatccaaat cgcgtgtgaa ccgatatcgc   2700
aagtcactgt aacatgatca tcgactgcgt ttcgcaattc tttaacgatt tcaagaggat   2760
gcactctgtc tgatttccaa tctgcaggca cctgctcacc ctcatgcata tattgtttta   2820
aatcagaaag gatcttctgc tcacgttccg caaagtctac tttcacagca tcgtgttcga   2880
tatgattgat cgtagatgga atatcaccga tcagttcaag atccggctgg taagcatgat   2940
caatgtcagc cagaatctcg tctaaatgga tgatcgtccg gtctccattg acattccaga   3000
atttcggatc atattcaatt gggtcatagc cgattgtcag aacaacatca gcctgctcaa   3060
gcagcagatc gccaggctgg ttgcggaata aaccgatccg gccaaaatac tgatcctcta   3120
aatctctcgt aagagtaccg gcagcttgat atgtttcaac gaatggaagc tgcacttttt   3180
tcaatagctt gcgaaccgct ttaatcgctt ccggtcttcc gcccttcatg ccgactaaaa   3240
cgacaggaag ttttgctgtt tgaatttttg caatggccat actgattgcg tcatctgctg   3300
cgggaccaag ttttggcgct gcgacagcac gtacgttttt tgtatttgtg acttcattca   3360
caacatcttg cggaaaactc acaaaagcgg ccccagcctg ccctgctgac gctatcctaa   3420
acgcatttgt aacagcttcc ggtatatttt ttacatcttg aacttctaca ctgtattttg   3480
taatcggctg gaatagcgcc gcattatcca aagattgatg tgtccgtttt aaacgatctg   3540
cacggatcac gttcccagca agcgcaacga cagggtcacc ttcagtgttt gctgtcagca   3600
gtcctgttgc caagttcgaa gcacctggtc ctgatgtgac taacacgact cccggttttc   3660
cagttaaacg gccgactgct tgcgccataa atgctgcatt ttgttcatgc cgggcaacga   3720
taatttcagg ccctttatct tgtaaagcgt caaataccgc atcaattttt gcacctggaa   3780
tgccaaatac atgtgtgaca ccttgctccg ctaagcaatc aacaacaagc tccgcccctc   3840
tgcttttcac aagggatttt tgttcttttg ttgcttttgt caacatgtcg actttatgtg   3900
atgattgatt gattgattgt acagtttgtt tttcttaata tctatttcga tgacttctat   3960
atgatattgc actaacaaga agatattata atgcaattga tacaagacaa ggagttattt   4020
gcttctcttt tatatgattc tgacaatcca tattgcgttg gtagtctttt ttgctggaac   4080
ggttcagcgg aaaagacgca tcgctctttt tgcttctaga agaaatgcca gcaaaagaat   4140
ctcttgacag tgactgacag caaaaatgtc tttttctaac tagtaacaag gctaagatat   4200
cagcctgaaa taaagggtgg tgaagtaata attaaatcat ccgtataaac ctatacacat   4260
atatgaggaa aaataataca aaagtgtttt aaatacagat acatacatga acatatgcac   4320
gtatagcgcc caaatgtcgg taatgggatc ggcgagctcc agcttttgtt ccctttagtg   4380
```

```
agggttaatt gcgcgcttgg cgtaatcatg gtcatagctg tttcctgtgt gaaattgtta   4440
tccgctcaca attccacaca acataggagc cggaagcata aagtgtaaag cctggggtgc   4500
ctaatgagtg aggtaactca cattaattgc gttgcgctca ctgcccgctt tccagtcggg   4560
aaacctgtcg tgccagctgc attaatgaat cggccaacgc gcggggagag gcggtttgcg   4620
tattgggcgc tcttccgctt cctcgctcac tgactcgctg cgctcggtcg ttcggctgcg   4680
gcgagcggta tcagctcact caaaggcggt aatacggtta tccacagaat caggggataa   4740
cgcaggaaag aacatgtgag caaaaggcca gcaaaaggcc aggaaccgta aaaaggccgc   4800
gttgctggcg tttttccata ggctccgccc ccctgacgag catcacaaaa atcgacgctc   4860
aagtcagagg tggcgaaacc cgacaggact ataaagatac caggcgtttc cccctggaag   4920
ctccctcgtg cgctctcctg ttccgaccct gccgcttacc ggatacctgt ccgcctttct   4980
cccttcggga agcgtggcgc tttctcatag ctcacgctgt aggtatctca gttcggtgta   5040
ggtcgttcgc tccaagctgg gctgtgtgca cgaacccccc gttcagcccg accgctgcgc   5100
cttatccggt aactatcgtc ttgagtccaa cccggtaaga cacgacttat cgccactggc   5160
agcagccact ggtaacagga ttagcagagc gaggtatgta ggcggtgcta cagagttctt   5220
gaagtggtgg cctaactacg gctacactag aaggacagta tttggtatct gcgctctgct   5280
gaagccagtt accttcggaa aaagagttgg tagctcttga tccggcaaac aaaccaccgc   5340
tggtagcggt ggtttttttg tttgcaagca gcagattacg cgcagaaaaa aaggatctca   5400
agaagatcct ttgatctttt ctacggggtc tgacgctcag tggaacgaaa actcacgtta   5460
agggattttg gtcatgagat tatcaaaaag gatcttcacc tagatccttt taaattaaaa   5520
atgaagtttt aaatcaatct aaagtatata tgagtaaact tggtctgaca gttaccaatg   5580
cttaatcagt gaggcaccta tctcagcgat ctgtctattt cgttcatcca tagttgcctg   5640
actccccgtc gtgtagataa ctacgatacg ggagggctta ccatctggcc ccagtgctgc   5700
aatgataccg cgagacccac gctcaccggc tccagattta tcagcaataa accagccagc   5760
cggaagggcc gagcgcagaa gtggtcctgc aactttatcc gcctccatcc agtctattaa   5820
ttgttgccgg gaagctagag taagtagttc gccagttaat agtttgcgca acgttgttgc   5880
cattgctaca ggcatcgtgg tgtcacgctc gtcgtttggt atggcttcat tcagctccgg   5940
ttcccaacga tcaaggcgag ttacatgatc ccccatgttg tgcaaaaaag cggttagctc   6000
cttcggtcct ccgatcgttg tcagaagtaa gttggccgca gtgttatcac tcatggttat   6060
ggcagcactg cataattctc ttactgtcat gccatccgta agatgctttt ctgtgactgg   6120
tgagtactca accaagtcat tctgagaata gtgtatgcgg cgaccgagtt gctcttgccc   6180
ggcgtcaata cgggataata ccgcgccaca tagcagaact ttaaaagtgc tcatcattgg   6240
aaaacgttct tcggggcgaa aactctcaag gatcttaccg ctgttgagat ccagttcgat   6300
gtaacccact cgtgcaccca actgatcttc agcatctttt actttcacca gcgtttctgg   6360
gtgagcaaaa acaggaaggc aaaatgccgc aaaaaaggga ataagggcga cacggaaatg   6420
ttgaatactc atactcttcc tttttcaata ttattgaagc atttatcagg gttattgtct   6480
catgagcgga tacatatttg aatgtattta gaaaaataaa caaatagggg ttccgcgcac   6540
atttccccga aaagtgccac ctgggtcctt ttcatcacgt gctataaaaa taattataat   6600
ttaaattttt taatataaat atataaatta aaaatagaaa gtaaaaaaag aaattaaaga   6660
aaaaatagtt tttgttttcc gaagatgtaa aagactctag ggggatcgcc aacaaatact   6720
accttttatc ttgctcttcc tgctctcagg tattaatgcc gaattgtttc atcttgtctg   6780
```

tgtagaagac cacacacgaa aatcctgtga ttttacattt tacttatcgt taatcgaatg 6840
tatatctatt taatctgctt ttcttgtcta ataaatatat atgtaaagta cgctttttgt 6900
tgaaattttt taaacctttg tttatttttt tttcttcatt ccgtaactct tctaccttct 6960
ttatttactt tctaaaatcc aaatacaaaa cataaaaata aataaacaca gagtaaattc 7020
ccaaattatt ccatcattaa aagatacgag gcgcgtgtaa gttacaggca agcgatccgt 7080
cctaagaaac cattattatc atgacattaa cctataaaaa taggcgtatc acgaggccct 7140
ttcgtc 7146

<210> SEQ ID NO 27
<211> LENGTH: 10231
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaatt cccgttttaa gagcttggtg agcgctagga gtcactgcca ggtatcgttt 240
gaacacggca ttagtcaggg aagtcataac acagtccttt cccgcaattt tctttttcta 300
ttactcttgg cctcctctag tacactctat attttttat gcctcggtaa tgattttcat 360 ttttttttt cccctagcgg atgactcttt ttttttctta gcgattggca ttatcacata 420
atgaattata cattatataa agtaatgtga tttcttcgaa gaatatacta aaaaatgagc 480
aggcaagata aacgaaggca aagatgacag agcagaaagc cctagtaaag cgtattacaa 540
atgaaaccaa gattcagatt gcgatctctt taaagggtgg tcccctagcg atagagcact 600
cgatcttccc agaaaaagag gcagaagcag tagcagaaca ggccacacaa tcgcaagtga 660
ttaacgtcca cacaggtata gggtttctgg accatatgat acatgctctg gccaagcatt 720
ccggctggtc gctaatcgtt gagtgcattg gtgacttaca catagacgac catcacacca 780
ctgaagactg cgggattgct ctcggtcaag cttttaaaga ggccctaggg gccgtgcgtg 840
gagtaaaaag gtttggatca ggatttgcgc ctttggatga ggcactttcc agagcggtgg 900
tagatctttc gaacaggccg tacgcagttg tcgaacttgg tttgcaaagg gagaaagtag 960
gagatctctc ttgcgagatg atcccgcatt ttcttgaaag ctttgcagag gctagcagaa 1020
ttaccctcca cgttgattgt ctgcgaggca agaatgatca tcaccgtagt gagagtgcgt 1080
tcaaggctct tgcggttgcc ataagagaag ccacctcgcc caatggtacc aacgatgttc 1140
cctccaccaa aggtgttctt atgtagtgac accgattatt taaagctgca gcatacgata 1200
tatatacatg tgtatatatg tatacctatg aatgtcagta agtatgtata cgaacagtat 1260
gatactgaag atgacaaggt aatgcatcat tctatacgtg tcattctgaa cgaggcgcgc 1320
tttccttttt tctttttgct ttttcttttt ttttctcttg aactcgacgg atctatgcgg 1380
tgtgaaatac cgcacagatg cgtaaggaga aaataccgca tcaggaaatt gtaaacgtta 1440
atattttgtt aaaattcgcg ttaaattttt gttaaatcag ctcatttttt aaccaatagg 1500
ccgaaatcgg caaaatccct tataaatcaa aagaatagac cgagataggg ttgagtgttg 1560
ttccagtttg gaacaagagt ccactattaa agaacgtgga ctccaacgtc aaagggcgaa 1620
aaaccgtcta tcagggcgat ggcccactac gtgaaccatc accctaatca agttttttgg 1680

-continued

```
ggtcgaggtg ccgtaaagca ctaaatcgga accctaaagg gagcccccga tttagagctt   1740
gacggggaaa gccggcgaac gtggcgagaa aggaagggaa gaaagcgaaa ggagcgggcg   1800
ctagggcgct ggcaagtgta gcggtcacgc tgcgcgtaac caccacaccc gccgcgctta   1860
atgcgccgct acagggcgcg tcgcgccatt cgccattcag gctgcgcaac tgttgggaag   1920
ggcgatcggt gcgggcctct tcgctattac gccagctggc gaaaggggga tgtgctgcaa   1980
ggcgattaag ttgggtaacg ccagggtttt cccagtcacg acgttgtaaa acgacggcca   2040
gtgagcgcgc gtaatacgac tcactatagg gcgaattggg taccggccgc aaattaaagc   2100
cttcgagcgt cccaaaacct tctcaagcaa ggttttcagt ataatgttac atgcgtacac   2160
gcgtctgtac agaaaaaaaa gaaaaatttg aaatataaat aacgttctta atactaacat   2220
aactataaaa aaataaatag ggacctagac ttcaggttgt ctaactcctt ccttttcggt   2280
tagagcggat gtggggggag ggcgtgaatg taagcgtgac ataactaatt acatgagcgg   2340
ccgcagatct ttaacccgca acagcaatac gtttcatatc tgtcatatag ccgcgcagtt   2400
tcttacctac ctgctcaatc gcatggctgc gaatcgcttc gttcacatca cgcagttgcc   2460
cgttatctac cgcgccttcc ggaatagctt tacccaggtc gcccggttgc agctctgcca   2520
taaacggttt cagcaacggc acacaagcgt aagagaacag atagttaccg tactcagcgg   2580
tatcagagat aaccacgttc atttcgtaca gacgcttacg ggcgatggtg ttggcaatca   2640
gcggcagctc gtgcagtgat tcataaatatg cagactcttc aatgatgccg gaatcgacca   2700
tggtttcgaa cgccagttca acgcccgctt tcaccatcgc aatcatcagt acgcctttat   2760
cgaagtactc ctgctcgccg attttgcctt catactgcgg cgcggtttca aacgcggttt   2820
tgccggtctc ttcacgccag gtcagcagtt tcttatcatc gttggcccag tccgccatca   2880
taccggaaga gaattcgccg gagatgatgt cgtccatatg tttctggaac aggggtgcca   2940
tgatctcttt cagctgttca gaaagcgcat aagcacgcag tttcgccggg ttagagagac   3000
ggtccatcat cagggtgatg ccgccctgtt tcagtgcttc ggtgatggtt tcccaaccga   3060
actgaatcag tttttctgcg tatgctggat cggtaccttc ttccaccagc ttgtcgaagc   3120
acagcagaga gccagcctgc aacataccgc acaggatggt ttgctcgccc atcaggtcag   3180
atttcacttc cgcaacgaag gacgattcca gcacacccgc acggtgacca ccggttgcag   3240
ccgcccaggc tttggcaatc gccatgcctt cgcctttcgg atcgttttcc gggtgaacgg   3300
caatcagcgt cggtacgccg aacccacgtt tgtactcttc acgcacttcg gtgcctgggc   3360
atttcggcgc aaccatcact acggtgatat ctttacggat ctgctcgccc acttcgacga   3420
tgttgaaacc gtgcgagtag cccagcgccg cgccgtcttt catcagtggc tgtacggtgc   3480
gcactacatc agagtgctgc ttgtccggcg tcaggttaat caccagatcc gcctgtggga   3540
tcagttcttc gtaagtaccc actttaaaac cattttcggt cgctttacgc caggacgcgc   3600
gcttctcggc aatcgcttct ttacgcagag cgtaggagat atcgagacca gaatcacgca   3660
tgttcaggcc ctggttcaga ccctgtgcgc cacagccgac gatgactact tttttaccct   3720
gaaggtagct cgcgccatcg gcgaattcat cgcggcccat ctcgagtcga aactaagttc   3780
tggtgtttta aaactaaaaa aaagactaac tataaaagta gaatttaaga agtttaagaa   3840
atagatttac agaattacaa tcaataccta ccgtctttat atacttatta gtcaagtagg   3900
ggaataattt cagggaactg gtttcaacct ttttttttcag ctttttccaa atcagagaga   3960
gcagaaggta atagaaggtg taagaaaatg agatagatac atgcgtgggt caattgcctt   4020
gtgtcatcat ttactccagg caggttgcat cactccattg aggttgtgcc cgttttttgc   4080
```

-continued ctgtttgtgc ccctgttctc tgtagttgcg ctaagagaat ggacctatga actgatggtt 4140
ggtgaagaaa acaatatttt ggtgctggga ttcttttttt ttctggatgc cagcttaaaa 4200
agcgggctcc attatattta gtggatgcca ggaataaact gttcacccag acacctacga 4260
tgttatatat tctgtgtaac ccgcccccta ttttgggcat gtacgggtta cagcagaatt 4320
aaaaggctaa ttttttgact aaataaagtt aggaaaatca ctactattaa ttatttacgt 4380
attctttgaa atggcgagta ttgataatga taaactggat cctcatccac ccaacttcga 4440
tttgtctctt actgcccct tatcggctga agtagccaat gaagcataag ccctaagggc 4500
gaaacttact tgacgttctc tatttttagg agtccaagcc ttatctcctc tggcatcttg 4560
tgcttctctt cttgcagcca attcagcgtc tgagacttgt aattggatac ctctatttgg 4620
gatatctatg gcgatcaaat ctccatcttc aatcaatcca atcgaaccac cagaagctgc 4680
ctctggtgat acgtgaccga tacttaaacc cgaagtgcca ccagagaatc taccgtcagt 4740
gataagggca caagcttttc ctagtcccat ggacttcaaa aatgaagttg ggtaaagcat 4800
ttcctgcata cctggtcctc cctttggtcc ctcatatctt atcactacca cgtctcctgc 4860
taccaccttt ccgccaagta tagcctcaac agcatcgtct tgactttcgt aaactttagc 4920
gggtccagta aatttcaaaa tactatcatc tacaccagca gttttcacaa tgcaaccatt 4980
ttcagcgaag tttccatata atactgctaa accaccatcc ttactataag catgctcaag 5040
cgatcttata catccatttg ctctatcatc gtccaaagtg tcccacctac agtcttgcga 5100
gaatgcttgg gtggttctga tccctgctgg acctgccctg aacatgtttt tcacggcatc 5160
atcttgagtt aacatgacat cgtattgctc taatgtctgt ggaagtgtta aacccaatac 5220
attcttcaca tccctgttta aaagaccggc tctgtccaac tcccctaaaa taccaataac 5280
ccctcctgca cgatgaacgt cttccatgtg atacttttga gttgatggtg caaccttaca 5340
taactgtgga accttacgtg aaagcttgtc gatatcagac atggtgaaat ctatctcagc 5400
ttcttgggct gcagctagaa gatgtaagac cgtgtttgta ctaccaccca ttgcaatatc 5460
caatgtcatg gcattttcga atgcagcctt tgaagctata ttcctcggta atgctgattc 5520
atcattttgt tcgtaatacc ttttcgttag ttccacaatt ctttttccgg catttaagaa 5580
caattgcttt ctgtctgcat gggtcgctaa taatgaacca tttcctggtt gagataaacc 5640
tagagcttca gtcaagcaat tcatagagtt agccgtgaac attccactgc aagaaccaca 5700
agttggacat gcacttcttt caacttggtc tgactgcgag tctgaaactt ttggatctgc 5760
accttgaatc attgcatcca caagatcaag tttgatgatc tgatcactta acttagtttt 5820
accagcctcc attgggccgc cagatacgaa gattactggg atgttcaatc tcaaggacgc 5880
catcaacata ccaggcgtta tcttatcaca attagagata caaaccattg catcggcaca 5940
atgagcatta accatatatt cgactgagtc tgcaattaat tctctcgatg gtaaagagta 6000
taacataccg ccatgcccca tagctatacc gtcgtccaca gcaatagtat taaactcttt 6060
tgcgacacca cctgcagctt caatttgttc ggcaacaagc ttacctagat cacgcaaatg 6120
gacatgaccc ggaacgaatt gtgtaaaaga gttgacgacg gcaatgattg gctttccgaa 6180
atctgcatca gtcatgccag tcatgtcgac aaacttagat tagattgcta tgctttcttt 6240
ctaatgagca agaagtaaaa aaagttgtaa tagaacaaga aaaatgaaac tgaaacttga 6300
gaaattgaag accgtttatt aacttaaata tcaatgggag gtcatcgaaa gagaaaaaaa 6360
tcaaaaaaaa aattttcaag aaaaagaaac gtgataaaaa tttttattgc ctttttcgac 6420
gaagaaaaag aaacgaggcg gtctcttttt tcttttccaa acctttagta cgggtaatta 6480

```
acgacaccct agaggaagaa agaggggaaa tttagtatgc tgtgcttggg tgttttgaag   6540
tggtacggcg atgcgcggag tccgagaaaa tctggaagag taaaaaagga gtagaaacat   6600
tttgaagcta tgagctccag cttttgttcc ctttagtgag ggttaattgc gcgcttggcg   6660
taatcatggt catagctgtt tcctgtgtga aattgttatc cgctcacaat tccacacaac   6720
ataggagccg gaagcataaa gtgtaaagcc tggggtgcct aatgagtgag gtaactcaca   6780
ttaattgcgt tgcgctcact gcccgctttc cagtcgggaa acctgtcgtg ccagctgcat   6840
taatgaatcg gccaacgcgc ggggagaggc ggtttgcgta ttgggcgctc ttccgcttcc   6900
tcgctcactg actcgctgcg ctcggtcgtt cggctgcggc gagcggtatc agctcactca   6960
aaggcggtaa tacggttatc cacagaatca ggggataacg caggaaagaa catgtgagca   7020
aaaggccagc aaaaggccag gaaccgtaaa aaggccgcgt tgctggcgtt tttccatagg   7080
ctccgccccc ctgacgagca tcacaaaaat cgacgctcaa gtcagaggtg gcgaaacccg   7140
acaggactat aaagatacca ggcgtttccc cctggaagct ccctcgtgcg ctctcctgtt   7200
ccgaccctgc cgcttaccgg atacctgtcc gcctttctcc cttcgggaag cgtggcgctt   7260
tctcatagct cacgctgtag gtatctcagt tcggtgtagg tcgttcgctc caagctgggc   7320
tgtgtgcacg aaccccccgt tcagcccgac cgctgcgcct tatccggtaa ctatcgtctt   7380
gagtccaacc cggtaagaca cgacttatcg ccactggcag cagccactgg taacaggatt   7440
agcagagcga ggtatgtagg cggtgctaca gagttcttga agtggtggcc taactacggc   7500
tacactagaa ggacagtatt tggtatctgc gctctgctga agccagttac cttcggaaaa   7560
agagttggta gctcttgatc cggcaaacaa accaccgctg gtagcggtgg tttttttgtt   7620
tgcaagcagc agattacgcg cagaaaaaaa ggatctcaag aagatccttt gatcttttct   7680
acggggtctg acgctcagtg gaacgaaaac tcacgttaag ggattttggt catgagatta   7740
tcaaaaagga tcttcaccta gatcctttta aattaaaaat gaagttttaa atcaatctaa   7800
agtatatatg agtaaacttg gtctgacagt taccaatgct taatcagtga ggcacctatc   7860
tcagcgatct gtctatttcg ttcatccata gttgcctgac tccccgtcgt gtagataact   7920
acgatacggg agggcttacc atctggcccc agtgctgcaa tgataccgcg agacccacgc   7980
tcaccggctc cagatttatc agcaataaac cagccagccg gaagggccga gcgcagaagt   8040
ggtcctgcaa ctttatccgc ctccatccag tctattaatt gttgccggga agctagagta   8100
agtagttcgc cagttaatag tttgcgcaac gttgttgcca ttgctacagg catcgtggtg   8160
tcacgctcgt cgtttggtat ggcttcattc agctccggtt cccaacgatc aaggcgagtt   8220
acatgatccc ccatgttgtg caaaaaagcg gttagctcct tcggtcctcc gatcgttgtc   8280
agaagtaagt tggccgcagt gttatcactc atggttatgg cagcactgca taattctctt   8340
actgtcatgc catccgtaag atgcttttct gtgactggtg agtactcaac caagtcattc   8400
tgagaatagt gtatgcggcg accgagttgc tcttgcccgg cgtcaatacg ggataatacc   8460
gcgccacata gcagaacttt aaaagtgctc atcattggaa aacgttcttc ggggcgaaaa   8520
ctctcaagga tcttaccgct gttgagatcc agttcgatgt aacccactcg tgcacccaac   8580
tgatcttcag catcttttac tttcaccagc gtttctgggt gagcaaaaac aggaaggcaa   8640
aatgccgcaa aaaagggaat aagggcgaca cggaaatgtt gaatactcat actcttcctt   8700
tttcaatatt attgaagcat ttatcagggt tattgtctca tgagcggata catatttgaa   8760
tgtatttaga aaaataaaca aataggggtt ccgcgcacat ttccccgaaa agtgccacct   8820
gaacgaagca tctgtgcttc attttgtaga acaaaaatgc aacgcgagag cgctaatttt   8880
```

```
tcaaacaaag aatctgagct gcatttttac agaacagaaa tgcaacgcga aagcgctatt   8940

ttaccaacga agaatctgtg cttcattttt gtaaaacaaa aatgcaacgc gagagcgcta   9000

atttttcaaa caaagaatct gagctgcatt tttacagaac agaaatgcaa cgcgagagcg   9060

ctattttacc aacaaagaat ctatacttct tttttgttct acaaaaatgc atcccgagag   9120

cgctattttt ctaacaaagc atcttagatt actttttttc tcctttgtgc gctctataat   9180

gcagtctctt gataactttt tgcactgtag gtccgttaag gttagaagaa ggctactttg   9240

gtgtctattt tctcttccat aaaaaaagcc tgactccact tcccgcgttt actgattact   9300

agcgaagctg cgggtgcatt ttttcaagat aaaggcatcc ccgattatat tctataccga   9360

tgtggattgc gcatactttg tgaacagaaa gtgatagcgt tgatgattct tcattggtca   9420

gaaaattatg aacggtttct tctattttgt ctctatatac tacgtatagg aaatgtttac   9480

attttcgtat tgttttcgat tcactctatg aatagttctt actacaattt ttttgtctaa   9540

agagtaatac tagagataaa cataaaaaat gtagaggtcg agtttagatg caagttcaag   9600

gagcgaaagg tggatgggta ggttatatag ggatatagca cagagatata tagcaaagag   9660

atacttttga gcaatgtttg tggaagcggt attcgcaata ttttagtagc tcgttacagt   9720

ccggtgcgtt tttggttttt tgaaagtgcg tcttcagagc gcttttggtt ttcaaaagcg   9780

ctctgaagtt cctatacttt ctagagaata ggaacttcgg aataggaact tcaaagcgtt   9840

tccgaaaacg agcgcttccg aaaatgcaac gcgagctgcg cacatacagc tcactgttca   9900

cgtcgcacct atatctgcgt gttgcctgta tatatatata catgagaaga acggcatagt   9960

gcgtgtttat gcttaaatgc gtacttatat gcgtctattt atgtaggatg aaaggtagtc  10020

tagtacctcc tgtgatatta tcccattcca tgcggggtat cgtatgcttc cttcagcact  10080

accctttagc tgttctatat gctgccactc ctcaattgga ttagtctcat ccttcaatgc  10140

tatcatttcc tttgatattg gatcatctaa gaaaccatta ttatcatgac attaacctat  10200

aaaaataggc gtatcacgag gccctttcgt c                                 10231
```

<210> SEQ ID NO 28
<211> LENGTH: 9404
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgcgtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctctag tacactctat atttttttat gcctcggtaa tgattttcat    360

ttttttttt ccccctagcgg atgactcttt ttttttctta gcgattggca ttatcacata    420

atgaattata cattatataa agtaatgtga tttcttcgaa gaatatacta aaaaatgagc    480

aggcaagata aacgaaggca aagatgacag agcagaaagc cctagtaaag cgtattacaa    540

atgaaaccaa gattcagatt gcgatctctt taaagggtgg tcccctagcg atagagcact    600

cgatcttccc agaaaaagag gcagaagcag tagcagaaca ggccacacaa tcgcaagtga    660
```

```
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctaggg gccgtgcgtg    840
gagtaaaaag gtttggatca ggatttgcgc ctttggatga ggcactttcc agagcggtgg    900
tagatctttc gaacaggccg tacgcagttg tcgaacttgg tttgcaaagg gagaaagtag    960
gagatctctc ttgcgagatg atcccgcatt ttcttgaaag ctttgcagag gctagcagaa   1020
ttaccctcca cgttgattgt ctgcgaggca agaatgatca tcaccgtagt gagagtgcgt   1080
tcaaggctct tgcggttgcc ataagagaag ccacctcgcc caatggtacc aacgatgttc   1140
cctccaccaa aggtgttctt atgtagtgac accgattatt taaagctgca gcatacgata   1200
tatatacatg tgtatatatg tatacctatg aatgtcagta agtatgtata cgaacagtat   1260
gatactgaag atgacaaggt aatgcatcat tctatacgtg tcattctgaa cgaggcgcgc   1320
tttccttttt tctttttgct tttctttttt ttttctcttg aactcgacgg atctatgcgg   1380
tgtgaaatac cgcacagatg cgtaaggaga aaataccgca tcaggaaatt gtaaacgtta   1440
atattttgtt aaaattcgcg ttaaattttt gttaaatcag ctcatttttt aaccaatagg   1500
ccgaaatcgg caaaatccct tataaatcaa aagaatagac cgagataggg ttgagtgttg   1560
ttccagtttg gaacaagagt ccactattaa agaacgtgga ctccaacgtc aaagggcgaa   1620
aaaccgtcta tcagggcgat ggcccactac gtgaaccatc accctaatca agttttttgg   1680
ggtcgaggtg ccgtaaagca ctaaatcgga accctaaagg gagcccccga tttagagctt   1740
gacggggaaa gccggcgaac gtggcgagaa aggaagggaa gaaagcgaaa ggagcgggcg   1800
ctagggcgct ggcaagtgta gcggtcacgc tgcgcgtaac caccacaccc gccgcgctta   1860
atgcgccgct acagggcgcg tcgcgccatt cgccattcag gctgcgcaac tgttgggaag   1920
ggcgatcggt gcgggcctct tcgctattac gccagctggc gaaaggggga tgtgctgcaa   1980
ggcgattaag ttgggtaacg ccagggtttt cccagtcacg acgttgtaaa acgacggcca   2040
gtgagcgcgc gtaatacgac tcactatagg gcgaattggg taccggccgc aaattaaagc   2100
cttcgagcgt cccaaaacct tctcaagcaa ggttttcagt ataatgttac atgcgtacac   2160
gcgtctgtac agaaaaaaaa gaaaaatttg aaatataaat aacgttctta atactaacat   2220
aactataaaa aaataaatag ggacctagac ttcaggttgt ctaactcctt ccttttcggt   2280
tagagcggat gtgggggggag ggcgtgaatg taagcgtgac ataactaatt acatgagcgg   2340
ccgcagatct ttaacccgca acagcaatac gtttcatatc tgtcatatag ccgcgcagtt   2400
tcttacctac ctgctcaatc gcatggctgc gaatcgcttc gttcacatca cgcagttgcc   2460
cgttatctac cgcgccttcc ggaatagctt tacccaggtc gcccggttgc agctctgcca   2520
taaacggttt cagcaacggc acacaagcgt aagagaacag atagttaccg tactcagcgg   2580
tatcagagat aaccacgttc atttcgtaca gacgcttacg ggcgatggtg ttggcaatca   2640
gcggcagctc gtgcagtgat tcataaatatg cagactcttc aatgatgccg gaatcgacca   2700
tggtttcgaa cgccagttca acgcccgctt tcaccatcgc aatcatcagt acgcctttat   2760
cgaagtactc ctgctcgccg attttgcctt catactgcgg cgcggtttca aacgcggttt   2820
tgccggtctc ttcacgccag gtcagcagtt tcttatcatc gttggcccag tccgccatca   2880
taccggaaga gaattcgccg gagatgatgt cgtccatatg tttctggaac aggggtgcca   2940
tgatctcttt cagctgttca gaaagcgcat aagcacgcag tttcgccggg ttagagagac   3000
ggtccatcat cagggtgatg ccgccctgtt tcagtgcttc ggtgatggtt tcccaaccga   3060
```

```
actgaatcag tttttctgcg tatgctggat cggtaccttc ttccaccagc ttgtcgaagc   3120
acagcagaga gccagcctgc aacataccgc acaggatggt ttgctcgccc atcaggtcag   3180
atttcacttc cgcaacgaag gacgattcca gcacacccgc acggtgacca ccggttgcag   3240
ccgcccaggc tttggcaatc gccatgcctt cgcctttcgg atcgttttcc gggtgaacgg   3300
caatcagcgt cggtacgccg aacccacgtt tgtactcttc acgcacttcg gtgcctgggc   3360
atttcggcgc aaccatcact acggtgatat ctttacggat ctgctcgccc acttcgacga   3420
tgttgaaacc gtgcgagtag cccagcgccg cgccgtcttt catcagtggc tgtacggtgc   3480
gcactacatc agagtgctgc ttgtccggcg tcaggttaat caccagatcc gcctgtggga   3540
tcagttcttc gtaagtaccc actttaaaac cattttcggt cgctttacgc caggacgcgc   3600
gcttctcggc aatcgcttct ttacgcagag cgtaggagat atcgagacca gaatcacgca   3660
tgttcaggcc ctggttcaga ccctgtgcgc cacagccgac gatgactact tttttaccct   3720
gaaggtagct cgcgccatcg gcgaattcat cgcggcccat ctcgagtcga aactaagttc   3780
tggtgtttta aaactaaaaa aaagactaac tataaaagta gaatttaaga agtttaagaa   3840
atagatttac agaattacaa tcaataccta ccgtctttat atacttatta gtcaagtagg   3900
ggaataattt cagggaactg gtttcaacct tttttttcag ctttttccaa atcagagaga   3960
gcagaaggta atagaaggtg taagaaaatg agatagatac atgcgtgggt caattgcctt   4020
gtgtcatcat ttactccagg caggttgcat cactccattg aggttgtgcc cgtttttttgc   4080
ctgtttgtgc ccctgttctc tgtagttgcg ctaagagaat ggacctatga actgatggtt   4140
ggtgaagaaa acaatatttt ggtgctggga ttcttttttt ttctggatgc cagcttaaaa   4200
agcgggctcc attatattta gtggatgcca ggaataaact gttcacccag acacctacga   4260
tgttatatat tctgtgtaac ccgcccccta ttttgggcat gtacgggtta cagcagaatt   4320
aaaaggctaa ttttttgact aaataaagtt aggaaaatca ctactattaa ttatttacgt   4380
attctttgaa atggcgagta ttgataatga taaactggat cctcatccac ccaacttcga   4440
tttgtctctt actgccccct tatcggctga agtagccaat gaagcataag ccctaagggc   4500
gaaacttact tgacgttctc tatttttagg agtccaagcc ttatctcctc tggcatcttg   4560
tgcttctctt cttgcagcca attcagcgtc tgagacttgt aattggatac ctctatttgg   4620
gatatctatg gcgatcaaat ctccatcttc aatcaatcca atcgaaccac cagaagctgc   4680
ctctggtgat acgtgaccga tacttaaacc cgaagtgcca ccagagaatc taccgtcagt   4740
gataagggca caagcttttc ctagtcccat ggacttcaaa aatgaagttg ggtaaagcat   4800
ttcctgcata cctggtcctc cctttggtcc ctcatatctt atcactacca cgtctcctgc   4860
taccaccttt ccgccaagta tagcctcaac agcatcgtct tgactttcgt aaactttagc   4920
gggtccagta aatttcaaaa tactatcatc tacaccagca gttttcacaa tgcaaccatt   4980
ttcagcgaag tttccatata atactgctaa accaccatcc ttactataag catgctcaag   5040
cgatcttata catccatttg ctctatcatc gtccaaagtg tcccacctac agtcttgcga   5100
gaatgcttgg gtggttctga tccctgctgg acctgccctg aacatgtttt tcacggcatc   5160
atcttgagtt aacatgacat cgtattgctc taatgtctgt ggaagtgtta aacccaatac   5220
attcttcaca tccctgttta aaagaccggc tctgtccaac tcccctaaaa taccaataac   5280
ccctcctgca cgatgaacgt cttccatgtg atacttttga gttgatggtg caaccttaca   5340
taactgtgga accttacgtg aaagcttgtc gatatcagac atggtgaaat ctatctcagc   5400
ttcttgggct gcagctagaa gatgtaagac cgtgtttgta ctaccaccca ttgcaatatc   5460
```

```
caatgtcatg gcattttcga atgcagcctt tgaagctata ttcctcggta atgctgattc   5520

atcattttgt tcgtaatacc ttttcgttag ttccacaatt ctttttccgg catttaagaa   5580

caattgcttt ctgtctgcat gggtcgctaa taatgaacca tttcctggtt gagataaacc   5640

tagagcttca gtcaagcaat tcatagagtt agccgtgaac attccactgc aagaaccaca   5700

agttggacat gcacttcttt caacttggtc tgactgcgag tctgaaactt ttggatctgc   5760

accttgaatc attgcatcca caagatcaag tttgatgatc tgatcactta acttagtttt   5820

accagcctcc attgggccgc cagatacgaa gattactggg atgttcaatc tcaaggacgc   5880

catcaacata ccaggcgtta tcttatcaca attagagata caaaccattg catcggcaca   5940

atgagcatta accatatatt cgactgagtc tgcaattaat tctctcgatg gtaaagagta   6000

taacataccg ccatgcccca tagctatacc gtcgtccaca gcaatagtat taaactcttt   6060

tgcgacacca cctgcagctt caatttgttc ggcaacaagc ttacctagat cacgcaaatg   6120

gacatgaccc ggaacgaatt gtgtaaaaga gttgacgacg gcaatgattg gctttccgaa   6180

atctgcatca gtcatgccag tcatgtcgac aaacttagat tagattgcta tgctttcttt   6240

ctaatgagca agaagtaaaa aaagttgtaa tagaacaaga aaaatgaaac tgaaacttga   6300

gaaattgaag accgtttatt aacttaaata tcaatgggag gtcatcgaaa gagaaaaaaa   6360

tcaaaaaaaa aattttcaag aaaaagaaac gtgataaaaa tttttattgc ctttttcgac   6420

gaagaaaaag aaacgaggcg gtctcttttt tcttttccaa acctttagta cgggtaatta   6480

acgacaccct agaggaagaa agaggggaaa tttagtatgc tgtgcttggg tgttttgaag   6540

tggtacggcg atgcgcggag tccgagaaaa tctggaagag taaaaaagga gtagaaacat   6600

tttgaagcta tgagctccag cttttgttcc ctttagtgag ggttaattgc gcgcttggcg   6660

taatcatggt catagctgtt tcctgtgtga aattgttatc cgctcacaat tccacacaac   6720

ataggagccg gaagcataaa gtgtaaagcc tggggtgcct aatgagtgag gtaactcaca   6780

ttaattgcgt tgcgctcact gcccgctttc cagtcgggaa acctgtcgtg ccagctgcat   6840

taatgaatcg gccaacgcgc ggggagaggc ggtttgcgta ttgggcgctc ttccgcttcc   6900

tcgctcactg actcgctgcg ctcggtcgtt cggctgcggc gagcggtatc agctcactca   6960

aaggcggtaa tacggttatc cacagaatca ggggataacg caggaaagaa catgtgagca   7020

aaaggccagc aaaaggccag gaaccgtaaa aaggccgcgt tgctggcgtt tttccatagg   7080

ctccgccccc ctgacgagca tcacaaaaat cgacgctcaa gtcagaggtg gcgaaacccg   7140

acaggactat aaagatacca ggcgtttccc cctggaagct ccctcgtgcg ctctcctgtt   7200

ccgaccctgc cgcttaccgg atacctgtcc gcctttctcc cttcgggaag cgtggcgctt   7260

tctcatagct cacgctgtag gtatctcagt tcggtgtagg tcgttcgctc caagctgggc   7320

tgtgtgcacg aaccccccgt tcagcccgac cgctgcgcct tatccggtaa ctatcgtctt   7380

gagtccaacc cggtaagaca cgacttatcg ccactggcag cagccactgg taacaggatt   7440

agcagagcga ggtatgtagg cggtgctaca gagttcttga agtggtggcc taactacggc   7500

tacactagaa ggacagtatt tggtatctgc gctctgctga agccagttac cttcggaaaa   7560

agagttggta gctcttgatc cggcaaacaa accaccgctg gtagcggtgg tttttttgtt   7620

tgcaagcagc agattacgcg cagaaaaaaa ggatctcaag aagatccttt gatcttttct   7680

acggggtctg acgctcagtg gaacgaaaac tcacgttaag ggattttggt catgagatta   7740

tcaaaaagga tcttcaccta gatcctttta aattaaaaat gaagttttaa atcaatctaa   7800

agtatatatg agtaaacttg gtctgacagt taccaatgct taatcagtga ggcacctatc   7860
```

```
tcagcgatct gtctatttcg ttcatccata gttgcctgac tccccgtcgt gtagataact   7920

acgatacggg agggcttacc atctggcccc agtgctgcaa tgataccgcg agacccacgc   7980

tcaccggctc cagatttatc agcaataaac cagccagccg gaagggccga gcgcagaagt   8040

ggtcctgcaa ctttatccgc ctccatccag tctattaatt gttgccggga agctagagta   8100

agtagttcgc cagttaatag tttgcgcaac gttgttgcca ttgctacagg catcgtggtg   8160

tcacgctcgt cgtttggtat ggcttcattc agctccggtt cccaacgatc aaggcgagtt   8220

acatgatccc ccatgttgtg caaaaaagcg gttagctcct tcggtcctcc gatcgttgtc   8280

agaagtaagt tggccgcagt gttatcactc atggttatgg cagcactgca taattctctt   8340

actgtcatgc catccgtaag atgcttttct gtgactggtg agtactcaac caagtcattc   8400

tgagaatagt gtatgcggcg accgagttgc tcttgcccgg cgtcaatacg ggataatacc   8460

gcgccacata gcagaacttt aaaagtgctc atcattggaa aacgttcttc ggggcgaaaa   8520

ctctcaagga tcttaccgct gttgagatcc agttcgatgt aacccactcg tgcacccaac   8580

tgatcttcag catcttttac tttcaccagc gtttctgggt gagcaaaaac aggaaggcaa   8640

aatgccgcaa aaaagggaat aagggcgaca cggaaatgtt gaatactcat actcttcctt   8700

tttcaatatt attgaagcat ttatcagggt tattgtctca tgagcggata catatttgaa   8760

tgtatttaga aaaataaaca aataggggtt ccgcgcacat ttccccgaaa agtgccacct   8820

gggtcctttt catcacgtgc tataaaaata attataattt aaatttttta atataaatat   8880

ataaattaaa aatagaaagt aaaaaaagaa attaaagaaa aaatagtttt tgttttccga   8940

agatgtaaaa gactctaggg ggatcgccaa caaatactac cttttatctt gctcttcctg   9000

ctctcaggta ttaatgccga attgtttcat cttgtctgtg tagaagacca cacacgaaaa   9060

tcctgtgatt ttacatttta cttatcgtta atcgaatgta tatctattta atctgctttt   9120

cttgtctaat aaatatatat gtaaagtacg ctttttgttg aaatttttta aacctttgtt   9180

tatttttttt tcttcattcc gtaactcttc taccttcttt atttactttc taaaatccaa   9240

atacaaaaca taaaaataaa taaacacaga gtaaattccc aaattattcc atcattaaaa   9300

gatacgaggc gcgtgtaagt tacaggcaag cgatccgtcc taagaaacca ttattatcat   9360

gacattaacc tataaaaata ggcgtatcac gaggcccttt cgtc                    9404
```

<210> SEQ ID NO 29
<211> LENGTH: 9404
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgcgtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctctag tacactctat atttttttat gcctcggtaa tgattttcat    360

tttttttttt cccctagcgg atgactcttt ttttttctta gcgattggca ttatcacata    420

atgaattata cattatataa agtaatgtga tttcttcgaa gaatatacta aaaaatgagc    480

aggcaagata aacgaaggca aagatgacag agcagaaagc cctagtaaag cgtattacaa    540
```

```
atgaaaccaa gattcagatt gcgatctctt taaagggtgg tcccctagcg atagagcact    600

cgatcttccc agaaaaagag gcagaagcag tagcagaaca ggccacacaa tcgcaagtga    660

ttaacgtcca cacaggtata gggtttctgg accatatgat acatgctctg gccaagcatt    720

ccggctggtc gctaatcgtt gagtgcattg gtgacttaca catagacgac catcacacca    780

ctgaagactg cgggattgct ctcggtcaag cttttaaaga ggccctaggg gccgtgcgtg    840

gagtaaaaag gtttggatca ggatttgcgc ctttggatga ggcactttcc agagcggtgg    900

tagatctttc gaacaggccg tacgcagttg tcgaacttgg tttgcaaagg gagaaagtag    960

gagatctctc ttgcgagatg atcccgcatt ttcttgaaag ctttgcagag gctagcagaa   1020

ttaccctcca cgttgattgt ctgcgaggca agaatgatca tcaccgtagt gagagtgcgt   1080

tcaaggctct tgcggttgcc ataagagaag ccacctcgcc caatggtacc aacgatgttc   1140

cctccaccaa aggtgttctt atgtagtgac accgattatt taaagctgca gcatacgata   1200

tatatacatg tgtatatatg tatacctatg aatgtcagta agtatgtata cgaacagtat   1260

gatactgaag atgacaaggt aatgcatcat tctatacgtg tcattctgaa cgaggcgcgc   1320

tttccttttt tctttttgct tttctttttt ttttctcttg aactcgacgg atctatgcgg   1380

tgtgaaatac cgcacagatg cgtaaggaga aaataccgca tcaggaaatt gtaaacgtta   1440

atattttgtt aaaattcgcg ttaaattttt gttaaatcag ctcatttttt aaccaatagg   1500

ccgaaatcgg caaaatccct tataaatcaa aagaatagac cgagataggg ttgagtgttg   1560

ttccagtttg gaacaagagt ccactattaa agaacgtgga ctccaacgtc aaagggcgaa   1620

aaaccgtcta tcagggcgat ggcccactac gtgaaccatc accctaatca agttttttgg   1680

ggtcgaggtg ccgtaaagca ctaaatcgga accctaaagg gagcccccga tttagagctt   1740

gacggggaaa gccggcgaac gtggcgagaa aggaagggaa gaaagcgaaa ggagcgggcg   1800

ctagggcgct ggcaagtgta gcggtcacgc tgcgcgtaac caccacaccc gccgcgctta   1860

atgcgccgct acagggcgcg tcgcgccatt cgccattcag gctgcgcaac tgttgggaag   1920

ggcgatcggt gcgggcctct tcgctattac gccagctggc gaaaggggga tgtgctgcaa   1980

ggcgattaag ttgggtaacg ccagggtttt cccagtcacg acgttgtaaa acgacggcca   2040

gtgagcgcgc gtaatacgac tcactatagg gcgaattggg taccggccgc aaattaaagc   2100

cttcgagcgt cccaaaacct tctcaagcaa ggttttcagt ataatgttac atgcgtacac   2160

gcgtctgtac agaaaaaaaa gaaaaatttg aaatataaat aacgttctta atactaacat   2220

aactataaaa aaataaatag ggacctagac ttcaggttgt ctaactcctt ccttttcggt   2280

tagagcggat gtggggggag ggcgtgaatg taagcgtgac ataactaatt acatgagcgg   2340

ccgcagatct ttaacccgca acagcaatac gtttcatatc tgtcatatag ccgcgcagtt   2400

tcttacctac ctgctcaatc gcatggctgc gaatcgcttc gttcacatca cgcagttgcc   2460

cgttatctac cgcgccttcc ggaatagctt tacccaggtc gcccggttgc agctctgcca   2520

taaacggttt cagcaacggc acacaagcgt aagagaacag atagttaccg tactcagcgg   2580

tatcagagat aaccacgttc atttcgtaca gacgcttacg ggcgatggtg ttggcaatca   2640

gcggcagctc gtgcagtgat tcataatatg cagactcttc aatgatgccg gaatcgacca   2700

tggtttcgaa cgccagttca acgcccgctt tcaccatcgc aatcatcagt acgcctttat   2760

cgaagtactc ctgctcgccg attttgcctt catactgcgg cgcggtttca aacgcggttt   2820

tgccggtctc ttcacgccag gtcagcagtt tcttatcatc gttggcccag tccgccatca   2880

taccggaaga gaattcgccg gagatgatgt cgtccatatg tttctggaac aggggtgcca   2940
```

```
tgatctcttt cagctgttca gaaagcgcat aagcacgcag tttcgccggg ttagagagac   3000
ggtccatcat cagggtgatg ccgccctgtt tcagtgcttc ggtgatggtt tcccaaccga   3060
actgaatcag tttttctgcg tatgctggat cggtaccttc ttccaccagc ttgtcgaagc   3120
acagcagaga gccagcctgc aacataccgc acaggatggt ttgctcgccc atcaggtcag   3180
atttcacttc cgcaacgaag gacgattcca gcacacccgc acggtgacca ccggttgcag   3240
ccgcccaggc tttggcaatc gccatgcctt cgcctttcgg atcgttttcc gggtgaacgg   3300
caatcagcgt cggtacgccg aacccacgtt tgtactcttc acgcacttcg gtgcctgggc   3360
atttcggcgc aaccatcact acggtgatat ctttacggat ctgctcgccc acttcgacga   3420
tgttgaaacc gtgcgagtag cccagcgccg cgccgtcttt catcagtggc tgtacggtgc   3480
gcactacatc agagtgctgc ttgtccggcg tcaggttaat caccagatcc gcctgtggga   3540
tcagttcttc gtaagtaccc actttaaaac cattttcggt cgctttacgc caggacgcgc   3600
gcttctcggc aatcgcttct ttacgcagag cgtaggagat atcgagacca gaatcacgca   3660
tgttcaggcc ctggttcaga ccctgtgcgc cacagccgac gatgactact tttttaccct   3720
gaaggtagct cgcgccatcg gcgaattcat cgcggcccat ctcgagtcga aactaagttc   3780
tggtgtttta aaactaaaaa aaagactaac tataaaagta gaatttaaga agtttaagaa   3840
atagatttac agaattacaa tcaataccta ccgtctttat atacttatta gtcaagtagg   3900
ggaataattt cagggaactg gtttcaacct tttttttcag ctttttccaa atcagagaga   3960
gcagaaggta atagaaggtg taagaaaatg agatagatac atgcgtgggt caattgcctt   4020
gtgtcatcat ttactccagg caggttgcat cactccattg aggttgtgcc cgtttttttgc   4080
ctgtttgtgc ccctgttctc tgtagttgcg ctaagagaat ggacctatga actgatggtt   4140
ggtgaagaaa acaatatttt ggtgctggga ttcttttttt ttctggatgc cagcttaaaa   4200
agcgggctcc attatattta gtggatgcca ggaataaact gttcacccag acacctacga   4260
tgttatatat tctgtgtaac ccgcccccta ttttgggcat gtacgggtta cagcagaatt   4320
aaaaggctaa ttttttgact aaataaagtt aggaaaatca ctactattaa ttatttacgt   4380
attctttgaa atggcgagta ttgataatga taaactggat cctcatccac ccaacttcga   4440
tttgtctctt actgcccccct tatcggctga agtagccaat gaagcataag ccctaagggc   4500
gaaacttact tgacgttctc tatttttagg agtccaagcc ttatctcctc tggcatcttg   4560
tgcttctctt cttgcagcca attcagcgtc tgagacttgt aattggatac ctctatttgg   4620
gatatctatg gcgatcaaat ctccatcttc aatcaatcca atcgaaccac cagaagctgc   4680
ctctggtgat acgtgaccga tacttaaacc cgaagtgcca ccagagaatc taccgtcagt   4740
gataagggca caagcttttc ctagtcccat ggacttcaaa aatgaagttg ggtaaagcat   4800
ttcctgcata cctggtcctc cctttggtcc ctcatatctt atcactacca cgtctcctgc   4860
taccaccttt ccgccaagta tagcctcaac agcatcgtct tgactttcgt aaactttagc   4920
gggtccagta aatttcaaaa tactatcatc tacaccagca gttttcacaa tgcaaccatt   4980
ttcagcgaag tttccatata atactgctaa accaccatcc ttactataag catgctcaag   5040
cgatcttata catccatttg ctctatcatc gtccaaagtg tcccacctac agtcttgcga   5100
gaatgcttgg gtggttctga tccctgctgg acctgccctg aacatgtttt tcacggcatc   5160
atcttgagtt aacatgacat cgtattgctc taatgtctgt ggaagtgtta aacccaatac   5220
attcttcaca tccctgttta aaagaccggc tctgtccaac tcccctaaaa taccaataac   5280
ccctcctgca cgatgaacgt cttccatgtg atacttttga gttgatggtg caaccttaca   5340
```

```
taactgtgga accttacgtg aaagcttgtc gatatcagac atggtgaaat ctatctcagc   5400
ttcttgggct gcagctagaa gatgtaagac cgtgtttgta ctaccaccca ttgcaatatc   5460
caatgtcatg gcattttcga atgcagcctt tgaagctata ttcctcggta atgctgattc   5520
atcattttgt tcgtaatacc ttttcgttag ttccacaatt ctttttccgg catttaagaa   5580
caattgcttt ctgtctgcat gggtcgctaa taatgaacca tttcctggtt gagataaacc   5640
tagagcttca gtcaagcaat tcatagagtt agccgtgaac attccactgc aagaaccaca   5700
agttggacat gcacttcttt caacttggtc tgactgcgag tctgaaactt ttggatctgc   5760
accttgaatc attgcatcca caagatcaag tttgatgatc tgatcactta acttagtttt   5820
accagcctcc attgggccgc cagatacgaa gattactggg atgttcaatc tcaaggacgc   5880
catcaacata ccaggcgtta tcttatcaca attagagata caaaccattg catcggcaca   5940
atgagcatta accatatatt cgactgagtc tgcaattaat tctctcgatg gtaaagagta   6000
taacataccg ccatgcccca tagctatacc gtcgtccaca gcaatagtat taaactcttt   6060
tgcgacacca cctgcagctt caatttgttc ggcaacaagc ttacctagat cacgcaaatg   6120
gacatgaccc ggaacgaatt gtgtaaaaga gttgacgacg gcaatgattg gctttccgaa   6180
atctgcatca gtcatgccag tcatgtcgac aaacttagat tagattgcta tgctttcttt   6240
ctaatgagca agaagtaaaa aaagttgtaa tagaacaaga aaaatgaaac tgaaacttga   6300
gaaattgaag accgtttatt aacttaaata tcaatgggag gtcatcgaaa gagaaaaaaa   6360
tcaaaaaaaa aattttcaag aaaaagaaac gtgataaaaa tttttattgc ctttttcgac   6420
gaagaaaaag aaacgaggcg gtctcttttt tcttttccaa acctttagta cgggtaatta   6480
acgacaccct agaggaagaa agaggggaaa tttagtatgc tgtgcttggg tgttttgaag   6540
tggtacggcg atgcgcggag tccgagaaaa tctggaagag taaaaaagga gtagaaacat   6600
tttgaagcta tgagctccag cttttgttcc ctttagtgag ggttaattgc gcgcttggcg   6660
taatcatggt catagctgtt tcctgtgtga aattgttatc cgctcacaat tccacacaac   6720
ataggagccg gaagcataaa gtgtaaagcc tggggtgcct aatgagtgag gtaactcaca   6780
ttaattgcgt tgcgctcact gcccgctttc cagtcgggaa acctgtcgtg ccagctgcat   6840
taatgaatcg gccaacgcgc ggggagaggc ggtttgcgta ttgggcgctc ttccgcttcc   6900
tcgctcactg actcgctgcg ctcggtcgtt cggctgcggc gagcggtatc agctcactca   6960
aaggcggtaa tacggttatc cacagaatca ggggataacg caggaaagaa catgtgagca   7020
aaaggccagc aaaaggccag gaaccgtaaa aaggccgcgt tgctggcgtt tttccatagg   7080
ctccgccccc ctgacgagca tcacaaaaat cgacgctcaa gtcagaggtg gcgaaacccg   7140
acaggactat aaagatacca ggcgtttccc cctggaagct ccctcgtgcg ctctcctgtt   7200
ccgaccctgc cgcttaccgg atacctgtcc gcctttctcc cttcgggaag cgtggcgctt   7260
tctcatagct cacgctgtag gtatctcagt tcggtgtagg tcgttcgctc caagctgggc   7320
tgtgtgcacg aaccccccgt tcagcccgac cgctgcgcct tatccggtaa ctatcgtctt   7380
gagtccaacc cggtaagaca cgacttatcg ccactggcag cagccactgg taacaggatt   7440
agcagagcga ggtatgtagg cggtgctaca gagttcttga agtggtggcc taactacggc   7500
tacactagaa ggacagtatt tggtatctgc gctctgctga agccagttac cttcggaaaa   7560
agagttggta gctcttgatc cggcaaacaa accaccgctg gtagcggtgg tttttttgtt   7620
tgcaagcagc agattacgcg cagaaaaaaa ggatctcaag aagatccttt gatcttttct   7680
acggggtctg acgctcagtg gaacgaaaac tcacgttaag ggattttggt catgagatta   7740
```

```
tcaaaaagga tcttcaccta gatcctttta aattaaaaat gaagttttaa atcaatctaa   7800

agtatatatg agtaaacttg gtctgacagt taccaatgct taatcagtga ggcacctatc   7860

tcagcgatct gtctatttcg ttcatccata gttgcctgac tccccgtcgt gtagataact   7920

acgatacggg agggcttacc atctggcccc agtgctgcaa tgataccgcg agacccacgc   7980

tcaccggctc cagatttatc agcaataaac cagccagccg gaagggccga gcgcagaagt   8040

ggtcctgcaa ctttatccgc ctccatccag tctattaatt gttgccggga agctagagta   8100

agtagttcgc cagttaatag tttgcgcaac gttgttgcca ttgctacagg catcgtggtg   8160

tcacgctcgt cgtttggtat ggcttcattc agctccggtt cccaacgatc aaggcgagtt   8220

acatgatccc ccatgttgtg caaaaaagcg gttagctcct tcggtcctcc gatcgttgtc   8280

agaagtaagt tggccgcagt gttatcactc atggttatgg cagcactgca taattctctt   8340

actgtcatgc catccgtaag atgcttttct gtgactggtg agtactcaac caagtcattc   8400

tgagaatagt gtatgcggcg accgagttgc tcttgcccgg cgtcaatacg ggataatacc   8460

gcgccacata gcagaacttt aaaagtgctc atcattggaa aacgttcttc ggggcgaaaa   8520

ctctcaagga tcttaccgct gttgagatcc agttcgatgt aacccactcg tgcacccaac   8580

tgatcttcag catcttttac tttcaccagc gtttctgggt gagcaaaaac aggaaggcaa   8640

aatgccgcaa aaaagggaat aagggcgaca cggaaatgtt gaatactcat actcttcctt   8700

tttcaatatt attgaagcat ttatcagggt tattgtctca tgagcggata catatttgaa   8760

tgtatttaga aaaataaaca aataggggtt ccgcgcacat ttccccgaaa agtgccacct   8820

gggtcctttt catcacgtgc tataaaaata attataattt aaatttttta atataaatat   8880

ataaattaaa aatagaaagt aaaaaaagaa attaaagaaa aaatagtttt tgttttccga   8940

agatgtaaaa gactctaggg ggatcgccaa caaatactac cttttatctt gctcttcctg   9000

ctctcaggta ttaatgccga attgtttcat cttgtctgtg tagaagacca cacacgaaaa   9060

tcctgtgatt ttacatttta cttatcgtta atcgaatgta tatctattta atctgctttt   9120

cttgtctaat aaatatatat gtaaagtacg ctttttgttg aaatttttta aacctttgtt   9180

tattttttt tcttcattcc gtaactcttc taccttcttt atttactttc taaaatccaa   9240

atacaaaaca taaaaataaa taaacacaga gtaaattccc aaattattcc atcattaaaa   9300

gatacgaggc gcgtgtaagt tacaggcaag cgatccgtcc taagaaacca ttattatcat   9360

gacattaacc tataaaaata ggcgtatcac gaggcccttt cgtc                    9404
```

```
<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

agtcacatca agatcgttta tgg                                             23


<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
```

gcacggaata tgggactact tcg 23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
actccacttc aagtaagagt ttg 23

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
tattgtctca tgagcggata c 21

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
acaacgagtg tcatggggag aggaagagg 29

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
gatcttcggc tgggtcatgt gaggcgg 27

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
acgctgaaca cgttggtgtc ttgc 24

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
aacccttagc agcatcggca acc 23

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
tattcatggg ccaatactac g 21

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gtagaagacg tcacctggta gaccaaagat g 31

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
catcgtgacg tcgctcaatt gactgctgct ac 32

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
actaagcgac acgtgcggtt tctgtggtat ag 32

<210> SEQ ID NO 42
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
gaaaccgcac gtgtcgctta gtttacattt ctttcc 36

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
tttgaagtgg tacggcgatg 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
aatcatatcg aacacgatgc 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
agctggtctg gtgattctac 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
tatcaccgta gtgatggttg 20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
gtcagcagtt tcttatcatc g 21

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
gcgaaactta cttgacgttc 20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
actttggacg atgatagagc 20

<210> SEQ ID NO 50
<211> LENGTH: 20

<212> TYPE: DNA
<213> ORGANISM: Artificial Sequence
<220> FEATURE:
<223> OTHER INFORMATION: Description of Artificial Sequence: Synthetic primer

<400> SEQUENCE: 50
gcgttagatg gtacgaaatc 20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
cttctaacac tagcgaccag 20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
aaagatgatg agcaaacgac 20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
cgagcaatac tgtaccaatg 20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
tcacggatga tttccagggt 20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
cacctgcgtt gttaccacaa 20

<210> SEQ ID NO 56
<211> LENGTH: 491
<212> TYPE: PRT
<213> ORGANISM: Escherichia coli

<400> SEQUENCE: 56

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415
```

```
Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490
```

<210> SEQ ID NO 57
<211> LENGTH: 14056
<212> TYPE: DNA
<213> ORGANISM: Artificial Sequence
<220> FEATURE:
<223> OTHER INFORMATION: pGV2227

<400> SEQUENCE: 57

```
ttggatcata ctaagaaacc attattatca tgacattaac ctataaaaat aggcgtatca     60

cgaggccctt tcgtctcgcg cgtttcggtg atgacggtga aaacctctga cacatgcagc    120

tcccggagac ggtcacagct tgtctgtaag cggatgccgg gagcagacaa gcccgtcagg    180

gcgcgtcagc gggtgttggc gggtgtcggg gctggcttaa ctatgcggca tcagagcaga    240

ttgtactgag agtgcaccat accacagctt ttcaattcaa ttcatcattt ttttttatt     300

cttttttttg atttcggttt ctttgaaatt tttttgattc ggtaatctcc gaacagaagg    360

aagaacgaag gaaggagcac agacttagat tggtatatat acgcatatgg caaattaaag    420

ccttcgagcg tcccaaaacc ttctcaagca aggttttcag tataatgtta catgcgtaca    480

cgcgtctgta cagaaaaaaa agaaaaattt gaaatataaa taacgttctt aatactaaca    540

taactataaa aaaataaata gggacctaga cttcaggttg tctaactcct tccttttcgg    600

ttagagcgga tgtgggggga gggcgtgaat gtaagcgtga cataactaat tacatgactc    660

gacctaggtt atttagtaaa atcaatgacc attcggcctt caatttttcc tgccttcatt    720

tcatcaataa tatcattgat ttcttccagt ttgcgtgtcg caacaattgg ttttacctta    780

ccttctgctc caaattgaaa agcttctgcc aagtcaagtc ttgttccgac aagtgaacct    840

gcaacctcca ctccgtcaaa aacaactgtt ggaactgata aagtcatctc agtattggga    900

agtgccacag caaccatttt gcccataggt ttcaaagaag caaccgcttg ttcaaaagca    960

atccttgcaa cagcacaaac tattgcactt tgcaccccta agccgccagt tatttttta    1020

atttcatcaa ctggatttac atcaccagaa ttgataatca catcagctcc aatttttta    1080

gctaaattta atttatcttg attaatatca acagcaatta cttttgctcc aaaaacattt   1140

ttagcatatt gaattgctaa atttccaagt cctccagcac caaaaattac ttgccaatca   1200

ccaggtttta ctcctgatac tttgattgct ttgtaagttg ttactccagc acaagtaatt   1260

gagctagctt caattgggtc aagtccgtca ggaactttga cagcataatc ggcaacaaca   1320

attgcttctt cagccattcc gccatcaact gaatatcctg catttttaac ttctcgacaa   1380

aaagtttcat taccagatac acagtattca cagtgaccac atccttcaaa gaaccaagcc   1440

actgaaaccc gatcaccaac ttgaagcgag cttacatcag ctccaatttc tttgacaatt   1500

ccaattcctt catgaccaag aacagtccct gctttgttgc cataatcacc tgctgcaacg   1560

tgcaaatcgg tatgacagac tccacaatac tccatgtcaa gcaaagcttc attaggtttg   1620
```

-continued

```
attgctcgaa gttccttttc aacaaggtcc gcataaccat ctggattgtg tcttactact   1680
gctgctttca ttggtaccta ttattgtatg ttatagtatt agttgcttgg tgttatgaaa   1740
gaaactaaga aaagaaaaat aaaataaaaa taaaagattg agacaaggga agaaaagata   1800
caaaataaga attaattaca attgcgtttg ctataaatac gtttttaaca atcaactctg   1860
gtaggaagat aatgcttttt ttttttatat atgcttggtg ccacttgtca catacaattc   1920
tacaaccttc gacaaaaatc caaatgatag taagatcaaa gccagaaagc aatggagaaa   1980
aaaaattaat gaaccacgat gaaccaaatg atcaatacaa ccaaagaaac taccctagtg   2040
aggtgtatgc tgacttggta tcacacttca tgaattttgc atatggcaaa gtccacgaaa   2100
gtgggcttca gaaaaaaggc gtgcggtgtg tagatgtatc aattagtgga tgccagtttt   2160
ggaacgggat tccactttcc gcaagttggt gcacgtcgtt agtgacataa cgccgcgttc   2220
atctttggga agaagcagat gctgagcgag gaggtactat agagtaaaga accctttcta   2280
tacccgcagc cccatggtaa gtgacagtgc agtaataata tgaaccaatt tatttttcgt   2340
tacataaaaa tgcttataaa actttaacta ataattagag attaaatcgc ggccgcaaaa   2400
gatccttagg atttattctg ttcagcaaac agcttgccca ttttcttcag taccttcggt   2460
gcgccttctt tcgccaggat cagttcgatc cagtacatac ggttcggatc ggcctgggcc   2520
tctttcatca cgctcacaaa ttcgttttcg gtacgcacaa ttttagacac aacacggtcc   2580
tcagttgcgc cgaaggactc cggcagttta gagtagttcc acatagggat atcgttgtaa   2640
gactggttcg gaccgtggat ctcacgctca acggtgtagc cgtcattgtt aataatgaag   2700
caaatcgggt tgatcttttc acgaattgcc agacccagtt cctgtacggt cagctgcagg   2760
gaaccgtcac cgatgaacag cagatgacga gattctttat cagcgatctg agagcccagc   2820
gctgccggga aagtatagcc aatgctaccc cacagcggct gaccgataaa atggcttttg   2880
gatttcagaa agatagaaga cgcgccgaaa aagctcgtac cttgttccgc cacgatggtt   2940
tcattgctct gggtcaggtt ctccacggcc tgccacaggc gatcctggga cagcagtgcg   3000
ttagatggta cgaaatcttc ttgctttttg tcaatgtatt tgcctttata ctcgatttcg   3060
gacaggtcca gcagagagct gatcaggctt tcgaagtcga agttctggat acgctcgttg   3120
aagattttac cctcgtcgat gttcaggcta atcattttgt tttcgttcag atggtgagtg   3180
aatgcaccgg tagaagagtc ggtcagttta acgcccagca tcaggatgaa gtccgcagat   3240
tcaacaaatt ctttcaggtt cggttcgctc agagtaccgt tgtagatgcc caggaaagac   3300
ggcagagcct cgtcaacaga ggacttgccg aagttcaggg tggtaatcgg cagtttggtt   3360
ttgctgatga attgggtcac ggtcttctcc agaccaaaag aaatgatttc gtggccggtg   3420
atcacgattg gtttctttgc gtttttcaga gactcctgga ttttgttcag gatttcctgg   3480
tcgctagtgt tagaagtgga gttttctttc ttcagcggca ggctcggttt ttccgcttta   3540
gctgccgcaa catccacagg caggttgatg taaactggtt tgcgttcttt cagcagcgca   3600
gacagaacgc ggtcgatttc cacagtagcg ttctctgcag tcagcagcgt acgtgccgca   3660
gtcacaggtt catgcatttt catgaagtgt ttgaaatcgc cgtcagccag agtgtggtgg   3720
acgaatttac cttcgttctg aactttgctc gttgggctgc ctacgatctc caccaccggc   3780
aggttttcgg cgtaggagcc cgccagaccg ttgacggcgc tcagttcgcc aacaccgaaa   3840
gtggtcagaa atgccgcggc tttcttggta cgtgcataac catctgccat gtagcttgcg   3900
ttcagttcgt tagcgttacc cacccatttc atgtctttat gagagatgat ctgatccagg   3960
aactgcagat tgtaatcacc cggaacgccg aagatttctt cgatacccag ttcatgcaga   4020
```

```
cggtccagca gataatcacc aacagtatac atgtcgagct tgttttatat ttgttgtaaa   4080
aagtagataa ttacttcctt gatgatctgt aaaaaagaga aaaagaaagc atctaagaac   4140
ttgaaaaact acgaattaga aaagaccaaa tatgtatttc ttgcattgac caatttatgc   4200
aagtttatat atatgtaaat gtaagtttca cgaggttcta ctaaactaaa ccacccccct   4260
ggttagaaga aaagagtgtg tgagaacagg ctgttgttgt cacacgattc ggacaattct   4320
gtttgaaaga gagagagtaa cagtacgatc gaacgaactt tgctctggag atcacagtgg   4380
gcatcatagc atgtggtact aaacccttc ccgccattcc agaaccttcg attgcttgtt   4440
acaaaacctg tgagccgtcg ctaggacctt gttgtgtgac gaaattggaa gctgcaatca   4500
ataggaagac aggaagtcga gcgtgtctgg gttttttcag ttttgttctt tttgcaaaca   4560
aatcacgagc gacggtaatt tctttctcga taagaggcca cgtgctttat gagggtaaca   4620
tcaattcaag aaggagggaa acacttcctt tttctggccc tgataatagt atgagggtga   4680
agccaaaata aaggattcgc gcccaaatcg gcatctttaa atgcaggtat gcgatagttc   4740
ctcactcttt ccttactcac gagtaattct tgcaaatgcc tattatgcag atgttataat   4800
atctgtgcgt cttgagttga gcctagaatt cttagaaaaa ctcatcgagc atcaaatgaa   4860
actgcaattt attcatatca ggattatcaa taccatattt ttgaaaaagc cgtttctgta   4920
atgaaggaga aaactcaccg aggcagttcc ataggatggc aagatcctgg tatcggtctg   4980
cgatcccgac tcgtccaaca tcaatacaac ctattaattt cccctcgtca aaaataaggt   5040
tatcaagtga gaaatcacca tgagtgacga ctgaatccgg tgagaatggc aaaagcttat   5100
gcatttcttt ccagacttgt tcaacaggcc agccattacg ctcgtcatca aaatcactcg   5160
cgtcaaccaa accgttattc attcgtgatt gcgcctgagc gaggcgaaat acgcgatcgc   5220
tgttaaaagg acaattacaa acaggaatcg aatgcaaccg gcgcaggaac actgccagcg   5280
catcaacaat attttcacct gaatcaggat attcttctaa tacctggaat gctgttttgc   5340
cggggatcgc agtggtgagt aaccatgcat catcaggagt acggacaaaa tgcttgatgg   5400
tcggaagagg cataaattcc gtcagccagt ttagtctgac catctcatct gcaacatcat   5460
tggcaacgct acctttgcca tgtttcagaa acaactctgg cgcatcgggc ttcccataca   5520
atcgatagat tgtcgcacct gattgcccga cattatcgcg agcccattta tacccatata   5580
aatcagcatc catgttggaa tttaatcgcg gcctcgaaac gtgagtcttt tccttaccca   5640
tactagtttt tagtttatgt atgtgttttt tgtagttata gatttaagca agaaaagaat   5700
acaaacaaaa aattgaaaaa gattgattta gaattaaaaa gaaaaatatt tacgtaagaa   5760
gggaaaatag taaatgttgc aagttcacta aactcctaaa ttatgctgcc ctttatattc   5820
cctgttacag cagccgagcc aaaggtatat aggctccttt gcattagcat gcgtaacaaa   5880
ccacctgtca gtttcaaccg aggtggtatc cgagagaatt gtgtgattgc tttaattaat   5940
ttcggagaat ctcacatgcc actgaagatt aaaaactgga tgccagaaaa ggggtgtcca   6000
ggtgtaacat caatagagga agctgaaaag tcttagaacg ggtaatcttc caccaacctg   6060
atgggttcct agatataatc tcgaagggaa taagtagggt gataccgcag aagtgtctga   6120
atgtattaag gtcctcacag tttaaatccc gctcacacta acgtaggatt attataactc   6180
aaaaaaatgg cattattcta agtaagttaa atatccgtaa tctttaaaca gcggccgcgg   6240
atcttcatcc tgccactgca attcttttca tatcggtcat atatcctctc agctttttac   6300
ccacctgttc tatagcatgt gaacgaatag cttcatttac gtctctcagt tggccattgt   6360
caaccgctcc ttccggaata gccttcccca aatcaccagg ttgtaactcg gccatgaagg   6420
```

-continued

```
gctttaacaa cgggacacat gcgtagctaa ataagtaatt accatattct gcagtgtctg   6480
atatgacaac attcatctcg taaagtcttt ttcttgcaat agtatttgct atcaaaggca   6540
attcatgcaa agactcatag tatgcagatt cttcaatgat accggagtca accatagttt   6600
cgaatgcaag ttctacccct gccttcacca tagctatcat caatactccc ttatcaaagt   6660
attcttgttc accaatttta ccttcgtatt gtggggctgt ctcgaatgcc gtcttgccgg   6720
tttcttctct ccacgtcaat aactttttat catcgtttgc ccaatctgcc atcattcctg   6780
aggaaaactc accggagata atatcgtcca tgtgcttttg gaataatggt gccatgatct   6840
cttttagttg ctcagataag gcgtaggctc ttagcttggc cggatttgaa agtctatcca   6900
tcatcaatgt tatgccacct tgtttaagtg cctcggtgat tgtctcccaa ccaaattgta   6960
tcaacttttc agcataggca ggatctgtac cctcttcgac caatttatca aagcatagta   7020
aagaccctgc ctgcaacatt ccgcacagaa tggtttgttc acccattaag tcactcttga   7080
cctcagctac gaaagaactc tctaacacac ccgctctatg acctccggtt gcggctgccc   7140
atgccttcgc aattgccata ccttcacctt tggggtcatt ttcaggatgt acggcgatca   7200
atgtaggtac accaaaaccc ctcttgtact cctctctgac ttccgtacct gggcactttg   7260
gtgcaaccat tacgactgtt atatcttttc tgatctgctc gcccacttca acgatattaa   7320
agccatgaga gtaacctaaa gctgccccat ccttcatcag cggttgaact gttcttacta   7380
cgtctgagtg aaccttatct ggtgttaggt taatcactaa atctgcctga gggatcagtt   7440
cttcgtaagt accaactttg aacccatttt ccgtcgcttt acgccaggag gccctctttt   7500
ctgcaattgc ctctttcctc aatgcatacg aaatatccag acctgaatct ctcatgttta   7560
aaccttggtt tagaccctga gcaccgcagc caacaattac tactttcttt ccttgcagat   7620
aagaagcacc atcagcaaac tcgtcccttc ccataaatct gcacttaccc agttgagcca   7680
attgttgtct caaatttaat gtgttaaaat agttggccat ctcgagtcga aactaagttc   7740
tggtgtttta aaactaaaaa aaagactaac tataaaagta gaatttaaga agtttaagaa   7800
atagatttac agaattacaa tcaataccta ccgtctttat atacttatta gtcaagtagg   7860
ggaataattt cagggaactg gtttcaacct tttttttcag ctttttccaa atcagagaga   7920
gcagaaggta atagaaggtg taagaaaatg agatagatac atgcgtgggt caattgcctt   7980
gtgtcatcat ttactccagg caggttgcat cactccattg aggttgtgcc cgtttttttgc  8040
ctgtttgtgc ccctgttctc tgtagttgcg ctaagagaat ggacctatga actgatggtt   8100
ggtgaagaaa acaatatttt ggtgctggga ttcttttttt ttctggatgc cagcttaaaa   8160
agcgggctcc attatattta gtggatgcca ggaataaact gttcacccag acacctacga   8220
tgttatatat tctgtgtaac ccgcccccta ttttgggcat gtacgggtta cagcagaatt   8280
aaaaggctaa ttttttgact aaataaagtt aggaaaatca ctactattaa ttatttacgt   8340
attctttgaa atggcgagta ttgataatga taaactggat ccgcggccgc ttacagatca   8400
gtaacacacc cttccgatgc aggacgggtt aatttagcga attttgccaa aactcccctg   8460
gtggctttcg gagttggctt ctgataatta gctcttctct ttgcgatttc ttcatcggaa   8520
actttcaggg atatagagtt gttgactgca tctatctcta ttatatcgtc atcttcaact   8580
aagccgatta gtccaccctc aacggcttca ggcacaatat ggccgacaac aaaaccgtga   8640
gtgccaccgg agaatctacc atccgtaatt aacgcgcaac ttttccctaa acccgcacca   8700
attaatgctg atgtaggctt cagcatttcg ggcataccag gtccgccgac gggacctata   8760
ttcctaatta ccgctacatc tccagcatgc aaacgaccag attctatgcc gtcgataaaa   8820
```

-continued

```
tgttgttcac catcaaagac tctggcagtg cctttgaaga actctccttc tttaccgcta   8880
atttttgcta cggaaccccc ttgagctaaa ttaccgtaca gaatctgcaa gtggccggtg   8940
gccttgatag gattctttag tggcctcatg atatcttgtg agtcgaaatc caagtctagg   9000
gcagtctcga cattctcggc taatgtttta cccgtcacag taaggcagtc accatgcaat   9060
tttccttcct ttagaaggta cttaagcact gctggcaagc ctccaatttt atgcaaatct   9120
tccatcatat atttacctga aggtttaaaa tcacctagta ctggagtaat gtcactaatt   9180
ctttggaagt catcctgagt tatttcgaca cctatcgcgt tagccattgc aataatatgc   9240
aagacagcat tagtactacc ccccaagacc atcacaatgg taatagcgtt ctcgaacgcc   9300
tccttagtca ttatatcact aggcttgatg tctttttcca aaagattctt aatggctaat   9360
ccaatctcat cacattcttc ttgtttttct tgagatactg cagggttcga agaagaatac   9420
ggcaatgaca tacctagtgt ttcgatagcg gcagctaagg tattagctgt gtacatcccc   9480
ccacatgccc cttgaccagg aatagcatta caaataacac cgtgataatc ttcatcagag   9540
atattgccgg taattttctg gcctagagat tcaaaagccg atacgatgtt caatttctca   9600
cctttatatt caccgtgttc tattgttcct ccatacacca taatgcttgg cctattaagt   9660
cttgccatac caataataga acctggcata tttttgtcac aacctgggat ggctacaatt   9720
gcatcatagt attcagcgcc agcgttggtt tcaatagagt cagctataac ttctctggaa   9780
acaagggagt atctcattcc caactttcca tttgctatcc catcagaaac tcctatcgta   9840
tgaaattgta agccgatcag accatctgtc tgatttactg agcttttaat ctttgatcca   9900
agggttccta aatgcatgtt gcatggattt ccatcccagt ccatcgacac tatacccact   9960
tgagctttct tgaaatcttc gtctttaaac ccgatgccgt aatacattgc ctgtgtggcg  10020
ggttgtgtgg gatcttgtgt caacgttttg ctgtacttat tcagttcaac agattcaact  10080
ttgccgttat acttaaactc catgtcgaca aacttagatt agattgctat gctttctttc  10140
taatgagcaa gaagtaaaaa aagttgtaat agaacaagaa aaatgaaact gaaacttgag  10200
aaattgaaga ccgtttatta acttaaatat caatgggagg tcatcgaaag agaaaaaaat  10260
caaaaaaaaa attttcaaga aaaagaaacg tgataaaaat ttttattgcc tttttcgacg  10320
aagaaaaaga aacgaggcgg tctctttttt cttttccaaa cctttagtac gggtaattaa  10380
cgacacccta gaggaagaaa gaggggaaat ttagtatgct gtgcttgggt gttttgaagt  10440
ggtacggcga tgcgcggagt ccgagaaaat ctggaagagt aaaaaaggag tagaaacatt  10500
ttgaagctat gagctccagc ttttgttccc tttagtgagg gttaattgcg cgcttggcgt  10560
aatcatggtc atagctgttt cctgtgtgaa attgttatcc gctcacaatt ccacacaaca  10620
taggagccgg aagcataaag tgtaaagcct ggggtgccta atgagtgagg taactcacat  10680
taattgcgtt gcgctcactg cccgctttcc agtcgggaaa cctgtcgtgc cagctgcatt  10740
aatgaatcgg ccaacgcgcg gggagaggcg gtttgcgtat tgggcgctct tccgcttcct  10800
cgctcactga ctcgctgcgc tcggtcgttc ggctgcggcg agcggtatca gctcactcaa  10860
aggcggtaat acggttatcc acagaatcag gggataacgc aggaaagaac atgtgagcaa  10920
aaggccagca aaaggccagg aaccgtaaaa aggccgcgtt gctggcgttt ttccataggc  10980
tccgcccccc tgacgagcat cacaaaaatc gacgctcaag tcagaggtgg cgaaacccga  11040
caggactata aagataccag gcgtttcccc ctggaagctc cctcgtgcgc tctcctgttc  11100
cgaccctgcc gcttaccgga tacctgtccg cctttctccc ttcgggaagc gtggcgcttt  11160
ctcatagctc acgctgtagg tatctcagtt cggtgtaggt cgttcgctcc aagctgggct  11220
```

-continued

```
gtgtgcacga acccccgtt cagcccgacc gctgcgcctt atccggtaac tatcgtcttg  11280
agtccaaccc ggtaagacac gacttatcgc cactggcagc agccactggt aacaggatta  11340
gcagagcgag gtatgtaggc ggtgctacag agttcttgaa gtggtggcct aactacggct  11400
acactagaag gacagtattt ggtatctgcg ctctgctgaa gccagttacc ttcggaaaaa  11460
gagttggtag ctcttgatcc ggcaaacaaa ccaccgctgg tagcggtggt ttttttgttt  11520
gcaagcagca gattacgcgc agaaaaaaag gatctcaaga agatcctttg atcttttcta  11580
cggggtctga cgctcagtgg aacgaaaact cacgttaagg gattttggtc atgagattat  11640
caaaaaggat cttcacctag atccttttaa attaaaaatg aagttttaaa tcaatctaaa  11700
gtatatatga gtaaacttgg tctgacagtt accaatgctt aatcagtgag gcacctatct  11760
cagcgatctg tctatttcgt tcatccatag ttgcctgact ccccgtcgtg tagataacta  11820
cgatacggga gggcttacca tctggcccca gtgctgcaat gataccgcga gacccacgct  11880
caccggctcc agatttatca gcaataaacc agccagccgg aagggccgag cgcagaagtg  11940
gtcctgcaac tttatccgcc tccatccagt ctattaattg ttgccgggaa gctagagtaa  12000
gtagttcgcc agttaatagt ttgcgcaacg ttgttgccat tgctacaggc atcgtggtgt  12060
cacgctcgtc gtttggtatg gcttcattca gctccggttc ccaacgatca aggcgagtta  12120
catgatcccc catgttgtgc aaaaaagcgg ttagctcctt cggtcctccg atcgttgtca  12180
gaagtaagtt ggccgcagtg ttatcactca tggttatggc agcactgcat aattctctta  12240
ctgtcatgcc atccgtaaga tgcttttctg tgactggtga gtactcaacc aagtcattct  12300
gagaatagtg tatgcggcga ccgagttgct cttgcccggc gtcaatacgg gataataccg  12360
cgccacatag cagaacttta aaagtgctca tcattggaaa acgttcttcg gggcgaaaac  12420
tctcaaggat cttaccgctg ttgagatcca gttcgatgta acccactcgt gcacccaact  12480
gatcttcagc atcttttact ttcaccagcg tttctgggtg agcaaaaaca ggaaggcaaa  12540
atgccgcaaa aaagggaata agggcgacac ggaaatgttg aatactcata ctcttccttt  12600
ttcaatatta ttgaagcatt tatcagggtt attgtctcat gagcggatac atatttgaat  12660
gtatttagaa aaataaacaa ataggggttc cgcgcacatt tccccgaaaa gtgccacctg  12720
aacgaagcat ctgtgcttca ttttgtagaa caaaaatgca acgcgagagc gctaattttt  12780
caaacaaaga atctgagctg catttttaca gaacagaaat gcaacgcgaa agcgctattt  12840
taccaacgaa gaatctgtgc ttcatttttg taaaacaaaa atgcaacgcg agagcgctaa  12900
tttttcaaac aaagaatctg agctgcattt ttacagaaca gaaatgcaac gcgagagcgc  12960
tattttacca acaaagaatc tatacttctt ttttgttcta caaaaatgca tcccgagagc  13020
gctatttttc taacaaagca tcttagatta cttttttct cctttgtgcg ctctataatg  13080
cagtctcttg ataacttttt gcactgtagg tccgttaagg ttagaagaag gctactttgg  13140
tgtctatttt ctcttccata aaaaaagcct gactccactt cccgcgttta ctgattacta  13200
gcgaagctgc gggtgcattt tttcaagata aaggcatccc cgattatatt ctataccgat  13260
gtggattgcg catactttgt gaacagaaag tgatagcgtt gatgattctt cattggtcag  13320
aaaattatga acggtttctt ctattttgtc tctatatact acgtatagga aatgtttaca  13380
ttttcgtatt gttttcgatt cactctatga atagttctta ctacaatttt tttgtctaaa  13440
gagtaatact agagataaac ataaaaaatg tagaggtcga gtttagatgc aagttcaagg  13500
agcgaaaggt ggatgggtag gttatatagg gatatagcac agagatatat agcaaagaga  13560
tacttttgag caatgtttgt ggaagcggta ttcgcaatat tttagtagct cgttacagtc  13620
```

```
cggtgcgttt ttggtttttt gaaagtgcgt cttcagagcg cttttggttt tcaaaagcgc  13680
tctgaagttc ctatactttc tagagaatag gaacttcgga ataggaactt caaagcgttt  13740
ccgaaaacga gcgcttccga aaatgcaacg cgagctgcgc acatacagct cactgttcac  13800
gtcgcaccta tatctgcgtg ttgcctgtat atatatatac atgagaagaa cggcatagtg  13860
cgtgtttatg cttaaatgcg tacttatatg cgtctattta tgtaggatga aaggtagtct  13920
agtacctcct gtgatattat cccattccat gcggggtatc gtatgcttcc ttcagcacta  13980
ccctttagct gttctatatg ctgccactcc tcaattggat tagtctcatc cttcaatgct  14040
atcatttcct ttgata                                                  14056
```

<210> SEQ ID NO 58
<211> LENGTH: 1716
<212> TYPE: DNA
<213> ORGANISM: Bacillus subtilis

<400> SEQUENCE: 58

```
atgttgacta aagctacaaa agagcagaaa tcattggtga aaaatagggg tgcagaactt     60
gttgtggact gtttggtaga acagggcgta acacatgttt ttggtatccc aggtgcaaaa    120
atcgacgccg tgtttgatgc attacaagac aagggtccag aaattattgt tgctagacat    180
gagcaaaatg ccgcatttat ggcgcaagct gtaggtaggc ttacaggtaa acctggtgtt    240
gtcctagtta cgtctggccc aggagcctcc aatttagcaa ctggtctatt gacagctaat    300
actgagggag atcctgtagt tgcgttagcc ggtaatgtaa ttagagctga taggcttaag    360
agaactcacc agtctctaga caacgctgct ttattccaac cgatcaccaa gtactcagta    420
gaggtacaag acgtaaagaa tatacctgaa gctgtgacaa acgcatttcg tatagcttct    480
gctggtcagg ctggtgccgc gtttgtttct tttcctcaag acgttgtcaa tgaagtgacc    540
aatactaaaa acgttagagc ggttgcagcc cctaaactag gtccagccgc agacgacgca    600
attagcgctg caattgctaa aattcagacg gcgaaactac cagtagtcct tgtcggtatg    660
aagggcggaa gaccagaagc aataaaagct gttcgtaagt tattgaagaa agtccaatta    720
cctttcgttg agacttacca agcagcaggt actttatcta gagatttaga ggatcagtat    780
tttggaagga taggtctatt tagaaaccaa ccaggagatt tactattaga acaagctgat    840
gttgtactta ctatcggtta tgatcctata gagtatgacc caaagttttg gaacataaat    900
ggggatagaa caattataca tctagacgag ataatcgccg acatcgatca cgcttatcaa    960
ccagatttag aactaatcgg agatatcccg tcaacaatca atcatattga acatgatgct   1020
gtaaaggttg agttcgctga acgtgagcag aaaatcttat ctgatctaaa gcaatatatg   1080
catgagggtg aacaagttcc agcagactgg aaatctgacc gtgcacatcc tttggaaatc   1140
gttaaggaac taagaaatgc ggtcgatgat catgtgactg ttacatgtga tatcggttca   1200
catgcaattt ggatgtcacg ttattttagg agctacgaac cattaacttt aatgatatct   1260
aacgggatgc aaactctggg ggttgcactt ccttgggcta ttggcgctag tttagttaag   1320
cccggtgaga aggtggtatc ggtatcaggt gatggtggct ttctgttttc ggctatggaa   1380
ttagaaactg cagtccgttt aaaagctccc attgtgcata ttgtctggaa tgattctact   1440
tacgacatgg ttgcttttca acagttgaag aaatacaata gaacttcggc tgtagacttt   1500
ggtaacatcg atattgtgaa atatgctgag tcttttggcg caacaggcct gagggtggaa   1560
agtccagatc agttagctga tgtgttgaga caagggatga atgccgaggg accggtaatc   1620
atagatgtgc cagttgacta ctcagacaat attaatttgg cttctgataa acttcctaaa   1680
```

gagtttggcg agctaatgaa gaccaaagcc ttataa 1716

<210> SEQ ID NO 59
<211> LENGTH: 1647
<212> TYPE: DNA
<213> ORGANISM: Lactococcus lactis

<400> SEQUENCE: 59
atgtatactg ttggtgatta tctgctggac cgtctgcatg aactgggtat cgaagaaatc 60
ttcggcgttc cgggtgatta caatctgcag ttcctggatc agatcatctc tcataaagac 120
atgaaatggg tgggtaacgc taacgaactg aacgcaagct acatggcaga tggttatgca 180
cgtaccaaga aagccgcggc atttctgacc actttcggtg ttggcgaact gagcgccgtc 240
aacggtctgg cgggctccta cgccgaaaac ctgccggtgg tggagatcgt aggcagccca 300
acgagcaaag ttcagaacga aggtaaattc gtccaccaca ctctggctga cggcgatttc 360
aaacacttca tgaaaatgca tgaacctgtg actgcggcac gtacgctgct gactgcagag 420
aacgctactg tggaaatcga ccgcgttctg tctgcgctgc tgaaagaacg caaaccagtt 480
tacatcaacc tgcctgtgga tgttgcggca gctaaagcgg aaaaaccgag cctgccgctg 540
aagaaagaaa actccacttc taacactagc gaccaggaaa tcctgaacaa aatccaggag 600
tctctgaaaa acgcaaagaa accaatcgtg atcaccggcc acgaaatcat ttcttttggt 660
ctggagaaga ccgtgaccca attcatcagc aaaaccaaac tgccgattac caccctgaac 720
ttcggcaagt cctctgttga cgaggctctg ccgtctttcc tgggcatcta caacggtact 780
ctgagcgaac cgaacctgaa agaatttgtt gaatctgcgg acttcatcct gatgctgggc 840
gttaaactga ccgactcttc taccggtgca ttcactcacc atctgaacga aaacaaaatg 900
attagcctga acatcgacga gggtaaaatc ttcaacgagc gtatccagaa cttcgacttc 960
gaaagcctga tcagctctct gctggacctg tccgaaatcg agtataaagg caaatacatt 1020
gacaaaaagc aagaagattt cgtaccatct aacgcactgc tgtcccagga tcgcctgtgg 1080
caggccgtgg agaacctgac ccagagcaat gaaaccatcg tggcggaaca aggtacgagc 1140
tttttcggcg cgtcttctat ctttctgaaa tccaaaagcc attttatcgg tcagccgctg 1200
tggggtagca ttggctatac tttcccggca gcgctgggct ctcagatcgc tgataaagaa 1260
tctcgtcatc tgctgttcat cggtgacggt tccctgcagc tgaccgtaca ggaactgggt 1320
ctggcaattc gtgaaaagat caacccgatt tgcttcatta ttaacaatga cggctacacc 1380
gttgagcgtg agatccacgg tccgaaccag tcttacaacg atatccctat gtggaactac 1440
tctaaactgc cggagtcctt cggcgcaact gaggaccgtg ttgtgtctaa aattgtgcgt 1500
accgaaaacg aatttgtgag cgtgatgaaa gaggcccagg ccgatccgaa ccgtatgtac 1560
tggatcgaac tgatcctggc gaaagaaggc gcaccgaagg tactgaagaa aatgggcaag 1620
ctgtttgctg aacagaataa atcctaa 1647

<210> SEQ ID NO 60
<211> LENGTH: 771
<212> TYPE: DNA
<213> ORGANISM: Drosophila melanogaster

<400> SEQUENCE: 60
atgtcgttta ctttgaccaa caagaacgtg attttcgttg ccggtctggg aggcattggt 60
ctggacacca gcaaggagct gctcaagcgc gatctgaaga acctggtgat cctcgaccgc 120
attgagaacc cggctgccat tgccgagctg aaggcaatca atccaaaggt gaccgtcacc 180

```
ttctacccct atgatgtgac cgtgcccatt gccgagacca ccaagctgct gaagaccatc    240

ttcgcccagc tgaagaccgt cgatgtcctg atcaacggag ctggtatcct ggacgatcac    300

cagatcgagc gcaccattgc cgtcaactac actggcctgg tcaacaccac gacggccatt    360

ctggacttct gggacaagcg caagggcggt cccggtggta tcatctgcaa cattggatcc    420

gtcactggat tcaatgccat ctaccaggtg cccgtctact ccggcaccaa ggccgccgtg    480

gtcaacttca ccagctccct ggcgaaactg gcccccatta ccggcgtgac ggcttacact    540

gtgaaccccg gcatcacccg caccaccctg gtgcacacgt tcaactcctg gttggatgtt    600

gagcctcagg ttgccgagaa gctcctggct catcccaccc agccctcgtt ggcctgcgcc    660

gagaacttcg tcaaggctat cgagctgaac cagaacggag ccatctggaa actggacttg    720

ggcaccctgg aggccatcca gtggaccaag cactgggact ccggcatcta a             771
```

<210> SEQ ID NO 61
<211> LENGTH: 1476
<212> TYPE: DNA
<213> ORGANISM: Artificial Sequence
<220> FEATURE:
<223> OTHER INFORMATION: Ec_ilvC_coSc_Q110V

<400> SEQUENCE: 61

```
atggccaact attttaacac attaaatttg agacaacaat tggctcaact gggtaagtgc     60

agatttatgg gaagggacga gtttgctgat ggtgcttctt atctgcaagg aaagaaagta    120

gtaattgttg gctgcggtgc tcagggtcta aaccaaggtt taaacatgag agattcaggt    180

ctggatattt cgtatgcatt gaggaaagag gcaattgcag aaaagagggc ctcctggcgt    240

aaagcgacgg aaaatgggtt caaagttggt acttacgaag aactgatccc tcaggcagat    300

ttagtgatta acctaacacc agataaggtt cactcagacg tagtaagaac agttcaaccg    360

ctgatgaagg atggggcagc tttaggttac tctcatggct ttaatatcgt tgaagtgggc    420

gagcagatca gaaaagatat aacagtcgta atggttgcac caaagtgccc aggtacggaa    480

gtcagagagg agtacaagag ggttttggt gtacctacat tgatcgccgt acatcctgaa    540

aatgacccca aaggtgaagg tatggcaatt gcgaaggcat gggcagccgc aaccggaggt    600

catagagcgg gtgtgttaga gagttctttc gtagctgagg tcaagagtga cttaatgggt    660

gaacaaacca ttctgtgcgg aatgttgcag gcagggtctt tactatgctt tgataaattg    720

gtcgaagagg gtacagatcc tgcctatgct gaaaagttga tacaatttgg ttgggagaca    780

atcaccgagg cacttaaaca aggtggcata acattgatga tggatagact ttcaaatccg    840

gccaagctaa gagcctacgc cttatctgag caactaaaag agatcatggc accattattc    900

caaaagcaca tggacgatat tatctccggt gagttttcct caggaatgat ggcagattgg    960

gcaaacgatg ataaaaagtt attgacgtgg agagaagaaa ccggcaagac ggcattcgag   1020

acagccccac aatacgaagg taaaattggt gaacaagaat actttgataa gggagtattg   1080

atgatagcta tggtgaaggc aggggtagaa cttgcattcg aaactatggt tgactccggt   1140

atcattgaag aatctgcata ctatgagtct ttgcatgaat tgcctttgat agcaaatact   1200

attgcaagaa aaagacttta cgagatgaat gttgtcatat cagacactgc agaatatggt   1260

aattacttat ttagctacgc atgtgtcccg ttgttaaagc ccttcatggc cgagttacaa   1320

cctggtgatt tggggaaggc tattccggaa ggagcggttg acaatggcca actgagagac   1380

gtaaatgaag ctattcgttc acatgctata gaacaggtgg gtaaaaagct gagaggatat   1440

atgaccgata tgaaaagaat tgcagtggca ggatga                             1476
```

<210> SEQ ID NO 62
<211> LENGTH: 1698
<212> TYPE: DNA
<213> ORGANISM: Artificial Sequence
<220> FEATURE:
<223> OTHER INFORMATION: Sc_ILV3 N20 deletion

<400> SEQUENCE: 62

```
atgaagaagc tcaacaagta ctcgtatatc atcactgaac ctaagggcca aggtgcgtcc     60
caggccatgc tttatgccac cggtttcaag aaggaagatt tcaagaagcc tcaagtcggg    120
gttggttcct gttggtggtc cggtaaccca tgtaacatgc atctattgga cttgaataac    180
agatgttctc aatccattga aaaagcgggt ttgaaagcta tgcagttcaa caccatcggt    240
gtttcagacg gtatctctat gggtactaaa ggtatgagat actcgttaca aagtagagaa    300
atcattgcag actcctttga aaccatcatg atggcacaac actacgatgc taacatcgcc    360
atcccatcat gtgacaaaaa catgcccggt gtcatgatgg ccatgggtag acataacaga    420
ccttccatca tggtatatgg tggtactatc ttgcccggtc atccaacatg tggttcttcg    480
aagatctcta aaaacatcga tatcgtctct gcgttccaat cctacggtga atatatttcc    540
aagcaattca ctgaagaaga aagagaagat gttgtggaac atgcatgccc aggtcctggt    600
tcttgtggtg gtatgtatac tgccaacaca atggcttctg ccgctgaagt gctaggtttg    660
accattccaa actcctcttc cttcccagcc gtttccaagg agaagttagc tgagtgtgac    720
aacattggtg aatacatcaa gaagacaatg gaattgggta ttttacctcg tgatatcctc    780
acaaaagagg cttttgaaaa cgccattact tatgtcgttg caaccggtgg gtccactaat    840
gctgttttgc atttggtggc tgttgctcac tctgcgggtg tcaagttgtc accagatgat    900
ttccaaagaa tcagtgatac tacaccattg atcggtgact tcaaaccttc tggtaaatac    960
gtcatggccg atttgattaa cgttggtggt acccaatctg tgattaagta tctatatgaa   1020
aacaacatgt tgcacggtaa cacaatgact gttaccggtg acactttggc agaacgtgca   1080
aagaaagcac caagcctacc tgaaggacaa gagattatta agccactctc ccacccaatc   1140
aaggccaacg gtcacttgca aattctgtac ggttcattgg caccaggtgg agctgtgggt   1200
aaaattaccg gtaaggaagg tacttacttc aagggtagag cacgtgtgtt cgaagaggaa   1260
ggtgccttta ttgaagcctt ggaaagaggt gaaatcaaga agggtgaaaa aaccgttgtt   1320
gttatcagat atgaaggtcc aagaggtgca ccaggtatgc ctgaaatgct aaagccttcc   1380
tctgctctga tgggttacgg tttgggtaaa gatgttgcat tgttgactga tggtagattc   1440
tctggtggtt ctcacgggtt cttaatcggc cacattgttc ccgaagccgc tgaaggtggt   1500
cctatcgggt tggtcagaga cggcgatgag attatcattg atgctgataa taacaagatt   1560
gacctattag tctctgataa ggaaatggct caacgtaaac aaagttgggt tgcacctcca   1620
cctcgttaca caagaggtac tctatccaag tatgctaagt tggtttccaa cgcttccaac   1680
ggttgtgttt tagatgct                                                 1698
```

<210> SEQ ID NO 63
<211> LENGTH: 14056
<212> TYPE: DNA
<213> ORGANISM: Artificial Sequence
<220> FEATURE:
<223> OTHER INFORMATION: pGV2247

<400> SEQUENCE: 63

```
ttggatcata ctaagaaacc attattatca tgacattaac ctataaaaat aggcgtatca     60
```

```
cgaggccctt tcgtctcgcg cgtttcggtg atgacggtga aaacctctga cacatgcagc    120
tcccggagac ggtcacagct tgtctgtaag cggatgccgg gagcagacaa gcccgtcagg    180
gcgcgtcagc gggtgttggc gggtgtcggg gctggcttaa ctatgcggca tcagagcaga    240
ttgtactgag agtgcaccat accacagctt ttcaattcaa ttcatcattt ttttttatt     300
cttttttttg atttcggttt ctttgaaatt tttttgattc ggtaatctcc gaacagaagg    360
aagaacgaag gaaggagcac agacttagat tggtatatat acgcatatgg caaattaaag    420
ccttcgagcg tcccaaaacc ttctcaagca aggttttcag tataatgtta catgcgtaca    480
cgcgtctgta cagaaaaaaa agaaaaattt gaaatataaa taacgttctt aatactaaca    540
taactataaa aaaataaata gggacctaga cttcaggttg tctaactcct tccttttcgg    600
ttagagcgga tgtggggggga gggcgtgaat gtaagcgtga cataactaat tacatgactc   660
gacctaggtt atttagtaaa atcaatgacc attcggcctt caatttttcc tgccttcatt    720
tcatcaataa tatcattgat ttcttccagt ttgcgtgtcg caacaattgg ttttacctta    780
ccttctgctc caaattgaaa agcttctgcc aagtcaagtc ttgttccgac aagtgaacct    840
gcaacctcca ctccgtcaaa aacaactgtt ggaactgata aagtcatctc agtattggga    900
agtgccacag caaccatttt gcccataggt ttcaaagaag caaccgcttg ttcaaaagca    960
atccttgcaa cagcacaaac tattgcactt tgcaccccta agccgccagt tattttttta   1020
atttcatcaa ctggatttac atcaccagaa ttgataatca catcagctcc aattttttta   1080
gctaaattta atttatcttg attaatatca acagcaatta cttttgctcc aaaaacattt   1140
ttagcatatt gaattgctaa atttccaagt cctccagcac caaaaattac ttgccaatca   1200
ccaggtttta ctcctgatac tttgattgct ttgtaagttg ttactccagc acaagtaatt   1260
gagctagctt caattgggtc aagtccgtca ggaactttga cagcataatc ggcaacaaca   1320
attgcttctt cagccattcc gccatcaact gaatatcctg catttttaac ttctcgacaa   1380
aaagtttcat taccagatac acagtattca cagtgaccac atccttcaaa gaaccaagcc   1440
actgaaaccc gatcaccaac ttgaagcgag cttacatcag ctccaatttc tttgacaatt   1500
ccaattcctt catgaccaag aacagtccct gctttgttgc cataatcacc tgctgcaacg   1560
tgcaaatcgg tatgacagac tccacaatac tccatgtcaa gcaaagcttc attaggtttg   1620
attgctcgaa gttccttttc aacaaggtcc gcataaccat ctggattgtg tcttactact   1680
gctgctttca ttggtaccta ttattgtatg ttatagtatt agttgcttgg tgttatgaaa   1740
gaaactaaga aaagaaaaat aaaataaaaa taaaagattg agacaaggga agaaaagata   1800
caaaataaga attaattaca attgcgtttg ctataaatac gtttttaaca atcaactctg   1860
gtaggaagat aatgcttttt ttttttatat atgcttggtg ccacttgtca catacaattc   1920
tacaaccttc gacaaaaatc caaatgatag taagatcaaa gccagaaagc aatggagaaa   1980
aaaaattaat gaaccacgat gaaccaaatg atcaatacaa ccaaagaaac taccctagtg   2040
aggtgtatgc tgacttggta tcacacttca tgaattttgc atatggcaaa gtccacgaaa   2100
gtgggcttca gaaaaaaggc gtgcggtgtg tagatgtatc aattagtgga tgccagtttt   2160
ggaacgggat tccactttcc gcaagttggt gcacgtcgtt agtgacataa cgccgcgttc   2220
atctttggga agaagcagat gctgagcgag gaggtactat agagtaaaga accctttcta   2280
tacccgcagc cccatggtaa gtgacagtgc agtaataata tgaaccaatt tatttttcgt   2340
tacataaaaa tgcttataaa actttaacta ataattagag attaaatcgc ggccgcaaaa   2400
gatccttagg atttattctg ttcagcaaac agcttgccca ttttcttcag taccttcggt   2460
```

-continued

```
gcgccttctt tcgccaggat cagttcgatc cagtacatac ggttcggatc ggcctgggcc   2520

tctttcatca cgctcacaaa ttcgttttcg gtacgcacaa ttttagacac aacacggtcc   2580

tcagttgcgc cgaaggactc cggcagttta gagtagttcc acatagggat atcgttgtaa   2640

gactggttcg gaccgtggat ctcacgctca acggtgtagc cgtcattgtt aataatgaag   2700

caaatcgggt tgatcttttc acgaattgcc agacccagtt cctgtacggt cagctgcagg   2760

gaaccgtcac cgatgaacag cagatgacga gattctttat cagcgatctg agagcccagc   2820

gctgccggga aagtatagcc aatgctaccc cacagcggct gaccgataaa atggcttttg   2880

gatttcagaa agatagaaga cgcgccgaaa aagctcgtac cttgttccgc cacgatggtt   2940

tcattgctct gggtcaggtt ctccacggcc tgccacaggc gatcctggga cagcagtgcg   3000

ttagatggta cgaaatcttc ttgctttttg tcaatgtatt tgcctttata ctcgatttcg   3060

gacaggtcca gcagagagct gatcaggctt tcgaagtcga agttctggat acgctcgttg   3120

aagattttac cctcgtcgat gttcaggcta atcattttgt tttcgttcag atggtgagtg   3180

aatgcaccgg tagaagagtc ggtcagttta acgcccagca tcaggatgaa gtccgcagat   3240

tcaacaaatt ctttcaggtt cggttcgctc agagtaccgt tgtagatgcc caggaaagac   3300

ggcagagcct cgtcaacaga ggacttgccg aagttcaggg tggtaatcgg cagtttggtt   3360

ttgctgatga attgggtcac ggtcttctcc agaccaaaag aaatgatttc gtggccggtg   3420

atcacgattg gtttctttgc gtttttcaga gactcctgga ttttgttcag gatttcctgg   3480

tcgctagtgt tagaagtgga gttttctttc ttcagcggca ggctcggttt ttccgcttta   3540

gctgccgcaa catccacagg caggttgatg taaactggtt tgcgttcttt cagcagcgca   3600

gacagaacgc ggtcgatttc cacagtagcg ttctctgcag tcagcagcgt acgtgccgca   3660

gtcacaggtt catgcatttt catgaagtgt ttgaaatcgc cgtcagccag agtgtggtgg   3720

acgaatttac cttcgttctg aactttgctc gttgggctgc ctacgatctc caccaccggc   3780

aggttttcgg cgtaggagcc cgccagaccg ttgacggcgc tcagttcgcc aacaccgaaa   3840

gtggtcagaa atgccgcggc tttcttggta cgtgcataac catctgccat gtagcttgcg   3900

ttcagttcgt tagcgttacc cacccatttc atgtctttat gagagatgat ctgatccagg   3960

aactgcagat tgtaatcacc cggaacgccg aagatttctt cgatacccag ttcatgcaga   4020

cggtccagca gataatcacc aacagtatac atgtcgagct tgttttatat ttgttgtaaa   4080

aagtagataa ttacttcctt gatgatctgt aaaaaagaga aaaagaaagc atctaagaac   4140

ttgaaaaact acgaattaga aaagaccaaa tatgtatttc ttgcattgac caatttatgc   4200

aagtttatat atatgtaaat gtaagtttca cgaggttcta ctaaactaaa ccaccccctt   4260

ggttagaaga aaagagtgtg tgagaacagg ctgttgttgt cacacgattc ggacaattct   4320

gtttgaaaga gagagagtaa cagtacgatc gaacgaactt tgctctggag atcacagtgg   4380

gcatcatagc atgtggtact aaaccctttc ccgccattcc agaaccttcg attgcttgtt   4440

acaaaacctg tgagccgtcg ctaggacctt gttgtgtgac gaaattggaa gctgcaatca   4500

ataggaagac aggaagtcga gcgtgtctgg gtttttttcag ttttgttctt tttgcaaaca   4560

aatcacgagc gacggtaatt tctttctcga taagaggcca cgtgctttat gagggtaaca   4620

tcaattcaag aaggagggaa acacttcctt tttctggccc tgataatagt atgagggtga   4680

agccaaaata aaggattcgc gcccaaatcg gcatctttaa atgcaggtat gcgatagttc   4740

ctcactcttt ccttactcac gagtaattct tgcaaatgcc tattatgcag atgttataat   4800

atctgtgcgt cttgagttga gcctagaatt cttagaaaaa ctcatcgagc atcaaatgaa   4860
```

```
actgcaattt attcatatca ggattatcaa taccatattt ttgaaaaagc cgtttctgta   4920
atgaaggaga aaactcaccg aggcagttcc ataggatggc aagatcctgg tatcggtctg   4980
cgatcccgac tcgtccaaca tcaatacaac ctattaattt cccctcgtca aaaataaggt   5040
tatcaagtga gaaatcacca tgagtgacga ctgaatccgg tgagaatggc aaaagcttat   5100
gcatttcttt ccagacttgt tcaacaggcc agccattacg ctcgtcatca aaatcactcg   5160
cgtcaaccaa accgttattc attcgtgatt gcgcctgagc gaggcgaaat acgcgatcgc   5220
tgttaaaagg acaattacaa acaggaatcg aatgcaaccg gcgcaggaac actgccagcg   5280
catcaacaat attttcacct gaatcaggat attcttctaa tacctggaat gctgttttgc   5340
cggggatcgc agtggtgagt aaccatgcat catcaggagt acggacaaaa tgcttgatgg   5400
tcggaagagg cataaattcc gtcagccagt ttagtctgac catctcatct gcaacatcat   5460
tggcaacgct acctttgcca tgtttcagaa acaactctgg cgcatcgggc ttcccataca   5520
atcgatagat tgtcgcacct gattgcccga cattatcgcg agcccattta tacccatata   5580
aatcagcatc catgttggaa tttaatcgcg gcctcgaaac gtgagtcttt tccttaccca   5640
tactagtttt tagtttatgt atgtgttttt tgtagttata gatttaagca agaaaagaat   5700
acaaacaaaa aattgaaaaa gattgattta gaattaaaaa gaaaaatatt tacgtaagaa   5760
gggaaaatag taaatgttgc aagttcacta aactcctaaa ttatgctgcc ctttatattc   5820
cctgttacag cagccgagcc aaaggtatat aggctccttt gcattagcat gcgtaacaaa   5880
ccacctgtca gtttcaaccg aggtggtatc cgagagaatt gtgtgattgc tttaattaat   5940
ttcggagaat ctcacatgcc actgaagatt aaaaactgga tgccagaaaa ggggtgtcca   6000
ggtgtaacat caatagagga agctgaaaag tcttagaacg ggtaatcttc caccaacctg   6060
atgggttcct agatataatc tcgaagggaa taagtagggt gataccgcag aagtgtctga   6120
atgtattaag gtcctcacag tttaaatccc gctcacacta acgtaggatt attataactc   6180
aaaaaaatgg cattattcta agtaagttaa atatccgtaa tctttaaaca gcggccgcgg   6240
atcttcatcc tgccactgca attcttttca tatcggtcat atatcctctc agctttttac   6300
ccacctgttc tatagcatgt gaacgaatag cttcatttac gtctctcagt tggccattgt   6360
caaccgctcc ttccggaata gccttcccca aatcaccagg ttgtaactcg gccatgaagg   6420
gctctaacaa cgggacacac gcgtagctaa ataagtaatt accatattct gcagtgtctg   6480
atatgacaac attcatctcg taaagtcttt ttcttgcaat agtatttgct atcaaaggca   6540
attcatgcaa agactcatag tatgcagatt cttcaatgat accggagtca accatagttt   6600
cgaatgcaag ttctacccct gccttcacca tagctatcat caatactccc ttatcaaagt   6660
attcttgttc accaatttta ccttcgtatt gtggggctgt ctcgaatgcc gtcttgccgg   6720
tttcttctct ccacgtcaat aactttttat catcgtttgc ccaatctgcc atcattcctg   6780
aggaaaactc accggagata atatcgtcca tgtgcttttg gaataatggt gccatgatct   6840
cttttagttg ctcagataag gcgtaggctc ttagcttggc cggatttgaa agtctatcca   6900
tcatcaatgt tatgccacct tgtttaagtg cctcggtgat tgtctcccaa ccaaattgta   6960
tcaacttttc agcataggca ggatctgtac cctcttcgac caatttatca aagcatagta   7020
aagaccctgc ctgcaacatt ccgcacagaa tggtttgttc acccattaag tcactcttga   7080
cctcagctac gaaagaactc tctaacacac ccgctctatg acctccggtt gcggctgccc   7140
atgccttcgc tattgccata ccttcacgtt tggggtcatt ttcaggatgt acggcgatca   7200
atgtaggtac accaaaaccc ctcttgtact cctctctgac ttccgtacct gggcactttg   7260
```

```
gcgcaaccat tacgactgtt atacctttc tgatctgctc gcccacttca acgatattaa   7320

agccatgaga gtaacctaaa gctgccccat ccttcatcag cggttgaact gttcttacta   7380

cgtctgagtg aaccttatct ggtgttaggt taatcactaa atctgcctga gggatcagtt   7440

cttcgtaagt accaactttg aacccatttt ccgtcgcttt acgccaatcg gcatcctttt   7500

ctgcaataga ctctttcctc aatgcatacg aaatatccag acctgaatct ctcatgttta   7560

aaccttggtt tagaccctga gcaccgcagc caacaattac tactttcttt ccttgcagat   7620

aagaagcacc atcagcaaac tcgtcccttc ccataaatct gcacttaccc agttgagcca   7680

attgttgtct caaatttaat gtgttaaaat agttggccat gtcgagtcga aactaagttc   7740

tggtgtttta aaactaaaaa aaagactaac tataaaagta gaatttaaga agtttaagaa   7800

atagatttac agaattacaa tcaataccta ccgtctttat atacttatta gtcaagtagg   7860

ggaataattt cagggaactg gtttcaacct tttttttcag ctttttccaa atcagagaga   7920

gcagaaggta atagaaggtg taagaaaatg agatagatac atgcgtgggt caattgcctt   7980

gtgtcatcat ttactccagg caggttgcat cactccattg aggttgtgcc cgtttttttgc   8040

ctgtttgtgc ccctgttctc tgtagttgcg ctaagagaat ggacctatga actgatggtt   8100

ggtgaagaaa acaatatttt ggtgctggga ttcttttttt ttctggatgc cagcttaaaa   8160

agcgggctcc attatattta gtggatgcca ggaataaact gttcacccag acacctacga   8220

tgttatatat tctgtgtaac ccgcccccta ttttgggcat gtacgggtta cagcagaatt   8280

aaaaggctaa ttttttgact aaataaagtt aggaaaatca ctactattaa ttatttacgt   8340

attctttgaa atggcgagta ttgataatga taaactggat ccgcggccgc ttacagatca   8400

gtaacacacc cttccgatgc aggacgggtt aatttagcga attttgccaa aactcccctg   8460

gtggctttcg gagttggctt ctgataatta gctcttctct ttgcgatttc ttcatcggaa   8520

actttcaggg atatagagtt gttgactgca tctatctcta ttatatcgtc atcttcaact   8580

aagccgatta gtccaccctc aacggcttca ggcacaatat ggccgacaac aaaaccgtga   8640

gtgccaccgg agaatctacc atccgtaatt aacgcgcaac ttttccctaa acccgcacca   8700

attaatgctg atgtaggctt cagcatttcg ggcataccag gtccgccgac gggacctata   8760

ttcctaatta ccgctacatc tccagcatgc aaacgaccag attctatgcc gtcgataaaa   8820

tgttgttcac catcaaagac tctggcagtg cctttgaaga actctccttc tttaccgcta   8880

atttttgcta cggaaccccc ttgagctaaa ttaccgtaca gaatctgcaa gtggccggtg   8940

gccttgatag gattctttag tggcctcatg atatcttgtg agtcgaaatc caagtctagg   9000

gcagtctcga cattctcggc taatgtttta cccgtcacag taaggcagtc accatgcaat   9060

tttccttcct ttagaaggta cttaagcact gctggcaagc ctccaatttt atgcaaatct   9120

tccatcatat atttacctga aggtttaaaa tcacctagta ctggagtaat gtcactaatt   9180

ctttggaagt catcctgagt tatttcgaca cctatcgcgt tagccattgc aataatatgc   9240

aagacagcat tagtactacc ccccaagacc atcacaatgg taatagcgtt ctcgaacgcc   9300

tccttagtca ttatatcact aggcttgatg tctttttcca aaagattctt aatggctaat   9360

ccaatctcat cacattcttc ttgtttttct tgagatactg cagggttcga agaagaatac   9420

ggcaatgaca tacctagtgt ttcgatagcg gcagctaagg tattagctgt gtacatcccc   9480

ccacatgccc cttgaccagg aatagcatta caaataacac cgtgataatc ttcatcagag   9540

atattgccgg taattttctg gcctagagat tcaaaagccg atacgatgtt caatttctca   9600

cctttatatt caccgtgttc tattgttcct ccatacacca taatgcttgg cctattaagt   9660
```

```
cttgccatac caataataga acctggcata tttttgtcac aacctgggat ggctacaatt    9720
gcatcatagt attcagcgcc agcgttggtt tcaatagagt cagctataac ttctctggaa    9780
acaagggagt atctcattcc caactttcca tttgctatcc catcagaaac tcctatcgta    9840
tgaaattgta agccgatcag accatctgtc tgatttactg agcttttaat ctttgatcca    9900
agggttccta aatgcatgtt gcatggattt ccatcccagt ccatcgacac tatacccact    9960
tgagctttct tgaaatcttc gtctttaaac ccgatgccgt aatacattgc ctgtgtggcg   10020
ggttgtgtgg gatcttgtgt caacgttttg ctgtacttat tcagttcaac agattcaact   10080
ttgccgttat acttaaactc catgtcgaca aacttagatt agattgctat gctttctttc   10140
taatgagcaa gaagtaaaaa aagttgtaat agaacaagaa aaatgaaact gaaacttgag   10200
aaattgaaga ccgtttatta acttaaatat caatgggagg tcatcgaaag agaaaaaaat   10260
caaaaaaaaa attttcaaga aaaagaaacg tgataaaaat ttttattgcc tttttcgacg   10320
aagaaaaaga aacgaggcgg tctctttttt cttttccaaa cctttagtac gggtaattaa   10380
cgacacccta gaggaagaaa gaggggaaat ttagtatgct gtgcttgggt gttttgaagt   10440
ggtacggcga tgcgcggagt ccgagaaaat ctggaagagt aaaaaaggag tagaaacatt   10500
ttgaagctat gagctccagc ttttgttccc tttagtgagg gttaattgcg cgcttggcgt   10560
aatcatggtc atagctgttt cctgtgtgaa attgttatcc gctcacaatt ccacacaaca   10620
taggagccgg aagcataaag tgtaaagcct ggggtgccta atgagtgagg taactcacat   10680
taattgcgtt gcgctcactg cccgctttcc agtcgggaaa cctgtcgtgc cagctgcatt   10740
aatgaatcgg ccaacgcgcg gggagaggcg gtttgcgtat tgggcgctct tccgcttcct   10800
cgctcactga ctcgctgcgc tcggtcgttc ggctgcggcg agcggtatca gctcactcaa   10860
aggcggtaat acggttatcc acagaatcag gggataacgc aggaaagaac atgtgagcaa   10920
aaggccagca aaaggccagg aaccgtaaaa aggccgcgtt gctggcgttt ttccataggc   10980
tccgcccccc tgacgagcat cacaaaaatc gacgctcaag tcagaggtgg cgaaacccga   11040
caggactata aagataccag gcgtttcccc ctggaagctc cctcgtgcgc tctcctgttc   11100
cgaccctgcc gcttaccgga tacctgtccg cctttctccc ttcgggaagc gtggcgcttt   11160
ctcatagctc acgctgtagg tatctcagtt cggtgtaggt cgttcgctcc aagctgggct   11220
gtgtgcacga accccccgtt cagcccgacc gctgcgcctt atccggtaac tatcgtcttg   11280
agtccaaccc ggtaagacac gacttatcgc cactggcagc agccactggt aacaggatta   11340
gcagagcgag gtatgtaggc ggtgctacag agttcttgaa gtggtggcct aactacggct   11400
acactagaag gacagtattt ggtatctgcg ctctgctgaa gccagttacc ttcggaaaaa   11460
gagttggtag ctcttgatcc ggcaaacaaa ccaccgctgg tagcggtggt ttttttgttt   11520
gcaagcagca gattacgcgc agaaaaaaag gatctcaaga agatcctttg atcttttcta   11580
cggggtctga cgctcagtgg aacgaaaact cacgttaagg gattttggtc atgagattat   11640
caaaaaggat cttcacctag atccttttaa attaaaaatg aagttttaaa tcaatctaaa   11700
gtatatatga gtaaacttgg tctgacagtt accaatgctt aatcagtgag gcacctatct   11760
cagcgatctg tctatttcgt tcatccatag ttgcctgact ccccgtcgtg tagataacta   11820
cgatacggga gggcttacca tctggcccca gtgctgcaat gataccgcga gacccacgct   11880
caccggctcc agatttatca gcaataaacc agccagccgg aagggccgag cgcagaagtg   11940
gtcctgcaac tttatccgcc tccatccagt ctattaattg ttgccgggaa gctagagtaa   12000
gtagttcgcc agttaatagt ttgcgcaacg ttgttgccat tgctacaggc atcgtggtgt   12060
```

```
cacgctcgtc gtttggtatg gcttcattca gctccggttc ccaacgatca aggcgagtta  12120
catgatcccc catgttgtgc aaaaaagcgg ttagctcctt cggtcctccg atcgttgtca  12180
gaagtaagtt ggccgcagtg ttatcactca tggttatggc agcactgcat aattctctta  12240
ctgtcatgcc atccgtaaga tgcttttctg tgactggtga gtactcaacc aagtcattct  12300
gagaatagtg tatgcggcga ccgagttgct cttgcccggc gtcaatacgg gataataccg  12360
cgccacatag cagaacttta aaagtgctca tcattggaaa acgttcttcg gggcgaaaac  12420
tctcaaggat cttaccgctg ttgagatcca gttcgatgta acccactcgt gcacccaact  12480
gatcttcagc atcttttact ttcaccagcg tttctgggtg agcaaaaaca ggaaggcaaa  12540
atgccgcaaa aaagggaata agggcgacac ggaaatgttg aatactcata ctcttccttt  12600
ttcaatatta ttgaagcatt tatcagggtt attgtctcat gagcggatac atatttgaat  12660
gtatttagaa aaataaacaa ataggggttc cgcgcacatt tccccgaaaa gtgccacctg  12720
aacgaagcat ctgtgcttca ttttgtagaa caaaaatgca acgcgagagc gctaattttt  12780
caaacaaaga atctgagctg catttttaca gaacagaaat gcaacgcgaa agcgctattt  12840
taccaacgaa gaatctgtgc ttcatttttg taaaacaaaa atgcaacgcg agagcgctaa  12900
tttttcaaac aaagaatctg agctgcattt ttacagaaca gaaatgcaac gcgagagcgc  12960
tattttacca acaaagaatc tatacttctt ttttgttcta caaaaatgca tcccgagagc  13020
gctatttttc taacaaagca tcttagatta cttttttctc cctttgtgcg ctctataatg  13080
cagtctcttg ataacttttt gcactgtagg tccgttaagg ttagaagaag gctactttgg  13140
tgtctatttt ctcttccata aaaaaagcct gactccactt cccgcgttta ctgattacta  13200
gcgaagctgc gggtgcattt tttcaagata aaggcatccc cgattatatt ctataccgat  13260
gtggattgcg catactttgt gaacagaaag tgatagcgtt gatgattctt cattggtcag  13320
aaaattatga acggtttctt ctattttgtc tctatatact acgtatagga aatgtttaca  13380
ttttcgtatt gttttcgatt cactctatga atagttctta ctacaatttt tttgtctaaa  13440
gagtaatact agagataaac ataaaaaatg tagaggtcga gtttagatgc aagttcaagg  13500
agcgaaaggt ggatgggtag gttatatagg gatatagcac agagatatat agcaaagaga  13560
tacttttgag caatgtttgt ggaagcggta ttcgcaatat tttagtagct cgttacagtc  13620
cggtgcgttt ttggtttttt gaaagtgcgt cttcagagcg cttttggttt tcaaaagcgc  13680
tctgaagttc ctatactttc tagagaatag gaacttcgga ataggaactt caaagcgttt  13740
ccgaaaacga gcgcttccga aaatgcaacg cgagctgcgc acatacagct cactgttcac  13800
gtcgcaccta tatctgcgtg ttgcctgtat atatatatac atgagaagaa cggcatagtg  13860
cgtgtttatg cttaaatgcg tacttatatg cgtctattta tgtaggatga aaggtagtct  13920
agtacctcct gtgatattat cccattccat gcggggtatc gtatgcttcc ttcagcacta  13980
ccctttagct gttctatatg ctgccactcc tcaattggat tagtctcatc cttcaatgct  14040
atcatttcct ttgata                                                  14056
```

<210> SEQ ID NO 64
<211> LENGTH: 1476
<212> TYPE: DNA
<213> ORGANISM: Artificial Sequence
<220> FEATURE:
<223> OTHER INFORMATION: Ec_ilvC_coSc_P2D1-A1

<400> SEQUENCE: 64

```
atggccaact attttaacac attaaatttg agacaacaat tggctcaact gggtaagtgc     60
```

```
agatttatgg gaagggacga gtttgctgat ggtgcttctt atctgcaagg aaagaaagta    120

gtaattgttg gctgcggtgc tcagggtcta aaccaaggtt taaacatgag agattcaggt    180

ctggatattt cgtatgcatt gaggaaagag tctattgcag aaaaggatgc cgattggcgt    240

aaagcgacgg aaaatgggtt caaagttggt acttacgaag aactgatccc tcaggcagat    300

ttagtgatta acctaacacc agataaggtt cactcagacg tagtaagaac agttcaaccg    360

ctgatgaagg atggggcagc tttaggttac tctcatggct ttaatatcgt tgaagtgggc    420

gagcagatca gaaaaggtat aacagtcgta atggttgcgc caaagtgccc aggtacggaa    480

gtcagagagg agtacaagag ggttttggt gtacctacat tgatcgccgt acatcctgaa     540

aatgacccca aacgtgaagg tatggcaata gcgaaggcat gggcagccgc aaccggaggt    600

catagagcgg gtgtgttaga gagttctttc gtagctgagg tcaagagtga cttaatgggt    660

gaacaaacca ttctgtgcgg aatgttgcag gcagggtctt tactatgctt tgataaattg    720

gtcgaagagg gtacagatcc tgcctatgct gaaaagttga tacaatttgg ttgggagaca    780

atcaccgagg cacttaaaca aggtggcata acattgatga tggatagact ttcaaatccg    840

gccaagctaa gagcctacgc cttatctgag caactaaaag agatcatggc accattattc    900

caaaagcaca tggacgatat tatctccggt gagttttcct caggaatgat ggcagattgg    960

gcaaacgatg ataaaaagtt attgacgtgg agagaagaaa ccggcaagac ggcattcgag   1020

acagccccac aatacgaagg taaaattggt gaacaagaat actttgataa gggagtattg   1080

atgatagcta tggtgaaggc aggggtagaa cttgcattcg aaactatggt tgactccggt   1140

atcattgaag aatctgcata ctatgagtct ttgcatgaat tgcctttgat agcaaatact   1200

attgcaagaa aaagacttta cgagatgaat gttgtcatat cagacactgc agaatatggt   1260

aattacttat ttagctacgc gtgtgtcccg ttgttagagc ccttcatggc cgagttacaa   1320

cctggtgatt tggggaaggc tattccggaa ggagcggttg acaatggcca actgagagac   1380

gtaaatgaag ctattcgttc acatgctata gaacaggtgg gtaaaaagct gagaggatat   1440

atgaccgata tgaaaagaat tgcagtggca ggatga                             1476

<210> SEQ ID NO 65
<211> LENGTH: 1713
<212> TYPE: DNA
<213> ORGANISM: Artificial Sequence
<220> FEATURE:
<223> OTHER INFORMATION: Ll_ilvD_coSc

<400> SEQUENCE: 65

atggagttta agtataacgg caaagttgaa tctgttgaac tgaataagta cagcaaaacg     60

ttgacacaag atcccacaca acccgccaca caggcaatgt attacggcat cgggtttaaa    120

gacgaagatt tcaagaaagc tcaagtgggt atagtgtcga tggactggga tggaaatcca    180

tgcaacatgc atttaggaac ccttggatca aagattaaaa gctcagtaaa tcagacagat    240

ggtctgatcg gcttacaatt tcatacgata ggagtttctg atgggatagc aaatggaaag    300

ttgggaatga gatactccct tgtttccaga gaagttatag ctgactctat tgaaaccaac    360

gctggcgctg aatactatga tgcaattgta gccatcccag gttgtgacaa aaatatgcca    420

ggttctatta ttggtatggc aagacttaat aggccaagca ttatggtgta tggaggaaca    480

atagaacacg gtgaatataa aggtgagaaa ttgaacatcg tatcggcttt tgaatctcta    540

ggccagaaaa ttaccggcaa tatctctgat gaagattatc acggtgttat ttgtaatgct    600

attcctggtc aaggggcatg tgggggggatg tacacagcta ataccttagc tgccgctatc   660
```

```
gaaacactag gtatgtcatt gccgtattct tcttcgaacc ctgcagtatc tcaagaaaaa    720
caagaagaat gtgatgagat tggattagcc attaagaatc ttttggaaaa agacatcaag    780
cctagtgata taatgactaa ggaggcgttc gagaacgcta ttaccattgt gatggtcttg    840
gggggtagta ctaatgctgt cttgcatatt attgcaatgg ctaacgcgat aggtgtcgaa    900
ataactcagg atgacttcca aagaattagt gacattactc cagtactagg tgattttaaa    960
ccttcaggta aatatatgat ggaagatttg cataaaattg gaggcttgcc agcagtgctt   1020
aagtaccttc taaaggaagg aaaattgcat ggtgactgcc ttactgtgac gggtaaaaca   1080
ttagccgaga atgtcgagac tgccctagac ttggatttcg actcacaaga tatcatgagg   1140
ccactaaaga atcctatcaa ggccaccggc cacttgcaga ttctgtacgg taatttagct   1200
caagggggtt ccgtagcaaa aattagcggt aaagaaggag agttcttcaa aggcactgcc   1260
agagtctttg atggtgaaca acattttatc gacggcatag aatctggtcg tttgcatgct   1320
ggagatgtag cggtaattag gaatataggt cccgtcggcg gacctggtat gcccgaaatg   1380
ctgaagccta catcagcatt aattggtgcg ggtttaggga aaagttgcgc gttaattacg   1440
gatggtagat tctccggtgg cactcacggt tttgttgtcg gccatattgt gcctgaagcc   1500
gttgagggtg gactaatcgg cttagttgaa gatgacgata taatagagat agatgcagtc   1560
aacaactcta tatccctgaa agtttccgat gaagaaatcg caaagagaag agctaattat   1620
cagaagccaa ctccgaaagc caccagggga gttttggcaa aattcgctaa attaacccgt   1680
cctgcatcgg aagggtgtgt tactgatctg taa                                1713
```

<210> SEQ ID NO 66
<211> LENGTH: 1023
<212> TYPE: DNA
<213> ORGANISM: Lactococcus lactis

<400> SEQUENCE: 66

```
ttatttagta aaatcaatga ccattcggcc ttcaattttt cctgccttca tttcatcaat     60
aatatcattg atttcttcca gtttgcgtgt cgcaacaatt ggttttacct taccttctgc    120
tccaaattga aaagcttctg ccaagtcaag tcttgttccg acaagtgaac ctgcaacctc    180
cactccgtca aaaacaactg ttggaactga taaagtcatc tcagtattgg gaagtgccac    240
agcaaccatt ttgcccatag gtttcaaaga agcaaccgct tgttcaaaag caatccttgc    300
aacagcacaa actattgcac tttgcacccc taagccgcca gttatttttt taatttcatc    360
aactggattt acatcaccag aattgataat cacatcagct ccaatttttt tagctaaatt    420
taatttatct tgattaatat caacagcaat tacttttgct ccaaaaacat ttttagcata    480
ttgaattgct aaatttccaa gtcctccagc accaaaaatt acttgccaat caccaggttt    540
tactcctgat actttgattg ctttgtaagt tgttactcca gcacaagtaa ttgagctagc    600
ttcaattggg tcaagtccgt caggaacttt gacagcataa tcggcaacaa caattgcttc    660
ttcagccatt ccgccatcaa ctgaatatcc tgcattttta acttctcgac aaaaagtttc    720
attaccagat acacagtatt cacagtgacc acatccttca aagaaccaag ccactgaaac    780
ccgatcacca acttgaagcg agcttacatc agctccaatt tctttgacaa ttccaattcc    840
ttcatgacca agaacagtcc ctgctttgtt gccataatca cctgctgcaa cgtgcaaatc    900
ggtatgacag actccacaat actccatgtc aagcaaagct tcattaggtt tgattgctcg    960
aagttccttt tcaacaaggt ccgcataacc atctggattg tgtcttacta ctgctgcttt   1020
cat                                                                 1023
```

<210> SEQ ID NO 67
<211> LENGTH: 13805
<212> TYPE: DNA
<213> ORGANISM: Artificial Sequence
<220> FEATURE:
<223> OTHER INFORMATION: pGV2082

<400> SEQUENCE: 67

```
ttggatcata ctaagaaacc attattatca tgacattaac ctataaaaat aggcgtatca     60
cgaggccctt tcgtctcgcg cgtttcggtg atgacggtga aaacctctga cacatgcagc    120
tcccggagac ggtcacagct tgtctgtaag cggatgccgg gagcagacaa gcccgtcagg    180
gcgcgtcagc gggtgttggc gggtgtcggg gctggcttaa ctatgcggca tcagagcaga    240
ttgtactgag agtgcaccat accacagctt ttcaattcaa ttcatcattt ttttttatt     300
cttttttttg atttcggttt ctttgaaatt tttttgattc ggtaatctcc gaacagaagg    360
aagaacgaag gaaggagcac agacttagat tggtatatat acgcatatgg caaattaaag    420
ccttcgagcg tcccaaaacc ttctcaagca aggttttcag tataatgtta catgcgtaca    480
cgcgtctgta cagaaaaaaa agaaaaattt gaaatataaa taacgttctt aatactaaca    540
taactataaa aaaataaata gggacctaga cttcaggttg tctaactcct tccttttcgg    600
ttagagcgga tgtgggggga gggcgtgaat gtaagcgtga cataactaat tacatgactc    660
gagcggccgc ttagatgccg gagtcccagt gcttggtcca ctggatggcc tccagggtgc    720
ccaagtccag tttccagatg gctccgttct ggttcagctc gatagccttg acgaagttct    780
cggcgcaggc caacgagggc tggtgggat  gagccaggag cttctcggca acctgaggct    840
caacatccaa ccaggagttg aacgtgtgca ccagggtggt gcgggtgatg ccggggttca    900
cagtgtaagc cgtcacgccg gtaatggggg ccagtttcgc cagggagctg gtgaagttga    960
ccacggcggc cttggtgccg gagtagacgg gcacctggta gatggcattg aatccagtga   1020
cggatccaat gttgcagatg ataccaccgg gaccgccctt gcgcttgtcc cagaagtcca   1080
gaatggccgt cgtggtgttg accaggccag tgtagttgac ggcaatggtg cgctcgatct   1140
ggtgatcgtc caggatacca gctccgttga tcaggacatc gacggtcttc agctgggcga   1200
agatggtctt cagcagcttg gtggtctcgg caatgggcac ggtcacatca taggggtaga   1260
aggtgacggt cacctttgga ttgattgcct tcagctcggc aatggcagcc gggttctcaa   1320
tgcggtcgag gatcaccagg ttcttcagat cgcgcttgag cagctccttg ctggtgtcca   1380
gaccaatgcc tcccagaccg gcaacgaaaa tcacgttctt gttggtcaaa gtaaacgaca   1440
tggtacctat tattgtatgt tatagtatta gttgcttggt gttatgaaag aaactaagaa   1500
aagaaaaata aaataaaaat aaaagattga gacaagggaa gaaaagatac aaaataagaa   1560
ttaattacaa ttgcgtttgc tataaatacg tttttaacaa tcaactctgg taggaagata   1620
atgctttttt tttttatata tgcttggtgc cacttgtcac atacaattct acaaccttcg   1680
acaaaaatcc aaatgatagt aagatcaaag ccagaaagca atggagaaaa aaaattaatg   1740
aaccacgatg aaccaaatga tcaatacaac caaagaaact accctagtga ggtgtatgct   1800
gacttggtat cacacttcat gaattttgca tatggcaaag tccacgaaag tgggcttcag   1860
aaaaaaggcg tgcggtgtgt agatgtatca attagtggat gccagttttg gaacgggatt   1920
ccactttccg caagttggtg cacgtcgtta gtgacataac gccgcgttca tctttgggaa   1980
gaagcagatg ctgagcgagg aggtactata gagtaaagaa ccctttctat acccgcagcc   2040
ccatggtaag tgacagtgca gtaataatat gaaccaattt atttttcgtt acataaaaat   2100
```

-continued

```
gcttataaaa ctttaactaa taattagaga ttaaatcgcg gccgcaaaag atccttagga   2160
tttattctgt tcagcaaaca gcttgcccat ttttcttcagt accttcggtg cgccttcttt   2220
cgccaggatc agttcgatcc agtacatacg gttcggatcg gcctgggcct ctttcatcac   2280
gctcacaaat tcgttttcgg tacgcacaat tttagacaca acacggtcct cagttgcgcc   2340
gaaggactcc ggcagtttag agtagttcca catagggata tcgttgtaag actggttcgg   2400
accgtggatc tcacgctcaa cggtgtagcc gtcattgtta ataatgaagc aaatcgggtt   2460
gatcttttca cgaattgcca gacccagttc ctgtacggtc agctgcaggg aaccgtcacc   2520
gatgaacagc agatgacgag attctttatc agcgatctga gagcccagcg ctgccgggaa   2580
agtatagcca atgctacccc acagcggctg accgataaaa tggcttttgg atttcagaaa   2640
gatagaagac gcgccgaaaa agctcgtacc ttgttccgcc acgatggttt cattgctctg   2700
ggtcaggttc tccacggcct gccacaggcg atcctgggac agcagtgcgt tagatggtac   2760
gaaatcttct tgctttttgt caatgtattt gcctttatac tcgatttcgg acaggtccag   2820
cagagagctg atcaggcttt cgaagtcgaa gttctggata cgctcgttga agattttacc   2880
ctcgtcgatg ttcaggctaa tcattttgtt ttcgttcaga tggtgagtga atgcaccggt   2940
agaagagtcg gtcagtttaa cgcccagcat caggatgaag tccgcagatt caacaaattc   3000
tttcaggttc ggttcgctca gagtaccgtt gtagatgccc aggaaagacg gcagagcctc   3060
gtcaacagag gacttgccga agttcagggt ggtaatcggc agtttggttt tgctgatgaa   3120
ttgggtcacg gtcttctcca gaccaaaaga aatgatttcg tggccggtga tcacgattgg   3180
tttctttgcg tttttcagag actcctggat tttgttcagg atttcctggt cgctagtgtt   3240
agaagtggag ttttctttct tcagcggcag gctcggtttt tccgctttag ctgccgcaac   3300
atccacaggc aggttgatgt aaactggttt gcgttctttc agcagcgcag acagaacgcg   3360
gtcgatttcc acagtagcgt tctctgcagt cagcagcgta cgtgccgcag tcacaggttc   3420
atgcattttc atgaagtgtt tgaaatcgcc gtcagccaga gtgtggtgga cgaatttacc   3480
ttcgttctga actttgctcg ttgggctgcc tacgatctcc accaccggca ggttttcggc   3540
gtaggagccc gccagaccgt tgacggcgct cagttcgcca acaccgaaag tggtcagaaa   3600
tgccgcggct ttcttggtac gtgcataacc atctgccatg tagcttgcgt tcagttcgtt   3660
agcgttaccc acccatttca tgtctttatg agagatgatc tgatccagga actgcagatt   3720
gtaatcaccc ggaacgccga agatttcttc gatacccagt tcatgcagac ggtccagcag   3780
ataatcacca acagtataca tgtcgagctt gttttatatt tgttgtaaaa agtagataat   3840
tacttccttg atgatctgta aaaaagagaa aaagaaagca tctaagaact tgaaaaacta   3900
cgaattagaa aagaccaaat atgtatttct tgcattgacc aatttatgca agtttatata   3960
tatgtaaatg taagtttcac gaggttctac taaactaaac cacccccttg gttagaagaa   4020
aagagtgtgt gagaacaggc tgttgttgtc acacgattcg gacaattctg tttgaaagag   4080
agagagtaac agtacgatcg aacgaacttt gctctggaga tcacagtggg catcatagca   4140
tgtggtacta aaccctttcc cgccattcca gaaccttcga ttgcttgtta caaaacctgt   4200
gagccgtcgc taggaccttg ttgtgtgacg aaattggaag ctgcaatcaa taggaagaca   4260
ggaagtcgag cgtgtctggg ttttttcagt tttgttcttt ttgcaaacaa atcacgagcg   4320
acggtaattt ctttctcgat aagaggccac gtgctttatg agggtaacat caattcaaga   4380
aggagggaaa cacttccttt ttctggccct gataatagta tgagggtgaa gccaaaataa   4440
aggattcgcg cccaaatcgg catctttaaa tgcaggtatg cgatagttcc tcactctttc   4500
```

```
cttactcacg agtaattctt gcaaatgcct attatgcaga tgttataata tctgtgcgtc   4560
ttgagttgag cctagaattc ttagaaaaac tcatcgagca tcaaatgaaa ctgcaattta   4620
ttcatatcag gattatcaat accatatttt tgaaaaagcc gtttctgtaa tgaaggagaa   4680
aactcaccga ggcagttcca taggatggca agatcctggt atcggtctgc gatcccgact   4740
cgtccaacat caatacaacc tattaatttc ccctcgtcaa aaataaggtt atcaagtgag   4800
aaatcaccat gagtgacgac tgaatccggt gagaatggca aaagcttatg catttctttc   4860
cagacttgtt caacaggcca gccattacgc tcgtcatcaa aatcactcgc gtcaaccaaa   4920
ccgttattca ttcgtgattg cgcctgagcg aggcgaaata cgcgatcgct gttaaaagga   4980
caattacaaa caggaatcga atgcaaccgg cgcaggaaca ctgccagcgc atcaacaata   5040
ttttcacctg aatcaggata ttcttctaat acctggaatg ctgtttttgcc ggggatcgca   5100
gtggtgagta accatgcatc atcaggagta cggacaaaat gcttgatggt cggaagaggc   5160
ataaattccg tcagccagtt tagtctgacc atctcatctg caacatcatt ggcaacgcta   5220
cctttgccat gtttcagaaa caactctggc gcatcgggct tcccatacaa tcgatagatt   5280
gtcgcacctg attgcccgac attatcgcga gcccatttat acccatataa atcagcatcc   5340
atgttggaat ttaatcgcgg cctcgaaacg tgagtctttt ccttacccat actagttttt   5400
agtttatgta tgtgtttttt gtagttatag atttaagcaa gaaaagaata caaacaaaaa   5460
attgaaaaag attgatttag aattaaaaag aaaaatattt acgtaagaag ggaaaatagt   5520
aaatgttgca agttcactaa actcctaaat tatgctgccc tttatattcc ctgttacagc   5580
agccgagcca aaggtatata ggctcctttg cattagcatg cgtaacaaac cacctgtcag   5640
tttcaaccga ggtggtatcc gagagaattg tgtgattgct ttaattaatt tcggagaatc   5700
tcacatgcca ctgaagatta aaaactggat gccagaaaag ggtgtccag gtgtaacatc   5760
aatagaggaa gctgaaaagt cttagaacgg gtaatcttcc accaacctga tgggttccta   5820
gatataatct cgaagggaat aagtagggtg ataccgcaga agtgtctgaa tgtattaagg   5880
tcctcacagt ttaaatcccg ctcacactaa cgtaggatta ttataactca aaaaaatggc   5940
attattctaa gtaagttaaa tatccgtaat ctttaaacag cggccgcgga tcttcatcct   6000
gccactgcaa ttcttttcat atcggtcata tatcctctca gctttttacc cacctgttct   6060
atagcatgtg aacgaatagc ttcatttacg tctctcagtt ggccattgtc aaccgctcct   6120
tccggaatag ccttccccaa atcaccaggt tgtaactcgg ccatgaaggg ctttaacaac   6180
gggacacatg cgtagctaaa taagtaatta ccatattctg cagtgtctga tatgacaaca   6240
ttcatctcgt aaagtctttt tcttgcaata gtatttgcta tcaaaggcaa ttcatgcaaa   6300
gactcatagt atgcagattc ttcaatgata ccggagtcaa ccatagtttc gaatgcaagt   6360
tctacccctg ccttcaccat agctatcatc aatactccct tatcaaagta ttcttgttca   6420
ccaattttac cttcgtattg tggggctgtc tcgaatgccg tcttgccggt ttcttctctc   6480
cacgtcaata actttttatc atcgtttgcc caatctgcca tcattcctga ggaaaactca   6540
ccggagataa tatcgtccat gtgcttttgg aataatggtg ccatgatctc ttttagttgc   6600
tcagataagg cgtaggctct tagcttggcc ggatttgaaa gtctatccat catcaatgtt   6660
atgccacctt gtttaagtgc ctcggtgatt gtctcccaac caaattgtat caacttttca   6720
gcataggcag gatctgtacc ctcttcgacc aatttatcaa agcatagtaa agaccctgcc   6780
tgcaacattc cgcacagaat ggtttgttca cccattaagt cactcttgac ctcagctacg   6840
aaagaactct ctaacacacc cgctctatga cctccggttg cggctgccca tgccttcgca   6900
```

```
attgccatac cttcaccttt ggggtcattt tcaggatgta cggcgatcaa tgtaggtaca   6960
ccaaaacccc tcttgtactc ctctctgact tccgtacctg ggcactttgg tgcaaccatt   7020
acgactgtta tatcttttct gatctgctcg cccacttcaa cgatattaaa gccatgagag   7080
taacctaaag ctgccccatc cttcatcagc ggttgaactg ttcttactac gtctgagtga   7140
accttatctg gtgttaggtt aatcactaaa tctgcctgag ggatcagttc ttcgtaagta   7200
ccaactttga acccattttc cgtcgcttta cgccaggagg ccctcttttc tgcaattgcc   7260
tctttcctca atgcatacga aatatccaga cctgaatctc tcatgtttaa accttggttt   7320
agaccctgag caccgcagcc aacaattact actttctttc cttgcagata agaagcacca   7380
tcagcaaact cgtcccttcc cataaatctg cacttaccca gttgagccaa ttgttgtctc   7440
aaatttaatg tgttaaaata gttggccatc tcgagtcgaa actaagttct ggtgttttaa   7500
aactaaaaaa aagactaact ataaaagtag aatttaagaa gtttaagaaa tagatttaca   7560
gaattacaat caatacctac cgtctttata tacttattag tcaagtaggg gaataatttc   7620
agggaactgg tttcaacctt ttttttcagc tttttccaaa tcagagagag cagaaggtaa   7680
tagaaggtgt aagaaaatga gatagataca tgcgtgggtc aattgccttg tgtcatcatt   7740
tactccaggc aggttgcatc actccattga ggttgtgccc gttttttgcc tgtttgtgcc   7800
cctgttctct gtagttgcgc taagagaatg gacctatgaa ctgatggttg gtgaagaaaa   7860
caatattttg gtgctgggat tctttttttt tctggatgcc agcttaaaaa gcgggctcca   7920
ttatatttag tggatgccag gaataaactg ttcacccaga cacctacgat gttatatatt   7980
ctgtgtaacc cgccccctat tttgggcatg tacgggttac agcagaatta aaaggctaat   8040
tttttgacta aataaagtta ggaaaatcac tactattaat tatttacgta ttctttgaaa   8100
tggcgagtat tgataatgat aaactggatc cgcggccgct tacagatcag taacacaccc   8160
ttccgatgca ggacgggtta atttagcgaa ttttgccaaa actcccctgg tggctttcgg   8220
agttggcttc tgataattag ctcttctctt tgcgatttct tcatcggaaa ctttcaggga   8280
tatagagttg ttgactgcat ctatctctat tatatcgtca tcttcaacta agccgattag   8340
tccaccctca acggcttcag gcacaatatg gccgacaaca aaaccgtgag tgccaccgga   8400
gaatctacca tccgtaatta acgcgcaact tttccctaaa cccgcaccaa ttaatgctga   8460
tgtaggcttc agcatttcgg gcataccagg tccgccgacg ggacctatat tcctaattac   8520
cgctacatct ccagcatgca aacgaccaga ttctatgccg tcgataaaat gttgttcacc   8580
atcaaagact ctggcagtgc ctttgaagaa ctctccttct ttaccgctaa tttttgctac   8640
ggaacccccct tgagctaaat taccgtacag aatctgcaag tggccggtgg ccttgatagg   8700
attctttagt ggcctcatga tatcttgtga gtcgaaatcc aagtctaggg cagtctcgac   8760
attctcggct aatgttttac ccgtcacagt aaggcagtca ccatgcaatt ttccttcctt   8820
tagaaggtac ttaagcactg ctggcaagcc tccaatttta tgcaaatctt ccatcatata   8880
tttacctgaa ggtttaaaat cacctagtac tggagtaatg tcactaattc tttggaagtc   8940
atcctgagtt atttcgacac ctatcgcgtt agccattgca ataatatgca agacagcatt   9000
agtactaccc cccaagacca tcacaatggt aatagcgttc tcgaacgcct ccttagtcat   9060
tatatcacta ggcttgatgt ctttttccaa aagattctta atggctaatc caatctcatc   9120
acattcttct tgtttttctt gagatactgc agggttcgaa gaagaatacg gcaatgacat   9180
acctagtgtt tcgatagcgg cagctaaggt attagctgtg tacatccccc cacatgcccc   9240
ttgaccagga atagcattac aaataacacc gtgataatct tcatcagaga tattgccggt   9300
```

```
aattttctgg cctagagatt caaaagccga tacgatgttc aatttctcac ctttatattc   9360
accgtgttct attgttcctc catacaccat aatgcttggc ctattaagtc ttgccatacc   9420
aataatagaa cctggcatat ttttgtcaca acctgggatg gctacaattg catcatagta   9480
ttcagcgcca gcgttggttt caatagagtc agctataact tctctggaaa caagggagta   9540
tctcattccc aactttccat ttgctatccc atcagaaact cctatcgtat gaaattgtaa   9600
gccgatcaga ccatctgtct gatttactga gcttttaatc tttgatccaa gggttcctaa   9660
atgcatgttg catggatttc catcccagtc catcgacact atacccactt gagctttctt   9720
gaaatcttcg tctttaaacc cgatgccgta atacattgcc tgtgtggcgg gttgtgtggg   9780
atcttgtgtc aacgttttgc tgtacttatt cagttcaaca gattcaactt tgccgttata   9840
cttaaactcc atgtcgacaa acttagatta gattgctatg ctttctttct aatgagcaag   9900
aagtaaaaaa agttgtaata gaacaagaaa aatgaaactg aaacttgaga aattgaagac   9960
cgtttattaa cttaaatatc aatgggaggt catcgaaaga gaaaaaaatc aaaaaaaaaa  10020
ttttcaagaa aaagaaacgt gataaaaatt tttattgcct ttttcgacga agaaaaagaa  10080
acgaggcggt ctcttttttc ttttccaaac ctttagtacg ggtaattaac gacaccctag  10140
aggaagaaag aggggaaatt tagtatgctg tgcttgggtg ttttgaagtg gtacggcgat  10200
gcgcggagtc cgagaaaatc tggaagagta aaaaaggagt agaaacattt tgaagctatg  10260
agctccagct tttgttccct ttagtgaggg ttaattgcgc gcttggcgta atcatggtca  10320
tagctgtttc ctgtgtgaaa ttgttatccg ctcacaattc cacacaacat aggagccgga  10380
agcataaagt gtaaagcctg gggtgcctaa tgagtgaggt aactcacatt aattgcgttg  10440
cgctcactgc ccgctttcca gtcgggaaac ctgtcgtgcc agctgcatta atgaatcggc  10500
caacgcgcgg ggagaggcgg tttgcgtatt gggcgctctt ccgcttcctc gctcactgac  10560
tcgctgcgct cggtcgttcg gctgcggcga gcggtatcag ctcactcaaa ggcggtaata  10620
cggttatcca cagaatcagg ggataacgca ggaaagaaca tgtgagcaaa aggccagcaa  10680
aaggccagga accgtaaaaa ggccgcgttg ctggcgtttt tccataggct ccgcccccct  10740
gacgagcatc acaaaaatcg acgctcaagt cagaggtggc gaaacccgac aggactataa  10800
agataccagg cgtttccccc tggaagctcc ctcgtgcgct ctcctgttcc gaccctgccg  10860
cttaccggat acctgtccgc ctttctccct tcgggaagcg tggcgctttc tcatagctca  10920
cgctgtaggt atctcagttc ggtgtaggtc gttcgctcca agctgggctg tgtgcacgaa  10980
ccccccgttc agcccgaccg ctgcgcctta tccggtaact atcgtcttga gtccaacccg  11040
gtaagacacg acttatcgcc actggcagca gccactggta acaggattag cagagcgagg  11100
tatgtaggcg gtgctacaga gttcttgaag tggtggccta actacggcta cactagaagg  11160
acagtatttg gtatctgcgc tctgctgaag ccagttacct tcggaaaaag agttggtagc  11220
tcttgatccg gcaaacaaac caccgctggt agcggtggtt tttttgtttg caagcagcag  11280
attacgcgca gaaaaaaagg atctcaagaa gatcctttga tcttttctac ggggtctgac  11340
gctcagtgga acgaaaactc acgttaaggg attttggtca tgagattatc aaaaaggatc  11400
ttcacctaga tccttttaaa ttaaaaatga agttttaaat caatctaaag tatatatgag  11460
taaacttggt ctgacagtta ccaatgctta atcagtgagg cacctatctc agcgatctgt  11520
ctatttcgtt catccatagt tgcctgactc cccgtcgtgt agataactac gatacgggag  11580
ggcttaccat ctggccccag tgctgcaatg ataccgcgag acccacgctc accggctcca  11640
gatttatcag caataaacca gccagccgga agggccgagc gcagaagtgg tcctgcaact  11700
```

```
ttatccgcct ccatccagtc tattaattgt tgccgggaag ctagagtaag tagttcgcca  11760
gttaatagtt tgcgcaacgt tgttgccatt gctacaggca tcgtggtgtc acgctcgtcg  11820
tttggtatgg cttcattcag ctccggttcc caacgatcaa ggcgagttac atgatccccc  11880
atgttgtgca aaaaagcggt tagctccttc ggtcctccga tcgttgtcag aagtaagttg  11940
gccgcagtgt tatcactcat ggttatggca gcactgcata attctcttac tgtcatgcca  12000
tccgtaagat gcttttctgt gactggtgag tactcaacca agtcattctg agaatagtgt  12060
atgcggcgac cgagttgctc ttgcccggcg tcaatacggg ataataccgc gccacatagc  12120
agaactttaa aagtgctcat cattggaaaa cgttcttcgg ggcgaaaact ctcaaggatc  12180
ttaccgctgt tgagatccag ttcgatgtaa cccactcgtg cacccaactg atcttcagca  12240
tcttttactt tcaccagcgt ttctgggtga gcaaaaacag gaaggcaaaa tgccgcaaaa  12300
aagggaataa gggcgacacg gaaatgttga atactcatac tcttcctttt tcaatattat  12360
tgaagcattt atcagggtta ttgtctcatg agcggataca tatttgaatg tatttagaaa  12420
aataaacaaa taggggttcc gcgcacattt ccccgaaaag tgccacctga acgaagcatc  12480
tgtgcttcat tttgtagaac aaaaatgcaa cgcgagagcg ctaatttttc aaacaaagaa  12540
tctgagctgc atttttacag aacagaaatg caacgcgaaa gcgctatttt accaacgaag  12600
aatctgtgct tcatttttgt aaaacaaaaa tgcaacgcga gagcgctaat tttcaaaca  12660
aagaatctga gctgcatttt tacagaacag aaatgcaacg cgagagcgct attttaccaa  12720
caaagaatct atacttcttt tttgttctac aaaaatgcat cccgagagcg ctattttct  12780
aacaaagcat cttagattac ttttttctc ctttgtgcgc tctataatgc agtctcttga  12840
taacttttg cactgtaggt ccgttaaggt tagaagaagg ctactttggt gtctattttc  12900
tcttccataa aaaaagcctg actccacttc ccgcgtttac tgattactag cgaagctgcg  12960
ggtgcatttt ttcaagataa aggcatcccc gattatattc tataccgatg tggattgcgc  13020
atactttgtg aacagaaagt gatagcgttg atgattcttc attggtcaga aaattatgaa  13080
cggtttcttc tattttgtct ctatatacta cgtataggaa atgtttacat tttcgtattg  13140
ttttcgattc actctatgaa tagttcttac tacaattttt ttgtctaaag agtaatacta  13200
gagataaaca taaaaaatgt agaggtcgag tttagatgca agttcaagga gcgaaaggtg  13260
gatgggtagg ttatataggg atatagcaca gagatatata gcaaagagat acttttgagc  13320
aatgtttgtg gaagcggtat tcgcaatatt ttagtagctc gttacagtcc ggtgcgtttt  13380
tggtttttg aaagtgcgtc ttcagagcgc ttttggtttt caaaagcgct ctgaagttcc  13440
tatactttct agagaatagg aacttcggaa taggaacttc aaagcgtttc cgaaaacgag  13500
cgcttccgaa aatgcaacgc gagctgcgca catacagctc actgttcacg tcgcacctat  13560
atctgcgtgt tgcctgtata tatatataca tgagaagaac ggcatagtgc gtgtttatgc  13620
ttaaatgcgt acttatatgc gtctatttat gtaggatgaa aggtagtcta gtacctcctg  13680
tgatattatc ccattccatg cggggtatcg tatgcttcct tcagcactac cctttagctg  13740
ttctatatgc tgccactcct caattggatt agtctcatcc ttcaatgcta tcatttcctt  13800
tgata                                                              13805
```

```
<210> SEQ ID NO 68
<211> LENGTH: 11561
<212> TYPE: DNA
<213> ORGANISM: Artificial Sequence
<220> FEATURE:
<223> OTHER INFORMATION: pGV2563
```

<400> SEQUENCE: 68

```
ttggatcata ctaagaaacc attattatca tgacattaac ctataaaaat aggcgtatca      60
cgaggccctt tcgtctcgcg cgtttcggtg atgacggtga aaacctctga cacatgcagc     120
tcccggagac ggtcacagct tgtctgtaag cggatgccgg gagcagacaa gcccgtcagg     180
gcgcgtcagc gggtgttggc gggtgtcggg gctggcttaa ctatgcggca tcagagcaga     240
ttgtactgag agtgcaccat accacagctt ttcaattcaa ttcatcattt ttttttttatt     300
cttttttttg atttcggttt ctttgaaatt tttttgattc ggtaatctcc gaacagaagg     360
aagaacgaag gaaggagcac agacttagat tggtatatat acgcatatgg caaattaaag     420
ccttcgagcg tcccaaaacc ttctcaagca aggttttcag tataatgtta catgcgtaca     480
cgcgtctgta cagaaaaaaa agaaaaattt gaaatataaa taacgttctt aatactaaca     540
taactataaa aaaataaata gggacctaga cttcaggttg tctaactcct tccttttcgg     600
ttagagcgga tgtggggggga gggcgtgaat gtaagcgtga cataactaat tacatgactc     660
gacctaggtt agtggtggtg gtggtggtgc ttcgtgaagt ctataaccat tctaccttca     720
atcttccccg ccttcatctc atcaatgatg tcattgattt cctccaactt tctggtagcg     780
acaataggct taaccttccc ttctgcaccg aattggaaag cttcggccaa atcgagtctt     840
gttccaacaa gactacctgc tacttcaact ccatcaaaca cgactgttgg cacagataat     900
gtcatttctg tgtttggcac agcaacggct accattttgc ccataggctt tagtgaggct     960
acagcctgct cgaatgcaat tctcgcaacg gcacatacaa tcgcggattg aacacctaaa    1020
ccgccagtga tctttttgat ttcgtctaca gggttaacgt caccagagtt aattgtgaca    1080
tcagcaccta tctttttggc aagattgagc ttatcttgat tgatatctac agcgatcacc    1140
ttcgcaccaa atacgttttt ggcgtactgg atagctaagt tgcccaggcc accagctccg    1200
aagataactt gccagtctcc tggcttaacg ccagacacct tgatagcttt gtaagtggtg    1260
acgcctgcac aagttataga tgatgcttct attggatcta ggccatctgg gactttaacg    1320
gcataatctg caaccacgat cgcttcctct gccattccac catcaacgct ataaccagcg    1380
tttttgactt ctcggcaaaa tgtctcgtta cctgacacac agtattcgca atgtccacac    1440
ccttcgaaaa accaagcaac actcactcta tcacctactt ggagagaact aacatcggca    1500
ccaatctctt tcacaatacc tataccttca tgtcctaaaa ctgtccctgc cttgttgccg    1560
aaatctccgg cagcaacatg taggtcagtg tgacagacac cgcagtattc catatccaac    1620
aatgcctcat ttggcttaat ggccctcaac tctttttcta caagatcagc gtacccatca    1680
ggattgtgac ggacaactgc agccttcatg gtacctatta ttgtatgtta tagtattagt    1740
tgcttggtgt tatgaaagaa actaagaaaa gaaaaataaa ataaaaataa aagattgaga    1800
caagggaaga aaagatacaa aataagaatt aattacaatt gcgtttgcta taaatacgtt    1860
tttaacaatc aactctggta ggaagataat gcttttttttt tttatatatg cttggtgcca    1920
cttgtcacat acaattctac aaccttcgac aaaaatccaa atgatagtaa gatcaaagcc    1980
agaaagcaat ggagaaaaaa aattaatgaa ccacgatgaa ccaaatgatc aatacaacca    2040
aagaaactac cctagtgagg tgtatgctga cttggtatca cacttcatga attttgcata    2100
tggcaaagtc cacgaaagtg ggcttcagaa aaaaggcgtg cggtgtgtag atgtatcaat    2160
tagtggatgc cagttttgga acgggattcc actttccgca agttggtgca cgtcgttagt    2220
gacataacgc cgcgttcatc tttgggaaga agcagatgct gagcgaggag gtactataga    2280
gtaaagaacc ctttctatac ccgcagcccc atgaattctt agaaaaactc atcgagcatc    2340
```

-continued

```
aaatgaaact gcaatttatt catatcagga ttatcaatac catatttttg aaaaagccgt   2400
ttctgtaatg aaggagaaaa ctcaccgagg cagttccata ggatggcaag atcctggtat   2460
cggtctgcga tcccgactcg tccaacatca atacaaccta ttaatttccc ctcgtcaaaa   2520
ataaggttat caagtgagaa atcaccatga gtgacgactg aatccggtga gaatggcaaa   2580
agcttatgca tttctttcca gacttgttca acaggccagc cattacgctc gtcatcaaaa   2640
tcactcgcgt caaccaaacc gttattcatt cgtgattgcg cctgagcgag gcgaaatacg   2700
cgatcgctgt taaaaggaca attacaaaca ggaatcgaat gcaaccggcg caggaacact   2760
gccagcgcat caacaatatt ttcacctgaa tcaggatatt cttctaatac ctggaatgct   2820
gttttgccgg ggatcgcagt ggtgagtaac catgcatcat caggagtacg gacaaaatgc   2880
ttgatggtcg gaagaggcat aaattccgtc agccagttta gtctgaccat ctcatctgca   2940
acatcattgg caacgctacc tttgccatgt ttcagaaaca actctggcgc atcgggcttc   3000
ccatacaatc gatagattgt cgcacctgat tgcccgacat tatcgcgagc ccatttatac   3060
ccatataaat cagcatccat gttggaattt aatcgcggcc tcgaaacgtg agtcttttcc   3120
ttacccatac tagtttttag tttatgtatg tgtttttttgt agttatagat ttaagcaaga   3180
aaagaataca aacaaaaaat tgaaaaagat tgatttagaa ttaaaaagaa aaatatttac   3240
gtaagaaggg aaaatagtaa atgttgcaag ttcactaaac tcctaaatta tgctgccctt   3300
tatattccct gttacagcag ccgagccaaa ggtatatagg ctcctttgca ttagcatgcg   3360
taacaaacca cctgtcagtt tcaaccgagg tggtatccga gagaattgtg tgattgcttt   3420
aattaatttc ggagaatctc acatgccact gaagattaaa aactggatgc cagaaaaggg   3480
gtgtccaggt gtaacatcaa tagaggaagc tgaaaagtct tagaacgggt aatcttccac   3540
caacctgatg ggttcctaga tataatctcg aagggaataa gtagggtgat accgcagaag   3600
tgtctgaatg tattaaggtc ctcacagttt aaatcccgct cacactaacg taggattatt   3660
ataactcaaa aaaatggcat tattctaagt aagttaaata tccgtaatct ttaaacagcg   3720
gccgcagatc cttagtggtg gtggtggtgg tgtcctgcca ctgcaattct tttcatatcg   3780
gtcatatatc ctctcagctt tttacccacc tgttctatag catgcgaacg aatagcttca   3840
tttacgtctc tcagttggcc attgtcaacc gctccttccg gaatagcctt ccccaaatca   3900
ccaggttgta actcggccat gaagggctct aacaacggga cacacgcgta gctaaataag   3960
taattaccat attctgcagt gtctgatatg acaacattca tctcgtaaag tctttttctt   4020
gcaatagtat ttgctatcaa aggcaattca tgcaaagact catagtatgc agattcttca   4080
atgataccgg agtcaaccat agtttcgaat gcaagttcta cccctgcctt caccatagct   4140
atcatcaata ctcccttatc aaagtattct tgttcaccaa ttttaccttc gtattgtggg   4200
gctgtctcga atgccgtctt gccggtttct tctctccacg tcaataactt tttatcatcg   4260
tttgcccaat ctgccatcat tcctgaggaa aactcaccgg agataatatc gtccatgtgc   4320
ttttggaata atggtgccat gatctctttt agttgctcag ataaggcgta ggctcttagc   4380
ttggccggat ttgaaagtct atccatcatc aatgttatgc caccttgttt aagtgcctcg   4440
gtgattgtct cccaaccaaa ttgtatcaac ttttcagcat aggcaggatc tgtaccctct   4500
tcgaccaatt tatcaaagca tagtaaagac cctgcctgca acattccgca cagaatggtt   4560
tgttcaccca ttaagtcact cttgacctca gctacgaaag aactctctaa cacacccgct   4620
ctatgacctc cggttgcggc tgcccatgcc ttcgctattg ccataccttc acgtttgggg   4680
tcattttcag gatgtacggc gatcaatgta ggtacaccaa aacccctctt gtactcctct   4740
```

```
ctgacttccg tacctgggca ctttggcgca accattacga ctgttatacc ttttctgatc   4800
tgctcgccca cttcaacgat attaaagcca tgagagtaac ctaaagctgc cccatccttc   4860
atcagcggtt gaactgttct tactacgtct gagtgaacct tatctggtgt taggttaatc   4920
actaaatctg cctgagggat cagttcttcg taagtaccaa ctttgaaccc attttccgtc   4980
gctttacgcc aatcggcatc cttttctgca atagactctt tcctcaatgc atacgaaata   5040
tccagacctg aatctctcat gtttaaacct tggtttagac cctgagcacc gcagccaaca   5100
attactactt tctttccttg cagataagaa gcaccatcag caaactcgtc ccttcccata   5160
aatctgcact tacccagttg agccaattgt tgtctcaaat ttaatgtgtt aaaatagttg   5220
gccatgtcga gtcgaaacta agttctggtg ttttaaaact aaaaaaaaga ctaactataa   5280
aagtagaatt taagaagttt aagaaataga tttacagaat tacaatcaat acctaccgtc   5340
tttatatact tattagtcaa gtaggggaat aatttcaggg aactggtttc aaccttttt    5400
ttcagctttt tccaaatcag agagagcaga aggtaataga aggtgtaaga aaatgagata   5460
gatacatgcg tgggtcaatt gccttgtgtc atcatttact ccaggcaggt tgcatcactc   5520
cattgaggtt gtgcccgttt tttgcctgtt tgtgcccctg ttctctgtag ttgcgctaag   5580
agaatggacc tatgaactga tggttggtga agaaaacaat attttggtgc tgggattctt   5640
ttttttctg gatgccagct taaaaagcgg gctccattat atttagtgga tgccaggaat    5700
aaactgttca cccagacacc tacgatgtta tatattctgt gtaacccgcc ccctattttg   5760
ggcatgtacg ggttacagca gaattaaaag gctaattttt tgactaaata aagttaggaa   5820
aatcactact attaattatt tacgtattct ttgaaatggc gagtattgat aatgataaac   5880
tggatccgcg gccgcttaca gatcagtaac acacccttcc gatgcaggac gggttaattt   5940
agcgaatttt gccaaaactc ccctggtggc tttcggagtt ggcttctgat aattagctct   6000
tctctttgcg atttcttcat cggaaacttt cagggatata gagttgttga ctgcatctat   6060
ctctattata tcgtcatctt caactaagcc gattagtcca ccctcaacgg cttcaggcac   6120
aatatggccg acaacaaaac cgtgagtgcc accggagaat ctaccatccg taattaacgc   6180
gcaacttttc cctaaacccg caccaattaa tgctgatgta ggcttcagca tttcgggcat   6240
accaggtccg ccgacgggac ctatattcct aattaccgct acatctccag catgcaaacg   6300
accagattct atgccgtcga taaaatgttg ttcaccatca aagactctgg cagtgccttt   6360
gaagaactct ccttctttac cgctaatttt tgctacggaa ccccccttgag ctaaattacc  6420
gtacagaatc tgcaagtggc cggtggcctt gataggattc tttagtggcc tcatgatatc   6480
ttgtgagtcg aaatccaagt ctagggcagt ctcgacattc tcggctaatg ttttacccgt   6540
cacagtaagg cagtcaccat gcaattttcc ttcctttaga aggtacttaa gcactgctgg   6600
caagcctcca attttatgca aatcttccat catatattta cctgaaggtt taaaatcacc   6660
tagtactgga gtaatgtcac taattctttg gaagtcatcc tgagttattt cgacacctat   6720
cgcgttagcc attgcaataa tatgcaagac agcattagta ctacccccca agaccatcac   6780
aatggtaata gcgttctcga acgcctcctt agtcattata tcactaggct tgatgtcttt   6840
ttccaaaaga ttcttaatgg ctaatccaat ctcatcacat tcttcttgtt tttcttgaga   6900
tactgcaggg ttcgaagaag aatacggcaa tgacatacct agtgtttcga tagcggcagc   6960
taaggtatta gctgtgtaca tccccccaca tgccccttga ccaggaatag cattacaaat   7020
aacaccgtga taatcttcat cagagatatt gccggtaatt ttctggccta gagattcaaa   7080
agccgatacg atgttcaatt tctcaccttt atattcaccg tgttctattg ttcctccata   7140
```

```
caccataatg cttggcctat taagtcttgc cataccaata atagaacctg gcatattttt   7200
gtcacaacct gggatggcta caattgcatc atagtattca gcgccagcgt tggtttcaat   7260
agagtcagct ataacttctc tggaaacaag ggagtatctc attcccaact ttccatttgc   7320
tatcccatca gaaactccta tcgtatgaaa ttgtaagccg atcagaccat ctgtctgatt   7380
tactgagctt ttaatctttg atccaagggt tcctaaatgc atgttgcatg gatttccatc   7440
ccagtccatc gacactatac ccacttgagc tttcttgaaa tcttcgtctt taaacccgat   7500
gccgtaatac attgcctgtg tggcgggttg tgtgggatct tgtgtcaacg ttttgctgta   7560
cttattcagt tcaacagatt caactttgcc gttatactta aactccatgt cgacaaactt   7620
agattagatt gctatgcttt ctttctaatg agcaagaagt aaaaaaagtt gtaatagaac   7680
aagaaaaatg aaactgaaac ttgagaaatt gaagaccgtt tattaactta aatatcaatg   7740
ggaggtcatc gaaagagaaa aaaatcaaaa aaaaaatttt caagaaaaag aaacgtgata   7800
aaaattttta ttgccttttt cgacgaagaa aaagaaacga ggcggtctct tttttctttt   7860
ccaaaccttt agtacgggta attaacgaca ccctagagga agaaagaggg gaaatttagt   7920
atgctgtgct tgggtgtttt gaagtggtac ggcgatgcgc ggagtccgag aaaatctgga   7980
agagtaaaaa aggagtagaa acattttgaa gctatgagct ccagcttttg ttccctttag   8040
tgagggttaa ttgcgcgctt ggcgtaatca tggtcatagc tgtttcctgt gtgaaattgt   8100
tatccgctca caattccaca caacatagga gccggaagca taaagtgtaa agcctggggt   8160
gcctaatgag tgaggtaact cacattaatt gcgttgcgct cactgcccgc tttccagtcg   8220
ggaaacctgt cgtgccagct gcattaatga atcggccaac gcgcggggag aggcggtttg   8280
cgtattgggc gctcttccgc ttcctcgctc actgactcgc tgcgctcggt cgttcggctg   8340
cggcgagcgg tatcagctca ctcaaaggcg gtaatacggt tatccacaga atcaggggat   8400
aacgcaggaa agaacatgtg agcaaaaggc cagcaaaagg ccaggaaccg taaaaaggcc   8460
gcgttgctgg cgtttttcca taggctccgc ccccctgacg agcatcacaa aaatcgacgc   8520
tcaagtcaga ggtggcgaaa cccgacagga ctataaagat accaggcgtt tccccctgga   8580
agctccctcg tgcgctctcc tgttccgacc ctgccgctta ccggatacct gtccgccttt   8640
ctcccttcgg gaagcgtggc gctttctcat agctcacgct gtaggtatct cagttcggtg   8700
taggtcgttc gctccaagct gggctgtgtg cacgaacccc ccgttcagcc cgaccgctgc   8760
gccttatccg gtaactatcg tcttgagtcc aacccggtaa gacacgactt atcgccactg   8820
gcagcagcca ctggtaacag gattagcaga gcgaggtatg taggcggtgc tacagagttc   8880
ttgaagtggt ggcctaacta cggctacact agaaggacag tatttggtat ctgcgctctg   8940
ctgaagccag ttaccttcgg aaaaagagtt ggtagctctt gatccggcaa acaaaccacc   9000
gctggtagcg gtggtttttt tgtttgcaag cagcagatta cgcgcagaaa aaaaggatct   9060
caagaagatc ctttgatctt ttctacgggg tctgacgctc agtggaacga aaactcacgt   9120
taagggattt tggtcatgag attatcaaaa aggatcttca cctagatcct tttaaattaa   9180
aaatgaagtt ttaaatcaat ctaaagtata tatgagtaaa cttggtctga cagttaccaa   9240
tgcttaatca gtgaggcacc tatctcagcg atctgtctat ttcgttcatc catagttgcc   9300
tgactccccg tcgtgtagat aactacgata cgggagggct taccatctgg ccccagtgct   9360
gcaatgatac cgcgagaccc acgctcaccg gctccagatt tatcagcaat aaaccagcca   9420
gccggaaggg ccgagcgcag aagtggtcct gcaactttat ccgcctccat ccagtctatt   9480
aattgttgcc gggaagctag agtaagtagt tcgccagtta atagtttgcg caacgttgtt   9540
```

```
gccattgcta caggcatcgt ggtgtcacgc tcgtcgtttg gtatggcttc attcagctcc   9600
ggttcccaac gatcaaggcg agttacatga tcccccatgt tgtgcaaaaa agcggttagc   9660
tccttcggtc ctccgatcgt tgtcagaagt aagttggccg cagtgttatc actcatggtt   9720
atggcagcac tgcataattc tcttactgtc atgccatccg taagatgctt ttctgtgact   9780
ggtgagtact caaccaagtc attctgagaa tagtgtatgc ggcgaccgag ttgctcttgc   9840
ccggcgtcaa tacgggataa taccgcgcca catagcagaa ctttaaaagt gctcatcatt   9900
ggaaaacgtt cttcggggcg aaaactctca aggatcttac cgctgttgag atccagttcg   9960
atgtaaccca ctcgtgcacc caactgatct tcagcatctt ttactttcac cagcgtttct  10020
gggtgagcaa aaacaggaag gcaaaatgcc gcaaaaaagg gaataagggc gacacggaaa  10080
tgttgaatac tcatactctt cctttttcaa tattattgaa gcatttatca gggttattgt  10140
ctcatgagcg gatacatatt tgaatgtatt tagaaaaata aacaaatagg ggttccgcgc  10200
acatttcccc gaaaagtgcc acctgaacga agcatctgtg cttcattttg tagaacaaaa  10260
atgcaacgcg agagcgctaa tttttcaaac aaagaatctg agctgcattt ttacagaaca  10320
gaaatgcaac gcgaaagcgc tattttacca acgaagaatc tgtgcttcat ttttgtaaaa  10380
caaaaatgca acgcgagagc gctaattttt caaacaaaga atctgagctg catttttaca  10440
gaacagaaat gcaacgcgag agcgctattt taccaacaaa gaatctatac ttcttttttg  10500
ttctacaaaa atgcatcccg agagcgctat ttttctaaca aagcatctta gattactttt  10560
tttctccttt gtgcgctcta taatgcagtc tcttgataac tttttgcact gtaggtccgt  10620
taaggttaga agaaggctac tttggtgtct attttctctt ccataaaaaa agcctgactc  10680
cacttcccgc gtttactgat tactagcgaa gctgcgggtg cattttttca agataaaggc  10740
atccccgatt atattctata ccgatgtgga ttgcgcatac tttgtgaaca gaaagtgata  10800
gcgttgatga ttcttcattg gtcagaaaat tatgaacggt ttcttctatt ttgtctctat  10860
atactacgta taggaaatgt ttacattttc gtattgtttt cgattcactc tatgaatagt  10920
tcttactaca atttttttgt ctaaagagta atactagaga taaacataaa aaatgtagag  10980
gtcgagttta gatgcaagtt caaggagcga aaggtggatg ggtaggttat atagggatat  11040
agcacagaga tatatagcaa agagatactt ttgagcaatg tttgtggaag cggtattcgc  11100
aatattttag tagctcgtta cagtccggtg cgtttttggt tttttgaaag tgcgtcttca  11160
gagcgctttt ggttttcaaa agcgctctga agttcctata ctttctagag aataggaact  11220
tcggaatagg aacttcaaag cgtttccgaa aacgagcgct tccgaaaatg caacgcgagc  11280
tgcgcacata cagctcactg ttcacgtcgc acctatatct gcgtgttgcc tgtatatata  11340
tatacatgag aagaacggca tagtgcgtgt ttatgcttaa atgcgtactt atatgcgtct  11400
atttatgtag gatgaaaggt agtctagtac ctcctgtgat attatcccat tccatgcggg  11460
gtatcgtatg cttccttcag cactaccctt tagctgttct atatgctgcc actcctcaat  11520
tggattagtc tcatccttca atgctatcat ttcctttgat a                      11561
```

<210> SEQ ID NO 69
<211> LENGTH: 9043
<212> TYPE: DNA
<213> ORGANISM: Artificial Sequence
<220> FEATURE:
<223> OTHER INFORMATION: pGV2164

<400> SEQUENCE: 69

```
ctgcttaatt aaccgttgat gacagcaatt cgggagggcg aaaaataaaa actggagcaa     60
```

-continued

```
ggaattacca tcaccgtcac catcaccatc atatcgcctt agcctctagc catagccatc    120
atgcaagcgt gtatcttcta agattcagtc atcatcatta ccgagtttgt tttccttcac    180
atgatgaaga aggtttgagt atgctcgaaa caataagacg acgatggctc tgccattgtt    240
atattacgct tttgcggcga ggtgccgatg ggttgctgag ggaagagtg tttagcttac     300
ggacctattg ccattgttat tccgattaat ctattgttca gcagctcttc tctaccctgt    360
cattctagta ttttttttt ttttttttg gttttacttt tttttcttct tgcctttttt      420
tcttgttact ttttttctag tttttttcc ttccactaag ctttttcctt gatttatcct     480
tgggttcttc tttctactcc tttagatttt tttttatat attaatttt aagtttatgt      540
attttggtag attcaattct ctttcccttt ccttttcctt cgctcccctt ccttatcaga    600
gctcgccgat cccattaccg acatttgggc gctatacgtg catatgttca tgtatgtatc    660
tgtatttaaa acacttttgt attatttttc ctcatatatg tgtataggtt tatacggatg    720
atttaattat tacttcacca ccctttattt caggctgata tcttagcctt gttactagtt    780
agaaaaagac atttttgctg tcagtcactg tcaagagatt cttttgctgg catttcttct    840
agaagcaaaa agagcgatgc gtcttttccg ctgaaccgtt ccagcaaaaa agactaccaa    900
cgcaatatgg attgtcagaa tcatataaaa gagaagcaaa taactccttg tcttgtatca    960
attgcattat aatatcttct tgttagtgca atatcatata gaagtcatcg aaatagatat   1020
taagaaaaac aaactgtaca atcaatcaat caatcatcac ataaagtcga catgttgaca   1080
aaagcaacaa aagaacaaaa atcccttgtg aaaagcagag gggcggagct tgttgttgat   1140
tgcttagcgg agcaaggtgt cacacatgta tttggcattc caggtgcaaa aattgatgcg   1200
gtatttgacg ctttacaaga taaagggcct gaaattatcg ttgcccggca tgaacaaaat   1260
gcagcattta tggcgcaagc agtcggccgt ttaactggaa aaccgggagt cgtgttagtc   1320
acatcaggac caggtgcttc gaacttggca acaggactgc tgacagcaaa cactgaaggt   1380
gaccctgtcg ttgcgcttgc tgggaacgtg atccgtgcag atcgtttaaa acggacacat   1440
caatctttgg ataatgcggc gctattccag ccgattacaa aatacagtgt agaagttcaa   1500
gatgtaaaaa atataccgga agctgttaca aatgcgttta ggatagcgtc agcagggcag   1560
gctggggccg cttttgtgag ttttccgcaa gatgttgtga atgaagtcac aaatacaaaa   1620
aacgtacgtg ctgtcgcagc gccaaaactt ggtcccgcag cagatgacgc aatcagtatg   1680
gccattgcaa aaattcaaac agcaaaactt cctgtcgttt tagtcggcat gaagggcgga   1740
agaccggaag cgattaaagc ggttcgcaag ctattgaaaa aagtgcagct tccattcgtt   1800
gaaacatatc aagctgccgg tactcttacg agagatttag aggatcagta ttttggccgg   1860
atcggtttat tccgcaacca gcctggcgat ctgctgcttg agcaggctga tgttgttctg   1920
acaatcggct atgacccaat tgaatatgat ccgaaattct ggaatgtcaa tggagaccgg   1980
acgatcatcc atttagacga gattctggct gacattgatc atgcttacca gccggatctt   2040
gaactgatcg gtgatattcc atctacgatc aatcatatcg aacacgatgc tgtgaaagta   2100
gactttgcgg aacgtgagca gaagatcctt tctgatttaa aacaatatat gcatgagggt   2160
gagcaggtgc ctgcagattg gaaatcagac agagtgcatc ctcttgaaat cgttaaagaa   2220
ttgcgaaacg cagtcgatga tcatgttaca gtgacttgcg atatcggttc acacgcgatt   2280
tggatgtcac gttatttccg cagctacgag ccgttaacat taatgattag taacggtatg   2340
caaacactcg gcgttgcgct tccttgggca atcggcgctt cattggtgaa accgggagaa   2400
aaagtagtat cagtctccgg tgatggcggt ttcttattct cagctatgga attagagaca   2460
```

-continued

```
gcagttcgtt taaaagcacc aattgtacac attgtatgga acgacagcac atatgacatg   2520
gttgcattcc agcaattgaa aaaatataat cgtacatctg cggtcgattt cggaaatatc   2580
gatatcgtga aatacgcgga aagcttcgga gcaactggct tacgcgtaga atcaccagac   2640
cagctggcag atgttctgcg tcaaggcatg aacgctgagg ggcctgtcat cattgatgtc   2700
ccggttgact acagtgataa cgttaattta gcaagtgaca agcttccgaa agaattcggg   2760
gaactcatga aaacgaaagc tctctaggga tcctcatgta attagttatg tcacgcttac   2820
attcacgccc tccccccaca tccgctctaa ccgaaaagga aggagttaga caacctgaag   2880
tctaggtccc tatttatttt tttatagtta tgttagtatt aagaacgtta tttatatttc   2940
aaatttttct ttttttctg tacagacgcg tgtacgcatg taacattata ctgaaaacct    3000
tgcttgagaa ggttttggga cgctcgaagg ctttaatttg ccctaggctc aactcaagac   3060
gcacagatat tataacatct gcataatagg catttgcaag aattactcgt gagtaaggaa   3120
agagtgagga actatcgcat acctgcattt aaagatgccg atttgggcgc gaatccttta   3180
ttttggcttc accctcatac tattatcagg gccagaaaaa ggaagtgttt ccctccttct   3240
tgaattgatg ttaccctcat aaagcacgtg gcctcttatc gagaaagaaa ttaccgtcgc   3300
tcgtgatttg tttgcaaaaa gaacaaaact gaaaaaaccc agacacgctc gacttcctgt   3360
cttcctattg attgcagctt ccaatttcgt cacacaacaa ggtcctagcg acggctcaca   3420
ggttttgtaa caagcaatcg aaggttctgg aatggcggga aagggtttag taccacatgc   3480
tatgatgccc actgtgatct ccagagcaaa gttcgttcga tcgtactgtt actctctctc   3540
tttcaaacag aattgtccga atcgtgtgac aacaacagcc tgttctcaca cactcttttc   3600
ttctaaccaa gggggtggtt tagtttagta gaacctcgtg aaacttacat ttacatatat   3660
ataaacttgc ataaattggt caatgcaaga aatacatatt tggtcttttc taattcgtag   3720
tttttcaagt tcttagatgc tttctttttc tctttttac agatcatcaa ggaagtaatt    3780
atctactttt tacaacaaat ataaaacaag ctcgacatgt atactgttgg tgattatctg   3840
ctggaccgtc tgcatgaact gggtatcgaa gaaatcttcg gcgttccggg tgattacaat   3900
ctgcagttcc tggatcagat catctctcat aaagacatga aatgggtggg taacgctaac   3960
gaactgaacg caagctacat ggcagatggt tatgcacgta ccaagaaagc cgcggcattt   4020
ctgaccactt tcggtgttgg cgaactgagc gccgtcaacg gtctggcggg ctcctacgcc   4080
gaaaacctgc cggtggtgga gatcgtaggc agcccaacga gcaaagttca gaacgaaggt   4140
aaattcgtcc accacactct ggctgacggc gatttcaaac acttcatgaa aatgcatgaa   4200
cctgtgactg cggcacgtac gctgctgact gcagagaacg ctactgtgga aatcgaccgc   4260
gttctgtctg cgctgctgaa agaacgcaaa ccagtttaca tcaacctgcc tgtggatgtt   4320
gcggcagcta aagcggaaaa accgagcctg ccgctgaaga aagaaaactc cacttctaac   4380
actagcgacc aggaaatcct gaacaaaatc caggagtctc tgaaaaacgc aaagaaacca   4440
atcgtgatca ccggccacga aatcatttct tttggtctgg agaagaccgt gacccaattc   4500
atcagcaaaa ccaaactgcc gattaccacc ctgaacttcg gcaagtcctc tgttgacgag   4560
gctctgccgt ctttcctggg catctacaac ggtactctga gcgaaccgaa cctgaaagaa   4620
tttgttgaat ctgcggactt catcctgatg ctgggcgtta aactgaccga ctcttctacc   4680
ggtgcattca ctcaccatct gaacgaaaac aaaatgatta gcctgaacat cgacgagggt   4740
aaaatcttca acgagcgtat ccagaacttc gacttcgaaa gcctgatcag ctctctgctg   4800
gacctgtccg aaatcgagta taaaggcaaa tacattgaca aaaagcaaga agatttcgta   4860
```

```
ccatctaacg cactgctgtc ccaggatcgc ctgtggcagg ccgtggagaa cctgacccag   4920
agcaatgaaa ccatcgtggc ggaacaaggt acgagctttt tcggcgcgtc ttctatcttt   4980
ctgaaatcca aaagccattt tatcggtcag ccgctgtggg gtagcattgg ctatactttc   5040
ccggcagcgc tgggctctca gatcgctgat aaagaatctc gtcatctgct gttcatcggt   5100
gacggttccc tgcagctgac cgtacaggaa ctgggtctgg caattcgtga aaagatcaac   5160
ccgatttgct tcattattaa caatgacggc tacaccgttg agcgtgagat ccacggtccg   5220
aaccagtctt acaacgatat ccctatgtgg aactactcta aactgccgga gtccttcggc   5280
gcaactgagg accgtgttgt gtctaaaatt gtgcgtaccg aaaacgaatt tgtgagcgtg   5340
atgaaagagg cccaggccga tccgaaccgt atgtactgga tcgaactgat cctggcgaaa   5400
gaaggcgcac cgaaggtact gaagaaaatg ggcaagctgt ttgctgaaca gaataaatcc   5460
taaggatctt ttgcggccta gtattgaatt cttatacagg aaacttaata gaacaaatca   5520
catatttaat ctaatagcca cctgcattgg cacggtgcaa cactacttca acttcatctt   5580
acaaaaagat cacgtgatct gttgtattga actgaaaatt ttttgtttgc ttctctctct   5640
ctctttcatt atgtgagatt taaaaaccag aaactacatc atcgaaaaag agttttaaac   5700
cattacaacc attgcgataa gccctctcaa actataacaa tactgacagt actaaataat   5760
tgcctacttg gcttcacata cgttgcatac gtcgatatag ataataatga taatgacagc   5820
aggattatcg taatacgtaa tagttgaaaa tctcaaaaat gtgtgggtca ttacgtaaat   5880
aatgatagga atgggattct tctatttttc ctttttccat tctagcagcc gtcgggaaaa   5940
cgtggcatcc tctctttcgg gctcaattgg agtcacgctg ccgtgagcat cctctctttc   6000
catatctaac aactgagcac gtaaccaatg gaaaagcatg agcttagcgt tgctccaaaa   6060
aagtattgga tggttaatac catttgtctg ttctcttctg actttgactc ctcaaaaaaa   6120
aaaaatctac aatcaacaga tcgcttcaat tacgccctca caaaaacttt tttccttctt   6180
cttcgcccac gttaaatttt atccctcatg ttgtctaacg gatttctgca cttgatttat   6240
tataaaaaga caaagacata atacttctct atcaatttca gttattgttc ttccttgcgt   6300
tattcttctg ttcttctttt tcttttgtca tatataacca taaccaagta atacatattc   6360
aaaatgtcca caaaatcata taccagtaga gctgagactc atgcaagtcc ggttgcatcg   6420
aaacttttac gtttaatgga tgaaaagaag accaatttgt gtgcttctct tgacgttcgt   6480
tcgactgatg agctattgaa acttgttgaa acgttgggtc catacatttg ccttttgaaa   6540
acacacgttg atatcttgga tgatttcagt tatgagggta ctgtcgttcc attgaaagca   6600
ttggcagaga aatacaagtt cttgatattt gaggacagaa aattcgccga tatcggtaac   6660
acagtcaaat tacaatatac atcgggcgtt taccgtatcg cagaatggtc tgatatcacc   6720
aacgcccacg gggttactgg tgctggtatt gttgctggct tgaaacaagg tgcgcaagag   6780
gtcaccaaag aaccaagggg attattgatg cttgctgaat tgtcttccaa gggttctcta   6840
gcacacggtg aatatactaa gggtaccgaa gcttggcgta atcatggtca tagctgtttc   6900
ctgtgtgaaa ttgttatccg ctcacaattc cacacaacat acgagccgga agcataaagt   6960
gtaaagcctg gggtgcctaa tgagtgagct aactcacatt aattgcgttg cgctcactgc   7020
ccgctttcca gtcgggaaac ctgtcgtgcc agctgcatta atgaatcggc caacgcgcgg   7080
ggagaggcgg tttgcgtatt gggcgctctt ccgcttcctc gctcactgac tcgctgcgct   7140
cggtcgttcg gctgcggcga gcggtatcag ctcactcaaa ggcggtaata cggttatcca   7200
cagaatcagg ggataacgca ggaaagaaca tgtgagcaaa aggccagcaa aaggccagga   7260
```

```
accgtaaaaa ggccgcgttg ctggcgtttt tccataggct ccgcccccct gacgagcatc   7320

acaaaaatcg acgctcaagt cagaggtggc gaaacccgac aggactataa agataccagg   7380

cgtttccccc tggaagctcc ctcgtgcgct ctcctgttcc gaccctgccg cttaccggat   7440

acctgtccgc ctttctccct tcgggaagcg tggcgctttc tcatagctca cgctgtaggt   7500

atctcagttc ggtgtaggtc gttcgctcca agctgggctg tgtgcacgaa ccccccgttc   7560

agcccgaccg ctgcgcctta tccggtaact atcgtcttga gtccaacccg gtaagacacg   7620

acttatcgcc actggcagca gccactggta acaggattag cagagcgagg tatgtaggcg   7680

gtgctacaga gttcttgaag tggtggccta actacggcta cactagaagg acagtatttg   7740

gtatctgcgc tctgctgaag ccagttacct tcggaaaaag agttggtagc tcttgatccg   7800

gcaaacaaac caccgctggt agcggtggtt tttttgtttg caagcagcag attacgcgca   7860

gaaaaaaagg atctcaagaa gatcctttga tcttttctac ggggtctgac gctcagtgga   7920

acgaaaactc acgttaaggg attttggtca tgagattatc aaaaaggatc ttcacctaga   7980

tccttttaaa ttaaaaatga agttttaaat caatctaaag tatatatgag taaacttggt   8040

ctgacagtta ccaatgctta atcagtgagg cacctatctc agcgatctgt ctatttcgtt   8100

catccatagt tgcctgactc cccgtcgtgt agataactac gatacgggag ggcttaccat   8160

ctggccccag tgctgcaatg ataccgcgag acccacgctc accggctcca gatttatcag   8220

caataaacca gccagccgga agggccgagc gcagaagtgg tcctgcaact ttatccgcct   8280

ccatccagtc tattaattgt tgccgggaag ctagagtaag tagttcgcca gttaatagtt   8340

tgcgcaacgt tgttgccatt gctacaggca tcgtggtgtc acgctcgtcg tttggtatgg   8400

cttcattcag ctccggttcc caacgatcaa ggcgagttac atgatccccc atgttgtgca   8460

aaaaagcggt tagctccttc ggtcctccga tcgttgtcag aagtaagttg gccgcagtgt   8520

tatcactcat ggttatggca gcactgcata attctcttac tgtcatgcca tccgtaagat   8580

gcttttctgt gactggtgag tactcaacca agtcattctg agaatagtgt atgcggcgac   8640

cgagttgctc ttgcccggcg tcaatacggg ataataccgc gccacatagc agaactttaa   8700

aagtgctcat cattggaaaa cgttcttcgg ggcgaaaact ctcaaggatc ttaccgctgt   8760

tgagatccag ttcgatgtaa cccactcgtg cacccaactg atcttcagca tcttttactt   8820

tcaccagcgt ttctgggtga gcaaaaacag gaaggcaaaa tgccgcaaaa aagggaataa   8880

gggcgacacg gaaatgttga atactcatac tcttcctttt tcaatattat tgaagcattt   8940

atcagggtta ttgtctcatg agcggataca tatttgaatg tatttagaaa aataaacaaa   9000

taggggttcc gcgcacattt ccccgaaaag tgccacctga cgt                     9043
```

<210> SEQ ID NO 70
<211> LENGTH: 7721
<212> TYPE: DNA
<213> ORGANISM: Artificial Sequence
<220> FEATURE:
<223> OTHER INFORMATION: pGV1954

<400> SEQUENCE: 70

```
ccagttaact gtgggaatac tcaggtatcg taagatgcaa gagttcgaat ctcttagcaa     60

ccattatttt tttcctcaac ataacgagaa cacacagggg cgctatcgca cagaatcaaa    120

ttcgatgact ggaaattttt tgttaatttc agaggtcgcc tgacgcatat accttttca    180

actgaaaaat tgggagaaaa aggaaaggtg agagcgccgg aaccggcttt tcatatagaa    240

tagagaagcg ttcatgacta aatgcttgca tcacaatact tgaagttgac aatattattt    300
```

```
aaggacctat tgttttttcc aataggtggt tagcaatcgt cttactttct aacttttctt    360
accttttaca tttcagcaat atatatatat atatttcaag gatataccat tctaatgtct    420
gcccctaaga agatcgtcgt tttgccaggt gaccacgttg gtcaagaaat cacagccgaa    480
gccattaagg ttcttaaagc tatttctgat gttcgttcca atgtcaagtt cgatttcgaa    540
aatcatttaa ttggtggtgc tgctatcgat gctacaggtg ttccacttcc agatgaggcg    600
ctggaagcct ccaagaaggc tgatgccgtt ttgttaggtg ctgtgggtgg tcctaaatgg    660
ggtaccggta gtgttagacc tgaacaaggt ttactaaaaa tccgtaaaga acttcaattg    720
tacgccaact taagaccatg taactttgca tccgactctc ttttagactt atctccaatc    780
aagccacaat ttgctaaagg tactgacttc gttgttgtca gagaattagt gggaggtatt    840
tactttggta agagaaagga agacgatggt gatggtgtcg cttgggatag tgaacaatac    900
accgttccag aagtgcaaag aatcacaaga atggccgctt tcatggccct acaacatgag    960
ccaccattgc ctatttggtc cttggataaa gctaatgttt tggcctcttc aagattatgg   1020
agaaaaactg tggaggaaac catcaagaac gaattcccta cattgaaggt tcaacatcaa   1080
ttgattgatt ctgccgccat gatcctagtt aagaacccaa cccacctaaa tggtattata   1140
atcaccagca acatgtttgg tgatatcatc tccgatgaag cctccgttat cccaggttcc   1200
ttgggtttgt tgccatctgc gtccttggcc tctttgccag acaagaacac cgcatttggt   1260
ttgtacgaac catgccacgg ttctgctcca gatttgccaa agaataaggt caaccctatc   1320
gccactatct tgtctgctgc aatgatgttg aaattgtcat tgaacttgcc tgaagaaggt   1380
aaggccattg aagatgcagt taaaaaggtt ttggatgcag gtatcagaac tggtgattta   1440
ggtggttcca acagtaccac cgaagtcggt gatgctgtcg ccgaagaagt taagaaaatc   1500
cttgcttaaa aagattctct ttttttatga tatttgtaca taaactttat aaatgaaatt   1560
cataatagaa acgacacgaa attacaaaat ggaatatgtt catagggtag acgaaactat   1620
atacgcaatc tacatacatt tatcaagaag gagaaaaagg aggatgtaaa ggaatacagg   1680
taagcaaatt gatactaatg gctcaacgtg ataaggaaaa agaattgcac tttaacatta   1740
atattgacaa ggaggagggc accacacaaa aagttaggtg taacagaaaa tcatgaaact   1800
atgattccta atttatatat tggaggattt tctctaaaaa aaaaaaaata caacaaataa   1860
aaaacactca atgacctgac catttgatgg agttgccggc ttgatcgaga atggcagctc   1920
ttatatacaa gttcttttag caagcgccgc tgcattattc aagtctcatc atatgaaatt   1980
tctttcgaga gattgtcata atcaaaaaat tgcataatgc atttcttgca acacattttc   2040
tgatataatc ttaccttaat gcaggtttac gtattagttt ttctaaaaga aacgcgacct   2100
ttggatatgg aggcttttcc cataaacgca tgtagtatgc atttacgatg agaatcaatt   2160
tttttccaag ggcgcaaaaa cgcataaacg cataaagtat gcatcagaag gattctcacc   2220
tggttgcaac catacaggtg ttagcgacag taatagaaaa aaaattaaaa taatggtgtt   2280
attgttattt gctttatttc cttggccttt gttgaaggaa ttcgtatacg tattacaaat   2340
aactagtatc gaggaacttg aaagagctga aatttttgca ttcttcttcg gtgattatgc   2400
ctaagccaat gaggtcgccc caaaagaccg caatcttgtc acgaccataa gccatataat   2460
cgcgaacaaa aacccgtttt taggaaggac agaggtccat atcaatataa ttaagaaggc   2520
atgttggcct ctgtttctta atatattcta aataagatgt aaggccttgt aattcagttt   2580
gttcacaaaa ttaaaaactg tttaatgttt tttgttttgt tgtagtattc gagcattaag   2640
gataaaaaaa gcttgtgaat aaaaatcttt cgctaaaaat caatataaga aaatggtaag   2700
```

```
cagctgaaag ataataaggt atggttaaag atcacaccac cctcttcaat tagctaagat   2760
catagctaaa ggtacaaaac cgaatacgaa agtaaataaa ttaatcagca taaaattaaa   2820
taataaacca cctaaaatat tagaagctaa tctttaacct ggaagacagg acagaaaagt   2880
aattacaaga acatatgtga aaaaaaatag ttgatatttt aaaccaaatc agaaatttat   2940
tatactaaaa ctatatctat gccaattatt tacctaaaca tctataacct tcaaaagtaa   3000
aaaaatacac aaacgttgaa tcatgagttt tatgttaatt agcggccgca gatcttcatc   3060
ctgccactgc aattcttttc atatcggtca tatatcctct cagcttttta cccacctgtt   3120
ctatagcatg tgaacgaata gcttcattta cgtctctcag ttggccattg tcaaccgctc   3180
cttccggaat agccttcccc aaatcaccag gttgtaactc ggccatgaag ggctttaaca   3240
acgggacaca tgcgtagcta aataagtaat taccatattc tgcagtgtct gatatgacaa   3300
cattcatctc gtaaagtctt tttcttgcaa tagtatttgc tatcaaaggc aattcatgca   3360
aagactcata gtatgcagat tcttcaatga taccggagtc aaccatagtt tcgaatgcaa   3420
gttctacccc tgccttcacc atagctatca tcaatactcc cttatcaaag tattcttgtt   3480
caccaatttt accttcgtat tgtggggctg tctcgaatgc cgtcttgccg gtttcttctc   3540
tccacgtcaa taacttttta tcatcgtttg cccaatctgc catcattcct gaggaaaact   3600
caccggagat aatatcgtcc atgtgctttt ggaataatgg tgccatgatc tcttttagtt   3660
gctcagataa ggcgtaggct cttagcttgg ccggatttga aagtctatcc atcatcaatg   3720
ttatgccacc ttgtttaagt gcctcggtga ttgtctccca accaaattgt atcaactttt   3780
cagcataggc aggatctgta ccctcttcga ccaatttatc aaagcatagt aaagaccctg   3840
cctgcaacat tccgcacaga atggtttgtt cacccattaa gtcactcttg acctcagcta   3900
cgaaagaact ctctaacaca cccgctctat gacctccggt tgcggctgcc catgccttcg   3960
caattgccat accttcacct ttggggtcat tttcaggatg tacggcgatc aatgtaggta   4020
caccaaaacc cctcttgtac tcctctctga cttccgtacc tgggcacttt ggtgcaacca   4080
ttacgactgt tatatctttt ctgatctgct cgcccacttc aacgatatta aagccatgag   4140
agtaacctaa agctgcccca tccttcatca gcggttgaac tgttcttact acgtctgagt   4200
gttgcttatc tggtgttagg ttaatcacta aatctgcctg agggatcagt tcttcgtaag   4260
taccaacttt gaacccattt tccgtcgctt tacgccagga ggccctcttt tctgcaattg   4320
cctctttcct caatgcatac gaaatatcca gacctgaatc tctcatgttt aaaccttggt   4380
ttagaccctg agcaccgcag ccaacaatta ctactttctt tccttgcaga taagaagcac   4440
catcagcaaa ctcgtccctt cccataaatc tgcacttacc cagttgagcc aattgttgtc   4500
tcaaatttaa tgtgttaaaa tagttggcca tctcgactat tgatatagtg tttaagcgaa   4560
tgacagaaga ttaatttctt ggtatgttag gaaagaataa aggagaataa gaataattag   4620
aacaatgtag gatggaaaga aagattatca agcatgccga ctttatatac ttgaacggag   4680
gcaaaggatg caaaatttc tcacatttct ttctgccgtt atgttggaag taagactccc   4740
attatcgcaa tactgcaaca cgaatatgca aaatttgctg agttatcgca gatagttgtt   4800
gcaaagatag cggcgtaggt ggccgcgaaa tggggaattc caaaacaaac ggttttttta   4860
ctcctgagaa atacttgtac gggataatcc agggcctacc acccacgctt cgaggattgg   4920
cttttatttt ttttttttg gtggcgtttt atttctttcc cgctttctgg gacttgtgcg   4980
gagttttgag aggggcgcgc ggcaaaggat tcccaaaacg gaaatcagac gccaatagcc   5040
agcactcaaa gcagttctgg acccattccg attttcccat ttggttcttg cgcgtgctga   5100
```

```
ttccgacacg cgcgtctata aatagcatga agtatccgca caccgcagcg ttagtgaggt   5160
gagggtggca gcaagctaat tcccgcatct ggaatctgaa ctgccccttt tggactaacc   5220
gtgtggttca tgggtgggcg aagtgcgcaa cctcgaaggt ttcttttgc gtgtcggatt    5280
ttacatccgg cggtagcgca tgatgccatg gctggctcca gatacatcct cagggcacca   5340
gcatctataa ttagattggc gcaacatggc tggctgcact gctgtcttca cttctttctt   5400
tttccggcaa tgaatgatgt atgttttgtg gcaaaagggt ccgcattgta cctgtttaca   5460
gttgagatta tcgtttttgg tagcccttca ttacggcata acgtattgag ctccagcttt   5520
tgttcccttt agtgagggtt aattgcgcgc ttggcgtaat catggtcata gctgtttcct   5580
gtgtgaaatt gttatccgct cacaattcca cacaacatag gagccggaag cataaagtgt   5640
aaagcctggg gtgcctaatg agtgaggtaa ctcacattaa ttgcgttgcg ctcactgccc   5700
gctttccagt cgggaaacct gtcgtgccag ctgcattaat gaatcggcca acgcgcgggg   5760
agaggcggtt tgcgtattgg gcgctcttcc gcttcctcgc tcactgactc gctgcgctcg   5820
gtcgttcggc tgcggcgagc ggtatcagct cactcaaagg cggtaatacg gttatccaca   5880
gaatcagggg ataacgcagg aaagaacatg tgagcaaaag gccagcaaaa ggccaggaac   5940
cgtaaaaagg ccgcgttgct ggcgtttttc cataggctcc gcccccctga cgagcatcac   6000
aaaaatcgac gctcaagtca gaggtggcga aacccgacag gactataaag ataccaggcg   6060
tttccccctg gaagctccct cgtgcgctct cctgttccga ccctgccgct taccggatac   6120
ctgtccgcct ttctcccttc gggaagcgtg gcgctttctc atagctcacg ctgtaggtat   6180
ctcagttcgg tgtaggtcgt tcgctccaag ctgggctgtg tgcacgaacc ccccgttcag   6240
cccgaccgct gcgccttatc cggtaactat cgtcttgagt ccaacccggt aagacacgac   6300
ttatcgccac tggcagcagc cactggtaac aggattagca gagcgaggta tgtaggcggt   6360
gctacagagt tcttgaagtg gtggcctaac tacggctaca ctagaaggac agtatttggt   6420
atctgcgctc tgctgaagcc agttaccttc ggaaaaagag ttggtagctc ttgatccggc   6480
aaacaaacca ccgctggtag cggtggtttt tttgtttgca agcagcagat tacgcgcaga   6540
aaaaaaggat ctcaagaaga tcctttgatc ttttctacgg ggtctgacgc tcagtggaac   6600
gaaaactcac gttaagggat tttggtcatg agattatcaa aaaggatctt cacctagatc   6660
cttttaaatt aaaaatgaag ttttaaatca atctaaagta tatatgagta aacttggtct   6720
gacagttacc aatgcttaat cagtgaggca cctatctcag cgatctgtct atttcgttca   6780
tccatagttg cctgactccc cgtcgtgtag ataactacga tacgggaggg cttaccatct   6840
ggccccagtg ctgcaatgat accgcgagac ccacgctcac cggctccaga tttatcagca   6900
ataaaccagc cagccggaag ggccgagcgc agaagtggtc ctgcaacttt atccgcctcc   6960
atccagtcta ttaattgttg ccgggaagct agagtaagta gttcgccagt taatagtttg   7020
cgcaacgttg ttgccattgc tacaggcatc gtggtgtcac gctcgtcgtt tggtatggct   7080
tcattcagct ccggttccca acgatcaagg cgagttacat gatcccccat gttgtgcaaa   7140
aaagcggtta gctccttcgg tcctccgatc gttgtcagaa gtaagttggc cgcagtgtta   7200
tcactcatgg ttatggcagc actgcataat tctcttactg tcatgccatc cgtaagatgc   7260
ttttctgtga ctggtgagta ctcaaccaag tcattctgag aatagtgtat gcggcgaccg   7320
agttgctctt gcccggcgtc aatacgggat aataccgcgc cacatagcag aactttaaaa   7380
gtgctcatca ttggaaaacg ttcttcgggg cgaaaactct caaggatctt accgctgttg   7440
agatccagtt cgatgtaacc cactcgtgca cccaactgat cttcagcatc ttttactttc   7500
```

accagcgttt ctgggtgagc aaaaacagga aggcaaaatg ccgcaaaaaa gggaataagg 7560
gcgacacgga aatgttgaat actcatactc ttcctttttc aatattattg aagcatttat 7620
cagggttatt gtctcatgag cggatacata tttgaatgta tttagaaaaa taaacaaata 7680
ggggttccgc gcacatttcc ccgaaaagtg ccacctgacg t 7721

<210> SEQ ID NO 71
<211> LENGTH: 7685
<212> TYPE: DNA
<213> ORGANISM: Artificial Sequence
<220> FEATURE:
<223> OTHER INFORMATION: pGV7024

<400> SEQUENCE: 71
ttggatcata ctaagaaacc attattatca tgacattaac ctataaaaat aggcgtatca 60
cgaggccctt tcgtctcgcg cgtttcggtg atgacggtga aaacctctga cacatgcagc 120
tcccggagac ggtcacagct tgtctgtaag cggatgccgg gagcagacaa gcccgtcagg 180
gcgcgtcagc gggtgttggc gggtgtcggg gctggcttaa ctatgcggca tcagagcaga 240
ttgtactgag agtgcaccat accacagctt ttcaattcaa ttcatcattt ttttttttatt 300 cttttttttg atttcggttt ctttgaaatt tttttgattc ggtaatctcc gaacagaagg 360
aagaacgaag gaaggagcac agacttagat tggtatatat acgcatatgg caaattaaag 420
ccttcgagcg tcccaaaacc ttctcaagca aggttttcag tataatgtta catgcgtaca 480
cgcgtctgta cagaaaaaaa agaaaaattt gaaatataaa taacgttctt aatactaaca 540
taactataaa aaaataaata gggacctaga cttcaggttg tctaactcct tccttttcgg 600
ttagagcgga tgtgggggga gggcgtgaat gtaagcgtga cataagaatt cttattcctt 660
tgccctcgga cgagtgctgg ggcgtcggtt tccactatcg gcgagtactt ctacacagcc 720
atcggtccag acggccgcgc ttctgcgggc gatttgtgta cgcccgacag tcccggctcc 780
ggatcggacg attgcgtcgc atcgaccctg cgcccaagct gcatcatcga aattgccgtc 840
aaccaagctc tgatagagtt ggtcaagacc aatgcggagc atatacgccc ggaggcgcgg 900
cgatcctgca agctccggat gcctccgctc gaagtagcgc gtctgctgct ccatacaagc 960
caaccacggc ctccagaaga ggatgttggc gacctcgtat tgggaatccc cgaacatcgc 1020
ctcgctccag tcaatgaccg ctgttatgcg gccattgtcc gtcaggacat tgttggagcc 1080
gaaatccgca tgcacgaggt gccggacttc ggggcagtcc tcggcccaaa gcatcagctc 1140
atcgagagcc tgcgcgacgg acgcactgac ggtgtcgtcc atcacagttt gccagtgata 1200
cacatgggga tcagcaatcg cgcatatgaa atcacgccat gtagtgtatt gaccgattcc 1260
ttgcggtccg aatgggccga acccgctcgt ctggctaaga tcggccgcag cgatcgcatc 1320
catggcctcc gcgaccggct ggagaacagc gggcagttcg gtttcaggca ggtcttgcaa 1380
cgtgacaccc tgtgcacggc gggagatgca ataggtcagg ctctcgctga actccccaat 1440
gtcaagcact tccggaatcg ggagcgcggc cgatgcaaag tgccgataaa cataacgatc 1500
tttgtagaaa ccatcggcgc agctatttac ccgcaggaca tatccacgcc ctcctacatc 1560
gaagctgaaa gcacgagatt cttcgccctc cgagagctgc atcaggtcgg agacgctgtc 1620
gaacttttcg atcagaaact tctcgacaga cgtcgcggtg agttcaggct ttttacccat 1680
actagttttt agtttatgta tgtgtttttt gtagttatag atttaagcaa gaaaagaata 1740
caaacaaaaa attgaaaaag attgatttag aattaaaaag aaaaatattt acgtaagaag 1800
ggaaaatagt aaatgttgca agttcactaa actcctaaat tatgctgccc tttatattcc 1860

```
ctgttacagc agccgagcca aaggtatata ggctcctttg cattagcatg cgtaacaaac   1920
cacctgtcag tttcaaccga ggtggtatcc gagagaattg tgtgattgct ttaattaatt   1980
tcggagaatc tcacatgcca ctgaagatta aaaactggat gccagaaaag ggtgtccag    2040
gtgtaacatc aatagaggaa gctgaaaagt cttagaacgg gtaatcttcc accaacctga   2100
tgggttccta gatataatct cgaagggaat aagtagggtg ataccgcaga agtgtctgaa   2160
tgtattaagg tcctcacagt ttaaatcccg ctcacactaa cgtaggatta ttataactca   2220
aaaaaatggc attattctaa gtaagttaaa tatccgtaat ctttaaacag cggccgcaga   2280
tctctcgagt cgaaactaag ttctggtgtt ttaaaactaa aaaaaagact aactataaaa   2340
gtagaattta agaagtttaa gaaatagatt tacagaatta caatcaatac ctaccgtctt   2400
tatatactta ttagtcaagt aggggaataa tttcagggaa ctggtttcaa cctttttttt   2460
cagctttttc caaatcagag agagcagaag gtaatagaag gtgtaagaaa atgagataga   2520
tacatgcgtg ggtcaattgc cttgtgtcat catttactcc aggcaggttg catcactcca   2580
ttgaggttgt gcccgttttt tgcctgtttg tgcccctgtt ctctgtagtt gcgctaagag   2640
aatggaccta tgaactgatg gttggtgaag aaaacaatat tttggtgctg ggattctttt   2700
tttttctgga tgccagctta aaaagcgggc tccattatat ttagtggatg ccaggaataa   2760
actgttcacc cagacaccta cgatgttata tattctgtgt aacccgcccc ctattttggg   2820
catgtacggg ttacagcaga attaaaaggc taattttttg actaaataaa gttaggaaaa   2880
tcactactat taattattta cgtattcttt gaaatggcga gtattgataa tgataaactg   2940
gatccgtcga caaacttaga ttagattgct atgctttctt tctaatgagc aagaagtaaa   3000
aaaagttgta atagaacaag aaaaatgaaa ctgaaacttg agaaattgaa gaccgtttat   3060
taacttaaat atcaatggga ggtcatcgaa agagaaaaaa atcaaaaaaa aaattttcaa   3120
gaaaaagaaa cgtgataaaa atttttattg cctttttcga cgaagaaaaa gaaacgaggc   3180
ggtctctttt ttcttttcca aacctttagt acgggtaatt aacgacaccc tagaggaaga   3240
aagaggggaa atttagtatg ctgtgcttgg gtgttttgaa gtggtacggc gatgcgcgga   3300
gtccgagaaa atctggaaga gtaaaaaagg agtagaaaca ttttgaagct atgagctcag   3360
atctgttaac cttgttttat atttgttgta aaaagtagat aattacttcc ttgatgatct   3420
gtaaaaaaga gaaaaagaaa gcatctaaga acttgaaaaa ctacgaatta gaaaagacca   3480
aatatgtatt tcttgcattg accaatttat gcaagtttat atatatgtaa atgtaagttt   3540
cacgaggttc tactaaacta aaccaccccc ttggttagaa gaaaagagtg tgtgagaaca   3600
ggctgttgtt gtcacacgat tcggacaatt ctgtttgaaa gagagagagt aacagtacga   3660
tcgaacgaac tttgctctgg agatcacagt gggcatcata gcatgtggta ctaaaccctt   3720
tcccgccatt ccagaacctt cgattgcttg ttacaaaacc tgtgagccgt cgctaggacc   3780
ttgttgtgtg acgaaattgg aagctgcaat caataggaag acaggaagtc gagcgtgtct   3840
gggttttttc agttttgttc tttttgcaaa caaatcacga gcgacggtaa tttctttctc   3900
gataagaggc cacgtgcttt atgagggtaa catcaattca agaaggaggg aaacacttcc   3960
tttttctggc cctgataata gtatgagggt gaagccaaaa taaaggattc gcgcccaaat   4020
cggcatcttt aaatgcaggt atgcgatagt tcctcactct ttccttactc acgagtaatt   4080
cttgcaaatg cctattatgc agatgttata atatctgtgc gtcttgagtt gagcctaggg   4140
agctccagct tttgttccct ttagtgaggg ttaattgcgc gcttggcgta atcatggtca   4200
tagctgtttc ctgtgtgaaa ttgttatccg ctcacaattc cacacaacat aggagccgga   4260
```

```
agcataaagt gtaaagcctg gggtgcctaa tgagtgaggt aactcacatt aattgcgttg   4320
cgctcactgc ccgctttcca gtcgggaaac ctgtcgtgcc agctgcatta atgaatcggc   4380
caacgcgcgg ggagaggcgg tttgcgtatt gggcgctctt ccgcttcctc gctcactgac   4440
tcgctgcgct cggtcgttcg gctgcggcga gcggtatcag ctcactcaaa ggcggtaata   4500
cggttatcca cagaatcagg ggataacgca ggaaagaaca tgtgagcaaa aggccagcaa   4560
aaggccagga accgtaaaaa ggccgcgttg ctggcgtttt tccataggct ccgcccccct   4620
gacgagcatc acaaaaatcg acgctcaagt cagaggtggc gaaacccgac aggactataa   4680
agataccagg cgtttccccc tggaagctcc ctcgtgcgct ctcctgttcc gaccctgccg   4740
cttaccggat acctgtccgc ctttctccct tcgggaagcg tggcgctttc tcatagctca   4800
cgctgtaggt atctcagttc ggtgtaggtc gttcgctcca agctgggctg tgtgcacgaa   4860
ccccccgttc agcccgaccg ctgcgcctta tccggtaact atcgtcttga gtccaacccg   4920
gtaagacacg acttatcgcc actggcagca gccactggta acaggattag cagagcgagg   4980
tatgtaggcg gtgctacaga gttcttgaag tggtggccta actacggcta cactagaagg   5040
acagtatttg gtatctgcgc tctgctgaag ccagttacct tcggaaaaag agttggtagc   5100
tcttgatccg gcaaacaaac caccgctggt agcggtggtt tttttgtttg caagcagcag   5160
attacgcgca gaaaaaaagg atctcaagaa gatcctttga tcttttctac ggggtctgac   5220
gctcagtgga acgaaaactc acgttaaggg attttggtca tgagattatc aaaaaggatc   5280
ttcacctaga tccttttaaa ttaaaaatga agttttaaat caatctaaag tatatatgag   5340
taaacttggt ctgacagtta ccaatgctta atcagtgagg cacctatctc agcgatctgt   5400
ctatttcgtt catccatagt tgcctgactc cccgtcgtgt agataactac gatacgggag   5460
ggcttaccat ctggccccag tgctgcaatg ataccgcgag acccacgctc accggctcca   5520
gatttatcag caataaacca gccagccgga agggccgagc gcagaagtgg tcctgcaact   5580
ttatccgcct ccatccagtc tattaattgt tgccgggaag ctagagtaag tagttcgcca   5640
gttaatagtt tgcgcaacgt tgttgccatt gctacaggca tcgtggtgtc acgctcgtcg   5700
tttggtatgg cttcattcag ctccggttcc caacgatcaa ggcgagttac atgatccccc   5760
atgttgtgca aaaaagcggt tagctccttc ggtcctccga tcgttgtcag aagtaagttg   5820
gccgcagtgt tatcactcat ggttatggca gcactgcata attctcttac tgtcatgcca   5880
tccgtaagat gcttttctgt gactggtgag tactcaacca agtcattctg agaatagtgt   5940
atgcggcgac cgagttgctc ttgcccggcg tcaatacggg ataataccgc gccacatagc   6000
agaactttaa aagtgctcat cattggaaaa cgttcttcgg ggcgaaaact ctcaaggatc   6060
ttaccgctgt tgagatccag ttcgatgtaa cccactcgtg cacccaactg atcttcagca   6120
tcttttactt tcaccagcgt ttctgggtga gcaaaaacag gaaggcaaaa tgccgcaaaa   6180
aagggaataa gggcgacacg gaaatgttga atactcatac tcttcctttt tcaatattat   6240
tgaagcattt atcagggtta ttgtctcatg agcggataca tatttgaatg tatttagaaa   6300
aataaacaaa taggggttcc gcgcacattt ccccgaaaag tgccacctga acgaagcatc   6360
tgtgcttcat tttgtagaac aaaaatgcaa cgcgagagcg ctaatttttc aaacaaagaa   6420
tctgagctgc atttttacag aacagaaatg caacgcgaaa gcgctatttt accaacgaag   6480
aatctgtgct tcatttttgt aaaacaaaaa tgcaacgcga gagcgctaat tttcaaaca    6540
aagaatctga gctgcatttt tacagaacag aaatgcaacg cgagagcgct attttaccaa   6600
caaagaatct atacttcttt tttgttctac aaaaatgcat cccgagagcg ctatttttct   6660
```

```
aacaaagcat cttagattac ttttttctc ctttgtgcgc tctataatgc agtctcttga   6720
taacttttg cactgtaggt ccgttaaggt tagaagaagg ctactttggt gtctattttc   6780
tcttccataa aaaaagcctg actccacttc ccgcgtttac tgattactag cgaagctgcg   6840
ggtgcatttt ttcaagataa aggcatcccc gattatattc tataccgatg tggattgcgc   6900
atactttgtg aacagaaagt gatagcgttg atgattcttc attggtcaga aaattatgaa   6960
cggtttcttc tattttgtct ctatatacta cgtataggaa atgtttacat tttcgtattg   7020
ttttcgattc actctatgaa tagttcttac tacaattttt ttgtctaaag agtaatacta   7080
gagataaaca taaaaaatgt agaggtcgag tttagatgca agttcaagga gcgaaaggtg   7140
gatgggtagg ttatataggg atatagcaca gagatatata gcaaagagat acttttgagc   7200
aatgtttgtg gaagcggtat tcgcaatatt ttagtagctc gttacagtcc ggtgcgtttt   7260
tggtttttg aaagtgcgtc ttcagagcgc ttttggtttt caaaagcgct ctgaagttcc   7320
tatactttct agagaatagg aacttcggaa taggaacttc aaagcgtttc cgaaaacgag   7380
cgcttccgaa aatgcaacgc gagctgcgca catacagctc actgttcacg tcgcacctat   7440
atctgcgtgt tgcctgtata tatatataca tgagaagaac ggcatagtgc gtgtttatgc   7500
ttaaatgcgt acttatatgc gtctatttat gtaggatgaa aggtagtcta gtacctcctg   7560
tgatattatc ccattccatg cggggtatcg tatgcttcct tcagcactac cctttagctg   7620
ttctatatgc tgccactcct caattggatt agtctcatcc ttcaatgcta tcatttcctt   7680
tgata                                                              7685
```

<210> SEQ ID NO 72
<211> LENGTH: 4105
<212> TYPE: DNA
<213> ORGANISM: Artificial Sequence
<220> FEATURE:
<223> OTHER INFORMATION: pGV2359

<400> SEQUENCE: 72

```
ctgcttaatt aagatcaggt cagtacaaac gcaacacgaa agaacaaaaa aagaagaaaa     60
cagaaggcca agacagggtc aatgagactg ttgtcctcct actgtcccta tgtctctggc    120
cgatcacgcg ccattgtccc tcagaaacaa atcaaacacc cacaccccgg gcacccaaag    180
tccccaccca caccaccaat acgtaaacgg ggcgcccccct gcaggccctc ctgcgcgcgg    240
cctcccgcct tgcttctctc cccttccttt tctttttcca gttttcccta ttttgtccct    300
ttttccgcac aacaagtatc agaatgggtt catcaaatct atccaaccta attcgcacgt    360
agactggctt ggtattggca gtttcgtagt tatatatata ctaccatgag tgaaactgtt    420
acgttacctt aaattctttc tccctttaat ttttctttat cttactctcc tacataagac    480
atcaagaaac aattgtatat tgtacacccc ccccctccac aaacacaaat attgataata    540
taaaggagaa ttcttataca ggaaacttaa tagaacaaat cacatattta atctaatagc    600
cacctgcatt ggcacggtgc aacactactt caacttcatc ttacaaaaag atcacgtgat    660
ctgttgtatt gaactgaaaa ttttttgttt gcttctctct ctctctttca ttatgtgaga    720
tttaaaaacc agaaactaca tcatcgaaaa agagttttaa accattacaa ccattgcgat    780
aagccctctc aaactataac aatactgaca gtactaaata attgcctact tggcttcaca    840
tacgttgcat acgtcgatat agataataat gataatgaca gcaggattat cgtaatacgt    900
aatagttgaa aatctcaaaa atgtgtgggt cattacgtaa ataatgatag gaatgggatt    960
cttctatttt tcctttttcc attctagcag ccgtcgggaa aacgtggcat cctctctttc   1020
```

```
gggctcaatt ggagtcacgc tgccgtgagc atcctctctt tccatatcta acaactgagc   1080
acgtaaccaa tggaaaagca tgagcttagc gttgctccaa aaaagtattg gatggttaat   1140
accatttgtc tgttctcttc tgactttgac tcctcaaaaa aaaaaaatct acaatcaaca   1200
gatcgcttca attacgccct cacaaaaact tttttccttc ttcttcgccc acgttaaatt   1260
ttatccctca tgttgtctaa cggatttctg cacttgattt attataaaaa gacaaagaca   1320
taatacttct ctatcaattt cagttattgt tcttccttgc gttattcttc tgttcttctt   1380
tttcttttgt catatataac cataaccaag taatacatat tcaaaatgtc cacaaaatca   1440
tataccagta gagctgagac tcatgcaagt ccggttgcat cgaaactttt acgtttaatg   1500
gatgaaaaga agaccaattt gtgtgcttct cttgacgttc gttcgactga tgagctattg   1560
aaacttgttg aaacgttggg tccatacatt tgccttttga aaacacacgt tgatatcttg   1620
gatgatttca gttatgaggg tactgtcgtt ccattgaaag cattggcaga gaaatacaag   1680
ttcttgatat ttgaggacag aaaattcgcc gatatcggta acacagtcaa attacaatat   1740
acatcgggcg tttaccgtat cgcagaatgg tctgatatca ccaacgccca cggggttact   1800
ggtgctggta ttgttgctgg cttgaaacaa ggtgcgcaag aggtcaccaa agaaccaagg   1860
ggattattga tgcttgctga attgtcttcc aagggttctc tagcacacgg tgaatatact   1920
aagggtaccg aagcttggcg taatcatggt catagctgtt tcctgtgtga aattgttatc   1980
cgctcacaat tccacacaac atacgagccg gaagcataaa gtgtaaagcc tggggtgcct   2040
aatgagtgag ctaactcaca ttaattgcgt tgcgctcact gcccgctttc cagtcgggaa   2100
acctgtcgtg ccagctgcat taatgaatcg gccaacgcgc ggggagaggc ggtttgcgta   2160
ttgggcgctc ttccgcttcc tcgctcactg actcgctgcg ctcggtcgtt cggctgcggc   2220
gagcggtatc agctcactca aaggcggtaa tacggttatc cacagaatca ggggataacg   2280
caggaaagaa catgtgagca aaaggccagc aaaaggccag gaaccgtaaa aaggccgcgt   2340
tgctggcgtt tttccatagg ctccgccccc ctgacgagca tcacaaaaat cgacgctcaa   2400
gtcagaggtg gcgaaacccg acaggactat aaagatacca ggcgtttccc cctggaagct   2460
ccctcgtgcg ctctcctgtt ccgaccctgc cgcttaccgg atacctgtcc gcctttctcc   2520
cttcgggaag cgtggcgctt tctcatagct cacgctgtag gtatctcagt tcggtgtagg   2580
tcgttcgctc caagctgggc tgtgtgcacg aaccccccgt tcagcccgac cgctgcgcct   2640
tatccggtaa ctatcgtctt gagtccaacc cggtaagaca cgacttatcg ccactggcag   2700
cagccactgg taacaggatt agcagagcga ggtatgtagg cggtgctaca gagttcttga   2760
agtggtggcc taactacggc tacactagaa ggacagtatt tggtatctgc gctctgctga   2820
agccagttac cttcggaaaa agagttggta gctcttgatc cggcaaacaa accaccgctg   2880
gtagcggtgg tttttttgtt tgcaagcagc agattacgcg cagaaaaaaa ggatctcaag   2940
aagatccttt gatcttttct acggggtctg acgctcagtg gaacgaaaac tcacgttaag   3000
ggattttggt catgagatta tcaaaaagga tcttcaccta gatcctttta aattaaaaat   3060
gaagttttaa atcaatctaa agtatatatg agtaaacttg gtctgacagt taccaatgct   3120
taatcagtga ggcacctatc tcagcgatct gtctatttcg ttcatccata gttgcctgac   3180
tccccgtcgt gtagataact acgatacggg agggcttacc atctggcccc agtgctgcaa   3240
tgataccgcg agacccacgc tcaccggctc cagatttatc agcaataaac cagccagccg   3300
gaagggccga gcgcagaagt ggtcctgcaa ctttatccgc ctccatccag tctattaatt   3360
gttgccggga agctagagta agtagttcgc cagttaatag tttgcgcaac gttgttgcca   3420
```

```
ttgctacagg catcgtggtg tcacgctcgt cgtttggtat ggcttcattc agctccggtt   3480

cccaacgatc aaggcgagtt acatgatccc ccatgttgtg caaaaaagcg gttagctcct   3540

tcggtcctcc gatcgttgtc agaagtaagt tggccgcagt gttatcactc atggttatgg   3600

cagcactgca taattctctt actgtcatgc catccgtaag atgcttttct gtgactggtg   3660

agtactcaac caagtcattc tgagaatagt gtatgcggcg accgagttgc tcttgcccgg   3720

cgtcaatacg ggataatacc gcgccacata gcagaacttt aaaagtgctc atcattggaa   3780

aacgttcttc ggggcgaaaa ctctcaagga tcttaccgct gttgagatcc agttcgatgt   3840

aacccactcg tgcacccaac tgatcttcag catcttttac tttcaccagc gtttctgggt   3900

gagcaaaaac aggaaggcaa aatgccgcaa aaaagggaat aagggcgaca cggaaatgtt   3960

gaatactcat actcttcctt tttcaatatt attgaagcat ttatcagggt tattgtctca   4020

tgagcggata catatttgaa tgtatttaga aaaataaaca aataggggtt ccgcgcacat   4080

ttccccgaaa agtgccacct gacgt                                         4105
```

```
<210> SEQ ID NO 73
<211> LENGTH: 8009
<212> TYPE: DNA
<213> ORGANISM: Artificial Sequence
<220> FEATURE:
<223> OTHER INFORMATION: pGV2157

<400> SEQUENCE: 73
```

```
ttggatcata ctaagaaacc attattatca tgacattaac ctataaaaat aggcgtatca     60

cgaggccctt tcgtctcgcg cgtttcggtg atgacggtga aaacctctga cacatgcagc    120

tcccggagac ggtcacagct tgtctgtaag cggatgccgg gagcagacaa gcccgtcagg    180

gcgcgtcagc gggtgttggc gggtgtcggg gctggcttaa ctatgcggca tcagagcaga    240

ttgtactgag agtgcaccat accacagctt ttcaattcaa ttcatcattt ttttttttatt    300

cttttttttg atttcggttt ctttgaaatt tttttgattc ggtaatctcc gaacagaagg    360

aagaacgaag gaaggagcac agacttagat tggtatatat acgcatatgt agtgttgaag    420

aaacatgaaa ttgcccagta ttcttaaccc aactgcacag aacaaaaacc tgcaggaaac    480

gaagataaat catgtcgaaa gctacatata aggaacgtgc tgctactcat cctagtcctg    540

ttgctgccaa gctatttaat atcatgcacg aaaagcaaac aaacttgtgt gcttcattgg    600

atgttcgtac caccaaggaa ttactggagt tagttgaagc attaggtccc aaaatttgtt    660

tactaaaaac acatgtggat atcttgactg atttttccat ggagggcaca gttaagccgc    720

taaaggcatt atccgccaag tacaattttt tactcttcga agacagaaaa tttgctgaca    780

ttggtaatac agtcaaattg cagtactctg cgggtgtata cagaatagca gaatgggcag    840

acattacgaa tgcacacggt gtggtgggcc caggtattgt tagcggtttg aagcaggcgg    900

cagaagaagt aacaaaggaa cctagaggcc ttttgatgtt agcagaattg tcatgcaagg    960

gctccctatc tactggagaa tatactaagg gtactgttga cattgcgaag agcgacaaag   1020

attttgttat cggctttatt gctcaaagag acatgggtgg aagagatgaa ggttacgatt   1080

ggttgattat gacacccggt gtgggtttag atgacaaggg agacgcattg ggtcaacagt   1140

atagaaccgt ggatgatgtg gtctctacag gatctgacat tattattgtt ggaagaggac   1200

tatttgcaaa gggaagggat gctaaggtag agggtgaacg ttacagaaaa gcaggctggg   1260

aagcatattt gagaagatgc ggccagcaaa actaaaaaac tgtattataa gtaaatgcat   1320

gtatactaaa ctcacaaatt agagcttcaa tttaattata tcagttatta ccctatgcgg   1380
```

-continued tgtgaaatac cgcacagatg cgtaaggaga aaataccgca tcaggaaatt gtaaacgtta 1440
atattttgtt aaaattcgcg ttaaattttt gttaaatcag ctcatttttt aaccaatagg 1500
ccgaaatcgg caaaatccct tataaatcaa aagaatagac cgagataggg ttgagtgttg 1560
ttccagtttg gaacaagagt ccactattaa agaacgtgga ctccaacgtc aaagggcgaa 1620
aaaccgtcta tcagggcgat ggcccactac gtgaaccatc accctaatca agttttttgg 1680
ggtcgaggtg ccgtaaagca ctaaatcgga accctaaagg gagcccccga tttagagctt 1740
gacggggaaa gccggcgaac gtggcgagaa aggaagggaa gaaagcgaaa ggagcgggcg 1800
ctagggcgct ggcaagtgta gcggtcacgc tgcgcgtaac caccacaccc gccgcgctta 1860
atgcgccgct acagggcgcg tcgcgccatt cgccattcag gctgcgcaac tgttgggaag 1920
ggcgatcggt gcgggcctct tcgctattac gccagctggc gaaaggggga tgtgctgcaa 1980
ggcgattaag ttgggtaacg ccagggtttt cccagtcacg acgttgtaaa acgacggcca 2040
gtgagcgcgc gtaatacgac tcactatagg gcgaattggg taccggccgc aaattaaagc 2100
cttcgagcgt cccaaaacct tctcaagcaa ggttttcagt ataatgttac atgcgtacac 2160
gcgtctgtac agaaaaaaaa gaaaaatttg aaatataaat aacgttctta atactaacat 2220
aactataaaa aaataaatag ggacctagac ttcaggttgt ctaactcctt ccttttcggt 2280
tagagcggat gtggggggag ggcgtgaatg taagcgtgac ataactaatt acatgactcg 2340
agcggccgcg gatcctcaag catctaaaac acaaccgttg gaagcgttgg aaaccaactt 2400
agcatacttg gatagagtac ctcttgtgta acgaggtgga ggtgcaaccc aactttgttt 2460
acgttgagcc atttccttat cagagactaa taggtcaatc ttgttattat cagcatcaat 2520
gataatctca tcgccgtctc tgaccaaccc gataggacca ccttcagcgg cttcgggaac 2580
aatgtggccg attaagaacc cgtgagaacc accagagaat ctaccatcag tcaacaatgc 2640
aacatcttta cccaaaccgt aacccatcag agcagaggaa ggctttagca tttcaggcat 2700
acctggtgca cctcttggac cttcatatct gataacaaca acggtttttt caccccttctt 2760 gatttcacct ctttccaagg cttcaataaa ggcaccttcc tcttcgaaca cacgtgctct 2820
acccttgaag taagtacctt ccttaccggt aattttaccc acagctccac ctggtgccaa 2880
tgaaccgtac agaatttgca agtgaccgtt ggccttgatt gggtgggaga gtggcttaat 2940
aatctcttgt ccttcaggta ggcttggtgc tttctttgca cgttctgcca aagtgtcacc 3000
ggtaacagtc attgtgttac cgtgcaacat gttgttttca tatagatact taatcacaga 3060
ttgggtacca ccaacgttaa tcaaatcggc catgacgtat ttaccagaag gtttgaagtc 3120
accgatcaat ggtgtagtat cactgattct ttggaaatca tctggtgaca acttgacacc 3180
cgcagagtga gcaacagcca ccaaatgcaa aacagcatta gtggacccac cggttgcaac 3240
gacataagta atggcgtttt caaaagcctc ttttgtgagg atatcacgag gtaaaatacc 3300
caattccatt gtcttcttga tgtattcacc aatgttgtca cactcagcta acttctcctt 3360
ggaaacggct gggaaggaag aggagtttgg aatggtcaaa cctagcactt cagcggcaga 3420
agccattgtg ttggcagtat acataccacc acaagaacca ggacctgggc atgcatgttc 3480
cacaacatct tctctttctt cttcagtgaa ttgcttggaa atatattcac cgtaggattg 3540
gaacgcagag acgatatcga tgtttttaga gatcttcgaa gaaccacatg ttggatgacc 3600
gggcaagata gtaccaccat ataccatgat ggaaggtctg ttatgtctac ccatggccat 3660
catgacaccg ggcatgtttt tgtcacatga tgggatggcg atgttagcat cgtagtgttg 3720
tgccatcatg atggtttcaa aggagtctgc aatgatttct ctactttgta acgagtatct 3780

```
cataccttta gtacccatag agataccgtc tgaaacaccg atggtgttga actgcatagc   3840

tttcaaaccc gctttttcaa tggattgaga acatctgtta ttcaagtcca atagatgcat   3900

gttacatggg ttaccggacc accaacagga accaaccccg acttgaggct tcttgaaatc   3960

ttccttcttg aaaccggtgg cataaagcat ggcctgggac gcaccttggc ccttaggttc   4020

agtgatgata tacgagtact tgttgagctt cttcatgtcg acaaacttag attagattgc   4080

tatgctttct ttctaatgag caagaagtaa aaaaagttgt aatagaacaa gaaaaatgaa   4140

actgaaactt gagaaattga agaccgttta ttaacttaaa tatcaatggg aggtcatcga   4200

aagagaaaaa aatcaaaaaa aaaattttca agaaaaagaa acgtgataaa aatttttatt   4260

gcctttttcg acgaagaaaa agaaacgagg cggtctcttt tttcttttcc aaacctttag   4320

tacgggtaat taacgacacc ctagaggaag aaagagggga aatttagtat gctgtgcttg   4380

ggtgttttga agtggtacgg cgatgcgcgg agtccgagaa aatctggaag agtaaaaaag   4440

gagtagaaac attttgaagc tatgagctcc agcttttgtt ccctttagtg agggttaatt   4500

gcgcgcttgg cgtaatcatg gtcatagctg tttcctgtgt gaaattgtta tccgctcaca   4560

attccacaca acataggagc cggaagcata aagtgtaaag cctggggtgc ctaatgagtg   4620

aggtaactca cattaattgc gttgcgctca ctgcccgctt tccagtcggg aaacctgtcg   4680

tgccagctgc attaatgaat cggccaacgc gcggggagag gcggtttgcg tattgggcgc   4740

tcttccgctt cctcgctcac tgactcgctg cgctcggtcg ttcggctgcg gcgagcggta   4800

tcagctcact caaaggcggt aatacggtta tccacagaat caggggataa cgcaggaaag   4860

aacatgtgag caaaaggcca gcaaaaggcc aggaaccgta aaaaggccgc gttgctggcg   4920

tttttccata ggctccgccc ccctgacgag catcacaaaa atcgacgctc aagtcagagg   4980

tggcgaaacc cgacaggact ataaagatac caggcgtttc cccctggaag ctccctcgtg   5040

cgctctcctg ttccgaccct gccgcttacc ggatacctgt ccgcctttct cccttcggga   5100

agcgtggcgc tttctcatag ctcacgctgt aggtatctca gttcggtgta ggtcgttcgc   5160

tccaagctgg gctgtgtgca cgaacccccc gttcagcccg accgctgcgc cttatccggt   5220

aactatcgtc ttgagtccaa cccggtaaga cacgacttat cgccactggc agcagccact   5280

ggtaacagga ttagcagagc gaggtatgta ggcggtgcta cagagttctt gaagtggtgg   5340

cctaactacg gctacactag aaggacagta tttggtatct gcgctctgct gaagccagtt   5400

accttcggaa aaagagttgg tagctcttga tccggcaaac aaaccaccgc tggtagcggt   5460

ggtttttttg tttgcaagca gcagattacg cgcagaaaaa aaggatctca agaagatcct   5520

ttgatctttt ctacggggtc tgacgctcag tggaacgaaa actcacgtta agggattttg   5580

gtcatgagat tatcaaaaag gatcttcacc tagatccttt taaattaaaa atgaagtttt   5640

aaatcaatct aaagtatata tgagtaaact tggtctgaca gttaccaatg cttaatcagt   5700

gaggcaccta tctcagcgat ctgtctattt cgttcatcca tagttgcctg actccccgtc   5760

gtgtagataa ctacgatacg ggagggctta ccatctggcc ccagtgctgc aatgataccg   5820

cgagacccac gctcaccggc tccagattta tcagcaataa accagccagc cggaagggcc   5880

gagcgcagaa gtggtcctgc aactttatcc gcctccatcc agtctattaa ttgttgccgg   5940

gaagctagag taagtagttc gccagttaat agtttgcgca acgttgttgc cattgctaca   6000

ggcatcgtgg tgtcacgctc gtcgtttggt atggcttcat tcagctccgg ttcccaacga   6060

tcaaggcgag ttacatgatc ccccatgttg tgcaaaaaag cggttagctc cttcggtcct   6120

ccgatcgttg tcagaagtaa gttggccgca gtgttatcac tcatggttat ggcagcactg   6180
```

```
cataattctc ttactgtcat gccatccgta agatgctttt ctgtgactgg tgagtactca   6240

accaagtcat tctgagaata gtgtatgcgg cgaccgagtt gctcttgccc ggcgtcaata   6300

cgggataata ccgcgccaca tagcagaact ttaaaagtgc tcatcattgg aaaacgttct   6360

tcggggcgaa aactctcaag gatcttaccg ctgttgagat ccagttcgat gtaacccact   6420

cgtgcaccca actgatcttc agcatctttt actttcacca gcgtttctgg gtgagcaaaa   6480

acaggaaggc aaaatgccgc aaaaaaggga ataagggcga cacggaaatg ttgaatactc   6540

atactcttcc tttttcaata ttattgaagc atttatcagg gttattgtct catgagcgga   6600

tacatatttg aatgtattta gaaaaataaa caaatagggg ttccgcgcac atttccccga   6660

aaagtgccac ctgaacgaag catctgtgct tcattttgta gaacaaaaat gcaacgcgag   6720

agcgctaatt tttcaaacaa agaatctgag ctgcattttt acagaacaga aatgcaacgc   6780

gaaagcgcta ttttaccaac gaagaatctg tgcttcattt ttgtaaaaca aaaatgcaac   6840

gcgagagcgc taatttttca aacaaagaat ctgagctgca tttttacaga acagaaatgc   6900

aacgcgagag cgctatttta ccaacaaaga atctatactt ctttttttgtt ctacaaaaat   6960

gcatcccgag agcgctattt ttctaacaaa gcatcttaga ttactttttt tctcctttgt   7020

gcgctctata atgcagtctc ttgataactt tttgcactgt aggtccgtta aggttagaag   7080

aaggctactt tggtgtctat tttctcttcc ataaaaaaag cctgactcca cttcccgcgt   7140

ttactgatta ctagcgaagc tgcgggtgca tttttttcaag ataaaggcat ccccgattat   7200

attctatacc gatgtggatt gcgcatactt tgtgaacaga aagtgatagc gttgatgatt   7260

cttcattggt cagaaaatta tgaacggttt cttctatttt gtctctatat actacgtata   7320

ggaaatgttt acattttcgt attgttttcg attcactcta tgaatagttc ttactacaat   7380

tttttttgtct aaagagtaat actagagata aacataaaaa atgtagaggt cgagtttaga   7440

tgcaagttca aggagcgaaa ggtggatggg taggttatat agggatatag cacagagata   7500

tatagcaaag agatactttt gagcaatgtt tgtggaagcg gtattcgcaa tattttagta   7560

gctcgttaca gtccggtgcg tttttggttt tttgaaagtg cgtcttcaga gcgcttttgg   7620

ttttcaaaag cgctctgaag ttcctatact ttctagagaa taggaacttc ggaataggaa   7680

cttcaaagcg tttccgaaaa cgagcgcttc cgaaaatgca acgcgagctg cgcacataca   7740

gctcactgtt cacgtcgcac ctatatctgc gtgttgcctg tatatatata tacatgagaa   7800

gaacggcata gtgcgtgttt atgcttaaat gcgtacttat atgcgtctat ttatgtagga   7860

tgaaaggtag tctagtacct cctgtgatat tatcccattc catgcggggt atcgtatgct   7920

tccttcagca ctacccttta gctgttctat atgctgccac tcctcaattg gattagtctc   7980

atccttcaat gctatcattt cctttgata                                      8009
```

```
<210> SEQ ID NO 74
<211> LENGTH: 8990
<212> TYPE: DNA
<213> ORGANISM: Artificial Sequence
<220> FEATURE:
<223> OTHER INFORMATION: pGV2163

<400> SEQUENCE: 74

ctgcttaatt aagatcaggt cagtacaaac gcaacacgaa agaacaaaaa aagaagaaaa     60

cagaaggcca agacagggtc aatgagactg ttgtcctcct actgtcccta tgtctctggc    120

cgatcacgcg ccattgtccc tcagaaacaa atcaaacacc cacaccccgg gcacccaaag    180

tccccaccca caccaccaat acgtaaacgg ggcgcccccct gcaggccctc ctgcgcgcgg    240
```

-continued

```
cctcccgcct tgcttctctc cccttccttt tctttttcca gttttcccta ttttgtccct    300
ttttccgcac aacaagtatc agaatgggtt catcaaatct atccaaccta attcgcacgt    360
agactggctt ggtattggca gtttcgtagt tatatatata ctaccatgag tgaaactgtt    420
acgttacctt aaattctttc tccctttaat tttcttttat cttactctcc tacataagac    480
atcaagaaac aattgtatat tgtacacccc ccccctccac aaacacaaat attgataata    540
taaaggagct cgccgatccc attaccgaca tttgggcgct atacgtgcat atgttcatgt    600
atgtatctgt atttaaaaca cttttgtatt atttttcctc atatatgtgt ataggtttat    660
acggatgatt taattattac ttcaccaccc tttatttcag gctgatatct tagccttgtt    720
actagttaga aaaagacatt tttgctgtca gtcactgtca agagattctt ttgctggcat    780
ttcttctaga agcaaaaaga gcgatgcgtc ttttccgctg aaccgttcca gcaaaaaaga    840
ctaccaacgc aatatggatt gtcagaatca tataaaagag aagcaaataa ctccttgtct    900
tgtatcaatt gcattataat atcttcttgt tagtgcaata tcatatagaa gtcatcgaaa    960
tagatattaa gaaaaacaaa ctgtacaatc aatcaatcaa tcatcacata aagtcgacat   1020
gttgacaaaa gcaacaaaag aacaaaaatc ccttgtgaaa agcagagggg cggagcttgt   1080
tgttgattgc ttagcggagc aaggtgtcac acatgtattt ggcattccag gtgcaaaaat   1140
tgatgcggta tttgacgctt tacaagataa agggcctgaa attatcgttg cccggcatga   1200
acaaaatgca gcatttatgg cgcaagcagt cggccgttta actggaaaac cgggagtcgt   1260
gttagtcaca tcaggaccag gtgcttcgaa cttggcaaca ggactgctga cagcaaacac   1320
tgaaggtgac cctgtcgttg cgcttgctgg gaacgtgatc cgtgcagatc gtttaaaacg   1380
gacacatcaa tctttggata atgcggcgct attccagccg attacaaaat acagtgtaga   1440
agttcaagat gtaaaaaata taccggaagc tgttacaaat gcgtttagga tagcgtcagc   1500
agggcaggct ggggccgctt ttgtgagttt tccgcaagat gttgtgaatg aagtcacaaa   1560
tacaaaaaac gtacgtgctg tcgcagcgcc aaaacttggt cccgcagcag atgacgcaat   1620
cagtatggcc attgcaaaaa ttcaaacagc aaaacttcct gtcgttttag tcggcatgaa   1680
gggcggaaga ccggaagcga ttaaagcggt tcgcaagcta ttgaaaaaag tgcagcttcc   1740
attcgttgaa acatatcaag ctgccggtac tcttacgaga gatttagagg atcagtattt   1800
tggccggatc ggtttattcc gcaaccagcc tggcgatctg ctgcttgagc aggctgatgt   1860
tgttctgaca atcggctatg acccaattga atatgatccg aaattctgga atgtcaatgg   1920
agaccggacg atcatccatt tagacgagat tctggctgac attgatcatg cttaccagcc   1980
ggatcttgaa ctgatcggtg atattccatc tacgatcaat catatcgaac acgatgctgt   2040
gaaagtagac tttgcggaac gtgagcagaa gatcctttct gatttaaaac aatatatgca   2100
tgagggtgag caggtgcctg cagattggaa atcagacaga gtgcatcctc ttgaaatcgt   2160
taaagaattg cgaaacgcag tcgatgatca tgttacagtg acttgcgata tcggttcaca   2220
cgcgatttgg atgtcacgtt atttccgcag ctacgagccg ttaacattaa tgattagtaa   2280
cggtatgcaa acactcggcg ttgcgcttcc ttgggcaatc ggcgcttcat tggtgaaacc   2340
gggagaaaaa gtagtatcag tctccggtga tggcggtttc ttattctcag ctatggaatt   2400
agagacagca gttcgtttaa aagcaccaat tgtacacatt gtatggaacg acagcacata   2460
tgacatggtt gcattccagc aattgaaaaa atataatcgt acatctgcgg tcgatttcgg   2520
aaatatcgat atcgtgaaat acgcggaaag cttcggagca actggcttac gcgtagaatc   2580
accagaccag ctggcagatg ttctgcgtca aggcatgaac gctgaggggc ctgtcatcat   2640
```

```
tgatgtcccg gttgactaca gtgataacgt taatttagca agtgacaagc ttccgaaaga   2700
attcggggaa ctcatgaaaa cgaaagctct ctagggatcc tcatgtaatt agttatgtca   2760
cgcttacatt cacgccctcc ccccacatcc gctctaaccg aaaaggaagg agttagacaa   2820
cctgaagtct aggtccctat ttattttttt atagttatgt tagtattaag aacgttattt   2880
atatttcaaa tttttctttt ttttctgtac agacgcgtgt acgcatgtaa cattatactg   2940
aaaaccttgc ttgagaaggt tttgggacgc tcgaaggctt taatttgccc taggctcaac   3000
tcaagacgca cagatattat aacatctgca taataggcat ttgcaagaat tactcgtgag   3060
taaggaaaga gtgaggaact atcgcatacc tgcatttaaa gatgccgatt tgggcgcgaa   3120
tcctttattt tggcttcacc ctcatactat tatcagggcc agaaaaagga agtgtttccc   3180
tccttcttga attgatgtta ccctcataaa gcacgtggcc tcttatcgag aaagaaatta   3240
ccgtcgctcg tgatttgttt gcaaaaagaa caaaactgaa aaaacccaga cacgctcgac   3300
ttcctgtctt cctattgatt gcagcttcca atttcgtcac acaacaaggt cctagcgacg   3360
gctcacaggt tttgtaacaa gcaatcgaag gttctggaat ggcgggaaag ggtttagtac   3420
cacatgctat gatgcccact gtgatctcca gagcaaagtt cgttcgatcg tactgttact   3480
ctctctcttt caaacagaat tgtccgaatc gtgtgacaac aacagcctgt tctcacacac   3540
tcttttcttc taaccaaggg ggtggtttag tttagtagaa cctcgtgaaa cttacattta   3600
catatatata aacttgcata aattggtcaa tgcaagaaat acatatttgg tcttttctaa   3660
ttcgtagttt ttcaagttct tagatgcttt ctttttctct tttttacaga tcatcaagga   3720
agtaattatc tactttttac aacaaatata aaacaagctc gacatgtata ctgttggtga   3780
ttatctgctg gaccgtctgc atgaactggg tatcgaagaa atcttcggcg ttccgggtga   3840
ttacaatctg cagttcctgg atcagatcat ctctcataaa gacatgaaat gggtgggtaa   3900
cgctaacgaa ctgaacgcaa gctacatggc agatggttat gcacgtacca agaaagccgc   3960
ggcatttctg accactttcg gtgttggcga actgagcgcc gtcaacggtc tggcgggctc   4020
ctacgccgaa aacctgccgg tggtggagat cgtaggcagc ccaacgagca aagttcagaa   4080
cgaaggtaaa ttcgtccacc acactctggc tgacggcgat ttcaaacact tcatgaaaat   4140
gcatgaacct gtgactgcgg cacgtacgct gctgactgca gagaacgcta ctgtggaaat   4200
cgaccgcgtt ctgtctgcgc tgctgaaaga acgcaaacca gtttacatca acctgcctgt   4260
ggatgttgcg gcagctaaag cggaaaaacc gagcctgccg ctgaagaaag aaaactccac   4320
ttctaacact agcgaccagg aaatcctgaa caaaatccag gagtctctga aaaacgcaaa   4380
gaaaccaatc gtgatcaccg gccacgaaat catttctttt ggtctggaga agaccgtgac   4440
ccaattcatc agcaaaacca aactgccgat taccaccctg aacttcggca agtcctctgt   4500
tgacgaggct ctgccgtctt tcctgggcat ctacaacggt actctgagcg aaccgaacct   4560
gaaagaattt gttgaatctg cggacttcat cctgatgctg ggcgttaaac tgaccgactc   4620
ttctaccggt gcattcactc accatctgaa cgaaaacaaa atgattagcc tgaacatcga   4680
cgagggtaaa atcttcaacg agcgtatcca gaacttcgac ttcgaaagcc tgatcagctc   4740
tctgctggac ctgtccgaaa tcgagtataa aggcaaatac attgacaaaa agcaagaaga   4800
tttcgtacca tctaacgcac tgctgtccca ggatcgcctg tggcaggccg tggagaacct   4860
gacccagagc aatgaaacca tcgtggcgga acaaggtacg agctttttcg gcgcgtcttc   4920
tatctttctg aaatccaaaa gccattttat cggtcagccg ctgtggggta gcattggcta   4980
tactttcccg gcagcgctgg gctctcagat cgctgataaa gaatctcgtc atctgctgtt   5040
```

```
catcggtgac ggttccctgc agctgaccgt acaggaactg ggtctggcaa ttcgtgaaaa   5100
gatcaacccg atttgcttca ttattaacaa tgacggctac accgttgagc gtgagatcca   5160
cggtccgaac cagtcttaca acgatatccc tatgtggaac tactctaaac tgccggagtc   5220
cttcggcgca actgaggacc gtgttgtgtc taaaattgtg cgtaccgaaa acgaatttgt   5280
gagcgtgatg aaagaggccc aggccgatcc gaaccgtatg tactggatcg aactgatcct   5340
ggcgaaagaa ggcgcaccga aggtactgaa gaaaatgggc aagctgtttg ctgaacagaa   5400
taaatcctaa ggatcttttg cggcctagta ttgaattctt atacaggaaa cttaatagaa   5460
caaatcacat atttaatcta atagccacct gcattggcac ggtgcaacac tacttcaact   5520
tcatcttaca aaaagatcac gtgatctgtt gtattgaact gaaaattttt tgtttgcttc   5580
tctctctctc tttcattatg tgagatttaa aaaccagaaa ctacatcatc gaaaaagagt   5640
tttaaaccat tacaaccatt gcgataagcc ctctcaaact ataacaatac tgacagtact   5700
aaataattgc ctacttggct tcacatacgt tgcatacgtc gatatagata ataatgataa   5760
tgacagcagg attatcgtaa tacgtaatag ttgaaaatct caaaaatgtg tgggtcatta   5820
cgtaaataat gataggaatg ggattcttct atttttcctt tttccattct agcagccgtc   5880
gggaaaacgt ggcatcctct ctttcgggct caattggagt cacgctgccg tgagcatcct   5940
ctctttccat atctaacaac tgagcacgta accaatggaa aagcatgagc ttagcgttgc   6000
tccaaaaaag tattggatgg ttaataccat ttgtctgttc tcttctgact ttgactcctc   6060
aaaaaaaaaa aatctacaat caacagatcg cttcaattac gccctcacaa aaactttttt   6120
ccttcttctt cgcccacgtt aaattttatc cctcatgttg tctaacggat ttctgcactt   6180
gatttattat aaaaagacaa agacataata cttctctatc aatttcagtt attgttcttc   6240
cttgcgttat tcttctgttc ttcttttttct tttgtcatat ataaccataa ccaagtaata   6300
catattcaaa atgtccacaa aatcatatac cagtagagct gagactcatg caagtccggt   6360
tgcatcgaaa cttttacgtt taatggatga aaagaagacc aatttgtgtg cttctcttga   6420
cgttcgttcg actgatgagc tattgaaact tgttgaaacg ttgggtccat acatttgcct   6480
tttgaaaaca cacgttgata tcttggatga tttcagttat gagggtactg tcgttccatt   6540
gaaagcattg gcagagaaat acaagttctt gatatttgag gacagaaaat tcgccgatat   6600
cggtaacaca gtcaaattac aatatacatc gggcgtttac cgtatcgcag aatggtctga   6660
tatcaccaac gcccacgggg ttactggtgc tggtattgtt gctggcttga aacaaggtgc   6720
gcaagaggtc accaaagaac caaggggatt attgatgctt gctgaattgt cttccaaggg   6780
ttctctagca cacggtgaat atactaaggg taccgaagct tggcgtaatc atggtcatag   6840
ctgtttcctg tgtgaaattg ttatccgctc acaattccac acaacatacg agccggaagc   6900
ataaagtgta aagcctgggg tgcctaatga gtgagctaac tcacattaat tgcgttgcgc   6960
tcactgcccg ctttccagtc gggaaacctg tcgtgccagc tgcattaatg aatcggccaa   7020
cgcgcgggga gaggcggttt gcgtattggg cgctcttccg cttcctcgct cactgactcg   7080
ctgcgctcgg tcgttcggct gcggcgagcg gtatcagctc actcaaaggc ggtaatacgg   7140
ttatccacag aatcagggga taacgcagga aagaacatgt gagcaaaagg ccagcaaaag   7200
gccaggaacc gtaaaaaggc cgcgttgctg gcgtttttcc ataggctccg cccccctgac   7260
gagcatcaca aaaatcgacg ctcaagtcag aggtggcgaa acccgacagg actataaaga   7320
taccaggcgt ttccccctgg aagctccctc gtgcgctctc ctgttccgac cctgccgctt   7380
accggatacc tgtccgcctt tctcccttcg ggaagcgtgg cgctttctca tagctcacgc   7440
```

```
tgtaggtatc tcagttcggt gtaggtcgtt cgctccaagc tgggctgtgt gcacgaaccc   7500

cccgttcagc ccgaccgctg cgccttatcc ggtaactatc gtcttgagtc caacccggta   7560

agacacgact tatcgccact ggcagcagcc actggtaaca ggattagcag agcgaggtat   7620

gtaggcggtg ctacagagtt cttgaagtgg tggcctaact acggctacac tagaaggaca   7680

gtatttggta tctgcgctct gctgaagcca gttaccttcg gaaaaagagt tggtagctct   7740

tgatccggca aacaaaccac cgctggtagc ggtggttttt ttgtttgcaa gcagcagatt   7800

acgcgcagaa aaaaaggatc tcaagaagat cctttgatct tttctacggg gtctgacgct   7860

cagtggaacg aaaactcacg ttaagggatt ttggtcatga gattatcaaa aaggatcttc   7920

acctagatcc ttttaaatta aaaatgaagt tttaaatcaa tctaaagtat atatgagtaa   7980

acttggtctg acagttacca atgcttaatc agtgaggcac ctatctcagc gatctgtcta   8040

tttcgttcat ccatagttgc ctgactcccc gtcgtgtaga taactacgat acgggagggc   8100

ttaccatctg gccccagtgc tgcaatgata ccgcgagacc cacgctcacc ggctccagat   8160

ttatcagcaa taaaccagcc agccggaagg gccgagcgca gaagtggtcc tgcaacttta   8220

tccgcctcca tccagtctat taattgttgc cgggaagcta gagtaagtag ttcgccagtt   8280

aatagtttgc gcaacgttgt tgccattgct acaggcatcg tggtgtcacg ctcgtcgttt   8340

ggtatggctt cattcagctc cggttcccaa cgatcaaggc gagttacatg atcccccatg   8400

ttgtgcaaaa aagcggttag ctccttcggt cctccgatcg ttgtcagaag taagttggcc   8460

gcagtgttat cactcatggt tatggcagca ctgcataatt ctcttactgt catgccatcc   8520

gtaagatgct tttctgtgac tggtgagtac tcaaccaagt cattctgaga atagtgtatg   8580

cggcgaccga gttgctcttg cccggcgtca atacgggata ataccgcgcc acatagcaga   8640

actttaaaag tgctcatcat tggaaaacgt tcttcggggc gaaaactctc aaggatctta   8700

ccgctgttga gatccagttc gatgtaaccc actcgtgcac ccaactgatc ttcagcatct   8760

tttactttca ccagcgtttc tgggtgagca aaaacaggaa ggcaaaatgc cgcaaaaaag   8820

ggaataaggg cgacacggaa atgttgaata ctcatactct tcctttttca atattattga   8880

agcatttatc agggttattg tctcatgagc ggatacatat ttgaatgtat ttagaaaaat   8940

aaacaaatag gggttccgcg cacatttccc cgaaaagtgc cacctgacgt              8990
```

```
<210> SEQ ID NO 75
<211> LENGTH: 8990
<212> TYPE: DNA
<213> ORGANISM: Artificial Sequence
<220> FEATURE:
<223> OTHER INFORMATION: pGV2360

<400> SEQUENCE: 75
```

```
ctgcttaatt aagatcaggt cagtacaaac gcaacacgaa agaacaaaaa aagaagaaaa     60

cagaaggcca agacagggtc aatgagactg ttgtcctcct actgtcccta tgtctctggc    120

cgatcacgcg ccattgtccc tcagaaacaa atcaaacacc cacaccccgg gcacccaaag    180

tccccaccca caccaccaat acgtaaacgg ggcgcccccct gcaggccctc ctgcgcgcgg    240

cctcccgcct tgcttctctc cccttccttt tctttttcca gttttcccta ttttgtccct    300

ttttccgcac aacaagtatc agaatgggtt catcaaatct atccaaccta attcgcacgt    360

agactggctt ggtattggca gtttcgtagt tatatatata ctaccatgag tgaaactgtt    420

acgttacctt aaattctttc tccctttaat ttttctttat cttactctcc tacataagac    480

atcaagaaac aattgtatat tgtacacccc ccccctccac aaacacaaat attgataata    540
```

```
taaaggagct cgccgatccc attaccgaca tttgggcgct atacgtgcat atgttcatgt    600
atgtatctgt atttaaaaca cttttgtatt atttttcctc atatatgtgt ataggtttat    660
acggatgatt taattattac ttcaccaccc tttatttcag gctgatatct tagccttgtt    720
actagttaga aaaagacatt tttgctgtca gtcactgtca agagattctt ttgctggcat    780
ttcttctaga agcaaaaaga gcgatgcgtc ttttccgctg aaccgttcca gcaaaaaaga    840
ctaccaacgc aatatggatt gtcagaatca tataaaagag aagcaaataa ctccttgtct    900
tgtatcaatt gcattataat atcttcttgt tagtgcaata tcatatagaa gtcatcgaaa    960
tagatattaa gaaaaacaaa ctgtacaatc aatcaatcaa tcatcacata aagtcgacat   1020
gttgacaaaa gcaacaaaag aacaaaaatc ccttgtgaaa agcagagggg cggagcttgt   1080
tgttgattgc ttagcggagc aaggtgtcac acatgtattt ggcattccag gtgcaaaaat   1140
tgatgcggta tttgacgctt tacaagataa agggcctgaa attatcgttg cccggcatga   1200
acaaaatgca gcatttatgg cgcaagcagt cggccgttta actggaaaac cgggagtcgt   1260
gttagtcaca tcaggaccag gtgcttcgaa cttggcaaca ggactgctga cagcaaacac   1320
tgaaggtgac cctgtcgttg cgcttgctgg gaacgtgatc cgtgcagatc gtttaaaacg   1380
gacacatcaa tctttggata atgcggcgct attccagccg attacaaaat acagtgtaga   1440
agttcaagat gtaaaaaata taccggaagc tgttacaaat gcgtttagga tagcgtcagc   1500
agggcaggct ggggccgctt ttgtgagttt tccgcaagat gttgtgaatg aagtcacaaa   1560
tacaaaaaac gtacgtgctg tcgcagcgcc aaaacttggt cccgcagcag atgacgcaat   1620
cagtatggcc attgcaaaaa ttcaaacagc aaaacttcct gtcgttttag tcggcatgaa   1680
gggcggaaga ccggaagcga ttaaagcggt tcgcaagcta ttgaaaaaag tgcagcttcc   1740
attcgttgaa acatatcaag ctgccggtac tcttacgaga gatttagagg atcagtattt   1800
tggccggatc ggtttattcc gcaaccagcc tggcgatctg ctgcttgagc aggctgatgt   1860
tgttctgaca atcggctatg acccaattga atatgatccg aaattctgga atgtcaatgg   1920
agaccggacg atcatccatt tagacgagat tctggctgac attgatcatg cttaccagcc   1980
ggatcttgaa ctgatcggtg atattccatc tacgatcaat catatcgaac acgatgctgt   2040
gaaagtagac tttgcggaac gtgagcagaa gatcctttct gatttaaaac aatatatgca   2100
tgagggtgag caggtgcctg cagattggaa atcagacaga gtgcatcctc ttgaaatcgt   2160
taaagaattg cgaaacgcag tcgatgatca tgttacagtg acttgcgata tcggttcaca   2220
cgcgatttgg atgtcacgtt atttccgcag ctacgagccg ttaacattaa tgattagtaa   2280
cggtatgcaa acactcggcg ttgcgcttcc ttgggcaatc ggcgcttcat tggtgaaacc   2340
gggagaaaaa gtagtatcag tctccggtga tggcggtttc ttattctcag ctatggaatt   2400
agagacagca gttcgtttaa aagcaccaat tgtacacatt gtatggaacg acagcacata   2460
tgacatggtt gcattccagc aattgaaaaa atataatcgt acatctgcgg tcgatttcgg   2520
aaatatcgat atcgtgaaat acgcggaaag cttcggagca actggcttac gcgtagaatc   2580
accagaccag ctggcagatg ttctgcgtca aggcatgaac gctgaggggc ctgtcatcat   2640
tgatgtcccg gttgactaca gtgataacgt taatttagca agtgacaagc ttccgaaaga   2700
attcggggaa ctcatgaaaa cgaaagctct ctagggatcc tcatgtaatt agttatgtca   2760
cgcttacatt cacgccctcc ccccacatcc gctctaaccg aaaaggaagg agttagacaa   2820
cctgaagtct aggtccctat ttattttttt atagttatgt tagtattaag aacgttattt   2880
atatttcaaa tttttctttt ttttctgtac agacgcgtgt acgcatgtaa cattatactg   2940
```

```
aaaaccttgc ttgagaaggt tttgggacgc tcgaaggctt taatttgccc taggctcaac   3000

tcaagacgca cagatattat aacatctgca taataggcat ttgcaagaat tactcgtgag   3060

taaggaaaga gtgaggaact atcgcatacc tgcatttaaa gatgccgatt tgggcgcgaa   3120

tcctttattt tggcttcacc ctcatactat tatcagggcc agaaaaagga agtgtttccc   3180

tccttcttga attgatgtta ccctcataaa gcacgtggcc tcttatcgag aaagaaatta   3240

ccgtcgctcg tgatttgttt gcaaaaagaa caaaactgaa aaaacccaga cacgctcgac   3300

ttcctgtctt cctattgatt gcagcttcca atttcgtcac acaacaaggt cctagcgacg   3360

gctcacaggt tttgtaacaa gcaatcgaag gttctggaat ggcgggaaag ggtttagtac   3420

cacatgctat gatgcccact gtgatctcca gagcaaagtt cgttcgatcg tactgttact   3480

ctctctcttt caaacagaat tgtccgaatc gtgtgacaac aacagcctgt tctcacacac   3540

tcttttcttc taaccaaggg ggtggtttag tttagtagaa cctcgtgaaa cttacattta   3600

catatatata aacttgcata aattggtcaa tgcaagaaat acatatttgg tcttttctaa   3660

ttcgtagttt ttcaagttct tagatgcttt ctttttctct tttttacaga tcatcaagga   3720

agtaattatc tactttttac aacaaatata aaacaagctc gacatgtata ctgttggtga   3780

ttatctgctg gaccgtctgc atgaactggg tatcgaagaa atcttcggcg ttccgggtga   3840

ttacaatctg cagttcctgg atcagatcat ctctcataaa gacatgaaat gggtgggtaa   3900

cgctaacgaa ctgaacgcaa gctacatggc agatggttat gcacgtacca agaaagccgc   3960

ggcatttctg accactttcg gtgttggcga actgagcgcc gtcaacggtc tggcgggctc   4020

ctacgccgaa aacctgccgg tggtggagat cgtaggcagc ccaacgagca aagttcagaa   4080

cgaaggtaaa ttcgtccacc acactctggc tgacggcgat ttcaaacact tcatgaaaat   4140

gcatgaacct gtgactgcgg cacgtacgct gctgactgca gagaacgcta ctgtggaaat   4200

cgaccgcgtt ctgtctgcgc tgctgaaaga acgcaaacca gtttacatca acctgcctgt   4260

ggatgttgcg gcagctaaag cggaaaaacc gagcctgccg ctgaagaaag aaaactccac   4320

ttctaacact agcgaccagg aaatcctgaa caaaatccag gagtctctga aaaacgcaaa   4380

gaaaccaatc gtgatcaccg gccacgaaat catttctttt ggtctggaga agaccgtgac   4440

ccaattcatc agcaaaacca aactgccgat taccaccctg aacttcggca agtcctctgt   4500

tgacgaggct ctgccgtctt tcctgggcat ctacaacggt actctgagcg aaccgaacct   4560

gaaagaattt gttgaatctg cggacttcat cctgatgctg ggcgttaaac tgaccgactc   4620

ttctaccggt gcattcactc accatctgaa cgaaaacaaa atgattagcc tgaacatcga   4680

cgagggtaaa atcttcaacg agcgtatcca gaacttcgac ttcgaaagcc tgatcagctc   4740

tctgctggac ctgtccgaaa tcgagtataa aggcaaatac attgacaaaa agcaagaaga   4800

tttcgtacca tctaacgcac tgctgtccca ggatcgcctg tggcaggccg tggagaacct   4860

gacccagagc aatgaaacca tcgtggcgga acaaggtacg agctttttcg gcgcgtcttc   4920

tatctttctg aaatccaaaa gccattttat cggtcagccg ctgtggggta gcattggcta   4980

tactttcccg gcagcgctgg gctctcagat cgctgataaa gaatctcgtc atctgctgtt   5040

catcggtgac ggttccctgc agctgaccgt acaggaactg ggtctggcaa ttcgtgaaaa   5100

gatcaacccg atttgcttca ttattaacaa tgacggctac accgttgagc gtgagatcca   5160

cggtccgaac cagtcttaca acgatatccc tatgtggaac tactctaaac tgccggagtc   5220

cttcggcgca actgaggacc gtgttgtgtc taaaattgtg cgtaccgaaa acgaatttgt   5280

gagcgtgatg aaagaggccc aggccgatcc gaaccgtatg tactggatcg aactgatcct   5340
```

```
ggcgaaagaa ggcgcaccga aggtactgaa gaaaatgggc aagctgtttg ctgaacagaa   5400
taaatcctaa ggatcttttg cggcctagta ttgaattctt atacaggaaa cttaatagaa   5460
caaatcacat atttaatcta atagccacct gcattggcac ggtgcaacac tacttcaact   5520
tcatcttaca aaaagatcac gtgatctgtt gtattgaact gaaaattttt tgtttgcttc   5580
tctctctctc tttcattatg tgagatttaa aaaccagaaa ctacatcatc gaaaaagagt   5640
tttaaaccat tacaaccatt gcgataagcc ctctcaaact ataacaatac tgacagtact   5700
aaataattgc ctacttggct tcacatacgt tgcatacgtc gatatagata ataatgataa   5760
tgacagcagg attatcgtaa tacgtaatag ttgaaaatct caaaaatgtg tgggtcatta   5820
cgtaaataat gataggaatg ggattcttct atttttcctt tttccattct agcagccgtc   5880
gggaaaacgt ggcatcctct ctttcgggct caattggagt cacgctgccg tgagcatcct   5940
ctctttccat atctaacaac tgagcacgta accaatggaa aagcatgagc ttagcgttgc   6000
tccaaaaaag tattggatgg ttaataccat ttgtctgttc tcttctgact ttgactcctc   6060
aaaaaaaaaa aatctacaat caacagatcg cttcaattac gccctcacaa aaactttttt   6120
ccttcttctt cgcccacgtt aaattttatc cctcatgttg tctaacggat ttctgcactt   6180
gatttattat aaaaagacaa agacataata cttctctatc aatttcagtt attgttcttc   6240
cttgcgttat tcttctgttc ttctttttct tttgtcatat ataaccataa ccaagtaata   6300
catattcaaa atgtccacaa aatcatatac cagtagagct gagactcatg caagtccggt   6360
tgcatcgaaa cttttacgtt taatggatga aaagaagacc aatttgtgtg cttctcttga   6420
cgttcgttcg actgatgagc tattgaaact tgttgaaacg ttgggtccat acatttgcct   6480
tttgaaaaca cacgttgata tcttggatga tttcagttat gagggtactg tcgttccatt   6540
gaaagcattg gcagagaaat acaagttctt gatatttgag gacagaaaat tcgccgatat   6600
cggtaacaca gtcaaattac aatatacatc gggcgtttac cgtatcgcag aatggtctga   6660
tatcaccaac gcccacgggg ttactggtgc tggtattgtt gctggcttga aacaaggtgc   6720
gcaagaggtc accaaagaac caaggggatt attgatgctt gctgaattgt cttccaaggg   6780
ttctctagca cacggtgaat atactaaggg taccgaagct tggcgtaatc atggtcatag   6840
ctgtttcctg tgtgaaattg ttatccgctc acaattccac acaacatacg agccggaagc   6900
ataaagtgta aagcctgggg tgcctaatga gtgagctaac tcacattaat tgcgttgcgc   6960
tcactgcccg ctttccagtc gggaaacctg tcgtgccagc tgcattaatg aatcggccaa   7020
cgcgcgggga gaggcggttt gcgtattggg cgctcttccg cttcctcgct cactgactcg   7080
ctgcgctcgg tcgttcggct gcggcgagcg gtatcagctc actcaaaggc ggtaatacgg   7140
ttatccacag aatcagggga taacgcagga aagaacatgt gagcaaaagg ccagcaaaag   7200
gccaggaacc gtaaaaaggc cgcgttgctg gcgtttttcc ataggctccg cccccctgac   7260
gagcatcaca aaaatcgacg ctcaagtcag aggtggcgaa acccgacagg actataaaga   7320
taccaggcgt ttccccctgg aagctccctc gtgcgctctc ctgttccgac cctgccgctt   7380
accggatacc tgtccgcctt tctcccttcg ggaagcgtgg cgctttctca tagctcacgc   7440
tgtaggtatc tcagttcggt gtaggtcgtt cgctccaagc tgggctgtgt gcacgaaccc   7500
cccgttcagc ccgaccgctg cgccttatcc ggtaactatc gtcttgagtc caacccggta   7560
agacacgact tatcgccact ggcagcagcc actggtaaca ggattagcag agcgaggtat   7620
gtaggcggtg ctacagagtt cttgaagtgg tggcctaact acggctacac tagaaggaca   7680
gtatttggta tctgcgctct gctgaagcca gttaccttcg gaaaaagagt tggtagctct   7740
```

```
tgatccggca aacaaaccac cgctggtagc ggtggttttt ttgtttgcaa gcagcagatt   7800

acgcgcagaa aaaaaggatc tcaagaagat cctttgatct tttctacggg gtctgacgct   7860

cagtggaacg aaaactcacg ttaagggatt ttggtcatga gattatcaaa aaggatcttc   7920

acctagatcc ttttaaatta aaaatgaagt tttaaatcaa tctaaagtat atatgagtaa   7980

acttggtctg acagttacca atgcttaatc agtgaggcac ctatctcagc gatctgtcta   8040

tttcgttcat ccatagttgc ctgactcccc gtcgtgtaga taactacgat acgggagggc   8100

ttaccatctg gccccagtgc tgcaatgata ccgcgagacc cacgctcacc ggctccagat   8160

ttatcagcaa taaaccagcc agccggaagg gccgagcgca gaagtggtcc tgcaacttta   8220

tccgcctcca tccagtctat taattgttgc cgggaagcta gagtaagtag ttcgccagtt   8280

aatagtttgc gcaacgttgt tgccattgct acaggcatcg tggtgtcacg ctcgtcgttt   8340

ggtatggctt cattcagctc cggttcccaa cgatcaaggc gagttacatg atcccccatg   8400

ttgtgcaaaa aagcggttag ctccttcggt cctccgatcg ttgtcagaag taagttggcc   8460

gcagtgttat cactcatggt tatggcagca ctgcataatt ctcttactgt catgccatcc   8520

gtaagatgct tttctgtgac tggtgagtac tcaaccaagt cattctgaga atagtgtatg   8580

cggcgaccga gttgctcttg cccggcgtca atacgggata ataccgcgcc acatagcaga   8640

actttaaaag tgctcatcat tggaaaacgt tcttcggggc gaaaactctc aaggatctta   8700

ccgctgttga gatccagttc gatgtaaccc actcgtgcac ccaactgatc ttcagcatct   8760

tttactttca ccagcgtttc tgggtgagca aaaacaggaa ggcaaaatgc cgcaaaaaag   8820

ggaataaggg cgacacggaa atgttgaata ctcatactct tcctttttca atattattga   8880

agcatttatc agggttattg tctcatgagc ggatacatat ttgaatgtat ttagaaaaat   8940

aaacaaatag gggttccgcg cacatttccc cgaaaagtgc cacctgacgt              8990
```

<210> SEQ ID NO 76
<211> LENGTH: 8990
<212> TYPE: DNA
<213> ORGANISM: Artificial Sequence
<220> FEATURE:
<223> OTHER INFORMATION: pGV2381

<400> SEQUENCE: 76

```
ctgcttaatt aagatcaggt cagtacaaac gcaacacgaa agaacaaaaa aagaagaaaa     60

cagaaggcca agacagggtc aatgagactg ttgtcctcct actgtcccta tgtctctggc    120

cgatcacgcg ccattgtccc tcagaaacaa atcaaacacc cacaccccgg gcacccaaag    180

tccccaccca caccaccaat acgtaaacgg ggcgcccccct gcaggccctc ctgcgcgcgg    240

cctcccgcct tgcttctctc cccttccttt tctttttcca gttttcccta ttttgtccct    300

ttttccgcac aacaagtatc agaatgggtt catcaaatct atccaaccta attcgcacgt    360

agactggctt ggtattggca gtttcgtagt tatatatata ctaccatgag tgaaactgtt    420

acgttacctt aaattctttc tccctttaat ttttctttttat cttactctcc tacataagac    480

atcaagaaac aattgtatat tgtacacccc cccctccac aaacacaaat attgataata    540

taaaggagct cgccgatccc attaccgaca tttgggcgct atacgtgcat atgttcatgt    600

atgtatctgt atttaaaaca cttttgtatt atttttcctc atatatgtgt ataggtttat    660

acggatgatt taattattac ttcaccaccc tttatttcag gctgatatct tagccttgtt    720

actagttaga aaaagacatt tttgctgtca gtcactgtca agagattctt ttgctggcat    780

ttcttctaga agcaaaaaga gcgatgcgtc ttttccgctg aaccgttcca gcaaaaaaga    840
```

```
ctaccaacgc aatatggatt gtcagaatca tataaaagag aagcaaataa ctccttgtct    900
tgtatcaatt gcattataat atcttcttgt tagtgcaata tcatatagaa gtcatcgaaa    960
tagatattaa gaaaaacaaa ctgtacaatc aatcaatcaa tcatcacata aagtcgacat   1020
gttgacaaaa gcaacaaaag aacaaaaatc ccttgtgaaa agcagagggg cggagcttgt   1080
tgttgattgc ttagcggagc aaggtgtcac acatgtattt ggcattccag gtgcaaaaat   1140
tgatgcggta tttgacgctt tacaagataa agggcctgaa attatcgttg cccggcatga   1200
acaaaatgca gcatttatgg cgcaagcagt cggccgttta actggaaaac cgggagtcgt   1260
gttagtcaca tcaggaccag gtgcttcgaa cttggcaaca ggactgctga cagcaaacac   1320
tgaaggtgac cctgtcgttg cgcttgctgg gaacgtgatc cgtgcagatc gtttaaaacg   1380
gacacatcaa tctttggata atgcggcgct attccagccg attacaaaat acagtgtaga   1440
agttcaagat gtaaaaaata taccggaagc tgttacaaat gcgtttagga tagcgtcagc   1500
agggcaggct ggggccgctt ttgtgagttt tccgcaagat gttgtgaatg aagtcacaaa   1560
tacaaaaaac gtacgtgctg tcgcagcgcc aaaacttggt cccgcagcag atgacgcaat   1620
cagtatggcc attgcaaaaa ttcaaacagc aaaacttcct gtcgttttag tcggcatgaa   1680
gggcggaaga ccggaagcga ttaaagcggt tcgcaagcta ttgaaaaaag tgcagcttcc   1740
attcgttgaa acatatcaag ctgccggtac tcttacgaga gatttagagg atcagtattt   1800
tggccggatc ggtttattcc gcaaccagcc tggcgatctg ctgcttgagc aggctgatgt   1860
tgttctgaca atcggctatg acccaattga atatgatccg aaattctgga atgtcaatgg   1920
agaccggacg atcatccatt tagacgagat tctggctgac attgatcatg cttaccagcc   1980
ggatcttgaa ctgatcggtg atattccatc tacgatcaat catatcgaac acgatgctgt   2040
gaaagtagac tttgcggaac gtgagcagaa gatcctttct gatttaaaac aatatatgca   2100
tgagggtgag caggtgcctg cagattggaa atcagacaga gtgcatcctc ttgaaatcgt   2160
taaagaattg cgaaacgcag tcgatgatca tgttacagtg acttgcgata tcggttcaca   2220
cgcgatttgg atgtcacgtt atttccgcag ctacgagccg ttaacattaa tgattagtaa   2280
cggtatgcaa acactcggcg ttgcgcttcc ttgggcaatc ggcgcttcat tggtgaaacc   2340
gggagaaaaa gtagtatcag tctccggtga tggcggtttc ttattctcag ctatggaatt   2400
agagacagca gttcgtttaa aagcaccaat tgtacacatt gtatggaacg acagcacata   2460
tgacatggtt gcattccagc aattgaaaaa atataatcgt acatctgcgg tcgatttcgg   2520
aaatatcgat atcgtgaaat acgcggaaag cttcggagca actggcttac gcgtagaatc   2580
accagaccag ctggcagatg ttctgcgtca aggcatgaac gctgaggggc ctgtcatcat   2640
tgatgtcccg gttgactaca gtgataacgt taatttagca agtgacaagc ttccgaaaga   2700
attcggggaa ctcatgaaaa cgaaagctct ctagggatcc tcatgtaatt agttatgtca   2760
cgcttacatt cacgccctcc ccccacatcc gctctaaccg aaaaggaagg agttagacaa   2820
cctgaagtct aggtccctat ttattttttt atagttatgt tagtattaag aacgttattt   2880
atatttcaaa tttttctttt ttttctgtac agacgcgtgt acgcatgtaa cattatactg   2940
aaaaccttgc ttgagaaggt tttgggacgc tcgaaggctt taatttgccc taggctcaac   3000
tcaagacgca cagatattat aacatctgca taataggcat ttgcaagaat tactcgtgag   3060
taaggaaaga gtgaggaact atcgcatacc tgcatttaaa gatgccgatt tgggcgcgaa   3120
tcctttattt tggcttcacc ctcatactat tatcagggcc agaaaaagga agtgtttccc   3180
tccttcttga attgatgtta ccctcataaa gcacgtggcc tcttatcgag aaagaaatta   3240
```

```
ccgtcgctcg tgatttgttt gcaaaaagaa caaaactgaa aaaacccaga cacgctcgac   3300
ttcctgtctt cctattgatt gcagcttcca atttcgtcac acaacaaggt cctagcgacg   3360
gctcacaggt tttgtaacaa gcaatcgaag gttctggaat ggcgggaaag ggtttagtac   3420
cacatgctat gatgcccact gtgatctcca gagcaaagtt cgttcgatcg tactgttact   3480
ctctctcttt caaacagaat tgtccgaatc gtgtgacaac aacagcctgt tctcacacac   3540
tcttttcttc taaccaaggg ggtggtttag tttagtagaa cctcgtgaaa cttacattta   3600
catatatata aacttgcata aattggtcaa tgcaagaaat acatatttgg tcttttctaa   3660
ttcgtagttt ttcaagttct tagatgcttt ctttttctct tttttacaga tcatcaagga   3720
agtaattatc tactttttac aacaaatata aaacaagctc gacatgtata ctgttggtga   3780
ttatctgctg gaccgtctgc atgaactggg tatcgaagaa atcttcggcg ttccgggtga   3840
ttacaatctg cagttcctgg atcagatcat ctctcataaa gacatgaaat gggtgggtaa   3900
cgctaacgaa ctgaacgcaa gctacatggc agatggttat gcacgtacca agaaagccgc   3960
ggcatttctg accactttcg gtgttggcga actgagcgcc gtcaacggtc tggcgggctc   4020
ctacgccgaa aacctgccgg tggtggagat cgtaggcagc ccaacgagca aagttcagaa   4080
cgaaggtaaa ttcgtccacc acactctggc tgacggcgat ttcaaacact tcatgaaaat   4140
gcatgaacct gtgactgcgg cacgtacgct gctgactgca gagaacgcta ctgtggaaat   4200
cgaccgcgtt ctgtctgcgc tgctgaaaga acgcaaacca gtttacatca acctgcctgt   4260
ggatgttgcg gcagctaaag cggaaaaacc gagcctgccg ctgaagaaag aaaactccac   4320
ttctaacact agcgaccagg aaatcctgaa caaaatccag gagtctctga aaaacgcaaa   4380
gaaaccaatc gtgatcaccg gccacgaaat catttctttt ggtctggaga agaccgtgac   4440
ccaattcatc agcaaaacca aactgccgat taccaccctg aacttcggca agtcctctgt   4500
tgacgaggct ctgccgtctt tcctgggcat ctacaacggt actctgagcg aaccgaacct   4560
gaaagaattt gttgaatctg cggacttcat cctgatgctg ggcgttaaac tgaccgactc   4620
ttctaccggt gcattcactc accatctgaa cgaaaacaaa atgattagcc tgaacatcga   4680
cgagggtaaa atcttcaacg agcgtatcca gaacttcgac ttcgaaagcc tgatcagctc   4740
tctgctggac ctgtccgaaa tcgagtataa aggcaaatac attgacaaaa agcaagaaga   4800
tttcgtacca tctaacgcac tgctgtccca ggatcgcctg tggcaggccg tggagaacct   4860
gacccagagc aatgaaacca tcgtggcgga acaaggtacg agctttttcg gcgcgtcttc   4920
tatctttctg aaatccaaaa gccattttat cggtcagccg ctgtggggta gcattggcta   4980
tactttcccg gcagcgctgg gctctcagat cgctgataaa gaatctcgtc atctgctgtt   5040
catcggtgac ggttccctgc agctgaccgt acaggaactg ggtctggcaa ttcgtgaaaa   5100
gatcaacccg atttgcttca ttattaacaa tgacggctac accgttgagc gtgagatcca   5160
cggtccgaac cagtcttaca acgatatccc tatgtggaac tactctaaac tgccggagtc   5220
cttcggcgca actgaggacc gtgttgtgtc taaaattgtg cgtaccgaaa acgaatttgt   5280
gagcgtgatg aaagaggccc aggccgatcc gaaccgtatg tactggatcg aactgatcct   5340
ggcgaaagaa ggcgcaccga aggtactgaa gaaaatgggc aagctgtttg ctgaacagaa   5400
taaatcctaa ggatcttttg cggcctagta ttgaattctt atacaggaaa cttaatagaa   5460
caaatcacat atttaatcta atagccacct gcattggcac ggtgcaacac tacttcaact   5520
tcatcttaca aaaagatcac gtgatctgtt gtattgaact gaaaattttt tgtttgcttc   5580
tctctctctc tttcattatg tgagatttaa aaaccagaaa ctacatcatc gaaaaagagt   5640
```

-continued

```
tttaaaccat tacaaccatt gcgataagcc ctctcaaact ataacaatac tgacagtact   5700

aaataattgc ctacttggct tcacatacgt tgcatacgtc gatatagata ataatgataa   5760

tgacagcagg attatcgtaa tacgtaatag ttgaaaatct caaaaatgtg tgggtcatta   5820

cgtaaataat gataggaatg ggattcttct atttttcctt tttccattct agcagccgtc   5880

gggaaaacgt ggcatcctct ctttcgggct caattggagt cacgctgccg tgagcatcct   5940

ctctttccat atctaacaac tgagcacgta accaatggaa aagcatgagc ttagcgttgc   6000

tccaaaaaag tattggatgg ttaataccat ttgtctgttc tcttctgact ttgactcctc   6060

aaaaaaaaaa aatctacaat caacagatcg cttcaattac gccctcacaa aaactttttt   6120

ccttcttctt cgcccacgtt aaattttatc cctcatgttg tctaacggat ttctgcactt   6180

gatttattat aaaaagacaa agacataata cttctctatc aatttcagtt attgttcttc   6240

cttgcgttat tcttctgttc ttcttttct tttgtcatat ataaccataa ccaagtaata   6300

catattcaaa atgtccacaa aatcatatac cagtagagct gagactcatg caagtccggt   6360

tgcatcgaaa cttttacgtt taatggatga aaagaagacc aatttgtgtg cttctcttga   6420

cgttcgttcg actgatgagc tattgaaact tgttgaaacg ttgggtccat acatttgcct   6480

tttgaaaaca cacgttgata tcttggatga tttcagttat gagggtactg tcgttccatt   6540

gaaagcattg gcagagaaat acaagttctt gatatttgag gacagaaaat tcgccgatat   6600

cggtaacaca gtcaaattac aatatacatc gggcgtttac cgtatcgcag aatggtctga   6660

tatcaccaac gcccacgggg ttactggtgc tggtattgtt gctggcttga aacaaggtgc   6720

gcaagaggtc accaaagaac caaggggatt attgatgctt gctgaattgt cttccaaggg   6780

ttctctagca cacggtgaat atactaaggg taccgaagct tggcgtaatc atggtcatag   6840

ctgtttcctg tgtgaaattg ttatccgctc acaattccac acaacatacg agccggaagc   6900

ataaagtgta aagcctgggg tgcctaatga gtgagctaac tcacattaat tgcgttgcgc   6960

tcactgcccg ctttccagtc gggaaacctg tcgtgccagc tgcattaatg aatcggccaa   7020

cgcgcgggga gaggcggttt gcgtattggg cgctcttccg cttcctcgct cactgactcg   7080

ctgcgctcgg tcgttcggct gcggcgagcg gtatcagctc actcaaaggc ggtaatacgg   7140

ttatccacag aatcagggga taacgcagga aagaacatgt gagcaaaagg ccagcaaaag   7200

gccaggaacc gtaaaaaggc cgcgttgctg gcgtttttcc ataggctccg cccccctgac   7260

gagcatcaca aaaatcgacg ctcaagtcag aggtggcgaa acccgacagg actataaaga   7320

taccaggcgt ttccccctgg aagctccctc gtgcgctctc ctgttccgac cctgccgctt   7380

accggatacc tgtccgcctt tctcccttcg ggaagcgtgg cgctttctca tagctcacgc   7440

tgtaggtatc tcagttcggt gtaggtcgtt cgctccaagc tgggctgtgt gcacgaaccc   7500

cccgttcagc ccgaccgctg cgccttatcc ggtaactatc gtcttgagtc caacccggta   7560

agacacgact tatcgccact ggcagcagcc actggtaaca ggattagcag agcgaggtat   7620

gtaggcggtg ctacagagtt cttgaagtgg tggcctaact acggctacac tagaaggaca   7680

gtatttggta tctgcgctct gctgaagcca gttaccttcg gaaaaagagt tggtagctct   7740

tgatccggca aacaaaccac cgctggtagc ggtggttttt ttgtttgcaa gcagcagatt   7800

acgcgcagaa aaaaaggatc tcaagaagat cctttgatct tttctacggg gtctgacgct   7860

cagtggaacg aaaactcacg ttaagggatt ttggtcatga gattatcaaa aaggatcttc   7920

acctagatcc ttttaaatta aaaatgaagt tttaaatcaa tctaaagtat atatgagtaa   7980

acttggtctg acagttacca atgcttaatc agtgaggcac ctatctcagc gatctgtcta   8040
```

```
tttcgttcat ccatagttgc ctgactcccc gtcgtgtaga taactacgat acgggagggc   8100

ttaccatctg gccccagtgc tgcaatgata ccgcgagacc cacgctcacc ggctccagat   8160

ttatcagcaa taaaccagcc agccggaagg gccgagcgca gaagtggtcc tgcaacttta   8220

tccgcctcca tccagtctat taattgttgc cgggaagcta gagtaagtag ttcgccagtt   8280

aatagtttgc gcaacgttgt tgccattgct acaggcatcg tggtgtcacg ctcgtcgttt   8340

ggtatggctt cattcagctc cggttcccaa cgatcaaggc gagttacatg atcccccatg   8400

ttgtgcaaaa aagcggttag ctccttcggt cctccgatcg ttgtcagaag taagttggcc   8460

gcagtgttat cactcatggt tatggcagca ctgcataatt ctcttactgt catgccatcc   8520

gtaagatgct tttctgtgac tggtgagtac tcaaccaagt cattctgaga atagtgtatg   8580

cggcgaccga gttgctcttg cccggcgtca atacgggata ataccgcgcc acatagcaga   8640

actttaaaag tgctcatcat tggaaaacgt tcttcggggc gaaaactctc aaggatctta   8700

ccgctgttga gatccagttc gatgtaaccc actcgtgcac ccaactgatc ttcagcatct   8760

tttactttca ccagcgtttc tgggtgagca aaaacaggaa ggcaaaatgc cgcaaaaaag   8820

ggaataaggg cgacacggaa atgttgaata ctcatactct tcctttttca atattattga   8880

agcatttatc agggttattg tctcatgagc ggatacatat ttgaatgtat ttagaaaaat   8940

aaacaaatag gggttccgcg cacatttccc cgaaaagtgc cacctgacgt              8990
```

<210> SEQ ID NO 77
<211> LENGTH: 561
<212> TYPE: PRT
<213> ORGANISM: Trichoderma atraviride

<400> SEQUENCE: 77

```
Met Thr Lys Asp Thr Val Asp Ile Leu Ile Asp Ser Leu Lys Ala Ala
1               5                   10                  15

Gly Val Lys Tyr Val Phe Gly Val Pro Gly Ala Lys Ile Asp Ser Val
            20                  25                  30

Phe Asn Ala Leu Ile Asp His Pro Asp Ile Lys Leu Val Val Cys Arg
        35                  40                  45

His Glu Gln Asn Ala Ala Phe Ile Ala Ala Ala Met Gly Lys Val Thr
    50                  55                  60

Gly Arg Pro Gly Val Cys Ile Ala Thr Ser Gly Pro Gly Thr Ser Asn
65                  70                  75                  80

Leu Val Thr Gly Leu Val Thr Ala Thr Asp Glu Gly Ala Pro Val Val
                85                  90                  95

Ala Ile Val Gly Ser Val Lys Arg Ser Gln Ser Leu Gln Arg Thr His
            100                 105                 110

Gln Ser Leu Arg Gly Ala Asp Leu Leu Ala Pro Val Thr Lys Lys Val
        115                 120                 125

Val Ser Ala Val Val Glu Asp Gln Val Ala Glu Ile Met Leu Asp Ala
    130                 135                 140

Phe Arg Val Ala Ala Ala Ser Pro Pro Gly Ala Thr Ala Val Ser Leu
145                 150                 155                 160

Pro Ile Asp Leu Met Thr Pro Ala Lys Ser Thr Ser Thr Val Thr Ala
                165                 170                 175

Phe Pro Ala Glu Cys Phe Ile Pro Pro Lys Tyr Gly Lys Ser Pro Glu
            180                 185                 190

Thr Thr Leu Gln Ala Ala Ala Asp Leu Ile Ser Ala Ala Lys Ala Pro
        195                 200                 205

Val Leu Phe Leu Gly Met Arg Val Ser Glu Ser Asp Asp Thr Ile Ser
```

```
    210                 215                 220

Ala Val His Gly Phe Leu Arg Lys His Pro Val Pro Val Val Glu Thr
225                 230                 235                 240

Phe Gln Ala Ala Gly Ala Ile Ser Lys Glu Leu Val His Leu Phe Tyr
                245                 250                 255

Gly Arg Ile Gly Leu Phe Ser Asn Gln Pro Gly Asp Gln Leu Leu Gln
            260                 265                 270

His Ala Asp Leu Val Ile Ala Ile Gly Leu Asp Gln Ala Glu Tyr Asp
        275                 280                 285

Ala Asn Met Trp Asn Ala Arg Gly Thr Thr Ile Leu His Val Asp Ile
    290                 295                 300

Gln Pro Ala Asp Phe Val Ala His Tyr Lys Pro Lys Ile Glu Leu Val
305                 310                 315                 320

Gly Ser Leu Ala Asp Asn Met Thr Asp Leu Thr Ser Arg Leu Asp Thr
                325                 330                 335

Val Ala Arg Leu Gln Leu Thr Lys Pro Gly Glu Ala Ile Arg Thr Asn
            340                 345                 350

Met Trp Glu Trp Gln Asn Ser Pro Glu Ala Ser Gly Arg Ser Thr Gly
        355                 360                 365

Pro Val His Pro Leu His Phe Ile Arg Leu Phe Gln Ser Ile Ile Asp
    370                 375                 380

Pro Ser Thr Thr Val Ile Ser Asp Val Gly Ser Val Tyr Ile Trp Leu
385                 390                 395                 400

Cys Arg Tyr Phe Tyr Ser Tyr Ala Arg Arg Thr Phe Leu Met Ser Asn
                405                 410                 415

Val Gln Gln Thr Leu Gly Val Ala Met Pro Trp Ala Ile Gly Val Ser
            420                 425                 430

Leu Ser Gln Thr Pro Pro Ser Ser Lys Lys Val Val Ser Ile Ser Gly
        435                 440                 445

Asp Gly Gly Phe Met Phe Ser Ser Gln Glu Leu Val Thr Ala Val Gln
    450                 455                 460

Gln Gly Cys Asn Ile Thr His Phe Ile Trp Asn Asp Gly Lys Tyr Asn
465                 470                 475                 480

Met Val Glu Phe Gln Glu Val Asn Lys Tyr Gly Arg Ser Ser Gly Val
                485                 490                 495

Asp Leu Gly Gly Val Asp Phe Val Lys Leu Ala Asp Ser Met Gly Ala
            500                 505                 510

Lys Gly Leu Arg Val Ser Ser Ala Gly Asp Leu Glu Ala Val Met Lys
        515                 520                 525

Glu Ala Leu Ala Tyr Asp Gly Val Cys Leu Val Asp Ile Glu Ile Asp
    530                 535                 540

Tyr Ser Gln Asn His Asn Leu Met Met Asp Leu Val Thr Ser Asp Val
545                 550                 555                 560

Ser

<210> SEQ ID NO 78
<211> LENGTH: 568
<212> TYPE: PRT
<213> ORGANISM: Talaromyces stipitatus

<400> SEQUENCE: 78

Met Ser Asn Arg Asn Pro Ser His Val Ile Val Glu Ser Leu Ser Asn
1               5                   10                  15

Ala Gly Val Lys Ile Val Phe Gly Ile Pro Gly Ala Lys Val Asp Gly
            20                  25                  30
```

```
Ile Phe Asp Ala Leu Ser Asp His Pro Thr Ile Lys Leu Ile Val Cys
        35                  40                  45

Arg His Glu Gln Asn Ala Ala Phe Met Ala Ala Ala Val Gly Arg Leu
    50                  55                  60

Thr Gly Ala Pro Gly Val Cys Leu Val Thr Ser Gly Pro Gly Thr Ser
65                  70                  75                  80

Asn Leu Val Thr Gly Leu Ala Thr Ala Thr Thr Glu Gly Asp Pro Val
                85                  90                  95

Leu Ala Ile Ala Gly Thr Val Ser Arg Leu Gln Ala Ala Arg His Thr
            100                 105                 110

His Gln Ser Leu Asp Val Asn Lys Val Leu Glu Gly Val Cys Lys Ser
        115                 120                 125

Val Ile Gln Val Gly Val Glu Asp Gln Val Ser Glu Val Ile Ala Asn
    130                 135                 140

Ala Phe Arg His Ala Arg Gln Phe Pro Gln Gly Ala Thr Ala Val Ala
145                 150                 155                 160

Leu Pro Met Asp Ile Ile Lys Ser Thr Ser Val Gly Val Pro Pro Phe
                165                 170                 175

Pro Ser Leu Ser Phe Glu Ala Pro Gly Tyr Gly Ser Ser Asn Thr Lys
            180                 185                 190

Leu Cys Lys Val Ala Val Asp Lys Leu Ile Ala Ala Lys Tyr Pro Val
        195                 200                 205

Ile Leu Leu Gly Met Arg Ser Ser Asp Pro Glu Ile Val Ala Ser Val
    210                 215                 220

Arg Arg Met Ile Lys Asp His Thr Leu Pro Val Val Glu Thr Phe Gln
225                 230                 235                 240

Ala Ala Gly Ala Ile Ser Glu Asp Leu Leu His Arg Tyr Tyr Gly Arg
                245                 250                 255

Val Gly Leu Phe Arg Asn Gln Pro Gly Asp Lys Val Leu Ala Arg Ala
            260                 265                 270

Asp Leu Ile Ile Ala Val Gly Tyr Asp Pro Tyr Glu Tyr Asp Ala Glu
        275                 280                 285

Thr Trp Asn Val Asn Asn Pro Ala Thr Ile His Asn Ile Ile His Ile
    290                 295                 300

Asp Tyr Thr His Ser Arg Val Ser Gln His Tyr Met Pro His Val Glu
305                 310                 315                 320

Leu Leu Gly Asn Pro Ala Asp Ile Val Asp Glu Leu Thr Ala Ser Leu
                325                 330                 335

Gln Ala Leu Lys Pro Asn Phe Trp Ser Gly Ala Glu Asp Thr Leu Glu
            340                 345                 350

Asn Ile Arg Gln Glu Ile Ala Arg Cys Glu Ala Thr Ala Thr His Thr
        355                 360                 365

Glu Ser Leu Gln Asp Gly Ala Val Gln Pro Thr His Phe Val Tyr Gln
    370                 375                 380

Leu Arg His Leu Leu Pro Lys Glu Thr Ile Val Ala Val Asp Val Gly
385                 390                 395                 400

Thr Val Tyr Ile Tyr Met Met Arg Tyr Phe Gln Thr Tyr Ser Pro Arg
                405                 410                 415

His Leu Leu Cys Ser Asn Gly Gln Gln Thr Leu Gly Val Gly Leu Pro
            420                 425                 430

Trp Ala Ile Ala Ala Ser Leu Ile Gln Glu Pro Pro Cys Ser Arg Lys
        435                 440                 445

Val Val Ser Ile Ser Gly Asp Gly Gly Phe Met Phe Ser Ser Gln Glu
```

-continued

```
    450                 455                 460

Leu Ala Thr Ala Val Leu Gln Lys Cys Asn Ile Thr His Phe Ile Trp
465                 470                 475                 480

Asn Asp Ser Gly Tyr Asn Met Val Glu Phe Gln Glu Glu Ala Lys Tyr
                485                 490                 495

Gly Arg Ser Ser Gly Ile Lys Leu Gly Gly Ile Asp Phe Val Lys Phe
            500                 505                 510

Ala Glu Ala Phe Asp Gly Ala Arg Gly Phe Arg Ile Asn Ser Thr Lys
        515                 520                 525

Glu Val Lys Glu Val Ile Lys Glu Ala Leu Ala Phe Glu Gly Val Ala
    530                 535                 540

Ile Val Asp Val Arg Ile Asp Tyr Ser Arg Ser His Glu Leu Met Lys
545                 550                 555                 560

Asp Ile Ile Pro Lys Asp Tyr Gln
                565
```

YEAST ORGANISM PRODUCING ISOBUTANOL AT A HIGH YIELD

CROSS-REFERENCE TO RELATED APPLICATIONS

This application claims priority to U.S. Provisional Application Ser. No. 61/219,173, filed Jun. 22, 2009, and is a continuation-in-part of U.S. application Ser. No. 12/696,645, filed Jan. 29, 2010, which is a divisional of U.S. application Ser. No. 12/343,375, filed Dec. 23, 2008, now U.S. Pat. No. 8,017,375 which claims, as does the present application, the benefit of U.S. Provisional Application Ser. No. 61/016,483, filed Dec. 23, 2007, all of which are herein incorporated by reference in their entireties for all purposes.

TECHNICAL FIELD

Metabolically engineered microorganisms and methods of producing such organisms are provided. Also provided are methods of producing metabolites that are biofuels by contacting a suitable substrate with metabolically engineered microorganisms and enzymatic preparations there from.

BACKGROUND

Biofuels have a long history ranging back to the beginning of the 20th century. As early as 1900, Rudolf Diesel demonstrated at the World Exhibition in Paris, France, an engine running on peanut oil. Soon thereafter, Henry Ford demonstrated his Model T running on ethanol derived from corn. Petroleum-derived fuels displaced biofuels in the 1930s and 1940s due to increased supply, and efficiency at a lower cost.

Market fluctuations in the 1970s coupled to the decrease in US oil production led to an increase in crude oil prices and a renewed interest in biofuels. Today, many interest groups, including policy makers, industry planners, aware citizens, and the financial community, are interested in substituting petroleum-derived fuels with biomass-derived biofuels. The leading motivations for developing biofuels are of economical, political, and environmental nature.

One is the threat of 'peak oil', the point at which the consumption rate of crude oil exceeds the supply rate, thus leading to significantly increased fuel cost results in an increased demand for alternative fuels. In addition, instability in the Middle East and other oil-rich regions has increased the demand for domestically produced biofuels. Also, environmental concerns relating to the possibility of carbon dioxide related climate change is an important social and ethical driving force which is starting to result in government regulations and policies such as caps on carbon dioxide emissions from automobiles, taxes on carbon dioxide emissions, and tax incentives for the use of biofuels.

Ethanol is the most abundant fermentatively produced fuel today but has several drawbacks when compared to gasoline. Butanol, in comparison, has several advantages over ethanol as a fuel: it can be made from the same feedstocks as ethanol but, unlike ethanol, it is compatible with gasoline at any ratio and can also be used as a pure fuel in existing combustion engines without modifications. Unlike ethanol, butanol does not absorb water and can thus be stored and distributed in the existing petrochemical infrastructure. Due to its higher energy content which is close to that of gasoline, the fuel economy (miles per gallon) is better than that of ethanol. Also, butanol-gasoline blends have lower vapor pressure than ethanol-gasoline blends, which is important in reducing evaporative hydrocarbon emissions.

Isobutanol has the same advantages as butanol with the additional advantage of having a higher octane number due to its branched carbon chain. Isobutanol is also useful as a commodity chemical and is also a precursor to isobutylene and isobutylene-derived fuels and chemicals. Isobutanol has been produced recombinantly in yeast microorganisms expressing a heterologous metabolic pathway (See, e.g., WO/2007/050671 to Donaldson et al., and WO/2008/098227 to Liao et al.). However, these yeast microorganisms fall short of commercial relevance due to their low performance characteristics, including low productivity, low titer, low yield, and the requirement for oxygen during the fermentation process. One of the primary reasons for the sub-optimal performance observed in existing isobutanol-producing microorganisms is the undesirable conversion of pathway intermediates to unwanted by-products.

Thus, there is an existing need to identify and reduce and/or eliminate the metabolic processes catalyzing the conversion of isobutanol pathway intermediates to unwanted by-products. The present inventors have addressed this need by providing recombinant microorganisms with reduced pyruvate decarboxylase (PDC) activity and reduced glycerol-3-phosphate dehydrogenase (GPD) activity.

SUMMARY OF THE INVENTION

The present inventors have observed that by combining the expression of a cytosolically localized acetolactate synthase enzyme with reduced pyruvate decarboxylase (PDC) activity and/or reduced glycerol-3-phosphate dehydrogenase (GPD) activity, an unexpectedly high flux from pyruvate to acetolactate can be achieved. Thus, the invention provides yeast cells that are engineered to exhibit an efficient conversion of pyruvate to acetolactate in the cytoplasm due to suppression of competing metabolic pathways. Therefore, as would be understood in the art, the present invention has utility for the production of any acetolactate-derived product, including, but not limited to, isobutanol, 2-butanol, 1-butanol, 2-butanone, 2,3-butanediol, valine, leucine, and 3-methyl-1-butanol.

Accordingly, in a first aspect, the invention provides a recombinant microorganism, such as a yeast cell, comprising a cytosolically-localized polypeptide having acetolactate synthase activity wherein the yeast cell is substantially free of an enzyme having pyruvate decarboxylase (PDC) activity and/or glycerol-3-phosphate dehydrogenase (GPD) activity, and wherein the cell converts pyruvate to acetolactate.

Thus, in various embodiments described herein, the present invention provides recombinant microorganisms engineered to include reduced pyruvate decarboxylase (PDC) activity as compared to a parental microorganism. In one embodiment, PDC activity is eliminated. PDC catalyzes the decarboxylation of pyruvate to acetaldehyde, which is reduced to ethanol by alcohol dehydrogenases via the oxidation of NADH to NAD+. In one embodiment, the recombinant microorganism includes a mutation in at least one PDC gene resulting in a reduction of PDC activity of a polypeptide encoded by said gene. In another embodiment, the recombinant microorganism includes a partial deletion of a PDC gene resulting in a reduction of PDC activity of a polypeptide encoded by said gene. In another embodiment, the recombinant microorganism comprises a complete deletion of a PDC gene resulting in a reduction of PDC activity of a polypeptide encoded by said gene. In yet another embodiment, the recombinant microorganism includes a modification of the regulatory region associated with at least one PDC gene resulting in a reduction of PDC activity of a polypeptide encoded by said gene. In yet another embodiment, the recombinant microorganism comprises a modification of the transcriptional regulator resulting in a reduction of PDC gene transcription. In yet another embodiment, the recombinant microorganism comprises mutations in all PDC genes resulting in a reduction of PDC activity of the polypeptides encoded by said genes. In another embodiment, the recombinant microorganism includes partial deletions of all PDC genes resulting in a reduction of PDC activity of the polypeptides encoded by said genes. In yet another embodiment, the recombinant microorganism comprises a deletion of all PDC genes resulting in the elimination of PDC activity of the polypeptides encoded by said genes.

In additional embodiments, the present invention provides recombinant microorganisms engineered to exhibit reduced glycerol-3-phosphate dehydrogenase (GPD) activity as compared to a parental microorganism. In one embodiment, GPD activity is eliminated. GPD catalyzes the reduction of dihydroxyacetone phosphate (DHAP) to glycerol-3-phosphate (G3P) via the oxidation of NADH to $NAD^+$. Glycerol is produced from G3P by Glycerol-3-phosphatase (GPP). In one embodiment, the recombinant microorganism includes a mutation in at least one GPD gene resulting in a reduction of GPD activity of a polypeptide encoded by said gene. In another embodiment, the recombinant microorganism includes a partial deletion of a GPD gene resulting in a reduction of GPD activity of a polypeptide encoded by the gene. In another embodiment, the recombinant microorganism comprises a complete deletion of a GPD gene resulting in a reduction of GPD activity of a polypeptide encoded by the gene. In yet another embodiment, the recombinant microorganism includes a modification of the regulatory region associated with at least one GPD gene resulting in a reduction of GPD activity of a polypeptide encoded by said gene. In yet another embodiment, the recombinant microorganism comprises a modification of the transcriptional regulator resulting in a reduction of GPD gene transcription. In another embodiment, the recombinant microorganism includes partial deletions of all GPD genes resulting in a reduction of GPD activity of the polypeptides encoded by said genes. In yet another embodiment, the recombinant microorganism comprises mutations in all GPD genes resulting in a reduction of GPD activity of the polypeptides encoded by said genes. In yet another embodiment, the recombinant microorganism comprises a deletion of all GPD genes resulting in the elimination of GPDs activity of the polypeptides encoded by said genes.

In an exemplary embodiment, the present invention provides a recombinant microorganism engineered to exhibit reduced pyruvate decarboxylase (PDC) activity and reduced glycerol-3-phosphate dehydrogenase (GPD) activity as compared to a parental microorganism.

In additional embodiments, the present invention provides recombinant microorganisms engineered to exhibit reduced pyruvate dehydrogenase (PDH) activity as compared to a parental microorganism. In one embodiment, the recombinant microorganism is engineered to have reduced pyruvate decarboxylase (PDC) activity and reduced pyruvate dehydrogenase (PDH) activity. In another embodiment, the recombinant microorganism is engineered to have reduced glycerol-3-phosphate dehydrogenase (GPD) activity and reduced pyruvate dehydrogenase (PDH) activity. In yet another embodiment, the recombinant microorganism is engineered to have reduced pyruvate decarboxylase (PDC) activity, reduced glycerol-3-phosphate dehydrogenase (GPD) activity, and reduced pyruvate dehydrogenase (PDH) activity.

In various embodiments described herein, the present invention provides recombinant microorganisms, including, but not limited to those, that comprise an isobutanol producing metabolic pathway. In some embodiments, the recombinant microorganisms can be engineered to express an isobutanol producing metabolic pathway comprising at least one exogenous gene that catalyzes a step in the conversion of pyruvate to isobutanol. In one embodiment, the recombinant microorganism may be engineered to express an isobutanol producing metabolic pathway comprising at least two exogenous genes. In another embodiment, the recombinant microorganism may be engineered to express an isobutanol producing metabolic pathway comprising at least three exogenous genes. In another embodiment, the recombinant microorganism may be engineered to express an isobutanol producing metabolic pathway comprising at least four exogenous genes. In another embodiment, the recombinant microorganism may be engineered to express an isobutanol producing metabolic pathway comprising five exogenous genes.

In various embodiments described herein, isobutanol producing metabolic pathway comprises at least one exogenous gene that catalyzes a step in the conversion of pyruvate to isobutanol. In one embodiment, the exogenous gene encodes a polypeptide selected from the group consisting of acetolactate synthase (ALS), ketol-acid reductoisomerase (KARI), dihydroxyacid dehydratase (DHAD), 2-keto-acid decarboxylase (KIVD), and alcohol dehydrogenase (ADH). In another embodiment, the exogenous gene encodes an acetolactate synthase (ALS). In an exemplary embodiment, the acetolactate synthase is a cytosolically-localized acetolactate synthase. In one specific embodiment, the cytosolically-localized acetolactate synthase is encoded by the *Lactococcus lactis* gene alsS. In another specific embodiment, the cytosolically-localized acetolactate synthase is encoded by the *Bacillus subtilis* gene alsS.

In additional embodiments, the recombinant microorganism comprises an isobutanol producing metabolic pathway comprising genes encoding an NADH-dependent KARI and an NADH-dependent ADH. In one embodiment, the KARI and/or the ADH show at least a 10-fold higher catalytic efficiency using NADH as the cofactor as compared to the wild-type *E. coli* KARI ilvC and a native *E. coli* ADH yqhD, respectively. In another embodiment, the KARI and/or the ADH have been modified or mutated to be NADH-dependent. In yet another embodiment, the KARI and/or the ADH has been identified in nature with increased activity using NADH as a cofactor as compared to the wild-type *E. coli* KARI ilvC and a native *E. coli* ADH yqhD, respectively.

In some embodiments, the invention provides a recombinant microorganism comprising an isobutanol producing metabolic pathway, wherein said recombinant microorganism comprises a reduction in pyruvate decarboxylase (PDC) activity as compared to a parental microorganism. In additional embodiments, the recombinant microorganism comprises a reduction in glycerol-3-phosphate dehydrogenase (GPD) activity as compared to a parental microorganism. In yet other embodiments, the recombinant microorganism comprises a reduction in pyruvate decarboxylase (PDC) activity and glycerol-3-phosphate dehydrogenase (GPD) activity as compared to a parental microorganism. In still yet other embodiments, the recombinant microorganism comprises a reduction in pyruvate decarboxylase (PDC) activity, a reduction in glycerol-3-phosphate dehydrogenase (GPD) activity, and a reduction in pyruvate dehydrogenase (PDH) activity as compared to a parental microorganism.

In various embodiments described herein, the present invention provides recombinant microorganisms that comprise a pathway for the fermentation of isobutanol from a.pentose sugar. In one embodiment, the pentose sugar is xylose. In one embodiment, the recombinant microorganism is engineered to express a functional xylose isomerase (XI). In another embodiment, the recombinant microorganism further comprises a deletion or disruption of a native gene encoding for an enzyme that catalyzes the conversion of xylose to xylitol. In one embodiment, the native gene is xylose reductase (XR). In another embodiment, the native gene is xylitol dehydrogenase (XDH). In yet another embodiment, both native genes are deleted or disrupted. In yet another embodiment, the recombinant microorganism further engineered to express, xylulose kinase which catalyzes the conversion of xylulose to xylulose-5-phosphate.

In some embodiments, the microorganisms of the present invention are engineered to grow on glucose independently of C2-compounds at a growth rate substantially equivalent to the growth rate of a parental microorganism without altered PDC activity.

In various embodiments described herein, the recombinant microorganisms may be microorganisms of the *Saccharomyces* clade, *Saccharomyces sensu strict* microorganisms, Crabtree-negative yeast microorganisms, Crabtree-positive yeast microorganisms, post-WGD (whole genome duplication) yeast microorganisms, pre-WGD (whole genome duplication) yeast microorganisms, and non-fermenting yeast microorganisms.

In some embodiments, the recombinant microorganisms may be yeast recombinant microorganisms of the *Saccharomyces* clade.

In some embodiments, the recombinant microorganisms may be *Saccharomyces sensu stricto* microorganisms. In one embodiment, the *Saccharomyces sensu stricto* is selected from the group consisting of *S. cerevisiae, S. kudriavzevii, S. mikatae, S. bayanus, S. uvarum, S. carocanis* and hybrids thereof.

In some embodiments, the recombinant microorganisms may be Crabtree-negative recombinant yeast microorganisms. In one embodiment, the Crabtree-negative yeast microorganism is classified into a genera selected from the group consisting of *Kluyveromyces, Pichia, Hansenula*, or *Candida*. In additional embodiments, the Crabtree-negative yeast microorganism is selected from *Kluyveromyces lactis, Kluyveromyces marxianus, Pichia anomala, Pichia stipitis, P. kudriavzevii, Hansenula anomala, Candida utilis* and *Kluyveromyces waltii*.

In some embodiments, the recombinant microorganisms may be Crabtree-positive recombinant yeast microorganisms. In one embodiment, the Crabtree-positive yeast microorganism is classified into a genera selected from the group consisting of *Saccharomyces, Kluyveromyces, Zygosaccharomyces, Debaryomyces, Candida, Pichia* and *Schizosaccharomyces*. In additional embodiments, the Crabtree-positive yeast microorganism is selected from the group consisting of *Saccharomyces cerevisiae, Saccharomyces uvarum, Saccharomyces bayanus, Saccharomyces paradoxus, Saccharomyces castelli, Saccharomyces kluyveri, Kluyveromyces thermotolerans, Candida glabrata, Z. bailli, Z. rouxii, Debaryomyces hansenii, Pichia pastorius, Schizosaccharomyces pombe*, and *Saccharomyces uvarum*.

In some embodiments, the recombinant microorganisms may be post-WGD (whole genome duplication) yeast recombinant microorganisms. In one embodiment, the post-WGD yeast recombinant microorganism is classified into a genera selected from the group consisting of *Saccharomyces* or *Candida*. In additional embodiments, the post-WGD yeast is selected from the group consisting of *Saccharomyces cerevisiae, Saccharomyces uvarum, Saccharomyces bayanus, Saccharomyces paradoxus, Saccharomyces castelli*, and *Candida glabrata*.

In some embodiments, the recombinant microorganisms may be pre-WGD (whole genome duplication) yeast recombinant microorganisms. In one embodiment, the pre-WGD yeast recombinant microorganism is classified into a genera selected from the group consisting of *Saccharomyces, Kluyveromyces, Candida, Pichia, Debaryomyces, Hansenula, Pachysolen, Yarrowia* and *Schizosaccharomyces*. In additional embodiments, the pre-WGD yeast is selected from the group consisting of *Saccharomyces kluyveri, Kluyveromyces thermotolerans, Kluyveromyces marxianus, Kluyveromyces waltii, Kluyveromyces lactis, Candida tropicalis, Pichia pastoris, Pichia anomala, Pichia stipitis, Debaryomyces hansenii, Hansenula anomala, Pachysolen tannophilis, Yarrowia lipolytica*, and *Schizosaccharomyces pombe*.

In some embodiments, the recombinant microorganisms may be microorganisms that are non-fermenting yeast microorganisms, including, but not limited to those, classified into a genera selected from the group consisting of *Tricosporon, Rhodotorula*, or *Myxozyma*.

In another aspect, the present invention provides methods of producing isobutanol using a recombinant microorganism of the invention. In one embodiment, the method includes cultivating the recombinant microorganism in a culture medium containing a feedstock providing the carbon source until a recoverable quantity of the isobutanol is produced and optionally, recovering the isobutanol. In one embodiment, the microorganism is selected to produce isobutanol from a carbon source at a yield of at least about 5 percent theoretical. In another embodiment, the microorganism is selected to produce isobutanol at a yield of at least about 10 percent, at least about 15 percent, about least about 20 percent, at least about 25 percent, at least about 30 percent, at least about 35 percent, at least about 40 percent, at least about 45 percent, at least about 50 percent, at least about 55 percent, at least about 60 percent, at least about 65 percent, at least about 70 percent, at least about 75 percent, at least about 80 percent, at least about 85 percent, at least about 90 percent, or at least about 95 percent theoretical.

In one embodiment, the microorganism is selected to produce isobutanol from a carbon source at a specific productivity of at least about 0.7 mg/L/hr per OD. In another embodiment, the microorganism is selected to produce isobutanol from a carbon source at a specific productivity of at least about 1 mg/L/hr per OD, at least about 10 mg/L/hr per OD, at least about 50 mg/L/hr per OD, at least about 100 mg/L/hr per OD, at least about 250 mg/L/hr per OD, or at least about 500 mg/L/hr per OD.

BRIEF DESCRIPTION OF DRAWINGS

Illustrative embodiments of the invention are illustrated in the drawings, in which.

DETAILED DESCRIPTION

Figure 1:
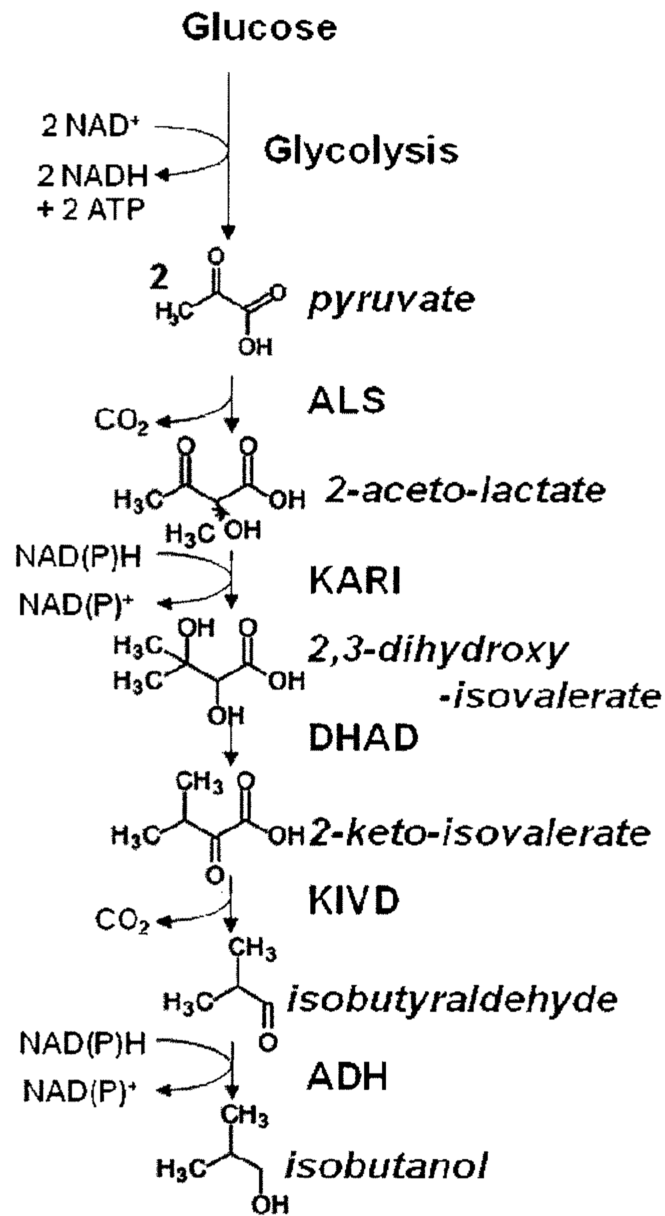
FIG. 1 illustrates an exemplary embodiment of an isobutanol pathway.

As used herein and in the appended claims, the singular forms "a," "an," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (Bacillus, Clostridia, *Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) *Bacteroides*, Flavobacteria; (7) *Chlamydia*; (8) Green sulfur bacteria; (9) Green non-sulfur bacteria (also anaerobic phototrophs); (10) *Radioresistant micrococci* and relatives; (11) *Thermotoga* and *Thermosipho* thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium.*

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces.*

The term "genus" is defined as a taxonomic group of related species according to the Taxonomic Outline of Bacteria and Archaea (Garrity, G. M., Lilburn, T. G., Cole, J. R., Harrison, S. H., Euzeby, J., and Tindall, B. J. (2007) The Taxonomic Outline of Bacteria and Archaea. TOBA Release 7.7, March 2007. Michigan State University Board of Trustees.

The term "species" is defined as a collection of closely related organisms with greater than 97% 16S ribosomal RNA sequence homology and greater than 70% genomic hybridization and sufficiently different from all other organisms so as to be recognized as a distinct unit.

The term "recombinant microorganism," "modified microorganism," and "recombinant host cell" are used interchangeably herein and refer to microorganisms that have been genetically modified to express or over-express endogenous polynucleotides, or to express heterologous polynucleotides, such as those included in a vector, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by PCR or by northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that are recognize and bind reacting the protein. See Sambrook et al., 1989, supra. The polynucleotide generally encodes a target enzyme involved in a metabolic pathway for producing a desired metabolite. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "wild-type microorganism" describes a cell that occurs in nature, i.e. a cell that has not been genetically modified. A wild-type microorganism can be genetically modified to express or overexpress a first target enzyme. This microorganism can act as a parental microorganism in the generation of a microorganism modified to express or overexpress a second target enzyme. In turn, the microorganism modified to express or overexpress a first and a second target enzyme can be modified to express or overexpress a third target enzyme.

Accordingly, a "parental microorganism" functions as a reference cell for successive genetic modification events. Each modification event can be accomplished by introducing a nucleic acid molecule in to the reference cell. The introduction facilitates the expression or overexpression of a target enzyme. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of heterologous polynucleotides encoding a target enzyme in to a parental microorganism The term "engineers" refers to any manipulation of a microorganism that result in a detectable change in the microorganism, wherein the manipulation includes but is not limited to inserting a polynucleotide and/or polypeptide heterologous to the microorganism and mutating a polynucleotide and/or polypeptide native to the microorganism. The term "metabolically engineered" or "metabolic engineering" involves rational pathway design and assembly of biosynthetic genes, genes associated with operons, and control elements of such polynucleotides, for the production of a desired metabolite. "Metabolically engineered" can further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway.

The terms "metabolically engineered microorganism" and "modified microorganism" are used interchangeably herein and refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "mutation" as used herein indicates any modification of a nucleic acid and/or polypeptide which results in an altered nucleic acid or polypeptide. Mutations include, for example, point mutations, deletions, or insertions of single or multiple residues in a polynucleotide, which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, an insertion, or a deletion of part or all of a gene. In addition, in some embodiments of the modified microorganism, a portion of the microorganism genome has been replaced with a heterologous polynucleotide. In some embodiments, the mutations are naturally-occurring. In other embodiments, the mutations are the results of artificial selection pressure. In still other embodiments, the mutations in the microorganism genome are the result of genetic engineering.

The term "biosynthetic pathway", also referred to as "metabolic pathway", refers to a set of anabolic or catabolic biochemical reactions for converting one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

The term "heterologous" as used herein with reference to molecules and in particular enzymes and polynucleotides, indicates molecules that are expressed in an organism other than the organism from which they originated or are found in nature, independently of the level of expression that can be lower, equal or higher than the level of expression of the molecule in the native microorganism.

On the other hand, the term "native" or "endogenous" as used herein with reference to molecules, and in particular enzymes and polynucleotides, indicates molecules that are expressed in the organism in which they originated or are found in nature, independently of the level of expression that can be lower equal or higher than the level of expression of the molecule in the native microorganism. It is understood that expression of native enzymes or polynucleotides may be modified in recombinant microorganisms.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a biofuel in a fermentation process. However, a feedstock may contain nutrients other than a carbon source.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, such as any biomass derived sugar, but also intermediate and end product metabolites used in a pathway associated with a metabolically engineered microorganism as described herein.

The term "C2-compound" as used as a carbon source for engineered yeast microorganisms with mutations in all pyruvate decarboxylase (PDC) genes resulting in a reduction of pyruvate decarboxylase activity of said genes refers to organic compounds comprised of two carbon atoms, including but not limited to ethanol and acetate.

The term "fermentation" or "fermentation process" is defined as a process in which a microorganism is cultivated in a culture medium containing raw materials, such as feedstock and nutrients, wherein the microorganism converts raw materials, such as a feedstock, into products. The term "cell dry weight" or "CDW" refers to the weight of the microorganism after the water contained in the microorganism has been removed using methods known to one skilled in the art. CDW is reported in grams.

The term "biofuel" refers to a fuel in which all carbon contained within the fuel is derived from biomass and is biochemically converted, at least in part, in to a fuel by a microorganism. A biofuel is further defined as a non-ethanol compound which contains less than 0.5 oxygen atoms per carbon atom. A biofuel is a fuel in its own right, but may be blended with petroleum-derived fuels to generate a fuel. A biofuel may be used as a replacement for petrochemically-derived gasoline, diesel fuel, or jet fuel.

The term "volumetric productivity" or "production rate" is defined as the amount of product formed per volume of medium per unit of time. Volumetric productivity is reported in gram per liter per hour (g/L/h).

The term "specific productivity" or "specific production rate" is defined as the amount of product formed per volume of medium per unit of time per amount of cells. Volumetric productivity is reported in gram or milligram per liter per hour per OD (g/L/h/OD).

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product. For example, the theoretical yield for one typical conversion of glucose to isobutanol is 0.41 g/g. As such, a yield of isobutanol from glucose of 0.39 g/g would be expressed as 95% of theoretical or 95% theoretical yield.

The term "titer" is defined as the strength of a solution or the concentration of a substance in solution. For example, the titer of a biofuel in a fermentation broth is described as g of biofuel in solution per liter of fermentation broth (g/L).

A "facultative anaerobic organism" or a "facultative anaerobic microorganism" is defined as an organism that can grow in either the presence or in the absence of oxygen.

A "strictly anaerobic organism" or a "strictly anaerobic microorganism" is defined as an organism that cannot grow in the presence of oxygen and which does not survive exposure to any concentration of oxygen.

An "anaerobic organism" or an "anaerobic microorganism" is defined as an organism that cannot grow in the presence of oxygen.

"Aerobic conditions" are defined as conditions under which the oxygen concentration in the fermentation medium is sufficiently high for an aerobic or facultative anaerobic microorganism to use as a terminal electron acceptor.

In contrast, "Anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of the fermentation until oxygen is unavailable to the microorganism as a terminal electron acceptor. Methods for the production of isobutanol under anaerobic conditions are described in commonly owned and co-pending applications U.S. Ser. No. 12/610,784 and PCT/US09/62952 (published as WO/2010/051527), the disclosures of which are herein incorporated by reference in their entireties for all purposes.

"Aerobic metabolism" refers to a biochemical process in which oxygen is used as a terminal electron acceptor to make energy, typically in the form of ATP, from carbohydrates. Aerobic metabolism occurs e.g. via glycolysis and the TCA cycle, wherein a single glucose molecule is metabolized completely into carbon dioxide in the presence of oxygen.

In contrast, "anaerobic metabolism" refers to a biochemical process in which oxygen is not the final acceptor of electrons contained in NADH. Anaerobic metabolism can be divided into anaerobic respiration, in which compounds other than oxygen serve as the terminal electron acceptor, and substrate level phosphorylation, in which the electrons from NADH are utilized to generate a reduced product via a "fermentative pathway."

In "fermentative pathways", NAD(P)H donates its electrons to a molecule produced by the same metabolic pathway that produced the electrons carried in NAD(P)H. For example, in one of the fermentative pathways of certain yeast strains, NAD(P)H generated through glycolysis transfers its electrons to acetaldehyde, yielding ethanol. Fermentative pathways are usually active under anaerobic conditions but may also occur under aerobic conditions, under conditions where NADH is not fully oxidized via the respiratory chain. For example, above certain glucose concentrations, Crabtree-positive yeasts produce large amounts of ethanol under aerobic conditions.

The term "byproduct" or "by-product" means an undesired product related to the production of a biofuel or biofuel precursor. Byproducts are generally disposed as waste, adding cost to a production process.

The term "substantially free" when used in reference to the presence or absence of enzymatic activities (PDC, GPD, PDH, etc.) in carbon pathways that compete with the desired metabolic pathway (e.g. an isobutanol-producing metabolic pathway) means the level of the enzyme is substantially less than that of the same enzyme in the wild-type host, wherein less than about 50% of the wild-type level is preferred and less than about 30% is more preferred. The activity may be less than about 20%, less than about 10%, less than about 5%, or less than about 1% of wild-type activity.

The term "non-fermenting yeast" is a yeast species that fails to demonstrate an anaerobic metabolism in which the electrons from NADH are utilized to generate a reduced product via a fermentative pathway such as the production of ethanol and $CO_2$ from glucose. Non-fermentative yeast can be identified by the "Durham Tube Test" (J. A. Barnett, R. W. Payne, and D. Yarrow. 2000. Yeasts Characteristics and Identification. 3rd edition. p. 28-29. Cambridge University Press, Cambridge, UK.) or by monitoring the production of fermentation productions such as ethanol and $CO_2$.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "operon" refers to two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

"Transformation" refers to the process by which a vector is introduced into a host cell. Transformation (or transduction, or transfection), can be achieved by any one of a number of means including chemical transformation (e.g. lithium acetate transformation), electroporation, microinjection, biolistics (or particle bombardment-mediated delivery), or *agrobacterium* mediated transformation.

The term "enzyme" as used herein refers to any substance that catalyzes or promotes one or more chemical or biochemical reactions, which usually includes enzymes totally or partially composed of a polypeptide, but can include enzymes composed of a different molecule including polynucleotides.

The term "protein," "peptide," or "polypeptide" as used herein indicates an organic polymer composed of two or more amino acidic monomers and/or analogs thereof. As used herein, the term "amino acid" or "amino acidic monomer" refers to any natural and/or synthetic amino acids including glycine and both D or L optical isomers. The term "amino acid analog" refers to an amino acid in which one or more individual atoms have been replaced, either with a different atom, or with a different functional group. Accordingly, the term polypeptide includes amino acidic polymer of any length including full length proteins, and peptides as well as analogs and fragments thereof. A polypeptide of three or more amino acids is also called a protein oligomer or oligopeptide The term "homolog", used with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

The term "analog" or "analogous" refers to nucleic acid or protein sequences or protein structures that are related to one another in function only and are not from common descent or do not share a common ancestral sequence. Analogs may differ in sequence but may share a similar structure, due to convergent evolution. For example, two enzymes are analogs or analogous if the enzymes catalyze the same reaction of conversion of a substrate to a product, are unrelated in sequence, and irrespective of whether the two enzymes are related in structure.

As used herein and as would be understood by one of ordinary skill in the art, "reduced activity and/or expression" of an endogenous protein such an enzyme can mean either a reduced specific catalytic activity of the protein (e.g. reduced activity) and/or decreased concentrations of the protein in the cell (e.g. reduced expression), while "deleted activity and/or expression" of an endogenous protein such an enzyme can mean either no or negligible specific catalytic activity of the enzyme (e.g. deleted activity) and/or no or negligible concentrations of the enzyme in the cell (e.g. deleted expression).

The term "reduced pyruvate decarboxylase activity" means either a decreased concentration of the pyruvate decarboxylase enzyme in the cell or reduced or no specific catalytic activity of the pyruvate decarboxylase enzyme.

The term "reduced glycerol-3-phosphate dehydrogenase activity" means either a decreased concentration of the glycerol-3-phosphate dehydrogenase enzyme in the cell or reduced or no specific catalytic activity of the glycerol-3-phosphate dehydrogenase enzyme.

The term "reduced pyruvate dehydrogenase activity" means either a decreased concentration of the pyruvate dehydrogenase enzyme in the cell or reduced or no specific catalytic activity of the pyruvate dehydrogenase enzyme.

The term "reduced xylose reductase activity" means either a decreased concentration of the xylose reductase enzyme in the cell or reduced or no specific catalytic activity of the xylose reductase enzyme.

The term "reduced xylitol dehydrogenase activity" means either a decreased concentration of xylitol dehydrogenase enzyme in the cell or reduced or no specific catalytic activity of the xylitol dehydrogenase enzyme.

The Microorganism in General

Native producers of 1-butanol, such as *Clostridium acetobutylicum*, are known, but these organisms also generate byproducts such as acetone, ethanol, and butyrate during fermentations. Furthermore, these microorganisms are relatively difficult to manipulate, with significantly fewer tools available than in more commonly used production hosts such as *E. coli* and yeast (e.g. *S. cerevisiae*).

Yeast cells produce pyruvate from sugars, which is then utilized in a number of pathways of cellular metabolism. Yeast cells can be engineered to produce a number of desirable products with the initial biosynthetic pathway step being conversion of endogenous pyruvate to acetolactate. The present inventors have observed that by combining the expression of a cytosolically localized acetolactate synthase enzyme with reduced pyruvate decarboxylase (PDC) activity and/or reduced glycerol-3-phosphate dehydrogenase (GPO) activity, an unexpectedly high flux from pyruvate to acetolactate can be achieved. Thus, the invention provides yeast cells that are engineered to exhibit an efficient conversion of pyruvate to acetolactate in the cytoplasm due to suppression of competing metabolic pathways. Therefore, as would be understood in the art, the present invention has utility for the production of any acetolactate-derived product, including, but not limited to, isobutanol, 2-butanol, 1-butanol, 2-butanone, 2,3-butanediol, valine, leucine, and 3-methyl-1-butanol.

Engineered biosynthetic pathways for synthesis of isobutanol are described in commonly owned and co-pending applications U.S. Ser. No. 12/343,375 (published as US 2009/0226991), U.S. Ser. No. 12/696,645, U.S. Ser. No. 12/610,784, PCT/US09/62952 (published as WO/2010/051527), and PCT/US09/69390, all of which are herein incorporated by reference in their entireties for all purposes. Additional pathways have been described for the synthesis of 1-butanol (See, e.g., commonly owned U.S. Provisional Application Nos. 60/940,877 and 60/945,576, as well as WO/2010/017230 and WO/2010/031772), 2-butanol (See, e.g., WO/2007/130518, WO/2007/130521, and WO/2009/134276), 2-butanone (See, e.g., WO/2007/130518, WO/2007/130521, and WO/2009/134276), 2,3-butanediol (See, e.g., WO/2007/130518, WO/2007/130521, and WO/2009/134276), valine (See, e.g., WO/2001/021772, and McCourt et al., 2006, *Amino Acids* 31: 173-210), leucine (See, e.g., WO/2001/021772, and McCourt et al., 2006, *Amino Acids* 31: 173-210), pantothenic acid (See, e.g., WO/2001/021772), and 3-methyl-1-butanol (See, e.g., WO/2008/098227, Atsumi et al., 2008, *Nature* 451: 86-89, and Connor et al., 2008, *Appl. Environ. Microbiol.* 74: 5769-5775). Each of these pathways shares the common intermediate acetolactate. Therefore, the product yield from these biosynthetic pathways will in part depend upon the amount of acetolactate that is available to downstream'enzymes of said biosynthetic pathways.

In various embodiments described herein, the present invention provides recombinant microorganisms that comprise an isobutanol producing metabolic pathway. Recombinant microorganisms provided herein can express a plurality of heterologous and/or native target enzymes involved in pathways for the production isobutanol from a suitable carbon source.

Accordingly, metabolically "engineered" or "modified" microorganisms are produced via the introduction of genetic material into a host or parental microorganism of choice and/or by modification of the expression of native genes, thereby modifying or altering the cellular physiology and biochemistry of the microorganism. Through the introduction of genetic material and/or the modification of the expression of native genes the parental microorganism acquires new properties, e.g. the ability to produce a new, or greater quantities of, an intracellular metabolite. As described herein, the introduction of genetic material into and/or the modification of the expression of native genes in a parental microorganism results in a new or modified ability to produce isobutanol. The genetic material introduced into and/or the genes modified for expression in the parental microorganism contains gene(s), or parts of genes, coding for one or more of the enzymes involved in a biosynthetic pathway for the production of isobutanol and may also include additional elements for the expression and/or regulation of expression of these genes, e.g. promoter sequences.

In addition to the introduction of a genetic material into a host or parental microorganism, an engineered or modified microorganism can also include alteration, disruption, deletion or knocking-out of a gene or polynucleotide to alter the cellular physiology and biochemistry of the microorganism. Through the alteration, disruption, deletion or knocking-out of a gene or polynucleotide the microorganism acquires new or improved properties (e.g., the ability to produce a new metabolite or greater quantities of an intracellular metabolite, improve the flux of a metabolite down a desired pathway, and/or reduce the production of byproducts).

Recombinant microorganisms provided herein may also produce metabolites in quantities not available in the parental microorganism. A "metabolite" refers to any substance produced by metabolism or a substance necessary for or taking part in a particular metabolic process. A metabolite can be an organic compound that is a starting material (e.g., glucose or pyruvate), an intermediate (e.g., 2-ketoisovalerate), or an end product (e.g., isobutanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

Exemplary metabolites include glucose, pyruvate, and isobutanol. The metabolite isobutanol can be produced by a recombinant microorganism metabolically engineered to express or over-express a metabolic pathway that converts pyruvate to isobutanol. An exemplary metabolic pathway that converts pyruvate to isobutanol may be comprised of an acetohydroxy acid synthase (ALS), a ketolacid reductoisomerase (KARI), a dihyroxy-acid dehydratase (DHAD), a 2-keto-acid decarboxylase (KIVD), and an alcohol dehydrogenase (ADH). Exemplary metabolic pathways that convert pyruvate to isobutanol are disclosed in WO/2007/050671, WO/2008/098227, and Atsumi et al., Nature, 2008 Jan. 3; 451(7174):86-9.

Accordingly, provided herein are recombinant microorganisms that produce isobutanol and in some aspects may include the elevated expression of target enzymes such as ALS, KARI, DHAD, KIVD, and ADH.

The disclosure identifies specific genes useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutation and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray of al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin of al. (1996) Nucl. Acids Res. 24: 216-218). Methodology for optimizing a nucleotide sequence for expression in a plant is provided, for example, in U.S. Pat. No. 6,015,891, and the references cited therein.

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as they modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for generating metabolites are encompassed by the microorganisms and methods provided herein.

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson W. R. Using the FASTA program to search protein and DNA sequence databases, Methods in Molecular Biology, 1994, 25:365-89, hereby incorporated herein by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutant protein thereof. See, e.g., GCG Version 6.1.

A typical algorithm used comparing a molecule sequence to a database containing a large number of sequences from different organisms is the computer program BLAST (Altschul, S. F., et al. (1990) "Basic local alignment search tool." J. Mol. Biol. 215:403-410; Gish, W. and States, D. J. (1993) "Identification of protein coding regions by database similarity search." Nature Genet. 3:266-272; Madden, T. L., et al. (1996) "Applications of network BLAST server" Meth. Enzymol. 266:131-141; Altschul, S. F., et al. (1997) "Gapped BLAST and PSI-BLAST: a new generation of protein database search programs." Nucleic Acids Res. 25:3389-3402; Zhang, J. and Madden, T. L. (1997) "PowerBLAST: A new network BLAST application for interactive or automated sequence analysis and annotation." Genome Res. 7:649-656), especially blastp or tblastn (Altschul, S. F., et al. (1997) "Gapped BLAST and PSI-BLAST: a new generation of protein database search programs." Nucleic Acids Res. 25:3389-3402). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, W. R. (1990) "Rapid and Sensitive Sequence Comparison with FASTP and FASTA" Meth. Enzymol. 183:63-98). For example, a percent sequence identity between amino acid sequences can be determined using FASTA with its default parameters (a word size of 2 and the PAM250 scoring matrix), as provided in GCG Version 6.1, hereby incorporated herein by reference.

The disclosure provides metabolically engineered microorganisms comprising a biochemical pathway for the production of isobutanol from a suitable substrate at a high yield. A metabolically engineered microorganism of the disclosure comprises one or more recombinant polynucleotides within the genome of the organism or external to the genome within the organism. The microorganism can comprise a reduction, disruption or knockout of a gene found in the wild-type organism and/or introduction of a heterologous polynucleotide and/or expression or overexpression of an endogenous polynucleotide.

In one aspect, the disclosure provides a recombinant microorganism comprising elevated expression of at least one target enzyme as compared to a parental microorganism or encodes an enzyme not found in the parental organism. In another or further aspect, the microorganism comprises a reduction, disruption or knockout of at least one gene encoding an enzyme that competes with a metabolite necessary for the production of isobutanol. The recombinant microorganism produces at least one metabolite involved in a biosynthetic pathway for the production of isobutanol. In general, the recombinant microorganisms comprises at least one recombinant metabolic pathway that comprises a target enzyme and may further include a reduction in activity or expression of an enzyme in a competitive biosynthetic pathway. The pathway acts to modify a substrate or metabolic intermediate in the production of isobutanol. The target enzyme is encoded by, and expressed from, a polynucleotide derived from a suitable biological source. In some embodiments, the polynucleotide comprises a gene derived from a prokaryotic or eukaryotic source and recombinantly engineered into the microorganism of the disclosure. In other embodiments, the polynucleotide comprises a gene that is native to the host organism.

It is understood that a range of microorganisms can be modified to include a recombinant metabolic pathway suitable for the production of isobutanol. In various embodiments, microorganisms may be selected from yeast microorganisms. Yeast microorganisms for the production of isobutanol may be selected based on certain characteristics:

One characteristic may include the property that the microorganism is selected to convert various carbon sources into isobutanol. The term "carbon source" generally refers to a substance suitable to be used as a source of carbon for prokaryotic or eukaryotic cell growth. Carbon sources include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose. The term "biomass" as used herein refers primarily to the stems, leaves, and starch-containing portions of green plants, and is mainly comprised of starch, lignin, cellulose, hemicellulose, and/or pectin. Biomass can be decomposed by either chemical or enzymatic treatment to the monomeric sugars and phenols of which it is composed (Wyman, C. E. 2003 Biotechnological Progress 19:254-62). This resulting material, called biomass hydrolysate, is neutralized and treated to remove trace amounts of organic material that may adversely affect the biocatalyst, and is then used as a feed stock for fermentations using a biocatalyst.

Accordingly, in one embodiment, the recombinant microorganism herein disclosed can convert a variety of carbon sources to products, including but not limited to glucose, galactose, mannose, xylose, arabinose, lactose, sucrose, and mixtures thereof.

The recombinant microorganism may thus further include a pathway for the fermentation of isobutanol from five-carbon (pentose) sugars including xylose. Most yeast species metabolize xylose via a complex route, in which xylose is first reduced to xylitol via a xylose reductase (XR) enzyme. The xylitol is then oxidized to xylulose via a xylitol dehydrogenase (XDH) enzyme. The xylulose is then phosphorylated via a xylulokinase (XK) enzyme. This pathway operates inefficiently in yeast species because it introduces a redox imbalance in the cell. The xylose-to-xylitol step uses NADH as a cofactor, whereas the xylitol-to-xylulose step uses NADPH as a cofactor. Other processes must operate to restore the redox imbalance within the cell. This often means that the organism cannot grow anaerobically on xylose or other pentose sugar. Accordingly, a yeast species that can efficiently ferment xylose and other pentose sugars into a desired fermentation product is therefore very desirable.

Thus, in one embodiment, the recombinant is engineered to express a functional exogenous xylose isomerase. Exogenous xylose isomerases functional in yeast are known in the art. See, e.g., Rajgarhia et al, US20060234364, which is herein incorporated by reference in its entirety. In another embodiment, the exogenous xylose isomerase gene is operatively linked to promoter and terminator sequences that are functional in the yeast cell.

In another embodiment, the recombinant microorganism has a deletion or disruption of a native gene that encodes for an enzyme (e.g. XR and/or XDH) that catalyzes the conversion of xylose to xylitol. Thus, in one embodiment, the recombinant microorganism is engineered to exhibit reduced xylose reductase (XR) activity. In another embodiment, the recombinant microorganism is engineered to exhibit reduced xylitol dehydrogenase (XDH) activity. In yet another embodiment, the recombinant microorganism also contains a functional, exogenous xylulokinase (XK) gene operatively linked to promoter and terminator sequences that are functional in the yeast cell. In one embodiment, the xylulokinase (XK) gene is overexpressed.

In one embodiment, the microorganism has reduced or no pyruvate decarboxylase (PDC) activity. PDC catalyzes the decarboxylation of pyruvate to acetaldehyde, which is then reduced to ethanol by ADH via an oxidation of NADH to NAD+. Ethanol production is the main pathway to oxidize the NADH from glycolysis. Deletion of this pathway increases the pyruvate and the reducing equivalents (NADH) available for the isobutanol pathway. Accordingly, deletion of PDC genes further increases the yield of isobutanol.

In another embodiment, the microorganism has reduced or no glycerol-3-phosphate dehydrogenase (GPD) activity. GPD catalyzes the reduction of dihydroxyacetone phosphate (DHAP) to glycerol-3-phosphate (G3P) via the oxidation of NADH to NAD+. Glycerol is then produced from G3P by Glycerol-3-phosphatase (GPP). Glycerol production is a secondary pathway to oxidize excess NADH from glycolysis. Reduction or elimination of this pathway increases the pyruvate and reducing equivalents (NADH) available for the isobutanol pathway. Thus, deletion of GPD genes further increases the yield of isobutanol.

In yet another embodiment, the microorganism has reduced or no PDC activity and reduced or no GPD activity.

Another characteristic may include the property that the wild-type or parental microorganism is non-fermenting. In other words, it cannot metabolize a carbon source anaerobically while the yeast is able to metabolize a carbon source in the presence of oxygen. Non-fermenting yeast refers to both naturally occurring yeasts as well as genetically modified yeast. During anaerobic fermentation with fermentative yeast, the main pathway to oxidize the NADH from glycolysis is through the production of ethanol. Ethanol is produced by alcohol dehydrogenase (ADH) via the reduction of acetaldehyde, which is generated from pyruvate by pyruvate decarboxylase (PDC). Thus, in one embodiment, a fermentative yeast can be engineered to be non-fermentative by the reduction or elimination of the native PDC activity. Thus, most of the pyruvate produced by glycolysis is not consumed by PDC and is available for the isobutanol pathway. Deletion of this pathway increases the pyruvate and the reducing equivalents available for the isobutanol pathway. Fermentative pathways contribute to low yield and low productivity of isobutanol. Accordingly, deletion of PDC may increase yield and productivity of isobutanol.

A third characteristic may include the property that the biocatalyst is selected to convert various carbon sources into isobutanol.

Figure 2:
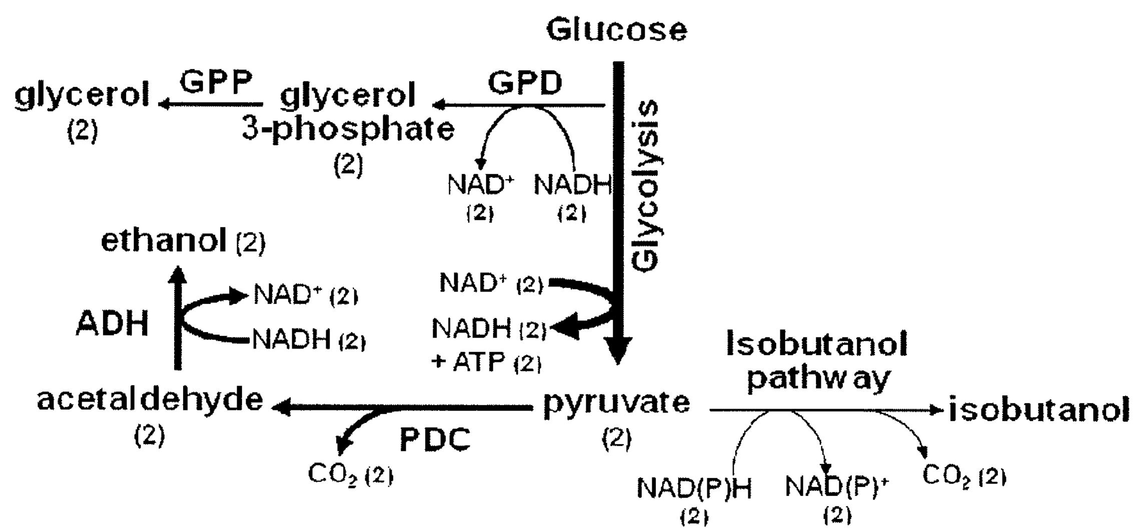
FIG. 2 illustrates production of pyruvate via glycolysis, together with an isobutanol pathway which converts pyruvate to isobutanol and a PDC pathway which converts pyruvate to acetaldehyde and carbon dioxide.

In one embodiment, the yeast microorganisms may be selected from the "*Saccharomyces* Yeast Clade", defined as an ascomycetous yeast taxonomic class by Kurtzman and Robnett in 1998 ("Identification and phylogeny of ascomycetous yeast from analysis of nuclear large subunit (26S) ribosomal DNA partial sequences." *Antonie van Leeuwenhoek* 73: 331-371, See FIG. 2 of Leeuwenhoek reference). They were able to determine the relatedness of approximately 500 yeast species by comparing the nucleotide sequence of the D1/D2 domain at the 5' end of the gene encoding the large ribosomal subunit 26S. In pair-wise comparisons of the D1/D2 nucleotide sequences of *S. cerevisiae* and the two most distant yeast from *S. cerevisiae, K. lactis* and *K. marxianus*, share greater than 80% identity.

The term "*Saccharomyces sensu stricto*" taxonomy group is a cluster of yeast species that are highly related to *S. cerevisiae* (Rainieri, S. et al 2003. *Saccharomyces Sensu Stricto*: Systematics, Genetic Diversity and Evolution. J. Biosci Bioengin 96(1)1-9. *Saccharomyces sensu stricto* yeast species include but are not limited to *S. cerevisiae, S. cerevisiae, S. kudriavzevii, S. mikatae, S. bayanus, S. uvarum, S. carocanis* and hybrids derived from these species (Masneuf et al. 1998. New Hybrids between *Saccharomyces Sensu Stricto* Yeast Species Found Among Wine and Cider Production Strains. *Yeast* 7(1)61-72).

An ancient whole genome duplication (WGD) event occurred during the evolution of the hemiascomycete yeast and was discovered using comparative genomic tools (Kellis et al 2004 "Proof and evolutionary analysis of ancient genome duplication in the yeast *S. cerevisiae.*" *Nature* 428: 617-624. Dujon et al 2004 "Genome evolution in yeasts." *Nature* 430:3544. Langkjaer et al 2003 "Yeast genome duplication was followed by asynchronous differentiation of duplicated genes." *Nature* 428:848-852. Wolfe and Shields 1997 "Molecular evidence for an ancient duplication of the entire yeast genome." *Nature* 387:708-713.) Using this major evolutionary event, yeast can be divided into species that diverged from a common ancestor following the WGD event (termed "post-WGD yeast" herein) and species that diverged from the yeast lineage prior to the WGD event (termed "pre-WGD yeast" herein).

Accordingly, in one embodiment, the yeast microorganism may be selected from a post-WGD yeast genus, including but not limited to *Saccharomyces* and *Candida*. The favored post-WGD yeast species include: *S. cerevisiae, S. uvarum, S. bayanus, S. paradoxus, S. castelli*, and *C. glabrata.*

In another embodiment, the yeast microorganism may be selected from a pre-whole genome duplication (pre-WGD) yeast genus including but not limited to *Saccharomyces, Kluyveromyces, Candida, Pichia, Issatchenkia, Debaryomyces, Hansenula, Yarrowia* and, *Schizosaccharomyces*. Representative pre-WGD yeast species include: *S. kluyveri, K. thermotolerans, K. marxianus, K. waltii, K. lactis, C. tropicalis, P. pastoris, P. anomala, P. stipitis, I. orientalis, I. occidentalis, I. scutulata, D. hansenii, H. anomala, Y. lipolytica*, and *S. pombe.*

A yeast microorganism may be either Crabtree-negative or Crabtree-positive. A yeast cell having a Crabtree-negative phenotype is any yeast cell that does not exhibit the Crabtree effect. The term "Crabtree-negative" refers to both naturally occurring and genetically modified organisms. Briefly, the Crabtree effect is defined as the inhibition of oxygen consumption by a microorganism when cultured under aerobic conditions due to the presence of a high concentration of glucose (e.g., 50 g-glucose $L^{-1}$). In other words, a yeast cell having a Crabtree-positive phenotype continues to ferment irrespective of oxygen availability due to the presence of glucose, while a yeast cell having a Crabtree-negative phenotype does not exhibit glucose mediated inhibition of oxygen consumption.

Accordingly, in one embodiment the yeast microorganism may be selected from yeast with a Crabtree-negative phenotype including but not limited to the following genera: *Kluyveromyces, Pichia, Issatchenkia, Hansenula*, and *Candida*. Crabtree-negative species include but are not limited to: *K. lactis, K. marxianus, P. anomala, P. stipitis, I. orientalis, I. occidentalis, I. scutulata, H. anomala*, and *C. utilis*.

In another embodiment, the yeast microorganism may be selected from a yeast with a Crabtree-positive phenotype, including but not limited to *Saccharomyces, Kluyveromyces, Zygosaccharomyces, Debaryomyces, Pichia* and *Schizosaccharomyces*. Crabtree-positive yeast species include but are not limited to: *S. cerevisiae, S. uvarum, S. bayanus, S. paradoxus, S. castelli, S. kluyveri, K. thermotolerans, C. glabrata, Z. bailli, Z. rouxii, D. hansenii, P. pastorius*, and *S. pombe*.

In some embodiments, the recombinant microorganisms may be microorganisms that are non-fermenting yeast microorganisms, including, but not limited to those, classified into a genera selected from the group consisting of *Tricosporon, Rhodotorula*, or *Myxozyma*.

In one embodiment, a yeast microorganism is engineered to convert a carbon source, such as glucose, to pyruvate by glycolysis and the pyruvate is converted to isobutanol via an engineered isobutanol pathway (See, e.g., WO/2007/050671, WO/2008/098227, and Atsumi et al., Nature, 2008 Jan. 3; 451(7174):86-9). Alternative pathways for the production of isobutanol have been described in WO/2007/050671 and in Dickinson et al., *Journal of Biological Chemistry* 273:25751-15756 (1998).

Accordingly, in one embodiment, the engineered isobutanol pathway to convert pyruvate to isobutanol can be comprised of the following reactions:

1. 2 pyruvate→acetolactate+$CO_2$
2. acetolactate+NAD(P)H→2,3-dihydroxyisovalerate+NAD$(P)^+$
3. 2,3-dihydroxyisovalerate→alpha-ketoisovalerate
4. alpha-ketoisovalerate→isobutyraldehyde+$CO_2$
5. isobutyraldehyde+NAD(P)H→isobutanol+NAD$(P)^+$ These reactions are carried out by the enzymes 1) Acetolactate Synthase (ALS), 2) Keto-acid Reducto-Isomerase (KARI), 3) Dihydroxy-acid dehydratase (DHAD), 4) Keto-isovalerate decarboxylase (KIVD), and 5) an Alcohol dehydrogenase (ADH).

In another embodiment, the yeast microorganism is engineered to overexpress these enzymes. For example, these enzymes can be encoded by native genes. Alternatively, these enzymes can be encoded by heterologous genes. For example, ALS can be encoded by the alsS gene of *B. subtilis*, alsS of *L. lactis*, or the ilvK gene of *K. pneumonia*. For example, KARI can be encoded by the ilvC genes of *E. coli, C. glutamicum, M. maripaludis*, or *Piromyces* sp E2. For example, DHAD can be encoded by the ilvD genes of *E. coli, C. glutamicum*, or *L. lactis*. KIVD can be encoded by the kivD gene of *L. lactis*. ADH can be encoded by ADH2; ADH6, or ADH7 of *S. cerevisiae*.

In one embodiment, pathway steps 2 and 5 may be carried out by KARI and ADH enzymes that utilize NADH (rather than NADPH) as a co-factor. Such enzymes are described in commonly owned and co-pending applications U.S. Ser. No. 12/610,784 and PCT/US09/62952 (published as WO/2010/051527), which are herein incorporated by reference in their entireties for all purposes. The present inventors have found that utilization of NADH-dependent KARI and ADH enzymes to catalyze pathway steps 2 and 5, respectively, surprisingly enables production of isobutanol under anaerobic conditions. Thus, in one embodiment, the recombinant microorganisms of the present invention may use an NADH-dependent KARI to catalyze the conversion of acetolactate (+NADH) to produce 2,3-dihydroxyisovalerate. In another embodiment, the recombinant microorganisms of the present invention may use an NADH-dependent ADH to catalyze the conversion of isobutyraldehyde (+NADH) to produce isobutanol. In yet another embodiment, the recombinant microorganisms of the present invention may use both an NADH-dependent KARI to catalyze the conversion of acetolactate (+NADH) to produce 2,3-dihydroxyisovalerate, and an NADH-dependent ADH to catalyze the conversion of isobutyraldehyde (+NADH) to produce isobutanol.

The yeast microorganism of the invention may be engineered to have increased ability to convert pyruvate to isobutanol. In one embodiment, the yeast microorganism may be engineered to have increased ability to convert pyruvate to isobutyraldehyde. In another embodiment, the yeast microorganism may be engineered to have increased ability to convert pyruvate to keto-isovalerate. In another embodiment, the yeast microorganism may be engineered to have increased ability to convert pyruvate to 2,3-dihydroxyisovalerate. In another embodiment, the yeast microorganism may be engineered to have increased ability to convert pyruvate to acetolactate.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum, Kluyveromyces* spp., including *K. thermotolerans, K. lactis*, and *K. marxianus, Pichia* spp., *Hansenula* spp., including *H. polymorpha, Candida* spp., *Trichosporon* spp., *Yamadazyma* spp., including *Y. stipitis, Torulaspora* spp, including *T. pretoriensis, Schizosaccharomyces* spp., including *S. pombe, Cryptococcus* spp., *Aspergillus* spp., *Neurospora* spp., or *Ustilago* spp. Sources of genes from anaerobic fungi include, but not limited to, *Piromyces* spp., *Orpinomyces* spp., or *Neocallimastix* spp. Sources of prokaryotic enzymes that are useful include, but not limited to, *Escherichia coli, Zymomonas mobilis, Staphylococcus aureus, Bacillus* spp., *Clostridium* spp., *Corynebacterium* spp., *Pseudomonas* spp., *Lactococcus* spp., *Enterobacter* spp., and *Salmonella* spp.

Methods in General

Identification of PDC in a Yeast Microorganism

Any method can be used to identify genes that encode for enzymes with pyruvate decarboxylase (PDC) activity. PDC catalyzes the decarboxylation of pyruvate to form acetaldehyde. Generally, homologous or similar PDC genes and/or homologous or similar PDC enzymes can be identified by functional, structural, and/or genetic analysis. In most cases, homologous or similar PDC genes and/or homologous or similar PDC enzymes will have functional, structural, or genetic similarities: Techniques known to those skilled in the art may be suitable to identify homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous genes, proteins, or enzymes, techniques may include, but not limited to, cloning a PDC gene by PCR using primers based on a published sequence of a gene/enzyme or by degenerate PCR using degenerate primers designed to amplify a conserved region among PDC genes. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity, then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein. Furthermore, PDC activity can be determined phenotypically. For example, ethanol production under fermentative conditions can be assessed. A lack of ethanol production may be indicative of a yeast microorganism with no PDC activity. Examples of yeast pyruvate decarboxylase genes that may be targeted for disruption may be found in U.S. Pat. No. 7,326,550. Target genes for disruption include, but are not limited, to PDC1 (GenBank Accession No. CAA97573.1), PDC5 (GenBank Accession No. CAA97705.1), and PDC6 (GenBank Accession No. CAA97089.1) from *S. cerevisiae*, as well as genes encoding pyruvate decarboxylases from *K. lactis* (GenBank Accession No. CAA59953.1), *K. marxianus* (AAA35267.1), *P. stipitis* (GenBank Accession No. AAC03164.3), *C. glabrata* (AAN77243.1), *S. pombe* (GenBank Accession No. NP_592796.2), and *Y. lipolytica* (CAG80835.1). Other target genes, such as those encoding pyruvate decarboxylase proteins having at least about 50-55%, 55%-60%, 60-65%, 65%-70%, 75-80%, 80-85%, 85%-90%, 90%-95%, or at least about 98% sequence identity to the *S. cerevisiae* pyruvate decarboxylases may be identified in the literature and in bioinformatics databases well known to the skilled person.

Identification of GPD in a Yeast Microorganism

Any method can be used to identify genes that encode for enzymes with glycerol-3-phosphate dehydrogenase (GPD) activity. GPD catalyzes the reduction of dihydroxyacetone phosphate (DHAP) to glycerol-3-phosphate (G3P) with the corresponding oxidation of NADH to NAD+. Generally, homologous or similar GPD genes and/or homologous or similar GPD enzymes can be identified by functional, structural, and/or genetic analysis. In most cases, homologous or similar GPD genes and/or homologous or similar GPD enzymes will have functional, structural, or genetic similarities. Techniques known to those skilled in the art may be suitable to identify homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous genes, proteins, or enzymes, techniques may include, but not limited to, cloning a GPD gene by PCR using primers based on a published sequence of a gene/enzyme or by degenerate PCR using degenerate primers designed to amplify a conserved region among GPD genes. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity, then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein. Furthermore, GPD activity can be determined phenotypically. For example, glycerol production under fermentative conditions can be assessed. A lack of glycerol production may be indicative of a yeast microorganism with no GPD activity. Examples of yeast glycerol-3-phosphate dehydrogenase genes that may be targeted for disruption may be found in US 2009/0053782. Other target genes, such as those encoding glycerol-3-phosphate dehydrogenase proteins having at least about 50-55%, 55%-60%, 60-65%, 65%-70%, 75-80%, 80-85%, 85%-90%, 90%-95%, or at least about 98% sequence identity to the *S. cerevisiae* glycerol-3-phosphate dehydrogenases may be identified in the literature and in bioinformatics databases well known to the skilled person.

Genetic Insertions and Deletions

Any method can be used to introduce a nucleic acid molecule into yeast and many such methods are well known. For example, transformation and electroporation are common methods for introducing nucleic acid into yeast cells. See, e.g., Gietz et al., *Nucleic Acids Res.* 27:69-74 (1992); Ito et al., *J. Bacteriol.* 153:163-168 (1983); and Becker and Guarente, *Methods in Enzymology* 194:182-187 (1991).

In an embodiment, the integration of a gene of interest into a DNA fragment or target gene of a yeast microorganism occurs according to the principle of homologous recombination. According to this embodiment, an integration cassette containing a module comprising at least one yeast marker gene and/or the gene to be integrated (internal module) is flanked on either side by DNA fragments homologous to those of the ends of the targeted integration site (recombinogenic sequences). After transforming the yeast with the cassette by appropriate methods, a homologous recombination between the recombinogenic sequences may result in the internal module replacing the chromosomal region in between the two sites of the genome corresponding to the recombinogenic sequences of the integration cassette. (Orr-Weaver et al., *Proc Natl Acad Sci USA* 78:6354-6358 (1981))

In an embodiment, the integration cassette for integration of a gene of interest into a yeast microorganism includes the heterologous gene under the control of an appropriate promoter and terminator together with the selectable marker flanked by recombinogenic sequences for integration of a heterologous gene into the yeast chromosome. In an embodiment, the heterologous gene includes an appropriate native gene desired to increase the copy number of a native gene(s).

The selectable marker gene can be any marker gene used in yeast, including but not limited to, HIS3, TRP1, LEU2, URA3, bar, ble, hph, and kan. The recombinogenic sequences can be chosen at will, depending on the desired integration site suitable for the desired application.

In another embodiment, integration of a gene into the chromosome of the yeast microorganism may occur via random integration (Kooistra, R., Hooykaas, P. J. J., Steensma, H. Y. 2004. *Yeast* 21: 781-792).

Additionally, in an embodiment, certain introduced marker genes are removed from the genome using techniques well known to those skilled in the art. For example, URA3 marker loss can be obtained by plating URA3 containing cells in FOA (5-fluoro-orotic acid) containing medium and selecting for FOA resistant colonies (Boeke, J. at al, 1984, *Mol. Gen. Genet,* 197, 345-47).

The exogenous nucleic acid molecule contained within a yeast cell of the disclosure can be maintained within that cell in any form. For example, exogenous nucleic acid molecules can be integrated into the genome of the cell or maintained in an episomal state that can stably be passed on ("inherited") to daughter cells. Such extra-chromosomal genetic elements (such as plasmids, etc.) can additionally contain selection markers that ensure the presence of such genetic elements in daughter cells. Moreover, the yeast cells can be stably or transiently transformed. In addition, the yeast cells described herein can contain a single copy, or multiple copies of a particular exogenous nucleic acid molecule as described above.

Reduction of Enzymatic Activity

Yeast microorganisms within the scope of the invention may have reduced enzymatic activity such as reduced pyruvate decarboxylase activity. The term "reduced" as used herein with respect to a particular enzymatic activity refers to a lower level of enzymatic activity than that measured in a comparable yeast cell of the same species. The term reduced also refers to the elimination of enzymatic activity than that measured in a comparable yeast cell of the same species. Thus, yeast cells lacking pyruvate decarboxylase activity are considered to have reduced pyruvate decarboxylase activity since most, if not all, comparable yeast strains have at least some pyruvate decarboxylase activity. Such reduced enzymatic activities can be the result of lower enzyme concentration, lower specific activity of an enzyme, or a combination thereof. Many different methods can be used to make yeast having reduced enzymatic activity. For example, a yeast cell can be engineered to have a disrupted enzyme-encoding locus using common mutagenesis or knock-out technology. See, e.g., Methods in Yeast Genetics (1997 edition), Adams, Gottschling, Kaiser, and Stems, Cold Spring Harbor Press (1998). In addition, certain point-mutation(s) can be introduced which results in an enzyme with reduced activity.

Alternatively, antisense technology can be used to reduce enzymatic activity. For example, yeast can be engineered to contain a cDNA that encodes an antisense molecule that prevents an enzyme from being made. The term "antisense molecule" as used herein encompasses any nucleic acid molecule that contains sequences that correspond to the coding strand of an endogenous polypeptide. An antisense molecule also can have flanking sequences (e.g., regulatory sequences). Thus antisense molecules can be ribozymes or antisense oligonucleotides. A ribozyme can have any general structure including, without limitation, hairpin, hammerhead, or axhead structures, provided the molecule cleaves RNA.

Yeast having a reduced enzymatic activity can be identified using many methods. For example, yeast having reduced pyruvate decarboxylase activity can be easily identified using common methods, which may include, for example, measuring ethanol formation via gas chromatography.

Overexpression of Heterologous Genes

Methods for overexpressing a polypeptide from a native or heterologous nucleic acid molecule are well known. Such methods include, without limitation, constructing a nucleic acid sequence such that a regulatory element promotes the expression of a nucleic acid sequence that encodes the desired polypeptide. Typically, regulatory elements are DNA sequences that regulate the expression of other DNA sequences at the level of transcription. Thus, regulatory elements include, without limitation, promoters, enhancers, and the like. For example, the exogenous genes can be under the control of an inducible promoter or a constitutive promoter. Moreover, methods for expressing a polypeptide from an exogenous nucleic acid molecule in yeast are well known. For example, nucleic acid constructs that are used for the expression of exogenous polypeptides within *Kluyveromyces* and *Saccharomyces* are well known (see, e.g., U.S. Pat. Nos. 4,859,596 and 4,943,529, for *Kluyveromyces* and, e.g., Gellissen et al., Gene 190(1):87-97 (1997) for *Saccharomyces*). Yeast plasmids have a selectable marker and an origin of replication. In addition certain plasmids may also contain a centromeric sequence. These centromeric plasmids are generally a single or low copy plasmid. Plasmids without a centromeric sequence and utilizing either a 2 micron (*S. cerevisiae*) or 1.6 micron (*K. lactis*) replication origin are high copy plasmids. The selectable marker can be either prototrophic, such as HIS3, TRP1, LEU2, URA3 or ADE2, or antibiotic resistance, such as, bar, ble, hph, or kan.

In another embodiment, heterologous control elements can be used to activate or repress expression of endogenous genes. Additionally, when expression is to be repressed or eliminated, the gene for the relevant enzyme, protein or RNA can be eliminated by known deletion techniques.

As described herein, any yeast within the scope of the disclosure can be identified by selection techniques specific to the particular enzyme being expressed, over-expressed or repressed. Methods of identifying the strains with the desired phenotype are well known to those skilled in the art. Such methods include, without limitation, PCR, RT-PCR, and nucleic acid hybridization techniques such as Northern and Southern analysis, altered growth capabilities on a particular substrate or in the presence of a particular substrate, a chemical compound, a selection agent and the like. In some cases, immunohistochemistry and biochemical techniques can be used to determine if a cell contains a particular nucleic acid by detecting the expression of the encoded polypeptide. For example, an antibody having specificity for an encoded enzyme can be used to determine whether or not a particular yeast cell contains that encoded enzyme. Further, biochemical techniques can be used to determine if a cell contains a particular nucleic acid molecule encoding an enzymatic polypeptide by detecting a product produced as a result of the expression of the enzymatic polypeptide. For example, transforming a cell with a vector encoding acetolactate synthase and detecting increased acetolactate concentrations compared to a cell without the vector indicates that the vector is both present and that the gene product is active. Methods for detecting specific enzymatic activities or the presence of particular products are well known to those skilled in the art. For example, the presence of acetolactate can be determined as described by Hugenholtz and Starrenburg, *Appl. Microbiol. Biotechnol.* 38:17-22 (1992).

Increase of Enzymatic Activity

Yeast microorganisms of the invention may be further engineered to have increased activity of enzymes. The term "increased" as used herein with respect to a particular enzymatic activity refers to a higher level of enzymatic activity than that measured in a comparable yeast cell of the same species. For example, overexpression of a specific enzyme can lead to an increased level of activity in the cells for that enzyme. Increased activities for enzymes involved in glycolysis or the isobutanol pathway would result in increased productivity and yield of isobutanol.

Methods to increase enzymatic activity are known to those skilled in the art. Such techniques may include increasing the expression of the enzyme by increased copy number and/or use of a strong promoter, introduction of mutations to relieve negative regulation of the enzyme, introduction of specific mutations to increase specific activity and/or decrease the Km for the substrate, or by directed evolution. See, e.g., Methods in Molecular Biology (vol. 231), ed. Arnold and Georgiou, Humana Press (2003).

Carbon Source

The biocatalyst herein disclosed can convert various carbon sources into isobutanol. The term "carbon source" generally refers to a substance suitable to be used as a source of carbon for prokaryotic or eukaryotic cell growth. Carbon sources include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose.

The term "C2-compound" as used as a carbon source for engineered yeast microorganisms with mutations in all pyruvate decarboxylase (PDC) genes resulting in a reduction of pyruvate decarboxylase activity of said genes refers to organic compounds comprised of two carbon atoms, including but not limited to ethanol and acetate The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a biofuel in a fermentation process. However, a feedstock may contain nutrients other than a carbon source.

The term "traditional carbohydrates" refers to sugars and starches generated from specialized plants, such as sugar cane, corn, and wheat. Frequently, these specialized plants concentrate sugars and starches in portions of the plant, such as grains, that are harvested and processed to extract the sugars and starches. Traditional carbohydrates are used as food and also to a lesser extent as carbon sources for fermentation processes to generate biofuels, such as and chemicals The term "biomass" as used herein refers primarily to the stems, leaves, and starch-containing portions of green plants, and is mainly comprised of starch, lignin, cellulose, hemicellulose, and/or pectin. Biomass can be decomposed by either chemical or enzymatic treatment to the monomeric sugars and phenols of which it is composed (Wyman, C. E. 2003 Biotechnological Progress 19:254-62). This resulting material, called biomass hydrolysate, is neutralized and treated to remove trace amounts of organic material that may adversely affect the biocatalyst, and is then used as a feed stock for fermentations using a biocatalyst.

The term "starch" as used herein refers to a polymer of glucose readily hydrolyzed by digestive enzymes. Starch is usually concentrated in specialized portions of plants, such as potatoes, corn kernels, rice grains, wheat grains, and sugar cane stems.

The term "lignin" as used herein refers to a polymer material, mainly composed of linked phenolic monomeric compounds, such as p-coumaryl alcohol, coniferyl alcohol, and sinapyl alcohol, which forms the basis of structural rigidity in plants and is frequently referred to as the woody portion of plants. Lignin is also considered to be the non-carbohydrate portion of the cell wall of plants.

The term "cellulose" as used herein refers is a long-chain polymer polysaccharide carbohydrate of beta-glucose of formula (C6H10O5)n, usually found in plant cell walls in combination with lignin and any hemicellulose.

The term "hemicellulose" refers to a class of plant cell-wall polysaccharides that can be any of several heteropolymers. These include xylane, xyloglucan, arabinoxylan, arabinogalactan, glucuronoxylan, glucomannan and galactomannan. Monomeric components of hemicellulose include, but are not limited to: D-galactose, L-galactose, D-mannose, L-rhamnose, L-fucose, D-xylose, L-arabinose, and D-glucuronic acid. This class of polysaccharides is found in almost all cell walls along with cellulose. Hemicellulose is lower in weight than cellulose and cannot be extracted by hot water or chelating agents, but can be extracted by aqueous alkali. Polymeric chains of hemicellulose bind pectin and cellulose in a network of cross-linked fibers forming the cell walls of most plant cells.

Microorganism Characterized by Producing Isobutanol at High Yield

For a biocatalyst to produce isobutanol most economically, it is desired to produce a high yield. Preferably, the only product produced is isobutanol. Extra products lead to a reduction in product yield and an increase in capital and operating costs, particularly if the extra products have little or no value. Extra products also require additional capital and operating costs to separate these products from isobutanol.

The microorganism may convert one or more carbon sources derived from biomass into isobutanol with a yield of greater than 5% of theoretical. In one embodiment, the yield is greater than 10%. In one embodiment, the yield is greater than 50% of theoretical. In one embodiment, the yield is greater than 60% of theoretical. In another embodiment, the yield is greater than 70% of theoretical. In yet another embodiment, the yield is greater than 80% of theoretical. In yet another embodiment, the yield is greater than 85% of theoretical. In yet another embodiment, the yield is greater than 90% of theoretical. In yet another embodiment, the yield is greater than 95% of theoretical. In still another embodiment, the yield is greater than 97.5% of theoretical.

More specifically, the microorganism converts glucose, which can be derived from biomass into isobutanol with a yield of greater than 5% of theoretical. In one embodiment, the yield is greater than 10% of theoretical. In one embodiment, the yield is greater than 50% of theoretical. In one embodiment the yield is greater than 60% of theoretical. In another embodiment, the yield is greater than 70% of theoretical. In yet another embodiment, the yield is greater than 80% of theoretical. In yet another embodiment, the yield is greater than 85% of theoretical. In yet another embodiment the yield is greater than 90% of theoretical. In yet another embodiment, the yield is greater than 95% of theoretical. In still another embodiment, the yield is greater than 97.5% of theoretical Microorganism Expressing a Cytosolically Localized Acetolactate Synthase (ALS)

In yeasts such as *S. cerevisiae*, the native acetolactate synthase, encoded in *S. cerevisiae* by the ILV2 gene, is naturally expressed in the yeast mitochondria. Unlike the endogenous acetolactate synthase of yeast, expression of heterologous, acetolactate synthases such as the *B. subtilis* alsS and the *L. lactis* alsS in yeast occurs in the yeast cytosol (i.e. cytosolically-localized). Thus, cytosolic expression of acetolactate synthase is achieved by transforming a yeast with a gene encoding an acetolactate synthase protein (EC 2.2.1.6).

ALS homologs that could be cytosolically expressed and localized in yeast are predicted to lack a mitochondrial targeting sequence as analyzed using mitoprot (Claros et al., 1996, *Eur. J. Biochem* 241: 779-86). Such cytosolically localized ALS proteins can be used as the first step in the isobutanol pathway. ALS homologs include, but are not limited to, the following: the *Serratia marcescens* ALS (GenBank Accession No. ADH43113.1) (probability of mitochondrial localization 0.07), the *Enterococcus faecalis* ALS (GenBank Accession No. NP_814940) (probability of mitochondrial localization 0.21), the *Leuconostoc mesenteroides (GenBank Accession No. YP*_818010.1) (probability of mitochondrial localization 0.21), the *Staphylococcus aureus* ALS (GenBank Accession No. YP_417545) (probability of mitochondrial localization 0.13), the *Burkholderia cenocepacia* ALS (GenBank Accession No. YP_624435) (probability of mitochondrial localization 0.15), *Trichoderma atroviride* ALS (SEQ ID NO: 77) probability of mitochondrial localization 0.19), *Talaromyces stipitatus* ALS (SEQ ID NO: 78) (probability of mitochondrial localization 0.19), and *Magnaporthe grisea* ALS (GenBank Accession No. EDJ99221) (probability of mitochondrial localization 0.02).

In alternative embodiments described herein, an ALS enzyme that is predicted to be mitochondrially localized may be mutated or modified to remove or modify an N-terminal mitochondrial targeting sequence (MTS) to remove or eliminate its ability to target the ALS enzyme to the mitochondria. Removal of the MTS can increase cytosolic localization of the ALS and/or increase the cytosolic activity of the ALS as compared to the parental ALS.

Methods for gene expression in yeasts are known in the art (See, e.g., *Methods in Enzymology,* 2004, Vol 194, *Guide to Yeast Genetics and Molecular and Cell Biology*). As is understood in the art, the expression of heterologous, prokaryotic genes in yeast typically requires a promoter, operably linked to a coding region of interest, and a transcriptional terminator. A number of yeast promoters can be used in constructing expression cassettes for genes encoding an acetolactate synthase, including, but not limited to constitutive promoters FBA, GPD1, ADH1, and GPM, and the inducible promoters GAL1, GAL10, and CUP1. Suitable transcriptional terminators include, but are not limited to FBA, GPD, GPM, ERG10, GAL1, CYC1, and ADH1.

Figure 3:
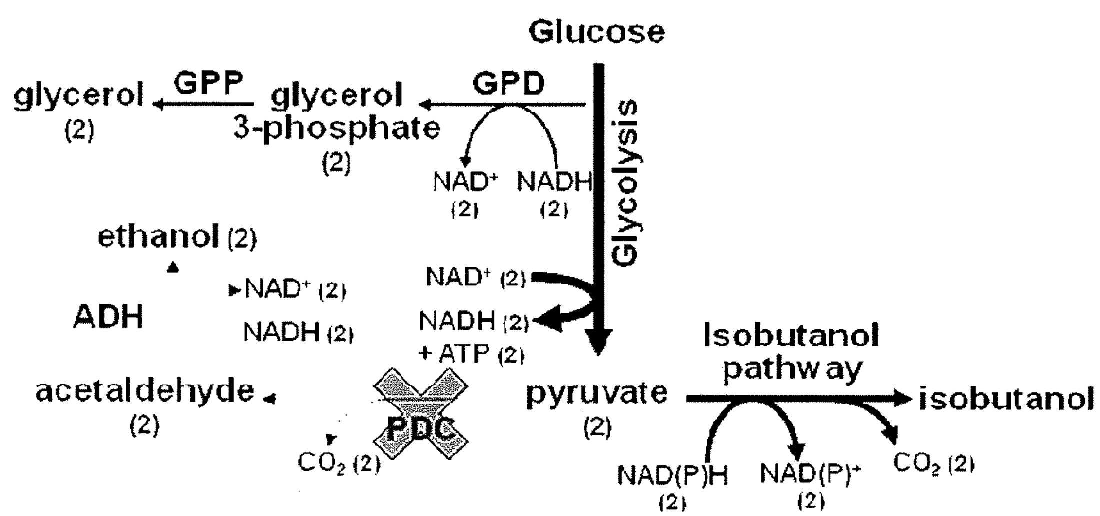
FIG. 3 illustrates an isobutanol pathway receiving additional pyruvate to form isobutanol at higher yield due to the deletion or reduction of the PDC pathway.

Microorganism Characterized by Production of Isobutanol from Pyruvate Via an Overexpressed Isobutanol Pathway and a Pdc-Minus Phenotype In yeast, the conversion of pyruvate to acetaldehyde is a major drain on the pyruvate pool (FIG. 2), and, hence, a major source of competition with the isobutanol pathway. This reaction is catalyzed by the pyruvate decarboxylase (PDC) enzyme. Reduction of this enzymatic activity in the yeast microorganism results in an increased availability of pyruvate and reducing equivalents to the isobutanol pathway and may improve isobutanol production and yield in a yeast microorganism that expresses a pyruvate-dependent isobutanol pathway (FIG. 3).

Reduction of PDC activity can be accomplished by 1) mutation or deletion of a positive transcriptional regulator for the structural genes encoding for PDC or 2) mutation or deletion of all PDC genes in a given organism. The term "transcriptional regulator" can specify a protein or nucleic acid that works in trans to increase or to decrease the transcription of a different locus in the genome. For example, in *S. cerevisiae*, the PDC2 gene, which encodes for a positive transcriptional regulator of PDC1,5,6 genes can be deleted; a *S. cerevisiae* in which the PDC2 gene is deleted is reported to have only ~10% of wildtype PDC activity (Hohmann, *Mol Gen Genet,* 241:657-666 (1993)). Alternatively, for example, all structural genes for PDC (e.g. in *S. cerevisiae*, PDC1, PDC5, and PDC6, or in *K. lactis*, PDC1) are deleted.

Crabtree-positive yeast strains such as *S. cerevisiae* strain that contains disruptions in all three of the PDC alleles no longer produce ethanol by fermentation. However, a downstream product of the reaction catalyzed by PDC, acetyl-CoA, is needed for anabolic production of necessary molecules. Therefore, the Pdc-mutant is unable to grow solely on glucose, and requires a two-carbon carbon source, either ethanol or acetate, to synthesize acetyl-CoA. (Flikweert M T, de Swaaf M, van Dijken J P, Pronk J T. FEMS Microbial Lett. 1999 May 1; 174(1):73-9. PMID: 10234824 and van Maris A J, Geertman J M, Vermeulen A, Groothuizen M K, Winkler A A, Piper M D, van Dijken J P, Prank J T. Appl Environ Microbial. 2004 January; 70(1):159-66. PMID: 14711638).

Thus, in an embodiment, such a Crabtree-positive yeast strain may be evolved to generate variants of the PDC mutant yeast that do not have the requirement for a two-carbon molecule and has a growth rate similar to wild type on glucose. Any method, including chemostat evolution or serial dilution may be utilized to generate variants of strains with deletion of three PDC alleles that can grow on glucose as the sole carbon source at a rate similar to wild type (van Maris et al., Directed Evolution of Pyruvate Decarboxylase-Negative *Saccharomyces cerevisiae, Yielding a C*2-Independent, Glucose-Tolerant, and Pyruvate-Hyperproducing Yeast, Applied and Environmental Microbiology, 2004, 70(1), 159-166).

Microorganism Characterized by Production of Isobutanol from Pyruvate Via an Overexpressed Isobutanol Pathway and a PDC-Minus GPD-Minus Phenotype Another pathway for NADH oxidation is through the production of glycerol. Dihydroxyacetone-phosphate, an intermediate of glycolysis is reduced to glycerol 3-phosphate by glycerol 3-phosphate dehydrogenase (GPD). Glycerol 3-phosphatase (GPP) converts glycerol 3-phosphate to glycerol. This pathway consumes carbon from glucose as well as reducing equivalents (NADH) resulting in less pyruvate and reducing equivalents available for the isobutanol pathway. These pathways contribute to low yield and low productivity of isobutanol. Accordingly, deletions of PDC and GPD would increase yield and productivity of isobutanol. As exemplified in Examples 9 and 13, the yield may increase to 70% by the additional deletion of GPD. In an embodiment, a yeast microorganism may include a recombinant microorganism having an engineered pathway to convert a carbon source, such as glucose, to isobutanol.

Figure 4:
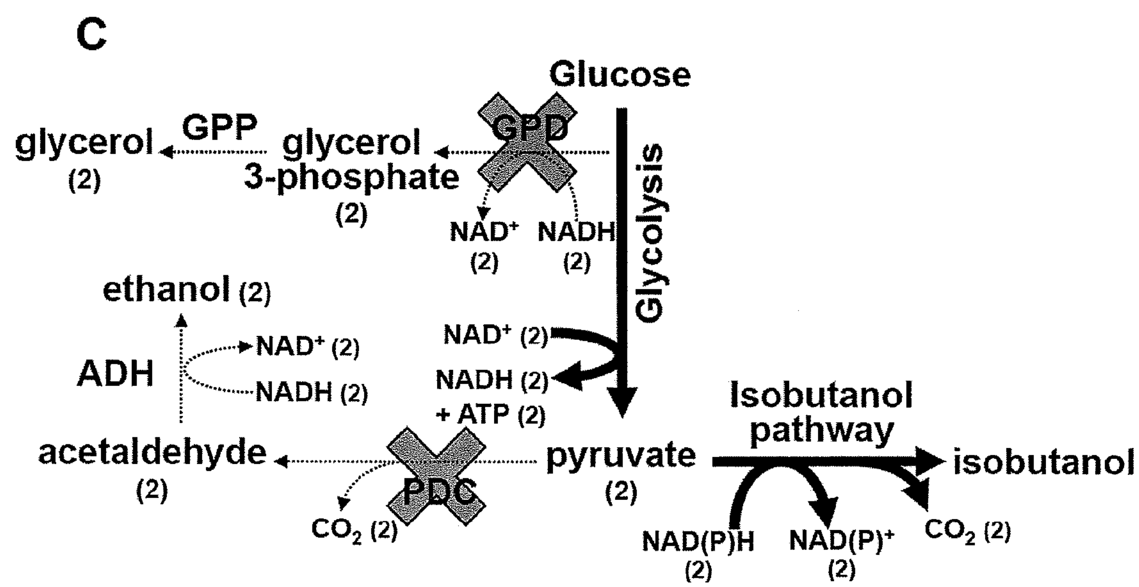
FIG. 4 illustrates an isobutanol pathway receiving additional pyruvate to form isobutanol at higher yield due to deletion or reduction of the PDC pathway and the deletion or reduction of the GPD pathway.

Looking at FIG. 4, an additional deletion of GPD results in a reduction in the production of glycerol 3-phosphate and glycerol. This results in an increase in the amount of carbon from glucose being converted to pyruvate and also a decrease in the consumption of reducing equivalents. Both of these factors combined results in a further increase in yield of isobutanol.

Yield of isobutanol can be increased also by reduction of the glycerol 3-phosphate dehydrogenase (GPD, EC1.1.1.8) activity, which is involved in the production of glycerol (FIG. 2). This enzyme catalyzes the reduction of the glycolysis intermediate, dihydroxyacetone-phosphate, to glycerol 3-phosphate. In this reaction, an NADH is oxidized to NAD+. Therefore, glycerol production would be a drain on the reducing equivalent (NADH) as well as on the carbon from glucose. This pathway can be eliminated by deleting the glycerol-3-phosphate dehydrogenases (e.g. GPD1 and GPD2 in *S. cerevisiae*, GPD1 in *K. lactis*) in the yeast.

Additionally, activities of other gene products may function as drains on metabolic intermediates. For example, reductions of the following activities may increase yield of isobutanol. Pyruvate dehydrogenase (PDH) activity, supplied by a multi-gene product complex, represents another route of pyruvate dissimilation. Reduction of PDH activity may increase pyruvate availability. Branched-chain amino acid transaminase (EC 2.6.1.42) interconverts valine↔keto-isovalerate in the cytosol, and may therefore reduce or limit available keto-isovalerate to isobutanol pathway. 3-methyl-2-oxobutanoate hydroxymethyltransferase (EC 2.1.2.11) directs the isobutanol pathway intermediate, keto-isovalerate, to the coenzyme A synthesis pathway. Alphaisopropylmalate isomerase (EC 4.1.3.12) directs the isobutanol pathway intermediate, keto-isovalerate, to the synthesis of leucine. Therefore, all of these enzymatic activities represent possible additional targets for disruption, deletion, or both.

Microorganism Characterized by Production of Isobutanol from Pyruvate Via an Overexpressed Balanced Isobutanol Pathway and a PDC-Minus GPD-Minus Phenotype To further increase yield from the pathway the imbalance in the use of reducing equivalents need to be corrected. Glycolysis generates 2 moles NADHs and 2 moles of pyruvate per mole of glucose, while the isobutanol pathway consumes either 2 NADPHs or 1 NADH and 1 NADPH for every 2 moles of pyruvate utilized. KARI enzymes typically use NADPH. There exists both an NADH and NADPH dependent alcohol dehydrogenase that can be used for the isobutanol pathway. For example, *S. cerevisiae* Adh2p is an NADH-dependent enzyme that is able to reduce isobutyraldehyde to isobutanol. Alternatively, this conversion can be performed by *S. cerevisiae* Adh6p or Adh7p, which are NADPH-dependent alcohol dehydrogenases. The additional NADPH can be obtained from the pentose phosphate pathway, but this results in a reduced yield as only 5 moles of pyruvate is generated from 3 moles of glucose, while glycolysis generates 6 moles of pyruvate from 3 moles of glucose.

This imbalance can be balanced in several ways. In one embodiment, glycolysis can be engineered to generate NADPH instead of NADH. This is accomplished by replacing the endogenous NAD+-dependent glyceraldehydes 3-phosphate dehydrogenase (GAPDH, EC 1.2.1.12) with an NADP+-dependent GAPDH (EC 1.2.1.13). Such NADP+-dependent GAPDHs have been identified in bacteria (i.e. gapB in *B. subtilis*), yeast (GDP1 in *K. lactis*) and plants. (Fillinger et al., *J Biol Chem.* 275:14031-14037, Verho et al., *Biochemistry,* 41:13833-13838) This may result in glycolysis producing 2 moles of NADPH which balances the 2 moles of NADPH that are consumed by the isobutanol pathway utilizing an NADPH-dependent alcohol dehydrogenase. See, for example, Richard, et al, U.S. Patent Application Publication Number US 2005/0106734 A1. In addition to balancing the pathway, this method may result in the reduction of available NADH and hence a reduction in the ability of the glycerol 3-phosphate dehydrogenase to generate glycerol.

In a second embodiment, an $NADP^+$-dependent GAPDH is co-expressed with the endogenous $NAD^+$-dependent GAPDH. This may allow the production of both NADPH and NADH from glycolysis and balance the consumption of 1 mole of NADPH and 1 mole of NADH by an isobutanol pathway utilizing an NADH-dependent alcohol dehydrogenase.

In yet another embodiment, the NADPH-dependent KARI enzyme in the pathway is engineered to use NADH. This has been shown with the *E. coli* KARI (ilvC) (Rane M J and Calvo K C, *Arch Biochem Biophys.,* 338(1):83-89). Alternatively, a KARI from *Methanococcus* species can be used. These KARI enzymes have been reported to be able to utilize NADH with roughly 60% the activity with NADPH (Xing et al., *Journal of Bacteriology* 1990). The use of these NADH-utilizing ilvC in combination with an NADH-dependent alcohol dehydrogenase also balances the NADH/NADPH imbalance.

Furthermore any of the genes encoding the foregoing enzymes (or any others mentioned herein (or any of the regulatory elements that control or modulate expression thereof) may be subject to directed evolution using methods known to those of skill in the art. Such action allows those of skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and S. uvarum, *Kluyveromyces* spp., including *K. thermotolerans, K. lactis*, and *K. marxianus, Pichia* spp., *Hansenula* spp., including *H. polymorpha, Candida* spp., *Trichosporon* spp., *Yamadazyma* spp., including *Y. stipitis, Torulaspora pretoriensis, Schizosaccharomyces* spp., incl. *Schizosaccharomyces pombe, Cryptococcus* spp., *Aspergillus* spp., *Neurospora* spp. or *Ustilago* spp. Sources of genes from anaerobic fungi include, but not limited to, *Piromyces* spp., *Orpinomyces* spp., or *Neocallimastix* spp. Sources of prokaryotic enzymes that are useful include, but not limited to, *Escherichia coli, Zymomonas mobilis, Staphylococcus aureus, Bacillus* spp., *Clostridium* spp., *Corynebacterium* spp., *Pseudomonas* spp., *Lactococcus* spp., *Enterobacter* spp., and *Salmonella* spp.

Microorganism Characterized by Balanced Isobutanol Pathway

In the various embodiments described herein, the engineered metabolic pathway may be balanced with respect to NADH and NADPH as compared to a native or unmodified metabolic isobutanol pathway from a corresponding parental microorganism, wherein the native or unmodified metabolic pathway is not balanced with respect to NADH and NADPH.

The ideal production microorganism produces a desirable product at close to theoretical yield. For example the ideal isobutanol producing organism produces isobutanol according to the following equation: 1 glucose→isobutanol+2 $CO_2$+$H_2O$.

Accordingly, 66% of the glucose carbon results in isobutanol, while 33% is lost as $CO_2$. In exemplary metabolic pathways for the conversion of pyruvate to isobutanol described by Atsumi et al. (WO/2008/098227, and Atsumi at al., *Nature,* 2008 Jan. 3; 451(7174):86-9), two of the five enzymes used to convert pyruvate into isobutanol according to the metabolic pathway outlined in FIG. 1 require the reduced cofactor nicotinamide adenine dinucleotide phosphate (NADPH). NADPH is produced only sparingly by the cell—the reduced cofactor nicotinamide adenine dinucleotide (NADH) is the preferred equivalent. Respiration is required to produce NADPH in the large quantities required to support high-level production of isobutanol.

Even if competing pathways can be eliminated or reduced in activity by metabolic engineering, yield is limited to about 83% of theoretical. Carbon loss to carbon dioxide ($CO_2$) remains the main limitation on yield in the aforementioned metabolic pathway for the production of isobutanol. Reducing the oxygen uptake rate (OUR) of the cells should decrease the loss of carbon to $CO_2$ because it decreases the metabolic flux through the $CO_2$-generating tricarboxylic acid (TCA) cycle and/or pentose phosphate pathway (PPP). However, a modified microorganism utilizing the aforementioned metabolic pathway for the production of isobutanol exhibits drastically decreased specific productivity under conditions where the OUR is decreased and isobutanol production under anaerobic conditions may not be possible.

The decreased yield and the loss of productivity upon $O_2$ limitation indicate that the strain uses one or more metabolic pathways to generate the NADPH needed to support isobutanol production. In a modified cell utilizing the aforementioned metabolic pathway the production of isobutanol from glucose results in an imbalance between the cofactors reduced during glycolysis and the cofactors oxidized during the conversion of pyruvate to isobutanol. While glycolysis produces two moles of NADH, the isobutanol pathway consumes two moles of NADPH. This leads to a deficit of two moles of NADPH and overproduction of two moles of NADH per isobutanol molecule produced, a state described henceforth as cofactor imbalance.

The terms “cofactor balance” or “balanced with respect to cofactor usage” refer to a recombinant microorganism comprising a metabolic pathway converting a carbon source to a fermentation product and a modification that leads to the regeneration of all redox cofactors within the recombinant microorganism producing said fermentation product from a carbon source and wherein the re-oxidation or re-reduction of said redox cofactors does not require the pentose phosphate pathway, the TCA cycle or the generation of additional fermentation products.

Stated another way, the terms “cofactor balance” or “balanced with respect to cofactor usage” can refer to an advantageous modification that leads to the regeneration of all redox cofactors within the recombinant microorganism producing a fermentation product from a carbon source and wherein said re-oxidation or re-reduction of all redox cofactors does not require the production of byproducts or co-products.

Stated another way, the terms “cofactor balance” or “balanced with respect to cofactor usage” can refer to an advantageous modification that leads to the regeneration of all redox cofactors within the recombinant microorganism producing a fermentation product from a carbon source under anaerobic conditions and wherein the production of additional fermentation products is not required for re-oxidation or re-reduction of redox cofactors.

Stated another way, the terms “cofactor balance” or “balanced with respect to cofactor usage” can refer to an advantageous modification that leads to the regeneration of all redox cofactors within the recombinant microorganism producing a fermentation product from a carbon source and wherein said modification increases production of said fermentation product under anaerobic conditions compared to the parental or wild type microorganism and wherein additional fermentation products are not required for the regeneration of said redox cofactors.

The cell has several options for resolving a cofactor imbalance. One is to change the relative fluxes going from glucose through glycolysis and through the pentose phosphate pathway (PPP). For each glucose molecule metabolized through the PPP, two moles of NADPH are generated in addition to the two moles of NADH that are generated through glycolysis (a total of 4 reducing equivalents). Therefore, use of the PPP results in the generation of excess reducing equivalents since only two moles are consumed during the production of isobutanol. Under anaerobic conditions, and without an alternate electron acceptor, the cell has no way to reoxidize or regenerate these extra cofactors to $NADP^+$ and metabolism thus stops. The excess reducing equivalents must instead be utilized for energy production through aerobic respiration which is only possible under aerobic conditions or for the production of byproducts. Another result of the flux through the PPP is that one additional molecule of $CO_2$ is lost per molecule of glucose consumed, which limits the yield of isobutanol that can be achieved under aerobic conditions.

Another way the cell can generate NADPH is via the TCA cycle. Flux through the TCA cycle results in carbon loss through $CO_2$ and in production of NADH in addition to the NADPH required for the isobutanol pathway. The NADH would have to be utilized for energy production through respiration under aerobic conditions (and without an alternate electron acceptor) or for the production of byproducts. In addition, the TCA cycle likely is not functional under anaerobic conditions and is therefore unsuitable for the production of stoichiometric amounts of NADPH in an anaerobic isobutanol process.

An economically competitive isobutanol process requires a high yield from a carbon source. Lower yield means that more feedstock is required to produce the same amount of isobutanol. Feedstock cost is the major component of the overall operating cost, regardless of the nature of the feedstock and its current market price. From an economical perspective, this is important because the cost of isobutanol is dependent on the cost of the biomass-derived sugars. An increase in feedstock cost results in an increase in isobutanol cost. Thus, it is desirable to utilize NADH-dependent enzymes for the conversion of pyruvate to isobutanol.

An enzyme is “NADH-dependent” if it catalyzes the reduction of a substrate coupled to the oxidation of NADH with a catalytic efficiency that is greater than the reduction of the same substrate coupled to the oxidation of NADPH at equal substrate and cofactor concentrations.

Thus, in one embodiment of the invention, a microorganism is provided in which cofactor usage is balanced during the production of a fermentation product.

In a specific aspect, a microorganism is provided in which cofactor usage is balanced during the production of isobutanol, in this case, production of isobutanol from pyruvate utilizes the same cofactor that is produced during glycolysis.

In another embodiment, a microorganism is provided in which cofactor usage is balanced during the production of a fermentation product and the microorganism produces the fermentation product at a higher yield compared to a modified microorganism in which the cofactor usage in not balanced.

In a specific aspect, a microorganism is provided in which cofactor usage is balanced during the production of isobutanol and the microorganism produces isobutanol at a higher yield compared to a modified microorganism in which the cofactor usage in not balanced.

In yet another embodiment, a modified microorganism in which cofactor usage is balanced during the production of a fermentation product may allow the microorganism to produce said fermentation product under anaerobic conditions at higher rates, and yields as compared to a modified microorganism in which the cofactor usage in not balanced during production of a fermentation product.

In a specific aspect, a modified microorganism in which cofactor usage is balanced during the production of isobutanol may allow the microorganism to produce isobutanol under anaerobic conditions at higher rates, and yields as compared to a modified microorganism in which the cofactor usage is not balanced during production of isobutanol.

One compound to be produced by the recombinant microorganism according to the present invention is isobutanol. However, the present invention is not limited to isobutanol. The invention may be applicable to any metabolic pathway that is imbalanced with respect to cofactor usage. One skilled in the art is able to identify pathways that are imbalanced with respect to cofactor usage and apply this invention to provide recombinant microorganisms in which the same pathway is balanced with respect to cofactor usage. One skilled in the art will recognize that the identified pathways may be of longer or shorter length, contain more or fewer genes or proteins, and require more or fewer cofactors than the exemplary isobutanol pathway. Further, one skilled in the art will recognize that in certain embodiments, such as a recombinant microbial host that produces an excess of NADPH, certain embodiments of the present invention may be adapted to convert NADPH to NADH.

Microorganisms Characterized by Providing Cofactor Balance Via Engineered Enzymes Conversion of one mole of glucose to two moles of pyruvate via glycolysis leads to the production of two moles of NADH. A metabolic pathway that converts pyruvate to a target product that consumes either two moles of NADPH or one mole of NADH and one mole of NADPH leads to cofactor imbalance. One example of such a metabolic pathway is the isobutanol metabolic pathway described by Atsumi et al. (Atsumi et al., 2008, *Nature* 451: 86-9), which converts two moles of pyruvate to one mole of isobutanol. In this five enzyme pathway, two enzymes are dependent upon NADPH: (1) KARI and (2) ADH, encoded by the *E. coli* ilvC and *E. coli* yqhD, respectively.

To resolve this cofactor imbalance, the present invention provides a recombinant microorganism in which the NADPH-dependent enzymes KARI and ADH are replaced with enzymes that preferentially depend on NADH (i.e. KARI and ADH enzymes that are NADH-dependent).

To further resolve this cofactor imbalance, the present invention in another embodiment provides recombinant microorganisms wherein the NADH-dependent KARI and ADH enzymes are overexpressed.

In one aspect, such enzymes may be identified in nature. In an alternative aspect, such enzymes may be generated by protein engineering techniques including but not limited to directed evolution or site-directed mutagenesis.

In one embodiment, the two NADPH-dependent enzymes within an isobutanol biosynthetic pathway that converts pyruvate to isobutanol may be replaced with ones that utilize NADH. These two enzymes may be KARI and an alcohol dehydrogenase (ADH).

In another embodiment, two NADH-dependent enzymes that catalyze the same reaction as the NADH-dependent enzymes are overexpressed. These two enzymes may be KARI and an alcohol dehydrogenase.

In one aspect, NADH-dependent KARI and ADH enzymes are identified in nature. In another aspect, the NADPH-dependent KARI and ADH enzymes may be engineered using protein engineering techniques including but not limited to directed evolution and site-directed mutagenesis.

There exist two basic options for engineering NADH-dependent isobutyraldehyde dehydrogenases or ketol-acid red uctoisomerases: (1) increase the NADH-dependent activity of an NADPH-dependent enzyme that is active towards the substrate of interest and/or (2) increase the activity of an NADH-dependent enzyme that is not sufficiently active towards the substrate of interest.

There exist two basic options for engineering NADH-dependent isobutyraldehyde dehydrogenases or ketol-acid reductoisomerases: (1) increase the NADH-dependent activity of an NADPH-dependent enzyme that is active towards the substrate of interest and/or (2) increase the activity of an NADH-dependent enzyme that is not sufficiently active towards the substrate of interest.

NADH-Dependent KARI Enzymes

As shown in FIG. 1, the ketol-acid reductoisomerase (KARI) enzyme of the isobutanol biosynthetic pathway as disclosed by Atsumi et al. (Atsumi at al., 2008, Nature 45: 86-9), requires the cofactor nicotinamide dinucleotide phosphate (NADPH) to convert acetolactate to 2,3-dihydroxyisovalerate. However, under anaerobic conditions, NADPH is produced only sparingly by the cell—nicotinamide adenine dinucleotide (NADH) is the preferred equivalent. Therefore, oxygen is required to produce NADPH in the large quantities to support high-level production of isobutanol. Thus, the production of isobutanol is feasible only under aerobic conditions and the maximum yield that can be achieved with this pathway is limited. Accordingly, KARI enzymes that preferentially utilize NADH rather than NADPH are desirable.

Other biosynthetic pathways utilize KARI enzymes for the conversion of acetolactate to 2,3-dihydroxyisovalerate. For example, KARI enzymes convert acetolactate to 2,3-dihydroxyisovalerate as part of the biosynthetic pathway for the production of 3-methyl-1-butanol (Atsumi et al., 2008, Nature 45: 86-9).

Yet other biosynthetic pathways utilize KARI to convert 2-aceto-2-hydroxy-butyrate to 2,3-dihydroxy-3-methylvalerate. This reaction is part of the biosynthetic pathway for the production of 2-methyl-1-butanol. (Atsumi et al., 2008, Nature 45: 86-9).

As used herein, the term “KARI” or “KARI enzyme” or “ketol-acid reductoisomerase” are used interchangeably herein to refer to an enzyme that catalyzes the conversion of acetolactate to 2,3-dihydroxyisovalerate and/or the conversion of 2-aceto-2-hydroxy-butyrate to 2,3-dihydroxy-3-methylvalerate. Moreover, these terms can be used interchangeably herein with the terms “acetohydroxy acid isomeroreductase” and “acetohydroxy acid red uctoisomerase.”

Enzymes for use in the compositions and methods of the invention include any enzyme having the ability to convert acetolactate to 2,3-dihydroxyisovalerate and/or the ability to convert 2-aceto-2-hydroxy-butyrate to 2,3-dihydroxy-3-methylvalerate. Such enzymes include, but are not limited to, the *E. coli* ilvC gene product and the *S. cerevisiae* ILV5 gene product, and the KARI enzyme from *Piromyces* sp, *Buchnera aphidicola, Spinacia oleracea, Oryza sativa, Chlamydomonas reinhardtii, Neurospora crassa, Schizosaccharomyces pombe, Laccaria bicolor, Ignicoccus hospitalis, Picrophilus torridus, Acidiphilium cryptum, Cyanobacteria/Synechococcus* sp., *Zymomonas mobilis, Bacteroides thetaiotaomicron, Methanococcus maripaludis, Vibrio fischeri, Shewanella* sp, *Gramella forsetti, Psychromonas ingrhamaii*, and *Cytophaga hutchinsonii.*

KARI sequences are available from a vast array of microorganisms, including, but not limited to, *Escherichia coli* (GenBank Nos: NP_418222 and NC_000913, *Saccharomy-*

*ces cerevisiae* (GenBank Nos: NP_013459 and NC_001144, *Methanococcus maripaludis* (GenBank Nos: CAF30210 and BX957220, and *Bacillus subtilis* (GenBank Nos: CA614789 and Z99118) and the KARI enzymes from *Piromyces* sp (GenBank No: CAA76356), *Buchnera aphidicola* (GenBank No: AAF13807), *Spinacia oleracea* (GenBank Nos: Q01292 and CAA40356), *Oryza sativa* (GenBank No: NP_001056384) *Chlamydomonas reinhardtii* (GenBank No: XP_001702649), *Neurospora crassa* (GenBank No: XP_961335), *Schizosaccharomyces pombe* (GenBank No: NP_001018845), *Laccaria bicolor* (GenBank No: XP_001880867), *Ignicoccus hospitalis* (GenBank No: YP_001435197), *Picrophilus torridus* (GenBank No: YP_023851), *Acidiphilium cryptum* (GenBank No: YP_001235669), *Cyanobacteria/Synechococcus* sp. (GenBank No: YP_473733), *Zymomonas mobilis* (GenBank No: YP_162876), *Bacteroides thetaiotaomicron* (GenBank No: NP_810987), *Methanococcus maripaludis* (GenBank No: YP_001097443), *Vibrio fischeri* (GenBank No: YP_205911), *Shewanella* sp (GenBank No: YP_732498), *Gramella forsetti* (GenBank No: YP_862142), *Psychromonas ingrhamaii* (GenBank No: YP_942294), and *Cytophaga hutchinsonii* (GenBank No: YP_677763).

As will be understood by one of ordinary skill in the art, modified KARI enzymes may be obtained by recombinant or genetic engineering techniques that are routine and well-known in the art. Mutant KARI enzymes can, for example, be obtained by mutating the gene or genes encoding the KARI enzyme of interest by site-directed or random mutagenesis. Such mutations may include point mutations, deletion mutations and insertional mutations. For example, one or more point mutations (e.g., substitution of one or more amino acids with one or more different amino acids) may be used to construct mutant KARI enzymes of the invention.

Ketol-acid reductoisomerase (KARI) catalyzes the reduction of acetolactate to 2,3-dihydroxyisovalerate. The two-step reaction involves an alkyl migration and a ketone reduction that occurs at a single active site on the enzyme without dissociation of any reaction intermediates. The enzyme is NADPH-dependent. The cofactor specificity may be expanded or switched so that it will utilize both cofactors and preferentially NADH during the production of isobutanol. A study published in 1997 (Rane, M. J. and K. C. Calvo, Archives of Biochemistry and Biophysics, 1997. 338: p. 83-89) describes a supposed cofactor-switched KARI quadruplet variant of the *E. coli* ilvC gene product with mutations R68D, K69L, K75V and R76D). However, in-house studies indicate that although the ratio NADH/NADPH was 2.5, the specific activity of this variant on NADH was actually worse than wildtype, rendering this enzyme not suited for the purpose of this disclosure.

Modified or Mutated KARI Enzymes

In accordance with the invention, any number of mutations can be made to the KARI enzymes, and in a preferred aspect, multiple mutations can be made to result in an increased ability to utilize NADH for the conversion of acetolactate to 2,3-dihydroxyisovalerate. Such mutations include point mutations, frame shift mutations, deletions, and insertions, with one or more (e.g., one, two, three, or four, etc.) point mutations preferred.

Mutations may be introduced into the KARI enzymes of the present invention using any methodology known to those skilled in the art. Mutations may be introduced randomly by, for example, conducting a PCR reaction in the presence of manganese as a divalent metal ion cofactor. Alternatively, oligonucleotide directed mutagenesis may be used to create the mutant KARI enzymes which allows for all possible classes of base pair changes at any determined site along the encoding DNA molecule. In general, this technique involves annealing an oligonucleotide complementary (except for one or more mismatches) to a single stranded nucleotide sequence coding for the KARI enzyme of interest. The mismatched oligonucleotide is then extended by DNA polymerase, generating a double-stranded DNA molecule which contains the desired change in sequence in one strand. The changes in sequence can, for example, result in the deletion, substitution, or insertion of an amino acid. The double-stranded polynucleotide can then be inserted into an appropriate expression vector, and a mutant or modified polypeptide can thus be produced. The above-described oligonucleotide directed mutagenesis can, for example, be carried out via PCR.

The invention further includes homologous KARI enzymes which are 5%, 10%, 20%, 30%, 40%, 50%, 60%, 70%, 75%, 80%, 85%, 90%, 95%, 96%, 97%, 98%, or 99% identical at the amino acid level to a wild-type KARI enzyme (e.g., encoded by the Ec_ilvC gene or *S. cerevisiae* ilv5 gene) and exhibit an increased ability to utilize NADH for the conversion of acetolactate to 2,3-dihydroxyisovalerate. Also included within the invention are KARI enzymes which are 50%, 60%, 70%, 75%, 80%, 85%, 90%, 95%, 96%, 97%, 98%, or 99% identical at the amino acid level to a KARI enzyme comprising the amino acid sequence set out in SEQ ID NO: 56 and exhibit an increased ability to utilize NADH for the conversion of acetolactate to 2,3-dihydroxyisovalerate. The invention also includes nucleic acid molecules which encode the above described KARI enzymes.

The invention also includes fragments of KARI enzymes which comprise at least 50, 100, 150, 200, 250, 300, 350, 400, 450, 500, 550, or 600 amino acid residues and retain one or more activities associated with KARI enzymes. Such fragments may be obtained by deletion mutation, by recombinant techniques that are routine and well-known in the art, or by enzymatic digestion of the KARI enzyme(s) of interest using any of a number of well-known proteolytic enzymes. The invention further includes nucleic acid molecules which encode the above described mutant KARI enzymes and KARI enzyme fragments.

By a protein or protein fragment having an amino acid sequence at least, for example, 50% "identical" to a reference amino acid sequence it is intended that the amino acid sequence of the protein is identical to the reference sequence except that the protein sequence may include up to 50 amino acid alterations per each 100 amino acids of the amino acid sequence of the reference protein. In other words, to obtain a protein having an amino acid sequence at least 50% identical to a reference amino acid sequence, up to 50% of the amino acid residues in the reference sequence may be deleted or substituted with another amino acid, or a number of amino acids up to 50% of the total amino acid residues in the reference sequence may be inserted into the reference sequence. These alterations of the reference sequence may occur at the amino (N—) and/or carboxy (C—) terminal positions of the reference amino acid sequence and/or anywhere between those terminal positions, interspersed either individually among residues in the reference sequence and/or in one or more contiguous groups within the reference sequence. As a practical matter, whether a given amino acid sequence is, for example, at least 50% identical to the amino acid sequence of a reference protein can be determined conventionally using known computer programs such as those described above for nucleic acid sequence identity determinations, or using the CLUSTAL W program (Thompson, J. D., et al., *Nucleic Acids Res.* 22:4673 4680 (1994)).

In one aspect, amino acid substitutions are made at one or more of the above identified positions (i.e., amino acid positions equivalent or corresponding to A71, R76, S78, or Q110 of *E. coli* IlvC). Thus, the amino acids at these positions may be substituted with any other amino acid including Ala, Asn, Arg, Asp, Cys, Gln, Glu, Gly, His, Ile, Leu, Lys, Met, Phe, Pro, Ser, Thr, Trp, Tyr, and Val. A specific example of a KARI enzyme which exhibits an increased ability to utilize NADH includes an *E. coli* IlvC KARI enzyme in which (1) the alanine at position 71 has been replaced with a serine, (2) the arginine at position 76 has been replaced with an aspartic acid, (3) the serine at position 78 has been replaced with an aspartic acid, and/or (4) the glutamine at position 110 has been replaced with valine (as described in commonly owned and co-pending applications U.S. Ser. No. 12/610,784 and PCT/US09/62952 (published as WO/2010/051527).

Polypeptides having the ability to convert acetolactate to 2,3-dihydroxyisovalerate and/or 2-aceto-2-hydroxy-butyrate to 2,3-dihydroxy-3-methylvalerate for use in the invention may be isolated from their natural prokaryotic or eukaryotic sources according to standard procedures for isolating and purifying natural proteins that are well-known to one of ordinary skill in the art (see, e.g., Houts, G. E., et al., J. Virol. 29:517 (1979)). In addition, polypeptides having the ability to convert acetolactate to 2,3-dihydroxyisovalerate and/or 2-aceto-2-hydroxy-butyrate to 2,3-dihydroxy-3-methylvalerate may be prepared by recombinant DNA techniques that are familiar to one of ordinary skill in the art (see, e.g., Kotewicz, M. L., et al., *Nucl. Acids Res.* 16:265 (1988); Soltis, D. A., and Skalka, A. M., *Proc. Natl. Acad. Sci. USA* 85:3372 3376 (1988)).

In accordance with the invention, one or more mutations may be made in any KARI enzyme of interest in order to increase the ability of the enzyme to utilize NADH, or confer other properties described herein upon the enzyme, in accordance with the invention. Such mutations include point mutations, frame shift mutations, deletions and insertions. Preferably, one or more point mutations, resulting in one or more amino acid substitutions, are used to produce KARI enzymes having an enhanced or increased ability to utilize NADH, particularly to facilitate the conversion of acetolactate to 2,3-dihydroxyisovalerate and/or the conversion of 2-aceto-2-hydroxy-butyrate to 2,3-dihydroxy-3-methylvalerate. In a preferred aspect of the invention, one or more mutations at positions equivalent or corresponding to position A71 (e.g., A71S), R76 (e.g., R76D), S78 (e.g. S78D), and/or Q110 (e.g. Q110V) and/or D146 (e.g. D146G), and/or G185 (e.g. G185R) and/or K433 (e.g. K433 E) of the *E. coli* IlvC KARI enzyme may be made to produce the desired result in other KARI enzymes of interest.

The corresponding positions of the KARI enzymes identified herein (e.g. *E. coli* IlvC may be readily identified for other KARI enzymes by one of skill in the art. Thus, given the defined region and the assays described in the present application, one with skill in the art can make one or a number of modifications which would result in an increased ability to utilize NADH, particularly for the conversion of acetolactate to 2,3-dihydroxyisovalerate, in any KARI enzyme of interest.

In a preferred embodiment, the modified or mutated KARI enzymes have from 1 to 4 amino acid substitutions in amino acid regions involved in cofactor specificity as compared to the wild-type KARI enzyme proteins. In other embodiments, the modified or mutated KARI enzymes have additional amino acid substitutions at other positions as compared to the respective wild-type KARI enzymes. Thus, modified or mutated KARI enzymes may have at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 different residues in other positions as compared to the respective wild-type KARI enzymes. As will be appreciated by those of skill in the art, the number of additional positions that may have amino acid substitutions will depend on the wild-type KARI enzyme used to generate the variants. Thus, in some instances, up to 50 different positions may have amino acid substitutions.

The nucleotide sequences for several KARI enzymes are known. For instance, the sequences of KARI enzymes are available from a vast array of microorganisms, including, but not limited to, *Escherichia coli* (GenBank No: NP_418222), *Saccharomyces cerevisiae* (GenBank Nos: NP_013459, *Methanococcus maripaludis* (GenBank No: YP_001097443), *Bacillus subtilis* (GenBank Nos: CAB14789), and the KARI enzymes from *Piromyces* sp (GenBank No: CAA76356), *Buchnera aphidicola* (GenBank No: AAF13807), *Spinacia oleracea* (GenBank Nos: Q01292 and CAA40356), *Oryza sativa* (GenBank No: NP_001056384) *Chlamydomonas reinhardtii* (GenBank No: XP_001702649), *Neurospora crassa* (GenBank No: XP_961335), *Schizosaccharomyces pombe* (GenBank No: NP_001018845), *Laccaria bicolor* (GenBank No: XP_001880867), *Ignicoccus hospitalis* (GenBank No: YP_001435197), *Picrophilus torridus* (GenBank No: YP_023851), *Acidiphilium cryptum* (GenBank No: YP_001235669), *Cyanobacteria/Synechococcus* sp. (GenBank No: YP_473733), *Zymomonas mobilis* (GenBank No: YP_162876), *Bacteroides thetaiotaomicron* (GenBank No: NP_810987), *Methanococcus maripaludis* (GenBank No: YP_001097443), *Vibrio fischeri* (GenBank No: YP_205911), *Shewanella* sp (GenBank No: YP_732498), *Gramella forsetti* (GenBank No: YP_862142), *Psychromonas ingrhamaii* (GenBank No: YP_942294), and *Cytophaga hutchinsonii* (GenBank No: YP_677763)

Improved NADH-Dependent Activity

In one aspect, the NADH-dependent activity of the modified or mutated KARI enzyme is increased.

In a preferred embodiment, the catalytic efficiency of the modified or mutated KARI enzyme is improved for the cofactor NADH. Preferably, the catalytic efficiency of the modified or mutated KARI enzyme is improved by at least about 5% as compared to the wild-type or parental KARI for NADH. More preferably the catalytic efficiency of the modified or mutated KARI enzyme is improved by at least about 15% as compared to the wild-type or parental KARI for NADH. More preferably, the catalytic efficiency of the modified or mutated KARI enzyme is improved by at least about 25% as compared to the wild-type or parental KARI for NADH. More preferably, the catalytic efficiency of the modified or mutated KARI enzyme is improved by at least about 50% as compared to the wild-type or parental KARI for NADH. More preferably, the catalytic efficiency of the modified or mutated KARI enzyme is improved by at least about 75% as compared to the wild-type or parental KARI for NADH. More preferably, the catalytic efficiency of the modified or mutated KARI enzyme is improved by at least about 100% as compared to the wild-type or parental KARI for NADH. More preferably, the catalytic efficiency of the modified or mutated KARI enzyme is improved by at least about 300% as compared to the wild-type or parental KARI for NADH. More preferably, the catalytic efficiency of the modified or mutated KARI enzyme is improved by at least about 500% as compared to the wild-type or parental KARI for NADH. More preferably, the catalytic efficiency of the modified or mutated KARI enzyme is improved by at least about 1000% as compared to the wild-type or parental KARI for NADH.

More preferably, the catalytic efficiency of the modified or mutated KARI enzyme is improved by at least about 5000% as compared to the wild-type or parental KARI for NADH.

In a preferred embodiment, the catalytic efficiency of the modified or mutated KARI enzyme with NADH is increased with respect to the catalytic efficiency of the wild-type or parental enzyme with NADPH. Preferably, the catalytic efficiency of the modified or mutated KARI enzyme is at least about 10% of the catalytic efficiency of the wild-type or parental KARI enzyme for NADPH. More preferably, the catalytic efficiency of the modified or mutated KARI enzyme is at least about 25% of the catalytic efficiency of the wild-type or parental KARI enzyme for NADPH. More preferably, the catalytic efficiency of the modified or mutated KARI enzyme is at least about 50% of the catalytic efficiency of the wild-type or parental KARI enzyme for NADPH. More preferably, the catalytic efficiency of the modified or mutated KARI enzyme is at least about 75%, 85%, 95% of the catalytic efficiency of the wild-type or parental KARI enzyme for NADPH.

In a preferred embodiment, the $K_M$ of the KARI enzyme for NADH is decreased relative to the wild-type or parental enzyme. A change in $K_M$ is evidenced by at least a 5% or greater increase or decrease in $K_M$ compared to the wild-type KARI enzyme. In certain embodiments, modified or mutated KARI enzymes of the present invention may show greater than 10 times decreased $K_M$ for NADH compared to the wild-type or parental KARI enzyme. In certain embodiments, modified or mutated KARI enzymes of the present invention may show greater than 30 times decreased $K_M$ for NADH compared to the wild-type or parental KARI enzyme.

In a preferred embodiment, the $k_{cat}$ of the KARI enzyme with NADH is increased relative to the wild-type or parental enzyme. A change in $k_{cat}$ is evidenced by at least a 5% or greater increase or decrease in $K_M$ compared to the wild-type KARI enzyme. In certain embodiments, modified or mutated KARI enzymes of the present invention may show greater than 50% increased $k_{cat}$ for NADH compared to the wild-type or parental KARI enzyme. In certain embodiments, modified or mutated KARI enzymes of the present invention may show greater than 100% increased $k_{cat}$ for NADH compared to the wild-type or parental KARI enzyme. In certain embodiments, modified or mutated KARI enzymes of the present invention may show greater than 200% increased $k_{cat}$ for NADH compared to the wild-type or parental KARI enzyme.

Cofactor Switch

In preferred embodiments, the cofactor specificity of the modified or mutated KARI enzyme is altered such that there is a cofactor switch from NADPH to NADH. In other words, these modified or mutated KARI enzymes will have an increase in NADH-dependent activity and a substantially simultaneous decrease in NADPH dependent activity. Thus, the methods of the present invention can be used to change the cofactor preference from NADPH to NADH.

"Cofactor specificity" is a measure of the specificity of an enzyme for one cofactor over another. Thus, the methods of the present invention may be used to alter the cofactor preference of the target enzyme, such that the preference for the less favored cofactor is increased by 20%, 50%, 100%, 300%, 500%, 1000%, up to 2000%. For example, a number of reductase enzymes have been described that favor NADPH over NADH (see WO/2002/022526; WO/2002/029019; Mittl et al., 1994, *Protein* 1504-14; Banta at al., (2002) *Protein Eng.,* 15: 131-140; all of which are hereby incorporated by reference in their entirety). As the availability of NADPH is often limiting, both in vivo and in vitro, the overall activity of the target protein is often limited. For target proteins that prefer NADPH as a cofactor, it would be desirable to alter the cofactor specificity of the target protein (e.g. a KARI enzyme) to a cofactor that is more readily available, such as NADH.

In a preferred embodiment, the cofactor specificity of the KARI enzyme is switched. By "switched" herein is meant, that the cofactor preference (in terms of catalytic efficiency ($k_{cat}/K_M$) of the KARI enzyme is changed to another cofactor Preferably, in one embodiment, by switching cofactor specificity, activity in terms of catalytic efficiency ($k_{cat}/K_M$) with the cofactor preferred by the wild-type KARI enzyme is reduced, while the activity with the less preferred cofactor is increased. This can be achieved, for example by increasing the $k_{cat}$ for less preferred cofactor over the preferred cofactor or by decreasing $K_M$ for the less preferred cofactor over the preferred cofactor or both.

In a preferred embodiment, the KARI enzyme is modified or a mutated to become NADH-dependent. The term "NADH-dependent" refers to the property of an enzyme to preferentially use NADH as the redox cofactor. An NADH-dependent enzyme has a higher catalytic efficiency ($k_{cat}/K_M$) with the cofactor NADH than with the cofactor NADPH as determined by in vitro enzyme activity assays. Accordingly, the term "NADPH-dependent" refers to the property of an enzyme to preferentially use NADPH as the redox cofactor. An NADPH dependent enzyme has a higher catalytic efficiency ($k_{cat}/K_M$) with the cofactor NADPH than with the cofactor NADH as determined by in vitro enzyme activity assays.

In a preferred embodiment, the catalytic efficiency of the KARI enzyme for NADH is enhanced relative to the catalytic efficiency with NADPH. The term "catalytic efficiency" describes the ratio of the rate constant $k_{cat}$ over the Michaelis-Menten constant $K_M$. In one embodiment, the invention is directed to a modified or mutated KARI enzyme that exhibits at least about a 1:10 ratio of catalytic efficiency ($k_{cat}/K_M$) with NADH over catalytic efficiency with NADPH. In another embodiment, the modified or mutated KARI enzyme exhibits at least about a 1:1 ratio of catalytic efficiency ($k_{cat}/K_M$) with NADH over catalytic efficiency with NADPH. In yet another embodiment, the modified or mutated KARI enzyme exhibits at least about a 10:1 ratio of catalytic efficiency ($k_{cat}/K_M$) with NADH over catalytic efficiency with NADPH. In yet another embodiment, the modified or mutated KARI enzyme exhibits at least about a 100:1 ratio of catalytic efficiency ($k_{cat}/K_M$) with NADH over catalytic efficiency with NADPH. In an exemplary embodiment, the modified or mutated KARI enzyme exhibits at least about a 100:1 ratio of catalytic efficiency ($k_{cat}/K_M$) with NADH over catalytic efficiency with NADPH.

In a preferred embodiment, the $K_M$ of the KARI enzyme for NADH is decreased relative to the $K_M$ of the KARI enzyme for NADPH. In one embodiment, the invention is directed to a modified or mutated KARI enzyme that exhibits at least about a 10:1 ratio of $K_M$ for NADH over $K_M$ for NADPH. In one embodiment, the invention is directed to a modified or mutated KARI enzyme that exhibits at least about a 1:1 ratio of $K_M$ for NADH over $K_M$ for NADPH. In a preferred embodiment, the invention is directed to a modified or mutated KARI enzyme that exhibits at least about a 1:10 ratio of $K_M$ for NADH over $K_M$ for NADPH. In yet another embodiment, the invention is directed to a modified or mutated KARI enzyme that exhibits at least about a 1:20, 1:100, 1:1000 ratio of $K_M$ for NADH over $K_M$ for NADPH.

In another preferred embodiment, the $k_{cat}$ of the KARI enzyme with NADH is increased relative to $k_{cat}$ with NADPH. In certain embodiments, modified or mutated KARI enzymes of the present invention may show greater than 0.8:1 ratio of $k_{cat}$ with NADH over $k_{cat}$ with NADPH. In certain embodiments, modified or mutated KARI enzymes of the present invention may show greater than 1:1 ratio of $k_{cat}$ with NADH over $k_{cat}$ with NADPH. In a preferred embodiment, modified or mutated KARI enzymes of the present invention may show greater than 10:1 ratio of $k_{cat}$ with NADH over $k_{cat}$ with NADPH. In certain embodiments, modified or mutated KARI enzymes of the present invention may show greater than 100:1 ratio of $k_{cat}$ with NADH over $k_{cat}$ with NADPH.

Identification of Corresponding Amino Acid Substitutions in Homologous Enzymes

An amino acid sequence alignment of 22 KARIs (including *E. coli* IlvC, spinach KARI and rice KARI) was described in commonly owned and co-pending applications U.S. Ser. No. 12/610,784 and PCT/US09/62952 (published as WO/2010/051527). Various KARIs aligned with the *E. coli* KARI sequence at amino acid positions 71, 76, 78, and 110 and this allows to conclude that the beneficial mutations found for *E. coli* KARI confer the same effects in these KARI enzymes.

A structure alignment of *E. coli* KARI (PDB ID NO. 1YRL) with rice KARI (PDB ID NO. 3FR8) as a representative of the shorter loop group has been performed and the sites of useful mutations in the *E. coli* context corresponded reasonably well with specific residues in the context of the shorter loop: Ser165, Lys166, and Ser167. Ser165 of (corresponding to A71 in *E. coli*) therefore may be substituted with aspartate. A charge reversal at position K166 (corresponding to position R76D) may yield the same result. Ser167 may correspond to Ser78 and a mutation to aspartate corresponds to a beneficial mutation at Q110, and thus can be transferable in the aligned KARIs.

NADH-Dependent ADH Enzymes

Several alcohol dehydrogenases may be suitable candidates for conversion into an NADH-dependent isobutyraldehyde dehydrogenase. Among the exemplary enzymes for conversion are *S. cerevisiae* ADH1, *Zymomonas mobilis* ADHII, *E. coli* YqhD, herein referred to as Ec_YqhD, and *S. cerevisiae* ADH7.

As described in WO/2008/098227, the *S. cerevisiae* ADH2 gene is expected to be functionally expressed from pSA55 and required for catalyzing the final step of the isobutanol biosynthetic pathway, namely the conversion of isobutyraldehyde to isobutanol. Thus, no isobutanol should be produced with the plasmid combination lacking ADH2 as adhE is deleted in JCL260. However, the results of a fermentation using a strain without overexpression of any gene encoding an enzyme with ADH activity for the conversion of isobutyraldehyde to isobutanol showed that overexpression of an ADH enzyme is not required for isobutanol production in *E. coli*. In fact, isobutanol production for the system lacking ADH2 was higher than for the system with ADH2 expression. Volumetric productivity and titer showed 42% increase, specific productivity showed 18% increase and yield 12% increase. This suggests strongly that a native *E. coli* dehydrogenase is responsible for the conversion of isobutyraldehyde to isobutanol.

Surprisingly, this last step of the isobutanol biosynthetic pathway was found to be carried out by a native *E. coli* dehydrogenase. Approximately −80% of the isobutyraldehyde reduction activity is due to Ec_YqhD under certain culture conditions. Available literature on Ec_YqhD suggests that while it does prefer long-chain alcohols, it also utilizes NADPH (versus NADH) (Perez et al., 2008, J. Biol. Chem. 283: 7346-53).

Switching the cofactor specificity of an NADPH-dependent alcohol dehydrogenase may be complicated by the fact that cofactor binding induces a conformational change, resulting in an anhydrous binding pocket that facilitates hydride transfer from the reduced cofactor to the aldehyde (Leskovac at al., 2002, *Ferns Yeast Research,* 2: 481-94; Reid et al., 1994, *Critical Reviews in Microbiology,* 20: p. 13-56). Mutations that are beneficial for binding NADH may have deleterious effects with respect to this conformational change.

Alternatively, isobutyraldehyde reduction activity of an NADH-dependent enzyme with little native activity towards this substrate may be increased. This approach has the advantages that (1) several specialized enzymes exist in nature that are highly active under fermentative conditions, (2) the binding sites of several of these enzymes are known, (3) mutational studies indicate that substrate specificity can easily be altered to achieve high activity on a new substrate.

Several alcohol dehydrogenase enzymes may be suitable candidates for conversion into an NADH-dependent isobutyraldehyde dehydrogenase: *S. cerevisiae* ADH1 and *Zymomonas* mobilis ADHII are NADH-dependent enzymes responsible for the conversion of acetaldehyde to ethanol under anaerobic conditions. These enzymes are highly active. The substrate specificity for these enzymes has been analyzed (Leskovac at al., 2002, *Ferns Yeast Research,* 2: 481-94; Rellos et al., 1997, *Protein Expression and Purification,* 9: 89-90), the amino acid residues comprising the substrate binding pocket are known (Leskovac at al., 2002, *Ferns Yeast Research,* 2: 481-94; Rellos at al., 1997, *Protein Expression and Purification,* 9: 89-90), and attempts to alter the substrate specificity by mutation have revealed that the substrate specificity can be altered (Rellos et al., 1997, *Protein Expression and Purification,* 9: 89-90; Green et al., 1993, *J. Biol. Chem.,* 268: 7792-98). Ec_YqhD and *S. cerevisiae* ADH7 are NADPH-dependent enzymes whose physiological functions are not as well understood. Ec_YqhD has been implicated in the protection of the cell from peroxide-derived aldehydes (Perez et al., 2008, J. Biol. Chem. 283: 7346-53). The substrate specificity of both enzymes is understood, and amino acids lining the substrate binding pocket are known (Perez et al., 2008, J. Biol. Chem. 283: 7346-53). Based on the known amino acid residues implicated in substrate binding (*S. cerevisiae* ADH1, Z. mobilis ADHII) or the cofactor binding site (Ec_yqhD), sites with the highest likelihood of affecting desired enzyme features such as substrate specificity or cofactor specificity may be mutated to generate the desired function.

One approach to increase activity of enzymes with NADH as the cofactor is saturation mutagenesis with NNK libraries at each of the residues that interact with the cofactor. These libraries can be screened for activity in the presence of NADPH and NADH in order to identify which single mutations contribute to increased activity on NADH and altered specificity for NADH over NADPH. Combinations of mutations at aforementioned residues can be investigated by any method known in the art. For example, a combinatorial library of mutants may be designed based on the results of the saturation mutagenesis studies. For example, a combinatorial library of mutants may be designed including only those mutations that do not lead to decrease in NADH-dependent activity.

Another approach to increase the NADH-dependent activity of the enzyme is to perform saturation mutagenesis of a first amino acid that interacts with the cofactor, then isolate the mutant with the highest activity using NADH as the cofactor, then perform saturation mutagenesis of a second amino acid that interacts with the cofactor, and so on. Similarly, a limited number of amino acids that interact with the cofactor may be targeted for randomization simultaneously and then be screened for improved activity with NADH as the cofactor. The selected, best mutant can then be subjected to the same procedure again and this approach may be repeated iteratively until the desired result is achieved.

Another approach is to use random oligonucleotide mutagenesis to generate diversity by incorporating random mutations, encoded on a synthetic oligonucleotide, into the cofactor binding region of the enzyme. The number of mutations in individual enzymes within the population may be controlled by varying the length of the target sequence and the degree of randomization during synthesis of the oligonucleotides. The advantages of this more defined approach are that all possible amino acid mutations and also coupled mutations can be found.

If the best variants from the experiments described above are not sufficiently active with NADH as the cofactor, directed evolution via error-prone PCR may be used to obtain further improvements. Error-prone PCR mutagenesis of the first domain containing the cofactor binding pocket may be performed followed by screening for ADH activity with NADH and/or increased specificity for NADH over NADPH as the cofactor.

Surprisingly, alcohol dehydrogenase enzymes that are not known to catalyze the reduction of isobutyraldehyde to isobutanol were identified that catalyze this reaction. Thus, in another aspect, such an alcohol dehydrogenase may be encoded by an NADH-dependent 1,3-propanediol dehydrogenase. In yet another aspect, such an alcohol dehydrogenase may be encoded by an NADH-dependent 1,2-propanediol dehydrogenase. Preferred enzymes of this disclosure include enzymes listed in Table 1 of co-pending and commonly owned U.S. Ser. No. 12/610,784 and PCT/US09/62952 (published as WO/2010/051527). These enzymes exhibit NADH-dependent isobutyraldehyde reduction activity, measured as Unit per minute per mg of crude cell lysate (U $min^{-1}$ $mg^{-1}$) that is approximately six-fold to seven-fold greater than the corresponding NADPH-dependent isobutyraldehyde reduction activity.

In addition to exhibiting increased activity with NADH as the cofactor as compared to the NADPH, alcohol dehydrogenases of the present invention may further be more active as compared to the native *E. coli* alcohol dehydrogenase Ec_YqhD. In particular, alcohol dehydrogenases of the present invention may exhibit increased activity and/or decreased $K_M$ values with NADH as the cofactor as compared to Ec_YqhD with NADPH as the cofactor. Exemplary enzymes that exhibit greater NADH-dependent alcohol dehydrogenase activity than the NADPH-dependent alcohol dehydrogenase activity are listed include the *Drosophila melanogaster* ADH, the *L. lactis* adhA, *K. pneumoniae* dhaT, and *E. coli* fucO (see Table 1 of U.S. Ser. No. 12/610,784).

Alcohol dehydrogenases of the present disclosure may also be utilized in metabolically-modified microorganisms that include recombinant biochemical pathways useful for producing additional alcohols such as 2-methyl-1-butanol, 3-methyl-1-butanol, 2-phenylethanol, 1-propanol, or 1-butanol via conversion of a suitable substrate by a modified microorganism.

Microorganisms producing such compounds have been described (WO/2008/098227). For example, these alcohols can be 1-propanol, 1-butanol, 2-methyl-1-butanol, 3-methyl-1-butanol or 2-phenylethanol and are generally produced from a metabolite comprising a 2-keto acid. In some aspects, the 2-keto acid includes 2-ketobutyrate, 2-ketovalerate, 2-keto-3-methylvalerate, 2-keto-4-methyl-pentanoate, or phenylpyruvate. The 2-ketoacid is converted to the respective aldehyde by a 2-ketoacid decarboxylase. For example, 2-ketobutyrate is converted to 1-propanal, 2-ketovalerate is converted to 1-butanal, 2-keto-3-methylvalerate is converted to 2-methyl-1-butanol, 2-keto-4-methyl-pentanoate is converted to 3-methyl-1-butanal, and phenylpyruvate is converted to phenylethanal by a 2-ketoacid decarboxylase. Thus, the recombinant microorganism includes elevated expression or activity of a 2-keto-acid decarboxylase, as compared to a parental microorganism. The 2-keto-acid decarboxylase may be encoded by kivD from *Lactococcus lactis*, or homologs thereof. The 2-keto-acid decarboxylase can be encoded by a polynucleotide derived from a gene selected from kivD from *L. lactis*, or homologs thereof.

In earlier publications (See, e.g., WO/2008/098227), only NADPH-dependent alcohol dehydrogenases are described that convert the aforementioned aldehyde to an alcohol. In particular, *S. cerevisiae* Adh2p is described that converts the aldehyde to the respective aldehyde.

Thus, in one embodiment of this disclosure, a microorganism is provided in which the cofactor dependent final step for the conversion of the aldehyde to the respective alcohol is catalyzed by an NADH-dependent alcohol dehydrogenase. In particular, NADH-dependent alcohol dehydrogenases are disclosed that catalyze the reduction aldehydes to alcohols, for example, of 1-propanal to 1propanol, 1-butanal to 1-butanol, 2-methyl-1-butanal to 2-methyl-1-butanol, 3-methyl-1-butanal to 3-methyl-1-butanol, or phenylethanal to phenylethanol.

In a specific aspect, such an alcohol dehydrogenase may be encoded by the *Drosophila melanogaster* alcohol dehydrogenase Dm_Adh or homologs thereof. In another specific aspect, such an alcohol dehydrogenase may be encoded by the *Lactococcus lactis* alcohol dehydrogenase (Ll_AdhA) or homologs thereof.

Surprisingly, alcohol dehydrogenase enzymes that are not known to catalyze the reduction of isobutyraldehyde to isobutanol were identified that catalyze this reaction. Thus, in another aspect, such an alcohol dehydrogenase may be encoded by an NADH-dependent 1,3-propanediol dehydrogenase. In yet another aspect, such an alcohol dehydrogenase may be encoded by an NADH-dependent 1,2-propanediol dehydrogenase.

In another embodiment, a method of producing an alcohol is provided. The method includes providing a recombinant microorganism provided herein; culturing the microorganism of in the presence of a suitable substrate or metabolic intermediate and under conditions suitable for the conversion of the substrate to an alcohol; and detecting the production of the alcohol. In various aspects, the alcohol is selected from 1-propanol, 1-butanol, 2-methyl 1-butanol, 3-methyl 1-butanol, and 2-phenylethanol. In another aspect, the substrate or metabolic intermediate includes a 2-keto acid-derived aldehyde, such as 1-propanal, 1-butanal, 2-methyl-1-butanal, 3-methyl-1-butanal, or phenylethanal.

Recombinant Host Cells Comprising a NADH-dependent KARI and/or ADH Enzymes

In an additional aspect, the present invention is directed to recombinant host cells (i.e. metabolically "engineered" or "modified" microorganisms) comprising NADH-dependent KARI and/or ADH enzymes of the invention. Recombinant microorganisms provided herein can express a plurality of additional heterologous and/or native target enzymes involved in pathways for the production of beneficial metabolites such as isobutanol from a suitable carbon source.

Accordingly, metabolically "engineered" or "modified" microorganisms are produced via the introduction of genetic material (i.e. a NADH-dependent KARI and/or ADH enzymes) into a host or parental microorganism of choice, thereby modifying or altering the cellular physiology and biochemistry of the microorganism. Through the introduction of genetic material and/or the modification of the expression of native genes the parental microorganism acquires new properties, e.g. the ability to produce a new, or greater quantities of, an intracellular metabolite. As described herein, the introduction of genetic material and/or the modification of the expression of native genes into a parental microorganism results in a new or modified ability to produce beneficial metabolites such as isobutanol. The genetic material introduced into and/or the genes modified for expression in the parental microorganism contains gene(s), or parts of genes, coding for one or more of the enzymes involved in a biosynthetic pathway for the production of isobutanol and may also include additional elements for the expression and/or regulation of expression of these genes, e.g. promoter sequences.

Recombinant microorganisms provided herein may also produce metabolites in quantities not available in the parental microorganism. A "metabolite" refers to any substance produced by metabolism or a substance necessary for or taking part in a particular metabolic process. A metabolite can be an organic compound that is a starting material (e.g., glucose or pyruvate), an intermediate (e.g., 2-ketoisovalerate), or an end product (e.g., 1-propanol, 1-butanol, isobutanol, 2-methyl-1-butanol, 3-methyl-1-butanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

Exemplary metabolites include glucose, pyruvate, 1-propanol, 1-butanol, isobutanol, 2-methyl-1-butanol, and 3-methyl-1-butanol.

The metabolite 1-propanol can be produced by a recombinant microorganism engineered to express or over-express a metabolic pathway that converts pyruvate to 1-propanol. An exemplary metabolic pathway that converts pyruvate to 1-propanol has been described in WO/2008/098227 and by Atsumi of al. (Atsumi et al., 2008, *Nature* 451(7174): 86-9), the disclosures of which are herein incorporated by reference in their entireties. In a preferred embodiment, metabolic pathway comprises a KARI and/or an ADH enzyme of the present invention.

The metabolite 1-butanol can be produced by a recombinant microorganism engineered to express or over-express a metabolic pathway that converts pyruvate to 3-methyl-1-butanol. An exemplary metabolic pathway that converts pyruvate to 3-methyl-1-butanol has been described in WO/2008/098227 and by Atsumi et al. (Atsumi et al., 2008, *Nature* 451(7174): 86-9), the disclosures of which are herein incorporated by reference in their entireties. In a preferred embodiment, metabolic pathway comprises a KARI and/or an ADH enzyme of the present invention.

The metabolite isobutanol can be produced by a recombinant microorganism engineered to express or over-express a metabolic pathway that converts pyruvate to isobutanol. An exemplary metabolic pathway that converts pyruvate to isobutanol may be comprised of a acetohydroxy acid synthase (ALS) enzyme encoded by, for example, alsS from *B. subtilis*, a ketolacid reductoisomerase (KARI) of the present invention, a dihydroxy-acid dehydratase (DHAD), encoded by, for example ilvD from *E. coli* or *L. lactis*, a 2-keto-acid decarboxylase (KIVD) encoded by, for example kivd from *L. lactis*, and an alcohol dehydrogenase (ADH) of the present invention.

The metabolite 3-methyl-1-butanol can be produced by a recombinant microorganism engineered to express or over-express a metabolic pathway that converts pyruvate to 3-methyl-1-butanol. An exemplary metabolic pathway that converts pyruvate to 3-methyl-1-butanol has been described in WO/2008/098227 and by Atsumi et al., (Atsumi et al., 2008, *Nature* 451(7174): 86-9), the disclosures of which are herein incorporated by reference in their entireties. In a preferred embodiment, metabolic pathway comprises a KARI and/or an ADH enzyme of the present invention.

The metabolite 2-methyl-1-butanol can be produced by a recombinant microorganism engineered to express or over-express a metabolic pathway that converts pyruvate to 2-methyl-1-butanol. An exemplary metabolic pathway that converts pyruvate to 2-methyl-1-butanol has been described in WO/2008/098227 and by Atsumi at al. (Atsumi et al., 2008, *Nature* 451: 86-9), the disclosures of which are herein incorporated by reference in their entireties. In an exemplary embodiment, metabolic pathway comprises a KARI and/or an ADH enzyme of the present invention.

The disclosure identifies specific genes useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutation and silent mutations. Such modified or mutated polynucleotides and polypeptides can be screened for expression of a functional enzyme using methods known in the art. In addition, homologs of enzymes useful for generating metabolites are encompassed by the microorganisms and methods provided herein.

Microorganism Characterized by Increased Capacity to Produce Intermediates of the Isobutanol Pathway As a consequence of increased yield of isobutanol, it follows that this yeast microorganism exhibits a higher capacity to produce the intermediates of the isobutanol pathway including, but not limited to, acetolactate, 2,3-dihydroxyisovalerate, keto-isovalerate, and isobutyraldehyde.

Method of Using Microorganism for High-Yield Isobutanol Fermentation

In a method to produce isobutanol from a carbon source at high yield, the yeast microorganism is cultured in an appropriate culture medium containing a carbon source.

Another exemplary embodiment provides a method for producing isobutanol comprising a recombinant yeast microorganism of the invention in a suitable culture medium containing a carbon source that can be converted to isobutanol by the yeast microorganism of the invention.

In certain embodiments, the method further includes isolating isobutanol from the culture medium. For example, isobutanol may be isolated from the culture medium by any method known to those skilled in the art, such as distillation, pervaporation, or liquid-liquid extraction.

EXAMPLES

General Methods

Sample preparation: Samples (2 mL) from the fermentation broth were stored at −20° C. for later substrate and product analysis. Prior to analysis, samples were thawed and then centrifuged at 14,000×g for 10 min. The supernatant was filtered through a 0.2 μm filter. Analysis of substrates and products was performed using authentic standards (>99%, obtained from Sigma-Aldrich), and a 5-point calibration curve (with 1-pentanol as an internal standard for analysis by gas chromatography).

Determination of optical density and cell dry weight: The optical density of the yeast cultures was determined at 600 nm using a DU 800 spectrophotometer (Beckman-Coulter, Fullerton, Calif., USA). Samples were diluted as necessary to yield an optical density of between 0.1 and 0.8. The cell dry weight was determined by centrifuging 50 mL of culture prior to decanting the supernatant. The cell pellet was washed once with 50 mL of milliQ $H_2O$, centrifuged and the pellet was washed again with 25 mL of milliQ $H_2O$. The cell pellet was then dried at 80° C. for at least 72 hours. The cell dry weight was calculated by subtracting the weight of the centrifuge tube from the weight of the centrifuge tube containing the dried cell pellet.

Gas Chromatography: Analysis of ethanol and isobutanol was performed on a HP 5890 gas chromatograph fitted with a DB-FFAP column (Agilent Technologies; 30 m length, 0.32 mm ID, 0.25 μM film thickness) or equivalent connected to a flame ionization detector (FID). The temperature program was as follows: 200° C. for the injector, 300° C. for the detector, 100° C. oven for 1 minute, 70° C./minute gradient to 235° C., and then hold for 2.5 min.

High Performance Liquid Chromatography: Analysis of glucose and organic acids was performed on a HP-1100 High Performance Liquid Chromatography system equipped with an Aminex HPX-87H Ion Exclusion column (Bio-Rad, 300×7.8 mm) or equivalent and an $H^+$ cation guard column (Bio-Rad) or equivalent. Organic acids were detected using an HP-1100 UV detector (210 nm, 8 nm 360 nm reference) while glucose was detected using an HP-1100 refractive index detector. The column temperature was 60° C. This method was Isocratic with 0.008N sulfuric acid in water as mobile phase. Flow was set at 0.6 mL/min. Injection size was 20 μL and the run time was 30 minutes.

Anaerobic batch fermentations: Anaerobic batch cultivations were performed at 30° C. in stoppered 100 mL serum bottles. A total of 20 mL of synthetic medium with an initial glucose concentration of 20 g-glucose $L^{-1}$ was used (Kaiser et al., Methods in Yeast Genetics, a Cold Spring Harbor Laboratory Manual (1994)). 2 mL samples are taken at 24 and 48 hours. The fermentation is ended after 48 hours or when all glucose is consumed. Samples are processed and analyzed by Gas Chromatography and/or High Performance Liquid Chromatography as described above.

Yeast transformations—*K. lactis*: Transformations were performed by electroporation according to Kooistra et al., *Yeast* 21:781-792 (2004).

Lithium Acetate transformations of *S. cerevisiae* strains were transformed by the Lithium Acetate method (Gietz et al., *Nucleic Acids Res.* 27:69-74 (1992). Cells were collected from overnight cultures grown in 50 mL of defined (SC) ethanol media at an $OD_{600}$ of approximately 0.8 to 1.0 by centrifugation at 2700 rcf for 2 minutes at room temperature. The cell pellet was resuspended in 50 mL sterile water, collected by centrifugation (2700 rcf; 2 min; room temp.), and resuspended in 25 mL sterile water. The cells were collected by centrifugation (2700 rcf; 2 min; room temp.) and resuspended in 1 mL 100 mM lithium acetate. The cell suspension was transferred to a sterile 1.5 mL tube and collected by centrifugation at full speed for 10 seconds. The cells were resuspended in 100 mM lithium acetate with a volume four times the volume of the cell pellet (e.g. 400 μL for 100 μL cell pellet). To the prepared DNA Mix (72 μl 50% PEG, 10 μl 1M Lithium Acetate, 3 μl boiled salmon sperm DNA, and 5 μl of each plasmid), 15 μl of the cell suspension was added and mixed by vortexing with five short pulses. The cell/DNA suspensions were incubated at 30° C. for 30 minutes and at 42° C. for 22 minutes. The cells were collected by centrifugation for 10 seconds at full speed and resuspended in 100 μl SOS (1M Sorbitol, 0.34% (w/v) Yeast Extract, 0.68% (w/v) Peptone, 6.5 mM CaCl). The cell suspensions were top spread over appropriate selective agar plates.

Yeast colony PCR: Yeast cells were taken from agar medium and transferred to 30 μl 0.2% SDS and heated for 4 mins at 90° C. The cells were spun down and 1 μl of the supernatant was used for PCR using standard Tag (NEB).

Molecular biology: Standard molecular biology methods for cloning and plasmid construction were generally used, unless otherwise-noted (Sambrook & Russell).

Media:

YP: contains 1% (w/v) yeast extract, 2% (w/v) peptone. YPD is YP containing 2% (w/v) glucose, YPE is YP containing 2% (w/v) Ethanol.

SC+Complete: 20 g/L glucose, 14 g/L Sigma™ Synthetic Dropout Media supplement (includes amino acids and nutrients excluding histidine, tryptophan, uracil, and leucine), and 6.7 g/L Difco™ Yeast Nitrogen Base. 0.076 g/L histidine, 0.076 g/L tryptophan, 0.380 g/L leucine, and 0.076 g/L uracil.

SC-HWUL: 20 g/L glucose, 14 g/L Sigma™ Synthetic Dropout Media supplement (includes amino acids and nutrients excluding histidine, tryptophan, uracil, and leucine), and 6.7 g/L Difco™ Yeast Nitrogen Base SC-WLU: 20 g/L glucose, 14 g/L Sigma™ Synthetic Dropout Media supplement (includes amino acids and nutrients excluding histidine, tryptophan, uracil, and leucine), 6.7 g/L Difco™ Yeast Nitrogen Base without amino acids, and 0.076 g/L histidine.

SC-HWU: 20 g/L glucose, 14 g/L Sigma™ Synthetic Dropout Media supplement (includes amino acids and nutrients excluding histidine, tryptophan, uracil, and leucine), 6.7 g/L Difco™ Yeast Nitrogen Base without amino acids, and 0.380 g/L leucine.

SC−Ethanol-HWU: 2% (w/v) ethanol, 14 g/L Sigma™ Synthetic Dropout Media supplement (includes amino acids and nutrients excluding histidine, tryptophan, uracil, and leucine), 6.7 g/L Difco™ Yeast Nitrogen Base, and 0.380 g/L leucine.

Solid versions of the above described media contain 2% (w/v) agar.

Strains, Plasmids and Primer Sequences

Table 1 details the genotype of strains disclosed herein:

| GEVO No. | Genotype and/or Reference |
|---|---|
| GEVO1187 | *S. cerevisiae* CEN.PK MAT a ho his3-leu2 trp1 ura3 PDC1 PDC5 PDC6 |
| GEVO1188 | *S. cerevisiae* CEN.PK MAT alpha ho his3-leu2 trp1 ura3 PDC1 PDC5 PDC6 |
| GEVO1287[1] | *K. lactis* MATα uraA1 trp1 leur2 lysA1 ade1 lac4-8 [pKD1] (ATCC #87365) |
| GEVO1537[2] | *S. cerevisiae* HO/HO pdc1::Tn5ble/pdc1::Tn5ble pdc5::Tn5ble/pdc5::Tn5ble pdc6::APT1/pdc6::APT1 HIS3/HIS, LEU2/LEU2, URA3/URA3, TRP1/TRP1 |

-continued

| GEVO No. | Genotype and/or Reference |
|---|---|
| Gevo1538 | *S. cerevisiae* MAT a/α, HIS3, LEU2, TRP1, URA3, pdc1::ble/pdc1::ble, pdc5::ble/pdc5::ble, pdc6::apt1(kanR)/pdc6::apt1(kanR), HO/HO |
| GEVO1581 | *S. cerevisiae* MAT a/alpha, his3/his3, trp1/trp1, ura3/ura3, LEU2/LEU2, pdc1::ble/pdc1::ble, pdc5::ble/pdc5::ble, pdc6::apt1(kanR)/pdc6::apt1(kanR), HO/HO |
| Gevo1715 | *S. cerevisiae* MAT α, leu2, ura3, pdc1::ble, pdc5::ble, pdc6::apt1(kanR), ho |
| GEVO1584 | *S. cerevisiae* MAT α, his3, trp1, ura3, leu2, pdc1::ble, pdc5::ble, pdc6::apt1(kanR), ho- |
| GEVO1742 | *K. lactis* MATα uraA1 trp1 leur2 lysA1 ade1 lac4-8 [pKD1] Klpdc1Δ::pGV1537 ($G418^R$)] |
| GEVO1794 | *K. lactis* MATalpha uraA1 trp1 leu2 lysA1 ade1 lac4-8 [pkD1] pdc1::kan {Ll-kivd; Sc-Adh7:KmURA3 integrated} |
| GEVO1818 | *K. lactis* MATalpha uraA1 trp1 leu2 lysA1 ade1 lac4-8 [pKD1] pdc1::kan {Ec-ilvC-deltaN; Ec-ilvD-deltaN(codon opt for *K. lactis*):Sc-LEU2 integrated} {Ll-kivd; Sc-Adh7:KmURA3 integrated} |
| GEVO1829 | *K. lactis* MATalpha uraA1 trp1 leu2 lysA1 ade1 lac4-8 [pKD1] pdc1::kan {Ec-ilvC-deltaN; Ec-ilvD-deltaN(codon opt for *K. lactis*):Sc-LEU2 integrated} {Ll-kivd; Sc-Adh7:KmURA3 integrated} {ScCUP1-1 promoter:Bs alsS, TRP1 random integrated} |
| Gevo1863 | *S. cerevisiae* MAT α, his3, trp1, ura3, leu2, pdc1::ble, pdc5::ble, pdc6::apt1(kanR), ho-, chemostat-evolved to be C2-independent. |

[1]same as ATCC200826

[2]The strains Gevo1537 and Gevo1538 were originally designated GG570 (derived from strain T2-3D)and was obtained from Paul van Heusden from the University of Leiden, the Netherlands. For complete references for both strains, see: Flikweert, M. T. et al., (1996) Yeast 12: 247-257.

Table 2 outlines the plasmids disclosed herein:

| GEVO No. | FIG. | Genotype or Reference |
|---|---|---|
| pGV1056 | 23 | bla(amp$^r$) S.c. TDH3 promoter - polylinker - CYC1 terminator CEN6/ARSH4 HIS3 pUC ori |
| pGV1062 | 24 | bla(amp$^r$) S.c. TDH3 promoter - polylinker - CYC1 terminator CEN6/ARSH4 URA3 pUC ori |
| pGV1102 | 25 | bla(amp$^r$) S.c. TEF1 promoter - HA tag - polylinker - CYC1 terminator 2micron URA3 pUC ori |
| pGV1103 | 26 | bla(amp$^r$) S.c. TDH3 promoter - myc tag - polylinker - CYC1 terminator 2micron HIS3 pUC ori |
| pGV1104 | 27 | bla(amp$^r$) S.c. TDH3 promoter - myc tag - polylinker - CYC1 terminator 2micron TRP1 pUC ori |
| pGV1106 | 28 | bla(amp$^r$) S.c. TDH3 promoter - myc tag - polylinker - CYC1 terminator 2micron URA3 pUC ori |
| pGV1254 | 16 | bla(amp$^r$) S.c. TEF1 promoter - HA-L.I. KIVD - S.c. TDH3 promoter - myc-S.c. ADH2 - CYC1 terminator 2micron URA3 pUC ori |
| pGV1295 | 17 | bla(amp$^r$) S.c. TDH3 promoter - myc-ilvC - CYC1 terminator 2micron TRP1 pUC ori |
| pGV1390 | 18 | bla(amp$^r$) S.c. CUP1-1 promoter - L.I. alsS - CYC1 terminator 2micron HIS3 pUC ori |
| pGV1438 | 19 | bla(amp$^r$) S.c. TDH3 promoter - myc-ilvD- CYC1 terminator 2micron LEU2 pUC ori |
| pGV1503 | 8 | bla(amp$^r$) S.c. TEF1 promoter - KanR pUC ori |
| pGV1537 | 9 | bla(amp$^r$) S.c. TEF1 promoter - KanR pUC ori *K. lactis* PDC1 5' region - Pm/l - *K. lactis* PDC1 3' region |
| pGV1429 | 10 | bla(amp$^r$) S.c. TDH3 promoter - myc tag - polylinker - CYC1 terminator 1.6micron TRP1 pUC ori |
| pGV1430 | 11 | bla(amp$^r$) S.c. TDH3 promoter - myc tag - polylinker - CYC1 terminator 1.6micron LEU2 pUC ori |
| pGV1431 | 12 | bla(amp$^r$) S.c. TDH3 promoter - myc tag - polylinker - CYC1 terminator 1.6micron K.m. URA3 pUC ori |
| pGV1472 | 13 | bla(amp$^r$) S.c. TEF1 promoter - AU1(x2)-L.I. alsS - CYC1 terminator 1.6micron LEU2 pUC ori |
| pGV1473 | 14 | bla(amp$^r$) S.c. TEF1 promoter - AU1(x2)-E.c. ilvD - S.c. TDH3 promoter - myc-E.c. ilvC - CYC1 terminator 1.6micron TRP1 pUC ori |
| pGV1475 | 15 | bla(amp$^r$) S.c. TEF1 promoter - HA-L.I. KIVD - S.c. TDH3 promoter - myc-S.c. ADH7 - CYC1 terminator 1.6micron K.m. URA3 pUC ori |
| pGV1590 | 20 | bla(amp$^r$) S.c. TEF1 promoter - L.I. KIVD - S.c. TDH3 promoter - S.c. ADH7 - CYC1 terminator 1.6micron K.m. URA3 pUC ori |
| pGV1726 | 21 | bla(amp$^r$) S.c. CUP1-1 promoter - B.s. alsS - CYC1 terminator TRP1 pUC ori |
| pGV1727 | 22 | bla(amp$^r$) S.c. TEF1 promoter - E.c. ilvD deltaN- S.c. TDH3 promoter - E.c. ilvC deltaN- CYC1 terminator LEU2 pUC ori |

-continued

| GEVO No. | FIG. | Genotype or Reference |
|---|---|---|
| pGV1649 | 29 | bla(amp$^r$) S.c. CUP1-1 promoter - B.s. alsS - CYC1 terminator 2micron TRP1 pUC ori |
| pGV1664 | 30 | bla(amp$^r$) S.c. TEF1 promoter - L.I. KIVD - S.c. TDH3 promoter - S.c. ADH7 - CYC1 terminator 2micron URA3 pUC ori |
| pGV1672 | 31 | bla(amp$^r$) S.c. CUP1-1 promoter - polylinker - CYC1 terminator CEN6/ARSH4 TRP1 pUC ori |
| pGV1673 | 32 | bla(amp$^r$) S.c. CUP1-1 promoter - B.s. alsS - CYC1 terminator CEN6/ARSH4 TRP1 pUC ori |
| pGV1677 | 33 | bla(amp$^r$) S.c. TEF1 promoter - E.c. ilvD deltaN- S.c. TDH3 promoter - E.c. ilvC deltaN- CYC1 terminator 2micron HIS3 pUC ori |
| pGV1679 | 34 | bla(amp$^r$) S.c. TEF1 promoter - E.c. ilvD deltaN- S.c. TDH3 promoter - E.c. ilvC deltaN- CYC1 terminator CEN6/ARSH4 HIS3 pUC ori |
| pGV1683 | 35 | bla(amp$^r$) S.c. TEF1 promoter - L.I. KIVD - S.c. TDH3 promoter - S.c. ADH7 - CYC1 terminator CEN6/ARSH4 URA3 pUC ori |

Table 3 outlines the primers sequences disclosed herein:

| No. | Name | SEQ ID NO: | Sequence |
|---|---|---|---|
| 489 | MAT common | 30 | AGTCACATCAAGATCGTTTATGG |
| 490 | MAT alpha | 31 | GCACGGAATATGGGACTACTTCG |
| 491 | MAT a | 32 | ACTCCACTTCAAGTAAGAGTTTG |
| 838 | pGV1423-seq1 (838) | 33 | TATTGTCTCATGAGCGGATAC |
| 965 | KIPDC1 -616 FOR | 34 | ACAACGAGTGTCATGGGGAGAGGAAGAGG |
| 966 | KIPDC1 +2528 REV | 35 | GATCTTCGGCTGGGTCATGTGAGGCGG |
| 995 | KIPDC1 internal | 36 | ACGCTGAACACGTTGGTGTCTTGC |
| 996 | KIPDC1 internal | 37 | AACCCTTAGCAGCATCGGCAACC |
| 1010 | KI-PDC1-prom-seq-c | 38 | TATTCATGGGCCAATACTACG |
| 1006 | KI-PDC1-prom-3c | 39 | GTAGAAGACGTCACCTGGTAGACCAAAGATG |
| 1009 | KI-PDC1-term-5c | 40 | CATCGTGACGTCGCTCAATTGACTGCTGCTAC |
| 1016 | KI-PDC1-prom-5-v2 (1016) | 41 | ACTAAGCGACACGTGCGGTTTCTGTGGTATAG |
| 1017 | KI-PDC1-term-3c-v2 (1017) | 42 | GAAACCGCACGTGTCGCTTAGTTTACATTTCTTTCC |
| 1019 | TEF1prom-5c (1019) | 43 | TTTGAAGTGGTACGGCGATG |
| 1321 | Bs-alsS-Q-A5 (1321) | 44 | AATCATATCGAACACGATGC |
| 1324 | Bs-alsS-Q-B3 (1324) | 45 | AGCTGGTCTGGTGATTCTAC |
| 1325 | Ec-ilvC-dN-Q-A5 (1325) | 46 | TATCACCGTAGTGATGGTTG |
| 1328 | Ec-ilvC-dN-Q-B3 (1328) | 47 | GTCAGCAGTTTCTTATCATCG |
| 1330 | Ec-ilvD-dN-co-KI-Q-A3 (1330) | 48 | GCGAAACTTACTTGACGTTC |
| 1331 | Ec-ilvD-dN-co-KI-Q-B5 (1331) | 49 | ACTTTGGACGATGATAGAGC |
| 1334 | LI-kivd-co-Ec-Q-A3 (1334) | 50 | GCGTTAGATGGTACGAAATC |
| 1335 | LI-kivd-co-Ec-Q-B5 (1335) | 51 | CTTCTAACACTAGCGACCAG |
| 1338 | Sc-ADH7-Q-A3 (1338) | 52 | AAAGATGATGAGCAAACGAC |

-continued

| No. | Name | SEQ ID NO: | Sequence |
|---|---|---|---|
| 1339 | Sc-ADH7-Q-B5 (1339) | 53 | CGAGCAATACTGTACCAATG |
| 1375 | HO +1300 F | 54 | TCACGGATGATTTCCAGGGT |
| 1376 | HO +1761 R | 55 | CACCTGCGTTGTTACCACAA |

Example 1

Construction and Confirmation of PDC Deletion in *K. lactis*

The purpose of this Example is to describe how a PDC-deletion variant of a member of the *Saccharomyces* clade, Crabtree-negative yeast, pre-WGD yeast *K. lactis* was constructed and confirmed.

Figure 8:
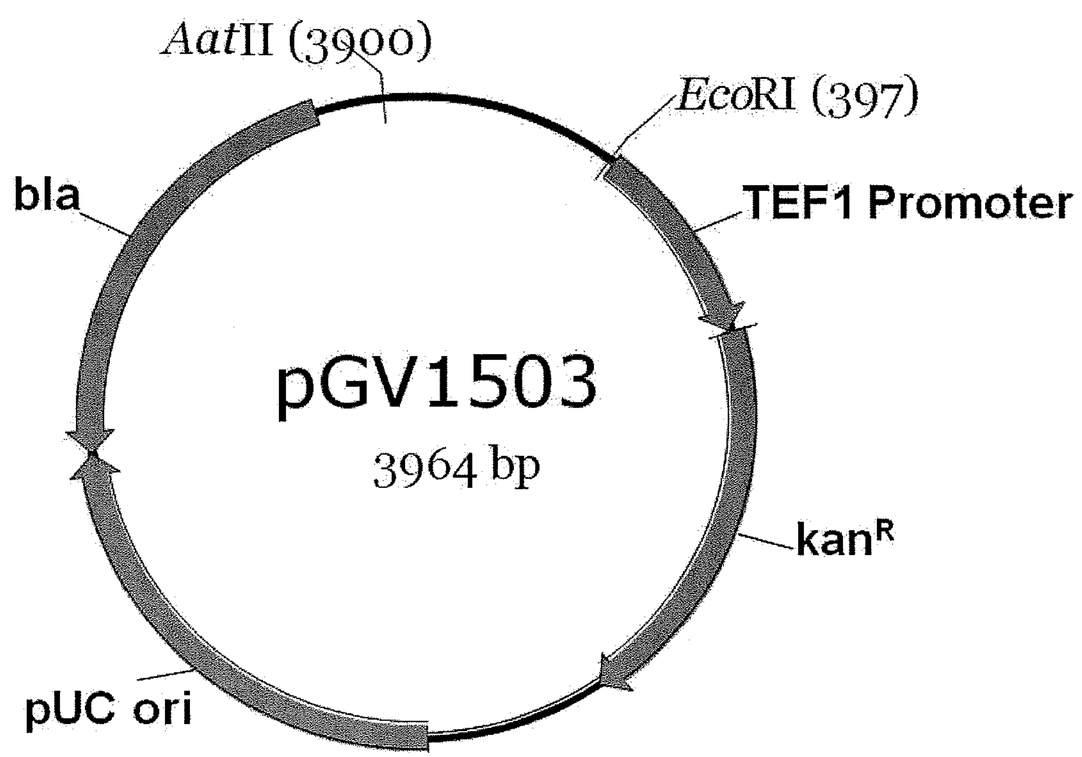
FIG. 8 illustrates a schematic map of plasmid pGV1503.
Figure 9:
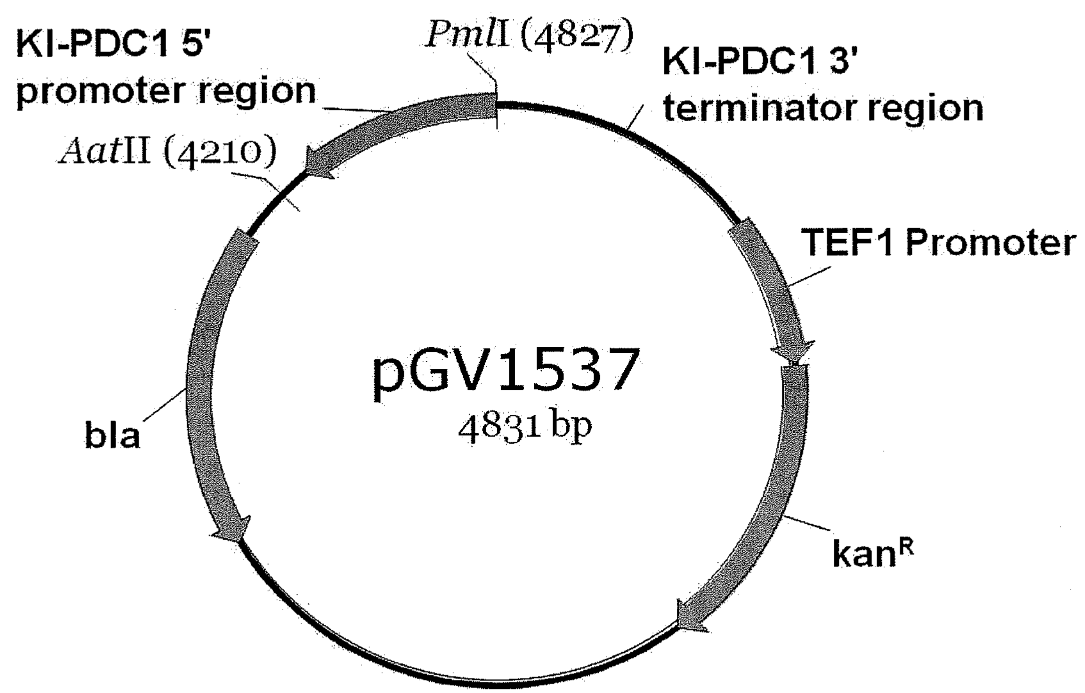
FIG. 9 illustrates a schematic map of plasmid pGV1537.

Construction of plasmid pGV1537: Plasmid pGV1537 (SEQ ID NO: 1) was constructed by the following series of steps. All PCR reactions carried out to generate pGV1537 used KOD polymerase (Novagen, Inc., Gibbstown, N.J.) and standard reaction conditions according to the manufacturer. A first round of two PCR reactions was carried out, wherein one PCR reaction contained primers 1006 and 1016 and used approximately 100 ng of genomic DNA from *K. lactis* strain GEVO1287 as a template. The other first-round PCR reaction contained primers 1017 and 1009 and approximately 100 ng of genomic DNA from *K. lactis* strain GEVO1287 as a template. The two resulting PCR products (approximately 530 bp and 630 bp in size, respectively) were gel purified using a Zymo Research Gel DNA Extraction kit (Zymo Research, Orange, Calif.) according to manufacturer's instructions and eluted into 10 μL of water. Two (2) microliters of each eluted PCR product were then used as a template for a final round of KOD polymerase-catalyzed PCR, which also included primers 1006 plus 1009. The resulting product was purified (Zymo Research DNA Clean & Concentrate kit, Zymo Research, Orange, Calif.), digested to completion with the enzymes MfeI and AatII, and the resulting product gel purified and eluted as described above. This DNA was ligated into the vector pGV1503 (FIG. 8), which had been digested with EcoRI plus AatII, treated with calf alkaline phosphatase, and gel purified as described above. Colonies arising from transformation of the ligated DNA were screened by restriction digest analysis and confirmed by DNA sequencing reactions using primers 838, 1010, and 1019. Correct recombinant DNA resulting from the ligation and subsequent analysis was named pGV1537 (FIG. 9).

Construction of a *K. lactis* Klpdc1Δ strain: Strain GEVO1287 was transformed with PmlI-digested, linearized plasmid pGV1537. Transformation was carried out by electroporation with approximately 300 ng of linearized pGV1537, essentially as described by Kooistra et al. (Kooistra, R., Hooykaas, P. J. J., and Steensman, H. Y. (2004) "Efficient gene targeting in *Kluyveromyces lactis*". *Yeast* 21:781-792). Transformed cells were selected by plating onto YPD plates containing 0.2 mg/mL geneticin (G418). Colonies arising from the transformation were further selected by patching colonies onto YPD plates and then replica plating onto YPD containing 5 μM (final concentration) of the respiratory inhibitor Antimycin A, as Pdc-variants of *K. lactis* are unable to grow on glucose in the presence of Antimycin A (Bianchi, M., et al., (1996). "The petite negative yeast *Kluyveromyces lactis* has a single gene expressing pyruvate decarboxylase activity". Molecular Microbiology 19(1):27-36) and can therefore be identified by this method. Of the 83 G418-resistant colonies patched onto YPD+Antimycin A, six colonies (~7%) were unable to grow and were therefore identified as candidate Klpdc1::pGV1537 disruption strains.

Confirmation of a *K. lactis* Klpdc1Δ strain by colony PCR: Candidate Klpdc1::pGV1537 disruption strains were confirmed by colony PCR analysis. To do so, genomic DNA from candidate lines was obtained by the following method. A small amount (equivalent to a matchhead) of yeast cells were resuspended in 50 μL of 0.2% SDS and heated to 95° C. for 6 minutes. The suspension was pelleted by centrifugation (30 sec, 16,000×g) and 1 μL of the supernatant was used as template in 50 μL PCR reactions. In addition to standard components, the reactions contained Triton X-100 at a final concentration of 1.5% and DMSO at a final concentration of 5%. The various primer sets used, and the expected amplicon sizes expected, are indicated in Table EX1-1. By these analyses, a correct Klpdc1Δ:::pGV1537 strain was identified and was named GEVO1742.

TABLE EX1-1

Primer pairs and expected amplicon sizes predicted for colony PCR screening of candidate Klpdc1Δ::pGV1537 cells.

| Primer Pair | Expected product size for Klpdc1Δ::pGV1537 | Expected product size for KlPDC1+ |
|---|---|---|
| 965 & 838 | 796 bp | (none) |
| 1019 & 966 | 947 bp | (none) |
| 995 & 996 | (none) | 765 bp |

Confirmation of GEVO1742 Klpdc1Δ::pGV1537 by fermentation: Strains of *K. lactis* lacking KLPdc1p (Klpdc1Δ) have been shown to produce significantly lower levels of ethanol when grown on glucose (Bianchi, M., at al., (1996). "The petite negative yeast *Kluyveromyces lactis* has a single gene expressing pyruvate decarboxylase activity". Molecular Microbiology 19(1):27-36). To confirm this phenotype, fermentations with strains GEVO1287 and GEVO1742 were carried out. Briefly, a saturated overnight (3 mL) culture of each strain grown in YPD was inoculated into 25 mL of YPD at a starting $OD_S$ of 0.1 and grown aerobically in a loosely-capped flask in a shaker for 24 hours at 30° C., 250 rpm. Following growth, 2 mL of culture were collected, the cells pelleted by centrifugation (5 minutes, 14,000×g) and the supernatant subjected to analysis by gas chromatography and liquid chromatography. A summary of the data from these analyses is summarized in Table EX1-2. The strongly diminished production of ethanol and the increased accumulation of pyruvate in the fermentation medium are characteristic of *K. lactis* strains in which PDC1 has been deleted. Thus, these observations confirm the molecular genetics conclusions that strain GEVO1742 is in fact Klpdc1Δ.

TABLE EX1-2

Ethanol and pyruvate produced and glucose consumed in aerobic fermentations of GEVO1287 and GEVO1742.

| STRAIN | Ethanol produced (g/L) | Pyruvate produced (g/L) | Glucose consumed (g/L) |
|---|---|---|---|
| GEVO1287 | 8.129 | (not detected) | 17.56 |
| GEVO1742 | 0.386 | 1.99 | 5.25 |

Example 2

Construction and Confirmation of PDC Deletion in *S. cerevisiae*

The purpose of this Example is to describe how a PDC deletion variant of a member of the *Saccharomyces sensu stricto* yeast group, the *Saccharomyces* yeast clade, a Crabtree-positive yeast, and a post-WGD yeast, *S. cerevisiae* was constructed and confirmed.

Strains GEVO1537 and GEVO1538 were incubated in 1% potassium acetate for 3-4 days which induces sporulation. The resulting haploid spores were recovered by random spore analysis. Briefly, a culture of sporulating cells was examined microscopically to ensure that a sufficient fraction of cells had sporulated (>10%). Five (5) mL of a culture of sporulated cells were collected by centrifugation (5 minutes at 3000×g) and washed once in 1 mL of water. The cells were resuspended in 5 mL water to which was added 0.5 mL of a 1 mg/mL solution (freshly made) of Zymolyase-T (in water) as well as 10 μL of β-mercaptoethanol. The cell suspension was incubated overnight at 30° C. in a shaker at 50 rpm. Five mL of 1.5% Triton X-100 were added and the mixture was incubated on ice for 15 minutes. The solution was sonicated three times for 30 seconds per cycle at 50% power, with 2 minutes rest on ice in between sonication cycles. The suspension was centrifuged (1200×g, 5 minutes) and washed twice with 5 mL of water. The final cell pellet was resuspended in 1 mL water and cells were plated to YP+2% EtOH.

Following this procedure, the separate individual spores, were plated onto solid medium to obtain colonies, all of genotype HO pdc1::Tn5ble pdc5::Tn5ble pdc6:APT1HIS3 LEU2 TRP1 URA3 and of unknown mating type. Some fraction of the cells were (homozygous) diploid due to the HO+gene status and resultant mating type switching and re-mating to form diploids.

The genotype of the mating type locus of the putative Pdc-minus colonies was confirmed by PCR using Taq DNA polymerase (New England BioLabs, Ipswich, Mass.) under standard conditions using primers specific for the MAT a locus (primers #489 and #491) or MAT a locus (primers #490 and #491). Colonies that generated a single PCR product with one of the two possible primer sets primer set and no product when tested with the other were putative haploid Pdc-minus strains. To confirm the mating type, such strains were crossed to Gevo1187 and Gevo1188 (CEN.PK). Resulting diploid progeny were selected on medium containing glucose (to select for the presence of PDC+ genes introduced by CEN.PK background) and also lacking at least one of the following nutrients: histidine, leucine, tryptophan, or uracil (to select for the appropriate prototrophy as provided by the wild-type allele of the corresponding gene from the Gevo1537 or GEVO1538 background.

Diploid cells were sporulated and germinated on agar plates containing YP+2% ethanol (to permit growth of Pdc-minus isolates). To identify Pdc-minus candidates, viable colonies were streaked on to YPD agar plates and colonies that were inviable on glucose were isolated. Inability to grow on glucose confirms that these candidates are pdc1::ble and pdc5::ble. The pdc6::apt1 was confirmed their ability to grow on YP+Ethanol plates containing the antibiotic G418. The genotype of the mating type locus of the putative Pdc-minus colonies was confirmed by PCR using Taq DNA polymerase (New England BioLabs, Ipswich, Mass.) under standard conditions using primers specific for the MAT a locus (primers #489 and #491) or MAT a locus (primers #490 and #491). The presence of a product from both sets of PCR reactions indicated that both mating type alleles were present in the population, as a consequence of mating type allele switching by an active HO-encoded enzyme. The presence of a PCR product for one set of MAT locus-specific primers but not the other indicated that the strain lacks this activity and was therefore ho-. Based upon these analyses, six candidates colonies were identified as ho-strains and one candidate #4 was HO.

These Pdc-minus strains were streaked to SC+Ethanol plates lacking one of: leucine, histidine, tryptophan, or uracil, to determine presence of auxotrophic mutations within these strains. One Pdc-minus strain, GEVO1581, was auxotrophic for histidine, uracil, and tryptophan, and thus carried three of the makers (his3, ura3, and trp1). Another Pdc-minus strain, GEVO1715, was auxotrophic for uracil and leucine and thus carried the two markers, ura3 and leu2.

GEVO1581 and GEVO1715 were screened by RFLP analysis to verify the presence of the ho allele. A 447 bp portion of the HO locus was amplified by PCR that contained the codon that is altered in the ho allele (H475L) using primers 1375 and 1376. This mutation introduces an AluI restriction site, and consequently, digestion with AluI (New England BioLabs, Ipswich, Mass.) yielded either a 447 bp fragment (HO) or a 122 bp fragment plus a 325 bp fragment (ho). Based upon RFLP analysis, GEVO1581 was HO and GEVO1715 was ho.

To obtain a Pdc-minus strain with all four auxotrophic markers, GEVO1715 was crossed to GEVO1188 and diploids generated as described above. The resulting diploid was sporulated and Pdc-minus candidates were isolated by plating onto YP+Ethanol containing both Phleomycin and G418. These candidates were then streaked onto YPD agar plates and tested for their inviability on glucose. Those that did not grow on glucose were isolated as this phenotype, in addition to their resistance to Phleomycin and G418 confirms that these candidates are pdc1::ble, pdc5::ble and pdc6::apt1. These isolates were streaked to SC+Ethanol plates lacking one of: leucine, histidine, tryptophan, or uracil, to determine presence of auxotrophic mutations within these strains. One of these Pdc-minus strains, GEVO1584, was auxotrophic for histidine, uracil, tryptophan and leucine and thus carried all four markers, his3, ura3, trp1, and leu2. GEVO1584 was also confirmed to be MATa and ho by colony PCR and RFLP analysis, respectively, as described above.

TABLE EX2-1

Summary table of *S. cerevisiae* Pdc-minus strains obtained

| GEVO No. | GENOTYPE | STRAIN SOURCE |
|---|---|---|
| 1537 | MAT a/α, HIS3, LEU2, TRP1, URA3, pdc1::ble/pdc1::ble, pdc5::ble/pdc5::ble, pdc6::apt1(kanR)/pdc6::apt1(kanR), HO/HO | Strain GG570 from Paul van Heusden, Univ. of Leiden, Netherlands |
| 1538 | MAT a/α, HIS3, LEU2, TRP1, URA3, pdc1::ble/pdc1::ble, pdc5::ble/pdc5::ble, pdc6::apt1(kanR)/pdc6::apt1(kanR), HO/HO | Strain GG570 from Paul van Heusden, Univ. of Leiden, Netherlands |
| 1581 | MAT a/α, his3/his3, trp1/trp1, ura3/ura3, LEU2/LEU2, pdc1::ble/pdc1::ble, pdc5::ble/pdc5::ble, pdc6::apt1(kanR)/pdc6::apt1(kanR), HO/HO | candidate #4 GEVO1537xGEVO1187 |
| 1584 | MAT a, his3, trp1, ura3, leu2, pdc1::ble, pdc5::ble, pdc6::apt1(kanR), ho | candidate #201 GEVO1715xGEVO1188 |
| 1715 | MAT a, leu2, ura3, pdc1::ble, pdc5::ble, pdc6::apt1(kanR), ho | candidate #104 GEVO1187x GEVO1537 |

Example 3

Other Pdc-Minus *S. cerevisiae* Strains

*S. cerevisiae* engineered to be deficient in PDC activity have been previously described: (Flikweert, M. T., van der Zanden, L., Janssen, W. M. T. M, Steensma, H. Y., van Dijken J. P., Pronk J. T. (1996) Yeast 12(3):247-57). Such strains may be obtained from these sources.

Example 4

Chemostat Evolution of *S. Cerevisiae* PDC Triple-Mutant

This example demonstrates that a PDC deletion variant of a member *Saccharomyces* sensu stricto yeast group, the *Saccharomyces* clade yeast, Crabtree-positive, post-WGD yeast, *S. cerevisiae*, can be evolved so that it does not have the requirement for a two-carbon molecule and has a growth rate similar to the parental strain on glucose.

A DasGip fermentor vessel was sterilized and filled with 200 ml of YNB (Yeast Nitrogen Base; containing per liter of distilled water 6.7 g YNB without amino acids from Difco, the following were added per liter of medium: 0.076 g histidine, 0.076 g tryptophan, 0.380 g leucine, and/or 0.076 g uracil; medium was adjusted pH to 5 by adding a few drops of HCL or KOH) and contained 2% w/v ethanol. The vessel was installed and all probes were calibrated according to DasGip instructions. The vessel was also attached to an off-gas analyzer of the DasGip system, as well as to a mass spectrometer. Online measurements of oxygen, carbon dioxide, isobutanol, and ethanol were taken throughout the experiment. The two probes that were inside the vessel measured pH and dissolved oxygen levels at all times. A medium inlet and an outlet were also set up on the vessel. The outlet tube was placed at a height just above the 200 ml level, and the pump rate was set to maximum. This arrangement helped maintain the volume in the vessel at 200 ml. Air was sparged into the fermentor at 12 standard liters per hour (slph) at all times. The temperature of the vessel was held constant at 31.8° C. and the agitation rate was kept at 300 rpm. The off-gas was analyzed for $CO_2$, $O_2$, ethanol and isobutanol concentrations. The amount of carbon dioxide ($X_{CO2}$) and oxygen ($X_{O2}$) levels in the off-gas were used to assess the metabolic state of the cells. An increase $X_{CO2}$ levels and decrease in $X_{O2}$ levels indicated an increase in growth rate and glucose consumption rate. The ethanol levels were monitored to ensure that there was no contamination, either from other yeast cells or from potential revertants of the mutant strain since the *S. cerevisiae* PDC triple-mutant (GEVO1584) does not produce ethanol. The minimum pH in the vessel was set to 5, and a base control was set up to pump in potassium hydroxide into the vessel when the pH dropped below 5.

GEVO1584 was inoculated into 10 ml of YNB medium with 2% w/v ethanol as the carbon source. The culture was incubated at 30° C. overnight with shaking. The overnight culture was used to inoculate the DasGip vessel. Initially, the vessel was run in batch mode, to build up a high cell density. When about 3 g CDW/L of cell biomass was reached, the vessel was switched to chemostat mode and the dilution of the culture began. The medium pumped into the vessel was YNB with 7.125 g/L glucose and 0.375 g/L of acetate (5% carbon equivalent). The initial dilution rate was set to 0.1 $h^{-1}$, but as the cell density started dropping, the dilution rate was decreased to 0.025 $h^{-1}$ to avoid washout. GEVO1584 was mating type a. A PCR check for the mating type of the chemostat population several days into the experiment indicated that the strain still present was mating type a.

Figure 5:
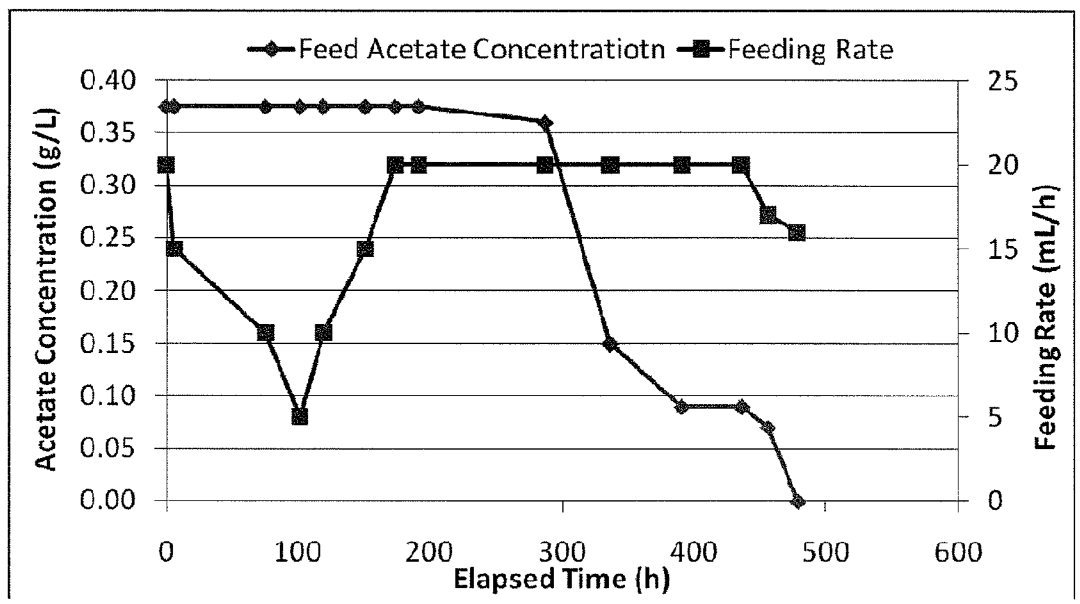
FIG. 5 illustrates the carbon source composition and feeding rate over time during chemostat evolution of the *S. cerevisiae* Pdc-minus strain GEVO1584. This graph shows how the acetate was decreased over a period of 480 hours from 0.375 g/L to 0 g/L. It also shows the total feeding rate. Higher feeding rate meant that growth rate was higher. Since the chemostat contained 200 ml of culture, dilution rate can be calculated by dividing the feeding rate by 200 ml.

The culture in the chemostat was stabilized and the dilution rate increased to 0.1 $h^{-1}$. After steady state was reached at the 0.1 $h^{-1}$ dilution rate, the concentration of acetate was slowly decreased. This was achieved by using a two pump system, effectively producing a gradient pumping scheme. Initially pump A was pumping YNB with 7.125 g/L glucose, and 0.6 g/L of acetate at a rate of 12.5 mL/h and pump C was pumping YNB with only 7.125 g/L glucose at a rate of 7.5 mL/h. The combined acetate going into the vessel was 0.375 g/L. Then, over a period of 3 weeks, the rate of pump A was slowly decreased and the rate of pump C was increased by the same amount so that the combined rate of feeding was always 20 mL/h. When the rate of pump A dropped below 3 mL/h the culture started to slowly wash out. To avoid complete washout the dilution rate was decreased to 0.075 $h^{-1}$ from 0.1 $h^{-1}$ (FIG. 5). At this dilution rate, the rate of pump A was finally reduced to 0, and the evolved strain was able to grow on glucose only. Over the period of about five weeks, a sample was occasionally removed, either from the vessel directly or from the effluent line. Samples were analyzed for glucose, acetate, and pyruvate using HPLC, and were plated on YNB with glucose, YNB with ethanol, and YNB (w/o uracil) plus glucose or ethanol as negative control. Strains isolated from the chemostat did not grow on the YNB plates without uracil. $OD_{600}$ was taken regularly to make sure the chemostat did not wash out.

Freezer stocks of samples of the culture were made regularly for future characterization of the strains.

Figure 6:
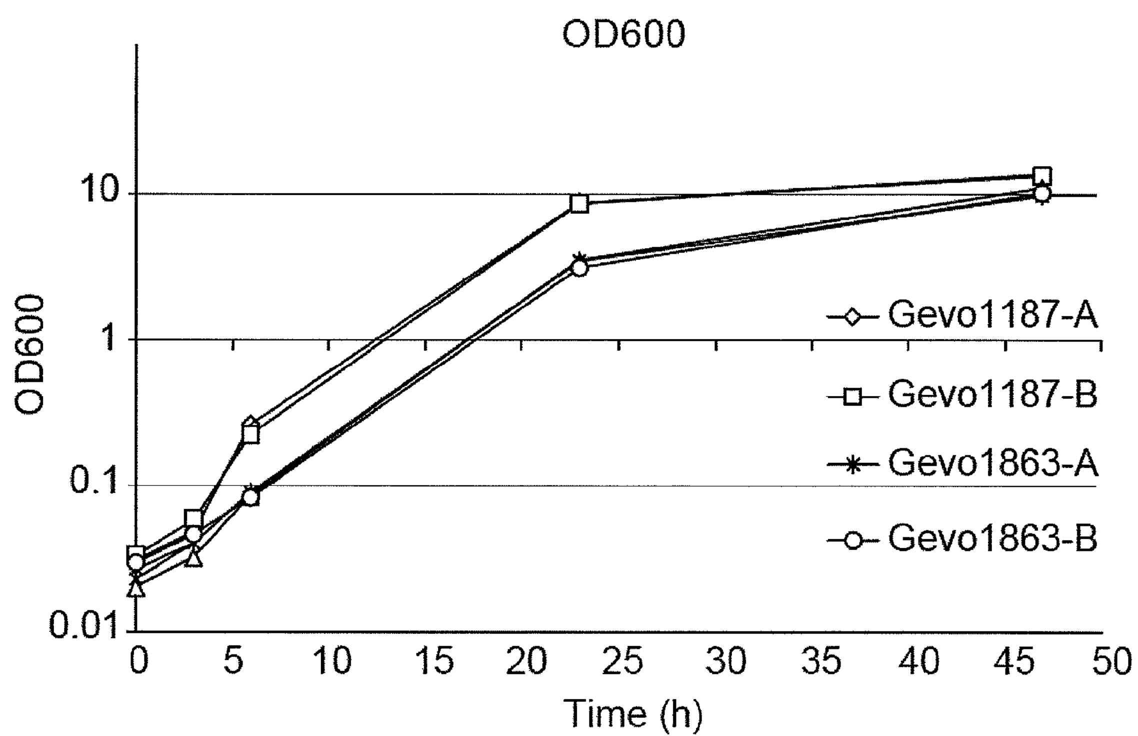
FIG. 6 illustrates growth of evolved Pdc-minus mutant strain GEVO1863 in YPD compared to the parental strain, GEVO1187.
Figure 7:
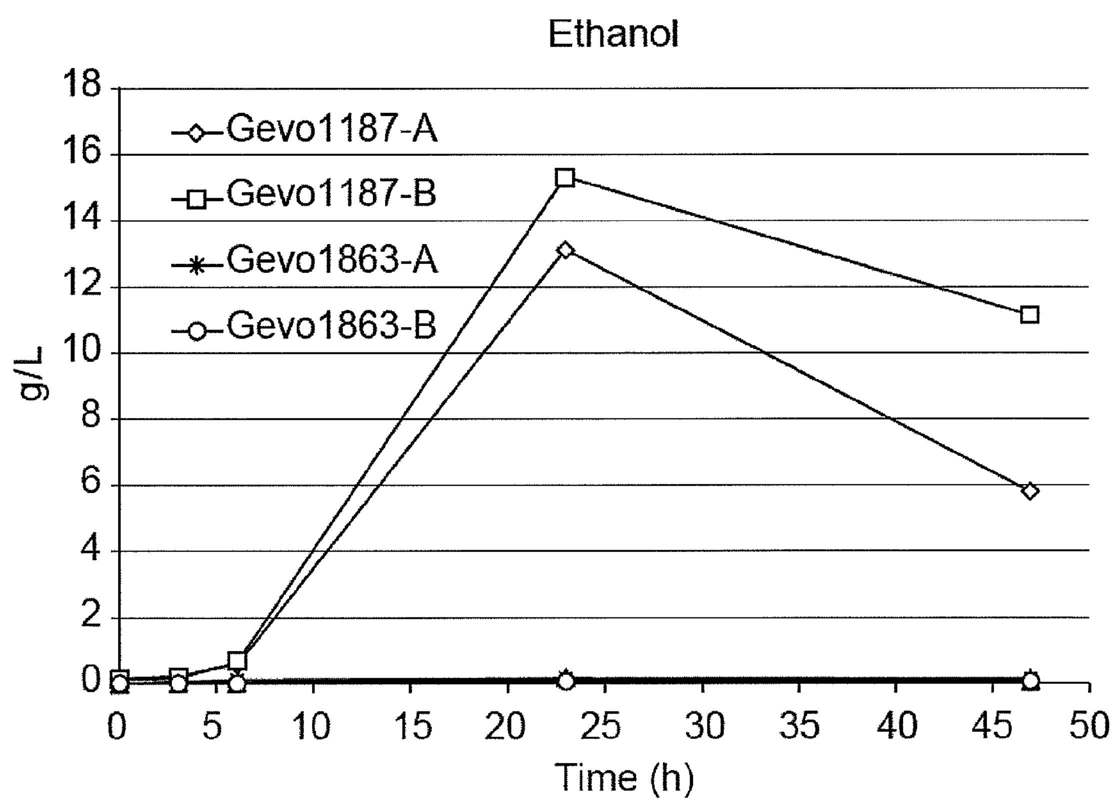
FIG. 7 illustrates that the evolved PCD mutant, GEVO1863, does not produce ethanol in YPD medium, unlike the parental strain GEVO1187.

To characterize growth of the evolved strains YNB, YPD (yeast extract, peptone, dextrose), and YPE (yeast extract, peptone, ethanol) were used with various concentrations of glucose or ethanol. The growth characterization was performed in either snap-cap test tubes or 48-well plates (7.5 ml). The snap-cap test tubes were not closed completely so that air would vent in/out of the tubes, and the 48-well plates were covered with an air permeable membrane to allow for oxygen transfer. To check for contaminations, YPD or YPE agar plates were used with the antibiotics G418 and Phleomycin. The PDC triple mutant strain (GEVO1584) has both G418 and Phleomycin resistance markers, so the progeny of that strain were able to grow on the antibiotics. Single colonies isolated from each chemostat sample were studied for growth rates. A single colony isolated from the 35-day chemostat population was selected because of high growth rates on glucose as a sole carbon source, was resistant to both G418 and Phleomycin, and grew without the need for ethanol or acetate. The single colony was further evolved through 24 successive serial transfers in test tubes on YPD at 30° C., 250 rpm shaking. The resulting strain, GEVO1863, grew similarly to the wild-type yeast parent on glucose (FIG. 6), did not produce ethanol (FIG. 7), and did not require ethanol or acetate for growth.

Example 5

Isobutanol Production in Pdc-Plus *K. lactis*

This example demonstrates isobutanol production in a member of the *Saccharomyces* clade, Crabtree-negative, pre-WGD yeast, *K lactis*.

Figure 10:
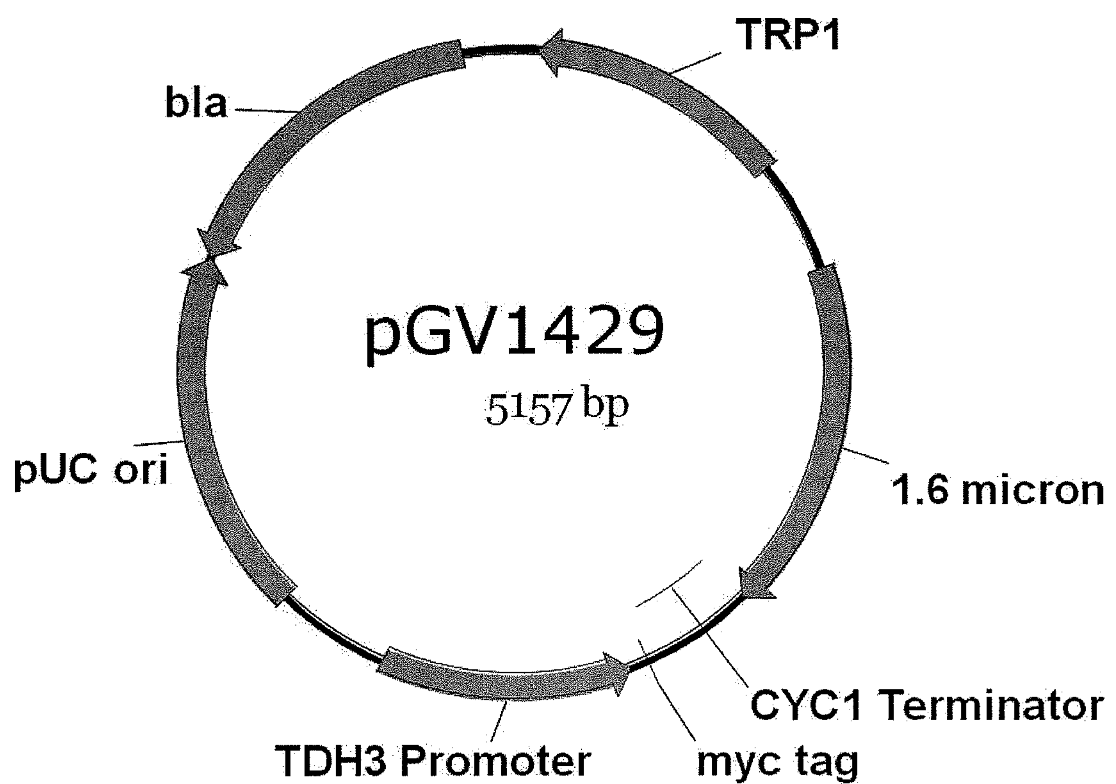
FIG. 10 illustrates a schematic map of plasmid pGV1429.
Figure 11:
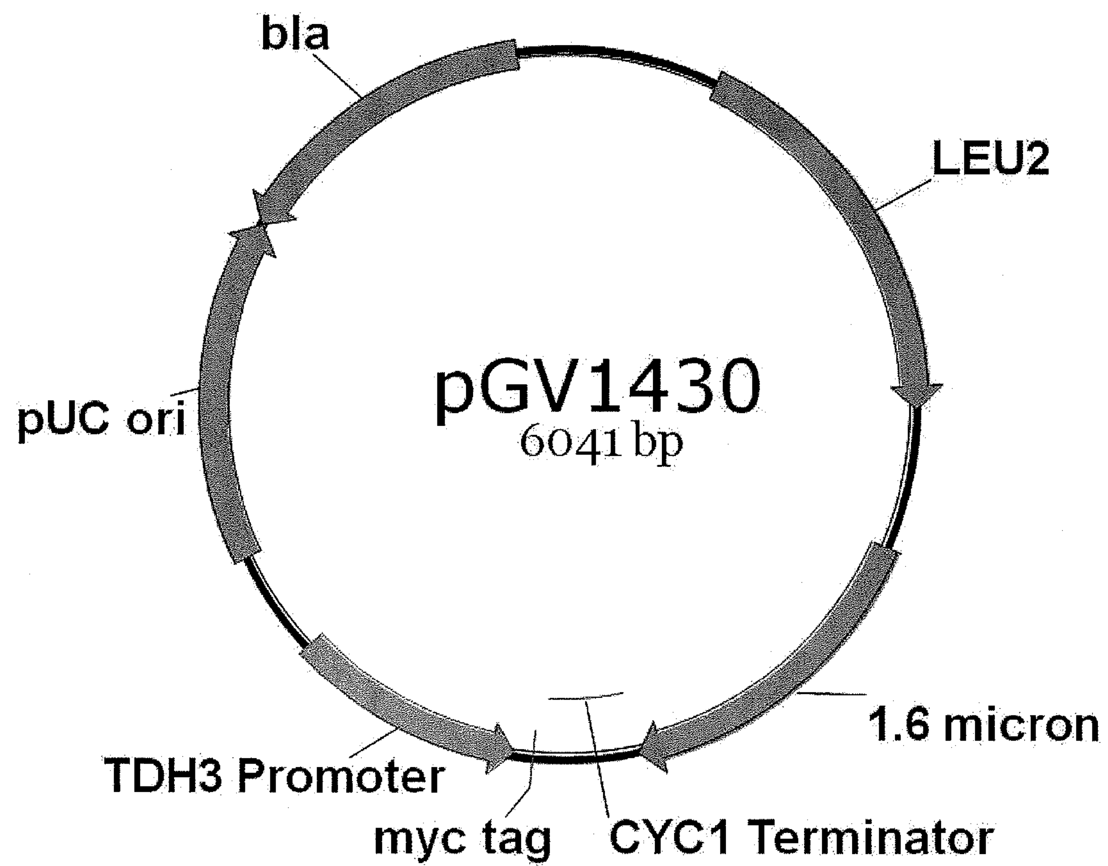
FIG. 11 illustrates a schematic map of plasmid pGV1430.
Figure 12:
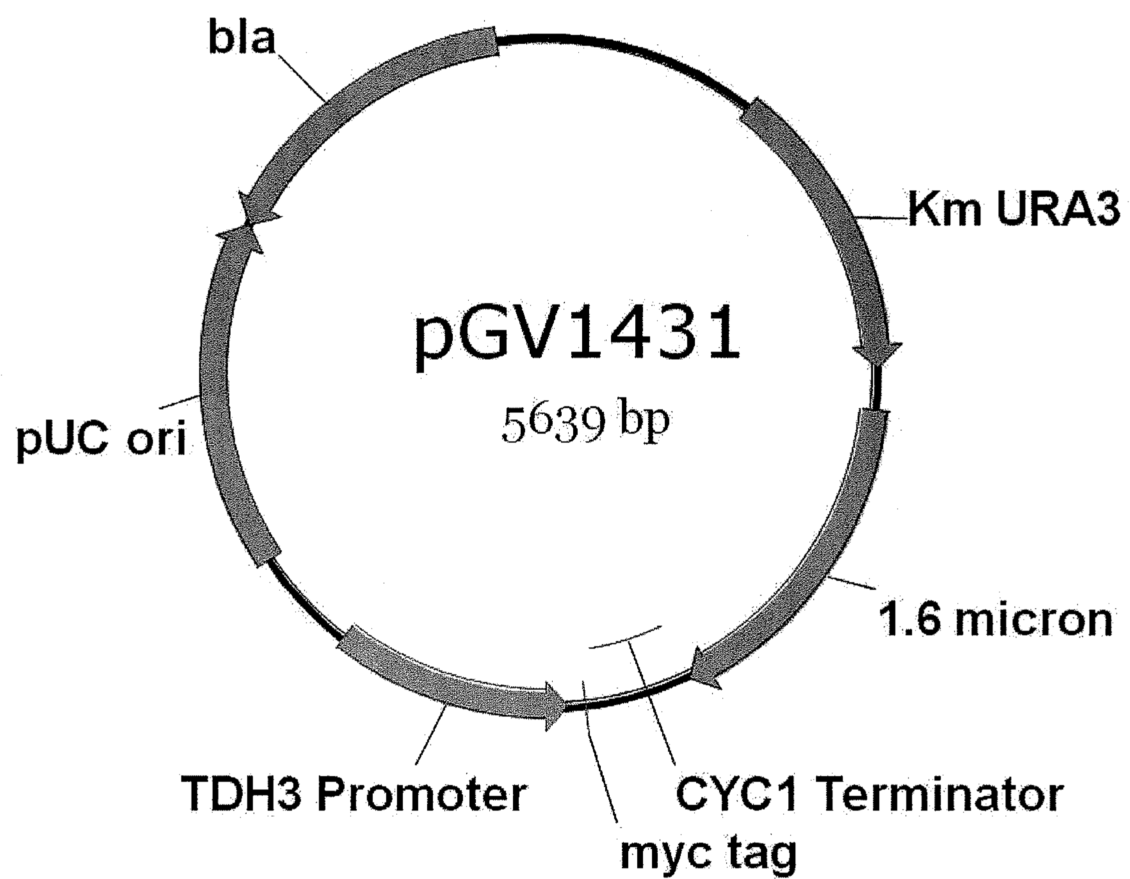
FIG. 12 illustrates a schematic map of plasmid pGV1431.
Figure 13:
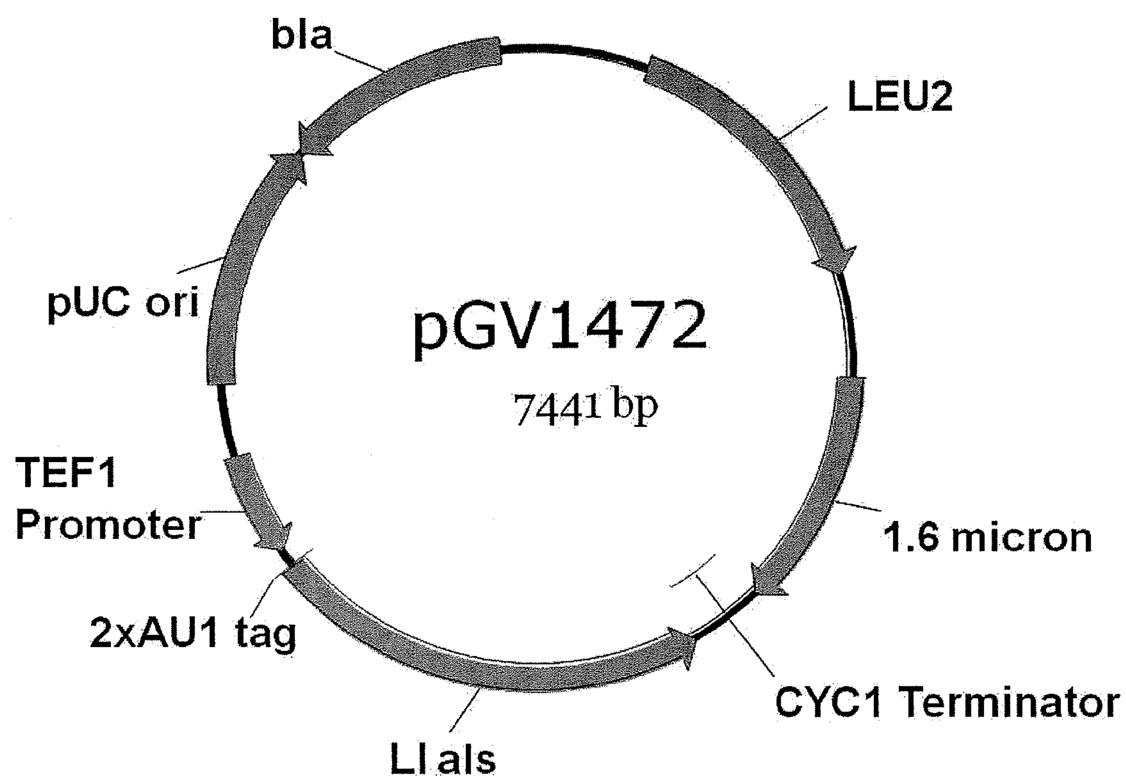
FIG. 13 illustrates a schematic map of plasmid pGV1472.
Figure 14:
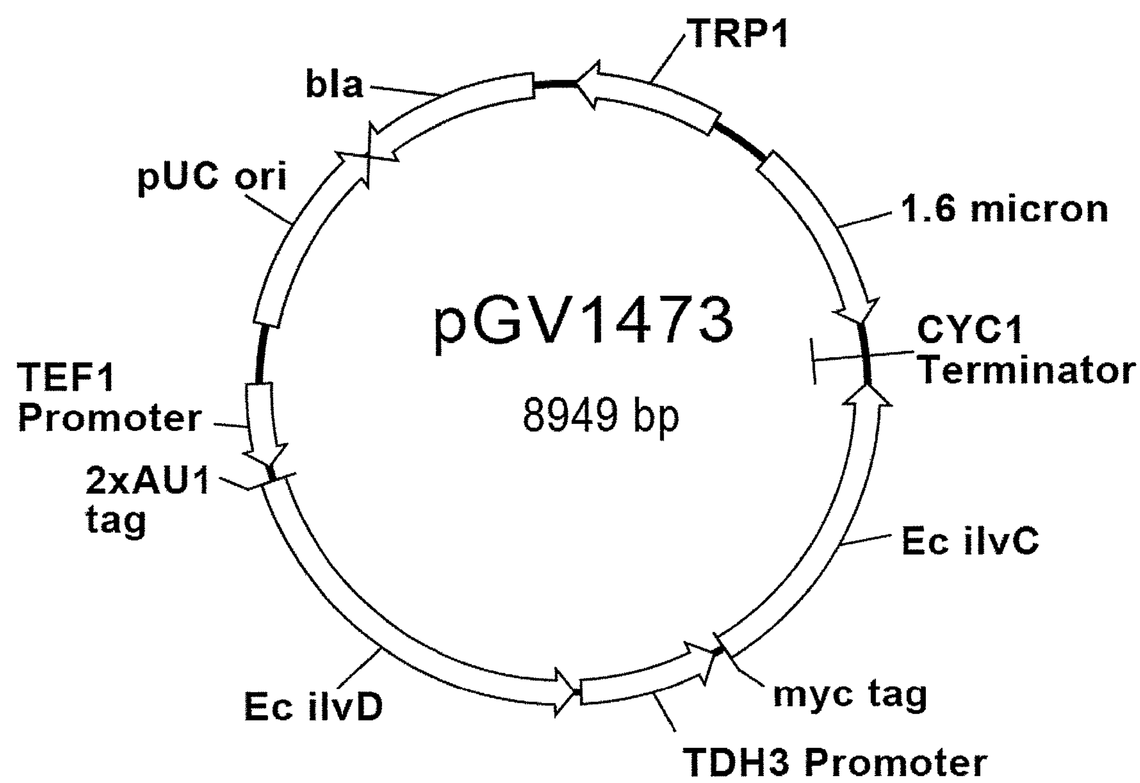
FIG. 14 illustrates a schematic map of plasmid pGV1473.
Figure 15:
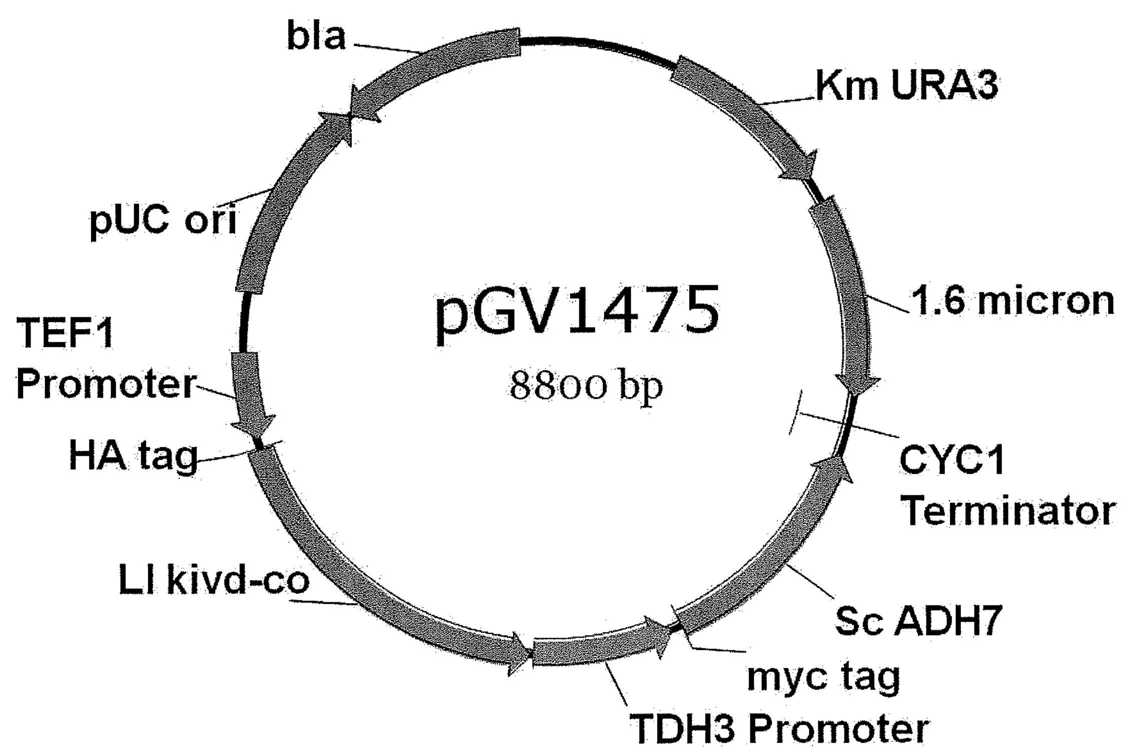
FIG. 15 illustrates a schematic map of plasmid pGV1475.

The isobutanol production pathway was cloned in a *K. lactis* vector-based expression system: a SacI-MluI fragment containing the TEF1 promoter. *Lactococcus lactis* alsS and part of the CYC1 terminator sequence was cloned into the same sites of the *K. lactis* expression plasmid, pGV1430 (FIG. 11), to generate pGV1472 (FIG. 13, SEQ ID NO: 2). A SacI-MluI fragment containing the TEF1 promoter, *E. coli* ilvD, TDH3 promoter, *E. coli* ilvC, and part of the CYC1 terminator was cloned into the same sites of the *K. lactis* expression plasmid, pGV1429 (FIG. 10), to generate pGV1473 (FIG. 14, SEQ ID NO: 3). A BssHII-NotI fragment containing the TEF1 promoter, *L. lactis* kivD, TDH3 promoter and *S. cerevisiae* ADH7. ScAdh7 was cloned into the *K. lactis* expression plasmid, pGV1431 (FIG. 12), to obtain pGV1475 (FIG. 15, SEQ ID NO: 4).

The *K. lactis* strain GEVO1287 was transformed with the above plasmids, pGV1472, pGV1473, and pGV1475 (Table EX5-1) to express the isobutanol pathway. As a control, *K. lactis* GEVO1287 was also transformed with empty vectors pGV1430, pGV1429, and pGV1431 (Table EX5-1).

TABLE EX5-1

*K. lactis* clones expressing an isobutanol pathway

| clone | Host | Plasmid 1 | Plasmid 2 | Plasmid 3 | ALS | KARI | DHAD | KIVD | ADH |
|---|---|---|---|---|---|---|---|---|---|
| iB165 | GEVO1287 | pGV1430 | pGV1429 | pGV1431 | — | — | — | — | — |
| iB173 | GEVO1287 | pGV1472 | pGV1473 | pGV1475 | Ptef1-Ll. alsS | Ec. ilvC | Ec. ilvD | Ll. Kivd | Sc. Adh7 |

Transformed cells were grown overnight and transferred to 100 mL fermentation bottles using 20 mL SC-WLU medium. Two mL samples were taken at 24 and 48 hours for GC analysis. At each time point, 2 mL of a 20% glucose was added after removing samples for GC analysis. At 48 hours the fermentation was ended. GC samples were processed as described. Results are shown in Table EX5-2 Up to 0.25 g/L isobutanol was produced in *K. lactis* transformed with an isobutanol pathway whereas the control strain without the pathway only produced 0.022 g/L in 48 hours.

TABLE EX5-2

*K. lactis* fermentation results

| clone | Isobutanol titer (mg/L) | Isobutanol yield (% theoretical) | Ethanol (g/L) |
|---|---|---|---|
| iB165 | 0.022 | 0.13 | 11.4 |
| iB173 | 0.25 | 1.5 | 12.6 |

To determine if isobutanol titers can be increased by using a rich complex media, fermentations were performed as described above with iB165 (vector only control) and iB173 using YPD instead of SC-WLU medium. In addition, fermentations were also carried out in 250 mL screw-cap flasks (microaerobic conditions) and in 125 mL metal-cap flasks (aerobic conditions). Samples were taken at 24, 48, and 72 and the isobutanol levels obtained are shown in Table EX5-3.

TABLE EX5-3

*K. lactis* fermentation results using YPD

| clone | Condition | Isobutanol titer (mg/L) | Isobutanol yield (% theoretical) | Ethanol (g/L) |
|---|---|---|---|---|
| iB165 | Anaerobic | 66 | 0.4 | 27.4 |
| iB165 | Microaerobic | 117 | 0.7 | 24.5 |
| iB165 | Aerobic | 104 | 0.6 | 11.7 |
| iB173 | Anaerobic | 297 | 1.8 | 25.8 |
| iB173 | Microaerobic | 436 | 2.6 | 23.4 |
| iB173 | Aerobic | 452 | 2.7 | 13.4 |

Example 6

Isobutanol Production in Pdc Plus *S. cerevisiae*

This example demonstrates isobutanol production in a member of *Saccharomyces sensu stricto* group, *Saccharomyces* clade, Crabtree-positive, post-WGD yeast, *S. cerevisiae.*

Figure 16:
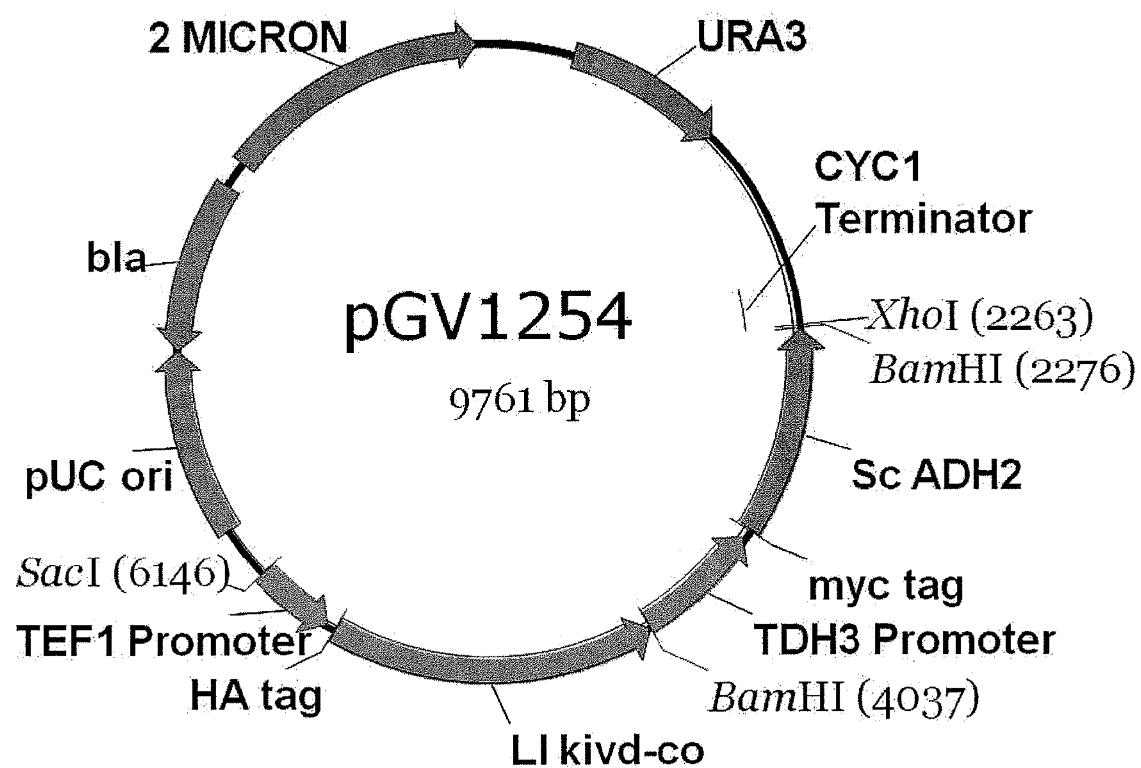
FIG. 16 illustrates a schematic map of plasmid pGV1254.
Figure 17:
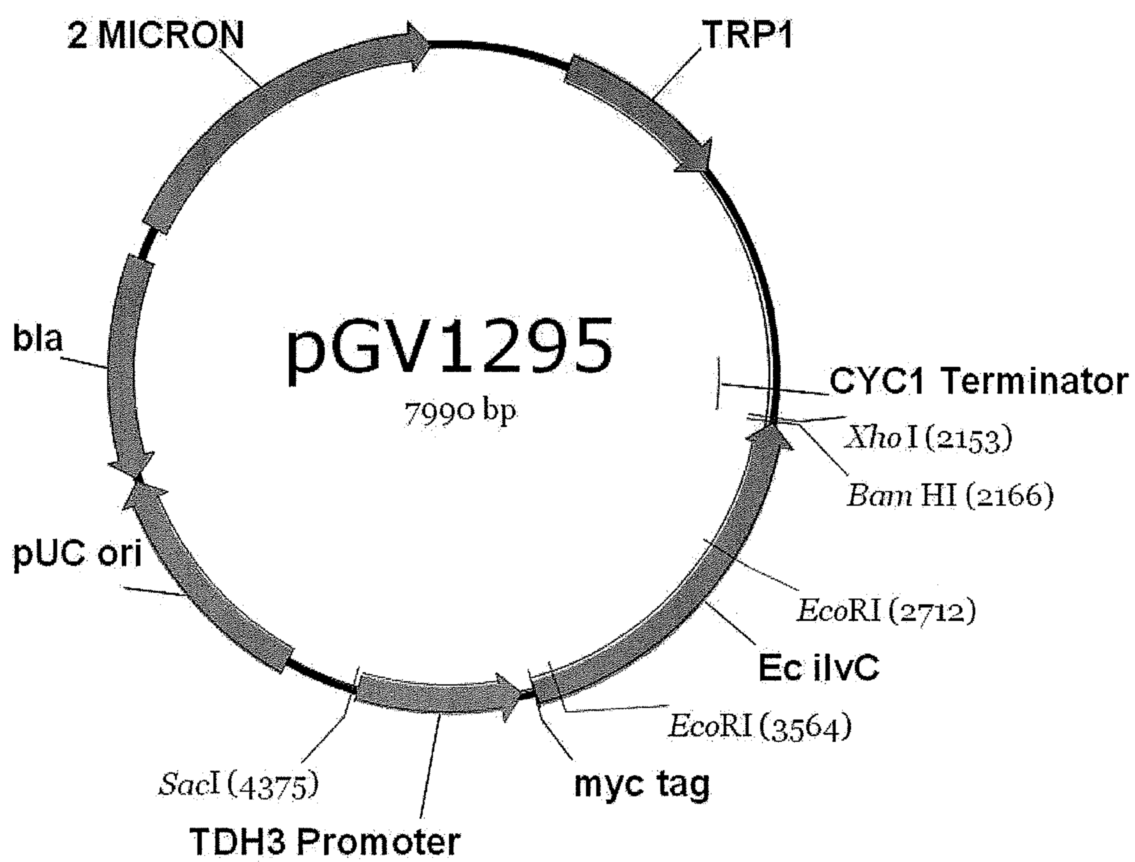
FIG. 17 illustrates a schematic map of plasmid pGV1295.
Figure 18:
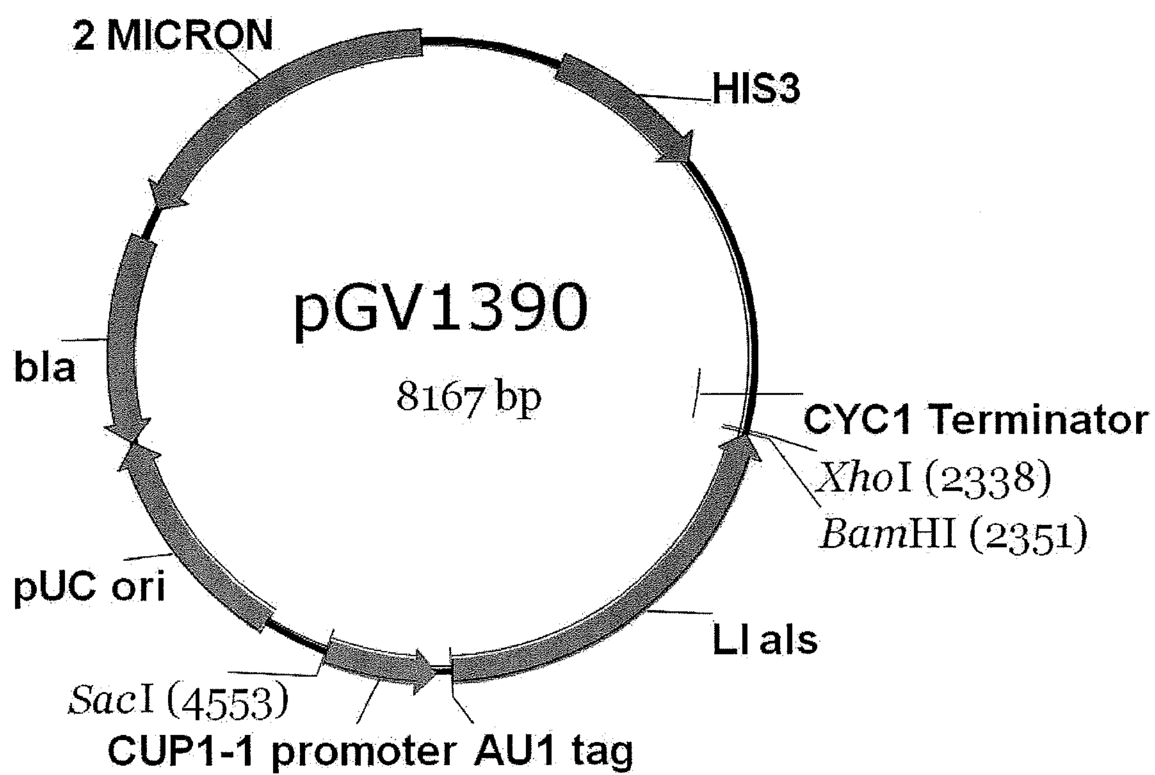
FIG. 18 illustrates a schematic map of plasmid pGV1390.
Figure 19:
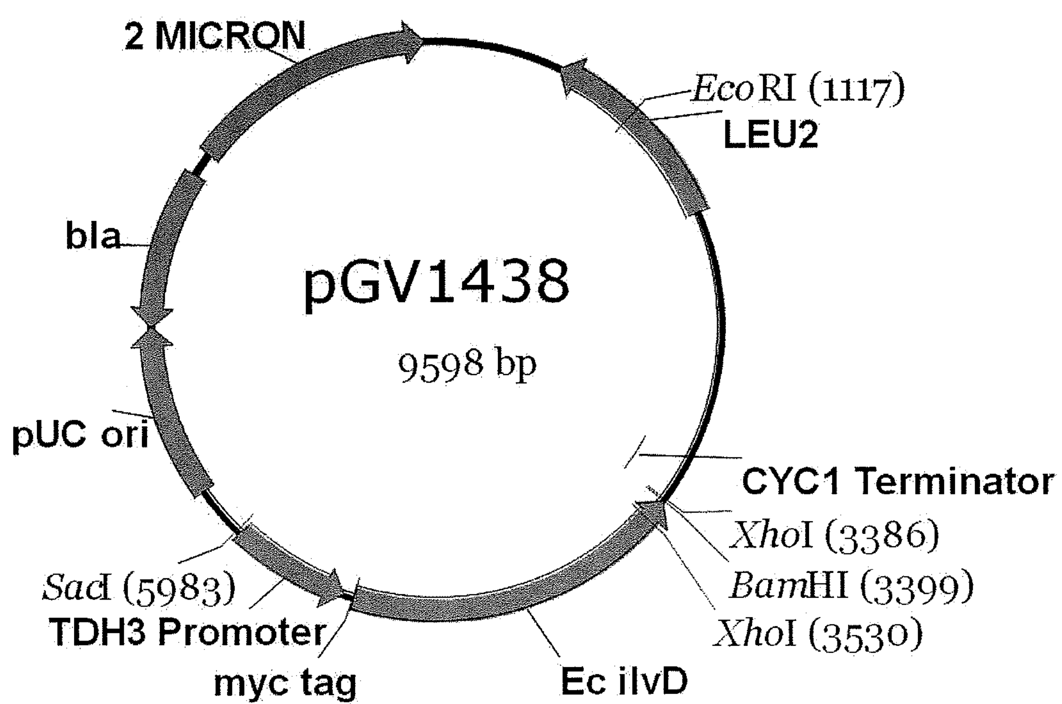
FIG. 19 illustrates a schematic map of plasmid pGV1438.

Various plasmids carrying the isobutanol production pathway were constructed for expression of this metabolic pathway in a Pdc-plus variant of *S. cerevisiae*, GEVO1187. Plasmids pGV1254 (FIG. 16; SEQ ID NO: 10), pGV1295 (FIG. 17; SEQ ID NO: 11) pGV1390 (FIG. 18; SEQ ID NO: 12), and pGV1438 (FIG. 19; SEQ ID NO: 13) were high copy *S. cerevisiae* plasmids that together expressed the five genes of the isobutanol pathway (TABLE EX6-1). pGV1390 was generated by cloning a SalI-BamHI fragment containing the *L.* lactis alsS (SEQ ID NO: 5) into the high copy *S. cerevisiae* expression plasmid, pGV1387, where the *L. lactis* alsS would be expressed under the CUP1 promoter. pGV1295 was generated by cloning a SalI-BamHI fragment containing the *E. coli* ilvC (SEQ ID NO: 6) into the high copy *S. cerevisiae* expression plasmid, pGV1266, where the *E. coli* ilvC would be expressed using the TDH3 promoter. pGV1438 was generated by cloning a SalI-BamHI fragment containing the *E. coli* ilvD (SEQ ID NO: 7) into the high copy *S. cerevisiae* expression plasmid, pGV1267, where the *E. coli* ilvD would be expressed using the TDH3 promoter. pGV1254 was made by cloning an EcoRI (filled in by Klenow polymerase treatment)-XhoI fragment containing the TDH3 promoter and *S. cerevisiae* ADH2 from pGV1241 into the BamHI (filled in by Klenow) and XhoI sites of pGV1186. pGV1186 was made by cloning a SalI-BamHI fragment containing the *L. lactis* kivD (SEQ ID NO: 8) into a high copy *S. cerevisiae* expression plasmid, pGV1102, where the *L. lactis* kivD would be expressed using the TEF1 promoter. pGV1241 was made by cloning a SalI-BamHI fragment containing the *S. cerevisiae* ADH2 (SEQ ID NO: 9) into a high copy *S. cerevisiae* expression plasmid, pGV1106, where the *S. cerevisiae* ADH2 would be expressed using the TDH3 promoter.

Figure 23:
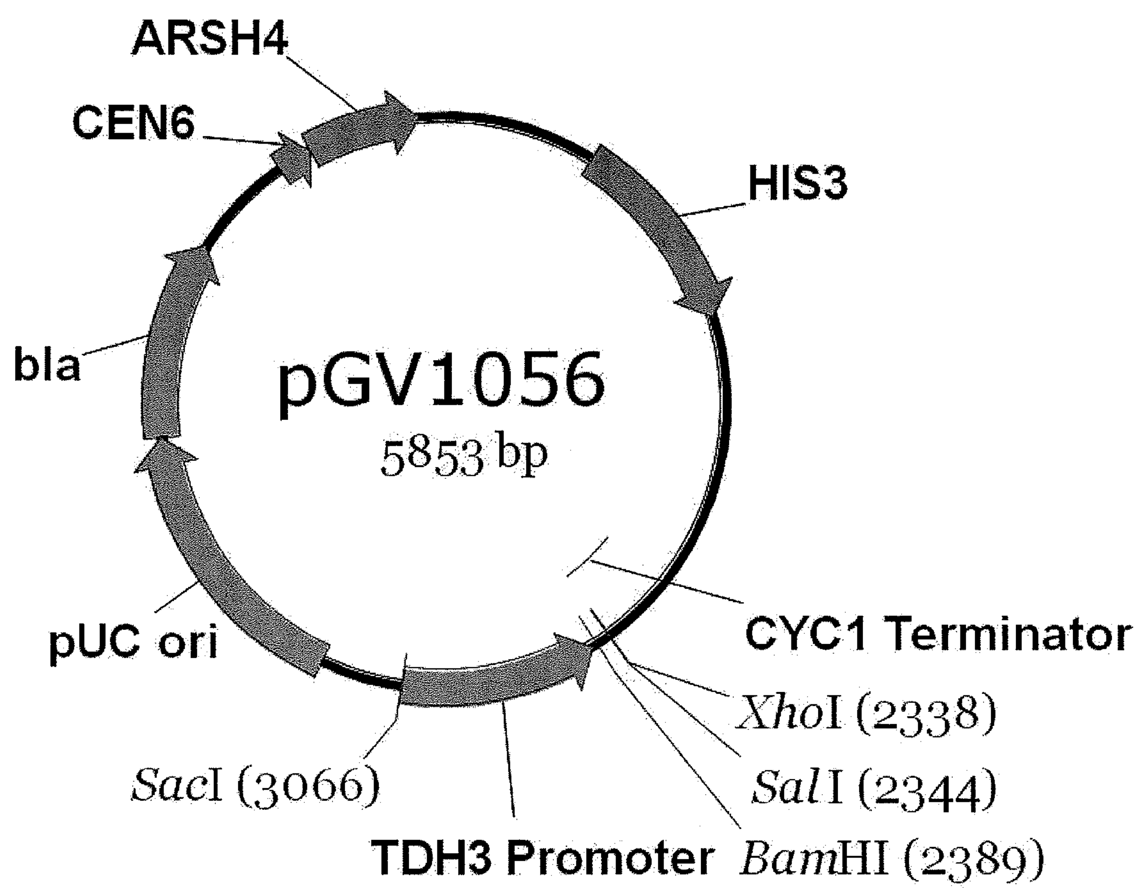
FIG. 23 illustrates a schematic map of plasmid pGV1056.

GEVO1187 was transformed with plasmids as shown in Table EX6-1. As a defective isobutanol pathway control, cells were transformed with pGV1056 (FIG. 23, empty vector control) instead of pGV1390. The transformants were plated onto appropriate selection plates. Single colonies from the transformation were isolated and tested for isobutanol production by fermentation.

TABLE EX6-1

| pGV# | Promoter | Gene | Plasmid type | Plasmid marker |
|---|---|---|---|---|
| pGV1254 | Sc TEF1 | *L. lactis* kivD | High copy | Sc URA3 |
| pGV1295 | Sc TDH3 | *E. coli* ilvC | High copy | Sc TRP1 |
| pGV1390 | Sc CUP1 | *L. lactis* alsS | High copy | Sc HIS3 |
| pGV1438 | Sc TDH3 | *E. coli* ilvD | High copy | Sc LEU1 |

The cells were grown overnight and anaerobic batch fermentations were carried out as described in General Methods. SC-HWUL was used as the media. 2 mL samples were taken at 24, 48 and 72 hours for GC At each time point, the cultures were fed 2 mL of a 40% glucose solution. The fermentation was ended after 72 hours. Samples were processed and analyzed as described. The results are shown in Table EX6-2. As shown, isobutanol was produced in GEVO1187 transformed with the isobutanol-pathway containing plasmids.

TABLE EX6-2

Isobutanol production in *S. cerevisiae*, GEVO1187, after 72 hours

| Strain | Plasmids | Isobutanol Titer [g $L^{-1}$] | Isobutanol Yield [%] | Ethanol Titer [$gL^{-1}$] | Ethanol Yield [%] |
|---|---|---|---|---|---|
| GEVO1187 | pGV1254, pGV1438, pGV1390, pGV1438 | 0.13 | 0.31 | 31 | 60 |
| GEVO1187 | pGV1056, pGV1295, pGV1438, pGV1254 | 0.04 | 0.10 | 42 | 82 |

This example demonstrates isobutanol production in a Pdc-minus member of the *Saccharomyces* clade, Crabtree-negative, pre-WGD yeast, *K. lactis*.

Figure 20:
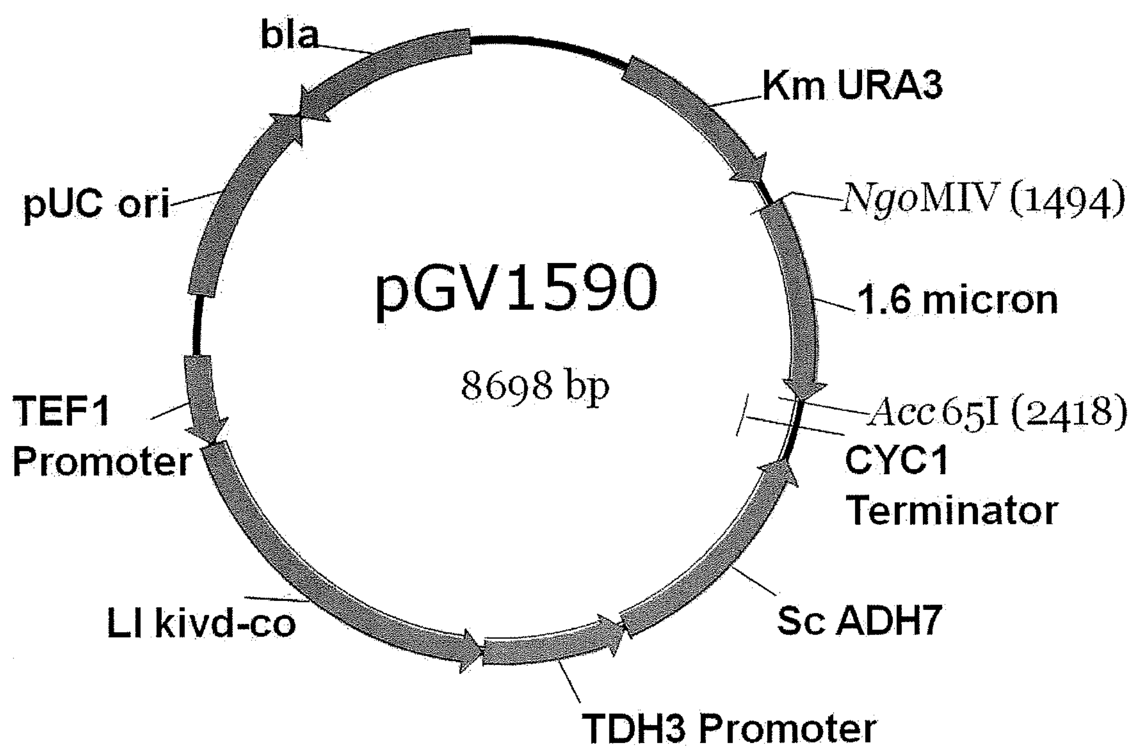
FIG. 20 illustrates a schematic map of plasmid pGV1590.
Figure 21:
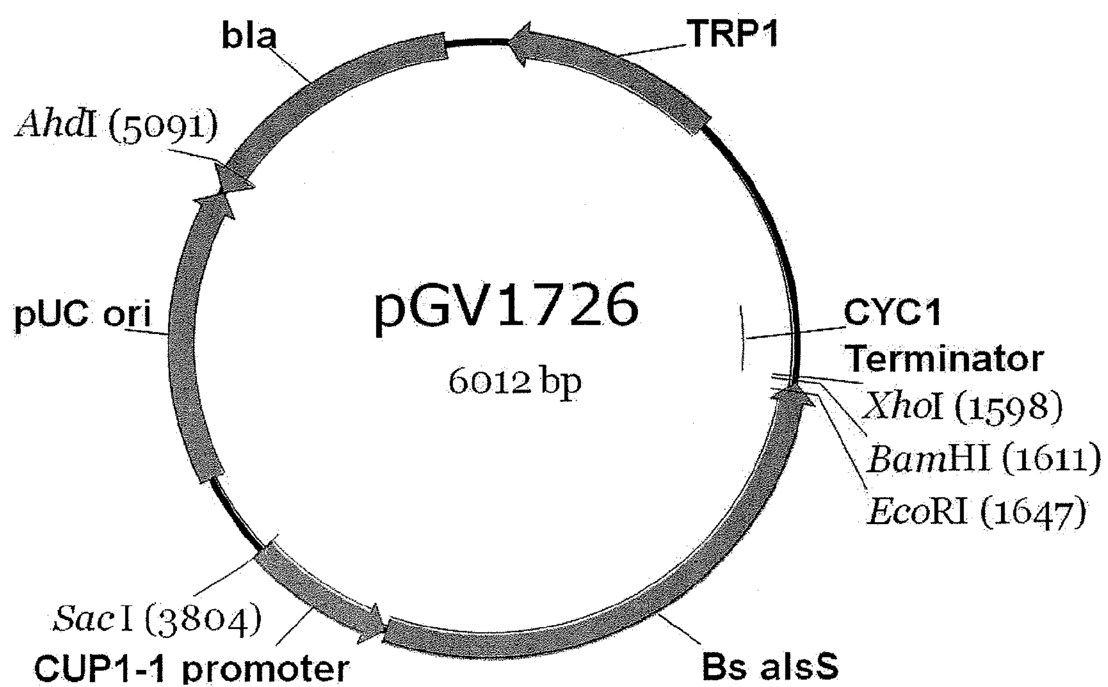
FIG. 21 illustrates a schematic map of plasmid pGV1726.
Figure 22:
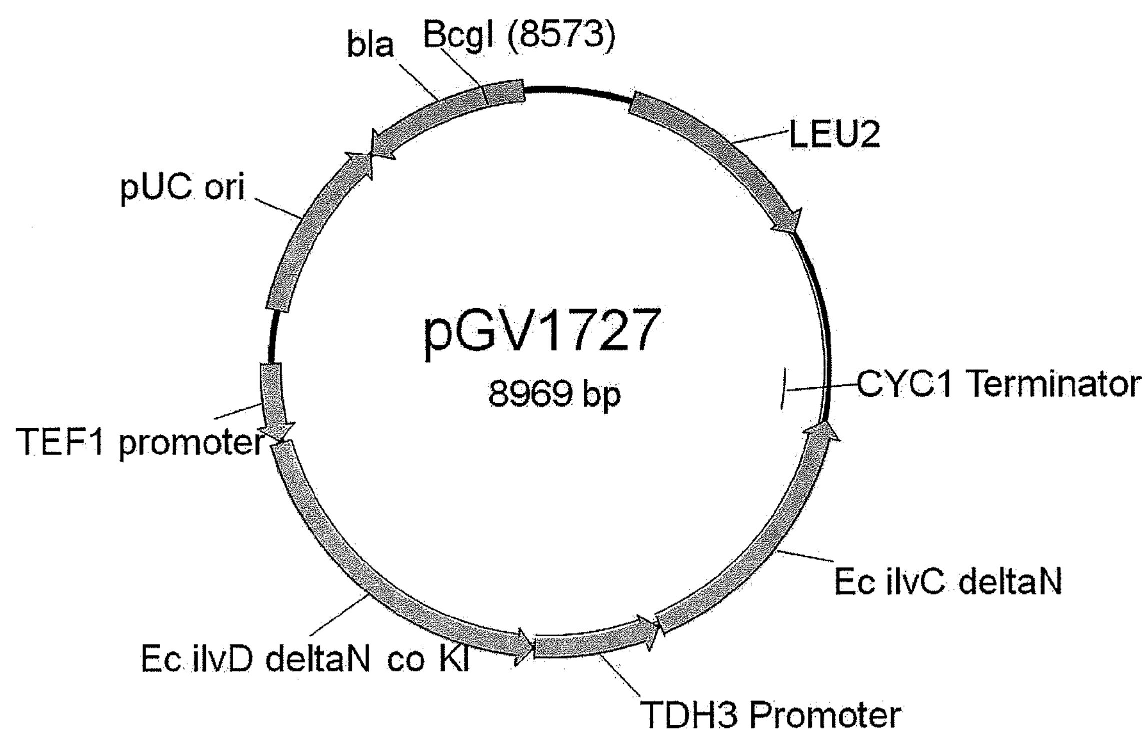
FIG. 22 illustrates a schematic map of plasmid pGV1727.

Description of plasmids pGV1590, pGV1726, pGV1727: pGV1590 (FIG. 20, SEQ ID NO: 14) is a *K. lactis* expression plasmid used to express *L. lactis* kivD (under TEF1 promoter) and *S. cerevisiae* ADH7 (under TDH3 promoter). This plasmid also carries the *K. marxianus* URA3 gene and the 1.6 micron replication origin that allow for DNA replication in *K. lactis*. pGV1726 (FIG. 21, SEQ ID NO: 15) is a yeast integration plasmid carrying the TRP1 marker and expressing *B. subtilis* alsS using the CUP1 promoter. pGV1727 (FIG. 22, SEQ ID NO: 16) is a yeast integration plasmid carrying the LEU2 marker and expressing *E. coli* ilvD under the TEF1 promoter and *E. coli* ilvC under the TDH3 promoter. Neither pGV1726 or pGV1727 carry a yeast replication origin.

Construction of GEVO1829, a *K. lactis* strain with pathway integrated: The isobutanol pathway was introduced into the Pdc-minus *K. lactis* strain GEVO1742 by random integrations of the pathway genes. GEVO1742 was transformed with the Acc65I-NgoMIV fragment of pGV1590 containing the *L. lactis* kivd and *S. cerevisiae* ADH7 but without the yeast replication origin, to generate GEVO1794. The presence of both *L. lactis* kivd and *S. cerevisiae* ADH7 was confirmed by colony PCR using primer sets 1334+1335 and 1338+1339, respectively. GEVO1794 was transformed with pGV1727, a yeast integration plasmid carrying *E. coli* ilvD (under the TEF1 promoter) and *E. coli* ilvC (under TDH3 promoter), that had been linearized by digesting with BcgI. The resulting strain, GEVO1818, was confirmed by colony PCR for the presence of *E. coli* ilvD and *E. coli* ilvC using primer sets 1330+1331 and 1325+1328, respectively. GEVO1818 was then transformed with pGV1726, a yeast integration plasmid carrying *B. subtilis* alsS (under the CUP1 promoter), that had been linearized by digesting with AhdI to generate GEVO1829. The presence of *B. subtilis* alsS was confirmed by colony PCR using primers 1321+1324.

Aerobic fermentations were carried out to test isobutanol production by the Pdc-minus strain carrying the isobutanol pathway, GEVO1829. The Pdc-minus strain without the isobutanol pathway, GEVO1742, was used as a control. These strains were cultured in YPD overnight at 30° C., 250 rpm, then diluted into 20 mL fresh YPD in a 125 mL flask and grown at 30° C., 250 rpm. 2 mL samples were taken at 24 and 48 hours, cells pelleted for 5 minutes at 14,000×g and the supernatant was analyzed for isobutanol by GC. In addition glucose concentrations were analyzed by LC. The results are shown in Table EX7-1. At 48 hours, the OD of the GEVO1742 strain had reached over 8.5 while the OD of the GEVO1829 was less than 5. GEVO1829 consumed around 15.7 g/L glucose while GEVO1742 consumed roughly 7.7 g/L glucose. GEVO1829 produced 0.17 g/L isobutanol while GEVO1742 did not produce any isobutanol above media background.

TABLE EX7-1

*K. lactis* fermentation results

| Clone | Isobutanol titer (mg/L) | Isobutanol yield (% theoretical) | Ethanol (mg/L) |
|---|---|---|---|
| GEVO1742 | 0 | 0 | 17 |
| GEVO1829 | 170 | 2.6 | 53 |

Example 8A

Isobutanol Production in Pdc-Minus *S. cerevisiae* GEVO1581

This example demonstrates isobutanol production in a Pdc-minus member of the *Saccharomyces sensu stricto* group, *Saccharomyces* clade yeast, Crabtree-positive yeast, post-WGD yeast, *S. cerevisiae.*

Figure 26:
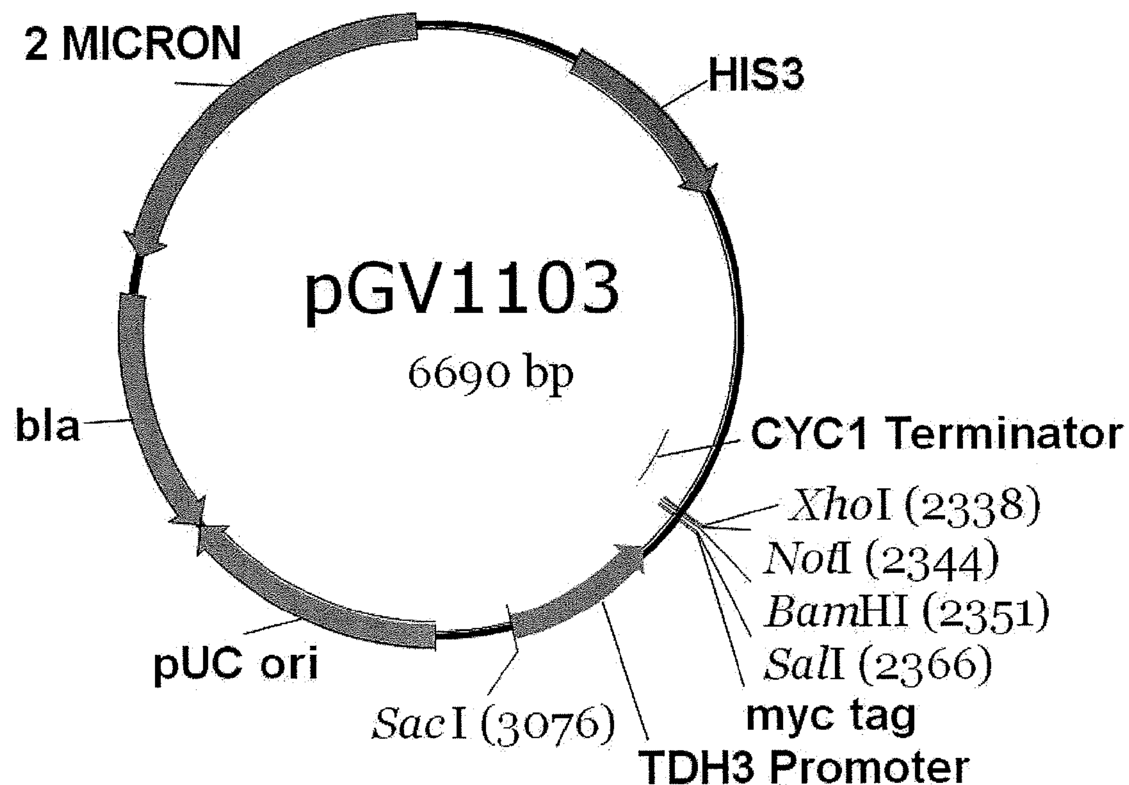
FIG. 26 illustrates a schematic map of plasmid pGV1103.
Figure 27:
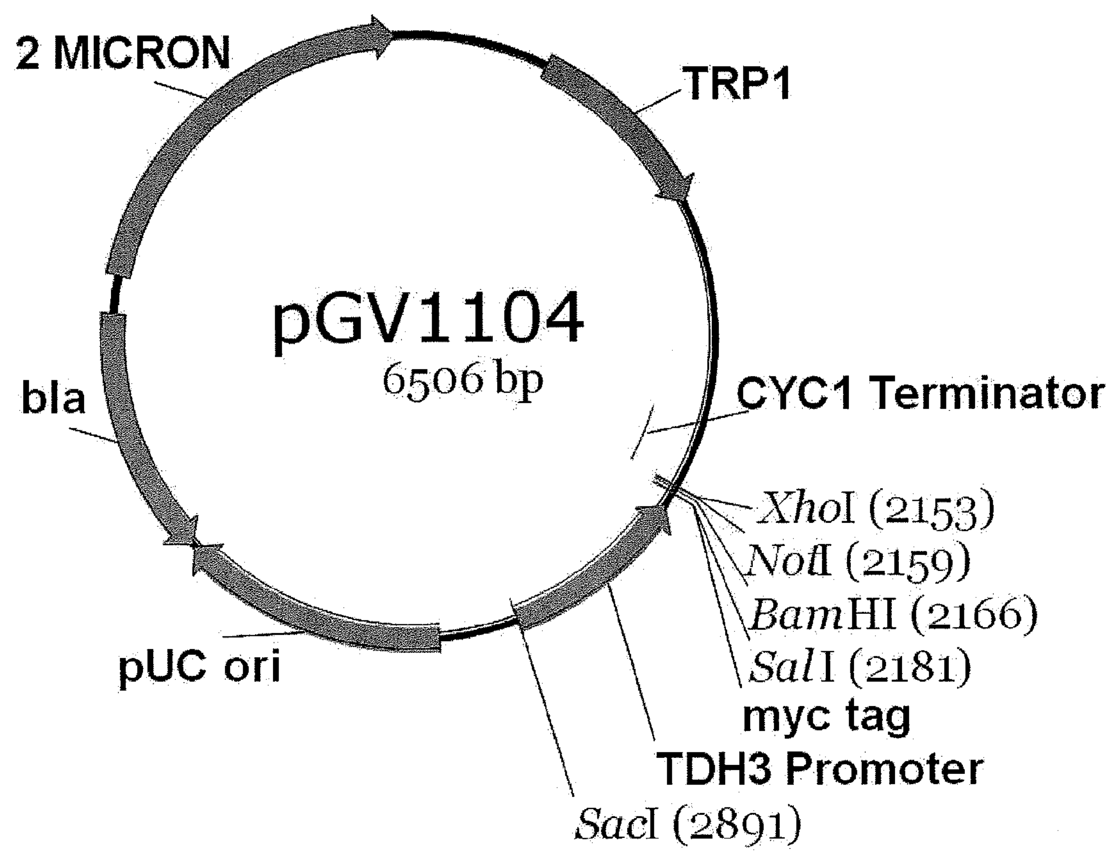
FIG. 27 illustrates a schematic map of plasmid pGV1104.
Figure 28:
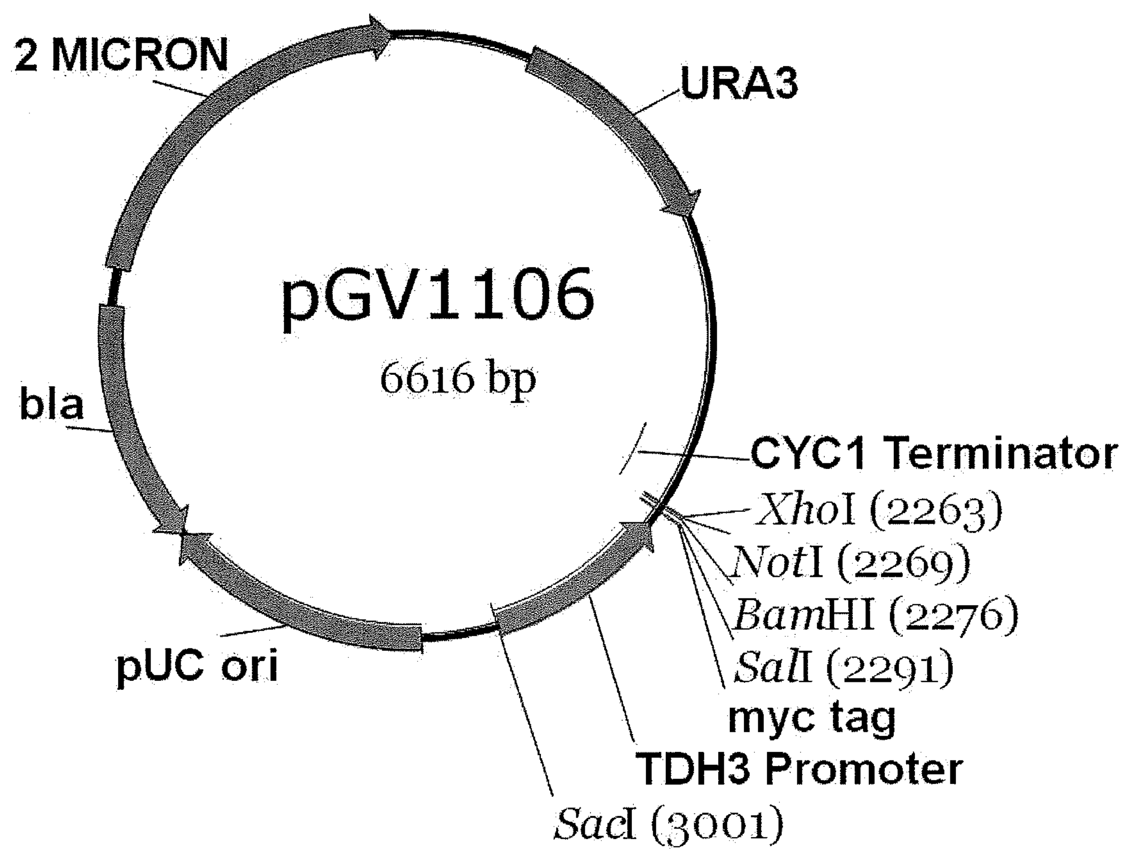
FIG. 28 illustrates a schematic map of plasmid pGV1106.
Figure 29:
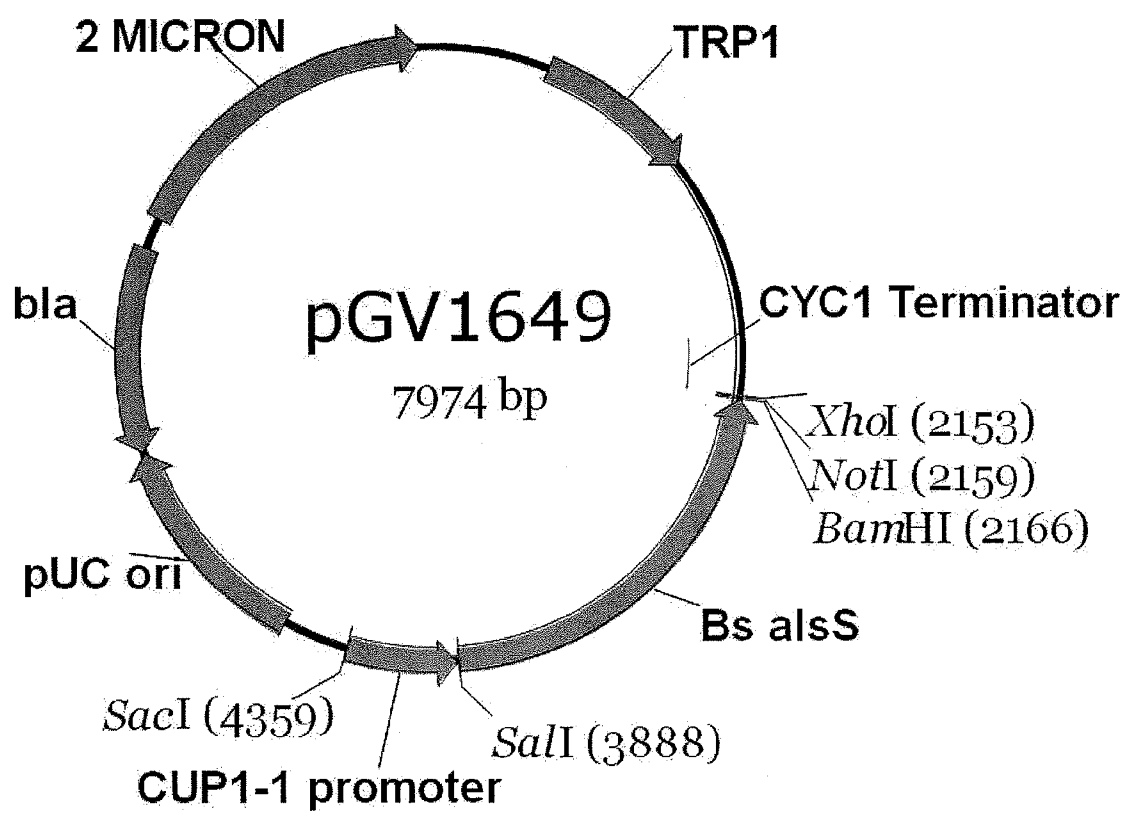
FIG. 29 illustrates a schematic map of plasmid pGV1649.
Figure 30:
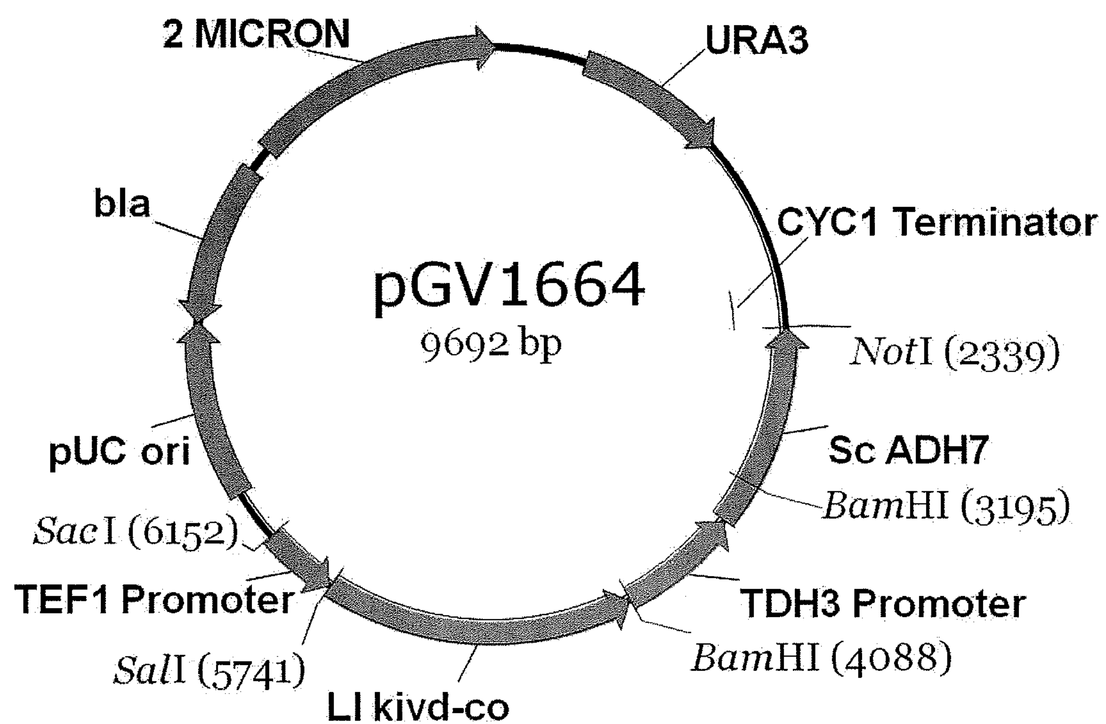
FIG. 30 illustrates a schematic map of plasmid pGV1664.
Figure 32:
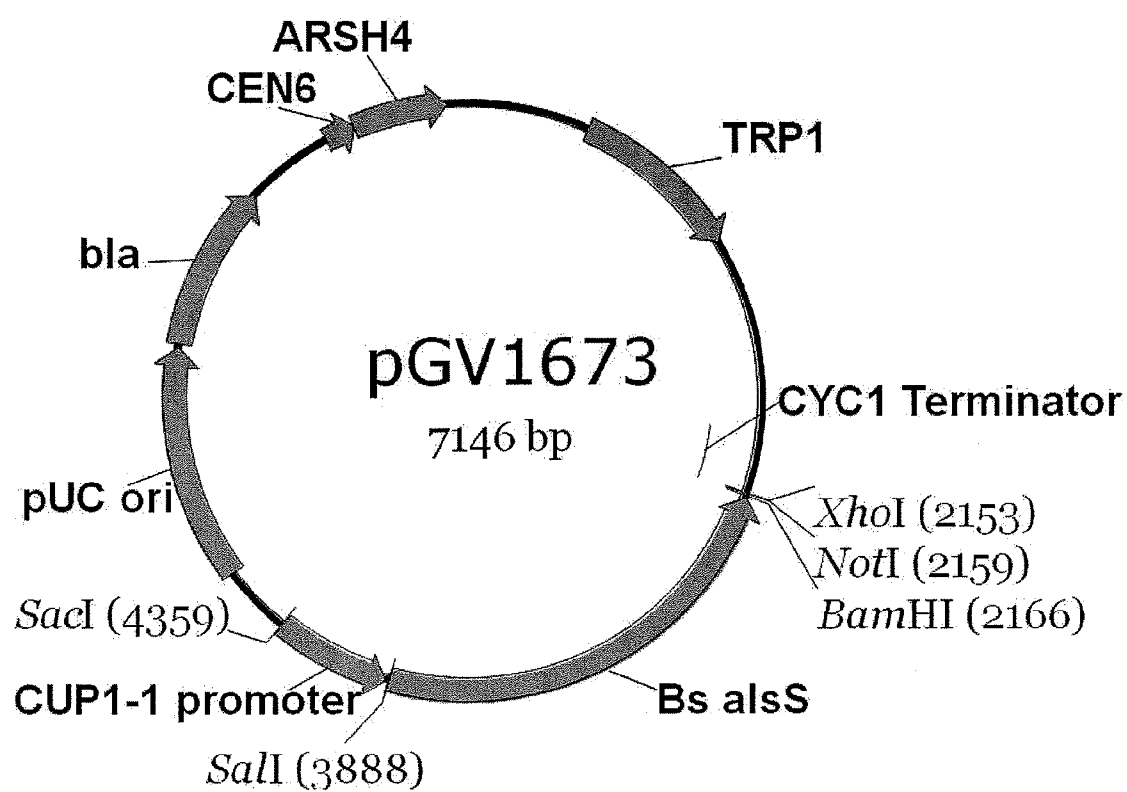
FIG. 32 illustrates a schematic map of plasmid pGV1673.
Figure 33:
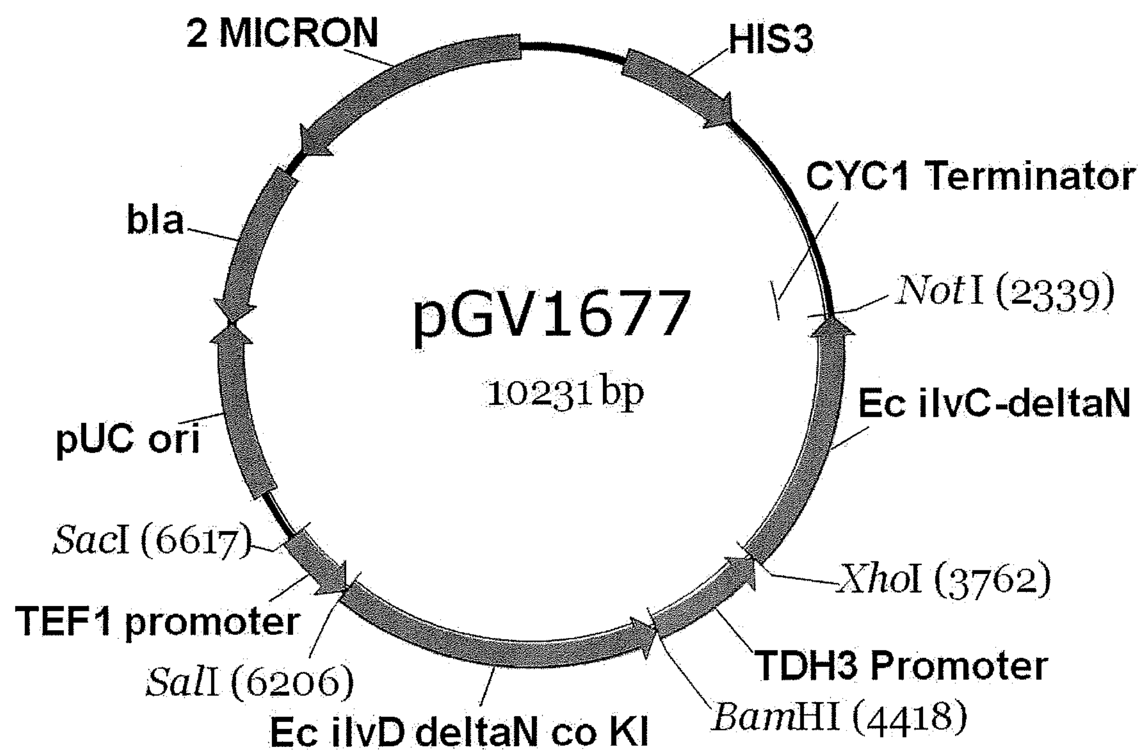
FIG. 33 illustrates a schematic map of plasmid pGV1677.

Strain GEVO1581 with the three genes encoding PDC activity deleted (pdc1Δ, pdc5Δ, and pdc6Δ) was used to produce isobutanol. Isobutanol pathway enzymes were encoded by genes cloned into three plasmids. pGV1103 (FIG. 26, SEQ ID NO: 20), pGV1104 (FIG. 27, SEQ ID NO: 21) and pGV1106 (FIG. 28, SEQ ID NO: 22) were empty high copy expression vectors that carry as marker genes, URA3, HIS3 and TRP1, respectively. The *B. subtilis* alsS gene, express using the CUP1 promoter, was encoded on either a low copy CEN plasmid, pGV1673 (FIG. 32, SEQ ID NO: 26) or a high copy plasmid, pGV1649 (FIG. 29, SEQ ID NO: 23). Both of these plasmids used TRP1 as a marker gene. *E. coli* ilvD (expressed using the TEF1 promoter) and *E. coli* ilvC (expressed using the TDH3 promoter) were expressed off of the high copy plasmid pGV1677 (FIG. 33, SEQ ID NO: 27). This plasmid utilized HIS3 as a marker gene. *L. lactis* kivD (expressed using the TEF1 promoter) and *S. cerevisiae* ADH7 (expressed using the TDH3 promoter) were expressed off of the high copy plasmid pGV1664 (FIG. 30, SEQ ID NO: 24). This plasmid utilized URA3 as a marker gene. Combination of these plasmids (Table EX8-1) to reconstitute the isobutanol pathway were introduced into GEVO1581 by lithium acetate transformation (described in General Methods).

TABLE EX8-1

Plasmids transformed into GEVO1581

| Fermentation # | Strain | Plasmids | Notes |
|---|---|---|---|
| iB250 | GEVO1581 | pGV1103, pGV1104, pGV1106 | Vector Control |
| iB251 | GEVO1581 | pGV1677, pGV1649, pGV1664 | iBuOH Pathway, alsS on 2 micron plasmid |
| iB252 | GEVO1581 | pGV1677, pGV1673, pGV1664 | iBuOH Pathway, alsS on CEN plasmid |

Fermentation experiments were carried out with GEVO1581 transformed with plasmids according to Table EX8-1 to determine the amount of isobutanol produced (titer) and the percentage of isobutanol to consumed glucose (yield).

Fermentations with Transformants of GEVO1581: Using cells grown in 3 mL defined (SC–Ethanol) medium, 20 mL cultures were inoculated with transformants of GEVO1581 (3 independent colonies per transformation set) to an $OD_{600}$ of approximately 0.1. The cultures were incubated at 30° C. at 250 RPM in 125 mL metal cap flasks until they reached an $OD_{600}$ of approximately 1. Glucose was added to a final concentration of 5% and a 2 mL aliquot was removed from each sample (T=0 sample). The $OD_S$ of each sample was measured, the cells in each sample were pelleted by centrifugation (14,000×g, 5 min), and the supernatant from each sample was stored at −20° C. The remaining cultures were incubated at 30° C. at 125 RPM for another 48 hours. Samples (2 mL) were removed after 24 and 48 hours and prepared as just described. The samples were thawed, and prepared as described in General Methods. Three individual transformants were used for each set of plasmids during the fermentations. The amount of glucose consumed and the amount of pyruvate, glycerol, ethanol, and isobutanol produced after 48 hours are listed in Table EX8A-2.

TABLE EX8A-2

48 hour time point data are shown as an average of three replicates

| | Glucose consumed (g/L) | Isobutanol (mg/L) | Yield (% theoretical) |
|---|---|---|---|
| iB250 | 3.6 ± .7 | 4.7 ± 0.00 | 0.31 ± 0.04 |
| iB251 | 2.8 ± 1.6 | 122 ± 41 | 11.0 ± 5.0 |
| iB252 | 1.2 ± .5 | 62 ± 11 | 12.8 ± 2.8 |

Again using cells grown in 3 mL defined (SC–Ethanol) medium, 20 mL cultures were inoculated with transformants of GEVO1581 to an $OD_{600}$ of approximately 0.1. The cultures were incubated at 30° C. at 250 RPM in 125 mL metal cap flasks until they reached an $OD_{600}$ of approximately 1. Biomass was pelleted and resuspended in 20 ml media with 2% glucose as the sole carbon source and a 2 mL aliquot was removed from each sample (T=0 sample). The $OD_{600}$ of each sample was measured and each sample was stored at −20° C. The remaining cultures were incubated at 30° C. at 125 RPM for another 48 hours. Samples (2 mL) were removed after 24 and 48 hours and stored at −20° C. The samples were thawed, and prepared as described in General Methods. The amounts of ethanol and isobutanol produced after 48 hours are listed in Table EX8A-3.

TABLE EX8A-3

48 hour time point data for fermentation in glucose, shown as an average of three replicates

| | Isobutanol (mg/L) | Isobutanol yield (% theoretical) | Ethanol (mg/L) | Ethanol yield (% theoretical) |
|---|---|---|---|---|
| iB250 | 0 | 0 | 0 | 0 |
| iB251 | 210 | 3.5 | 110 | 1.8 |

Example 8B

Isobutanol Production in Pdc-Minus *S. cerevisiae* Gevo1584

This example demonstrates isobutanol production in a Pdc-minus member of the *Saccharomyces sensu stricto* group, *Saccharomyces* clade, Crabtree-positive yeast, WGD yeast, *S. cerevisiae.*

GEVO1581 is a diploid strain, thus, a second backcross of a Pdc-minus yeast into the CEN.PK background was performed, yielding a Pdc-minus haploid strain GEVO1584 with the required auxotrophic markers for plasmid propagation.

Figure 24:
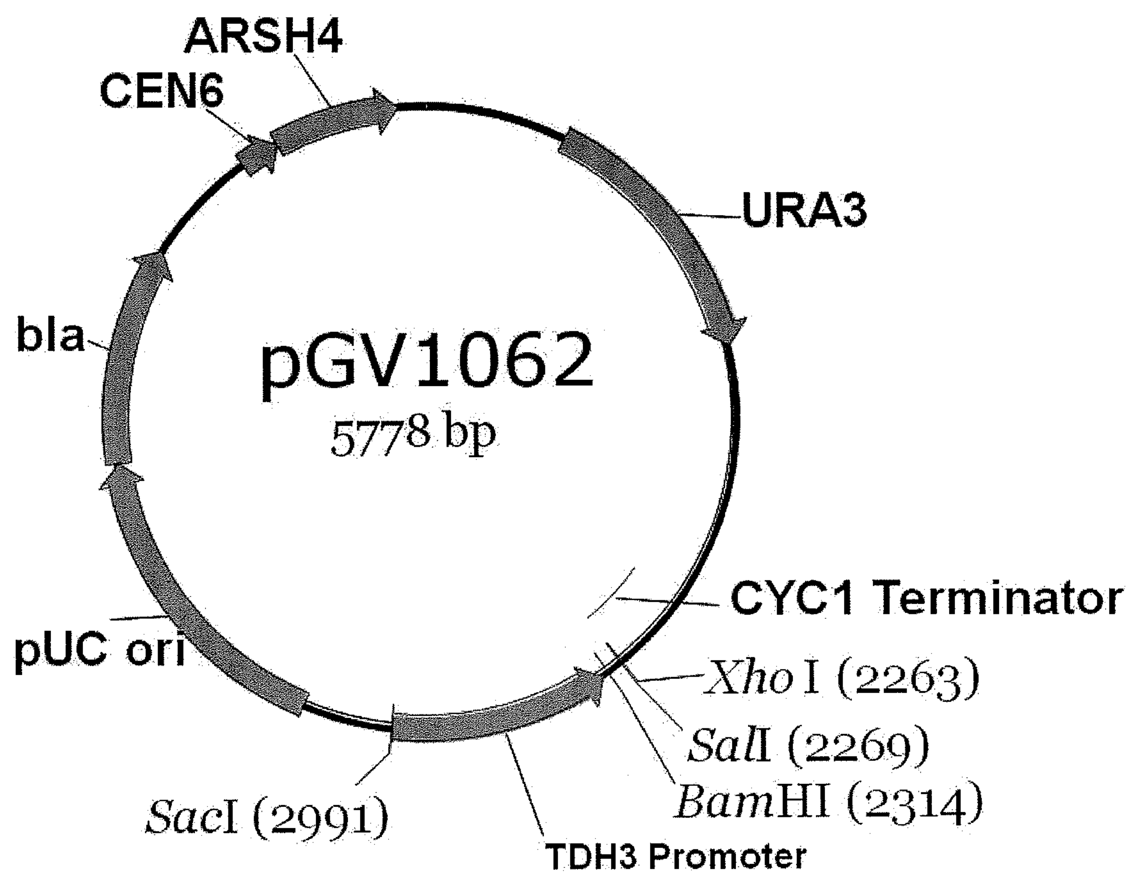
FIG. 24 illustrates a schematic map of plasmid pGV1062.
Figure 25:
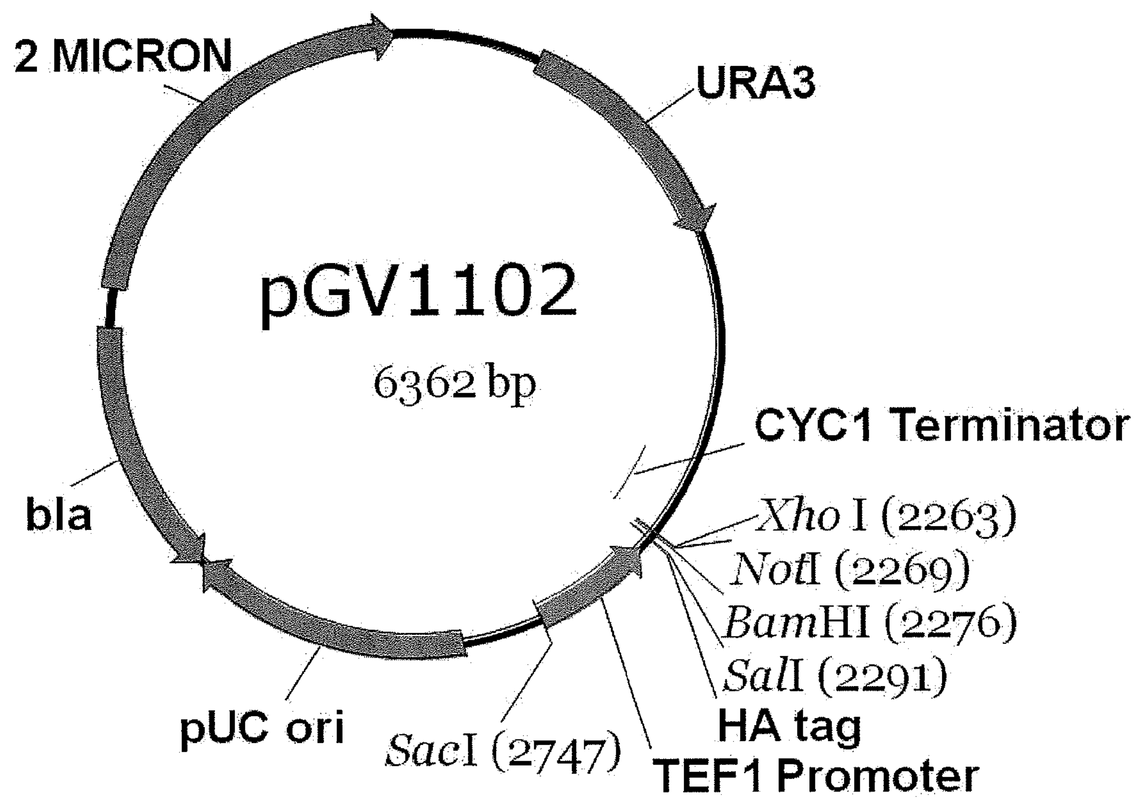
FIG. 25 illustrates a schematic map of plasmid pGV1102.
Figure 31:
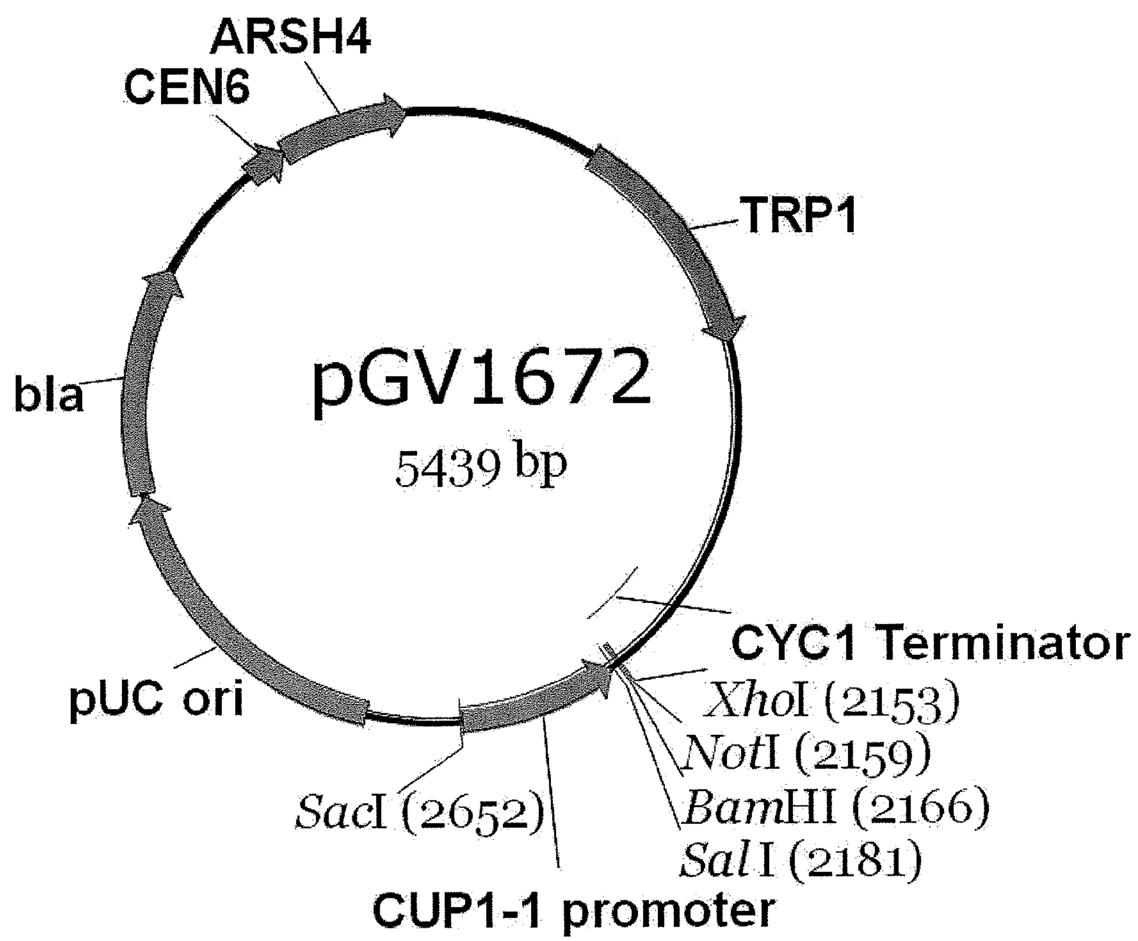
FIG. 31 illustrates a schematic map of plasmid pGV1672.
Figure 34:
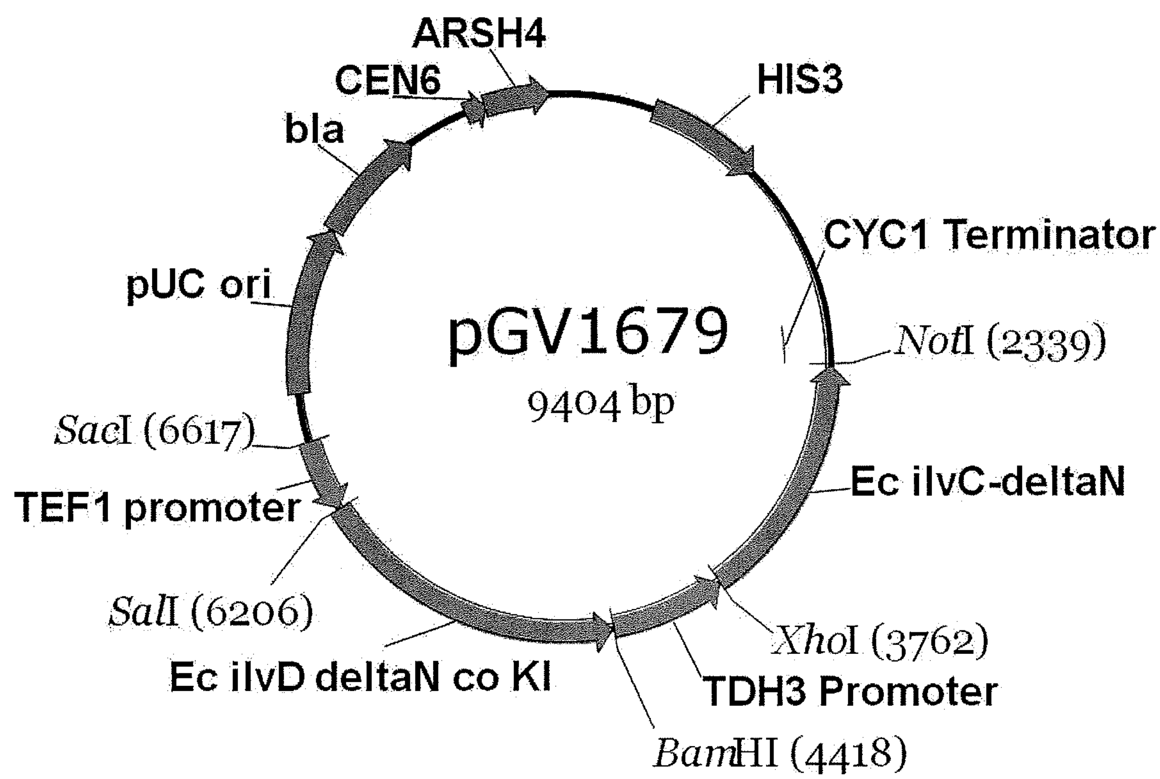
FIG. 34 illustrates a schematic map of plasmid pGV1679.
Figure 35:
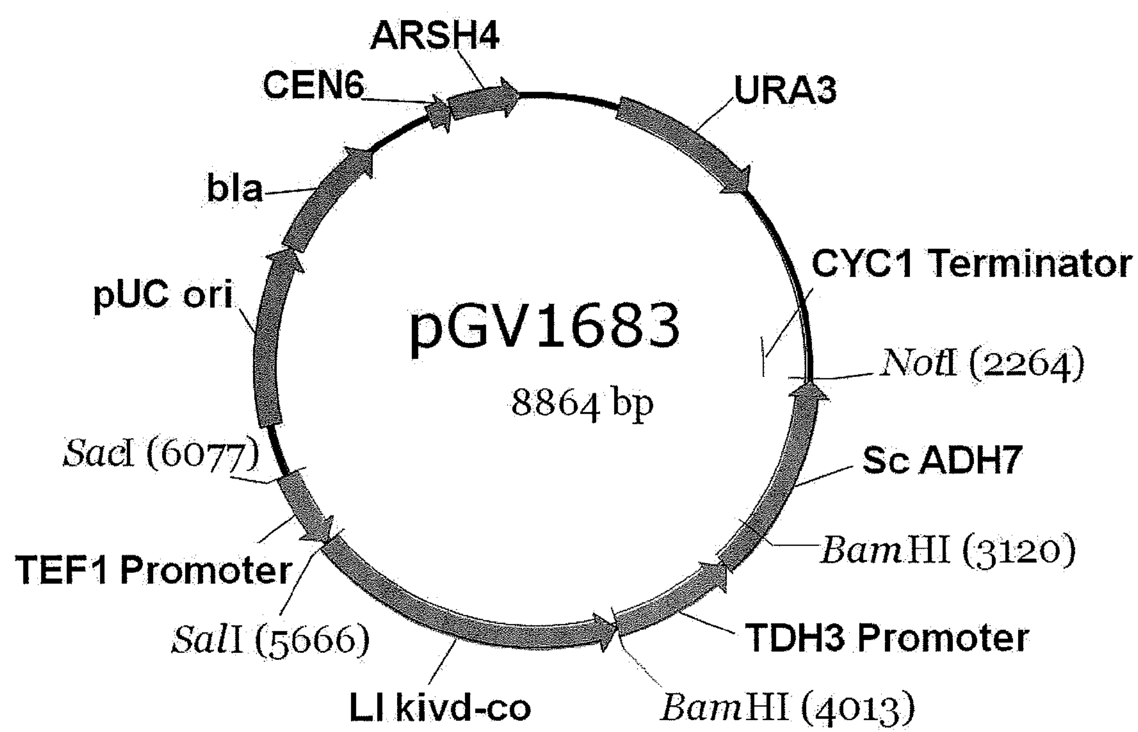
FIG. 35 illustrates a schematic map of plasmid pGV1683.

Transformations of GEVO1584: The following combinations of plasmids were transformed into GEVO1584 (Table EX8B-1) using lithium acetate transformation (described in General Methods) followed by selection on appropriate minimal media. pGV1672 (FIG. 31, SEQ ID NO: 25), pGV1056 (FIG. 23, SEQ ID NO: 17), and pGV1062 (FIG. 24, SEQ ID NO: 18) were empty low copy CEN expression vectors that carry as marker genes, TRP1, HIS3, and URA3. pGV1103 (FIG. 26, SEQ ID NO: 20), pGV1104 (FIG. 27, SEQ ID NO: 21) and pGV1102 (FIG. 25, SEQ ID NO: 19) were empty high copy expression vectors that carry as marker genes, URA3, HIS3 and TRP1, respectively. The isobutanol pathway was expressed off of low copy CEN plasmids pGV1673 (FIG. 32, SEQ ID NO: 26), pGV1679 (FIG. 34, SEQ ID NO: 28) and pGV1683 (FIG. 35, SEQ ID NO: 29). pGV1673 carried the *B. subtilis* alsS under the CUP1 promoter and utilized the TRP1 marker gene. pGV1679 carried the *E. coli* ilvD and *E. coli* ilvC genes expressed using the TEF1 and TDH3 promoters, respectively, and utilized the HIS3 marker gene. pGV1683 carried the *L. lactis* kivd and the *S. cerevisiae* ADH7 genes expressed using the TEF1 and TDH3 promoters, respectively, and utilized the URA3 marker gene. The isobutanol pathway was also expressed off of high copy plasmids pGV1649 (FIG. 29, SEQ ID NO: 23), pGV1677 (FIG. 33, SEQ ID NO: 27) and pGV1664 (FIG. 30, SEQ ID NO: 24). pGV1649 carried the *B. subtilis* alsS under the CUP1 promoter and utilized the TRP1 marker gene. pGV1677 carried the *E. coli* ilvD and *E. coli* ilvC genes expressed using the TEF1 and TDH3 promoters, respectively, and utilized the HIS3 marker gene. pGV1664 carried the *L. lactis* kivd and the *S. cerevisiae* ADH7 genes expressed using the TEF1 and TDH3 promoters, respectively, and utilized the URA3 marker gene.

TABLE EX8B-1

| Fermentation # | Strain | Plasmids | Notes |
|---|---|---|---|
| iB300 | GEVO1584 | pGV1672, pGV1056, pGV1062 | Vector Control (CEN plasmids) |
| iB301 | GEVO1584 | pGV1673, pGV1679, pGV1683 | Isobutanol pathway (CEN plasmids) |
| iB302 | GEVO1584 | pGV1103, pGV1104, pGV1102 | Vector Control (2μ plasmids) |
| iB303 | GEVO1584 | pGV1677, pGV1649, pGV1664 | Isobutanol pathway (2μ plasmids) |

Fermentations with Transformants of GEVO1584: Using cells grown in 3 mL defined (SC) media containing ethanol (SC+Ethanol-HWU), 200 mL cultures were inoculated with transformants of GEVO1584 and incubated in SC+Ethanol-HWU at 30° C. at 250 RPM in 500 mL shake flasks for 72 hours. The $OD_{600}$ values measured after 72 hours ranged from 1.4 to 3.5. The cultures were diluted 1:10 into fresh 250 mL SC+Ethanol-HWU media and incubated at 30° C. at 250 RPM in 500 mL shake for 24 hours. The cells were collected by centrifugation at 3000 RPM for 3 minutes and resuspended in 20 mL SC+Glucose-HWU media in 125 mL metal cap flasks. 250 μL of 100% ethanol was added to each culture to bring the concentration of ethanol to 1%. A 2 mL aliquot was removed, the $OD_{600}$ was measured using 100 μL, and the remaining aliquot was centrifuged to pellet cells (14,000×g, 5 min) and the supernatants were stored at −20° C. The cultures were incubated at 125 rpm at 30° C. A 2 mL aliquot was removed from each culture after 24 and 48 hours of incubation, and the $OD_S$ was measured as before (see Table 3, t=24 and t=48) and the sample centrifuged and stored as described above. The samples were thawed, and the samples were prepared and analyzed via GC and HPLC as described in General Methods. Results are shown in Table EX8B-2.

TABLE EX8B-2

48 hour time point data are shown as an average of three replicates

| Fermentation # | | Isobutanol Titer (g/L) | Glucose Consumed (g/L) | Ethanol Consumed (g/L) | Yield (% theor.)] |
|---|---|---|---|---|---|
| iB300 | Vector Control (CEN plasmids) | 0.012 ± 0.003 | 9.75 ± 4.17 | 2.47 ± 0.30 | 0.30% |
| iB301 | Isobutanol pathway (CEN plasmids) | 0.392 ± 0.087 | 9.31 ± 5.03 | 0.95 ± 0.64 | 10.27% |
| iB302 | Vector Control (2μ plasmids) | 0.013 ± 0.006 | 8.61 ± 4.51 | 0.64 ± 0.17 | 0.37% |
| iB303 | Isobutanol pathway (2μ plasmids) | 0.248 ± 0.032 | 9.51 ± 1.25 | 0.77 ± 0.59 | 6.36% |

All Pdc-minus yeast (GEVO1584) consumed approximately 10 g/L of glucose and less than 2 g/L of ethanol after 48 hours. All strains accumulated ~1.5 g/L pyruvate, except for those carrying the isobutanol pathway on 2p plasmids (<0.5 g/L). The accumulation of pyruvate and failure of the yeast to produce ethanol from glucose is confirmation that all lacked PDC activity. After 48 hours, the Pdc-minus yeast with the isobutanol pathway encoded on 2p plasmids generated 0.248±0.032 g/L isobutanol at a theoretical yield of 6.36% of the consumed glucose (Table EX8B-2). The CEN plasmid isobutanol pathway strain generated 0.392±0.087 g/L isobutanol at a yield of 10.27% (Table EX8B-2). Isobutanol titers were well above the equivalent vector control strains.

Example 9

High-Yield Isobutanol Fermentation Using Crabtree-Negative Pdc-Minus and GPD-Minus *K. lactis*

In yeast, excess NADH is oxidized to NAD+ through the generation of glycerol. The key enzyme involved in this reaction is the glycerol 3-phosphate dehydrogenase. Deletion of the gene encoding this protein, Kl-Gpd1p, would eliminate loss of NADH as well as carbons from glucose. This would lead to an increased yield of isobutanol.

Figure 36:
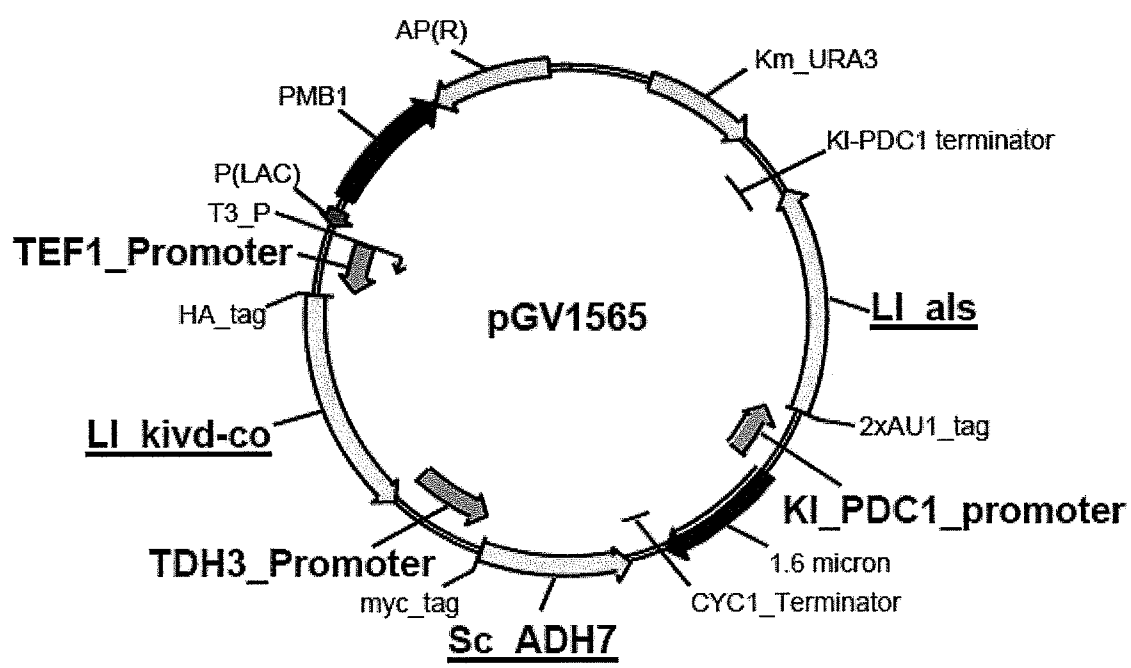
FIG. 36 illustrates a schematic map of plasmid pGV1565.
Figure 37:
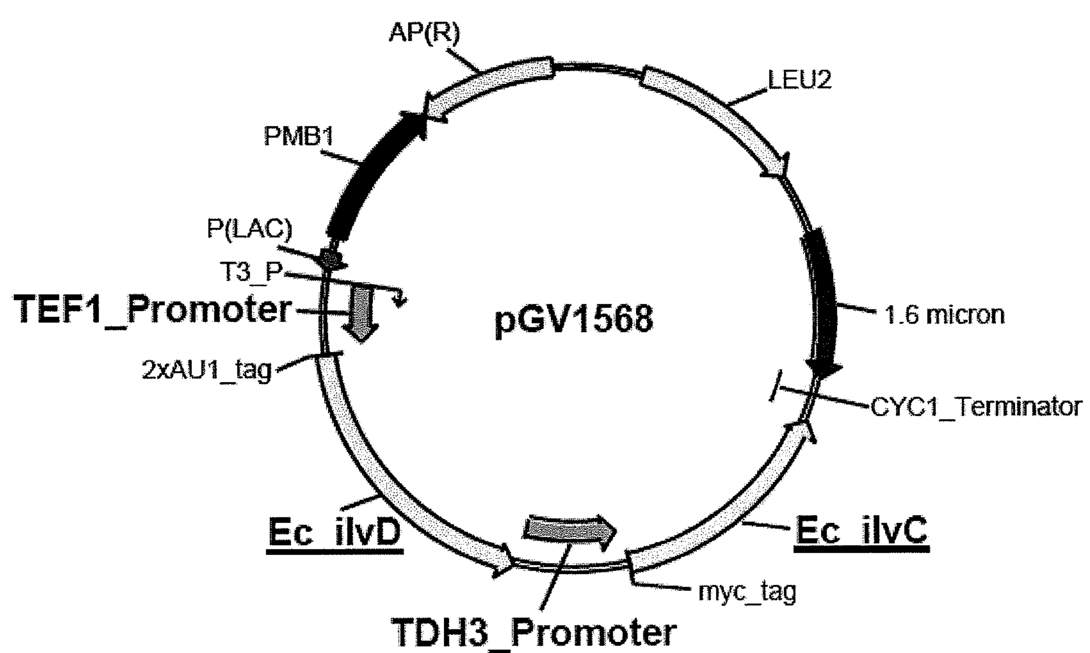
FIG. 37 illustrates a schematic map of plasmid pGV1568.
Figure 38:
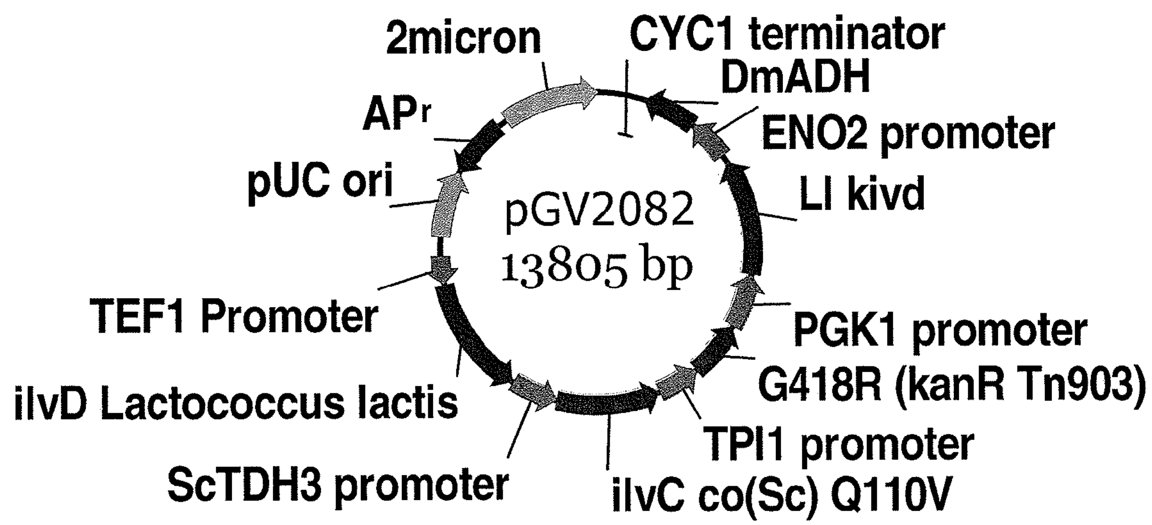
FIG. 38 illustrates a schematic map of plasmid pGV2082.
Figure 39:
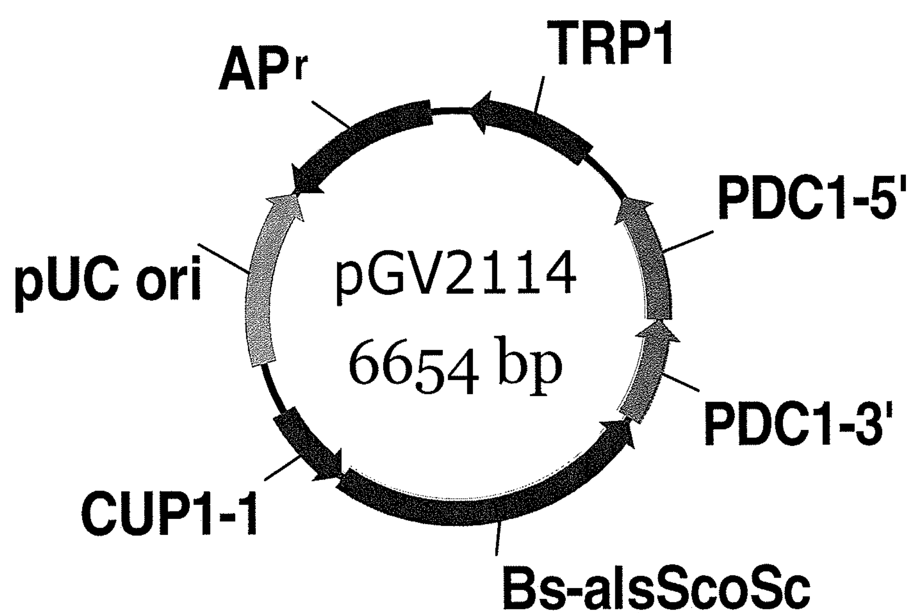
FIG. 39 illustrates a schematic map of plasmid pGV2114.
Figure 40:
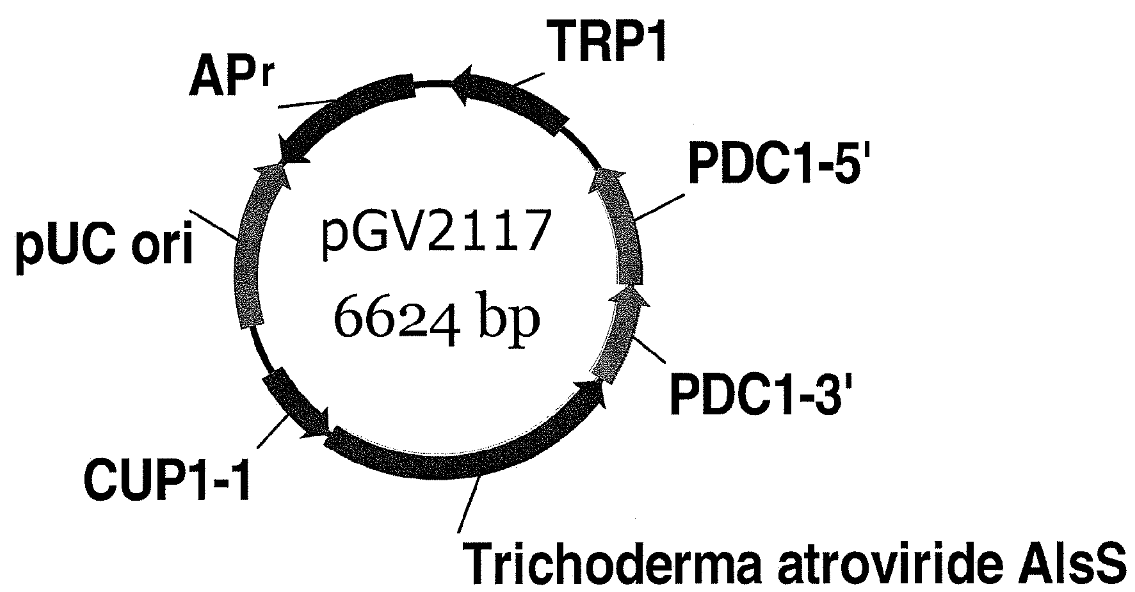
FIG. 40 illustrates a schematic map of plasmid pGV2117.
Figure 41:
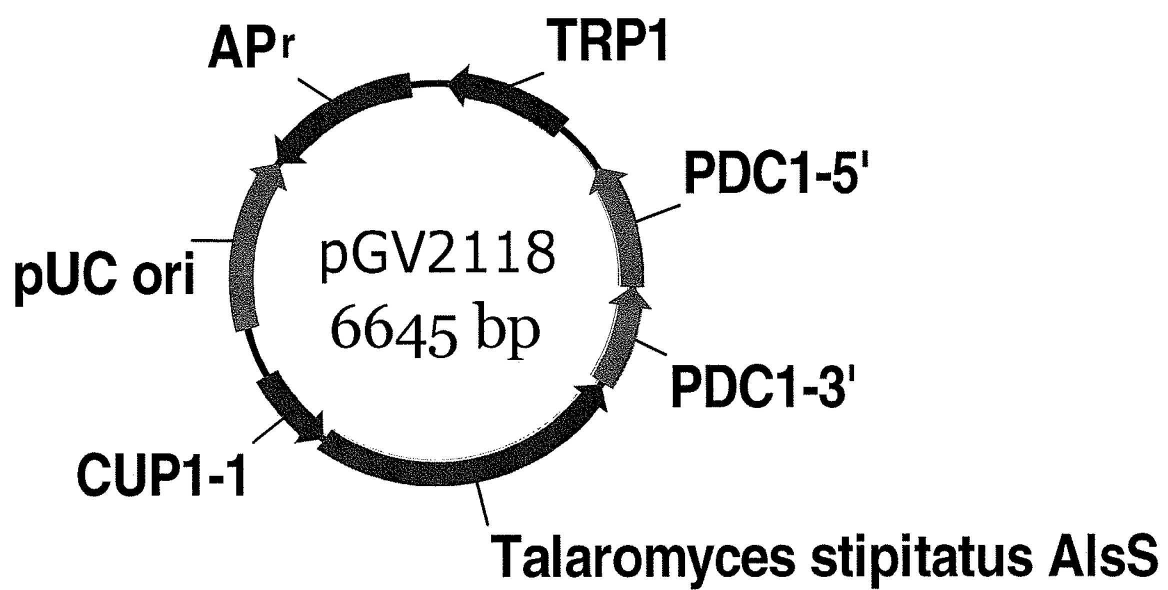
FIG. 41 illustrates a schematic map of plasmid pGV2118.

The PDC-minus *K. lactis* strain, GEVO1488, is engineered to delete GPD1 gene of *K. lactis*. This PDC-minus GPD-minus strain is transformed with pGV1565 and pGV1568 (FIG. 36 and FIG. 37). These transformants are then subjected to anaerobic batch fermentation and samples analyzed as described. As shown in Table EX9-1, the additional deletion of GPD1 is expected to result in a significant increase in isobutanol yield.

Example 10

High-Yield Isobutanol Fermentation Using Crabtree-Negative PDC-Minus and GPD-Minus *K. lactis* with Balanced Isobutanol Pathway Yield is further increased by the use of a pathway in which there is a balanced usage of NADH and NADPH. This balance is accomplished by the use of an engineered ilvC which is able to utilize NADH and the NADH-dependent alcohol dehydrogenase, Adh2. These constructs are used to express the isobutanol pathway in a PDC-minus and GPD-minus *K. lactis*. This strain is subjected to anaerobic batch fermentation as described above and samples are analyzed for isobutanol. As shown in Table EX9-1, the yield of isobutanol using this pathway in a PDC-minus *K. lactis* is expected to result in a significant increase in yield.

Example 11

High-Yield Isobutanol Fermentation Using Crabtree-Negative PDC-Minus and GPD-Minus *K. lactis* with Balanced Isobutanol Pathway An alternative route to balancing the NADH and NADPH usage is to overexpress an $NADP^+$-dependent glyceraldehyde 3-phosphate dehydrogenase (GAPDH) in addition to the endogenous $NAD^+$-dependent GAPDH, such that both NADH and NADPH are generated from glycolysis. The isobutanol pathway can utilize an NADPH-dependent KARI enzyme and the NADH-dependent Adh2p. In this case, PDC-minus and GPD-minus *K. lactis* is transformed with a construct expressing a NADP+-dependent GAPDH and an isobutanol pathway using Adh2. This strain is subjected to anaerobic batch fermentation as described above and samples analyzed for isobutanol. As shown in Table EX9-1, introduction of this $NADP^+$-dependent GAPDH is expected to result in a significant increase in productivity of isobutanol.

Example 12

High-Yield Isobutanol Fermentation Using Crabtree-Negative PDC-Minus and GPD-Minus *K. lactis* with Balanced Isobutanol Pathway Yet another alternative route to balancing the NADH and NADPH usage is to replace the endogenous $NAD^+$-dependent GAPDH with an $NADP^+$-dependent GAPDH in a PDC-minus and GPD-minus *K. lactis*. This strain is transformed with the isobutanol pathway and subjected to anaerobic batch fermentation as described above and samples analyzed for isobutanol. As shown in Table EX9-1, introduction of this $NADP^+$-dependent GAPDH is expected to result in a significant increase in productivity of isobutanol.

TABLE EX9-1

Isobutanol productivity in *K. lactis* strains after 48 hours. (Listed numbers for the pdc-minus strains are expected numbers).

| | | Isobutanol | | Ethanol | |
|---|---|---|---|---|---|
| Genotype | Plasmid | Titer [g $L^{-1}$] | Yield [%] | Titer [g $L^{-1}$] | Yield [%] |
| PDC+ GPD+ | pathway genes | 0.25 | 1.5 | 12.6 | 62 |
| pdc− GPD+ | pathway genes | 8.2 | 50 | 0.01 | 0.05 |
| pdc− gpd− | pathway genes | 11.5 | 70 | 0.01 | 0.05 |
| pdc− gpd− | balanced pathway (NADH utilizing pathway) | 13.2 | 80 | 0.01 | 0.05 |
| pdc− gpd− | balanced pathway (NADH and NADPH production from glycolysis) | 13.2 | 80 | 0.01 | 0.05 |
| pdc− gpd− | balanced pathway (NADPH production from glycolysis) | 13.2 | 80 | 0.01 | 0.05 |

Example 13

High-Yield Isobutanol Fermentation Using Crabtree-Positive PDC-Minus and GPD-Minus *S. cerevisiae*

The PDC-minus *S. cerevisiae* strain is engineered to delete both GPD1 and GPD2. This PDC-minus GPD-minus strain is transformed with plasmids expressing the isobutanol pathway in *S. cerevisiae*. These transformants are then subjected to anaerobic batch fermentation and samples analyzed as described. As is seen in Table EX13-1, the additional deletions of GPD1 and GPD2 is expected to result in a significant increase in isobutanol yield.

Example 14

High-Yield Isobutanol Fermentation Using Crabtree-Positive PDC-Minus and GPD-Minus *S. cerevisiae* with Balanced Isobutanol Pathway Yield is further increased by the use of a pathway in which there is balanced usage of NADH and NADPH usage. This balance is accomplished by the use of an engineered KARI which is able to utilize NADH and the NADH-dependent alcohol dehydrogenase, Adh2p. These constructs are used to express the isobutanol pathway in a PDC-minus and GPD-minus *S. cerevisiae*. This strain is subjected to anaerobic batch fermentation as described above and samples are analyzed for isobutanol. As shown in Table EX13-1, the yield of isobutanol using this pathway in a PDC-minus *S. cerevisiae* is expected to result in a significant increase in yield.

Example 15

High-Yield Isobutanol Fermentation Using Crabtree-Positive PDC-Minus GPO-Minus *S. cerevisiae* with Balanced Isobutanol Pathway An alternative route to balancing the NADH and NADPH usage is to overexpress an $NADP^+$-dependent glyceraldehydes 3-phosphate dehydrogenase (GAPDH) in addition to the endogenous $NAD^+$-dependent GAPDH, such that both NADH and NADPH are generated from glycolysis. The isobutanol pathway can utilize an NADPH-dependent KARI enzyme and the NADH-dependent Adh2. In this case, PDC-minus and GPD-minus *S. cerevisiae* is transformed with a construct expressing a $NADP^+$-dependent GAPDH and an isobutanol pathway using Adh2. This strain is subjected to anaerobic batch fermentation as described above and samples analyzed for isobutanol. As shown in Table EX13-1, introduction of this $NADP^+$-dependent GAPDH is expected to result in a significant increase in productivity of isobutanol.

Example 16

High-Yield Isobutanol Fermentation Using Crabtree-Positive PDC-Minus *S. cerevisiae* with Balanced Isobutanol Pathway Yet another alternative route to balancing the NADH and NADPH usage is to replace the endogenous $NAD^+$-dependent GAPDH with an $NADP^+$-dependent GAPDH in a PDC-minus and GPD-minus *S. cerevisiae*. This strain is transformed with the isobutanol pathway and subjected to anaerobic batch fermentation as described above and samples analyzed for isobutanol. As shown in Table EX13-1, introduction of this $NADP^+$-dependent GAPDH is expected to result in a significant increase in productivity of isobutanol.

TABLE EX13-1

Isobutanol productivity in *S. cerevisiae* strains after 48 hours. (Listed numbers for the pdc-minus strains are expected numbers).

| | | Isobutanol | | Ethanol | |
|---|---|---|---|---|---|
| Genotype | Plasmid | Titer [g $L^{-1}$] | Yield [%] | Titer [g $L^{-1}$] | Yield [%] |
| WT | pathway genes | 0.13 | 0.31 | 31 | 60 |
| pdc− | pathway genes | 8.2 | 50 | 0.01 | 0.05 |
| pdc− gpd− | pathway genes | 9.9 | 70 | 0.01 | 0.05 |
| pdc− gpd− | balanced pathway (NADH utilizing pathway) | 13.2 | 80 | 0.01 | 0.05 |
| pdc− gpd− | balanced pathway (NADH and NADPH production from glycolysis) | 13.2 | 80 | 0.01 | 0.05 |
| pdc− gpd− | balanced pathway (NADPH production from glycolysis) | 13.2 | 80 | 0.01 | 0.05 |

Example 17

High-Yield Isobutanol Fermentation Using Crabtree-Negative PDC-Minus GPD-Minus Evolved *K. lactis* with Balanced Isobutanol Pathway In an embodiment, the yield for isobutanol may be increased by further engineering yeast microorganism to reduce production of minor byproducts. Isobutanol may be produced at a yield of about 90% theoretical.

Example 18

High-Yield Isobutanol Fermentation Using Crabtree-Positive PDC-Minus GPD-Minus Evolved *S. corevisiae* with Balanced Isobutanol Pathway In another embodiment, the yield for isobutanol may be increased by further engineering a yeast microorganism to reduce production of minor byproducts. Isobutanol may be produced at a yield of about 90% theoretical.

General Methods for Examples 19-24

Sample preparation: Samples were prepared from various timepoints for analysis by liquid chromatography and gas chromatography. 2 mL of media was removed and centrifuged at 14,000×g for 10 min. The supernatant was removed and stored at 4° C. until analysis.

Determination of optical density: The optical density of the yeast cultures was determined at 600 nm using a DU 800 spectrophotometer (Beckman-Coulter, Fullerton, Calif., USA). Samples were diluted as necessary to yield an optical density of between 0.1 and 0.8.

Gas Chromatography: Analysis of ethanol and isobutanol was performed on a HP 5890 gas chromatograph fitted with a ZB-FFAP column (Phenomenex; 30 m length, 0.32 mm ID, 0.25 μM film thickness) or equivalent connected to a flame ionization detector (FID). The temperature program was as follows: 200° C. for the injector with Agilent cyclo-splitter insert, 300° C. for the detector, 100° C. oven for 1 minute, 70° C./minute gradient to 235° C., and then hold until a final run time of 5.54 min. Injection volume was 0.5 μl, with a split ratio of 50:1; Helium flow rate was approximately 2.3 ml/min using a constant pressure of 0.88 bar.

High Performance Liquid Chromatography: Analysis of glucose and organic acids was performed on a HP-1100 High Performance Liquid Chromatography system equipped with two Rezex RFQ-"Fast Fruit" columns in series (Phenomenex, 100×7.8 mm, 8 μm particles), or equivalent, and an $H^+$ cation guard column (Bio-Rad) or equivalent. Pyruvate and HMF were detected using an HP-1100 UV detector (210 nm, 8 nm 360 nm reference) while all other organic acids and glucose were detected using an HP-1100 refractive index detector. The column and R1 temperatures were 60° C. This method was Isocratic with 0.018N sulfuric acid in water as mobile phase. Flow was set at 1.1 mL/min. Injection size was 20 μL and the run time was 15 minutes Lithium Acetate transformations of *S. cerevisiae* strains were transformed by the Lithium Acetate method (Gietz et al., *Nucleic Acids Res.* 27:69-74 (1992). Cells were collected from overnight cultures grown in 50 mL of defined (SC) ethanol media at an $OD_{600}$ of approximately 0.8 to 1.0 by centrifugation at 2700 rcf for 2 minutes at room temperature. The cell pellet was resuspended in 50 mL sterile water, collected by centrifugation (2700 rcf; 2 min; room temp.), and resuspended in 25 mL sterile water. The cells were collected by centrifugation (2700 rcf; 2 min; room temp.) and resuspended in 1 mL 100 mM lithium acetate. The cell suspension was transferred to a sterile 1.5 mL tube and collected by centrifugation at full speed for 10 seconds. The cells were resuspended in 100 mM lithium acetate with a volume four times the volume of the cell pellet (e.g. 400 μL for 100 μL cell pellet). To the prepared DNA Mix (72 μl 50% PEG, 10 μl 1M Lithium Acetate, 3 μl boiled salmon sperm DNA, and 5 μl of each plasmid), 15 μl of the cell suspension was added and mixed by vortexing with five short pulses. The cell/DNA suspensions were incubated at 30° C. for 30 minutes and at 42° C. for 22 minutes. The cells were collected by centrifugation for 10 seconds at full speed and resuspended in 100 μl SOS (1M Sorbitol, 0.34% (w/v) Yeast Extract, 0.68% (w/v) Peptone, 6.5 mM CaCl). The cell suspensions were top spread over appropriate selective agar plates.

Yeast colony PCR: Yeast cells were taken from agar medium and transferred to 30 μl 0.2% SDS and heated for 4 mins at 90° C. The cells were spun down and 1 μl of the supernatant was used for PCR using standard Taq (NEB).

Molecular biology: Standard molecular biology methods for cloning and plasmid construction were generally used, unless otherwise noted (Sambrook & Russell).

Media:

YP: contains 1% (w/v) yeast extract, 2% (w/v) peptone.

YPD is YP containing 2% (w/v) glucose, YPE is YP containing 2% (w/v) Ethanol.

YPD80 medium (Difco) is YP containing 80 g/L glucose, 0.2 g/L G418 antibiotic, 20 μM $CuSO_4$, and 1% ethanol.

SC+Complete: 20 g/L glucose, 14 g/L Sigma™ Synthetic Dropout Media supplement (includes amino acids and nutrients excluding histidine, tryptophan, uracil, and leucine), and 6.7 g/L Difco™ Yeast Nitrogen Base. 0.076 g/L histidine, 0.076 g/L tryptophan, 0.380 g/L leucine, and 0.076 g/L uracil.

Solid versions of the above described media contain 2% (w/v) agar.

Strains, Plasmids and Primer Sequences for Examples 19-24

TABLE EX 19-1

Genotype of strains for Examples 19-24.

| GEVO No. | Genotype and/or Reference |
|---|---|
| GEVO2712 | *S. cerevisiae* CEN.PK2; MATa ura3 leu2 his3 trp1 pdc1::{$P_{CUP1}$-Bs_alsS2, TRP1} pdc5::{$P_{TEF1}$:Sc_ILV3ΔN $P_{TDH3}$:Ec_ilvC_coSc$^{Q110V}$, LEU2} pdc6::{$P_{TEF1}$: LI_kivd2_coEc $P_{TDH3}$:Dm_ADH, URA3}, evolved for C2 supplement-independence, glucose tolerance and faster growth |
| GEVO2843 | *S. cerevisiae*, MATa ura3 leu2 his3 trp1 pdc1Δ::$P_{CUP1}$:[Bs_alsS1_coSc:$T_{CYC1}$: $P_{PGK1}$: LI_kivD2: $P_{ENO2}$: Sp_HIS5] pdc5Δ::[LEU2-bla-$P_{TEF1}$: ILV3ΔN: $P_{TDH3}$: Ec_ilvC_coSc$^{Q110V}$] pdc6Δ::[URA3: bla; $P_{TEF1}$: LI_kivD2: $P_{TDH3}$: Dm_ADH] {evolved for C2 supplement-independence, glucose tolerance and faster growth} |
| GEVO2962 | *S. cerevisiae* CEN.PK2; MATa ura3 leu2 his3 trp1 pdc1::PCUP1-Bs_alsS_coSc-TCYC1-PPGK1-LI_kivd-PENO2-Sp_HIS5 pdc5::LEU2-bla-PTEF1-ILV3ΔN-PTDH3-ilvC_coSc_Q110V pdc6::URA3-bla-PTEF1-LI_kivd-PTDH3-DmADH {evolved for C2 supplement-independence, glucose tolerance and faster growth} pGV2227 |
| GEVO2994 | *S. cerevisiae* CEN.PK2; MATa ura3 leu2 his3 trp1 pdc1::$P_{CUP1}$-Bs_alsS1_coSc-$T_{CYC1}$-$P_{PGK1}$-LI_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-LI_ilvD_coSc_$P_{TDH3}$-Ec_ilvC_coSc_P2D1-A1-$P_{ENO2}$-LI_adhA-$P_{FBA1}$-Sc_TRP1 {evolved for C2 supplement-independence, glucose tolerance and faster growth} |
| GEVO3059 | *S. cerevisiae* CEN.PK2; MATa ura3 leu2 his3 trp1 gpd1::$T_{KI\_URA3\_short}$-$P_{FBA1}$-KI_URA3-$T_{KI\_URA3}$ pdc1::$P_{CUP1}$-Bs_alsS1_coSc-$T_{CYC1}$-$P_{PGK1}$-LI_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-LI_ilvD_coSc_$P_{TDH3}$-Ec_ilvC_coSc_P2D1-A1-$P_{ENO2}$-LI_adhA-$P_{FBA1}$-Sc_TRP1 {evolved for C2 supplement-independence, glucose tolerance and faster growth} |
| GEVO3061 | *S. cerevisiae* CEN.PK2; MATa ura3 leu2 his3 trp1 gpd2::$T_{KI\_URA3\_short}$-$P_{FBA1}$-KI_URA3-$T_{KI\_URA3}$ pdc1::$P_{CUP1}$-Bs_alsS1_coSc-$T_{CYC1}$-$P_{PGK1}$-LI_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-LI_ilvD_coSc_$P_{TDH3}$-Ec_ilvC_coSc_P2D1-A1-$P_{ENO2}$-LI_adhA-$P_{FBA1}$-Sc_TRP1 {evolved for C2 supplement-independence, glucose tolerance and faster growth} |
| GEVO3124 | *S. cerevisiae* CEN.PK2; MATa ura3 leu2 his3 trp1 gpd1::$T_{Ki\_URA3\_short}$-$P_{FBA1}$-Ki_URA3-$T_{Ki\ URA3}$ gpd2::$P_{CCW12}$-Hph pdc1::$P_{CUP1}$-Bs_alsS1_coSc-$T_{CYC1}$-$P_{PGK1}$-Ll_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-Ll_ilvD_coSc_$P_{TDH3}$-Ec_ilvC_coSc_P2D1-A1-$P_{ENO2}$-Ll_adhA-$P_{FBA1}$-Sc_TRP1 {evolved for C2 supplement-independence, glucose tolerance and faster growth} |
| GEVO3128 | *S. cerevisiae* CEN.PK2; MATa ura3 leu2 his3 trp1 gpd1::$P_{CCW12}$-Hph gpd2::$T_{Ki\_URA3\_short}$-$P_{FBA1}$-Ki_URA3-$T_{Ki\_URA3}$ pdc1::$P_{CUP1}$-Bs_alsS1_coSc-$T_{CYC1}$-$P_{PGK1}$-Ll_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-Ll_ilvD_coSc_$P_{TDH3}$-Ec_ilvC_coSc_P2D1-A1-$P_{ENO2}$-Ll_adhA-$P_{FBA1}$-Sc_TRP1 {evolved for C2 supplement-independence, glucose tolerance and faster growth} |
| GEVO3158 | *S. cerevisiae* CEN.PK2; MATa ura3 leu2 his3 trp1 gpd1::$T_{Ki\_URA3\_short}$-$P_{FBA1}$-Ki_URA3-$T_{Ki\_URA3}$ gpd2::$P_{CCW12}$-Hph pdc1::$P_{CUP1}$-Bs_alsS1_coSC-$T_{CYC1}$-$P_{PGK1}$-Ll_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-Ll_ilvD_coSc_$P_{TDH3}$-Ec_ilvC_coSc_P2D1-A1-$P_{ENO2}$-Ll_adhA-$P_{FBA1}$-Sc_TRP1 [pGV2227] {evolved for C2 supplement-independence, glucose tolerance and faster growth} |
| GEVO3159 | *S. cerevisiae* CEN.PK2; MATa ura3 leu2 his3 trp1 gpd1::$T_{Ki\_URA3\_short}$-$P_{FBA1}$-Ki_URA3-$T_{Ki\_URA3}$ gpd2::$P_{CCW12}$-Hph pdc1::$P_{CUP1}$-Bs_alsS1_coSc-$T_{CYC1}$-$P_{PGK1}$-Ll_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-Ll_ilvD_coSc_$P_{TDH3}$-Ec_ilvC_coSc_P2D1-A1-$P_{ENO2}$-Ll_adhA-$P_{FBA1}$-Sc_TRP1 [pGV2082] {evolved for C2 supplement-independence, glucose tolerance and faster growth} |
| GEVO3160 | *S. cerevisiae* CEN.PK2; MATa ura3 leu2 his3 trp1 gpd1::$P_{CCW12}$-Hph gpd2::$T_{Ki\_URA3\_short}$-$P_{FBA1}$-Ki_URA3-$T_{Ki\_URA3}$ pdc1::$P_{CUP1}$-Bs_alsS1_coSc-$T_{CYC1}$-$P_{PGK1}$-Ll_kivd2_coEc-$P_{ENO2}$-Sp_his5 pdc5::LEU2-bla-$P_{TEF1}$-ILV3ΔN20-$P_{TDH3}$-Ec_ilvC_coSc_Q110V pdc6::$P_{TEF}$-Ll_ilvD_coSc_$P_{TDH3}$-Ec_ilvC_coSc_P2D1-A1-$P_{ENO2}$-Ll_adhA-$P_{FBA1}$-Sc_TRP1 [pGV2247] {evolved for C2 supplement-independence, glucose tolerance and faster growth} |
| GEVO3532 | *S. cerevisiae* CEN.PK2; MATa ura3 leu2 his3 trp1 gpd1::$T_{Ki\_URA3}$ gpd2::$T_{Ki\_URA3}$ pdc1::$P_{CUP1}$-Bs_alsS1_coSc-$T_{CYC1}$-$P_{PGK1}$-Ll_kivd2_coEc-$P_{ENO2}$-Sp_HIS5 pdc5::$T_{Ki\_URA3\_short}$-$P_{FBA1}$-Ki_URA3-$T_{Ki\_URA3}$ pdc6::$P_{TEF1}$-Ll_ilvD_$P_{TDH3}$-Ec_ilvC_coSc$^{P2D1\text{-}A1}$-$P_{ENO2}$-Ll_adhA-$P_{FBA1}$-Sc_TRP1 {evolved for C2 supplement-independence, glucose tolerance and faster growth} (first described here) |

TABLE EX 19-2

Plasmids disclosed for Examples 19-24.

| GEVO No. | Genotype or Reference |
|---|---|
| pGV2082 | $P_{TEF1}$-Ll__ilvD__coSc-$P_{TDH3}$-Ec__ilvC__coSc__Q110V-$P_{TPI1}$-G418R-$P_{PGK1}$-Ll__kivD2__coEc-$P_{ENO2}$-Dm__ADH, 2μ ori, bla, pUC-ori. |
| pGV2227 | $P_{TEF1}$-Ll__ilvD__coSc-$P_{TDH3}$-Ec__ilvC__coSc$^{Q110V}$-$P_{TPI1}$-G418R-$P_{PGK1}$-Ll__kivd2__coEc-PDC1-3'region-$P_{ENO2}$-Ll__adhA 2μ bla, pUC-ori |
| pGV2247 | $P_{TEF1}$-Ll__ilvD__coSc-$P_{TDH3}$-Ec__ilvC__coSc__P2D1-A1-$P_{TPI1}$-G418R-$P_{PGK1}$-Ll__kivD2__coEc-$P_{ENO2}$-Ll__adhA, 2μ ori, bla, pUC-ori. |
| pGV2563 | $P_{TEF1}$-Ll__ilvD__coSc, $P_{TDH3}$-Ec__ilvC__coSc$^{P2D1-A1-his6}$, $P_{ENO2}$-Ll__adhA__coSc$^{RE1-his6}$, 2μ-ori, pUC ori, bla, G418r |

Example 19

Isobutanol Production in Pdc-Yeast

This example demonstrates isobutanol production at greater than 30% yield in a Pdc-minus member of the *Saccharomyces sensu stricto* group, *Saccharomyces* clade yeast, Crabtree-positive yeast, post-WGD yeast *S. cerevisiae.*

GEVO2962 is a modified yeast biocatalyst that contains genes within the chromosome of the biocatalyst which encode a pathway of enzymes that convert pyruvate into isobutanol. GEVO2962 is GEVO2843 transformed with pGV2227 (SEQ ID NO: 57), which is a high copy yeast expression plasmid used to overexpress Ec_ilvC Q110V (*Escherichia coli* ilvC containing a Q to V mutation at position 110), Ll_ilvD (Lactococcus lactis ilvD), Ll_kivD2 (Lactococcus lactis kivD), and Ll_AdhA (*Lactococcus lactis* adhA). The strain GEV02843 is PDC-deficient and able to grow in high glucose media without addition of C2-compounds. GEVO2843 has integrated into the PDC1 locus the Bs_alsS1_coSc (*Bacillus subtilis* alsS; SEQ ID NO: 58) and Ll_kivD2_coEc (*Lactococcus lactis* kivD, SEQ ID NO: 59) genes under the CUP1 and PGK1 promoters, respectively. This strain also has the Ll_kivD2_coEc (*Lactococcus lactis* kivD, SEQ ID NO: 59) and Dm_ADH (*Drosophila melanogaster* ADH, SEQ ID NO: 60) under the TEF1 and TDH3 promoters, respectively, integrated into the PDC6 locus. Lastly, this strain has the Ec_ilvC_coSc_Q110V (SEQ ID NO: 61) and Sc_ILV3ΔN20 (SEQ ID NO: 62) under the TDH3 and TEF1 promoters, respectively, integrated at the PDC5 locus.

When the biocatalyst GEVO2962 was contacted with glucose in a medium suitable for growth of the biocatalyst, at about 30° C., the biocatalyst produced isobutanol from the glucose. A 24-hour starter culture was started in a 50 mL conical tube with GEVO2962 cells from a frozen glycerol stock. The tube contained a 5 mL volume of YPD80 medium (Difco) at a starting $OD_{600}$ of about 1.0. The starter culture was grown for approximately 24 hrs in a 30° C. shaker at 250 rpm. The entire contents of the starter culture were then transferred to a flask seed culture. The flask seed culture was 1 L of YPD80 medium in a 2.8 L baffled Fernbach flask. The seed flask culture was grown for approximately 24 hrs in a 30° C. shaker at 250 rpm.

A portion of the flask seed culture was transferred to a 2 L DasGip seed fermenter containing about 750 mL of YPD80 medium to achieve a 1 $OD_{600}$ initial cell concentration. The fermenter vessel was attached to a computer control system to monitor and control pH at 5.0 through addition of base, temperature at 30° C., oxygen transfer rate (OTR), and agitation. The vessel was agitated, with a fixed agitation of 1000 rpm and 2 sL/h air flow overlay. Cells were grown until the $OD_{600}$ was about 10. Some of the seed fermenter culture was then transferred to a 2 L DasGip fermenter vessel containing about 1100 mL of YPD80. The vessel was attached to a computer control system to monitor and control pH at 6.0 through addition of base, temperature at about 30° C., dissolved oxygen, and agitation. Initially, during the cell growth phase, the vessel was agitated with a variable agitation of 400-600 rpm using a 10 sL/h air sparge until the $OD_{600}$ was about 8. Cell growth continued for approximately 16 hrs, after which time, the agitation was fixed at 600 rpm with 5 sL/h airflow. The dissolved oxygen was approximately zero throughout this experiment with an OTR of about 4-8 mM/h. Continuous measurement of the fermentor vessel off-gas by mass spectrometer analysis was performed for oxygen, isobutanol, ethanol, and carbon dioxide throughout the experiment. Samples were aseptically removed from the fermenter vessel throughout the experiment and used to measure $OD_{600}$, glucose concentration, and isobutanol concentration in the broth.

At about 48 h intervals throughout the 470 h experiment, the fermenter whole broth was removed from the fermenter, cells were separated from the broth using centrifugation at about 20° C. and 4000×g in 500 mL centrifuge bottles. The cell pellets were resuspended in fresh YPD medium that contained 80 g/L glucose, 0.2 g/L G418 antibiotic, 20 μM $CuSO_4$, and 1% ethanol and returned to the fermenter. At six points throughout the fermentation, about 1 L of a flask culture of GEVO2962 at about 7 $OD_{600}$ was concentrated to 50-100 mL by centrifugation and then added to the fermenter vessel aseptically.

The fermenter vessel was attached by tubing to a smaller 400 mL fermenter vessel that served as a flash tank and operated in a recirculation loop with the fermenter. Whole fermentation broth was recirculated between the flash tank and fermenter at a rate of about 10-30 mL per min. The volume in the flash tank was approximately 100 mL and the hydraulic retention time in the flash tank was about 3-10 minutes. Heat and vacuum were applied to the flash tank. The vacuum level applied to the flash tank was initially set at about 60 mBar and the flash tank was set at approximately 36° C. Generally, the vacuum ranged from 50-65 mBar and the flash tank temperature ranged from 35° C. to 37° C. throughout the experiment. Vapor from the heated flash tank was condensed into a collection vessel as distillate. Whole fermentation broth was continuously returned from the flash tank back to the fermentation vessel. When the concentration of isobutanol in the broth dropped below 1.5 g/L, the flash recycle system was turned off. The flash recycle was turned back on when the broth concentration of isobutanol reached above 2.5 g/L.

The distillate recovered in the experiment was strongly enriched for isobutanol. Isobutanol formed an azeotrope with water and lead to a two phase distillate: an isobutanol rich top phase and an isobutanol lean bottom phase. Distillate samples were analyzed by GC for isobutanol concentration.

Isobutanol production reached a maximum at around 470 hrs with a total effective titer of about 111 g/L. The isobutanol production rate was about 0.24 g/L/h on average over the course of the experiment. The percent theoretical yield of isobutanol was approximately 36% at the end of the experiment.

Example 20

Isobutanol Production in Pdc- Gpd-Yeast

This example demonstrates isobutanol production at greater than 70% yield in a Pdc-minus, Gpd-minus member of the *Saccharomyces sensu stricto* group, *Saccharomyces* clade yeast, Crabtree-positive yeast, post-WGD yeast, *S. cerevisiae.*

The modified yeast biocatalyst, GEVO3158, encodes a heterologous pathway of enzymes that convert pyruvate into isobutanol. Genes for the pathway are located on the chromosome and on a single plasmid. GEVO3158 is GEVO3124 transformed with pGV2247 (SEQ ID NO: 63), which is a high copy yeast expression plasmid used to overexpress Ec_ilvC_Q110V (*Escherichia coli* ilvC containing a Q to V mutation at position 110), Ll_ilvD (*Lactococcus lactis* ilvD), Ll_kivD (*Lactococcus lactis* kivD), and Ll_adhA (*Lactococcus lactis* adhA). The strain GEVO3124 is both GPD-deficient, PDC-deficient and able to grow in high glucose media without addition of C2-compounds. GEVO3124 has integrated into the PDC1 locus the Bs_alsS1_coSc (*Bacillus subtilis* alsS; SEQ ID NO: 58) and Ll_kivD2_coEc (*Lactococcus lactis* kivD, SEQ ID NO: 59) genes under the CUP1 and PGK1 promoters, respectively. This strain also has the Ec_ilvC_coSc_P2D1-A1 (*Escherichia coli* ilvC variant; SEQ ID NO: 64), Ll_ilvD coSc, and Ll_adhA (*Lactococcus lactis* adhA, SEQ ID NO: 66) under the TDH3, TEF1 and ENO2 promoters, respectively, integrated into the PDC6 locus. Lastly, this strain has the Ec_ilvC_coSc_Q110V (*Escherichia coli* ilvC containing a Q to V mutation at position 110; SEQ ID NO: 61) and Sc_ILV3ΔN20 (SEQ ID NO: 62) under the TDH3 and TEF1 promoters, respectively, integrated at the PDC5 locus.

GEVO3124 was generated by deletion of GPD2 using Hph as marker in strain GEVO3059. Deletion of GPD2 was carried out by transforming a hygromycin resistance marker, Hph, flanked by the GPD2 5' and 3' targeting sequences. This gpd2::Hph disruption cassette was generated by multiple rounds of SOE PCR. First, the GPD2 5' targeting sequence was amplified from pGV2164 (SEQ ID NO: 69), the CCW12 promoter was amplified from pGV1954 (SEQ ID NO: 70), the Hph ORF was amplified from pGV2074 (SEQ ID NO: 71), and the GPD2 3' targeting sequence was also amplified. Second, the GPD2 5' targeting sequence and the CCW12 promoter were stitched together by SOE-PCR, and the Hph ORF and GPD2 3' targeting sequence were stitched together by SOE-PCR. Lastly, these two SOE-PCR products were stitched together in another round of SOE-PCR. The resulting product was then transformed into GEVO3059 recovered overnight in YPD+1% EtOH+G418 or YPD+1% EtOH+G418+1 g/L glycerol, and selected on YPD+G418+Hygro+1 g/L glycerol or YPD+G418+Hygro+10 g/L glycerol plates. Twelve colonies were re-streaked for singles and colony PCRs were performed in single colony isolates to test for correct 5' and 3' junctions and the loss of GPD2.

GEVO3059 was generated by deletion of GPD1 using KI_URA3 as marker in strain GEVO2994. Deletion of GPD1 was carried out by a bipartite integration scheme using the KI_URA3 marker. The 5' bipartite fragment contained the GPD1_5' targeting sequence-$T_{KI\_URA3\_short}$-$P_{FBA1}$-KI_URA3_3' truncated and was generated by PCR with pGV2359 (SEQ ID NO: 72) as template. The 3' bipartite fragment contained KI_URA3_5' truncated-$T_{kI\_URA3}$-GPD1_3' targeting sequence and was generated by PCR with pGV2157 (SEQ ID NO: 73) as template. The 3' truncated and 5' truncated KI_URA3 overlapped by 347 bp to allow for recombination between the KI_URA3 sequences and reconstitution of a functional KI_URA3 gene. The 5' and 3' bipartite fragments were co-transformed into GEVO2994 and selected on SCD-U+1 g/L glycerol plates.

GEVO2994 was generated by integrating the Ec_ilvC_coSc_P2D1-A1 (*Escherichia coli* ilvC variant; SEQ ID NO: 64), Ll_ilvD_coSc, (*Lactococcus lactis* ilvD, SEQ ID NO: 65) and Ll_adhA (*Lactococcus lactis* adhA, SEQ ID NO: 66) under the TDH3, TEF1 and ENO2 promoters, respectively, into the PDC6 locus of GEVO2843. This integration replaced the Ll_kivD2_coEc (*Lactococcus lactis* kivD, SEQ ID NO: 59) and the Dm_ADH (*Drosophila melanogaster* ADH, SEQ ID NO: 60) that were present at the PDC6 locus in GEVO2843. GEVO2843 was generated by integrating the Bs_alsS1_coSc (*Bacillus subtilis* alsS; SEQ ID NO: 58) and Ll_kivD2_coEc (*Lactococcus lactis* kivD, SEQ ID NO: 59) into the PDC1 locus of GEVO2712

When the biocatalyst GEVO3158 was contacted with glucose in a medium suitable for growth of the biocatalyst, at about 30° C., the biocatalyst produced isobutanol from the glucose. A 24-hour starter culture was started in a 50 mL conical tube with GEVO3158 cells from a frozen glycerol stock. The tube contained a 5 mL volume of YPD80 at a starting $OD_{600}$ of about 1.0. The starter culture was grown for approximately 24 hrs in a 30° C. shaker at 250 rpm. The entire contents of the starter culture were then transferred to a flask seed culture. The flask seed culture was 80 mL of YPD80 medium in a 500 mL baffled Erlenmeyer flask. The seed flask culture was grown for approximately 24 hrs in a 30° C. shaker at 250 rpm.

A portion of the flask seed culture was transferred to a 2 L DasGip fermenter containing about 750 mL of YPD80 medium to achieve a 0.5 $OD_{600}$ initial cell concentration. The fermenter vessel was attached to a computer control system to monitor and control pH at 6.0 through addition of base, temperature at 30° C., oxygen transfer rate (OTR), and agitation. The vessel was agitated, with a fixed agitation of 700 rpm to maintain an OTR of about 10 mM/h using a 5 sL/h air overlay until the $OD_{600}$ was about 8-10. After continuing growth for approximately 20 hrs, the OTR was decreased to approximately 0.2-0.7 mM/h by reducing agitation to a fixed 250-350 rpm and continued 5 sL/h airflow overlay. Measurement of the fermentor vessel off-gas by mass spectrometer was included for ethanol, isobutanol, carbon dioxide, and oxygen. Continuous measurement of off-gas concentrations of carbon dioxide and oxygen were also measured by a DasGip off-gas analyzer throughout the experiment. Samples were aseptically removed from the fermenter vessel throughout the experiment and used to measure $OD_{600}$, glucose concentration by HPLC, and isobutanol concentration in the broth by GC.

Isobutanol production reached a maximum at around 7 days with a titer of about 10 g/L. Yield of the fermentation, calculated when the titer of isobutanol was between 3.7 g/L and 10 g/L, was approximately 74% maximum theoretical. Yield of the fermentation, calculated when the titer of isobutanol was between 0 g/L and 10 g/L, was approximately 52% maximum theoretical. Yield of the fermentation, calculated when the titer of isobutanol was between 0.5 g/L and 10 g/L, was approximately 61% maximum theoretical.

Example 21

Isobutanol Production in Pdc- Gpd-Yeast

This example demonstrates isobutanol production at greater than 70% yield in a Pdc-minus, Gpd-minus member of the *Saccharomyces sensu stricto* group, *Saccharomyces* clade yeast, Crabtree-positive yeast, post-WGD yeast, *S. cerevisiae.*

The modified yeast biocatalyst, GEVO3159, encodes a heterologous pathway of enzymes that convert pyruvate into isobutanol. Genes for the pathway are located on the chromosome and on a single plasmid. GEVO3159 is GEVO3124 transformed with pGV2082 (SEQ ID NO: 67), which is a high copy yeast expression plasmid used to overexpress Ec_ilvC_Q110V (*Escherichia coli* ilvC containing a Q to V mutation at position 110), Ll_ilvD (Lactococcus lactis ilvD), Ll_kivD2 (Lactococcus lactis kivD), and Dm_ADH (*Drosophila melanogaster* ADH).

The strain GEVO3124 is both GPD-deficient, PDC-deficient and able to grow in high glucose media without addition of C2-compounds. GEVO3124 has integrated into the PDC1 locus the Bs_alsS1_coSc (*Bacillus subtilis* alsS; SEQ ID NO: 58) and Ll_kivD2 coEc (*Lactococcus lactis* kivD, SEQ ID NO: 59) genes under the CUP1 and PGK1 promoters, respectively. This strain also has the Ec_ilvC_coSc_P2D1-A1 (*Escherichia coli* ilvC variant; SEQ ID NO: 64), Ll_ilvD_coSc (*Lactococcus lactis* ilvD, SEQ ID NO: 65), and Ll_adhA (Lactococcus lactis adhA, SEQ ID NO: 66) under the TDH3, TEF1 and ENO2 promoters, respectively, integrated into the PDC6 locus. Lastly, this strain has the Ec_ilvC_coSc_Q110V (*Escherichia coli* ilvC containing a Q to V mutation at position 110; SEQ ID NO: 61) and Sc_ILV3ΔN20 (SEQ ID NO: 62) under the TDH3 and TEF1 promoters, respectively, integrated at the PDC5 locus.

GEVO3124 was generated by deletion of GPD2 using Hph as marker in strain GEVO3059. Deletion of GPD2 was carried out by transforming a hygromycin resistance marker, Hph, flanked by the GPD2 5' and 3' targeting sequences. This gpd2::Hph disruption cassette was generated by multiple rounds of SOE-PCR. First, the GPD2 5' targeting sequence was amplified from pGV2164 (SEQ ID NO: 69), the CCW12 promoter was amplified from pGV1954 (SEQ ID NO: 70), the HPH ORF was amplified from pGV2074 (SEQ ID NO: 71), and the GPD2 3' targeting sequence was also amplified. Second, the GPD2 5' targeting sequence and the CCW12 promoter were stitched together by SOE-PCR, and the Hph ORF and GPD2 3' targeting sequence were also stitched together by SOE-PCR. Lastly, these two SOE-PCR products were stitched together in another round of SOE-PCR. The resulting product was then transformed into GEVO3059 recovered overnight in YPD+1% EtOH+G418 or YPD+1% EtOH+G418+1 g/L glycerol, and selected on YPD+G418+ Hygro+1 g/L glycerol or YPD+G418+Hygro+10 g/L glycerol plates. Twelve colonies were re-streaked for singles and colony PCRs were performed in single colony isolates to test for correct 5' and 3' junctions and the loss of GPD2.

GEVO3059 was generated by deletion of GPD1 using KI_URA3 as marker in strain GEVO2994. Deletion of GPD1 was carried out by a bipartite integration scheme using the KI_URA3 marker. The 5' bipartite fragment contained the GPD1_5' targeting sequence-$T_{KI\_URA3\_short}$-$P_{FBA1}$-KI_URA3_3' truncated and was generated by PCR with pGV2359 (SEQ ID NO: 72) as template. The 3' bipartite fragment contained KI_URA3_5' truncated-$T_{KI\_URA3}$-GPD1_3' targeting sequence and was generated by PCR with pGV2175 (SEQ ID NO: 73) as template. The 3' truncated and 5' truncated KI_URA3 overlapped by 347 bp to allow for recombination between the KI_URA3 sequences and reconstitution of a functional KI_URA3 gene. The 5' and 3' bipartite fragments were co-transformed into GEVO2994 and selected on SCD-U+1 g/L glycerol plates.

GEVO2994 was generated by integrating the Ec_ilvC_coSc_P2D1-A1 (*Escherichia coli* ilvC variant; SEQ ID NO: 64), Ll_ilvD_coSc (*Lactococcus lactis* ilvD, SEQ ID NO: 65), and Ll_adhA (*Lactococcus lactis* adhA, SEQ ID NO: 66) under the TDH3, TEF1 and ENO2 promoters, respectively, into the PDC6 locus of GEVO2843. GEVO2843 was generated by integrating the Bs_alsS1_coSc (*Bacillus subtilis* alsS; SEQ ID NO: 58 and Ll_kivD2_coEc (*Lactococcus lactis* kivD, SEQ ID NO: 59) into the PDC1 locus of GEVO2712.

When the biocatalyst GEVO3159 was contacted with glucose in a medium suitable for growth of the biocatalyst, at about 30° C., the biocatalyst produced isobutanol from the glucose. A 24-hour starter culture was started in a 50 mL conical tube with GEVO3159 cells from a frozen glycerol stock. The tube contained a 5 mL volume of YPD80 at a starting $OD_{600}$ of about 1.0. The starter culture was grown for approximately 24 hrs in a 30° C. shaker at 250 rpm. The entire contents of the starter culture were then transferred to a flask seed culture. The flask seed culture was 80 mL of YPD80 in a 500 mL baffled Erlenmeyer flask. The seed flask culture was grown for approximately 24 hrs in a 30° C. shaker at 250 rpm.

A portion of the flask seed culture was transferred to a 2 L DasGip fermenter containing about 750 mL of YPD80 medium to achieve a 0.5 $OD_{600}$ initial cell concentration. The fermenter vessel was attached to a computer control system to monitor and control pH at 6.0 through addition of base, temperature at 30° C., oxygen transfer rate (OTR), and agitation. The vessel was agitated, with a fixed agitation of 700 rpm to maintain an OTR of about 10 mM/h using a 5 sL/h air overlay until the $OD_{600}$ was about 8-10. After continuing growth for approximately 20 hrs, the OTR was decreased to approximately 0.2-0.7 mM/h by reducing agitation to a fixed 250-350 rpm and continued 5 sL/h airflow overlay. Measurement of the fermentor vessel off-gas by mass spectrometer was included for ethanol, isobutanol, carbon dioxide, and oxygen. Continuous measurement of off-gas concentrations of carbon dioxide and oxygen were also measured by a DasGip off-gas analyzer throughout the experiment. Samples were aseptically removed from the fermenter vessel throughout the experiment and used to measure $OD_{600}$, glucose concentration by HPLC, and isobutanol concentration in the broth by GC.

Isobutanol production reached a maximum at around 5 days with a titer of about 8.5 g/L. Yield of the fermentation, calculated when the titer of isobutanol was between 3.2 g/L and 8.5 g/L, was approximately 75% maximum theoretical. Yield of the fermentation, calculated when the titer of isobutanol was between 0 g/L and 8.5 g/L, was approximately 48% maximum theoretical. Yield of the fermentation, calculated when the titer of isobutanol was between 1 g/L and 8.5 g/L, was approximately 58% maximum theoretical.

Example 22

Isobutanol Production in Pdc- Gpd-, Co-Factor Balanced Yeast

This example demonstrates isobutanol production at greater than 70% yield in a Pdc-minus, Gpd-minus member of the *Saccharomyces sensu stricto* group, *Saccharomyces* clade yeast, Crabtree-positive yeast, post-WGD yeast, *S. cerevisiae*, expressing an NADH-dependent isobutanol biosynthetic pathway.

The recombinant yeast microorganism, GEVO3160, encodes a heterologous biosynthetic pathway that converts pyruvate into isobutanol. Genes for the pathway are located on the chromosome and on a single plasmid. GEVO3160 is GEVO3128 transformed with pGV2247(SEQ ID NO: 63), which is a high copy yeast expression plasmid used to overexpress Ec_ilvC_P2D1-A1 (*Escherichia coli* ilvC variant), Ll_ilvD (*Lactococcus lactis* ilvD), Ll_kivD (*Lactococcus lactis* kivD), and Ll_adhA (*Lactococcus lactis* adhA). The strain GEVO3128 is both GPD-deficient, PDC-deficient and able to grow in high glucose media without addition of C2-compounds. GEVO3128 has integrated into the PDC1 locus the Bs_alsS1_coSc (*Bacillus subtilis* alsS; SEQ ID NO: 58) and Ll_kivD2_coEc (*Lactococcus lactis* kivD, SEQ ID NO: 59) genes under the CUP1 and PGK1 promoters, respectively. This strain also has the Ec_ilvC_coSc_P2D1-A1 (*Escherichia coli* ilvC variant; SEQ ID NO: 64), Ll_ilvD_coSc (*Lactococcus lactis* ilvD, SEQ ID NO: 65), and Ll_adhA (*Lactococcus lactis* adhA, SEQ ID NO: 66) under the TDH3, TEF1 and ENO2 promoters, respectively, integrated into the PDC6 locus. Lastly, this strain has the Ec_ilvC_coSc_Q110V (*Escherichia coli* ilvC containing a Q to V mutation at position 110; SEQ ID NO: 61) and Sc_ILV3ΔN20 (SEQ ID NO: 62) under the TDH3 and TEF1 promoters, respectively, integrated at the PDC5 locus.

GEVO3128 was generated by deletion of GPD1 using Hph as marker in strain GEVO3061. To obtain a gpd1 gpd2 double deletion, deletion of GPD1 was pursued in the gpd2::KI_URA3 deletion strains GEVO3061 Deletion of GPD1 was carried out by transforming a hygromycin resistance marker, Hph, flanked by the GPD1 5' and 3' targeting sequences. This gpdt:Hph disruption cassette was generated by multiple rounds of SOE PCR. First, the GPD1 5' targeting sequence was amplified from pGV2163 (SEQ ID NO: 74), the CCW12 promoter was amplified from pGV1954 (SEQ ID NO: 70), the Hph ORF was amplified from pGV2074 (SEQ ID NO: 71), and the GPD1 3' targeting sequence was amplified by PCR. Second, the GPD1 5' targeting sequence and the CCW12 promoter were stitched together by SOE-PCR, and the Hph ORF and GPD1 3' targeting sequence were also stitched together by SOE-PCR. Lastly, these two SOE-PCR products were stitched together in another round of SOE-PCR. The resulting product was then transformed into GEVO3061, recovered overnight in YPD+1% EtOH+G418 or YPD+1% EtOH+G418+1 g/L glycerol, and selected on YPD+G418+Hygro+1 g/L glycerol or YPD+G418+Hygro+10 g/L glycerol plates GEVO3061 was generated by deletion of GPD2 using KI_URA3 as marker in strain GEVO2994. Deletion of GPD2 was carried out by a bipartite integration scheme using the KI_URA3 marker. The 5' bipartite fragment contained the GPD2__5' targeting sequence-$T_{KI\_URA3\_short}$-$P_{FBA1}$-KI_URA3__3' truncated and was generated by PCR with pGV2360 (SEQ ID NO: 75) as template. The 3' bipartite fragment contained KI_URA3__5' truncated-$T_{KI\_URA3}$-GPD2__3' targeting sequence and was generated by PCR with pGV2381(SEQ ID NO: 76) as a template. The 3' truncated and 5' truncated KI_URA3 overlapped by 347 bp to allow for recombination between the KI_URA3 sequences and reconstitution of a functional KI_URA3 gene. The 5' and 3' bipartite fragments were co-transformed into GEVO2994 and selected on SCD-U+1 g/L glycerol plates.

GEVO2994 was generated by integrating the Ec_ilvC_coSc_P2D1-A1 (*Escherichia coli* ilvC variant; SEQ ID NO: 64), Ll_ilvD_coSc (*Lactococcus lactis* ilvD, SEQ ID NO: 65), and Ll_adhA (*Lactococcus lactis* adhA, SEQ ID NO: 66) under the TDH3, TEF1 and ENO2 promoters, respectively, into the PDC6 locus of GEVO2843. GEVO2843 was generated by integrating the Bs_alsS1_coSc (*Bacillus subtilis* alsS; SEQ ID NO: 58) and Ll_kivD2_coEc (*Lactococcus lactis* kivD, SEQ ID NO: 59) into the PDC1 locus of GEVO2712.

When the biocatalyst GEVO3160 was contacted with glucose in a medium suitable for growth of the biocatalyst, at about 30° C., the biocatalyst produced isobutanol from the glucose. A 24-hour starter culture was started in a 50 mL conical tube with GEVO3160 cells from a frozen glycerol stock. The tube contained a 5 mL volume of YPD80 medium at a starting $OD_{600}$ of about 1.0. The starter culture was grown for approximately 24 hrs in a 30° C. shaker at 250 rpm. The entire contents of the starter culture were then transferred to a flask seed culture. The flask seed culture was 80 mL of YPD80 medium in a 500 mL baffled Erlenmeyer flask. The seed flask culture was grown for approximately 24 hrs in a 30° C. shaker at 250 rpm.

A portion of the flask seed culture was transferred to a 2 L DasGip fermenter containing about 750 mL of YPD80 medium to achieve a 0.5 $OD_{600}$ initial cell density. The fermenter vessel was attached to a computer control system to monitor and control pH at 6.0 through addition of base, temperature at 30° C., oxygen transfer rate (OTR), and agitation. The vessel was agitated, with a fixed agitation of 700 rpm to maintain an OTR of about 10 mM/h using a 5 sL/h air overlay until the $OD_{600}$ was about 8-10. After continuing growth for approximately 20 hrs, the OTR was decreased to approximately 0.2-0.4 mM/h by reducing agitation to a fixed 200 rpm and continued 5 sL/h airflow overlay. Measurement of the fermentor vessel off-gas by mass spectrometer was included for ethanol, isobutanol, carbon dioxide, and oxygen. Continuous measurement of off-gas concentrations of carbon dioxide and oxygen were also measured by a DasGip off-gas analyzer throughout the experiment. Samples were aseptically removed from the fermenter vessel throughout the experiment and used to measure $OD_{600}$, glucose concentration by HPLC, and isobutanol concentration in the broth by GC. Isobutanol production reached a maximum at around 7 days with a titer of about 10.5 g/L.

Yield of the fermentation, calculated when the titer of isobutanol was between 5.7 g/L and 10.2 g/L, was approximately 74% of theoretical (max yield calculation). Yield of the fermentation, calculated when the titer of isobutanol was between 0 g/L and 10.5 g/L, was approximately 48% of theoretical (yield calculation including growth of biomass). Yield of the fermentation, calculated when the titer of isobutanol was between 0.6 g/L and 10.5 g/L, was approximately 57% of theoretical (yield calculation for production phase only).

Example 23

Isobutanol Production in Pdc- Gpd-Yeast

This example demonstrates isobutanol production at greater than 70% yield in a Pdc-minus, Gpd-minus member of the *Saccharomyces sensu stricto* group, *Saccharomyces* clade yeast, Crabtree-positive yeast, post-WGD yeast, *S. cerevisiae*, expressing an NADH-dependent isobutanol biosynthetic pathway.

The recombinant yeast microorganism, GEVO3160, encodes a heterologous biosynthetic pathway that converts pyruvate into isobutanol. Genes for the pathway are located on the chromosome and on a single plasmid. GEVO3160 is GEVO3128 transformed with pGV2247 (SEQ ID NO: 63), which is a high copy yeast expression plasmid used to overexpress Ec_ilvC_P2D1-A1 (*Escherichia coli* ilvC variant), Ll_ilvD (*Lactococcus lactis* ilvD), Ll_kivD (*Lactococcus lactis* kivD), and Ll_adhA (*Lactococcus lactis* adhA). The strain GEVO3128 is both GPD-deficient, PDC-deficient and able to grow in high glucose media without addition of C2-compounds. GEVO3128 has integrated into the PDC1 locus the Bs_alsS1_coSc (*Bacillus subtilis* alsS; SEQ ID NO: 58) and Ll_kivD2_coEc (*Lactococcus lactis* kivD, SEQ ID NO: 59) genes under the CUP1 and PGK1 promoters, respectively. This strain also has the Ec_ilvC_coSc_P2D1-A1 (*Escherichia coli* ilvC variant; SEQ ID NO: 64), Ll_ilvD_coSc (*Lactococcus lactis* ilvD, SEQ ID NO: 65), and Ll_adhA (*Lactococcus lactis* adhA, SEQ ID NO: 66) under the TDH3, TEF1 and ENO2 promoters, respectively, integrated into the PDC6 locus. Lastly, this strain has the Ec_ilvC_coSc_Q110V (*Escherichia coli* ilvC containing a Q to V mutation at position 110; SEQ ID NO: 61) and Sc_ILV3ΔN20 (SEQ ID NO: 62) under the TDH3 and TEF1 promoters, respectively, integrated at the PDC5 locus.

GEVO3128 was generated by deletion of GPD1 using Hph as marker in strain GEVO3061. To obtain a gpd1 gpd2 double deletion, deletion of GPD1 was pursued in the gpd2::KI_URA3 deletion strains GEVO3061 Deletion of GPD1 was carried out by transforming a hygromycin resistance marker, Hph, flanked by the GPD1 5' and 3' targeting sequences. This gpd1::Hph disruption cassette was generated by multiple rounds of SOE PCR. First, the GPD1 5' targeting sequence was amplified from pGV2163 (SEQ ID NO: 74), the CCW12 promoter was amplified from pGV1954 (SEQ ID NO: 70), the Hph ORF was amplified from pGV2074 (SEQ ID NO: 71), and the GPD1 3' targeting sequence was amplified by PCR. Second, the GPD1 5' targeting sequence and the CCW12 promoter were stitched together by SOE-PCR, and the Hph ORF and GPD1 3' targeting sequence were also stitched together by SOE-PCR. Lastly, these two SOE-PCR products were stitched together in another round of SOE-PCR. The resulting product was then transformed into GEVO3061, recovered overnight in YPD+1% EtOH+G418 or YPD+1% EtOH+G418+1 g/L glycerol, and selected on YPD+G418+Hygro+1 g/L glycerol or YPD+G418+Hygro+10 g/L glycerol plates GEVO3061 was generated by deletion of GPD2 using KI_URA3 as marker in strain GEVO2994. Deletion of GPD2 was carried out by a bipartite integration scheme using the KI_URA3 marker. The 5' bipartite fragment contained the GPD2__5' targeting sequence-$T_{KI\_URA3\_short}$-$P_{FBA1}$-KI_URA3__3' truncated and was generated by PCR with pGV2360 (SEQ ID NO: 75) as template. The 3' bipartite fragment contained KI_URA3__5' truncated-$T_{KI\_URA3}$-GPD2__3' targeting sequence and was generated by PCR with pGV2381 (SEQ ID NO: 76) as template. The 3' truncated and 5' truncated KI_URA3 overlapped by 347 bp to allow for recombination between the KI_URA3 sequences and reconstitution of a functional KI_URA3 gene. The 5' and 3' bipartite fragments were co-transformed into GEVO2994 and selected on SCD-U+1 g/L glycerol plates.

GEVO2994 was generated by integrating the Ec_ilvC_coSc_P2D1-A1 (*Escherichia coli* ilvC variant; SEQ ID NO: 64), Ll_ilvD_coSc (*Lactococcus lactis* ilvD, SEQ ID NO: 65), and Ll_adhA (*Lactococcus lactis* adhA, SEQ ID NO: 66) under the TDH3, TEF1 and ENO2 promoters, respectively, into the PDC6 locus of GEVO2843. GEVO2843 was generated by integrating the Bs_alsS1_coSc (*Bacillus subtilis* alsS; SEQ ID NO: 58) and Ll_kivD2 coEc (*Lactococcus lactis* kivD, SEQ ID NO: 59) into the PDC1 locus of GEVO2712.

When the biocatalyst GEVO3160 was contacted with glucose in a medium suitable for growth of the biocatalyst, at about 30° C., the biocatalyst produced isobutanol from the glucose. A 24-hour starter culture was started in a 50 mL conical tube with GEVO3160 cells from a frozen glycerol stock. The tube contained a 5 mL volume of YPD80 medium at a starting $OD_{600}$ of about 1.0. The starter culture was grown for approximately 24 hrs in a 30° C. shaker at 250 rpm. The entire contents of the starter culture were then transferred to a flask seed culture. The flask seed culture was 80 mL of YPD80 medium in a 500 mL baffled Erlenmeyer flask. The seed flask culture was grown for approximately 24 hrs in a 30° C. shaker at 250 rpm.

A portion of the flask seed culture was transferred to a 2 L DasGip fermenter containing about 750 mL of YPD80 medium to achieve a 0.5 $OD_{600}$ initial cell concentration. The fermenter vessel was attached to a computer control system to monitor and control pH at 6.0 through addition of base, temperature at 30° C., oxygen transfer rate (OTR), and agitation. The vessel was agitated, with a fixed agitation of 700 rpm to maintain an OTR of about 10 mM/h using a 5 sL/h air overlay until the $OD_{600}$ was about 8-10. After continuing growth for approximately 20 hrs, the OTR was decreased to approximately 0.3-0.8 mM/h by reducing agitation to a fixed 180-350 rpm and continued 5 sL/h airflow overlay. Measurement of the fermentor vessel off-gas by mass spectrometer was included for ethanol, isobutanol, carbon dioxide, and oxygen. Continuous measurement of off-gas concentrations of carbon dioxide and oxygen were also measured by a DasGip off-gas analyzer throughout the experiment. Samples were aseptically removed from the fermenter vessel throughout the experiment and used to measure $OD_{600}$, glucose concentration by HPLC, and isobutanol concentration in the broth by GC.

Isobutanol production reached a maximum at around 7 days with a titer of about 14 g/L. Yield of the fermentation, calculated when the titer of isobutanol was between 7.2 g/L and 12.6 g/L, was approximately 71% maximum theoretical. Yield of the fermentation, calculated when the titer of isobutanol was between 0 g/L and 14 g/L, was approximately 52% maximum theoretical. Yield of the fermentation, calculated when the titer of isobutanol was between 0.5 g/L and 14 g/L, was approximately 60% maximum theoretical.

Example 24

Isobutanol Production in Pdc- Gpd-Yeast

This example demonstrates isobutanol production at greater than 70% yield in a Pdc-minus, Gpd-minus member of the *Saccharomyces sensu stricto* group, *Saccharomyces* clade yeast, Crabtree-positive yeast, post-WGD yeast, *S. cerevisiae*, expressing an NADH-dependent isobutanol biosynthetic pathway.

GEVO3647 contains $P_{ADH1}$-Bs_alsS1_coSc (*Bacillus subtilis* alsS; SEQ ID NO: 58) with two copies of the *Lactococcus lactis* kivD gene (SEQ ID NO: 59) integrated at the PDC1 locus. The strain is a transformation product of the parent strain GEVO3532 with plasmid pGV2563 (SEQ ID NO: 68).

Medium used for the fermentation was YP+80 g/L glucose+1% v/v Ethanol+0.2 g/L G418. The medium was filter sterilized using a 1 L bottle top Corning PES 0.22 μm filter (431174). Medium was pH adjusted 6.0 in the fermenter vessels using 6N KOH. Table EX 15-1 outlines medium components per liter of Di-$H_2O$.

Inoculum cultures were started from patch plates and placing them in 500 mL baffled flasks containing 80 ml YP+20 g/L glucose+1% v/v ethanol+0.2 g/L G418 medium. The cultures were incubated for 32.5 h at 30° C. in an orbital shaker at 250 rpm. Cell density after incubation was as at $OD_{600}$ of 2.5. Batch fermentations were conducted using a 2 L top drive motor DasGip vessel with a working volume of 1.2 L per vessel. The operating conditions are summarized in Table EX15-1 below.

TABLE EX15-1

| Process control parameters. | | |
|---|---|---|
| Initial volume | mL | 1200 |
| Temperature | ° C. | 30 |
| pH | | 6.0 |
| Growth Phase (0-32 hours): | | |
| Oxygen transfer rate (OTR) | mM/h | 10.0 |
| Air flow (overlay) | slph | 5.0 |
| Agitation | rpm | 900 |
| Dissolved oxygen (DO) | % | Not controlled |
| Production phase (32-84.3 hours): | | |
| Oxygen transfer rate (OTR) | mM/h | 0.5 |
| Air flow (overlay) | slph | 5.0 |
| Agitation | rpm | 300 |
| Dissolved oxygen (DO) | % | Not controlled |

Fermenter vessels were sterilized, along with the appropriate dissolved oxygen probes and pH probes, for 60 minutes at 121° C. pH probes were calibrated prior to sterilization however, dissolved oxygen probes were calibrated post sterilization in order to achieve complete polarization prior to calibration. Table EX15-1 outlines the process control parameters used during the fermentation. Note that pH was controlled using 6N KOH and 2N $H_2SO_4$.

The fermentation was run for 84.3 h. Vessels were sampled every 6-10 h or 3 times daily. Sterile 5 mL syringes were used to collect 3 mL of fermenter broth via a sterile sample port. The sample was placed in a 2 mL microfuge tube and a portion was used to measure cell density ($OD_{600}$) on a Genesys 10 spectrophotometer (Thermo Scientific). The remaining sample was filtered through a 0.22 μm Corning filter. The supernatant from each vessel was refrigerated in a 96-well deep well plate, and stored at 4° C. prior to gas and liquid chromatography analysis.

Analysis of volatile organic compounds, including ethanol and isobutanol was performed on a HP 5890/6890/7890 gas chromatograph fitted with an HP 7673 Autosampler, a DB-FFAP column (J&W; 30 m length, 0.32 mm ID, 0.25-μM film thickness) or equivalent connected to a flame ionization detector (FID). The temperature program was as follows: 200° C. for the injector, 300° C. for the detector, 100° C. oven for 1 minute, 70° C./minute gradient to 230° C., and then hold for 2.5 min. Analysis was performed using authentic standards (>99%, obtained from Sigma-Aldrich, and a 5-point calibration curve with 1-pentanol as the internal standard).

Analysis of organic acid metabolites was performed on an HP-1200 High Performance Liquid Chromatography system equipped with two Restek RFQ 150×4.6 mm columns in series. Organic acid metabolites were detected using an HP-1100 UV detector (210 nm) and refractive index. The column temperature was 60° C. This method was isocratic with 0.0180 $NH_2SO_4$ in Milli-Q water as mobile phase. Flow was set to 1.1 mL/min. Injection volume was 20 μL and run time was 16 min. Analysis was performed using authentic standards (>99%, obtained from Sigma-Aldrich, with the exception of DHIV (2,3-dihydroxy-3-methyl-butanoate, CAS1756-18-9), which was custom synthesized at Caltech (Cioffi, E. et al. Anal Biochem 104 pp. 485 (1980)), and a 5-point calibration curve.

Additionally, on-line continuous measurement of the fermenter vessel off-gas by GC-MS analysis was performed for oxygen, isobutanol, ethanol, carbon dioxide, and nitrogen throughout the experiment.

At the end of the fermentation, the isobutanol titer had reached 6.4 g/L. Yield of the fermentation, calculated over the entire production phase, i.e. from 32 to 84.3 hours, was approximately 71% of theoretical.

Example 25

Cytosolic ALS Homologs that Support Isobutanol Production

This example demonstrates isobutanol production using expression of cytosolically localized ALS genes in the presence of the rest of the isobutanol pathway. The ALS genes were integrated into the PDC1 locus of *S. cerevisiae* strain GEVO1187 and isobutanol production was achieved by expression from plasmid of the other genes in the isobutanol pathway. Isobutanol production in strains carrying the ALS genes from *T. atroviride* (Ta_ALS) and *T. stipitatus* (Ts_ALS) was compared to isobutanol production in strains carrying the ALS gene from *B. subtilis* (either Bs_alsS2 or Bs_alsS1_coSc). Strains, and plasmids are listed in Tables EX16-1 and EX16-2, respectively.

TABLE EX16-1

| Genotype of strains disclosed herein | |
|---|---|
| GEVO No. | Genotype |
| Gevo 1187 | *S. cerevisiae*, CEN.PK; MATa ura3 leu2 his3 trp1 |
| Gevo 2280 | *S. cerevisiae* MATa ura3 leu2 his3 trp1 ADE2 pdc1::$P_{CUP1-1}$-Bs_AlsS2, TRP1 Note that this is TRP1 +. Transformed with plasmid pGV1730. Original isolate A2 |
| Gevo 2618 | *S. cerevisiae*, MATa ura3 leu2 his3 trp1 pdc1::$P_{CUP1-1}$-Bs_AlsS1_coSc, TRP1. Transformed with plasmid pGV2114. |
| Gevo 2621 | *S. cerevisiae*, MATa ura3 leu2 his3 trp1 pdc1::$P_{CUP1-1}$-Ta_Als, TRP1. Transformed with plasmid pGV2117. |
| Gevo 2622 | *S. cerevisiae*, MATa ura3 leu2 his3 trp1 pdc1::$P_{CUP1-1}$-Ts_Als, TRP1. Transformed with plasmid pGV2118. |

TABLE EX16-2

| Plasmids disclosed herein | | |
|---|---|---|
| Plasmid name | Relevant Genes/Usage | Genotype |
| pGV1730 | Integration plasmid that will integrate $P_{CUP1-1}$:Bs_alsS2 into PDC1 using digestion with NruI for targeting. This was the parent vector for cloning the ALS homologs. | $P_{CUP1-1}$:Bs_alsS2, pUC ORI, $Amp^R$, TRP1, PDC1 3'-fragment-NruI-PDC1 5'-fragment. |
| pGV1773 | Vector with *Bacillus subtilis* AlsS codon optimized for *S. cerevisiae*. | $P_{PDC1}$:Bs_AlsS1_coSc, $P_{TDH3}$:Ll_kivD, $P_{ADH1}$:Sc_ADH7_coSc, URA3 5'-end, pUC ORI, $kan^R$. |
| pGV1802 | DNA2.0 plasmid carrying the *Trichoderma atroviride* ALS. | Ta_ALS_coSc in DNA 2.0 vector |
| pGV1803 | DNA2.0 plasmid carrying the *Talaromyces stipitatus* ALS. | Ts_ALS_coSc in DNA 2.0 vector |
| pGV2082 | High copy 2μ plasmid with 4 isobutanol pathway genes without an ALS gene. | Ec_ilvC_$coSc^{Q110V}$, Ll_ilvD_coSc, Ll_kivD2_coEc, and Dm_ADH, 2μ ori, bla, G418R. |
| pGV2114 | Integration plasmid that will integrate into PDC1 using digestion with NruI for targeting. It carries the *Bacillus subtilis* AlsS gene codon optimized for *S. cerevisiae*. | $P_{CUP1-1}$:Bs_alsS1_coSc, pUC ORI, $Amp^R$, TRP1, PDC1 3'-fragment-NruI-PDC1 5'-fragment. |
| pGV2117 | Integration plasmid that will integrate into PDC1 using digestion with NruI for targeting. It carries the *Trichoderma atroviride* ALS gene codon optimized for *S. cerevisiae*. | $P_{CUP1-1}$:Ta_ALS_coSc, pUC ORI, $Amp^R$, TRP1, PDC1 3'-fragment-NruI-PDC1 5'-fragment. |
| pGV2118 | Integration plasmid that will integrate into PDC1 using digestion with NruI for targeting. It carries the *Talaromyces stipitatus* ALS gene codon optimized for *S. cerevisiae*. | $P_{CUP1-1}$:Ts_ALS coSc, pUC ORI, $Amp^R$, TRP1, PDC1 3'-fragment-NruI-PDC1 5'-fragment. |

Materials and Methods for Example 25

Standard molecular biology methods for cloning and plasmid construction were generally used, unless otherwise noted (Sambrook, J., Russel, D. W. *Molecular Cloning, A Laboratory Manual.* 3rd ed. 2001, Cold Spring Harbor, N.Y.: Cold Spring Harbor Laboratory Press).

Cloning techniques included digestion with restriction enzymes, gel purification of DNA fragments (using the Zymoclean Gel DNA Recovery Kit, Cat# D4002, Zymo Research Corp, Orange, Calif.), ligations of two DNA fragments (using the Roche rapid ligation kit, Cat® 11 635 379 001, Roche Diagnostics, Mannheim, Germany), Klenow treatment of fragments to give blunt ends (using the NEB DNA Polymerase I, Large (Klenow), cat# M0210S, Ipswich, Mass.), and bacterial transformations into chemically competent *E. coli* cells made at GEVO (TOP10). Plasmid DNA was purified from *E. coli* cells using the Qiagen QIAprep Spin Miniprep Kit (Cat#27106, Qiagen, Valencia, Calif.).

PCR was performed on an Eppendorf Mastercycler (Cat#71086, Novagen, Madison Wis.). The following PCR program was followed for all primer sets unless otherwise noted: 94° C. for 2 min then 40 cycles of (94° C. 30 sec, 54° C. 30 sec, 72° C. 1 min) then 72° C. for 10 min. Yeast colony PCR used the FailSafe™ PCR System EPICENTRE® Biotechnologies, Madison, Wis.; Catalog #FS99250). A PCR cocktail containing 15 μl of Master Mix E buffer, 10.5 μl water, 2 μl of each primer at 10 μM concentration, 0.5 μl polymerase enzyme mix from the kit was added to a 0.2 mL PCR tube for each sample (30 μl each). For each candidate a small amount of cells was added to the reaction tube using a sterile P10 pipette tip. Presence of the positive PCR product was assessed using agarose gel electrophoresis. The following primer pairs were used. Primers 1432 and 1433 for the 5'-ends of all integrations (800 bp band), primers 1435 and 2233 for the 3'-ends of pGV2114 integrations (1.1 Kb band), primers 1435 and 2234 for the 3'-end of the pGV2115 integrations (1.1 Kb band), primers 1435 and 2236 for the 3'-ends of the pGV2117 integrations (1.1 Kb band), primers 1435 and 2237 for the 3'-ends of the pGV2118 integrations (1.1 Kb band).

Transformation of integration plasmids was performed according to the lithium acetate protocol described above. Integration plasmids were digested with NruI, checked by gel electrophoresis for complete digestion and used directly from digestion. Integrative transformants were selected by plating the transformed cells on SCD-Trp agar medium. Once the transformants were single colony purified they were maintained on SCD-Trp plates. Once transformants were screened by PCR as described above for proper integration, each strain was transformed with the plasmid pGV2082. Transformants were plated to YPD plates containing 0.2 g/L G418.

SCD-Trp: 20 g/L glucose, 14 g/L Sigma™ Synthetic Drop-out Media supplement (includes amino acids and nutrients excluding histidine, tryptophan, uracil, and leucine), and 6.7 g/L Difco™ Yeast Nitrogen Base. 0.076 g/L histidine, 0.380 g/L leucine, and 0.076 g/L uracil.

Fermentations

Strains with integrated ALS genes expressed from the CUP1 promoter were transformed with pGV2082 (which carries the other 4 isobutanol pathway genes Ec_ilvC_coScQ110V (SEQ ID NO: 61), Ll_ilvD (SEQ ID NO: 65), Ll_kivd2_coEc (SEQ ID NO: 59), and Dm_ADH (SEQ ID NO: 60)). Strains were patched onto YPD plates containing 0.2 mg/mL G418. The following morning cells were removed from the plate with a sterile toothpick and resuspended in 4 mL of YPD with 0.2 mg/mL G418. The $OD_{600}$ was determined for each culture. Cells were added to 50 mL YP with 5% dextrose and 0.2 mg/mL G418 such that a final $OD_{600}$ of 0.1 was obtained. 1 mL of media was removed and the $OD_{600}$ for this undiluted sample determined, leftover media was stored at 4° C. to act as media blank for the analytics submission, and to act as the t=0 sample for the fermentation. At t=24 h, 2 mL of media was removed and 25 μL used at a 1:40 dilution to determine $OD_{600}$. The remaining culture was centrifuged in a microcentrifuge at maximum speed for 10 min and a 1:10 dilution read on the YSI. 50% glucose containing 0.2 mg/mL G418 was added to a final concentration of 100 g/L glucose. 1 mL of supernatant was analyzed by gas chromatography as described above. At t=48 h, 2 mL of media was removed and 25 μL used at a 1:40 dilution to determine $OD_{600}$. The remaining culture was centrifuged in a microcentrifuge at maximum speed for 10 min and a 1:10 dilution read on the YSI. 50% glucose plus water (with 0.2 mg/mL G418) were added to give a final concentration of glucose of 100 g/L. 1 mL of supernatant was analyzed by gas chromatography. At t=72 h, 2 mL of media was removed and 25 μL used at a 1:40 dilution to determine $OD_{600}$). The remaining culture was centrifuged in a microcentrifuge at maximum speed for 10 min and a 1:10 dilution read on the YSI. 1 mL of supernatant was analyzed by gas chromatography and high performance liquid chromatography.

Yeast Strain Construction

GEVO2280 was constructed by transforming GEVO1187 with the integration plasmid pGV1730. The plasmid pGV1730 was first linearized with NruI, which cuts such that the linear plasmid will integrate into the PDC1 locus, and the DNA was transformed using the standard yeast transformation protocol. Transformants were selected by plating to SCGaI-Trp plates. Individual integrants were verified using colony PCR with primers 1432 and 1433 to detect proper integration at the 5'-end (803 bp fragment) and primers 1220 and 1435 to detect proper integration at the 3'-end (772 bp).

GEVO2618 was constructed by transforming GEVO1187 with the integration plasmid pGV2114. The plasmid was first linearized with NruI, which cuts such that the linear plasmid will integrate into the PDC1 locus, and the DNA was transformed using the standard yeast transformation protocol described above. Correct integration was verified with colony PCR using primers 1432 and 1433 to check the 5'-end of the integration (800 bp band) and primers 1435 and 2233 for the 3'-end of pGV2114 integration (1,100 bp band).

GEVO2621 was constructed by transforming GEVO1187 with the integration plasmid pGV2117. The plasmid was first linearized with NruI, which cuts such that the linear plasmid will integrate into the PDC1 locus, and the DNA was transformed using the standard yeast transformation protocol described above. integration was verified with colony PCR using primers 1432 and 1433 to check the 5'-end of the integration (800 bp band) and primers 1435 and 2236 for the 3'-end of pGV2117 integration (1,100 bp band).

GEVO2622 was constructed by transforming GEVO1187 with the integration plasmids pGV2118. The plasmid was first linearized with NruI, which cuts such that the linear plasmid will integrate into the PDC1 locus, and the DNA was transformed using the standard yeast transformation protocol described above. Twelve transformants were single colony purified. Correct integration was verified with colony PCR using primers 1432 and 1433 to check the 5'-end of the integration (800 bp band) and primers 1435 and 2237 for the 3'-end of pGV2118 integration (1,100 bp band).

Each ALS-containing strain was transformed with the 4 component pathway plasmid, pGV2082 (SEQ ID NO: 67), as described above. Control strains GEVO2280 (Bs_alsS2) and GEVO1187 (no ALS) were also transformed with pGV2082. Transformants were single colony purified and maintained on YPD plates with 0.2 mg/mL G418.

Plasmid Construction

Construction of plasmid pGV2082. The plasmid pGV2044 carries the genes Ec_ilvC_coSc$^{Q110V}$, Bs_AlsS2, Ll_ilvD_coSc and Dm_ADH. The plasmid pGV2082 was created from pGV2044 by replacing the Bs_AlsS2 with Ll_kivD2_coEc as follows: the Ll_kivD2_coEc gene and associated PGK1 promoter were removed from pGV2047 by digestion with AvrII and NcoI. The 2530 bp fragment was purified by gel electrophoresis and the fragment was prepared using the Zymoclean kit described above. Plasmid pGV2044 was digested with EcoRI and SbfI to remove the Bs_AlsS2 gene and associated CUP1 promoter and the 11275 bp vector fragment was gel purified. The vector and insert were treated with Klenow fragment to produce blunt ends. The pGV2044 vector fragment and the $P_{PGK1}$:Ll_kivD2_coEc insert were ligated using standard methods in an approximately 5:1 insert:vector molar ratio and transformed into TOP10 chemically competent *E. coli* cells. Plasmid DNA was isolated and correct clones were confirmed using restriction enzyme analysis consisting of digestion of potential clones with the following enzymes: EcoRV to give correct fragments of 6.3 and 7.5 kb, EcoRV plus NruI to give correct fragments of 2.9, 3.4, and 7.5 kb), EcoRI plus NcoI to give correct fragments of 2.5 and 11.2 Kb.

pGV1730 was digested with BamHI and SalI and the vector fragment of 4.9 kb was gel purified by agarose gel electrophoresis. pGV1773 was digested with BamHI and SalI and the 1.7 Kb fragment containing the Bs_AlsS_coSc was gel purified by agarose gel electrophoresis. The pGV1730 vector fragment was ligated to the pGV1773 insert fragment using the Roche rapid ligation kit in a ratio of 5:1 insert to vector ratio and transformed into TOP10 chemically competent *E. coli* cells. Plasmid DNA was isolated and correct clones were confirmed using restriction enzyme analysis consisting of digestion of potential clones with ScaI plus PstI to give correct fragments of 2.7, 1.7, 1.4 and 0.9 Kb, AflII to give correct fragments of 1.5 and 5.1 kb, NaeI plus StuI to give correct fragments of 1.4, 5.2 kb.

Construction of pGV2117: pGV1730 was digested with BamHI and SalI and the vector fragment of 4.9 kb was gel purified by agarose gel electrophoresis. pGV1802 was digested with BamHI and SalI and the 1.8 kb fragment containing the Ta_ALS was gel purified by agarose gel electrophoresis. The pGV1730 vector fragment w:as ligated to the pGV1802 insert fragment using the Roche rapid ligation kit in a ration of 5:1 insert to vector ratio and transformed into TOP-10 chemically competent *E. coli* cells. Plasmid DNA was isolated and correct clones were confirmed using restriction enzyme analysis consisting of digestion of potential clones with BamHI plus StuI to give correct fragments of 1.4 and 5.2 kb, SalI plus PstI to give correct fragments of 0.7 and 5.9 kb, and AhdI to give correct fragments of 1.9 and 4.7 kb.

Construction of pGV2118: pGV1730 was digested with BamHI and SalI and the vector fragment of 4.9 kb was gel purified by agarose gel electrophoresis. pGV1803 was digested with BamHI and SalI and the 1.8 kb fragment containing the Ts_ALS gel purified by agarose gel electrophoresis. The pGV1730 vector fragment was ligated to the pGV1803 insert fragment using the Roche rapid ligation kit in a ration of 5:1 insert to vector ratio and transformed into TOP-10 chemically competent *E. coli* cells. Plasmid DNA was isolated and correct clones were confirmed using restriction enzyme analysis consisting of digestion of potential clones with NaeI to give correct bands of 2.9 and 3.7 kb, EcoRV to give correct bands of 0.7 and 5.9 kb, and HpaI plus SacI to give correct bands of 1.9 and 4.7 kb.

Results

Fermentations of GEVO1187, GEVO2280, GEVO2618, GEVO2621, GEVO2622 and transformed with pGV2082 were carried out as described above (except G418 was not added to the glucose at 24 h). In this experiment strains containing the ALS genes Ta_ALS_coSc and Ts_ALS_coSc produced more isobutanol than the strain containing the Bs_Als2. The Bs_Als1_coSc produced the most isobutanol. Table EX16-3 shows the final OD, glucose consumption, and isobutanol titer for each of the strains. The integration of the cytosolic genes Ta_ALS coSc and Ts_ALS_coSc led to production of isobutanol that was in each case 6-fold above that of a strain without an integrated ALS gene, demonstrating that these strains are producing isobutanol using a cytosolic pathway.

TABLE EX16-3

Results of fermentation with cytosolic ALS homologs, at 72 h

| Strain | $OD_{600}$ | Glucose consumed g/L | Isobutanol produced g/L |
|---|---|---|---|
| GEVO1187 | 10.9 ± 0.3 | 233 ± 36 | 0.3 ± 0.0 |
| GEVO2280 | 9.9 ± 0.3 | 274 ± 26 | 1.3 ± 0.11 |
| GEVO2618 | 9.4 ± 0.2 | 138 ± 9 | 2.6 ± .09 |
| GEVO2621 | 9.9 ± 0.3 | 161 ± 52 | 1.9 ± .18 |
| GEVO2622 | 10.8 ± 0.6 | 182 ± 47 | 1.8 ± .15 |

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

What is claimed is:

1. A recombinant yeast microorganism for producing isobutanol, the recombinant yeast microorganism comprising an isobutanol producing metabolic pathway, wherein said isobutanol producing metabolic pathway comprises the following substrate to product conversions:

(i) pyruvate to acetolactate;

(ii) acetolactate to 2,3-dihydroxyisovalerate;

(iii) 2,3-dihydroxyisovalerate to α-ketoisovalerate;

(iv) α-ketoisovalerate to isobutyraldehyde; and (v) isobutyraldehyde to isobutanol;

wherein the recombinant yeast microorganism expresses (a) an acetolactate synthase to catalyze the conversion of pyruvate to acetolactate;

(b) a ketol-acid reductoisomerase to catalyze the conversion of acetolactate to 2,3-dihydroxyisovalerate;

(c) a dihydroxyacid dehydratase to catalyze the conversion of 2,3-dihydroxyisovalerate to α-ketoi sovalerate;

(d) an α-ketoisovalerate decarboxylase from *Laciococcus lactis* to catalyze the conversion of α-ketoisovalerate to isobutyraldehyde; and (e) an alcohol dehydrogenase to catalyze the conversion of isobutyraldehyde to isobutanol;

wherein the recombinant yeast microorganism has been engineered to:

(A) disrupt, mutate, or delete one or more endogenous pyruvate decarboxylase (PDC) genes; and (B) disrupt, mutate, or delete one or more endogenous glycerol-3-phosphate dehydrogenase (GPD) genes;

wherein said recombinant yeast microorganism has reduced endogenous PDC and reduced endogenous GPD activity as compared to the corresponding yeast microorganism that has not been engineered to have reduced endogenous PDC activity and reduced endogenous GPD activity; and wherein the recombinant yeast microorganism produces isobutanol at a yield which is at least 10% of the theoretical yield of isobutanol from glucose.

2. The recombinant yeast microorganism of claim 1, wherein all endogenous PDC genes and all endogenous GPD genes are disrupted, mutated, or deleted.

3. The recombinant yeast microorganism of claim 1, wherein said acetolactate synthase is a cytosolically-localized acetolactate synthase.

4. The recombinant yeast microorganism of claim 3, wherein said cytosolically-localized acetolactate synthase is encoded by the *Lactococcus lactis* alsS gene.

5. The recombinant yeast microorganism of claim 3, wherein said cytosolically-localized acetolactate synthase is encoded by the *Bacillus subtilis* alsS gene.

6. The recombinant yeast microorganism of claim 1, wherein said recombinant yeast microorganism has been engineered to disrupt or delete an endogenous pyruvate dehydrogenase (PDH) gene.

7. The recombinant yeast microorganism of claim 1, wherein said recombinant yeast microorganism has an increased capacity to produce acetolactate as compared to the corresponding yeast microorganism that has not been engineered to have reduced endogenous PDC activity and reduced endogenous GPD activity.

8. The recombinant yeast microorganism of claim 1, wherein said recombinant yeast microorganism is a yeast of a genus selected from the group consisting of *Saccharomyces, Kluyveromyces, Candida, Pichia, Issatchenkia, Debaryomyces, Hansenula, Yarrowia*, and *Schizosaccharomyces.*

9. A method of producing isobutanol, comprising:

(a) providing a recombinant yeast microorganism according to claim 1;

(b) cultivating the microorganism in a culture medium containing a feedstock providing the carbon source, until the isobutanol is produced; and (c) recovering the isobutanol.

* * * * *

UNITED STATES PATENT AND TRADEMARK OFFICE

CERTIFICATE OF CORRECTION

PATENT NO. : 8,455,239 B2
APPLICATION NO. : 12/820505
DATED : June 4, 2013
INVENTOR(S) : Reid M. Renny Feldman et al.

It is certified that error appears in the above-identified patent and that said Letters Patent is hereby corrected as shown below:

In the Claims

Column 393, line 39, claim 1, "α-ketoi sovalerate" should read --α-ketoisovalerate--.

Column 393, line 40, claim 1, "*Laciococcus*" should read --*Lactococcus*--.

Signed and Sealed this
Twenty-third Day of July, 2013

Teresa Stanek Rea
*Acting Director of the United States Patent and Trademark Office*